US006821765B2

(12) United States Patent
Ye et al.

(10) Patent No.: US 6,821,765 B2
(45) Date of Patent: Nov. 23, 2004

(54) ISOLATED HUMAN KINASE PROTEINS, NUCLEIC ACID MOLECULES ENCODING HUMAN KINASE PROTEINS, AND USES THEREOF

(75) Inventors: Jane Ye, Boyds, MD (US); Chunhua Yan, Boyds, MD (US); Valentina Di Francesco, Rockville, MD (US); Ellen M Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 10/667,442

(22) Filed: Sep. 23, 2003

(65) Prior Publication Data

US 2004/0043466 A1 Mar. 4, 2004

Related U.S. Application Data

(62) Division of application No. 10/254,869, filed on Sep. 26, 2002, now Pat. No. 6,653,117, which is a division of application No. 09/801,876, filed on Mar. 9, 2001, now Pat. No. 6,492,155.

(51) Int. Cl.[7] .......................... C12N 9/12; C12N 15/00; C12N 5/00; C12N 1/20; C07H 21/04

(52) U.S. Cl. .................... 435/194; 435/320.1; 435/325; 435/252.3; 435/6; 536/23.2

(58) Field of Search ......................... 435/194, 6, 252.3, 435/325, 320.1; 536/23.2

(56) References Cited

PUBLICATIONS

No References cited.*

* cited by examiner

*Primary Examiner*—Maryam Monshipouri
(74) *Attorney, Agent, or Firm*—Celera Genomics; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

12 Claims, 90 Drawing Sheets

```
   1 CCATGGGAGC GAACACTTCA AGAAAACCAC CAGTGTTTGA TGAAAATGAA
  51 GATGTCAACT TTGACCACTT TGAAATTTTG CGAGCCATTG GGAAAGGCAG
 101 TTTTGGGGAG GTCTGCATTG TACAGAAGAA TGATACCAAG AAGATGTGCG
 151 CAATGAAGTA CATGAATAAA CAAAAGTGCG TGGAGCGCAA TGAAGTGAGA
 201 AATGTCTTCA AGGAACTCCA GATCATGCAG GGTCTGGAGC ACCCTTTCCT
 251 GGTTAATTTG TGGTATTCCT TCCAAGATGA GGAAGACATG TTCATGGTGG
 301 TGGACCTCCT GCTGGGTGGA GACCTGCGTT ATCACCTGCA ACAGAACGTC
 351 CACTTCAAGG AAGAAACAGT GAAGCTCTTC ATCTGTGAGC TGGTCATGGC
 401 CCTGGACTAC CTGCAGAACC AGCGCATCAT TCACAGGGAT ATGAAGCCTG
 451 ACAATATTTT ACTTGACGAA CATGGGCACG TGCACATCAC AGATTTCAAC
 501 ATTGCTGCGA TGCTGCCCAG GGAGACACAG ATTACCACCA TGGCTGGCAC
 551 CAAGCCTTAC ATGGCACCTG AGATGTTCAG CTCCAGAAAA GGAGCAGGCT
 601 ATTCCTTTGC TGTTGACTGG TGGTCCCTGG GAGTGACGGC ATATGAACTG
 651 CTGAGAGGCC GGAGACCGTA TCATATTCGC TCCAGTACTT CCAGCAAGGA
 701 AATTGTACAC ACGTTTGAGA CGACTGTTGT AACTTACCCT TCTGCCTGGT
 751 CACAGGAAAT GGTGTCACTT CTTAAAAAGC TACTCGAACC TAATCCAGAC
 801 CAACGATTTT CTCAGTTATC TGATGTCCAG AACTTCCCGT ATATGAATGA
 851 TATAAACTGG GATGCAGTTT TTCAGAAGAG GCTCATTCCA GGTTTCATTC
 901 CTAATAAAGG CAGGCTGAAT TGTGATCCTA CCTTTGAACT TGAGGAAATG
 951 ATTTTGGAGT CCAAACCTCT ACATAAGAAA AAAAAGCGTC TGGCAAAGAA
1001 GGAGAAGGAT ATGAGGAAAT GCGATTCTTC TCAGACATGT CTTCTTCAAG
1051 AGCACCTTGA CTCTGTCCAG AAGGAGTTCA TAATTTTCAA CAGAGAAAAA
1101 GTAAACAGGG ACTTTAACAA AAGACAACCA AATCTAGCCT TGGAACAAAC
1151 CAAAGACCCA CAAGGTGAGG ATGGTCAGAA TAACAACTTG TAAAGGCCTC
1201 ATGTCTTCTT CTTGGGACAA TCTCATGCCA GAAACTTCTA ATTACATATG
1251 TCAAGAAAAG CTGACAGTAG CTCCTGCCAC TCCACACACC ATGACTTAGA
1301 AAATGTGAAT GAATATATTT CAAAAAAGGC AGCACAACAC AGTGAAGGGT
1351 CCTGGGCCTG AGCTCCTGGA AAGTCATTTC ACATCAATCA ACTGTGTGAT
1401 CTAGAGCAAG TCACTTAGCC ACTTTCTGTG CTTTACTTTA TTTATCTAAA
1451 ATGAGAGGGT TATACTAAAA AAAAAAAAAA AAAAA
     (SED NO:1)
5'UTR:         1 - 2
Start Codon:   3
Stop Codon:    1191
3'UTR:         1194
Homologous proteins:
Top 10 BLAST Hits                                                      Score      E
CRA|87000000001426 /altid=gi|7161864  /def=emb|CAB76566.1| (AJ25...     560    e-158
CRA|87000000001314 /altid=gi|8923754  /def=ref|NP_060871.1| gene...     557    e-157
CRA|103000001515936 /altid=gi|10946600 /def=ref|NP_067277.1| hy...      514    e-145
CRA|108000024647823 /altid=gi|12730486 /def=ref|XP_003392.2| ge...      395    e-109
CRA|18000005184360 /altid=gi|7505957  /def=pir||T23688 hypotheti...     328    8e-89
CRA|18000005004115 /altid=gi|1730069  /def=sp|P54644|KRAC_DICDI ...     226    5e-58
CRA|18000004912236 /altid=gi|464395   /def=sp|P28178|PK2_DICDI PR...    209    8e-53
CRA|18000004991065 /altid=gi|1362152  /def=pir||S56639 ribosomal...     204    3e-51
CRA|18000004952305 /altid=gi|462434   /def=sp|P34099|KAPC_DICDI C...    203    6e-51
CRA|107000045076305 /altid=gi|12322721 /def=gb|AAG51345.1|AC012...      202    8e-51

EST:                                                                   Score     E
gi|12432521 /dataset=dbest /taxon=96...                                1362     0.0
gi|12425892 /dataset=dbest /taxon=96...                                 864     0.0
gi|9811536  /dataset=dbest /taxon=960...                                708     0.0

EXPRESSION INFORMATION FOR MODULATORY USE:
gi|12432521 brain hippocampus
gi|12425892 Breast mammary adenocarcinoma cell line
gi|9811536  Bladder carcinoma cell line
Tissue expression:
Human brain
Human fetal brain
Human fetal heart
Human kidney
Human uterus
```

FIGURE 1

```
  1 MGANTSRKPP VFDENEDVNF DHFEILRAIG KGSFGEVCIV QKNDTKKMCA
 51 MKYMNKQKCV ERNEVRNVFK ELQIMQGLEH PFLVNLWYSF QDEEDMFMVV
101 DLLLGGDLRY HLQQNVHFKE ETVKLFICEL VMALDYLQNQ RIIHRDMKPD
151 NILLDEHGHV HITDFNIAAM LPRETQITTM AGTKPYMAPE MFSSRKGAGY
201 SFAVDWWSLG VTAYELLRGR RPYHIRSSTS SKEIVHTFET TVVTYPSAWS
251 QEMVSLLKKL LEPNPDQRFS QLSDVQNFPY MNDINWDAVF QKRLIPGFIP
301 NKGRLNCDPT FELEEMILES KPLHKKKKRL AKKEKDMRKC DSSQTCLLQE
351 HLDSVQKEFI IFNREKVNRD FNKRQPNLAL EQTKDPQGED GQNNNL
 (SEQ ID NO:2)
```

FEATURES:
Functional domains and key regions:
[1] PDOC00001 PS00001 ASN_GLYCOSYLATION
N-glycosylation site Number of matches: 2

```
     1       4-7 NTSR
     2     43-46 NDTK
```

---

[2] PDOC00005 PS00005 PKC_PHOSPHO_SITE
Protein kinase C phosphorylation site

Number of matches: 7

```
     1       5-7 TSR
     2       6-8 SRK
     3   194-196 SRK
     4     45-47 TKK
     5   122-124 TVK
     6   193-195 SSR
     7       6-8 SRK
```

---

[3] PDOC00006 PS00006 CK2_PHOSPHO_SITE
Casein kinase II phosphorylation site

Number of matches: 4

```
     1     33-36 SFGE
     2     89-92 SFQD
     3   212-215 TAYE
     4   230-233 SSKE
```

---

[4] PDOC00008 PS00008 MYRISTYL
N-myristoylation site

Number of matches: 3

```
     1       2-7 GANTSR
     2   197-202 GAGYSF
     3   391-396 GQNNNL
```

---

[5] PDOC00009 PS00009 AMIDATION
Amidation site 218-221 RGRR

---

[6] PDOC00100 PS00107 PROTEIN_KINASE_ATP
Protein kinases ATP-binding region signature 29-52 IGKGSFGEVCIVQKNDTKKMCAMK

---

[7] PDOC00100 PS00108 PROTEIN_KINASE_ST
Serine/Threonine protein kinases active-site signature 142-154 IIHRDMKPDNILL

---

<u>Membrane spanning structure and domains:</u>

| Helix | Begin | End | Score | Certainity |
|---|---|---|---|---|
| 1 | 197 | 217 | 0.690 | Putative |

FIGURE 2A

```
BLAST Alignment t  T p Hit:
Alignment to top blast hit:
>CRA|87000000001426 /altid=gi|7161864 /def=emb|CAB76566.1| (AJ250840)
             serine/threonine protein kinase [Mus musculus] /org=Mus
             musculus /taxon=10090 /dataset=nraa /length=414
           Length = 414

 Score =  560 bits (1428), Expect = e-158
 Identities = 278/403 (68%), Positives = 320/403 (78%), Gaps = 7/403 (1%)
 Frame = +3

Query: 3    MGANTSRKPPVFDENEDVNFDHFEILRAIGKGSFGEVCIVQKNDTKKMCAMKYMNKQKCV 182
             MG N S KPPVFDENE+VNFDHF+ILRAIGKGSFG+VCIVQK DTKKM AMKYMNKQKCV
Sbjct: 1    MGGNHSHKPPVFDENEEVNFDHFQILRAIGKGSFGKVCIVQKRDTKKMYAMKYMNKQKCV 60

Query: 183  ERNEVRNVFKELQIMQGLEHPFLVNLWYSFQDEEDMFMVVDLLLGGDLRYHLQQNVHFKE 362
             ER+EVRNVF+ELQIMQGLEHPFLVNLWYSFQDEEDMFMVVDLLLGGDLRYHLQQNVHF E
Sbjct: 61   ERDEVRNVFRELQIMQGLEHPFLVNLWYSFQDEEDMFMVVDLLLGGDLRYHLQQNVHFTE 120

Query: 363  ETVKLFICELVMALDYLQNQRIIHRDMKPDNILLDEHGHVHITDFNIAAMLPRETQITTM 542
              TVKL+ICEL +AL+YLQ   IIHRD+KPDNILLDEHGHVHITDFNIA +L     + ++M
Sbjct: 121  GTVKLYICELALALEYLQRYHIIHRDIKPDNILLDEHGHVHITDFNIATVLKGSEKASSM 180

Query: 543  AGTKPYMAPEMFS--SRKGAGYSFAVDWWSLGVTAYELLRGRRPYHIRSSTSSKEIVHTF 716
             AGTKPYMAPE+F      G GYS+ VDWWSLGVTAYELLRG RPY I S+T   EI++ F
Sbjct: 181  AGTKPYMAPEVFQVYVDGGPGYSYPVDWWSLGVTAYELLRGWRPYEIHSATPIDEILNMF 240

Query: 717  ETTVVTYPSAWSQEMVSLLKKLLEPNPDQRFSQLSDVQNFPYMNDINWDAVFQKRLIPGF 896
             +   V Y S W + MVSLLKKLL  +P+ R S L D+Q+  Y+ D+NWDAVF+K L+PGF
Sbjct: 241  KVERVHYSSTWCEGMVSLLKKLLTKDPESRLSSLRDIQSMTYLADMNWDAVFEKALMPGF 300

Query: 897  IPNKGRLNCDPTFELEEMILESKPLHKKKKRLAK-KEKDMRKCDSSQTCLLQEHLDSVQK 1073
             +PNKGRLNCDPTFELEEMILESKPLHKKKKRLAK + +D  K         LQ+ L++V+K
Sbjct: 301  VPNKGRLNCDPTFELEEMILESKPLHKKKKRLAKHRSRDSTKDSCPLNGHLQQCLETVRK 360

Query: 1074 EFIIFNREKVNR----DFNKRQPNLALEQTKDPQGEDGQNNNL 1190
             EFIIFNREK+ R    D      +   +        + +DG+NNN+
Sbjct: 361  EFIIFNREKLRRQQGHDGQLSDLDGRIGSQTSSKLQDGRNNNI 403 (SEQ ID NO:4)

>CRA|87000000001314 /altid=gi|8923754 /def=ref|NP_060871.1| gene for
             serine/threonine protein kinase [Homo sapiens] /org=Homo
             sapiens /taxon=9606 /dataset=nraa /length=414
           Length = 414

 Score =  557 bits (1419), Expect = e-157
 Identities = 275/403 (68%), Positives = 319/403 (78%), Gaps = 7/403 (1%)
 Frame = +3

Query: 3    MGANTSRKPPVFDENEDVNFDHFEILRAIGKGSFGEVCIVQKNDTKKMCAMKYMNKQKCV 182
             MG N S KPPVFDENE+VNFDHF+ILRAIGKGSFG+VCIVQK DTKKM AMKYMNKQKC+
Sbjct: 1    MGGNHSHKPPVFDENEEVNFDHFQILRAIGKGSFGKVCIVQKRDTKKMYAMKYMNKQKCI 60

Query: 183  ERNEVRNVFKELQIMQGLEHPFLVNLWYSFQDEEDMFMVVDLLLGGDLRYHLQQNVHFKE 362
             ER+EVRNVF+ELQIMQGLEHPFLVNLWYSFQDEEDMFMVVDLLLGGDLRYHLQQNVHF E
Sbjct: 61   ERDEVRNVFRELQIMQGLEHPFLVNLWYSFQDEEDMFMVVDLLLGGDLRYHLQQNVHFTE 120

Query: 363  ETVKLFICELVMALDYLQNQRIIHRDMKPDNILLDEHGHVHITDFNIAAMLPRETQITTM 542
              TVKL+ICEL +AL+YLQ   IIHRD+KPDNILLDEHGHVHITDFNIA ++     + ++M
Sbjct: 121  GTVKLYICELALALEYLQRYHIIHRDIKPDNILLDEHGHVHITDFNIATVVKGAERASSM 180

Query: 543  AGTKPYMAPEMFS--SRKGAGYSFAVDWWSLGVTAYELLRGRRPYHIRSSTSSKEIVHTF 716
             AGTKPYMAPE+F     +G GYS+ VDWWSLG+TAYELLRG RPY I S T   EI++ F
Sbjct: 181  AGTKPYMAPEVFQVYMDRGPGYSYPVDWWSLGITAYELLRGWRPYEIHSVTPIDEILNMF 240

Query: 717  ETTVVTYPSAWSQEMVSLLKKLLEPNPDQRFSQLSDVQNFPYMNDINWDAVFQKRLIPGF 896
             +   V Y S W + MV+LL+KLL  +P+ R S L D+Q+ PY+ D+NWDAVF+K L+PGF
Sbjct: 241  KVERVHYSSTWCKGMVALLRKLLTKDPESRVSSLHDIQSVPYLADMNWDAVFKKALMPGF 300

Query: 897  IPNKGRLNCDPTFELEEMILESKPLHKKKKRLAK-KEKDMRKCDSSQTCLLQEHLDSVQK 1073
             +PNKGRLNCDPTFELEEMILESKPLHKKKKRLAK + +D  K         LQ  L++V++
Sbjct: 301  VPNKGRLNCDPTFELEEMILESKPLHKKKKRLAKNRSRDGTKDSCPLNGHLQHCLETVRE 360

Query: 1074 EFIIFNREKVNRDFNKRQPNLALEQTKDPQG----EDGQNNNL 1190
             EFIIFNREK+ R   +    L  +      Q      +DG NNNL
Sbjct: 361  EFIIFNREKLRRQQGQGSQLLDTDSRGGGQAQSKLQDGCNNNL 403 (SEQ ID NO:5)
```

FIGURE 2B

```
>CRA|103000001515936 /altid=gi|10946600 /def=ref|NP_067277.1|
          hypothetical serine/threonine protein kinase [Mus
          musculus] /org=Mus musculus /taxon=10090 /dataset=nraa
          /length=488
        Length = 488

 Score =  514 bits (1310), Expect = e-145
 Identities = 250/389 (64%), Positives = 304/389 (77%), Gaps = 4/389 (1%)
 Frame = +3

Query: 18   SRKPPVFDENEDVNFDHFEILRAIGKGSFGEVCIVQKNDTKKMCAMKYMNKQKCVERNEV 197
             S + PVFD+ EDVNFDHF+ILRAIGKGSFG+VCIVQK DT+KM AMKYMNKQ+C+ER+EV
Sbjct: 77   SARRPVFDDKEDVNFDHFQILRAIGKGSFGKVCIVQKRDTEKMYAMKYMNKQQCIERDEV 136

Query: 198  RNVFKELQIMQGLEHPFLVNLWYSFQDEEDMFMVVDLLLGGDLRYHLQQNVHFKEETVKL 377
             RNVF+EL+I+Q +EH FLVNLWYSFQDEEDMFMVVDLLLGGDLRYHLQQNV F E+TV+L
Sbjct: 137  RNVFRELEILQEIEHVFLVNLWYSFQDEEDMFMVVDLLLGGDLRYHLQQNVQFSEDTVRL 196

Query: 378  FICELVMALDYLQNQRIIHRDMKPDNILLDEHGHVHITDFNIAAMLPRETQITTMAGTKP 557
             +ICE+ +ALDYL++Q IIHRD+KPDNILLDE GH H+TDFNIA ++     + T +AGTKP
Sbjct: 197  YICEMALALDYLRSQHIIHRDVKPDNILLDEQGHAHLTDFNIATIIKDGERATALAGTKP 256

Query: 558  YMAPEMFSS--RKGAGYSFAVDWWSLGVTAYELLRGRRPYHIRSSTSSKEIVHTFETTVV 731
             YMAPE+F S    G GYSF VDWWS+GV AYELLRG RPY I SS + + +V  F T  V
Sbjct: 257  YMAPEIFHSFVNGGTGYSFEVDWWSVGVMAYELLRGWRPYDIHSSNAVESLVQLFSTVSV 316

Query: 732  TYPSAWSQEMVSLLKKLLEPNPDQRFSQLSDVQNFPYMNDINWDAVFQKRLIPGFIPNKG 911
              Y   WS+EMV+LL+KLL  NP+ RFS L D+Q  P +  + WD + +K++ PGF+PNKG
Sbjct: 317  QYVPTWSKEMVALLRKLLTVNPEHRFSSLQDMQTAPSLAHVLWDDLSEKKVEPGFVPNKG 376

Query: 912  RLNCDPTFELEEMILESKPLHKKKKRLAKKEKDMRKCDSSQT--CLLQEHLDSVQKEFII 1085
             RL+CDPTFELEEMILES+PLHKKKKRLAK +        DSSQ+    LQ+ LD++Q++F+I
Sbjct: 377  RLHCDPTFELEEMILESRPLHKKKKRLAKNKSRDSSRDSSQSENDYLQDCLDAIQQDFVI 436

Query: 1086 FNREKVNRDFNKRQPNLALEQTKDPQGED 1172
             FNREK+     KR   L  E   P+  D
Sbjct: 437  FNREKL-----KRSQELMSEPPPGPETSD 460 (SEQ ID NO:6)

>CRA|108000024647823 /altid=gi|12730486 /def=ref|XP_003392.2| gene for
          serine/threonine protein kinase [Homo sapiens] /org=Homo
          sapiens /taxon=9606 /dataset=nraa /length=330
        Length = 330

 Score =  395 bits (1004), Expect = e-109
 Identities = 199/316 (62%), Positives = 237/316 (74%), Gaps = 7/316 (2%)
 Frame = +3

Query: 264  YSFQDEEDMFMVVDLLLGGDLRYHLQQNVHFKEETVKLFICELVMALDYLQNQRIIHRDM 443
             YSFQDEEDMFMVVDLLLGGDLRYHLQQNVHF E TVKL+ICEL +AL+YLQ   IIHRD+
Sbjct: 4    YSFQDEEDMFMVVDLLLGGDLRYHLQQNVHFTEGTVKLYICELALALEYLQRYHIIHRDI 63

Query: 444  KPDNILLDEHGHVHITDFNIAAMLPRETQITTMAGTKPYMAPEMFS--SRKGAGYSFAVD 617
             KPDNILLDEHGHVHITDFNIA ++     + ++MAGTKPYMAPE+F      +G GYS+ VD
Sbjct: 64   KPDNILLDEHGHVHITDFNIATVVKGAERASSMAGTKPYMAPEVFQVYMDRGPGYSYPVD 123

Query: 618  WWSLGVTAYELLRGRRPYHIRSSTSSKEIVHTFETTVVTYPSAWSQEMVSLLKKLLEPNP 797
             WWSLG+TAYELLRG RPY I S T   EI++ F+    V Y S W + MV+LL+KLL  +P
Sbjct: 124  WWSLGITAYELLRGWRPYEIHSVTPIDEILNMFKVERVHYSSTWCKGMVALLRKLLTKDP 183

Query: 798  DQRFSQLSDVQNFPYMNDINWDAVFQKRLIPGFIPNKGRLNCDPTFELEEMILESKPLHK 977
             + R S L D+Q+ PY+ D+NWDAVF+K L+PGF+PNKGRLNCDPTFELEEMILESKPLHK
Sbjct: 184  ESRVSSLHDIQSVPYLADMNWDAVFKKALMPGFVPNKGRLNCDPTFELEEMILESKPLHK 243

Query: 978  KKKRLAK-KEKDMRKCDSSQTCLLQEHLDSVQKEFIIFNREKVNRDFNKRQPNLALEQTK 1154
             KKKRLAK + +D  K          LQ  L++V++EFIIFNREK+ R    +     L  +
Sbjct: 244  KKKRLAKNRSRDGTKDSCPLNGHLQHCLETVREEFIIFNREKLRRQQGQGSQLLDTDSRG 303

Query: 1155 DPQG----EDGQNNNL 1190
               Q      +DG NNNL
Sbjct: 304  GGQAQSKLQDGCNNNL 319 (SEQ ID NO: 7)

>CRA|18000005184360 /altid=gi|7505957 /def=pir||T23688 hypothetical
          protein M03C11.1 - Caenorhabditis elegans
          /org=Caenorhabditis elegans /taxon=6239 /dataset=nraa
          /length=379
        Length = 379
```

FIGURE 2C

```
 Score =  328 bits (833), Expect = 8e-89
 Identities = 156/353 (44%), Positives = 226/353 (63%), Gaps = 2/353 (0%)
 Frame = +3

Query: 66   HFEILRAIGKGSFGEVCIVQKNDTKKMCAMKYMNKQKCVERNEVRNVFKELQIMQGLEHP 245
            HF ++R+IG+G+FG+VCIVQ+  TKK  A+KYMNK++C+E+    NV +EL ++  + HP
Sbjct: 27   HFSVIRSIGRGAFGKVCIVQERKTKKYFALKYMNKRRCIEKGVAANVIRELTLLSKMSHP 86

Query: 246  FLVNLWYSFQDEEDMFMVVDLLLGGDLRYHLQQNVHFKEETVKLFICELVMALDYLQNQR 425
            F+VNLWY+FQD + M+MV DLLLGGDLRYHL Q   F E+  KL++CE+ +A++YL   +
Sbjct: 87   FIVNLWYTFQDGDYMYMVSDLLLGGDLRYHLSQQGKFAEDRAKLYLCEICLAVEYLHEMK 146

Query: 426  IIHRDMKPDNILLDEHGHVHITDFNIAAMLPRETQITTMAGTKPYMAPEMFSS--RKGAG 599
            I+HRD+KP+NILLDE GH H+TD N+A  L  +   T+ +GT+PYMAPE++++      G
Sbjct: 147  IVHRDIKPENILLDEQGHAHLTDLNLATQLEDDQLATSYSGTRPYMAPEIYATYLEIEDG 206

Query: 600  YSFAVDWWSLGVTAYELLRGRRPYHIRSSTSSKEIVHTFETTVVTYPSAWSQEMVSLLKK 779
            Y   VDWW+LGV  YE+LRGR P+   S T +E    F  + + YP+ W  +++  +  
Sbjct: 207  YDSRVDWWALGVCFYEMLRGRTPFEFSSRTKPEEAYVAFRESSIPYPAHWPTDLIQFINS 266

Query: 780  LLEPNPDQRFSQLSDVQNFPYMNDINWDAVFQKRLIPGFIPNKGRLNCDPTFELEEMILE 959
            +L+ + ++R   L  ++    Y   I++ +VF+K+  P FIP K  LNCDP +ELEE IL 
Sbjct: 267  MLKFDKEKRLVGLEAIKKHSYTERIDFKSVFEKKPSPVFIPCKEGLNCDPMYELEERILV 326

Query: 960  SKPLHKKKKRLAKKEKDMRKCDSSQTCLLQEHLDSVQKEFIIFNREKVNRDFN 1118
            S P+H  ++R        R     Q   L E    V K FI F+R  V  + N
Sbjct: 327  STPIH--RRRTNHNNSSGRSSSEPQNAALVE----VSKAFIDFSRHNVKIEPN 373 (SEQ ID NO: 8)
```

Hmmer search results (Pfam):

Scores for sequence family classification (score includes all domains):

| Model | Description | Score | E-value | N |
|---|---|---|---|---|
| PF00069 | Eukaryotic protein kinase domain | 241.7 | 1e-68 | 1 |
| CE00359 | E00359 bone_morphogenetic_protein_receptor | 18.9 | 0.00012 | 1 |
| PF00433 | Protein kinase C terminal domain | 8.8 | 0.2 | 1 |
| CE00022 | CE00022 MAGUK_subfamily_d | 8.6 | 0.02 | 1 |
| CE00203 | CE00203 ERBB_RECEPTOR | 6.0 | 0.25 | 1 |
| CE00031 | CE00031 VEGFR | 5.1 | 0.12 | 1 |
| CE00528 | CE00528 CDC14_PHOSPHATASE | 1.7 | 8 | 1 |
| CE00292 | CE00292 PTK_membrane_span | -44.9 | 1.9e-06 | 1 |
| CE00287 | CE00287 PTK_Eph_orphan_receptor | -45.1 | 2.4e-05 | 1 |
| CE00286 | E00286 PTK_EGF_receptor | -59.9 | 1.7e-07 | 1 |
| CE00291 | CE00291 PTK_fgf_receptor | -81.9 | 0.00049 | 1 |
| CE00290 | CE00290 PTK_Trk_family | -158.8 | 0.00022 | 1 |
| CE00016 | CE00016 GSK_glycogen_synthase_kinase | -216.0 | 0.00011 | 1 |
| CE00288 | CE00288 PTK_Insulin_receptor | -225.8 | 0.21 | 1 |

FIGURE 2D

Parsed for domains:

| Model | Domain | seq-f | seq-t | | hmm-f | hmm-t | | score | E-value |
|---|---|---|---|---|---|---|---|---|---|
| CE00031 | 1/1 | 134 | 168 | .. | 1059 | 1093 | .. | 5.1 | 0.12 |
| CE00203 | 1/1 | 136 | 172 | .. | 855 | 891 | .. | 6.0 | 0.25 |
| CE00359 | 1/1 | 142 | 191 | .. | 272 | 326 | .. | 18.9 | 0.00012 |
| CE00022 | 1/1 | 133 | 223 | .. | 133 | 226 | .. | 8.6 | 0.02 |
| CE00288 | 1/1 | 23 | 238 | .. | 1 | 269 | [] | -225.8 | 0.21 |
| CE00528 | 1/1 | 251 | 260 | .. | 608 | 617 | .] | 1.7 | 8 |
| CE00292 | 1/1 | 23 | 276 | .. | 1 | 288 | [] | -44.9 | 1.9e-06 |
| CE00287 | 1/1 | 23 | 276 | .. | 1 | 260 | [] | -45.1 | 2.4e-05 |
| CE00291 | 1/1 | 23 | 278 | .. | 1 | 285 | [] | -81.9 | 0.00049 |
| CE00286 | 1/1 | 23 | 278 | .. | 1 | 263 | [] | -59.9 | 1.7e-07 |
| CE00290 | 1/1 | 23 | 279 | .. | 1 | 282 | [] | -158.8 | 0.00022 |
| PF00069 | 1/1 | 23 | 281 | .. | 1 | 278 | [] | 241.7 | 1e-68 |
| PF00433 | 1/1 | 282 | 301 | .. | 1 | 20 | [. | 8.8 | 0.2 |
| CE00016 | 1/1 | 1 | 331 | [. | 1 | 433 | [] | -216.0 | 0.00011 |

FIGURE 2E

```
   1 TCCCTCTCTC ATACCATTTA ATTGGTTGCT TCCTAATTAA TGACTCTCTT
  51 TGCTCTCTAT TTAATGATTC TTGCTAAAGT CCATAAGGCA CTTTGCCAGC
 101 AGTTGGTTTT TAGTATGAAA AGTAGCATTT CCTTAATGAG TCTGAGTCTG
 151 CCTTCCAAAT GAAGGGTTTA CTTACATTTT CCTAATGGGA AAACGAGCTT
 201 TTCTTCTACG CTTCCTTAGG GGTTTCATAA GTTCTTTTTC AATAACTCAT
 251 CCTTAACACT TTCTCCAATT CTGCCTGTAA TCAATATTCC CTTCACATGT
 301 AAAGAGCTCA GGAGGAAATC AACTATTTTT TTAAAAATAC GCAATAAGGA
 351 AATTCTGCTA CTCTTAGAAA TAGCAGGAGC TAACATTCAT TCTTTGCATA
 401 TCATGTGCTA GGCATTGTGC CAATTACCTT ATATACATTG TCTCATTATA
 451 TGTATCCATG ACCATATATG TGCTAAGCAT GAAATTTTCT TAAGCCAGAT
 501 AGCTGAGTAG AATTTTAAAA TATTATTTTG TACAAAATCT AGACCTTTAC
 551 CCCATTTGGG GGATAGATCT GAAGATCTGG GCTCATGTTT CCATGTGGTG
 601 ACAATCTGTT TGATCTGAGC ACAATTACTT TATTTGGATG GAGCCATTGC
 651 CACCATTGTC TGCCCAATGC ACTAATGTTA AATGCCCAGT CTGGCTCACT
 701 CATTTGCATC ATCTGCCTGG CTCCTATAGG GATCCCAGCT TGTCACTCCT
 751 GAGGTAGACA CTGTCATTTC CCCCATTCTA GAGGTGAGAG GTTACATAAC
 801 TGGGCCAAAG GCATTATCAG TGTCAGTTTT AGGACTGGAA CACAGGATGC
 851 TGCCTCTCTT TACCATTATG TTTTAAAGTG GAGCAAAGCC GTAGTTTTCA
 901 GGATCTTTTC TTGTTCACAC ATATCATTTA ATTTGAGCCT CAGAGCGGCT
 951 AACAGTTTTG AGCACTTATG CTATGAAAAT GTTTTGTGTA TTCAGTTAAA
1001 TGTATGCATA TCATACATTT ATGTAACTCA ATACATATAT ATAAATGTGA
1051 TATAACATAC GTATGATATA ACAGAGTTAT ATATATGTGT ATTATTTAAC
1101 TTAATATATA ATGAGTTAAG TGTATGCATA TCATAGATTT ATGTAACTCA
1151 ATATATAAAG AGTTATATAA TACAACAGAG TTGATATATA TATAAATGTT
1201 GTATATAAAC ATAATATATA CGTTAATATA TATTAACAAA GAGTTGTATA
1251 ATACAACACA GAGTTAATAA TATATAAATA CAACACAAAG AGTTATATAT
1301 GTGTGTATTA TACATTTAAC TTAATATATA ATGAGTTAAA TGTATGTCTG
1351 TCCCATTCAA CTCTCCATTG AGGAAAGTAC CATTATCTTC CCCAAGTTCA
1401 GAAGAAGAAA ACAGAGAAAT ATATTGAAAT TCAGCAATTT GCTGGTGTGG
1451 TCAAGTCCAA CCCAGAACTT GCTTCTTTTA CATTGTAGTA CCCTCCAGGG
1501 TATGCAGAAA CAGATAGCTA GTGCATCTTT ATGACTAAAA AAGAAAATTT
1551 TTGTTGTTGA TTACCCAGTA ACAACAAGAC AGTATAAAAT CAGCATATTT
1601 TCTCAACAAT ATTTTCATTT TATAGTTGTT GAATAAAGTA TTGCTGACTT
1651 CATTTTAAAC TTTTCTACAT ACTTTGAAAA ATATGTTGCT TTCCTCCCAT
1701 TTTGTAAGTC TAGGTCTGCT ATTGATGAGC CATGCAGTGT TTTCTCCTGT
1751 TGCTTGATGT TTTTATTCTG AAATCATGGT TGGTTTTCAA ACACAAAAGT
1801 TTTCACTACA GTGATACAGA TGAGGTTTAT GTTTCCGCCA CAGTCTATAC
1851 TCAGGGTGCC TAGAGTATAG CATATTATTA GGGTACTATT TCTTTTCCTA
1901 TCCTAGATAT CCAACTAAGG CTTCGGGACA TGTTTTGAGC GAAGATGGGT
1951 GTTTCTGCCC GGATAGTATA AATCGAGGAT CCAGGTCTGG GCAGATTCAA
2001 CCATGGGAGC GAACACTTCA AGAAAACCAC CAGTGTTTGA TGAAAATGAA
2051 GATGGTAAGA AATATGGGAT AGTGGCATAT AAAAAATAGA ATTTTGCAAA
2101 ATTCAAGTAT ATGCTTCTAG TTTCATAAGT TAAGCATAAG CATGGTCTGT
2151 AGGGCCTTGA AGGAAAAAGG CAAAGCTGCA TGAGTGAGTC TGAGGACTTT
2201 GTAGGCTCAT AGCTAGGTTT TACCTTCCAC TTTCCATGGG ACCTTTGGCA
2251 GCTTTCCTAA TCTCCACTAT ACCAATGTCC TTTGTCCAAA GGGAGCTGCA
2301 GTTGGGCATG TGGTGGATAG TTAAATGATT TGTTTGTCCT CTGTGCTGTT
2351 CCTTGGCAGT TGAAGTTACC CCCATTGCTC ATTGTTACAG AAAATACATT
2401 ATCAACATGT ACATGAATGA TAACCAGTGC TCATAATATT ATAGAATGAA
2451 GCTGTGCCTT CTGAATTTCC AACTGCCAAG CTTTTGTGTA CTAGACAAAT
2501 CCCATAATGC TACGTCATAG AAAAAAGAAT CAGTTGTATT GGAGAAAAGG
2551 GAAACTTTCC AGGCCAGACT CAGCAAGACA AGAATAAAGG CATGAGTCCT
2601 CCTGATTCTC CCATCAGTGA GGCATGCTGG AACTGGGCAA TGCCTCCTCA
2651 TGTCCCTCTT CCTTCCTATA TGTTAAGTCT GAACAGCATT GGCGTATGCA
2701 GGTGGCAGCT GTTTATAGGT TGTCTGGGGG AAAAAAATGC CCCAAGCCCC
2751 AGGTAGTAAG TTGTCCAGAC CTCTGAGAGG GAGCTCTTCC GAGTAATTCC
2801 CAGAGAGCTC TGCTAATTGG AACAGGGAGG AAAAGAATGG ACTGAAATTC
2851 AGGAAATCTG ACACCAGTCC TACTACCAGT TACTTGCTAG GCCCAAGCAG
2901 CTTATTTACT GACTCTATCT TCAATTTTGT TATCAATAAA GTGAGGAGAT
2951 AGGTTCCTTC CCACTCAAGA AGTTTATCAT TTTGAGATCC TAAAGCAACT
3001 TTGTGAATTC TGAAGAAGCT TCTAAATCAT CAAGGAAAGT TTATTGGGTT
3051 AGAATGCAAG TTTGATTGCT GAAATGAAAA CTACAAATAA CAGTGGCTTA
```

FIGURE 3A

3101 AGCCAAATGG AAATGTTTAT CTTTCTCATG TGACAATCTA GGCATAAGTA
3151 ATCCAGGTGA TGTGTGGTTC CAGCAGCTTA GGGACTCTGA CGCCAACTAC
3201 TTGCCTTTTT CCCTCTCTTC CCATTTCTAG AGTGGTACCC TCAGAGTGGC
3251 TAACCAACAC AACAAATTCC AGCCAGTGAG AAAGGTGGAA AGTAGGAGAG
3301 GTTATGCCCA CTTATTTATA GGATTTGCTC TGGCTTGTCA CTTTCGTTCA
3351 CTTCCACTTA CCTAGATACA AGAAAGACTG GGAAATTCAG TTTGTTATCT
3401 TGGGTGGCCA TGAACCTTCT AAAAATAAGG AGTTCTGTTT TATTACAAAA
3451 GAAAAGAAGA ATTAGGAGTT TGTCATGATT GGGGACAACT ACGTCTGCTG
3501 TAGTTGGGGC AAACAATCTT AGTTTTGAAT CTTGGGATGG AAATACTTTT
3551 AAAAACAAAA TATGGGCCAG GCGCGGTGGC TCACGCCTGT AATCCCAGCA
3601 CTTTGGGAGG CCGAGGCGGG CGGATCACGA GGTCAGGAGA TCGAGACCAT
3651 CCTGGCTAAC ACGGTGAAAC CCCGTCTCTA CTAAAAAATA CAAAAAATTA
3701 GCCGGGCGTG GTGGTGGACG CCTGTAGTCC CAGCTACTCG GGAGGCTGAG
3751 GCAGGAGAAT GGCGGGAACC CGGGAGGTGG AGCTTGCAGT GAGCCGAGAT
3801 CCGGCCACTG CACTCCAGCC TGGGCGACAG AGCGAGACTC CATCTCAAAA
3851 CAAACAAACA AACAAACAAG CAAAAAAACC CAAAATATAT GGCTGATCAG
3901 GACGCCTTGT TTCAAGCTAT TCACTATCAG TTTGGAGGCC CATTCTTACT
3951 ATTTCTACAG AATAGTTCAT AGGAACTTTG AAATTATATA GCTGGAAAGG
4001 GGTCTTAAGA AAACTTTTTT TTCATGGCTA TTGTGATTGC CTTGCTTTAA
4051 CTTATCAAAT AGTAAAAGCA AAGATCTAGA GACTAGTGAT ATTACTTAAT
4101 TTTTCTGTCT CTAAAATGGA AAGACAAATA GGCTTGCTTT TCATTTAGTT
4151 GGTTTCCTCT GCTTCCTCTG GACTCAGAGC TAATGTTGTA CATGAGGCTG
4201 GTCGTCAGAG AATAGGGTGG AAAAGAGAGG CCAGCTGCAT ACTTTTAACT
4251 TGCTGGGCTA CATTTGAAGG TAGTAGAATA GCATTATGAT GAGAAAACAC
4301 AGAAATGCAT AACTCTTCCT TGATTCAGCC AGGCTTTGTT CTTGCGGGAT
4351 GCCCAAGAAA GCTACATAAC CAAAGAATTG TGACAATTGG GAAATAAGAT
4401 ACCCCTTTTT AGTTACTTTA AAGGACTCTA GAAAAACTAG GTTGAAGGAG
4451 AGTTAGGCTT AGGGACCAGA CAGGTCTTTC TTAACACCCT CTAGGTCACC
4501 ACCTTTTCTG TTGTCTGGCT TCTCAGCCCA ATGAGATGAA CCCACTGCAG
4551 CACCCATAAA GGAAAGATCT GAGCATAGCA ACAAGTCTGT GCCTCCCAAA
4601 GGTGCTAGGC TCTCTGTCTG TTTATGCAGA CAGTTGCAAG GCAAAGGAAG
4651 TAGGAGGGCA AGTCCACCTA CTATAAACCT GTCACTCTCT AGACATGAAG
4701 AATAGAGGAG GAAACAAGTT GGTCCTTGCT CTGTCATTGT GAACCCCATG
4751 TTCTGATGAT GGAAGGCTGA CAATAAAAAG GTAAATAATA CATAAACCAG
4801 ATAATTTCAC AGTGCCTTAA AGTGCCACCA AGGAAATGAC TCCTAGTGAT
4851 CTTACAGACA GTGACAGTGA TGGTGAGGAG GCCACTTTAG ATAGGGTGGC
4901 TGCGGTTGTC TTTCTAAGGA GGTGACATTT GGGCTGAAGC CTGAAAGATG
4951 AGAAGAAGCC ATCTATGAAA TGACATGAAA AGAATAGTTC AAGAACAGGA
5001 AAAACAAGTC CAAAATCCAA ATAATGACAA AATCAGGATT GAATAGTTGC
5051 CTATATCTTA ACGTTCTCTC ATGAGCACTA GTTTGCCAAA GAGACTGCAT
5101 TTATTGCCAT GTTAACTTAT TTCTTCAAAA GATGATTGAT TTGAGGAGAA
5151 AAAGTATGCC ATTCTAGGGA ATTTACTTTG CTTTAAAATT CAGTACATTT
5201 TGTAAAGTTC ATTTGACTCT TCACATAAAT CTGGATTGAG CACAAGGTAA
5251 AATTGTATCT GATTGCTGTG AAGCTCCTGA CCAAGAAAAA GCAACCAAAA
5301 AGCACTGATT AACCAAACAA CATTAATGCT TATGTCATTT TTGATATCCA
5351 TATTTTTATA TACATAATCA TAATGTATAA TCAAACTGGG CCAGTATCAA
5401 GGGCACTAAA ATGAGCCAAC TTAATTATTT AAAAAATATT GCTGAAAAGA
5451 ATCCCAATAT GTGATTTTTA AAAAGTTTTT TAAAATTTTT AAAAAGATTT
5501 TTTAAAAGAT TTTTAAAAAT ATTTTCTTCA AACTGTTTAA TATTTCCAAT
5551 ATATAGATAT GAGAAAAACA TTTAACCAAT AATTTTCCCA AGTAATGTTT
5601 CAAGAATTCT CTCTTATGGA AAAAGTGTTT TTGTTCACTT TGAAGGTAAT
5651 TAAGGAGCAA GATAAGAGGT TATTGGATGT CCCTTGAGAT AAGCTATTCT
5701 TGCCAGAATT CATCCTGACA CTTGTATTTC ATGTTGTTCC ATCTGATATC
5751 TGATCTTGAA CACATAATTT TATTAGTTAC TTATGTTGAT CTTTATTCAG
5801 CAAAAACAAA GTAGGAGATT TTCAGGCTAG GCATGGTTGC TTACGCCTGT
5851 AATCCCAGCA CTTCAGGAGG CCGAGGCGGG CAGATCACGA GGTCAAGAGA
5901 TCGAAACCAT CCTGGCCAAC ATGGTGAAAC CCCATCTCTA CTAAAAAATA
5951 CAAAAAAAAT TAGCTGGGCA TGCCAGTGTG CGCCTGTAGT CCCAGCTATT
6001 CAGGAGGCTG AGGCAGGAGA ATCTCTTGAA CCTGGGAGGT GAAGTTTGCA
6051 GTGAGCTGAG ATTGCTCCAC TGCACTCCAG CCTGGCAACA GAGCAAGACT
6101 CTGTCCAAAA AAAAACGGCT TGCTTATTTG ATTATATAAG ATATCTTTCA
6151 TAAATTAGAT CTCAAATTAT ACTATTGTTT TGCAGTTTTA GCTTTTATGT

FIGURE 3B

6201 TTTAGGGCAA ATCTTAAGTC CTAATTACTT TTTTTTTATT ATTGTGGTAA
6251 AATGTATATA ACAAAATGTA CCATTTAATC ATTTTAGAAT ATACGGTTTA
6301 TGACATTAAG CACATTCACG TTATCATGCA ACCATCACCA CTACCCATCC
6351 TCAGAACATT TCTCTTCTCG AATTGAAACT TGGTACCTCT GAAACAATAA
6401 CATCCACATT CCATCCCCTC CCCAGTCCCT GTTAAACAAC CATTTGACTT
6451 TATGTCTCTA TGAATTTAAC TACTCTATGT ACCTCATATA AATGGAACAT
6501 ATAAGATTTG TTCTTTTGCA TCTGGTTTAT TTCATTTAGC ATATATTTTT
6551 AAGGTTCATC CATGTTGCAG CATGTGTCAA GATTCTCTTT CTTTTTAAGT
6601 CTGAGTCGTA TTCCATTGTA TGGATATACC ACATTTTGTT TATCTTTTCA
6651 TTAGTTGACA TTGATTGTCC TCACCTTTTG ATTTTTGTGA ATAAGGCTGC
6701 TATAAACATT GGTGTGCAAA TATCTGTTCA AGTCCCTGTT TTCAATTCTT
6751 CAGGGTATAT ACCTAGAAGT GGAAGCACTG GATCATATAA TTCCTTGTTT
6801 GACTCTCTGA GGAACCATCA TACTGTCTTC TACCTAATTA TGCTTTGTGT
6851 TTTAGTAATG GGACACAGCC TGGCATGATG GGCTAGAGTA TTGGAAAGGC
6901 ATGCACAGGT TCAAGTCTCA GCTGTGCCAC GTGCCAGTAA TCTACATGTT
6951 TCTATGAGAA GAGTCAAAGA GGATATAGCC TGGTCAACCA TTATCAGACA
7001 CTGGAGTCAG TTTGACTAAT TATATGGTGT TCTAAGGAAA CTTGAGGTAC
7051 CACAAGAAAA GTCTCCAAAT CTAAATAATT ACTAATGAAT TAATTGAGGG
7101 GGAAACTTAT TTAACCTTTG TAAGCCTCAG TTTCTTTGTA TGTAAAATGC
7151 AGGTAATAAT TGGGCATACT TCATTAGGTC TTTGTGAGGA TTGAATAAAT
7201 AATGCAAGTA AAACACTTAG CAAAGTATTT CCCATAAAGT AACCACTCAA
7251 TTAATGCTAA TTAAGTGTTA TTTACTAACA TCAGAGTTTC CTAGTGTGAA
7301 CTCTTTGAAG TACTTTAAGT TCTGAGAAAA ACAAAATTAA TTAAATGCAA
7351 CTCTGTCGAT TCCACAGTTA ATTAGACCTA TTCATGTTTC TATTGACTGG
7401 ATTAACAGAA CGGCAGATTT TATGGATTCT GTTAAAACCT ATATAAAAAC
7451 ACTTTAAAAG AAGCCAAGTT ATTGACTGCA CAAAAACATA ATCTCATCTG
7501 ATATCTTTTT TATCCCCCTG AGGTTATTGT GTTTTTGTTT AAGGCAAAAT
7551 CAAGAACTAA TTGGGATGAA AATAACTAAA GTTTACTTTG TCTGATTTAA
7601 GTCCCAAACT GACTAATAAG TAATCCCATT TGATCAACAG ATTCAGTGAA
7651 AACTGTCCCC CATTCTCAAC TACCATATGG ATATTCTGAG AAATAATTAA
7701 TGATGCAGAA AAACATTTTT TGTTTTCTGA AATAAAAGAA TAGACGTGCA
7751 AGTGACACTT CTTTTTAATG CTTACAACCT TTTTTTAAAA ATCTACTTTA
7801 TTTTCTCTAT CTGAATGCAC TAGATTTTGT TTGTTTGTTT TTGTGGTTGG
7851 TTGGTATGGT TTTGCTTATT GAGGTTTTCA GGCTGATTTA GAAAAAAGAA
7901 ATTTTTACAG GAGAGAGTGG ACTTGTTTAC AATTCAGAGT TGAGGCAACA
7951 AAAAAAAATC TTGCAGTCAT TATGAGTAAT ATGTGTATCC AAGTTTATAC
8001 AAAGAATGTA AAGGTGATAA AGTTGGCTTA GTTAAATCAA GAGACAGCCT
8051 TCTTCTAGAA TATTATAGCT AAGAAAATTT GGACTTAAGT TTAAAAAGCT
8101 GCTCTAAAGA GTTCATCAAT GCCCTGAGTT TGCAGAGAGT TCAATTATTG
8151 CATTATTCTT TGGACTTGCT GAAAACTCAG TGTTCTACTT TTATTTGGCA
8201 ACACCATCTC CTAGGATATG TGGCTGTTTC CAGTTTTCCA GCATCTTCAG
8251 TGACAGAGGC AATGGGATCC TTTAAAATGT TGGGCCAAGA AAATTGGCCA
8301 CAGATTTGCA ATCCAAAAGA AATAGGAGGT TGCTAAATTG ATTCCAGCTA
8351 TGAAGGACAT CGAAAATTTC TTTTGTTATT TGACTGTCTA TCATGGTCTA
8401 TTTGCACTCA ATTTAATAGG CAAATGAATT TCCGACTTTC CCTTAGCAGC
8451 CTTGAGTAAT GCTGTCTCGT ATTTATTATT TTGCATTAGA ATGGTTGGAA
8501 AAGTTAAAGG AAAATTTCCC TAGCAAGAAT TGGCTTCTTA AAAAAATAAG
8551 TCATCTTGGA CAACCTAACA TTTAGTAAAG GCATTTGTCA TAAATAACCT
8601 CAAGTCCAAT TTATGGCAAG GGTTTTAATT TGTAAGGGCT TTATTTCTCC
8651 ATACAAAGGG ATTGGAGAAA CAAACTAGAA AGCCAGAAAA CAGACCACAA
8701 ACACTGAGCT AGTGGTTCCA ACTGGAGTGT TCCCTGAGCA GTGACTTATG
8751 AATACTTGTT TAGAAGAATC AACTCAAACA AATTTAGGAA AGTCACATCC
8801 TGCCTTTAGA GCTTCCAGTG TTTGTTAGCA TATTAAAGTC TCTGAAATGA
8851 CCTACAATAT TGAAATCTCA GTCTTCTGCT ATTTTTAATA TTTATTTCAA
8901 AATGAAATAA TTTTTGTGAA AAACATTTTA ATGTCTGTGG CTCATAATAT
8951 TCTGTGGATC TCAGTTTGGG AAATGAAAGA TTATAATCGT ATCTACTCTT
9001 TATCTGTTGG AAACATCTTT CCATTTATTT TTCCTGCTGG TTTAATGGCA
9051 ACAAATTTTT ACATGTGAAA TATTTGTAAT GTGATTTATA TGAAAAAATG
9101 TAATTTTCTT ATTACACGAT CAAAAGTGGT TATGCTCCTC TGTAAGTTTT
9151 TCCTTACAAG TTTTTATGTT GCATAATTTA TATCTATTTG GTTTAATGAG
9201 TACAACACAA GATAGCTCAG TTTAATTCTG GGATGTTGGA TGTTTCTAGT
9251 TAAAGTACAA GTTGGATTTG ATGAAAATTC ATTGCTTCTT TATGATTTTT

FIGURE 3C

9301 TAAAACTCAA GAACATGTTA GTTAAAGAGT GTCTTCTGAA CAAATTCTTG
9351 TGAAGTAGTT GCTGATTATT AAGTAACACT CATGCTACCG TAACTTTTTA
9401 TACTATCCAA AGCTATAGAC ATTTTTAATT TTCAACTTGC AACTACCTAG
9451 GTTGAAAAAT TAAATCTGCA AGCCAGTTTC ATTATTCAGA CAATTTGGTT
9501 ATCACTTCAA GCCTACTATC TTCAAAGAAA ATGGGAGTGC AGGCCTTCAT
9551 GGGAGCTGAC TTCTGCTGTA TGGCCTTGCA AATGTCAACT CGATTAGAGT
9601 GACCAGTGTT AGCCCTCAAT TCACAAACTC AGGTCCCATG AAATATACAC
9651 GGATTTCTAC TATGCATTAC TATGTGACCA TTCATGGAAG TTTCGTTTGG
9701 AAACACAGAC ATTAAAAAGC CAGTCATGGA ATAACATTCT TGTTAAAACA
9751 GGACATTGGC AAAAAGGACT AGAAAACTTC TGGCTATAGA TTTTGAATCC
9801 AATAGCCTTG CATAGGCTTT TCTGTTTCCT CCTAAACTAT GTCTTCTGTC
9851 CTTTCTGGAG GCATATTTAT AGTAAAATAA ACAAAATTAA CCTTGTTTTA
9901 CACTTGAGTA ACCTATACCT TTGGTTATTT ACGAGAATTA CTTAAAGCAG
9951 AGTTGGCAAC TTTTTCTGTG ATGGGCCTGA TACTAAATAT TTTACACTTT
10001 CCAAGTAATA CAGTCTCTGT CACAACTACT CAACTCTGCC ACTGTAGCAT
10051 AAAAGCACAC TTAGACAATG CAGAAACAAA TGAACATGGC TTTGTTCCAA
10101 TAAAACTTTA TTTATGGACA CTGAAATGTG AATTTCAAAA ATATTTTTTG
10151 CATAAGATCA AATATTATTC TTTTGATTTT TTTCCAATCA ATAAAAAGTG
10201 TAAAAATTGG CCGGGCATGG TGGCTCATGC CTGTAATCCC AGCACTTTGG
10251 GAGGCCGAGG TGGGCAGATC ACCTGAGGTC ACGAGTTCGA GACCAGCCTG
10301 ACCAACATGG AGAAACCCTG TCTATATTAA AAATACAAAA TTAGCTGGGT
10351 GTGGTGGGGC CTACCTGTAA TCCCAGCTAC TCGGGAGGCT GAGGCAGGAG
10401 AATCGCTTGA ATGCAGGAGG CAGAGGTTGC GGTGAGCCCA GATTGCACCA
10451 TTGCACTCCA GCCGGGGCAA CAAGAGCAAA ACTCCGTCTC AAAAAAAAAA
10501 AAAAAAAAAA GTGTAAAAAC CATTCTTAGT TCATGAGCTA TACAAAAATA
10551 GATAGTGAGT TAGATTTGGC CCATGGGGCT TATTTTGCTG ACTCCTGCTC
10601 TAAGCATCTT GCAGACATTT CTTCATATGC CCTAGGAGAT TTCTGATATC
10651 CCCTCATAAT ACCCTGGCCT TACACCAAGA CTACAATCTG TTCTTTGCAG
10701 ATGCTTAATA AATTCATTCT TCCCTGTCAT TCAGTTGATC TGTGTGAGCC
10751 AGTGGAAATA CTTGGGCCAA TAAATCTAGT GTGTTTGAGG GTAAAATATG
10801 CTATTTTTGT AAGATATATT ATTTAATGGC CACACAACCT AAATTCAATT
10851 AAATGGTTAC AACCTGTAAC GCATTTAAAA TATGACTAGG CAGAATTTGC
10901 TTCCTACTAA AGACATTTAT TCGATTGAGG AGCATCCAAC AGTTGATGTT
10951 GATCCCCCCA TCCTGCCCCA CTGTTCTACT TTGCAATTTG TTTGAAAGAA
11001 ATTGTCAATA TATTTCTGAC TTCTGAGCAA ATCCATGAAT CGGGATCCAG
11051 CAACAGGAAA AGAAGCTGTT GCTGCCCATT GCTTGGTTTT GGCACCAGGA
11101 ATGGATAAAT CCCAGACTTC CTGGGGCACG TGTTTTATAA AAGGGAAGTG
11151 CTGACAGTGC AAACAGCTGC CATCAATTGG CCTTGGAGAC TACTTCCCTG
11201 GAGAAGCTCC AATTATATTC TTAAAGGACC CACCAAGCTC TTCAAGTGTT
11251 AGTGGCAACC ATTTGCTGCC AACCATTTGA AATGATGAAG TAATTTTTTT
11301 TTATTAGTGG ATCCTAAGTG ATAGGCTCTA GAACTGATCT TCAACCTTAA
11351 CTAATATCAT GGCATCAGAG GGCTACAGAT TAAATCAGTG GTTCCCAGTC
11401 ACTCTCTGTG GACAAGTAGC AACTACGACA AAGCTTTTCT TAGTCTATGG
11451 TGGAAGAGAA AAATTAGGAC AATGTAATAA GCATCCCATA AACTTATTAA
11501 ACCTATTAAA ATTTAATTTT AAGATTATGT CATTTTTTGT ATGTGTGTAT
11551 GCTTAGTATT TATGGATTGT GGAAATAGAA TTTTTTTTTT ATAGTGAGAA
11601 CCTAGGTAAG TGACTTACCT CTCTGATCCC CCATTTTCTC ATATGTAGAA
11651 GGGGGCTAAT AATAGTATCT GTCTCATAGT TTTTGTGAGA ATAAAAAAAT
11701 TGTCCAGGTA AAATGCTTAG CTGGTGACTG GCACACAGTA ATTGCTCAAT
11751 AAATGTTAGC TATTATTGCT ATCATTATAT AATCATCATG GTTTCCAATG
11801 CCTTTACTTG GCAAATAAAA GAACAAAAGT CACCCGATAT TGATCTCCCT
11851 TTTCTTCCCT AGTTTTCTGG GGGGTGGGAG GCAGAGACCG AATTTTCTGA
11901 TCTGTGAAAT CTGAATTTAT CATTGTAATT TTCCATAAGT GCTATGTAGA
11951 GAACTCATTT AAGTTGCTGG GATGAAAAAA AATCAAAAGT GGCCTATTGT
12001 GCTGGGTGCA GTGGTTCACG CCTGCAATCC CAGCACTTTG GGAGGCTGAG
12051 GGGGGTGGAT CGCCTGAGGT CAGGAGTTCA AGACCAGCCT GGCCAACATG
12101 GTGAAACCTT GACTCTACTA AAAATACAAA AATTAGCCTG GCATGATGGT
12151 GGGCACCTGT AATCCCAGCT ACTCAGGAGG CTGAGGCAGG AGAATCCCTT
12201 GAACCCAGGA GGTGGAGGAT TCAGTGAGCC GAGATCTACT GCACTCCAGC
12251 CTGGGCAACA GAGTAAGCCT CTGTCTCGAA AAAAAAAAAA AAAAAAAAAA
12301 AAAAAGTGGC CTCATCTTCA TTTCAGTGAA AGATGATAGT ATCTGGACTC
12351 ACAGTGTGGC AGTGCAGACG GAAAGCTGAG AGTTTATTCA ACATTTATTT

FIGURE 3D

12401 TCAATATAAA ATAATTAGGT GTTACTGATG GCTTGAATGT GGGGTAAGAT
12451 GGAAAGAACA AAATCAAGGA TAAATCCTAG GTTTTTGCTT GAGTAGTTAT
12501 GTGGATGACT GTGACATTTT ACTAAGATGG AGATGCGTGG GAACGGAGGG
12551 GTTTGGGACC CTGCTCACAT ACAGTCTAGA GTTCACTTTT GGAGGCATAC
12601 AGTGATTATG GGACAGCTAA ATGATGGTGC CAAGTAGGAG CTGGAGTAGA
12651 GTATCCAGCA ATGAGTGGAA ACATCTGGGA TGGAGACAGA AAGACACGGG
12701 TATTAATTCT ACGGGGATGG CTAAGTCTGC TCTGAGAGAC AGTGTGGAGA
12751 CCAAGGAGAA GAGGAATCCT AATATTTAGA AACAAGGCAG TGGATAGCAA
12801 TCTAGCTATG GAAAGTGGAA GGAAAGAGAT AGTTGATCAT CCAGTTCAAC
12851 ACTACTCTTG TTGTAGTTCA CTTATGTTGA ATGCTTCTGT GTGACTAAGT
12901 CGGTGAGAAA AATCTATGGG AGTAGGCAAC ATGGAGGATG TTGGTATTCA
12951 CAAAAGCAGT TTAGTGGAGT GTGGAGGCCT GAGCCAGACT AGAATGAGTT
13001 AGGAGTAGAT GGAAGATAAG AATGCAGATA TGGGCCCAGC GCGGTGGCTC
13051 ACGCCTGTAA TCCCAGCACT TTGGGAGGCC AAGGTGAGCA GATCACAAGG
13101 TCAGGAGATC GAGACCATCC TGGCTAACAC CGTGAAACCC CATCTCTACT
13151 AAAAATACAA AAAATTAGCC GGGCCTGGTG GCGGGTGCCT GTAGTCCCAG
13201 CTACTCGGGA GGCTGAGGCA GGAGAATGGC GTGAACCCGG GAGGTGGAGC
13251 TGGCAGTGAG CCGAGATGGT GCCACTGCAC TCCAGCCTGG GCAACAGAGC
13301 AAGACTCCAT CTCAAAAAAA AAAAAAAAAA AAGAATGCAG ATATGGCAAG
13351 TATAGACAAG CTTCAAGAAG TTTGGTCTAA AAGGAAGCGG AGAAATAAAC
13401 AAAGAGATGA TGCCTAATAT AATTCAGCTA AATGTAATAT AATGGATTTT
13451 TTTAAGATGA GGTACTAGAG CATGTAATAT AAATCTATTA AATTGGGTGG
13501 CCAGGAACCA GGACTGGCTC ATCAGCATGG ACCAGGCTAG ACGCACAGGG
13551 CCTTATATCC AGAAGGACAT CACCTTTGGG TTTTAATGCT CTGCACTTGC
13601 TGTCTCCAAA TTCTAACTGT CTCTTAGGCT CTCATCAACA CCCACCTCCA
13651 TATCCAGATA TTGAGTACCT CAGGGAGTTC AATTTGGAAG CAAATGATGT
13701 GAAAATGTAC TTTACTATCC AGTAACATTC TTGTTAGGGA GTGTTGGCAG
13751 AGATTGTCGA ACAACCATAA TGCATTTTAT CATTCGATCA GTCTACAATT
13801 TAAACATAGC AGGACTGGAC AGAGGCACAG GAAGATTAAG CCACTGACCT
13851 TAAGTCAGAC AGTCACATGG GTAGATCCGG AATCTTGATC TAAAATGAAT
13901 ACCATTTTTT CAGTTATAGC TATCTTCCCA GGATGGCCAA CCAGAATGCA
13951 TATATAAAAT TTCAAAAACA AACATTGGGA ATTGCTCTTC AGCAAGAATA
14001 CATCAAACAC CCATTATGTG CCTAACTCTA AATCTTACTT TCAGAGAGCT
14051 AAAAACAATT TCATTTCACA GTGACATTCA TCTTCGCTTC TGCCGTAACT
14101 CACATGCATA TGCCTTAGAC CACATTATTA ATGAAGTATT GGGGGGTTCC
14151 ATCTAGAGCA CCTTTTCTTC CCTGGAGTTA ATCATCCAGT TCAGCACCAC
14201 TCTTGAGCTT TGCTTAGCTT CTTCTACCCA TTTGGATTTT AAGGACAACA
14251 ATTCCAATGG CCTTTATCCA TGTATTTAAC AATTCATTAT GAGCCAGGTG
14301 AAGTGGATCA CACCTCTAAT CCCAACACTT TGGGAGGCTG AGGCAGGTGG
14351 ATCGCTGGAG CCCAGGAGTT CACAACCAGC CTGGGCAACA TGGTGAGACT
14401 CCATCTCTAC CATTTTTTTT TTAATTAGTT GGGTATGGTG GCAGGAGATC
14451 AAGGCTACGG TGAGCTGTAA TTGCACCACT GCACACTAGC CTGGGCAACA
14501 GAGCAAGACC CTGTCTCACC AAAAACAAAA ACAATTTATT TCATCATCAT
14551 TGTCATCATC ATTGTCACTG CTCACTCTTC AACATTTTTT AGGTCAACTT
14601 AATTAATATG ATACCTTGTG GGATAATTTT TATTTATTTT TATAAAATAT
14651 TGAAGTTTTT GCCACTTTGA TAACTTCTTC ATTTTCTGTC CAGAGTATAA
14701 CATACCAGGG AAAAGGCTCT AAAATAAGGC TTGAGGTATT AAAAAGATCT
14751 TCTGTTTAAG TCTTATGTTC CTAATCAATA ACTAGAATTG GCCTGATTGC
14801 TTTCCTCAGT GGGTTTTCTG GTAGTCCTGA TATGATATCG AGGCTGTCAT
14851 ATAGTCCTGA AATATCCTAT CATTAACATT TGTGGTGGTA TCTGATATAA
14901 AGGTAGATGA ACTTCATTGC AGCTATTCTT AGGAAATGCG TATTTAAATG
14951 CATAGTTAAA AGCAAGATTT ACAATTATAG AAGGAATGCA AATGAGTTGT
15001 AGAAAGCTCA TAAAATAAAA ATCAAGAAGA AAGAATTACC CATCATGCCT
15051 CAGCCCAGTG ATAACCACTG CTAATATTTT TGGCTGTTTT CATTTGCAAC
15101 CCCATCTCCA TTCTAGCAGC CCTCATCCCT CCTACCCACT ATGTTTTTCA
15151 CTATATTTCT TGTTTAAATT TACTTAATTA TTTGTTAATT ATGTTTTTCC
15201 TCTCACTAGA AAGTGAACTC CATGAGGGCC AGGGATTTTT GCTATTTTGT
15251 TCACTTTTGT ATCCTTAGCA CCTACTTTGT TGATTAAGTG AATGCATTAA
15301 TGATCTATTT TTAATCTGTG TATGTGTATA AAAGACACTT GATATATCTG
15351 GGATGATATT CAATATACTT TTGTATCCTC ATTTTCACCA TAGGTAGTTT
15401 ATGTCAATTC CTTGAAATTT GTTGATTTTC TTGAATAATT TAGCAGTTGT
15451 ACAATTCTAA AACATAAATA TAATTTGCTT AAATATACAT ACCATTTTAA

FIGURE 3E

15501 ACATATTTAA ATGTGAAAAT ACAGTTGAGT TCTCTTAGAT TGCAATTTTG
15551 TAACTTTTGA TAATCCTTTG ATCCTGAAAA AAATTTTTTG GCATGAGGGA
15601 AGAGATGAAT ATTTCTTTTG GAGTATTTAA ATCATCTCTG CAATAATCCT
15651 TTGATCCTGA AAAAAAATTT GTGGCATGAG GGAAGAGAAG AATATTTCTT
15701 TTGGAGTGTT TAAATCATCT CTACAATTAA TAATATCTAA AGCAGTTTGG
15751 TTGGTTTATT TAGGTAGGAT TAATTTTCAG TATGAATATT ATTTAAAAAA
15801 CAAATATAGT CAGTTGAATT GCTGTGGAGG TTTCTGTACG ATTTACTCAA
15851 AGCTGGCTCT TTTTCTGTAC GCACTACCAC GCCCGGCTAA TTTTTGCATT
15901 TTTTTGGTAG AGATGGGGGT TTCACCATGT TGGCCAGGCT GGTCTTGAAC
15951 TCCTGATCTC AAGTGATCCA CCCACCTCAG CCTCTCAAGG TGCTGGGATT
16001 ACAGGCATAA GCCACCATGC CCAGCCTGCA TTTATCCTTA CATGATGGTG
16051 AAAAATAATG TTTGTACTTC CTTCAGAATA ATTTCAAGAA GGATCCCTGG
16101 AGTCAGCTAA TGATTAGAGT CAGGACTGTG CCTTAGTTGA TGGCCCATAT
16151 AGCACTACTG AACATGCCAG AGCTTTTGCT TATCCATACT GGAGGAGGGA
16201 GTGCTTAGAA GGCAAACGTA TATCATTTTA TTTTCATTCA AAATGTACTG
16251 ATAGCAAAGA ATTTCAATGG CTGGCAGATT CAGTTAAGGA CAAAAATAAT
16301 TCACAGCAGA AACTTTTTCT TGGTCTCCCT CCTCCAAGTG CTAAGCATGG
16351 CACAAGTAGA TATCATGGAA TTCTAGAACC CTCTCTTCAT AGATCTTAAA
16401 AACTACTCTC TTTCCCTGCT TGAGTACTTT CTCAAATCTG TGTCTGTGTG
16451 CAAATTTTCC TTCTAAGGAC ACCAGCCATA CCGGATTCAG GGCCCACTCT
16501 ACTCCATTTT GATACTGTAC CATCTTAACC GAACATGTTA TATCTGCAAC
16551 AACCCCATTC TCAAATAAAT TTCACAGTCT GACATACTAG GGGTTAGGAC
16601 TTCAACCTAT CTTTTTGGGA GACACCTTTG GTTTGACTGC TTCTTCAACT
16651 CTTACCAGCT CTATGAGCTT GAGCAGGTTA CATACTCTTT TCAAGTCTTA
16701 GTGCTTCACT TGTATTTTGG GGCTAATAAG GATTATACGA AATAATGCAG
16751 GTTAAATGCC TAGCACTTTG CTTTACATAC TAAGGGTTCC CAAGTGCTTT
16801 ATTATTAGGT TTCTGAATGT TATATATAAA GTTTCAGTGC TGCAAAAGGA
16851 ATAGCACTCG AATATAACAT TTTCTTTTTA ATTCTCAGCA AGGCAACGTA
16901 CTTCTATATA GAAGGGTGCA CCCTTACAGA TAGAATAATG GTGGGCGCAC
16951 ACTTGGACAA GGGAGGAGAA GGGGTTCTTA TCCCCCACGC ACGTGGCCCC
17001 TGCTCCTGTG TCGTTCCCCT ATTGGCTAGG GTTAGACCAC ACAGGCTAAC
17051 CTAATTCTGA TTGGCTAATT TAAAGAGAAT GACGGGGTGA GGGCTTTGGC
17101 AGAGTCAGGG CAGAGCAGAT AGCAGGTAAT CGGACTGAGT TAGGGTGGAG
17151 CAGGTGATCT GAATGAGTCA GGGTGGAGCA ATCAAAAAGG TTGCTTTATG
17201 AGGAAGTTAC GTTTAAAAGT AGAAGGCAGG CTGGGCGCGG TGGCTCACGC
17251 CTGTAATCCC AGCACTTTGG GAGGCAGAGG TGGGCGGATC ACGAGGTCAG
17301 GAGATGCAGA CCATCCTGGC TAACACGGTG AAACCCCGTC TCTACTAAAA
17351 ATACAAAAAA ATTAGCTGGG CGTGGTGGCA GGCACCTGTA GTCCCAGCTA
17401 CTCAGGAGGC TGAGGCGGGA GAATGGCATG AACCCAGGAG GCGGAGCTTG
17451 CAGTGAGGCG AGATCCTGCC ATTGCACGCC AGCCTGGGCG ACAGAGACTC
17501 CACCTCAAAA ACAAAACAAA AAAGTAGAAG GCAAAGAATT GAACATACTG
17551 ACATATTAAG TCTTTGAAAA GAAATTTAGA ACTCATATCT AACAATCCCT
17601 CCCCTTGTAT TTCCTTACAG CTTTCTTTTC AAACTTTTTT TTAATATGCC
17651 TTGGCTTAGT AGTTTTGCTT CATTTTCCAA AAGAAGAAGC TTCTCTGGAT
17701 AAGGTGGAGG TTAGTTAAGG GAGGTTTCAG TAAGTGACAT TTTTATGAGC
17751 CTCTGCATCT ACTTACGGAT GCACAGTATG ACACAGCACC CGACAAGAAT
17801 AAGTCCACCT ATTACGGCTG CGAGGGAAGT AAGAATTGAG GCTATTATTC
17851 CTTCTCATTT ACCAAACTAC TTTTCTAGCC ATCTTATAAA GGGGTCATTT
17901 ACCCCTGAGT TGCTGGCTAA CTTATTGGAT AGAGCAGTCA GACCATGCAG
17951 TGCCTTTCTA ATACTTCCAT TAGGGGCAGT GTTGTTTGGG ATGAAGGTGC
18001 AACATTGAGT TTTAATTATG ATGCAAACTA CCCCTCTTTC TGCTACTATC
18051 ATGTCTAAGG CTATTTTATT TTGCCAAGCC ATCTGGCTAG TAGCCCCTAA
18101 TTGCTCAGCT ATTCCATTAA CAGCATCTCT AGTGTAGTTA ATAAATCACT
18151 GTTGGTTGTA GTAGCTGTAG TTTATCCAAT CTACATTTTT ATTAATTGTC
18201 ACTCACCAAA ATATTGACTT AAATCCTGCG GCTATTTGAT TTTGGGCTTT
18251 AAATTGATCT GGTATTCCTC ATGGGACCCT AATTGTGTCT AAATAGACGT
18301 GAGAGTTGAA AGACCCATAA GGGGCTTCTC TCGCTTTACG ATGTCTTATT
18351 TTTCCTTCCT CTGGTTGATG AAATGCCAGG GTGAAAGGGA TAGCCAATTG
18401 GACTAAAGCA CAAGTGCCAC TCCAGTTATT TGGCAGAGTG TCCAGTAAAG
18451 GTCCACCACA ATACCACCAC ACATCCACAC ATCCGCTCGG GGATGAATAA
18501 GGGCTGACTG ATTGATAAGC TCTTGAAAAT TCTTAAGCTC ACTGCATCCC
18551 TTCAGGTCTC CAAGGAACGC TAAGTTTCCT CCCTGTCATG AGAGACACTA

FIGURE 3F

18601 AGTGAACTAG TTTTGGGAGA CAGAAGCTGG ATGGCCCTTG GGGGCTGACC
18651 TGCAGGGTAC CAGACTTCGG GATATAGCAG AGAGAGAGCT TGGAACGACT
18701 TATTACTCCA GGCTGTAGAA TCCCTGGAAA AGAGCTACCA TGCAGCCCAT
18751 GCCTGGTTGA CTGGAGGACC ACCCTAGTGG AAAGGGGACA ATCTGGAATA
18801 CTTGATCCAT TCTAACCAGG CATTTGCATC TTGGTATCCT GTCTTAGTTG
18851 CCAAAGTTTG CTTTAAGTCT TTGTTTTTTT GTTGTTTTGT TTTGTTTTTT
18901 GAGACGGAGT TTCGCTACTT GTTGCCCAGG CTGGAGTGCA ATGGCGCAAT
18951 CTTGGCTCAC TGCAACCTCT GCTTCCCAGG TTCAAGCAAT TCTCCTGTCT
19001 CAGCCTCCCG AGTAGCTGGG ATTACAGGCA TGCACCACCA TGCCTGGCTA
19051 AGTTTGTATT TTTAGTAGAG ACGGTGGTTT CTCCATGTTG GTCAGGCTGG
19101 TCTTGAACTC CCAACCTCAG GTGATCCCCC TGCCTCGGCC TCCCAAAGTG
19151 CTGGGATTAC AGGCGTGAGC CACCGAGCCT GACCTGTTTT AAGTCTTTAG
19201 TTTTTACAAT AGCTATCTTG GTCTTGTTGT TAGATGGAGG AGGAGCAACT
19251 GTTCCGTTGT GAGAGGTTTT GGAAGAAGGC TTACAGGAAG GTGCAGGCGG
19301 TGGGGATCAA AGAAATGCAT TTTAAATAAT CTAATAGGGT TTGTCCCTGA
19351 AACCTCAGCC CCTATAGCAT AAAACTGACT TAAAGAAGGG AACTGGCTTA
19401 GAAAAGGGGA AGAAATTTGA GAGTTTGAGA TAATAACCTG TAGAGAATTA
19451 TAGATAATAA CCTGTATAGG TTTAGCTGAC AGCTGGGGGG AGGGCTGTCT
19501 CTTTAGTAAA ATGAGTGTAT GGTTTTAGTA AATTACAAAA ACTGGTTGGG
19551 GCAATCCCTT CTTGCTATTT AGTGGTCCAC AGAACATTGG ACCAACTACA
19601 GCATAAAAGC TCTACGTCGG GGGCGGGGCG GGGGGTAGGA CTCTGGGTTG
19651 ACATTGGGGT CTTTATTGAA ATTTCCCCGG ATTAAATGGT CCCAATTCAC
19701 TAATGCCCAG TCTGATGACA GTCAGGAGGC ACAGAGGTAT TTTTTCTGAA
19751 ATAGAGAGGT GTCTTTGACT TGGCAAATCC CCACAGGGTA TAACAAGGCA
19801 AGCATTAAGT GCAATAGTTT GAGGCAAAAT TGACTTGGTT ATGTTAATAA
19851 CTAGATGGTC AGCAATAGAG CCAGTAAAGA AGAAAGAGTA ATAGAATAGA
19901 TAAAAGAGAG TTAAATTTTT CTTAGCTTTA GTTTGGCAGG GCTTTCCCCT
19951 GGGGCTGTGG CCCACAACTC TGGAGGGGGC GGCGCTTTCT TGACTCGGGT
20001 GTGATGAGTC CATCCCTTTT TCACTGTAGA AACAGCAGTC TTGGTGGTGA
20051 GCAGCACAAG GTAGGGTCCT TCCCAGGCTG GCTCGAGTTT TCCTTCTTTC
20101 CACCCTTTGA TAAGAACGTG ATCTTCAGGC TGGTGTTGGT TTACCGGAAA
20151 TTCTAGGGGT GGTACCTGTG CTAAAAGACT TTTAGTTTTG AGGGAAAGGA
20201 AAATGGAAGA TAAACCAAGT ATATAATTTC TAAGAAATGG ACCTTTTGTT
20251 TTAAATGTGG GGACATCAGC AGTGGACTTT ATAGTCCTTG GTGCCTTTTT
20301 ACTGAGAAAT TTCCTTTAGC ACCTATTTTT ATTAGATTTT AGACCAAAGA
20351 AGGCCAAACA CCATTTTATA TTTAACAGTG CTTCCTGTAT GATTCTTATA
20401 CCAGATAAGC TAAGTTTCAC CTTTATATTA GCAAGTTGTT AAACTTAATT
20451 TTAATAAAAC TTTGTAGACA TATTTATCCA ATTTTTAATG TCTGACCATA
20501 ATGTATGATT CTTATAGACT CTTTTTAACC TTTTATAATT TTTGTTAAAG
20551 AGCAGGTTAG TGCTTTAAGA AATACCTGTT GTGCTTTTAT TTTAATGTCC
20601 AGTTCACAGA AAAACTGTAT GATACCCCTT AAACTTTAGC CAATATGTTT
20651 ACACACAGAA TTTCCTTTAT AATTAACATT TCAAAACTTG CTTAAACCTT
20701 TAAAACAAAA TATTTGTTTA TTTTTAAACT TTTAATGTAG GTAAAAATCC
20751 ACATTCTTAT GGCTCCTTAT AATCCTTTTA CCAAAGGCAT ATTTTACTTT
20801 CCTTATACAC CTTGCACATA AACTGTTTCT TCAATAGCTT TACATTCAGG
20851 AGGCTTAATT ACTTTTAAAT TATACAACAT TTCTTACATA AATTCCCTTT
20901 TAAAACTTTT TTTTCCTTCA CAACTTTCAC AGACAATTCT TTGACATGCC
20951 TCAACTTTCT GACTTGTTGT AAACATCCCT TTCTTTAAAC AACTAGTTAA
21001 TTTATTTTAG GACAAGAATT TACTATATAA CATTCTTTTT ACATAAATTC
21051 TCCCTCTCCT TTTTTTTTTT AAGATAATCA TTCTTCTCCA AAGCCAACTT
21101 CCTTTATGTC TGTGGACAAG ACTGTCTAAG GCCACAAGAT TTGAAGTTAG
21151 GATAATACAT GTTACACTGT TAACTTTTAG CTAAATTTAC TTTTGTTGAA
21201 AACCTCTAAG TTTGGGATTT CAATTATTCT TTGCTATTAA TAAGACCTTG
21251 TTTAGTCAAA ATTAACTCAG AATTGGTATA GATGGCTTTT TTTTATTATT
21301 ATTATTATTC TGTAAGTACT TTAAGGCTTG GCTGAGTGCA AACAGCTCTC
21351 ACGTTTGAAC AGCACCAATT ATTAGGCAGT TTTCCTAACT CTGCTTCTAC
21401 AAGTGTTTCC TTATCACTTC CTGAATACTC ATTGTGTCTT TTTCCCTCAA
21451 TCACCCGGGA GGAACCTGTC CTGAAGGGAT TTAGATCCCC TGTTAGGCAA
21501 ACCTGCTGGG TTAAGGGGAA TTTTCAGTGG TTAATGTTAA ATCATCTTTT
21551 TCTAACAGTA ATAGCCCCAT ACTTTAAGAT TTTTGAGTTA GTAAGCTACA
21601 TTTTCACTTT TTATATATTT TTTGACTTAG GGTAGTTCTG AACTGGTGAG
21651 GTGTGCTCAC AATGAGGTTT CCTCTAAAAG TTACTTTTCT ACTTCCTTCT

FIGURE 3G

21701 GTTAGCAAAG CAGTTGCGGC TACAGATTGA ATGTATTCAG GCCATCCGCG
21751 GGTTACTGGG TTAAGGATTT TTGATAGGAA GGCTACTGGT TGTCAGTGGC
21801 CTCAGTGCTT TCAGGCTATG CCCTTGTTTA TACTTACAAC AAGGTGGTAC
21851 TGGAGTGTTA TAGGGTCACC GAGAAGACCT TCGATTATCA GTTATAGGTT
21901 TTAAATTTAC CCTGGCTTTT TTTTTTTTAT TATTATACTT TAAGTCCTAG
21951 GGTACATGTG CACAACGTGC AGGTTTGTTA CATATTTATA CATGTGCCAC
22001 GTTGGTGTGC TGCACCTATT AACTAAGGAA TAGGGTACAC TGTTTTTTCT
22051 TTACTACTTC TATCTCTTTC TTTCCCTCTC TGACTTTCTG TCTCTTTCTT
22101 TCTGACTCCC TCTTTGTAGC TCTGCCTCTC TTTCTCTCTC TCTGCCTCTC
22151 TCCTCTCTGT CTCTCTCTTC TCTGTCTCTG TCCTGTTTCT CTCTCTCTCT
22201 TGTTTCTCTC TCCTCTGTCT CTCTCCTCTC TCCCTCTCTT CTGTCTCTCT
22251 CTCCTGTCTC TCTCTTTCTC TCTCCTCTCT CTCTCTCCCC TCTTGTCTCT
22301 CACTCCTGGC TGTCTCTCTC TCTCTCCTCT CTGTCTCTCT CTCTCCTCTC
22351 TGTGTCTCTT TGTCCTCTCT CTCTTTCTCT CTCCTCTGTC TCTTTGTCCT
22401 CTCTCTTTCT CTCTCCTGTC TCTCCTCTCT CTCTCTCCCC TCTCTCCTGT
22451 CTCTCGCTCT CCTCTGTCTC TGGCTCTGTC TCCTCTCTGG CCCTCTCTCT
22501 CTCTTCTCTG GCTCTCTCTC CTGGCTCTCT CCTCTCTGAC TCTCTCTCTC
22551 TCTCCTCTCT CTCTCCNNNN NNNNNNNNNN NNNNNNNNNN NNNNNNNNNN
22601 NNNNNNNNNN NNNNNNNNNN NNNNNNNNNN NNNNNNNNNN NNNNNNNNNN
22651 NNNNNNNNNN NNNNNNNNNN NNNNNNNNNN NNNNNNNNNN NNNNNNNNNN
22701 NNNNNNNNNN NNNNNNNNNN NNNNNNNNNN NNNNNNNNNN NNNNNNNNNN
22751 NNNNNNNNNN NNNNNNNNNN NNNNNNNNNN NNNNNNNNNN NNNNNNNNNN
22801 NNNNNNNNNN NNNNNNNNNN NNNNNNNNNN NNNNNNNNNN NNNNNNNNNN
22851 NNNNNNNNNN NNNNNNNNNN NNNNNNNNNN NNNNNNNNNN NNNNNNNNNN
22901 NNNNNNNNNN NNNNNNNNNN NNNNNNNNNN NNNNNNNNNN NNNNNNNNNN
22951 NNNNNNNNNN NNNNNNNNNN NNNNNNNNNN NNNNNNNNNN NNNNNNNNNN
23001 NNNNNNNNNN NNNNNNNNNN NNNNNNNNNN NNNNNNNNNN NNNNNNNNNN
23051 NNNNNNNNNN NNNNNNNNNN NNNNNNNNNN NNNNNNNNNN NNNNNNNNNN
23101 NNNNNNNNNN NNNNNNNNNN NNNNNNNNNN NNNNNNNNNN NNNNNNNNNN
23151 NNNNNNNNNN NNNNNNNNNN NNNNNNNNNN NNNNNNNNNN NNNNNNNNNN
23201 NNNNNNNNNN NNNNNNNNNN NNNNNNNNNN NNNNNNNNNN NNNNNNNNNN
23251 NNNNNNNNNN NNNNNNNNNN NNNNNNNNNN NNNNNNNNNN NNNNNNNNNN
23301 NNNNNNNNNN NNNNNNNNNN NNNNNNNNNN NNNNNNNNNN NNNNNNNAAA
23351 AAAGGTTGCT TTACGAGGAA GTTAAATTTA AAAGTAGAAG GCAAAGAATT
23401 GAACATACTG ACATATTAAT TCTTTGAAAA GAAATTTATA ACTGATATCT
23451 AACACTGAAG GAGGCTTATG CTTAGGGTTT TATGTTAGGA GTTTGGTTTA
23501 GAGCATAGCA TCTTTTATTT AGAAGAAATC TAATTCTTAA TATGGAATTC
23551 ACAAGTAGGA TTATGAGGAA CCCTGAAAAT TATATACAAA GTTTATTTTG
23601 TGTATTTGAA TTATTTTTTC TCTTTGGAAA AGGCATGTAT TCACCAAAGG
23651 AGTCCATGCT ATCCCCCCCA AGCTAAGACT GCTTCTGCTC ATCCTCAGCG
23701 ATTCATAGTT GCCTTAGGAT ACATTTATAG GGGACCCTCA ATTTTAAAAA
23751 CTTAGCACTG AATCAGAGAG AAAACTTGAG AGGCATTTGC GAGGTTAAAT
23801 GAGAGTGACC GATGCTGTAC AAGAGTAGGT CTCGAAATGT GGTACTTTTC
23851 TTGGGTTATC TCGTCTTATT CTCATCACAA ATGGTGAAGA AATGGTCAGC
23901 CACATTAAAG AGCAGATACT GAGATTCAGC AAGTGAGAAA ACCTGTCCTG
23951 GTTCACACAG CCAGGAAGAG GCAGAGGCAG AATCCTCACC CCACTTCTGT
24001 TTGCCTCCAA AGCTCAAGGA GAGTGAGCTT TACCCTTCAT ATTTACTCAT
24051 CCTCTTACTA ATTTGACTCT TAAGATAATC CTGAGATTTA AACCAGAAAA
24101 CTATTATGAT CCCCTTATTT GAATGAGAAT ATATGTCTAA AAATGATTTT
24151 TAAAAACACT ATTAAAGGTC ACAAAGCCAG TGAATGATAA AGGGATTGGT
24201 ACCTCTGGCT CCTATAGTTA GTTCATCCTT CAAAGAACAA AAATAGCCCC
24251 CATTTATTGA GTGCCTACTA AACTCTAGAT ATGTTTTTAA TATATGCTAT
24301 CTCATTTAAT ACCTACCACA TTCCTGTAAG GTAGGTATCA TTCATTATAC
24351 CTATTTTACA GATCAGGAAA AAACAAAACA AAACAAAAAA AAACAAGACT
24401 TTCTAGGGAA AGATGCTGAA TAGAACACAT TCTTCTACAT CCATTCCTTT
24451 CTGAAGATCT TCCTAATATG ACAGGTAGGG ATTTGTCTTA AGATTTAAAC
24501 CCACAAGGTA TGAAGAGACA GGCAGAAGAG CTTCACTATC AACGTTGCAG
24551 AAACTGGAAA GGAGACAGAG AACTAGAAGC AACATAACTG AGTCCTAAGC
24601 TTCTAGAAGG GGAAGGTGAG AAATAACCAG ACCCATGCCG TAGAACCCTC
24651 CAAAGACTCG GGAATTGGCA CTGTCATGTG CCTCTAGAGC TAGAGGTGAA
24701 GGGGAAGAGC TAAAGTAAAT GACATTGTTT GGATATCTAT TTAAAAACTA
24751 GTCATGTCCC TTCTACCAAC TTGGAAAAAG ACAAAAAAAA ATTCTCCACT

FIGURE 3H

```
24801 CCATACTATG GTTTATCCTC TGAAGAAGAA GTTTTCTTAG TGGGGAAGTT
24851 GAGTGCAGAA GATGCCTTGC TGAAAATGGA GGGATCGGGT AGATAAATGC
24901 ATACTGGATA CTGGGGCACC CAGCCTCCTC TTCCCACTTG GCTCTGATAA
24951 TACTGGCAGC CAAGGACTCA CCCTCCAGTA AAGAGAACGA CAGAATATTT
25001 TCTGGAGATT TTGACCAATC CAAGAAGGAA GATTTAAAAT TATCAACATT
25051 GGAGATTTTC TAATTCAACA TCCAGGCCAC AGCTAGAAGC AACACTATAG
25101 AAGTTTATTG CTGGCAAGAG CCACATACTC AGAATGTCCA AACAGGGGTT
25151 TAGGTCTCCA CACTTAAATA TGAGCAGACA ACCAAGGATT CTCAGGCTTT
25201 TGGGGAAGCC CTCTAATATG ACTGATAGAG ACTAAAACAA ATGAACAGGG
25251 AAAAAGTTAG CAAAAAGTAT AAGAAAGGTA AGAGAAAGCT ATGAAAACCA
25301 AAAAACAAAT AACCAGACAA AAAACAAACA AACAAAATAG ATACCAAGAA
25351 AATAGCTTTT GGAGAGCAAA AATTTGCTTT GGGAAAAAAA TTACAGCATG
25401 AATGGAAAAA TCCAAAGAAG ATTTAGAAGA TATATTTAAA GAAAATTTCC
25451 AGAATAATGA GCAAACAAAG ATATAAAATA AGGGTAAATA TAAGAACATT
25501 TAACGGCCAG GTGAGGAGTT CTAGTTTCTA AATAATAGGT ATAGAAAGAG
25551 AGAAAGAGAA AATGGAAGGG GCAATAATTA TTACATATTT TAAGAAAAAG
25601 AGTCCAGAAT TGAAGAACAT AAGTTTTCAG ATTAAAGGAG CCTATTAAAT
25651 GCCCAGCACA ATGAATAAAT CATAACATAT CAAAACATTC AACACAAGTA
25701 TATAAGACTA GAAGTTTCTA GAGAAGAAAA CTGTTACATC AAAAGGATCA
25751 GGCATCAAAA TAGCTCTAGA CTTCTCAACA GCAATGTGTG AAAAGGTAGA
25801 AGATAAGAGC AAAGCCTTCA AATTCTGAAG GAAACAATTT CCAACCTAGA
25851 ATTCAATAGT CAGCCAAACT ATTAGTCAAG TGTGAATACA ATAAAAATAT
25901 TTTTCATGGA TATATAATAT TTCAAAAAAT ATATCTCCCA TGCAATCCTT
25951 CTTACAAAGC TGTTTTAAAA TGTGCTTCAG TAAAACAAGA AAGAAGGGGG
26001 CACTGCATGC AAGAGCCAGG AATCTATCCT TAAAGAGGCA TGAAGGAAAT
26051 CCCCAGGGTG ATGGTGAAGG GAATACCAGG AAGACAGCTG TGCAGGAATA
26101 GAGATAAATA GTCCAGACTG GATTATGTCT GAGGAGAGAC ATTTTCAGGA
26151 AGATGACAAT GTGCCTGATG CACCTGAGCA TTATGAAAGG GAACTAGACA
26201 ACTGGAGAAG GGTTTGGGAT TGGATTGGGA AGGAGATGTA GAAAAGTCAA
26251 CATGTGTAAA CAAGACTGTT ACTAATTCCA GGGAAAGCCA AAAATTGTGC
26301 AAGAAAAGAA AACTAATCAT AGTTTACTAC AACTCAATTG AGCCTACCAT
26351 TTCTGTATTC ATAATAATGG AAATACCGAA TATTGATCTA ATTAAAATTA
26401 TTATGCCAGA TGTATTAGAA AGATGGAGGC ATGTTGGGAT AAAACCAAAG
26451 GAGCAAGAAC ATGAGCTAAA TCCCCATCTA CCACCTTGAA TATTCAATAA
26501 CTAATGCCTA AAATGAAAAA GAAAGGACAA TAAAATTATA CTCTTTAGGG
26551 ACATGGTGGA GATCACCCAA TGCATATCTA AAGAGAGGTA AAAGTGGTTG
26601 CTCCTTGGCT GGGAGAGATT AGAAGGGGGG TAAGTAGATC ATAGGACTGC
26651 CATTTTCTCC TTTTTAAAAA ATAACAAATC TTTTAGAACT ATTTGATTAT
26701 TTAAGCTATA TAAAGATATA GATAGTTATG GACACAAAAC TTGAAAAAAT
26751 GAAAACATTA AAAAGACTGA AATAGAGCAA AATATGAATC ATGGTTATCT
26801 TTAGATGGTT TTGTTTTTCT TCTTTATACT TTGCTGTATT TTTTATACTG
26851 ATAGCATATT CGTTTTATAT ATATGTGTGT ATATATATAT TTTACAATTA
26901 TATATACAAT TTTATATATT TTATATATAT ATTTATATAT ATACTCTTCA
26951 TTGTAAACAA GAAATTGAAG TTCAGAAAAG TCAGATAAAT TTCCTAATTT
27001 CAAATATCTT GTAAATGGTA GAGCTAGGAT TCCACTGCAA GTCTGTCTGA
27051 TGTGAAGCAT TTTTATCTTT CATCAAAGCA TTCAATCTTC GTTAAAATCC
27101 GAGAGGCAAA ATTGTCATGC CTCACCATTC TCTCCCATCT CTGAAGGTCC
27151 ATAGTGCCTC TTTTGTACAC CATACAAAAT AACACTTGAT TGGTTTCATT
27201 ATTTGTTTAC TTATTTGTCT ATCTATACAT TTATTCATAT TCATCTAATT
27251 TTAGAAAGAT GAGAGAATGG ATTCCAAAGG TACATAGATT ATAGCAAAAT
27301 AAAATAAAGT TACAAAAATG AAACAAGGGA CATTTGATTA TTCAGGTTTT
27351 GTTTTGTCAG ACTGCTAAAT GAGGCACACT CAGTTTTCCT TCTCTGCTTG
27401 GGGAGGGTAA GTGTCCTGGG ACTGAGTCCC AAGCTTCTTA TGTTTTTCCA
27451 TCAGTGCCTA GGAAAGTCCT GGGTACACAG ATACTCAATG AATGTTTGTT
27501 GGTTTGACTT GCCAGCAAAG CCGTGGCTCC TAGGGAAGTG ACTTCAGCTT
27551 CTTTATCTTC TTGGTGTGAC TATCTTAAAA GGGAGTAAGT GAGCCTTTCT
27601 TTGTAACTGA CTGTATTTGA GAATGCAGCA TGACAGACAA AACATTCATC
27651 TCATTCATGG AGAATTGTAA AATCCAGCAG AAGAGCTCTC TTTTTAACCA
27701 GTGCTTACAA TTTGTCCTTT TTCACCCTTC CTTGGCAAAT CACGCAATAT
27751 TCCTTCTTAA AAATGGGTAA AGTGCCAGCC GAACTTAGAA GAGGGACTGA
27801 TTCTATCTCT ATTCTGACCA GGTATACGGT AGACTGTAAT TTAATGTCAG
27851 CACCTTTCTG TTGCCATAAT GAGGTATATT TATTTCTGTT CAAAGATCAT
```

FIGURE 3I

27901 GCAGCCCTGA CAAAGCAAAT ACCCTCTGAC TCCCACTGTT AATTATCCTT
27951 CAGTTGCTAC AGGGTTTTCA TCCATGTCCT CACTTAGGAG AGTTGGCGGT
28001 TGTGAAGCAG ATGGAGTCCA CAATCTCAGT GGCAGTTCTT AATGCTTTGA
28051 GCTCAAAGTG TGAGTAAGTC GATGAGTGAG GCTTTTAAGA TGTAAATCCA
28101 ATATCTGCAG AGAAATCTGA AGCTGTAATA TTAGAACAAC ATTCAAATGA
28151 GGACTTCATT GACTAGCTCA TTAAGAAGTC CTTTGATAAT AGCATGTTGG
28201 TAAGACTTTT CTTAGAAGGT ACATATTATA AATGATGATG TGCTAAGAAA
28251 TCAACATAAA GGAAAATAGA AAAATTTTCC CCAAATCCAT CCTTTTTCTG
28301 TAGAACTTTA ATGATGATAC CTCATTCCTT TGTAACTTAA TTTTAAAAAG
28351 TTAATTATGC ACCTACTATG ATACGTCCAA AATGTTTTTA GGTGATGTGG
28401 ATATAGCGAA GAACAAGACA CACCCAGTGT CTTCCTTCAT GGAGTCTATA
28451 TTCTTGGCAC TGTTGGTCCT GTGTGAAGTC CTAACATTAT TTTGCTTAAT
28501 GTTTTGGCAA GAGAGGCAAC ATTGGCTGGG CGTGATGGCT CATACCTGTA
28551 ATCCCAGCAC TTTGGGAGGC TGAGGTGGAT GGATCACCTG AGGTAGGGAG
28601 TTCAAGACCA GCCTGATAAC ATAGAGAAAC CCTGCCTCTC CTAAAAATAC
28651 AAAATTAGCC AGGCATGGTG GTGCGTGTCT GTAATCCCAG CTACTCTGGA
28701 GGCTGAGGCA GGAGAATCAC TTAAACCTGG GAGGCAGAGG TTGTGGTGAG
28751 CCGAGATTGT GCCATTGCAC TTGTACTCCA GCCTGGGCAA CAAGATTGAA
28801 ACTCCATCTC AAAAAAAAAA AACCAACAGG CAACATTCTG GGCTGAAACA
28851 AAGGTAATTC ATCTGGTAAC AATAGCAATA ACATAAATAG CAGTAATAAT
28901 TATACATTAT TGAGTTCCTA TTCTCTGCCA AAAATGGTTG ATAAGCACCT
28951 TTGATATGGC TTATTTTACC TAGTCCTCAT TATAACCTTA GAAGGTATAT
29001 TGTATCTGGT CAAAATTGAA AGAAGAAATT GAAACTCACA GAGGGTAAAT
29051 AATTAAAGTT CATAGCTAGT AAGTAGTACA GACAAACCCA AAAGCAGAGT
29101 TTCATGCTCA TAGTCACCAT AATGTATTCA GAAACTTTTA GGACTCATCA
29151 CAATATTAAA ATCATGGAAC TTGGAGCCAC AAAAAGTCAG ATTTAAGTCC
29201 AAACCCTGAC CCTGGGTAAT TTAACTTTTC TGGGTTTATG TAACATATCT
29251 ATAAAGTAGC AATAATAATA TTACCACCTC ATGCTGTTTT GGTAAAAAGT
29301 AAATAAGATA ATGTATATTA AGGTATTTGG ATAGTGCCTA TAGATGTATA
29351 TATGCTACTT AATAGACAGT AATGTAATTA TTAACTATGA CCTAAGATGT
29401 GGCACAGTGC AGGTAGCAGA AGTTCTATCA TTAATCATTT ACAGATACTT
29451 ATTAAATTGC TTCAAACCCA TAAGGATAGA GGCAAGATGG AGGGGGAAGT
29501 CTAAGAAATT GATTGAGTCA ACATTTATAT AAATACTTAT CTACTGAGAG
29551 CTTCTTCACC TCAGGGTTTG GGTCACTTTA AATGCATCCT CCCTGACCTC
29601 CTCTGCCTGG CTACCTTTGG AACTCCAACC CATTCTGCAA GACCCAGTTA
29651 AAATGCTGCC CATTCCTGAA GCTTTCTTAT TTTCTAAAGT AGGAAGAGAT
29701 TTCTCCCACC TTAGAACTCC TATAAACATC TGCAGACTAG TTCTAGGCAG
29751 CCTTTAACAA AATCCTCATG GGATCTTTGA AAATACAGAT TCCCAGGTCC
29801 AGCCTCCAGA GAATCTGATT CAGATAAGGC CAATGAATCT GAATTTAAAA
29851 ACATGTATTT GTGTGATTTT GATGGGTGGA CACACTTGAG AATCACGTCA
29901 GGACCATTTA TGTGGCTCTC AATTACATAT ACACTACTTT ATATTGCAGT
29951 TGTTTATTTA TGTTATATTG CAGTTATTTA TTTATGTTTC ATCTCTTTTC
30001 CTGAGAAATT ACCTTCCTGA TAATCCAATG CAGAGATAAA TTAAGAAAAT
30051 CTGTAGGAAA GAATAGATCA TCAAGTCCCT TGCAACATTC TTCTGAGGTT
30101 GTAATAATCT CCTCTAGGAT GCTTTGCTGG ATTTCCCTGG ACTAGGTTGT
30151 CTTTTCCTGC TACTTTCTCC CATTACAGGT CTCCCTACGG CAGCACTGCT
30201 TATATCACTT GGAACTTGAA TCTATTTTGG TAAAAAAAAA GTTAAAAATT
30251 AAATTATCAG AAGGATATTG GGGATGCCTG CAGAGTAATC AAAATAGGAT
30301 CTATATTGTT ATAGAGCCAG GCACATTAAT GCCATCAGCT TTAGCCCTTT
30351 ATGTTGTGAT TTTACTTTAT TCCAAATGTC AGCTTTATCC TGTTGGATGT
30401 GCTGATCTTT TTTCTCTACA TTCAGCCAGT TCCATTCTCA TGTTCTGGAA
30451 GCTTGTGACA GAGGGGGAAT ATGCATTTCA AGATCAGAAG ATCCAGAGTG
30501 AAAATGATTG GAATGGCCTG AGTCACAGTT CCAATCCTAG AACAAGGCAT
30551 CTTGCTAGGG ATGTGAGAGA TGATAAGTGA CAGATACAGT GACAGCAAGT
30601 GGTTGATGGG ATCTGAGTTG TGAGAGAGGG TCTGTGAAAA ATGAAAGACC
30651 TGCATAAGAA GAGGAGAAGC AGAAATATGA ACATTGTTGT GAGTCAGGTC
30701 TTTACCCAAC TCTGTGCTGC TTATTCTACT TTTTTGTGCA AGATTGATTA
30751 TGTGTGTTTA ATAGAATGCA GTAAAGAACA GTGTTGGAGG GCAGCTGTGG
30801 AGTCCACTTG AGTGGGACTC TACCACTCTG CCACTTACCT ACTTTGTGGC
30851 CTTGAGAAAG GTACTTAATT TCCCTGGGTT GCAGTTTGTT CACCTAAAAA
30901 CGTGGCAATA ATAGTAATAC TGTTTCAGAG TTGGCGCAAA ATTAGGATAA
30951 TATATGTAAC ATATTTAGAA TAATGATGGG TATTCCTTAT GTAAATGTTA

FIGURE 3J

31001 GATGTTAGCT ACTGTGAATT TTTCTGTTGT TCCACTAGAC TGTAGGACCC
31051 CTGAAGGCAG GCAACCTTGG GCTTCTTTCT CCCAGCACCT AGCACAATGG
31101 CTGTTACTTA GTAAGCAGTC AGTAATGGTG TGTTGTTGTC AGTGAACACA
31151 GACTGAGTTC AGTGAGCAAT GTCTTGGAAA GCCTCTACTG CACCTAGGAC
31201 TTTCAGCTAT ACTGAGACAG AAAAATGAAA TCCTCTCTGG ACTGGAAAGC
31251 AGAAGCCAGA CATGTAGGCA ACCAAACTGT AACTGTTTCC ATGTCGAATT
31301 GACTTTGCCT TTAGCGAATC ATAGCACTGA GGAGTGTCAC GTTTAAGCAG
31351 CAAATTTGTA TAGCAAATTA ACATGCCAAA AAAGGCATGC AAGACTTTTA
31401 CTTGATTTTT TTCCCCTCCT CTCTGGGGAA TTTATCTTAT TTGGGTCTTA
31451 TCTTGGAATT TATCTTATCT TGAACTTATT CAGACTGCAT TGGTTTAATT
31501 TGCTATCAAC TGGGGCTATA TAGTGCACTG GAATTTAATG TGTTGTATAT
31551 GTGAAATATT TACCAAATAA CCACATAACC AAGATATGGA GGACCTACTT
31601 TAAGAGGAGA TTCTTGCAAA GCACCTTAAA AGCATACACT CAATAATCAC
31651 AATGGCATGA CTGCATACAG GGAGATAATC AGTTGTTTTA ACTTTTAATT
31701 TAAGCAGTAG CAGAATGACT TTTTGGGAAC TTAGGAATTT GGAAACCTTT
31751 TTATTCTATG TATTGAATAT CAACTATGTA ATTTAGTCTA AGGTTATATG
31801 CTAGAAACAT TTCAAAAACG AAAGCAGCAG CAATGACATC AAAAATGCAT
31851 GTCAAAAGCA AATGGTTTTA AATAGAAATA CATCATTTTA ACAATCTTGA
31901 AGTTTAAAAG ATCCTATAAA AATCACAAAC CCAGAAGGAC AAACAAGAAA
31951 AGATTGATAC ATTTAACTAC ATAAAATTTA AAACTACATT ACTGAAAAAA
32001 AATCTGAGAC AGGGTCTCTG TCACCCAGGC TGGGGTGCAG TGGTGCGATC
32051 ACAGCTTACT GCAGCCTTGA CTTCCCAGGC TTAAGGGCTC ATGTAATCCT
32101 CCCATCTTAG CCTCCCAAGT AGATGGGACC ACAGGCATGC ATCACCACAC
32151 TCGACTAATG TTTAATTTTT TTGTTGTTGA GACAGTCTCC CTATGTTGCT
32201 CAGGCTGGTC TCTAACTCCT GGGCTCAAGT GATTCTCCTG CCTCAGCCTC
32251 TCAAAGTGCT AGAATTACAG GTATGAACCA CTGAGCCTGG CTTTAAAAGT
32301 TTTTAAAATC AAAAGCCAAA TGGACAACCT AGAAAAAATA CTCCTGAGAT
32351 ATGTTAAACA GAGTTAATTT ACTTGCCATT TTTAAGTGTG CTTACATATC
32401 AAAAAATCTA ATAACTCATT AAAGATATGT AAAATATATA CAAAGGCAGT
32451 TTGCTGAAAA AATACACATA TAAATATATG CAGCTTCACT CAGCATTCAA
32501 GAAATAAAGT AAATCAATAA TTCAATCTTT TTCACTTGTC AGATGAAGAA
32551 CAGTTAATGT AGTAGTGTTG GCAAGGTGGT GGACAAAAAG TTATTTTTAT
32601 ATGTTTTTGA TATCAAGAAG ATTTGATGCA ACATCTTTGA AGAGCCAGTT
32651 AATAATATCT GTAAAATTAG AAAATTAACA TATTCTTTGC CCAGCATTTC
32701 TACTTTTATC AACTTTGCTT GTAAACAGAC ACAGAAGCCC ATCAAGAATG
32751 CTCAAGGTAG TTTTGGTAAT CATAGATAAT TTTTTTTTTT TTTTGACGGT
32801 GTCTTGCTCT GTCACCCAGG CTGGAGTGCA ATGGCACAAT CTTGGCTCAC
32851 TGCAATGTCC GCCTCCTGGG TTCAAGGGTG TTGCAGGAAG TCAGGGACCC
32901 CAAACGGAGG GACTGGCTAA AACCATGGCA GAAGAACATG GACTGTGAAG
32951 ATTTCATGGA CATTTATTAG ATCCCCCAAA TTAATACTTT TATAATTTCT
33001 TATGCCTGTC TTTACTGCAA TCTCTGANNN NNNNNNNNNN NNNNNNNNNN
33051 NNNNNNNNNN NNNNNNNNNN NNNNNNNNNN NNNNNNNNNN NNNNNNNNNN
33101 NNNNNNNNNN NNNNNNNNNN NNNNNNNNNN NNNNNNNNNN NNNNNNNNNN
33151 NNNNNNNNNN NNNNNNNNNN NNNNNNNNNN NNNNNNNNNN NNNNNNNNNN
33201 NNNNNNNNNN NNNNNNNNNN NNNNNNNNNN NNNNNNNNNN NNNNNNNNNN
33251 NNNNNNNNNN NNNNNNNNNN NNNNNNNNNN NNNNNNNNNN NNNNNNNNNN
33301 NNNNNNNNNN NNNNNNNNNN NNNNNNNNNN NNNNNNNNNN NNNNNNNNNN
33351 NNNNNNNNNN NNNNNNNNNN NNNNNNNNNN NNNNNNNNNN NNNNNNNNNN
33401 NNNNNNNNNN NNNNNNNNNN NNNNNNNNNN NNNNNNNNNN NNNNNNNNNN
33451 NNNNNNNNNN NNNNNNNNNN NNNNNNNNNN NNNNNNNNNN NNNNNNNNNN
33501 NNNNNNNNNN NNNNNNNNNN NNNNNNNNNN NNNNNNNNNN NNNNNNNNNN
33551 NNNNNNNNNN NNNNNNNNNN NNNNNNNNNN NNNNNNNNNN NNNNNNNNNN
33601 NNNNNNNNNN NNNNNNNNNN NNNNNNNNNN NNNNNNNNNN NNNNNNNNNN
33651 NNNNNNNNNN NNNNNNNNNN NNNNNNNNNN NNNNNNNNNN NNNNNNNNNN
33701 NNNNNNNNNN NNNNNNNNNN NNNNNNNNNN NNNNNNNNNN NNNNNNNNNN
33751 NNNNNNNNNN NNNNNNNNNN NNNNNNNNNN NNNACTCCCT CCCCCTTTTGA
33801 AAATCCCTAA TAAAAACTTG CTGGTTTTAC AGCTCGGGGG CATCACGGAA
33851 CCTACCGACA TGTGATGTCT CCCCCAGATG TCCAGCCTTA AAATTTCTCT
33901 CTTTTGTACT CTGTCCCTTT ATTTTTCAAC GCAGCTGATG CTTAGGGAAA
33951 ATAGAAAAGA ACCTACGTGA CTATCAGGGG CAGGTTCCCC GACACAAGGG
34001 ATTTTCCTCC CTCAGCCTCC TGAGTAGCTG GGATTATAGG CACACACCAC
34051 CACACCCGGC TAATTTTTGT ATTTTTAGTA GAGACTGGGT TTCACCATGT

FIGURE 3K

34101 TGGCCAGGGT GGTCTCAAAC TCCTGACCTC TGGTCATCCA CCCGCCTCAG
34151 CCTCCCAAAG TGCTGGGATT ACAGGCGTTA GCCACTGCAC TCAGCAATCA
34201 CAGATAATTA AACCATCTTT CAAAATCCAT CAATAAGTTA AATATTTTAT
34251 GGTACATTTA CACAATAAAA TACAAATTAG CTACTTAAAA ATAATGAGAT
34301 CTATATGTGA TGGTATGAAT GGACAGAGGC AATGTGTTAT ACAGAAAGGG
34351 TTTAACAATG TATGCTCCCA TTGGAATGAT AGTATGTTGC TATTGCTGTT
34401 AGGAAGGAGT ACATATATGC AGAGAGAATC TCTTAAAGGG TACACAAGGA
34451 TTTGTTAATA ATGGTTGCTT CATGGAACTG GAACTGCAAA CTTGGAAGAG
34501 GAAGATAGCT TAGTTTTCAC TGAATAATTG TTGTACTTAA AAAAATTTGT
34551 AATTTTTAGT TTTCAGTGGA CCAGATATTT TGCTTCTGGT TTATAATGTC
34601 TCATCTTCAA AGTCAGCTGA GTTAGGTTTA ATTAGCTCCA TTTTACAGAC
34651 AGAGACATTG TTATTTGAAA GATTGAGTAA CTAGTCTAAG GTTACACAGC
34701 TGGTGTCCTC GTTGCCTGTT CAGTAGAAAG GTTTACATAA ACAGCAAGGT
34751 GTGCTGTTCT CAATAGACTC ACTTATGTTC ATGATTTGGT ACTTGCTCAA
34801 GCTGGAATCA ATTTTTAGAA AAAATAAAAT CTTTTGCAAA GATTTTTACC
34851 TCAAAAATAG AAAAAAAGGG CATTCCTGCC TTACCTTCTA CAAGGGTCTT
34901 CTCTGAAATT CCAAGCATCA GGGTGTTATA ACAGACTCTA AAAAGGGTTT
34951 CCTTTTTTCT TTCCTTTAAC ATTGCTTATT GCACAGCATA TTGAGACAGA
35001 GAAGATGGTA AGTGAAATAA AACAAAGGAA ATAAAAAGTA TCATCACTGG
35051 GTTTCAGAAT CAGCATGGTT TATGCTAAGG GAAAGACTTG GAAACCTTGA
35101 TTCAACATAT AATTCTAAAA AGAGACAGGA AGAAATCCCA CCTTGTTTCC
35151 TCTGATTCTA CCTTTGGGAT GGGTAGGTAT GTTATACAAT AAGAATAACA
35201 TTGAGATGAC TGCTATAAAA ATAGTGGTTA AGAGCCTGGG TCCAGAATGA
35251 GAAAGGTGGA TATTGAATTT ACCTGAGTGC AACTAGGCAG ACTCAAGTGA
35301 GTTGATTTTA CCCACTCCTC CACTCAAATA CTGGGTATGG CTTTGCAAAA
35351 ACATTCAACC AGTTATCCAC ATAGTTGGTC TTAACTTTCC ATGTGACTAT
35401 AATGAATATA AACTTGCTAA TGAGCAGAGT GTGATTTTAG TGTTTAAACT
35451 ATTTTTTCCC GAATAATAGT TCCTAGATGC AGTTAATGAG CCTTATTGGG
35501 TACCCACACA AAGGAGATAG AATTGTCTGT TGGACTTTTT GAAAAACTTT
35551 CTTGGTTTTA AAAAAGGTAC ATTTCTAAAG GATTTTTATG TGTAGTTTTG
35601 ACTAAACAAG TCTTTGCCTT ACTTTCTGTT TTTAAAATCT AACCTCAACA
35651 TTAATATGTC ACTATACTGG TTATAACCAT AACAAATTAT TTCATCTCTC
35701 TGAGCCTGAG TACCCTCAAC TGTATACACT ATAAGGATGT GAAGATAGAA
35751 AGTGACATAA AAATGAAACA TGTACTGACC ACCCTCATAA ACAGATCCCT
35801 CATACATATA GAATGTCTGT GCCTGGTTGA TTAGTGAAGG AATGTGTACT
35851 CACCCAAAAG AAAAACTCTG AAATAAGTAC TTTTAGATAT TTACTTTTTC
35901 AATATTCCAA GTAATTATCA CAACATTAAG GTGCATTCAG CTTTGTGTGT
35951 TAACGTGGTA TACCTCCAGG CAACTTTTAG GATACTGTAC AGATACAATG
36001 GCTGTGAAGG CTGGGATGAA AAGACCTGTG CGAAGCAGGA CTGAGGCACT
36051 TAAGGAAGGC CTCAGAGTTA CATCTCCTTT GCCTGTTTTC TTGCAGGCCA
36101 CATACCCTAG CCCAGCCCTG TCAGCATGAG TGAGAACCAG GCTCTGCCTT
36151 TGCCCACACT AAACCACTAC CTTCAAGGCC CCACAAAGAC CCAGTGTCTC
36201 CAGACGGTCT TTCTGTCTTC TTAACACTCA GAGCTCCATG AACCAGAATG
36251 AAAGTTTTGG AACATGATCC AAGTAAAAGA CTCAAGAAGT AAACACCACT
36301 AAGGTTAACT TTGCTTTAGA GGTTAGAGAA AACACTGCAA GGACACCACA
36351 CCAGAGACTA TGAAAACCCC AAATGTATTG AAATGATGCT GATTCCATTT
36401 ACCTCCATAT TGCCTGATAA TACCCAGGTG CTACCATGGC AGCTTAAGGT
36451 GGTATTTGCT GGGAGCTATG ATACTCTTTA AGAAGTAATA GCACTACTAG
36501 TAAAAGCAGT TAGTTCCAGG CAATATTCTA TGCACATGAC CCATTTCATC
36551 TTCTTATAAA CCTCATGAAG AATATATTAT TTTCATCCTC ATTTTATAGA
36601 TGCAGAAAGG GAAGCATAGA CGTAAATTTC CAAGATTACA CAGCTATTTA
36651 TTGTTGGAAC TGAGATTTGA ATTCAGGTTG TCTGTCTTCA GGGACTGTGC
36701 TCTTAATCTC AGTGGTCATC AAACTTTTCT GTAAAGAGCC ATCCAGTAAA
36751 TATTGTGGGT TTATATACAT TCTCTATTGC ATATCCATTG GTTTTCAAAA
36801 ATAATCCTAT ACAAATTCAA AAACCATTCT TAGCTCATAG ACTACACAAA
36851 AACAGATTGC AAGTCCAGTT TGGCATTTAC TGTTCCTATT GATCAAGGGT
36901 TTAAGAACAT AGTGAGTACA CTATTCCACA TTCCCCTTAG GCAAATCCTG
36951 TATGTTTATA GTACTGTTAG ATTTCTGTTG ACAAAATAAT CCACAATTCT
37001 GACTTCATCT CTCTCTCTCT CTCTCTTTCT GATTTTGTTT GAATTTATGA
37051 GGTTTAGTTG CATTTTCAAG TTAGTCTTCC TGCTAACGAG TGATTCTTTT
37101 GTTGAACATT TAAAAAGGGA CTGTCAGGAT TGAATAAGAG AACCTCTTCC
37151 AGTCACTTTT TTTTTTGAGA AAGGATCTCA CCTGTTGCCC AGGCTGGTGT

FIGURE 3L

37201 GCAGTGGTGC AATCACAGAT AACTGCAGCC TCAACCTCTT AGGTTCAAGT
37251 TCCCCCTGCC TCAATTTCTG AGTAGCTGGG ACTACAGATG TGCACCACCA
37301 TGCCTAGCAA ATTTTTAATT TTTTGTAGAG ATGGGGCCTC ACTACATTAC
37351 CCAAGCTAGT CTTGAACTCC TGGGCTCAAG CAATGCTCCT GCCTCGGCCT
37401 CCCAAAGTGC TGGGATTACA GGTGTGAGTG ACTGCATCCA GCCTCTTATA
37451 GTCACTTTTA ATCTATCATT GGCTTTCCCA TTAGATTGTA CTGTTATACA
37501 AGGAAGTGAC TTCAGACAGT ATGGCACTAG ACTAGAGGCT GTGTTTTTCT
37551 TTAATAAAGG CATAAATGAG ATGAATTGCT CTAAGGCTTT AGGCTTGTCC
37601 CTTTTCTGAG AAGTGACCTT TGGGAGGTCA CATTTAGTTA AAGCAGTTTT
37651 GCTAGTATAA ATTTACCAGG ATCCTGACAT GTAATCCTGT ATCATTTTCA
37701 GTAAGGTTAA AATGGTATAT GAAAGGAGGT GGTTCACGAA ATGGATTAAT
37751 ATCAACATGG AACTTCATGC TTTCTAGGTA CCTGCTGCAT CCTTGGAGAT
37801 TCAAAATGTC ATCATGGCAT TCTAGGCTAG ACTGGCAGTG GAGAAATCAC
37851 TGTGAGTTAT TGGATTTGCT CAAGATAAAA TCTTGAATTT GCAAATAAAT
37901 CCTGGTCAGC TTTTTTTAAC ACTCTTGTGG TAAATAATAC ACAACTCAGA
37951 TTCATGTAAT GGGTGTAAGA AAATCATTGC TTTGGTTATT TCAGTATGAA
38001 ACTCAAGAGA AAACTTACTG AAGTGTTTTT AAAATTATTC TGACCACAAC
38051 CCAAGGTAAA ACATAAGCCA AAAAACATAT CATGACATAG TAAATGAAGC
38101 CAGGATTGTA TATATATGTC TACTCAAGTA TATGAAATGG AAACAACAGT
38151 TTCAGAGGCA GTACTATGCT TACTACATTT GAGGCATTTC TGGTATTTTC
38201 TATTCTATTT AATTAAATTT TTAGTACTTC TTATTTTAGC TACATTTATT
38251 TCATAACTCA TTAATGGGTT TTGACTCACA GCTCAAAAAC ACTGCCTTAG
38301 AGAATCCAAA TGTTCACACT ATCCATATTT ATAAGAAGTA ATTGTTCTGG
38351 GGTTCTTGTG TATTCTTATA GCTTAGTTTG ATTTATTTGC TAAGACCTGG
38401 CTAAGTGAGA ACTGCAAAGA GTTATGCCTT CAACTACCTA AGCCAGGAAT
38451 TTTCTGAGGT GGCAGGGGAA CCAGGGTGAG CAGAAGGACA TATCATCCCC
38501 ACCCTCATTA AGCTTATGCT ATAGTGGATG AAATAAACTC AGAAGTCAAG
38551 GAGTTTCAGA AGAGAAGTCA TTCCCTTGAG TAACTATGTT AAGTACGTAA
38601 ACAGCTTTAG TAGTGCTTTC TTAGTACAAG GTGTTTTCTT CTGATCTAGG
38651 AGAGTCAGTC CAATTTTTTT CTTTTGAGAA AATGGAGGCT CAAAGAGTCT
38701 GTCATTTATC TCCAGTCTCT TCATTATTTT GAGTCCAAGT ACAGGATTAT
38751 TTGTAATATA CATGCTGCCT CACATGACTA AGTGGGTTTT GTGATAGAAA
38801 GGGAATTTGG AGTTGAGAAG AGAAAGTGAT GATTAAGTCA CATCATTAAA
38851 ATGTTTGACT CTCAGATATC TTGGAAAGAC TTTGAAGGCA CTCTAGCCAA
38901 ACTTTTTCCT TCAGAAGGAG CTTATCTAAT TATTCTAGAT AATAGAGAAA
38951 AACTAGGTCT TTTAAAGAGA CAAATTATAT ACCATTTAGT GTTTCACAAT
39001 ATTTTCTGAA TAAACTTAAA ATCCCTTATT TGGAATTTAA CTCATCTAAA
39051 TCCTTATTTC AAAAACCAGG AAACAGAGTC AAACATTTTC TCAGTTATCA
39101 AGGCAGTAAA CCAAAGATTG TCACCTGCAC AGGAGAATCT ATGATTTGTT
39151 CTTCTCATCA TTATACATTT CACGAGCATT GACTCAAAAA ACCATGCTAC
39201 CTATAAACTA ATCAACAATT GCTTCTTCTA GGGACTGAAA TTTTAAAATT
39251 TCAGACGTGG AGGATCGACT CTACTTCAAA GCAAAATTCA GTGGACTTCT
39301 GCACACATAT CCATTCTAAT CTGTTACAAG TCTGCACTTT GGAGATTAGT
39351 TCATGCTACA CACTTAGAGG TGTAATATTT TCCTACTTGG GAAAATTGAA
39401 ATTACTTAGA TACAAAAGAG TGGTTGTAGT AAGAAAATAG GCAAGGAGAA
39451 CATTTTAAAG TGCTGATCCT CGGTAAAGCC ATACATAGGA TGCACCTGGG
39501 AGCAGATCTT TCTGAAGTCA TTCTGTGCTC AGAGATGTTT CTCCTTACCT
39551 TGCTGCCTAT GTCAAATTCT CTGTGATATG TTCTTAGAGC CCCATGACCT
39601 CTCTTCTTAA CTTGCAGTGG GAGCTTGAAT TTTCCATTTA TTTTTGTGAC
39651 CATTTAGTCT ATAAGAGTCT CCGTCTTTAC AGGGCCCTCA CCTGACTACA
39701 GACTCCATAA AGGCAGAGAT TCTATTTTTA CTCTATTATT ACTGTATTCC
39751 CAGCACTAAG CACTAGGATT AATACATAGT AAGTGTTCAA CAGATGTTTA
39801 CTGGATGATT AGATTGGCAT TTTAAGGTAG TCTGAGATCA CGTTTTAGAC
39851 AAGATACTTC AGTTTAGTCC AATCTTTATT ATTTATTAGC TACTAAAGAG
39901 AAATTGATAA TTACTCATGA TATTCTTCTT TTTTGTTTTA CAGTCAACTT
39951 TGACCACTTT GAAATTTTGC GAGCCATTGG GAAAGGCAGT TTTGGGAAGG
40001 TGAGAACAAA TTGAAATGAT TAACCACCAG CAGGGTTATG TAGCCCAGGG
40051 AACAGAGGGT CCAGAAATGT TCACATTATT GAGTTGCTGG GACCACAAGG
40101 AAAGATAATT AAGTGAAAAT GTTTTTGTAA TGGATTTTTA TAAAATTGTC
40151 ACCACAGTTT AAGAAAAGCG TGTGACAGGC AGCTACATAA TGAACATATA
40201 CTGTTGTCAG AATAATCTCA TTAAACTCAA ATCTGTTTAC TCTCAGTAAA
40251 CTTTAAGGCT TTTCTCTCTA CCCTAAAGGA GATGAAGATT TCAGAATCAT

FIGURE 3M

40301 TTTCAGATTC TACCAGCTGT ATGCCCAGTA ATAGTTATCT TGTTTATGGA
40351 AGAGTTACTT ATTTTCATGT GGGAAAGAAG TCATCCGATT TCTATTTGTT
40401 TCCTCATTTG TCTAATGTTT TTATCTTAAG AAAAATACAT ATTCAGTTTA
40451 ATTTTTTTTG CAAGAAACTT CTGTATTCAA ACCCTGATTA CTAGTTTCTC
40501 AATGGAGACG TACTTTAAGA GAATAATATT TCATATAAAA CTTGCATTTT
40551 AAAATCATTT TCTGTTTACT TTTTCAGGCA TTATACAGAC CTCTAAAGAA
40601 ATTTCAAAAA CATGGACATC ATATTTAGTG TTTTTCCAGT CCTTAAAGTC
40651 CTTTTTGGTT ATATCATGTA TGGGTTGTAA ACAGAAATTC TTTGCACAGT
40701 ATTATTCAGC TTGACAGTTC AGTCATGTCT ATTTCAGTCA CTCAAAGCAG
40751 GATTAAGGAT GTTACTTGTT ATTGGAATAT TCCTGACATG GAGGCAGCTA
40801 TTTTCACCAA AATGCTGTCT TAAAAGCCCA AAAAGCAATA CCAGGCAAAA
40851 TTGTTTGAGA AAAAAGAGAT CCAAGAATTG AACTGGTGCA TAGAAAAGAA
40901 AATGAAATTT TTAATCTAAA ATCAGAGCTA AGTGGGAGCT TTTAACATCA
40951 TATAATTTGC AAATGTTAAG GATCCAAGCC ACAGCAAAGA ACATGTCTTG
41001 TTCTGTCTCT CATCACCATG ATCCATTATC TCCCTAATCA CTCTCTCACT
41051 CGGGTTTTCA CCATTAGGTC TGCATTGTAC AGAAGAATGA TACCAAGAAG
41101 ATGTACGCAA TGAAGTACAT GAATAAACAA AAGTGCGTGG AGCGCAATGA
41151 AGTGAGAAAT GTCTTCAAGG AACTCCAGAT CATGCAGGGT CTGGAGCACC
41201 CTTTCCTGGT TAATTTGTGG TGAGTAATTT TACTGGACCT CTGAATAGAG
41251 ACACTCCTGT TATCGGTGGG CTAGGGGAGG TCCCCAAATG CCTCTGGGAC
41301 CTCAGCCCTG GCTGGTATCC AGGCTCTTGA CACAATTGCA AGAAAGAGTT
41351 CAAGGATGAG TTGGAAAACA GTGAAAGTAC AGAGATTTAT TGCAAAGTGG
41401 AAAAGTACAC ACTCAAGAGA GGGGAGCATG GGTGAACTCC AGCGAATGTC
41451 ATGTAAGGGG GGGTTTGAGG CTGCTGCCAT AATGGGTTTC TTTAACCAAG
41501 GGGTGAAACA TTCATGATGA TTCCTGAAAA AAGATGGAGA TTTCTTGGAA
41551 CTGTGGTGCC AGCTATTTTT ACACCAAATA TGAATGTTCC TGGAACTGTC
41601 ATGGTGCTGG TGGGTGTATG ATTTAGTATG TTAATGAGTG TATGATGAGG
41651 TCCTAGGTGA AACCTAGGTC AAATCCAGCA CAATGGAGAG GACCCACAGA
41701 CTCTCTGAAG GAAACGACTG CTCCTGCAGG ACCCAGGCAA CTCCCCCAAA
41751 ACTGTGAGTA CCCCAACTGT GGAGGTGGGA AAGAGAGACC CTCCTCTCCC
41801 AAACACACAC CCCCACTGGA GAAGCTGAAG GTCTGTTTGC TGGAGAAGTT
41851 TCTGACTTTA CCTGGAGCTG AGTGGACTTG AAGAGCCCAG TGAAATACAC
41901 GGGGAGAAGA AGCAGCAGAA AGGCCCTGGG AGCTTGCTGG GTCCACAAGC
41951 AGGCCATTCC TGCCTGGCAC CACAGGGATC CAATGGGAGA GGAGCGGGGG
42001 TAAAATTCCA TAGGGAGAAG CAAATCTCTA GCTGAACTTG GTGACAATTT
42051 GAACAGGGTG AGAAAGCGCC TGGCCAGAAC TCAGGAGAGG GCACAAATCC
42101 AGTGTGCAGA CTCCGGGGGC AGGGGATAAA CCAAGCTCTT TTATTTCCCA
42151 GCTGGGAGCG GGGAGCCTGG GGCAGGTTTT CAAGCAGGTA TTGCTTCTCT
42201 ACTTAGAAAC AACCTGGGAG CTGTGTTGGC GGGGGAGGGG GGTTGGGGAT
42251 GGGGGAGGGG GGTGGTGGAA AGCACGGTGG GAGTGAGACC GGCCCTTCGG
42301 TTTTCATGGG AGCTGGGTGA GGCCTGTGAC TGCCAGCTTT TCCCCACTTC
42351 CTGACAATCT GCATGTTTCT GCAGAGACAG CCATAATCCT CCTAGGTACA
42401 CAACTCCAGT GACCTGGGAA TCCCACCCCC ATTCCCCACA GCAGCAGCAG
42451 CAGCAAGGCC CACCCAAAGG AGTCTGAGCT CAGAGACACC TAGCCCTGCC
42501 CCCACCTGAT GGTCCTTCCT ACTCACTCTG GTATCGGAAA ACAAAGGGCA
42551 TATAATCTTG GGAGTTCTAG GGCCCTGCCC ACTGCCAGTT TCTCCCCATA
42601 ATACCAAAGC TGATGCTCTC TGGAAAAGCA CCACCTCCTG GCAGGAGGAC
42651 AACAGCACAA AAATAGAATA TTAACCAAAG CTAAGAACCC TTACAGAGTC
42701 CATTGTACTC CCTGCCACCT CCACCAGAAT AGGCACTGGT ATCCACAGCT
42751 GAGAGACTCA TAGATGGTTC ACATCACAGG ACTCTGTGCA GACGACTTCC
42801 AGTACCAGCC TGGAGCTGGG TAGGCTAGCT GGGTGGCTAG ACCCAGAATA
42851 GAGATAACAA TCACTGCAGT TCAGCTCACA AGAAACCATA TCCATAGGAA
42901 AGGAGGAGAG TACTACATCA AAGGAACACC CAGTGGGACG AAAGAGTCTG
42951 AACAAGACTT TCCCTCTGAA AGAGCCTACC CAAGTGAGAA GGAACCAGTA
43001 ATATGACAAA ACAAGGCTCT TGATGCCCCC CAAAAATCAC ACTAGTTCAC
43051 CAGCAATGGA TCCAAACCAA GAAGAAATCC CTGATTTACC TGAAAAAGAA
43101 TTCAGGAGGT TAGCTATTAA GCTAATCAGG GAGGAACCAG AGAAAGGTGA
43151 AGCTCAGTGC AAGGGAATCC AAAATATGAT ACAAGAAGTG AAGGGAGAAA
43201 TATTCAAGCA AATAGATAGC TTAAAGAAAA AACAATACAA AATTCAGGAA
43251 ACTTTAGACA CACTTTAAAA ATTGCAAAAT GCTCTAGAAA GTGTCAGCAA
43301 TAGAATTGAA CAAGTAGAAG AAAGAAATTC AGAGCTCGAA GACAAAGTCT
43351 TCAAATTAAC CCAATCAAAC AAAGACAAAG CAAAAAGAAT AAGAAAATAT

FIGURE 3N

```
43401 AAACAAAACT CCCAAGAAGT CTGATATTAT GTTAAATGAC CAAACCTAAG
43451 AATAATGGGT GTCCCTGAGG AAGAAGAGAA TTTTAAAAGC TTGGAAAACA
43501 TATCTGAGGG AATAATTGAG GAAAACTTCC CCGGCCTTGC TAGAAATCTA
43551 GACATCCAAA TACAAGAAGC ACAAAAAACA CCTGGGTAAT TCATCGCAAA
43601 AAGGTATTTG CTTAGGCACA CTGTCATCAG ATTATCCAAA GTTAAGATGA
43651 AGGAAAGAAT CTTAAGAGAT ATGAGACAGA AGCACCAGGA AACCTACAAA
43701 GGAAAACCTA TTAGATTAAC AGCAGATTTC TCAGCAGAAA CCCTACAAGC
43751 TAGAAGGGAT TGGAGCCCTA TCTCTGGCCT CCTCAAAACA ATTATTAGCC
43801 AAGAATTTTG TATCCAGTGA AACTAAGCAT CATATATGAA GGAAAGATAC
43851 AGTCATTTTC AGACAAACAA ATGCTGAGAG AAATTGCCAT TACCAAGTCA
43901 CCACTACAAG AACCGCTAAA AGGAGCTCTA AATCTTAAAA CAAATCCTGG
43951 AAACACATCA AAATGGAACC TCTTTAAAGC ATAAATCACA GAGGATCTAC
44001 AAAATAAAAA TACAAGTTAA AAAGCAAAAA CAAAACCAAA AAAATCTGCA
44051 GGACCCAGGA GACCACCCCC AAAAAAATGT GAGTGCTCCA ACTGTGGAAG
44101 TAGGAAAGGA AGAGCATCCT TTCCTGAACA CACACCCCCA CTGGAGAAGC
44151 TGAAGGTCTG TTTGTGGGAA GAACAGCTTT AGCTCTTTTT TGGTTTTTTG
44201 GAAAAAAACC CAAAGTACAC AGGCAACAAA GAGCATGATG AATGCCAACG
44251 GTACCCTCAC ATTTCAATAC TAACATTGGA ATGTAAATGG CCTAAATGCT
44301 CCACTTAAAA GATACAGAAT CACAGAATGG ATAAGAACTC ACCAACCTAC
44351 TATGTGCTGC CTTCAGGAGA CTCACCTAGT ACATAAGTAC TCACATAAAC
44401 ATAAAGTAAA GGTGTGGGGA AAGGAATTTC ATGCAAATGG ACACCAAAAG
44451 CGAGGAGGGG TAGCTATTCT TATATCAGAC AAAACAAACT TTAAAGTAAC
44501 AGCAGTTAAA AGAGAGACAA AGAGGGACAT TATATAATGG TAAAAGGCCT
44551 TGTTCAACAG GAAAATGTCA CAATCCTAAA CATATAAGCA CCTAACACTG
44601 GAGCTCCCAA ATTTATAAAA CAATTACTAA TTGACCTAAG AAATGAGACA
44651 GACAGCAACA CAATAATAGT GAAGGATTTT AATACTCCAC TGACAGCACT
44701 AGACAGGTCA TCAAGAGAGA AAGTCAACAA AGAAACAATG GATTTAAACT
44751 ATACCTTGAA ACAAATGGAT TTAACAGATA TATACAGAAC ATTTCATCCA
44801 ACAACTGCAG AATACACATT CTATTCAACA GAGCATGGAA GTTTCTCCAA
44851 GATAGACCAT ATGATAGGCC ATATAATGAG CCTCAATAAA TTTAAGAATA
44901 TTCATATTAT ATCAACATTC TCTCAGACCA CAGTGGAATA AAACTGGAAA
44951 TGAACTCCAA AAGGAAACTT CAAAACCATG CAAATACATG GAAATTAAAT
45001 AACCTGCTCC TGAATGGCAT TGGGTCAAAA ACAAAATCAA GATGAAAATT
45051 TAAAAATTCT TCAAACTGAA TGACAATAAT GACACAACCT ATCAAAACCT
45101 CTAGGATACA GCAAAGGCGG TGCTAAAAGC AAAGTTGATA GCCCTAAACG
45151 CCCACATTGA AAAGACTGAA AGAGCACAAA CTGACACTCT AAGGTCACAC
45201 CTGAAGGGAC TAGAGAAACA AGAATAAACC AAACCCAAAC CCGGCAGAAG
45251 AAAGGAAATA ACCAAGATCA AAGCAGAACT AAATGAAATT GAAACAAAAA
45301 AAAAAAAAGA AAGATAAATA AAACAAAAAG ATGGTTCTTT GAAAAGATAA
45351 ACAAAATTGG TAGACTATTG GCAAGATTAA CCAAGAAAAC AAGGGAGAAA
45401 ATCTAAATAA CCTCACAAAG AAATGAAACA AGAGATATTA CAACTGACAC
45451 CACTGAAATA CAAAAGATCA TTCAAGGCTA CTATGAACAC CTTTATGCAC
45501 ATAAACTAGA AAACCTAGAA GATATGGATA AATTCCTGGA AAAATATAAC
45551 TCTCCTAGCT TAAATCAGGA AGAATTAAAT ACCCTGAACA GATCAATAGC
45601 AAGCAGCGAG ATTGAAACGG TAATTTAAAA ATTACCAAGA AAAATGCCCA
45651 GGACCAGATG GATTCACAGC AGAATTATAT CAGACATTCA AAGAAGAATT
45701 GGTACCAATT CTTTTGACAC TAAGGAAACC TCCCCTAATT CATCCTATGA
45751 AGCCAGCATC ACCCTAATAC CAAAACCATG AAAGAACATA ACCTAAAAAG
45801 AAAACTGCAG ACCAATATCA TTGATGAACA CAGATGCTGA AATCCTTAAC
45851 AAAATACTAG CTAACTGAAT CCAACAGCAT ATCAAAAAGA TAATCCACCA
45901 TGATCAAGTG GGTTTCATAT CAGGGATGCA GGAATGGCTT AACATACACA
45951 AGTCAATAAA TGTGACACAC CACATAAACA GAATTTTTTA AAAAATCACA
46001 TGATCATCTC AGTAGGTGCA GAAAAAGCAT TCAACAAAAT CCAGCATCCT
46051 TTTATGATTA AAACCCTCAG CAAAATCAGC ATACAAGGGA CATAGGCCTT
46101 AATGTAATAA AAGCCATCTA TGACAAACCC ACAGCCAACA TAAAACTGAA
46151 CACATTCCCT CTGAGAACCA GAATGAGACA AGTATGCCCA CTCTCACTGC
46201 TCCTCTTCAA TGTAGTACTG GAAGTCCTAG CCAGAGCAAT AAGACAAGAG
46251 AAAGAAATAA AGGTCATCTA AATCAGTAAA GAGGAAGTCA AACTGTCACT
46301 GCTTATTGGC GATATGATCG TTTAACTTGA AAACCCTAAG GACTCTTCCA
46351 GAAAGCTCCT AGAACTGATA AAAGAATTCA GCAAAGTTTC CGGATACAAG
46401 ATTAATGTAC ACAAATCAGT AGCTCTCCTA TACACCAACA GCAACCAAGT
46451 AGAGAACCAA ATCAAGAACT CAATCCCTTT TACAATAGCT GCAAAAAAAA
```

FIGURE 3O

46501 CAAAACAAAA CAAGACAAAA CAAAAAAACA AAAAAAAACA AATACTTAGG
46551 AATATACTTA ACCAAGGAGT AGAAAGACCT CTACAAGGGA AAATTACAAA
46601 ACACTGCTGG AAGGAATCAT AGATGACACA AACAAATGGA AACATGTCCC
46651 ATGCTCATGG ATGAGTAAAA TCAGTATTGT GAAAAATAAC CATACTGCCA
46701 AAAGCAATCT ATAAATTCAA TGCAATTTCC ATCAAAATAC CACCATCATT
46751 CTTCACAGAA TTAGAAAAAA CAATTCTAAA ATTCATATGG AACCAAAAAA
46801 GAACCTGCAT AGCCAAAGCA AGACTAAGCA AAAAGATCAA ATCTGGAGGC
46851 ATCACACTAC CTGATTTCAA ACTATACCAT AAGCCCACAG TCACCAAAAC
46901 AGCATGGTAC TGGTACAAAA ATAGGCACAT AGACCAATGG AACAGAATAG
46951 AGAACACAGA AATAAACTCA AATACTTACA GCCAACTGAT CTTTGATAAA
47001 GCAAATGAAA ACATAAAGTG GGAAAAGGAC ACCCTTTTCA ACAAATGGTG
47051 CTGGGATAAT TGAATAGCCA CAAGTAGGAG AATGAAACTG GATCGTCATC
47101 TCTCACCTTA TACAAAAATC AACTGAAGAT GGATTAAGGA CTTAAACCTA
47151 AGACCTGAAA CTATAAAAAT TCTAGAAGAT AACATTGGAA AAACCCTTCT
47201 AGACATTGGC TTAAGCAAGG GTTTCATGAC CAAGAACCCA AAAGCAAATG
47251 CAATAAAAAC AAAGATAAAT TGCTGGTACC TAATTAAACT AAAGAGCTTT
47301 TGCATGGCAA ACGGAAGTCA GCAAACAGCC CACAGAGTGG AAGAAAATCT
47351 TCACAATCTA TACATCTGAC AAAGGATGAA TATCCAGAAT CCTACAATGA
47401 ACTCAAGTAA ATCAGTAAGG AAAAAACAAT CCTATCAAAA AGTGGGCTAA
47451 GGACATGAAT AGACAGTTCT CAAAAGAAGA TATACAAATG GCCAGCAAAC
47501 ATATGAAAAA ATGCTCAACA TCACTAATGA TCAGGGAAAT GCAAATCAAA
47551 ACCATAATGT GATTCCACCT TACTCCTGCA AGAATGGTTA TAATAAAAAA
47601 AAAATCAAAA AACAGCAGAT GTTGGCATGG ATGCAGTGAA CAGGGAACAC
47651 TTTCTACACT GCTGGTGGGA ATGTAAACTA GTACAGCCAC TATTGAAAAC
47701 AGTGTGGAAA TTACTTAAAG AACTAAAAGT AGAACTACCA TTTGATCCAG
47751 CAATCCCTCT ACTGGGTATC TACTCAGAGG AAAATAAGTC ATTATTCAAA
47801 AAAGATACTT ACACATGCAT GTTTACAGAG CACAGAGTTG CAACCCAAAT
47851 GCCCATCAAT CAATGAGTGG ATAAAGAAAC TGTGGTATAT GTATACATGA
47901 TGGAATACTA TGCAGCCATA AAAAGGAATG AACTAACAGC ATTTGCAGTG
47951 ACCTGGATGA GATTGGAGAC TATTATTCTA AGTGACGTAA TTCAGGAATT
48001 GAAAACCAAA CATCATATGT TCTCACTGAT ATGTGGAAGC TAAGCTATGA
48051 GGATGCAAAG CAATGAGAAT GATACAATGG ACTTTGGAGA CTTAGGGGGA
48101 AGAGTGGGAG GGGGGCGAGG GATACAAGAC TACAAATGTG GTGTAGTGTA
48151 TACTGCTCAG GTGATGGGTG CAACAAAATC TCACAATCAC CACTAAAGAA
48201 CTTACCCATG TAACCAAAAC CACCTTTACC CCAATAACTT ATGGAAAAAT
48251 AATCCAGCAC CACATTAGGT TTAGTCGGAC TTAGCCAGCT TGGCTTACAC
48301 CCTGGTTTTT CAGGTTCTTA TCATTCCCAG TTTATGCAGC TGTTTCAACA
48351 TTTTCCTTTT GCTAGTCATG TGAAACTGCT GTCTGGAATT TTCTTTTCTC
48401 CTGCTACCAC CCTTTATTAT TCCTGTCTCA CTTTCATCTT CATCCCTACT
48451 GTTACATAAA TGCATCTTGA TTTCTAGGCA AGCATTTGTC AAATTCTCAT
48501 TAGGATCTTC CTCAGGGTCT TTTGTTCTCC TTAGTTTCTT TGGCTTTATA
48551 GTGAAAGAAC ATTTTTCTTT TATTGTCACT AACAAATACT TCTTGGTCAG
48601 TTGTCACAGT TCCCCTTGTC CTTGAGGTCA ATATATATAT ATTTTTAAAC
48651 ATTGTAATTA AATATGCTGA CTGGGAAGGA GTTCAGATGT CTTACTAGTT
48701 ATTAGATACT TTCTTTCCCC ATGAACTGCA CGGGAGGAAC TTTGGTTACA
48751 AAGCTTGGCC TCATCAGCTG ACTTGAGGTT GATATTTAGA ATTTATACGA
48801 AGCACTTTCT CCCTTAAAAT AACTGGCAAT AAAACTGTTG CTTTGTAGCG
48851 TATTTCTTAG GCAGCCACAT ATATACCTGT AAGTTAGACA AGGATAGGTG
48901 CTTCCTTTGT CAACAAATAG CTTTTGCAGA GCTGAAGCTA ACTTGTATCA
48951 ATGACTAGAC ATTAAGTGAC TGTGATCTGC GCTCCAAGCT ATTTCCATAA
49001 TCCAAGGCAT AGAAAATGGC AGAGAAGCTT GCAGTATCTG TTACCTCCTG
49051 TTCTTTTCTT GTGTGTCAAG GTCTTTGTGT GTCACCTTCC ATTTTATTTT
49101 ACATTTTAAT GCGTCCATTA TGTTAAGTGG TGTTTCTTAA AGCTAATTCA
49151 GGATGACTGT TATTTAAATA TGCATACCAA GAAGTTCTGA CTTACCAGCA
49201 AAGAAAAAAA AGGGTCTTTA TTCAGAGAAT GCTAATGGAA AAATAATTGA
49251 GGTTTTACTC TGTGTTTAGG GACATCCTTC TGGAGAAATC AGTACATAAA
49301 ACCTGCCTCC ATCCATCTTT AATTATTACA GTTCATTTAA TATACAATTT
49351 GCTCAAAGCC TCTATGCCAC AGTTGAAAAG AAGATGGTTT TATGTGACTT
49401 GGAAATAGGT CTATTACAGT TTATGCACTA CTCGGATATG GTAGAGTCTA
49451 ATTTCAGCTT AAGCTCAGTG TATTTAATCA GTATCTTAGA GTGGCCTATT
49501 CAAAATGCTG CCATGTAAAA AGCTAAAATG GATGCAGCTC TTTCTTCCCT
49551 ACCCTTAGCA ATCATCAAAT TGCCTTTCTT CCCCTCTCTC TGCATCCTGA

FIGURE 3P

```
49601 GAATGACAAG ATACTGTCAC TTCACAACCT CCCTTTGTTC AAAGTCACAT
49651 TTTTCTTCTT AAAAAGTTTA ACCAACTAAT TTTTTTTTTT TTAAGACCAG
49701 GGACCCATGA TAAGGCCTTA GCATTTTACC TTCTCATATT TGTCTTTCAT
49751 CGCTGTGTGG GCAAAGTTGA TTTCATTCTG TTCCTTTTTT TAAGAAAATG
49801 GGTATTGTGA GGCTTTAAGC TGGCCAAAGA TGATAGATTT TGCTGTTTGC
49851 TAATTTGGTG TCATTCCAGA CAACATTCTG TTCTCCATGC ATACTGACCT
49901 GGTGATAACA TGACATATAA CCTATTCTTT CCTTCTCACT TCTCACATTG
49951 AACCTCACAG TGGAACACTA GGCATCATTA ACAATGATAG AAGAAAGAGA
50001 GGAGACTTAC CTCCACCCAG TGATTCTGGT ACTACATTCA AAACTAGAAA
50051 CTAACTGGGA GGGGGAATTC TTAAAGTACA ACAGCAACTC CCTTTGTCTT
50101 CCAAACCATG AGAAAAATCT TCACAAATCT GTATCATTCT TCCTAATAAA
50151 TGCTTTTTGT TTTAGTAAGT ACAATATATT CAATGTAAGT TTATCTTTCC
50201 ACATTTATAA ACCATCTTGC AGTGCTTTTG AAGGTGTGAT TGTGAGTGTA
50251 TTAGTCAGTT CTCACATTGC TATAAAGAAA TACCTGAGAC TGGGTAATTT
50301 TTAAAGAAAA GAAGTTTAAG TGGCTCATGG TTCTGCAGGC TGTGCAGGAA
50351 GCATAGTGGC TTCTGCTTTG GGGAGGACTC AGGAAGCTTC CAATCATTGT
50401 GGAAGGCAAA AAGGGGAGCA GGGCATCTCA CATGGTGGGA GCAGGAGCAA
50451 GAGAGAGGAG GAGAGAGTCA CTACACACTT TTAAATGACC AGCTCTCTTA
50501 AGACCTCTAT CACGAGAACA GCACCAAGAG GATGGTGTGA AACCATTCAT
50551 GAGGATCCAC CCCCATGATC CAATCACCTC CCACCAGGCC CCACCTCCAG
50601 CATTGGGGAT TACAATTCAA CATGAGATTT GGGTGGGGAT AGAGATGCAA
50651 ACCATATCAG TGAGTAATTT ACTTCATCAT TTTTAAGTCA CATGGTTATA
50701 AGATAGGGTT AATGTGTGTA ACTTTACATT TATAAATGAA ATGAATAAAG
50751 TGCTATGGCC AGTACCCAGC ACATAGTAAC AGGTGTCTTA CAAATATTCG
50801 TTCTTTCCTT CCTTACTTCA TGAAGTTATG ACATTCTGAA CTTGCCCATC
50851 TCCTATGGTT CATTGTGGAC ATCCAAAGGA CAAATCTAAA TGGTGCTTGG
50901 CCCCAGGACA TCATGGAAAG CTGTATGTGC AGTGTCAAGG GGGTTATCTT
50951 CAACTCATTC TCTATAAGAG CATATGTTGC TTGTTTTGTT TTGTTTTCTA
51001 TCCTCATTCT GCAANNNNNN NNNNNNNNNN NNNNNNNNNN NNNNNNNNNN
51051 NNNNNNNNNN NNNNTATCTT TACCACCCGA AAGCATTAAA AGCTTAAGAA
51101 GCATTGTATT ATTTATAAAG TAACAGCAAT ACTTTTAAAA TTTCTGCCTT
51151 CTTTGTGTAC TCTATTTTAT GGATATGCTG TGTAGGCCTC TCAATAATAC
51201 TTTCAATAAT CTCATTCATG CTAAAATGCC CCTAGCTTCT GGAGATTTAT
51251 AAAATTCTAG TTTTCAGGCT GAGGGTAAAC AAATTGTTCC TTTTTTAAGT
51301 GAGTTAAGAT TAAAAAGTTT GTGTGTGTGA ATAGGTATAA ATGTATACAT
51351 ACATATGCAT ATATTTATAC ATTTATACCT ATACACACAC AAACATATGT
51401 TTTTCAATAT CATATATATG TATTATATAT ATGAATATCA CATATATATG
51451 TGTGTGTATA TATATATGTG ATATTTGAAA ACTCTTCTGC TCATTGCAGT
51501 CAACTTGAAA AACAGAAAAT TACCTAGAAA AATGAAAATT CTTCAATAAT
51551 TCTTATCACC TTGTAACAAT CACTTCTAAC ATGTTGGTGT ATGCTTTTCA
51601 GTAAAATGTC TGCATTTGAT TTTCTGTTTT TGATCATGCA TTAGCCTCAA
51651 TCATTCCTTC TTTCACCTAT ATGTTTACTG AGCATCGAAA ACAAGTTATA
51701 ATTTGATTGC TAGGTGAAAT ACAAGATGCA CAGTTATATT TGAATTTCAG
51751 ATAAACAACC AATAATTTTT AGTATATGGC CCAAATATCA CGAGATATAT
51801 TTTTACTGAA AATTTTTATT TATCTGAATC TGAAGTTTAA TTATGCATGT
51851 TGTACTTTTA TTGGTTAAAT CTGGCAATCT TAACTGTAGT AGAAACCCAT
51901 GCTATGGGGA TATCTTGGTG AGCAGAAATA GACGGAGCCC TGATATTAAT
51951 CAAATGGCAC ATGAATATAT AAACTGTGAG AAGTATATAA AGAGAGTAAG
52001 TATGAAGAAC TGTGTGTGTG GTGTGTGGGT ATGTATGTGT TGGGGTTTCA
52051 GAGAAAGAAG GTAAGTAGTC TGGGGGCAGG GACGTTAAGG AGGAAAGAAC
52101 ATTTGGAAAT AAAATTCAAC CTGACTTGCC TCCAGGGACC TGGCTACACT
52151 CAGGAACAGT CTTCAAATGT AGGCCATGTT ATCAAGTGAA TGCTGCCAGA
52201 CAGGGCTGGC ATCCAGGAAA AGTAAATAAA ATCTTCTTGT GCGTCTGTCT
52251 CTGAGGGCTC TTCACAAAGC CCTGGCAACC CACAGCCTGA AAACAAATAG
52301 GCCCCAGTCT TTCCCAGCAT AGTTGATTCC CCAGGTGGCT TTTGTTAATT
52351 GAGATTAAAC CTGTAGCTGC ACACAACTCC TCAGGGCCTC TATCTCTTTA
52401 CTCATGTCTT TGTCCCTGTG GATAGAAGGG GTCCACATGT GGTTTCAGGA
52451 AATTAGGACA CCAGATCATC TGTTTTAACT GGAAAGAACT ACCTGTACTG
52501 AGAGTGTGAC AAGGTCCTTT CAGACTCTGA ACATAGCCCA ATAAATGGTA
52551 TCAACCTTAA ATAACGAGAT TCTGAAAATA TGATTAAGTA TCGAGTTTGC
52601 TGGAGCCCAG AGCTTGAGGA TGCCCACCTG GGAGCACAGA TTCACTTTGC
52651 CCAGAATGTA CACTCCAATT AGCAGCAGTT ATAAGTGGGG TTTTAAGAAA
```

FIGURE 3Q

```
52701 AAAAGACAAG GCAGTTCCTA AGTTATTTAC CAAAAATTTA CATTAAAATA
52751 ATGTAAGCTA TTGATGGACT ATGCATTATT CTTTATATCA CAAATTACAG
52801 GAACACAAAG ATAATGGGTG AGGCAGCTAG TCAGGAACAA AATGGCTTTA
52851 AAATACTGTC CTTGAGCATG GGTTTGAGGC TGTGACTGAC ATCCCATACT
52901 CATGTTTCTC TAAACCTAAT AAATTGTGCA TATCTCATAT AGCTCAGACT
52951 GCTCTGAGCT ATTTTTGTTT TCTCATTTCC CCCCTTTTCA TCAAGATTTT
53001 GCAAAGAAAG CATTGTGGAT GAACTTAAGC AGTTTTGGCT CCTTTTATGT
53051 TCAGGAACTT AGTCCTGCAT TGCTAGGAAG TCTTATTCCC AGATGGTCCT
53101 GTCCCACATT TGGGGGAAGG GGAAAGGATG AGTCTTAGTG GGGATTTTAA
53151 CACCATCAGA AGCAAAATTG GGATGGCATC GCAGGGTGCC ACAAATGAGA
53201 CCTCACCCAA GTCACTAATT TATGTAGCTA CTGTTGCTTG TGGGATCATC
53251 TCCAGGCTTC AGAATACCAT GCAGTTAGTT TTCTCGGAAT AAGTAAAACA
53301 ATGAGCTATA CATAGTAGAA ATATAATACA CATAACAATT ACAATTAAAA
53351 AAAAAAAAGA ATTTCTATGC CTGAATGAAA AAAATATCTA TTCCATTGGA
53401 AAGTCAACTA AAAACATCAT GAAGAAAATT AAAATCCAGT CCTTTCTTAG
53451 AGACTTGTTG TAGCAGGAAA TAATTCAAGA TTTAGATCAA ATTGTAGGAA
53501 AATAATAAAA ACTAGAAAAC AATGGTCAGG GCTGAATTTA AAAACAGGTG
53551 TGCTATAATT TTCTTCTGAA CCATAATTTC TCTCTCTTCA GTTCACTATT
53601 TCTACCCAAG ATAAATGTTA TCAGGACCAA CATACTTGTA AAATAAGCTT
53651 TAGTATTATA TTTGGCCTAA TTATTTGCAT TAAGTGCAAC AAAAATAATG
53701 AATGGCCATG TACGCATTTT TAAGTTGGCT TTGCTGGAAC TTTTTCATAA
53751 GGAATCTCAG ATTAGACTTT TAAAAGCCTC TCTAAACTAG ATATTGAAGC
53801 CAATAATTCA CCATCAAACT GCCTGTAGCA TCTACATAAA TTGGGTGAAT
53851 TTCTCCCTTC TTCAGGTTCT GAAATATATT GAGGTTTCTA GGCCTGTCAA
53901 ATGATGACAT TCTTTACTTA CTGCAAGGTC AAAAAACTTG TGAGGGTACC
53951 ATGTAGACAA GGTATCAGGT CAGTTTTCCA AAAGGACTAT TGATTTGGCT
54001 CTATAAAGTC AACTTCAATT CATCAAAGCA GTTTGGTCAT ATCTGAAAGT
54051 ATGTCATTTC ACCCAAAGCC TTGGTAAAAT GACCAGCCTT AGTAAAATGA
54101 CCAGTGTCTC CAACTGTGTA CTGTTACAGA AGAAAACAGG TTCTTACTGA
54151 ACTTACACAA ATAACAATAT TGCCATAAAT AAAGAGTATT CACAAATAGT
54201 TTCCAAATTC TGGAGGAATC AGGTAGAGAG TAAGATGTTT CAATTTTGCT
54251 CATAAAAGTA TACTTTACTT AATTGTTGTA AGCTCTAAAT AGCTCAAAAA
54301 AAATTCTTGA CTTTGGAAAA CAAAACAAAA AGAATCAGCA ATGTTCCAAA
54351 CAAAAAAAGT CATTAAAAAA ATTTCAGTCC TGGCCAGGTG CAGTGGCTGA
54401 TGCCTATAAT CCCAGCATTT TGGGAGGCCA AGGCAGGTGG ATCACCTGAG
54451 GTCGGGAGTT CAAGACCAGC CTGACCAACA TGGAGAAACC CTCTAAAAAT
54501 ACAAAATTAG CCGACGTGGG TGGCACATGC CTGTAATCCC AGCTACTCGG
54551 GAGGCTGAGG CAGAAGAATT GCTTGAACCT GGGAGGTGGA GGTTGCGTTG
54601 AGCTGAGATC ACATCATTGC ACTCCAGCCT GGGCAACAAG AGTGAAACTT
54651 CATCTCAAAA AAAAAAAGAA AAATTTAGTT CTCTATCAGT TCAGTTCCAT
54701 GTAGTTAACT CTTGTTCTGT TTGATATTGG GTTAGCAATC TTCACGAACT
54751 GATGAACTTT TATATTAGAA TTCTGAAAGT TTTTACATAA TCCATTGATA
54801 TGATTTCCAA AACCTTCAGA AACTTGTATT CGAGAGTACT TCTCAGAATC
54851 CTTTTCATGA ATTTCCTTGA AGGATAAGCA AATTTTGGAC TGTAGCTGAT
54901 TATAAACCAC TTTTTATGAA GAATCTAAGT AAAATAATAA TTGTCTGTAG
54951 ATGACAAAAG ACTTAAAGCA GTCTTAGTTA AAGACACAAT TGACCAGGAA
55001 ATTTGGTTAT GCCTGTAGCA TACAACAACT TGACATAACA ATCGTAATTA
55051 TTACTGATCA TATATACCAA AACATATTGG AACTTTTGGA ATCTCATTCA
55101 ATTTTGGAAC AGATATTAAT CATATTAATA CATTTATACA AATATATTCA
55151 AAGAAAGTTA AACATCATTT CTTATTTGAC AATGCTTTCT GTATGATTTA
55201 AACATATCAA ATAAGCCTGA TCTGCCTCTC TGTAACTTCT AGGGGACCTC
55251 ATATCTGAAA AGTTATTTCG AGGTAAAAAA AAAAAAAAAA AAAAAAAGGA
55301 CTAAATTTTA ATTTGAAATA TGATTTTGGA AAGTTTGTCA AATATCAAAG
55351 GTTTAAAAAA CTTACTCAAA ATATTTTTAC AGGTCACTGT AAAATAATAG
55401 TCATTTATTT AGCCAAAGTG ATAATTCCAA GATTTCAAAA GCAAAAACTT
55451 TTACTATTTG GTAGAAAGGA GACTGCGTTC CCAATCAAGA GACCTAATAG
55501 GGACAGCATG AGGCAAACTC TTCCCTCCTT TTTATAAGGA ATCTCAGATT
55551 TTACCTTAAA AAGCCTCTCA AGGCTAGGTA TCTTTGAGAG GTTACCTTTT
55601 TTTTTTTCTG TTTTTCTTTT TGAAGTTTAA TCAAAAGGCA AACAAATCTT
55651 TTACTGTCTC TTATTAATAC TATATAAAAT TCTTATTCAA AGGAGAATGC
55701 CAAATTTATA TTAGTGTGTT GTCAATACTA AAGCTAATTT TAATTAAACA
55751 TTATAAACAA ATCCATACAA TCTCAGTCAG CTTTGACTGC AGAAGATAAG
```

FIGURE 3R

55801 ATTTTCATAA ATCTTTTATA ACCTATTACA ATTTTCTATT AAAGAGAAGA
55851 TCAATGTTTC AAGAAAACCC TGTGGTTCCA AAAGAGGGGC CCAGACTCTG
55901 GCCTTGCACC AGTGAGCTTT TGAGATTAAT GTTCACTTTT TAGAAAAACT
55951 TATAAACAAT TCTCTTCTAA TTTTAGCCAA CTTGATCACA CACAAAATTC
56001 CTTTCACAAG ATTAATCTTC CATAAACCCA CAACTTGCTT AAACCTTCAG
56051 TTTTGTCCTA TACTTCTTTT ATTTTGAGAC GGAGTCTCAC TCTGCCCAGC
56101 CTGGAGTGCA GTGGCATGAT CTCGGCTCGC TGCAACCTCC GCCTCCTGGG
56151 TTCAAGCAAT TCTTCTGCCT CAGCCTCCCG AGTAGCTGAA ACTACAGGCA
56201 TGCACCACCA TGCCGGGCTA ATTTTTGTAT TTTTAGTACA GACGGGGTTT
56251 CACCATATTG GCCAGGCTGG TATACTTCTT TTTTAGATTG GCATTCTATC
56301 TTAGGACAAA ATCTACTTTC CTTTCTCCCT TATCATTTTG ACCACACAAT
56351 GCTCTCTTTC ATGCAAATGA AAAATTACTG TCATTTCAAC TCCCTTTACC
56401 AAAAACACAT CTTAATTTCT TTATATACCT TATGTATAGA ATTGTCTCTC
56451 TTATATCTAG TCATTTTTTT TTTCTTTTTT CTTTTTTTCT TTTTGAGATG
56501 GAGTCTCACT CTGTCGCACA GACTGGAGTG CAATGGTGCG ATCTTGGCTC
56551 ACTGCAACCT CTGCCTCCTG GGTTCAAGCA ATTCTCTTGC TTCAGCCTCC
56601 CAAGTAGCTG GGACTACAGG CATGTGCCAC CACACCTGGC TATTTTTTTG
56651 TATTTTTAGG AGAGACAGGG TTTCACTGTG TTTGCCAGGG TGGTCTCGAT
56701 CTCCTGACCG CATGATCTGC CCGCCTCGGC CTCCCAAAGT GCTGGGATAA
56751 CAGGCATGAG CCACCGCGTC TGGCCATATC TAGTCATTTA AATTACATAC
56801 GATAACTACA ATTTTAACTC TTAGGAACGC TAATTTACAG TGAAATCTGA
56851 GGAAGTAATT TTGAGCTGTT TTATGCCAGT ATTTATAGAT GAAAACCATT
56901 TCATAATTTT TATAAAGTTG TTTCCTCAAT TATTTTGTTT ATTAACAGAT
56951 CTAAATATAT TTAGCTTTTC TACACCATAT AACTCAGACA TTTTATGGTT
57001 ACACAATGCT TAATTTAACA TGACTTTACG ATTTAGTTAC TGAAAAAGAT
57051 TTTTGAAACT GAAAAGTTCA TTTATACACT TCTATCTCAT TTACATTCAT
57101 TTAATTTAGT TTATTCATTC TTAACAATTA TGCTTGAATA GTTCATTAAA
57151 CAAAAGTAGC CACCATCAAG TTATTTCTTT GTTAATCATT TTTATAGCCT
57201 GCAAATGTCA GGCAGTTGCC ACCTAAGCAA GAACCCGAAA GCTAAAACAG
57251 AGATATTTTG CTGATCAGAA GGCACGGTGG CTTTCATTAA ACCAACAGTA
57301 TTAACTGGTC TTATTTACCG AAGATTTACC CAAGTTATGT GAACTAAAAG
57351 GGATTTGAGT TATTTTCTAT TTTTCTGATA AAATATTTAA GTGTTTCCTT
57401 TCTCTTTTGG CCAATTAGAA CTCATTCATA TATTTTTGTA ATAAATTTTA
57451 CATACACATG ACACATATAA ACATGCAGAC ACACACAGGC AGATTTTATA
57501 GCTTTGTAAG TTTCTTCATT TGCCAGTTTT CAATAGTTTC TCTCCCACCT
57551 TTAGACTGTC AAGCCCTAAA CAATTGTTAG CTAGGCAACC TTAAATTTGT
57601 ACTTCTAAAG GGATGACTCT TAGCTGAAAC AAAGTAAAAA AAAATAAAAA
57651 TTACACTTCA AAAACACAGA GCGGAGCTCA AACTAAGGGA GCAGGTGTAT
57701 ATAGGTAAAG GTCCAGTTAA GACAAGATGG CCAAGGAAAG CATCTTAAGT
57751 AAAGGTAGGA CTTGTATAGA TTTAAACCAA TGTTAAATTT CTCATGACTC
57801 AGCTCTCCCT CTCCTCCAGG TGCACAGAGG CAGAAACCCT TACAAATGGA
57851 GATTTCCTTT ATCAATGTAA ATTTCAATAT AGCCAGCTAA ATGCCAGCAA
57901 GGTATATTTT GGAGAACTGT TAGAGGCAGT GAATCTGTAT GTGTCTGCAG
57951 CAACTTCAAT TCTTGCCTAC TCTCAAAATA AAAAATTCAA CTGAGGGGCA
58001 TAAGGTAGAA TGAAAGACAG AGGCAATTTT TAGAGCAAAA GGGAAAGTTT
58051 ATTTTAAAAG TTTTAGAGCA GGAATTAAAG GAAGTAAAGT ACACTTGGAA
58101 GAGGGCCAGA TGGGCAGCTT GAGAGATTCA AGCACACGGT TTGACCTTTG
58151 ACTTGGAGTT TTATATGTTG GCAGGCTTCT CGGGGGTTGT TGCTTCTCCC
58201 CTGATTCTTC CTTTGGGGTG GACTGTCCGC ATGTGCAGCA GCCTGCCGGC
58251 ACTTGGGAGA GGCCGCATGT GCAGTGTGTT TACTGAAGTT ATGTGCATGC
58301 TTACTTGAGG CATCTTTTTT TCCTTACCAG TTGACTGTTC CTAGAGGAAG
58351 GTCATATACC AGTTAAACTC TACCATTTTT GCCTCTTAGT GTGCATGCTT
58401 GAGCCTACTC GCCCACCTCC TGAGATCTTA TCAGGAACCT ACTGATCATC
58451 AGTTTCAGGG TTTTTCTATC TACTGGGAGA TTGCCTTTTC CTGGCGCCGG
58501 CTGCAACCAA ATATTATTTG AGAGAGACAG TTTAACAACC ACCTGACCAT
58551 CACCTAATGG TTGTCTGACA TTCCTTGGTG GAGGTTGGGG GTGATCTCCT
58601 GCCTTGCCCA TGTCTGCCTG CCTACTGTAA CAGACCAACT TAGTTAAATA
58651 GGTGGGCTTT TCAACTTAGT TTGTTTCTTG GTGAGATGAC TGACATCATT
58701 GTGAAGCTCT TTAATGAACA GGGCAAAGAA AGCCTTCTCT ATGCCTGGAC
58751 TCGGCATGGA CAGCTCTGGG AAAGAAGAAA GCCTATTTTA CCTGAGGGCC
58801 TATCTTTTAT AAATATTTTG TTCAAATTCT TTCTTTTAAA ACAAAGGTTC
58851 TTTTTCAATG ACTTACCAAA CCAATACACC TTAACCAAGG TTATGTCTAA

FIGURE 3S

58901 ACCAAGGATC AACTAGGCAT TTCCAAAGAG TGGCAAAGTA GTCCTCACAA
58951 GATCCAGAAC CAAAGACAGC TCAAAGAAAC AAATGTCTTG CTCACTGCAA
59001 ATAGAATACA ACCCATATTT CTGTCCAGCC GTATTTTCAA GGATCTCAGC
59051 TTCTCTGTTG AGCACCTACT CACGGAGGCC CCAAAGCCCT ATATGCCCCA
59101 CAGATAGAGA CAGGAAATCA AAAGCTGTCT CTGGAAGGGA AAAGAATCAA
59151 TAACAAATGG GTACCTCAGA AGGTCAAGAG TTATACAAAT GATTTTAAAC
59201 AAATAGGACT GCTTTCCTGA CTGGGAATCA AACCTGGGCT GCAGTCATGA
59251 AAGCAGAATC TTAGCTGGTA GACCACAGAG TGGAGTGCTT TTTTGTAAAT
59301 CCTTCAGGAG ATCCAAGCAG GCAGTTTGAG CATATAAAGG ATTTCAACTC
59351 ATTTCAGATC TGATCACAGC TGGAATGCTG TTTAGCTAAT TTCCTGCATG
59401 TTAATATTTC AAAGATATGA TGAGATTTGT ATCTGCAAGG GATTGTGAAG
59451 TCCAGCAGGG CATTTGAAGG ATATTGTCTG GGCCGGGCAT GGTGACTTAA
59501 ATGTGCTGGC TTAAAATCCC AGCACTTTGG GAGGCCAAGG CGGGTGAATC
59551 ACTTGAGGTC AGGAGTTTGA GACCAGTCTG GTTCACATGG TGAAATCCCA
59601 TCTCTACTAA AAAATACAAA AAATTAGCTG AATGTGGTGG CACGTGCCTG
59651 TAATCTCAGC TACTCAGGAG GCTTAGGCAG GAGAATTGCT TGAACCTGGG
59701 AGGTAGAGGC TGTAGTGAGC TGAGATCACA CCACTGCACT CTATCCTGGT
59751 GACAGAGCAA GACTCTGTCT CAAAAAAAAA AAAAAAAATA CTATCTGATG
59801 TTGGGTCAAG AAATCATCAG TGTCATTCAT TAGACCTGGT ATAGACAAAA
59851 GTTTGTTGGA TCTGTATTTT TATAATCTCT GTAGTATCAT TCTTGTTCTG
59901 TAGTTGTTTC ATTTGTTCTC TCTGTTTAAA AATTATCTTC CTAGGAGATG
59951 GATGGGAGCT GAGGGAATGA GCAGAAAGGG ATGAGTTTAG ATCACAGGAG
60001 TAGGAGGAGA TGGAGCAGTT AGAGGTGAAA GAGAAAACCT CCAAAATCTT
60051 ATTAAATTTA GAAATAGTTT CAAACATACT TTTGTTCACC TCTTGAATGG
60101 AGGCAATTTT TTCTTTTAGG ATTTCTTTTA GAAACTTGTA GGTACTATTG
60151 GAAGTAAGTC TCTCACTCAA TTTGGTTCTA AAACTAGCTT TTTCTAATTG
60201 TGTGTGCAAA CAAACTAATT TAGGTATTTT AAAAGGTACC ACATTTTGGC
60251 CATTGTCAGT TGGAATCATT CTGAGTTATG CTCTACTAGT TTTCTAAATA
60301 TTTGCATGAA GAGGCATGGT AAGTATTCAG TATGAATCGA GCTGGCATTT
60351 CTAATGGTGG ATCTCTTCTT AAGGAGGAAA CCTCAGTTTT AGATAGTTGA
60401 ACTGCCTTCA GAATCTGGCC AGTTTTAAAA ACTACAGTTG TTTTTTCTTA
60451 AGCCACAAAG ATTTACTTAT TTTTCAAGAG AAACTATATT CTTCTTGGCC
60501 AAATTTTGTA TTAGAGGAAA GGTTACAAAC TCTAATGAAT AAGACAAAGA
60551 AAACCTTAAC TTCAGAGAAA AGTGAAAATC ACAAAACAAA GTAAATATAA
60601 TCTCTAGAGA ATAACACATG AAACTCCTGT CTTTCAGTAG AGTTTCAATT
60651 CCAATCCCGC AGAGTTAAGA ATGTGTATGG CTTGAATAAA GTCTGAATCC
60701 TCAACTAACC TGGGAGTATT TGGATACCGA GATGGCTGCC AGATCTGGTG
60751 AGGTTGGGTG AACCAAGCTG TTGATTCTGG TACTGTTACA GGAAAGCAGT
60801 CCTGATCCAT ACCCCAAGAG AGGGTTCTTG GATCTCACGC AAGAAAGAAT
60851 TCAGGGCAAG TTTGCAGAGT AAGGTGAAAG CAAGTTTATT AAGAAAGTAA
60901 AGGAACAAAA GAATGGCTAC TCCATAGACA GAGCAGCCCT GAGGACTGCT
60951 GGTTGATCAT TTTTATGGTT TTTTTAATAA TATGCCAAAC AAGGGGTGGA
61001 TTATTCCCTT CCCTTTTTAG ATCATATAGG GTAACTTCCT GACATTGCCA
61051 TGGCATTTGT AAACTGTCAT GGTGCTGGTG GGAGTGTAGC ATTGAGGACG
61101 ACCAGAGATC ACTCTCATCG TCATCTTGGT TTTGGCCGGC TTCTTTGCCG
61151 CAACTTGTTT TATCAGGAAG GTCTTCATGA CCCGTATCTT GTGCTGACCT
61201 CCTATCTCAT CCTGTGACTT AGAATGCCTT AACTGTCTGG AAATGCAGCT
61251 CAGTAGGTTT CAGCCTCATT TTACCCAGCT CCTATTTAAG ATGGAGTTGC
61301 TCTGGTTCAC ACGCCTCTGA CAGTACCAAC ATTCCAATTG TCACGAACTT
61351 GAGGGGATCA CTGAAGCTCC ACTTTAGATC CCATCTGGGG TGGTAAAATG
61401 TCAACGTGAA ACAAGATTCA GAAAATATGA TTAAGTATAG CATTTATTGG
61451 GGCTCAAAGC TTGAAAATTG TTATCCGGGA GCATAGATTC AAGTTGCCCT
61501 GAATATACTC CAATTAACAG CAGCGACAAG TGGGTTTCTA CGGAAAAAAG
61551 AAGAGGCAGT TTCTAACTTG TTCGCCAAAA ATTTACGTTA AAGTAACGTA
61601 AGCTATTGAT AGGCTACACG TTATTCTTTG TATCACAAAT TCCAGGATCA
61651 CGATGATAAT GAGCCAGGCA GCTAGTCAGA AACAAAATCC CAGGCATCAG
61701 TGTGGGGATA TGACTGAAGT CCCATACTCC TGTCTCTCTG GGCCTGACAC
61751 ATTTTGCATA GTTCATATAG CTCAGCCTTC TCTGAGCTAT TTCTCTCTTC
61801 TCAGTGGCTT TCCTGGAAGC AGCCTCCATC ATATGTGACT CAGAGTGCTA
61851 GCATTTCTTC ATGGGTTTAT AAACCATAAG AACTCAAGGT GGCCTTCAGA
61901 GCCACAGCAT CAACAATATT AACTTCCCTA TTAGTAGTGT TCTATTACTT
61951 TGGGTTTTAC ATATATTATC TCATTTATTC ATCATAACAA CCTGGTTGAT

FIGURE 3T

62001 AGGGATTATT ATTCCCATTC TATTCCTGAA GAAACTGAGG CTCAAAGGAG
62051 CTAAAATATT TTCCTATAGT CACACAGCTA GGAAGTGGCA GAGCGAGGAC
62101 TCAAACCCAA GAATCCTGAC TTCAAAGCCT CTGCTCTTCC TGCTGCACTA
62151 TACCATCCCT ATACACATCT CTGAGACTCC TGTAAAAATA TGTAAGGAAC
62201 AGGATTTATT TCATTTATTG TCTTTCATAT CCCACAAGAA TACAAACTGT
62251 GTAAGGCAGG TATGTCTGTA TGTTTTTTAT CACTGCCTCA TTCCCCATCT
62301 TCCACAACAG TGCCTACCGC ACAGTAAGTG CTCGATAAAT ATCTTTTAAA
62351 TGAGCATGTG AATGAATGTG TGTTAGTGTT AGGGCTAAGG CCTTTGGCTT
62401 CTGGTTAATT GCCCTTTTTG CCATTATGCC AATGTCATTT GCACACTCAC
62451 AAACATACCC TCATATAATC ATATGCACTT CAGTTTCTTT GCAGGTCCTG
62501 GGTTCAGACA AATCTGAGTT TGAATTTCTG TTCCACCACT GGGTAACTGA
62551 GTGAATTTGG TCAGTTATGT TTGGTATTTT ACTTAGTTTC CTCACCTGTA
62601 ATTAGGAATA ACAGGAATAC TCATGTCAGT ACTACTTTGA ATGACAGTGA
62651 TAAGAATATG TACTTCAAGC ACCTCACAAA GTACGTGGTT GATAAATGGT
62701 GACTTTACAC AACAACTGAG TGACACTTCT TCTGGCACAG GGGCCAAGGG
62751 AAAATTTCCC CTTCACCCTC TGAAGGTTCA CTGAGAATCA ACTGATAAAA
62801 GGCAGATTAA TAGGAGAAAA AGCACACAAA ATTTGTTTGC AATATGGAAA
62851 TTCACAGAAA GGGGTAGATG GTTGACACTT TTATGCCATC TTGAGGTTAC
62901 AGAAAGAGCT TGGAAAAATA GATTATGGGT GAAGGGAGAG AAAGAAAGTC
62951 CTGGGGCAAA GGTGGTCCTT GTTATGTAGA TGAAATCTCA CAAGTAGCAA
63001 CTCTCAGAAA GAATAGATGA TAGTCTGTGG TTGGGAGATC TGATCATGGG
63051 GAGGTCCTCA GAGAATGCCT GGTTGTTTAT TTCACTAATG TATTTTTTTT
63101 TCCTATAGAT ACAAATCATC TCCATGAAAG GTAGCTTTTC AGGGTTATTC
63151 CTGTGTGCAT GCCTTCTTCT GAAGCACCAT CTCAAGATAT GTCAAATAAG
63201 TGTATTTGGG GTGAAATATT TTTGGTTTCC TTTGCTAGAA ATGAAATGTC
63251 CCTGCTTCCC CATAGCCAGA AAAGATTCTT GAGTGGACAA CTGCACCTAA
63301 ACTTGAACCT GAGCACTAGA AAGTCTTTTG TTTTATTCTA TGTTTTTATA
63351 AATTTAAATC TAATTTTTTG AATATAAAAT AATACATATT TTGTAAATGT
63401 GGAAACACAG AAAGTTCTAA TGAAAAAATA AAAACCTGTA TTTCATCACG
63451 CAGAAATATC TGCTGTATTA GTTTTCCGTT GCTGCGGTAA CAAATTGCCA
63501 CAAACCTGGT GGCTTGAGAC ATCATAGATT TAGTATCTTA CAATTCTGGA
63551 AGTCAGAAGT CCAAAATCAG TCTCCCTAGG CTAAAATCAA TGTGTCACCA
63601 GGGCTGTGTT TCTTCCAGAG CCTCCAGGTG AGAATCTGTT TCATTATCTT
63651 TTCTAGCTTC TTGAGGCTGC CTGTATTCTC GGCTTGTGGC CCCTTCCTTT
63701 ATCTTCAAAG CCAGCAGCAT ACTATCTTCA AACCTCTCTC TGACTCTGAC
63751 TTCATGTTCT CCTTATTCAT CTTTTAAGGC CCCTTGTGAT TACATTGGGC
63801 CTACTTGGAT AATGCAGGAT CACCTCTCTA TCTGATGATG GGCCTTAAAG
63851 TCCCTTTTGC CACAAAAGAA AACATATTTG CAGGTTCTGG AGATTATAAT
63901 GTGGACAGCT TTGGGGAGCC TTTATTCTGC TTATTACAAA CACTATTAGT
63951 ATTTAGTGCA ATTCATTCCC ATTGTTTTCC CTATATTTTT CAACATATTT
64001 CACTTTTTAC TATCTATGCC ATTCACAAGA TTGCTTATTT CAAGCAACGT
64051 TTTATTGTAA TTGTTTTCTG TTATCAACAT AAAGTAATCA AAAGGGTCAG
64101 AATCTAGTTT AAAGTGAGTT TATTCGAGTA CAAAGTTTGA GGACAAGCCC
64151 CCCAGGAAAC AGAATTCAAG GAATGGAAGT CAGAGTTCCA AAGTGTAGAC
64201 ATTGGGGATC ATTTATAGAC AAAGTTCAGG GAAGTTTAAC AGAATTTCAC
64251 CATCTTTCTA TGTAAGGTTT AATGCATAGT TACAACAATC TGATTAGTCA
64301 AAGTGGTCTT TTTCTTTTGA GAAATGTATA TTTAAACATT CTACTCTGAA
64351 GATGTAATTG TCATGGGGCC TTGGGCACCA TCATGTCTGA GTTAGGTACA
64401 AGACTATAGG GAGGCAGTTA ATCTATAACA AAGATCAGTG ATTGGAAAGG
64451 GGAGGTCTGG TCTCTTCTAG TCATTTATAG AATAAGAACA ATGAGGAAGA
64501 GAGGTAAGCT ATAATCTAAG ATGCAGAATT GCAGACATGC CATGCGACTC
64551 ACTCAGTTTC CAGGGCTTAA CTTCCCCCTT GTCAAAATCA ATTTAGAAGA
64601 TCCTGAAATT TTATTTTATT TTATACTTAT ATTATTAAAC ATGTTTTATT
64651 AGAATGTTTC ATTGTTGTGG GGAGAATTCC TAAATTTCCT AAGCATAAAC
64701 ACTCTTTGTT TCTTTTCAGT ATATATTTCT TCCCAGTACA TGTTATTTGG
64751 ACCTAAGTCT TCTGGGATGG CAATAGAGAT GCAATGGAGG TCAAATTCCA
64801 TCCTTTTTAG AGGAATCTAT ACAAATTAGA GCTAGTAAGG ATATAAAAGA
64851 TCATTTTATC AGGTGCATCA TCCCTAAACA TACATACACA TTTACACACA
64901 TAATGTAAAA TCCTGTTAAA AGAAGACGCT TCCCAATATT CAAGGGCTGT
64951 ATAGACGTGC TTTTAGATTA AGAATTAGAT GCATTATGAC AGATTTTGCT
65001 ATGTAACAAA CTGCCCCAAA ACTTATTAAC TCAAAACAGC AAGTATTGAT
65051 GTCTCATGAT TCTGTAGATT GGCCAGGAAG TTCTTCCAGT CTGGGCTGTT

FIGURE 3U

65101 ATGTGAGTCA GTGATTCAAA ACTATCCATC TAGGCCTTGA AGGCGGGGGC
65151 TAGCCTAACC TTTTTCTTCT GCCATGAGAC TAACCCTGGC TTCTTCACGT
65201 GCGGGTGGAA GGGTTCCTAA CAGCAACAGC TGACAAACTT AATGAGCAAG
65251 CACTTTTTCA GCCTCTGCCA CAGTCACATT TTCTATCCTA TTGGCTAAAG
65301 TAAATCACGA AGTCAGGCTC AGATTCAAGG GGTGTAGAAA TAGGCTCCAC
65351 TTCTGATGAG TGGCACGGCA AAGTCAACAT TGCAAAAAGC CAGGCAGAGA
65401 TATTACTGTG GCCAGTTTTG CAAACAATCC ACCGTAATAC ATAAAATATG
65451 TTTAAGCAGT CCACAAAATG ATCAAGGAAA TGGTAGAAAC TATAAACACT
65501 GCAAGAACTC AGAGCCACAT GATGTTATTG AGTCCTTGTA GTGCTCTGAA
65551 AGGGTTCAAG GAAGAAGTTG TTTTGGCATA TGACCCTGAT GAACTTGCAA
65601 AAGTAGAGAA GAAGGGAGCA CAGTTTCTGA AGAAGAACTT AGTAGAGAAG
65651 TGTTATTCTG TGGCCAGTAC GCAGTAATTG TTCCACCTAG AGATGTTGAC
65701 TGACTGATGA ACAGGAAGCT GAGTCTTTAT AATGCAGATA TTCACATATT
65751 CATTTACTCA TCCTTTATTG AAAACAACGC AAGGAGCCAC TAGAAAATTT
65801 AAGCTCAAAA GAAACTCACT GGATGGATAT GGGGTAAAGA TTCAGAAGCA
65851 CAGCTGAAGT AGCAGGTTTC ACAAAGATTA GGGACAAAGG GCAATCTGGA
65901 AATCTAGGTA GCAGGAACTA TTGAATAGAC TCTTAAGCTG TCTGGGCGGA
65951 CATGAGTCAG CTCCAACCAA TTTTCTAACC TTGTGTCACC CACTCAAGAT
66001 TGAAAGTCCT GGGAGAGAAT CCAACTGGCC TTGCTCAGAA AACATTCCTG
66051 CCCCTTAGCT CAAAGAAAGA ATAAAATAAA TGACTCCTGG ATTGTTAGCC
66101 TAAGCAACTT AGATGATCAT GTCATTCATT TAGATGGGGA GATTGGAGGA
66151 GGAGCAGATT CATTGTGAAA ATCAGGAAAA CTCTTTTAGC TCTGTTAATT
66201 TTGAACTGCC CCTTAGTAAT TCAGATAGAG CTCTTGAATA GGCAGTAAGT
66251 GAATCTGGAG TTCAAAGGGA AATTCAGGGA GTATAAAGTC CAACAAAACA
66301 AAAATATGGG AATCACTGGC TGTTAGATGC CATTTAGACC AGGGACTTGA
66351 AGGGAGCACC TTGGGAAAGA GACTAGATGG AACAGAAAGT CTGAGGACTA
66401 AAGACATTGC TCTCTAATAG TTCTGGTAGA GGAGGAAGAT TCAGGAAACT
66451 AGACAGAAAG ACAACAGTCA TGAAGCTAAT CAACAAGCTA TGGGTAAGTC
66501 AGGGGAGTCT GCCATCCTGG AATCTTCCAG AGAGAAAAGT TTTTCAGAAA
66551 GGAAGGAGGG AAAACCATTT CAGATGCTGC TGCAAGGTCA AGAAGAAGAA
66601 GACAAAAAGA GCAGACCCCT TACTTGAGAA GATAAATATT GTGACCTTGT
66651 CCCAGTGTTT TGGGAGGCTG AGGCAGGAGG ATCACTTGAG GTCAGGAGTT
66701 TGAGGCCAGC CTAGGCAACA TAGTGAGAAC TCATCTCTAC AAAATATAAG
66751 AATAAAATAA TTAGCTGAGT AATCTCAGCT TCTTTGGAGG CTGAGGTGGG
66801 AGGATCCCTT GGGCCAGGAG TTTGAAGTGA TTACTCCACT GCACTCCAGC
66851 CTGGGTGACA GGGCAAGACT CTGCTCTAAA AAACTAAAAA AAAAATTAAA
66901 AAAATATATT GAGATTGTTG CAGAACTTTC TCCTTAGGTC AGCTAAAACT
66951 GGGCTCTTGT CACATGACCA GGGAAGATTA GGCTTGCAGA CACATAGAAG
67001 GGTGAGGAAA ACATTTATTG GGAGAAAAGG AAAAAGAAAG AAAAACCCTC
67051 AGCAAAGCGA GAGGGAGTCT TGCCAACAAC CTCCTGCCTC ACAGATAGGT
67101 TACCACACGG AAACTGAAGA GGCCAGGCTC CTCCCCCTGC AAACAGCGCG
67151 AACTTCCCCT GGCTCCACCC ACTTCCCTCA GTGCGCAAGT GGGCATTATT
67201 TAGAGAGAAT GAGCCAGGAA AGCGCGGGCT TCATCCAGGA CCAGCAGTCC
67251 GGTTTTTCAG CCTTCAGGCT GTTTTAGACT TGGAGGCTGG GTTTCTCCGG
67301 GACCCTTGGC TGTCTCCTGT CTCTATCAAG ATCTTAATAA GAGCCAACTC
67351 CACATGGTGG GACAAAAGAC CAAAGGGAGT AAAGGGAGAG GCTTAATGAG
67401 AAAATGAGAA ATTAAATCAT TTAATGAGTG ATTTTATTTT CCAAGTAGAG
67451 GAGGAGAGGT ACAAAATGAG TTTTGAGATT CATGTTGTGA CAGGTAGCAA
67501 TAGTGTCTTG CCATTTCTGT ATTGTATTCC ATTGTATAAA TACTCCATGG
67551 TTCATTTACG TTTTTTACCA TTGATAGGCA TTTGGATCGT TTGCAATTTG
67601 AGACTTTCGC AGAGTACTAC TATTAACATT CTTATTTGTT CTTTTGGCAA
67651 ACTCCAAAAT ATGTGTACTT TTGTACACAT GTAAACCCTA GGACCCAGTG
67701 GAGCGTAGTA CTTGATTTTA CGNCGTGTAG ATTAGAGTGC AACAGATCTT
67751 TAGTATACTT TAGCTGAGTA GAGTAGCAGA TAATGCTGGA CGAAGACGAT
67801 TGTCGTGCTC GTGTAGTAAC CTGTTCTAGT CTTGCGTGAG AGCACCTCTC
67851 TAGCCGCTGT GACGTCGTAC CTAGTGTTCA AGTAGCTGAG GAGCAGTGTC
67901 ACAGTAGGAC GTCCGCACCA GAGTTTAGTT CGGGTCGACT ATGATGTATG
67951 TGTACTAGTA GTGTAGTATA GTAGTACACG AGTCGTAGAG GAGTAGCCTT
68001 AGAGANNNNN NNNNNNNNNN NNNNNNNNNN NNNNNNNNNN NNNNNNNNNN
68051 NNNNNATTGG AATCCTCCCC TGTGCTCTAA AGATGTGTAC TTCTTATTTT
68101 TCTACACATA TTTTGGAATA TAAACTTAAG AATTAAATCA CTGGGTCCTA
68151 GGGTTTACAT AGGTTTAGCT GGCAAACAAT TTTCCAAAGA GCTTGTGCCA

FIGURE 3V

68201 GTTTATACTC ACATCCGCAA TGTATGAAAA GTCAAGTTGC TCCAAAGCAT
68251 CACCAACACT GGATATTATC AGTTTATTTA ACTCTGGGTG TTCCAGCAAA
68301 TGTGTAATGG TATCTCCCTG TGGTTTTAAT TTGCATTTTT CTGGTGACTT
68351 ATGAGTTTGG GCATATTTTT GCTTATTGAC CATTTATAAT CCCTTTGTTG
68401 GGAAGTGCTT GTTTGACTCT TTTAACCATC TTTCTATCGG TTGCCTCTTT
68451 TTCTTATTGA TCCATGAAAG CTCTTTATAT ATTCTATATA CAAGTCTTTT
68501 TAAAAGTTTT TTAAAAACTT TTATTTAGCA CATACCAAGT CAGGTGTTGT
68551 TCCAGGTGCT GAAATGGAGG AGAAGGAAAT TTTCAGAAGA TATGTGGCAA
68601 AGAGAAAAAA GCGTTAACCT TTGTGATTTG TGTTATTTGT TACTATCAAG
68651 TTGGCAATAA TAAATATTTA TTATAATTTG TAACACATAT TTAAAATGTA
68701 TTATATATAA TATTTTATAT TGTATCATAT ATAAAATCAA CAGATTTTAA
68751 TTAATTCAAA ATTCAGTATC TTCACTGACA TGTGTTAGCT TCCTAGCACT
68801 GGAATGTCAT TTGCTTGCTT ACATATAAAG GTATAATAAA ATTTTAAATC
68851 TTCTGCTCAG ATAAAGAAGT AGTGAATTAT CTAAGATGTT TGGAATGACT
68901 TAACATAAAT ATTTCTAAAG GGAAAGGGAT AAATCACATA ATTTTTCTGC
68951 ATGGAAACCA AATAAAACAA ATAAAAAGAA AGATGCGTTT ATCAGTAGGG
69001 AAAGTGTCTA GAAAAAGTAC ATATAACTAT GCCTGACAAT AGGCATATAG
69051 CCTACATGTA ATTGATACAT TTTAGAAGAA AGTGTGGAAT CATTTTTAAT
69101 ATTATGTATG TAGAACTCTA CCCTGAGTCA GGAGTTTCTT GTCATATGTT
69151 GAGGAGGGTA GAACAGAGTT ACTAACACTA AATGAGACAT TGAATAACCT
69201 ATCTTTTGTT TTTATGGGTA AAAAATATAG CGACCATAAT ATACCAGAAG
69251 TAAAAGAAAT ACAAATTAAT ATCTAATTTA TTATATATAT GGAATGAGCT
69301 GTGAAACTTC ACCAAGAAGT CTTTCTTTGG GGCATATAAA CTATTTGCAC
69351 AATCTCTGAC CTTCTTTTTC ACTGCAATAA TGGTTTTTTT TTTAACAATA
69401 AAAAATGTTT GGACTTAATG TGGTACAATT TATCAATCTT TTTCTTTATG
69451 CGTAGTGATT TCTGTGTTCT CTTTAAGAAA TTTTTGTCTG GCTGGGGACA
69501 GTGACTCACG CTTGTAATCC CAGCACTGTG GAAGGCCGAG GCAGGCAGAT
69551 CACTTGAGGC CAGGAGCTTG AGACAAGCCT GGCCAACATG GTGAAACACC
69601 ATCTCTATTA AAAATACAAA TATTAGCCGG GCGTAATGGC ACATGCCTGT
69651 AAATCCCAGC TACTTGGGAA GCTGAGGCAT GAGAATCCCA TGAATCCTAG
69701 AGGTGGAGGT TGCAGTGTGC CGAGATCATG GCGCCAATGC ACTCCAGGTT
69751 GGGCGACAGA TCCAGACGCT GTCTCAAAAA AAAAAAAAAA AAAAAAAAAA
69801 TCTTTGCCTA TGCCAACGTG GAGCTATTCT ATCCTGTTTC CTAGAAGCTT
69851 CACTGTTTTA GCTTTCACAT TTAGATCTAC AGTCTAGGAT CAAGTTTTAT
69901 TTTGTCTTCA TATAAATAAG TAATTGACCC TTAGCCATTT GTTGATAAGC
69951 TTATACTTTC CTTACGTCAC CACAGAACCA CATTTGTTAT TAATCAAGTC
70001 ACCATCTATG TATGGGTTTC CTGACTCTGT TCCATTGATT CATTTGTATA
70051 CTCTTGCATA TTTATCACTC TGTTTTAATT ACTGTAGTTT TATACTGGAT
70101 TTTCAGTAAT TCATCTTTGG ATTATGTTGG CTACAGTTGG TTCTTTAAAA
70151 TTCCATATAA ATTTCATAAG TAGCTTTTCA ATTTGTATTT TAAAGCTGCT
70201 GGTATGTATA TTGGGTACAT GGAGTCTATA GATTAATTCA GGGATAACTA
70251 ACATCTTTTT AAAATATCAA ATTTCCAATT CATACATTTT ATATATATAT
70301 ATATATGTGT GTGTACATGC ATATACATAT ATATGCGTAT ACATTTCCTT
70351 ATTTATGTAG ATATTCCTTA ATTTCTCTCT TTGGTTTTAG TTTTTCATGT
70401 AGAGGTCTAG CGTATTTGTC TTTAGACTGA TGACTAGGTA TTTGATAAGA
70451 TTACAAGTGG TATTATTTAT CAAAATTGTA TTTCTTGCTA GTTTGGTGCT
70501 TATATACTAA AATACAATTG ATTATTAATA TTGACTTTGT GTTCAGTGAC
70551 CTGGCTAAAT TCTCTTATTA ATTATACTAG TTGTCCCATA GGTTTTCTTG
70601 GATTTTCAAT ATTTACATTC ATGTGATTTA CTAATAGTGG CAGGTTCATT
70651 TCTTCCCTTT CAATCTTGCC TTTTCTTTCC ATGCATATTG CACATGCATT
70701 GAGAACAATG TTGAATAAAA GTAGTGATAA TGGACATCTT TGTCTCTTTT
70751 TCCCGAGTTC ACAGGGAAGG TTTTCAATAT ATCAAGAGTT TATAAAATAT
70801 TTGCTGTAGG CTATTTGTAG ATATCCTTTA TCACAATAAG AAAGTTTCTT
70851 TTCTGTCCTA AGTCACTAGA AGTTTTTTTT TTTTTTAACA TGAATGAGTA
70901 CAATATTTTA TCAAATACTT TTGTTTTACT GAGGTCATTT CTATTGTGAG
70951 TGAAGCAAGT TGATTTGTAA ATATTAAAGC AATCTTGATT TCCAAAAGTA
71001 AATGCTAGTT GGTCATGTTC TATTATCCTC TTGTGTATAT TACTGGCTAC
71051 AATAAAATAT TTGTTTTTTA TATTTTTTAT ATTATTATTC ATACATTATT
71101 TATGTATGTT ATTTATTATT TATAAATATG TATTCTATTT ATATATATTC
71151 CTACATATAT TTTAGGATGT ACATAGACAA GTTTGAATGG TAACAAGAAT
71201 GAGCCAACTG AGAGGAAGAA ATTGGTAATG TAGTAAAGAG CGGGGATGAT
71251 TGCCAAGTCA GGTCCTGCAG GTGGTGAGAT GAATGTGACT CAGGGCACAG

FIGURE 3W

71301 GTGAATGAGC TGACCTTAGG TGGAAGTGGG GACCCTTCCT TCATGTACTA
71351 GGAGAGAAAG CAGAGTTTGA AGTCTGTATG TGTGTGAGCT GCTGGGCTTC
71401 TCAGAGGGCA GATGAAATAG TTCTTATGCC ATTGCCTGTG TTTTCCCTGT
71451 GGTATATGAG GCCATCCACT GAGAATGAAG GTGGTCAGAG TATAGGAAAT
71501 TTTGAGATGC CGAGAAGATC TGTGAAATTA GTAGAGAATT AGAATAGGAT
71551 TTTCTAAGTA TCCATTTGAG ACTTGTAGTT ATAATTAAAC AAGAATCTAT
71601 CCTGCAGATT TGTATTTTTC TCCTTAGATT GCACTTAATA GATCACCAGT
71651 TCATTTTTGT TGCTGTTTAA AAGCATATTG AGTTTAAGCA GGATTGGAGT
71701 TTAATTGGGT GAGGTATTCT CACTGTGACT AAGTTTGATG AATTGAAAAG
71751 CGTAGTTGTA GAAAGGAAAC TCAAGAAGGA AATTCTTGGG GAAACTTAAA
71801 GAATCGTATA TATGCAATGT CACTTTTTAA GACAACTAAT ATTTTTAAGA
71851 ATTTACTACT TTTGAGGTGC TGTACTAATA TATTACATGT ATAATTTCAT
71901 ATATCTTCAA CTACTAGTTC CTGTAAATAA GTATGCTGAT GATGACACGT
71951 TCCATTTCTT TCGATAGCCA CAAAAACAGG AAGTGATGAC AAAGCTGGAT
72001 TCTAACTCCT GACTCCCAAA TTCTCTAAGA CCCTCAGCAT TAACATATAT
72051 TTTATTTTAA TGTTATTATA TATGTATCAT TACTTTTACA ACTCTTAAAC
72101 CAAACATTTT AAAATTAGCT ACAACTGCAA AATCAACTTA AAAATTTCAA
72151 AGAGCCATTT AACATGATAA ATTAAAATAT TTTAGTAAAA CAAAATCACC
72201 ACTGATACTT TAATATTCTT AGGTCTGAGA AAAACCATTA TGTCGTATTA
72251 TTCCTGCGTT CCTGGTAGCG TTTCTACTGC TGGACATCAG AAATAGAGAA
72301 TAGTAGAGCC CCTGAGATAA GAGCAGAGAC AGGGGAAAAG CAAAACATTT
72351 CTGAAGAGGC AGTTGGTCTA GTTTGGCTAT AATCACTAGA CGGGTAAAGG
72401 AACATTGGGT GCATTAAAAG TAGAGAGCCT GGGATGAAGG CGTGAAGGCT
72451 GAGTAAGAAT CTCTTCACTT GGTAGTAATT CTAGTTCATC CCCCTCTGAC
72501 CTGCAATTCT GAACATGGTG TAGCTTGGTC AATAAGGAAA TAAATTGCCT
72551 TTCTGGCTGG AGAGGCAAAG GGTAGACAAT ACATTGTGCC AGCTGAACTT
72601 CCTGTCTCTC CGCTCTGGAG AAGAGCCAGT CACAATGTAT GACTCAGCAC
72651 GCCGGGCACC TCTCCCACGC CAGCCAGGCC TGCCCAGCCA CTTGCTGAAT
72701 CACAAGTGGC CATTTCCAAT CCCATCAGTG ACCCAAGCTC TCCAACTTAG
72751 ACTAGTTTCT CTGTGATCGG TCTATGATTG TCATGGAGCA CAAAAAGTAT
72801 TAACTTCTAA CATTTATTTT TCTTTCCTGG ATGCTTGATG AACTTTATAA
72851 GCAAGAGACT GATTTAATTG TTCCTCATTA TCATCTGAGC ATGCCGTCTT
72901 GGCTTGCCCT TTTATATGGA GAGCAAAATG TTGTTATTCC CCTTTGCCTG
72951 ATTACTGGCT GTATTATTCT CTGAGGTGGC CATCTCAAGA GATTCTGTAG
73001 AAAATAATAA TAGCAAAATT TCTCCCTTGA GAAGCTTCAT AAATTAAATC
73051 TCCAGAGCCA GTATATGTAA GCCGACAGAT TATGAAATAT GATTTAATGC
73101 TCTGTCCAGA GAAAGGTCAG GGCTTCAGAA AAATCATCAT AATATCAAGA
73151 AAAACTAATC TGCAACCTGT TATATGATTT TTAAAAATCA CCCCCCATCT
73201 TTTTTACTGT GCAAACTGTA GATTTTTGTT TATTTTATTT GAGGCTATAG
73251 TTTATGTCTT GAATCACACA CATATGAGTA TTACTTTCTG TGAAGTTTTC
73301 ATGACCCCTG CAATCAAACT TGGGTCCTTC TGTTAGTTTC TATCACAGTA
73351 TCCTTCACTT TTCTTTCACA ATTCTTGCCA TATTCTATAA CTACATATTT
73401 GTTTGTTAAA TATTTGTTTA TCTTTTATAG ATGATTGGCT TCAGGAAGAG
73451 GGAAACCATG TCCTTTTGTT CAGTCCTTTA TTCTCAGCAC CTTGCACAAC
73501 ATGAATATAC AAAAAATATT TGTAAAATGA CCATCGAATG AACAAGTGCT
73551 CATTAAGTAC CAAGCTATAT GCCAGGGGTT GCTGATGGTT AGAAATGAGC
73601 AGGGCACAAA ATTCTTTGTT CAATTAGTGA GCAATTCAGG CAAAAAGAAA
73651 ATATTAATGG TGATTATACA ATATAATGCA ATGCAGCCAT CTGCCACTAG
73701 ATTTACTGAA GTGTTTTGTT TTGTTTTTAA GAGACAGAGT CTTGCTCTGT
73751 CACCCAGACT GGAGTACAGT GGGTAAAATC ATAGCTCACT TCAGTCTCGA
73801 ACTCCTGGGC TCAAGGAATC CTCTCACCTC AACCTCTTAA GTAGCTGGGA
73851 CTACAGGTGC ATGCCACTAT ACTGGCTAAT TTAAAAACAG AAGCCAACAA
73901 ACAAAAAACA CACCTTTTTA AGACTGGGTC TCACTATGTT GCCCAGGCTG
73951 GCCTTGAACT CCTGGCCTCA AGCGATCATC CTGCCTTCCA AAGTGCTACC
74001 TTCTAGAGTA TTGGGATTAC AAGCGTGAGT CATCTGCACC AGGCCTGAAG
74051 CATTCTGTAA TGGAGAAATA CCTGGGTGCT ATGGAAGGGC AGAGGGGGAA
74101 ACACAGAGGA GTAACATCTA GTTTACGTTT GTCAAGGAGA GGCCAGGAAA
74151 GACTAACTAC AGGGGAGATA AACTCCAACC AAGAGTCTTT AAGTCTTCCA
74201 AGACTTACGT ACAAGTTTCT TATTGCTAAA ATGGAAGTTT TAATGAACAT
74251 TTATTTATTT ATTTGAGATG GGGTTTCACT CTTGTTGCCC AGGCTGGTGT
74301 GCAATGGCAC AATCTTGGCT TACTGCAACC TCTGCCCCCC AGGTTCAGGT
74351 GATTATCCTG CCTCAGCCTC CAAAGTAGCT GGAATACAGG AGCCTGCCAC

FIGURE 3X

74401 CATGCCCAGC TAATTTTTTT TTGTATTTGT AGTAGAGACG GGGTTTTGCC
74451 ATATTGGCCA TGCTTGTCTC AAACTCCTGA TCTCAGGTGA TCCACCCACC
74501 TCGGCCTTCC AAAGTGCTGG GATTACAGGT GTGAACCACT GCCCCCGGCC
74551 TGAACACTTA CTATAAATAT TATATGGTAG TTCTCTCAAA TTCATTCTGT
74601 TTACTGCCCA AAAGAGCTAC ATAAATTCTA AGTTGTCCAC ATTTATGAAT
74651 TTTAGATATA TGGCTGTTTA TTCTGGATAA ACACACAAAA TACACAAGAG
74701 TGGGTGCGAT CACTTATATG TGTTAAAGAA GGCATTCAAG GTGCATTTTT
74751 TCTTTGGAAA AGCTTTGTAA GGCTGCTTAT GAGACAGAGA AGTAAGTATT
74801 TTATAAATTC CAAAGCTTCT TGGTCTATTG ATGAGTTTTT CTGCTGTTAA
74851 AAACCTCTGA AAATTTGACA ACGTACTCTA GAGAGAGAAA GCGCTGAAAT
74901 AGGCACTGAC GTACTGCTGG TGGCAATTCA AAATGATATG CACCCTATGG
74951 AGATAAATTT GGCAATATCA AGCAAACATT ACATATACCT TTGCCCTTTG
75001 TTTTGACAAA TCTTTGTTTT AGCAAACCCT CTTCTATACA TCTATAATGA
75051 CATTAGACTG CCCAGAATAC AAGAAGGCAA CCACAGTGGG CCAGTACTAC
75101 TACTGGGCTA GATGTGGTGG CTCACACCTG TAACCACAAC ATTTTGGGAG
75151 GCTAAGGTAG GAAGGCTGCT TGAGGCCAGC CTGGGCAACA TAGTGAGACC
75201 TCATCTCTAC AAAAAAAAAA AAAAAAAAAA AATTAGCCAG TCATGGTGGT
75251 ACATGCCTGT AGTCTCAGCT ACTCAGGAGG CTGAGATGGA AGGACAGGTT
75301 GAGCCTTGGA AGTGGAGGCT GCGGGGAACT ATGAATATGC CACAGCACTC
75351 CAGCCTGTGC TACAGAGAGA GACTCCGTCT TAAAAAACAA AACAAAATAA
75401 CAACAACAAC AAACAAAGAT AGATGCATAG AGTTTTTCAC TGTTGCACTA
75451 TTTATATTAG CCAAAAACCG GGAAACAACC TGAATATTCA TCAAGTGGGG
75501 ACAGGTTGAG TAATCATGTG ACATACATAA ATTGCAGCAC TGCACACTTG
75551 AGAAAAGAAG TGAGAAATGT CTCTATTTCC TAGTGTGGTT TGCTCTCCAG
75601 AGTATACTGT TAAGTGAAAA AAGCACTGTG GCCTCAAATT TATCTATAGA
75651 TTCTATACAA TCCCCATCAA AATCTCAGCT GGCTTCTTTG CAGAAATTCA
75701 CAAGCTGATC TTAAAATGTG TATAGAAATC CAAGGGACTC AAAATTCAAT
75751 AAATTCAAAG ACTAGCCAAA ACAATCTTGA AAAAGAAGAG CAAAGTTGGA
75801 GGGCTCATAC TTTTCAGTTT CGAAAGTTGT TATGAAGCTA CAATAATCAA
75851 GATAGGGTGG TCCTGGCATA AGGATAAACA TGGAACAGAA TTGAGCATCT
75901 AAAAATAAAG CCTCATATTT CCAGTCAATT GACTTTTAAC CAGGGTGCCA
75951 AGAAAATTCA ATGGGGGAAG AATTTGTCTT TTCAACAACT GGTGCTGGGA
76001 CAACTGTATA TCCAAATGTA AAAGAATGAA ATTGGAACCC TACCTCACAC
76051 CATGTACAAA ATTAGCTCAA AATGGAAAAC AGAGGTAAAT ATAAGAACTT
76101 AATGTATAAA ATTCTTCGAA GAAAATACAG AAGTAGATGA TCAAGACCTT
76151 GTAATCACTA ATTGTTCCTC AGATATGACC CCAAAAGAAC AAGTACTAAA
76201 AAAAAAAGTA GACAAATTGG ACACCATCAA AATTGAAAAC TTTTATGCTT
76251 TTTATACTTC AAAGTCACTA TCAAAAAAGT GAAAAGTCAC CCCAGAGAAT
76301 GGGGAGAAAA TATTTGCAAA TCATATATCT ACTAAAGGAT GTGCATTTAC
76351 AATATACAAA GGGGCCAGGC GCTGTGGCTC ATGCCTGTAA TCCCAGCAAA
76401 TCGGGAGGCC AAGGTGGGTG GATCACCTGA GGTCAGGAGT TCAAGACCAG
76451 CCTGATCAAC ATGGTGAAAC CCTGTCTCTA CTAAAAATAT AAAAATTAGC
76501 TGGGTGTGGT GTCAGGTACC TGTATCCCCA GCTACTTGGG AGGCTGAGGC
76551 AGGAGAATCA CTTGAACCTG GGAGGTAGAG GTTGCAGGGC GTGGAGATTG
76601 TGCCATTGCA CTCCAGCCTG GGCAACAAGA GCGAAACTCC ATATCAAAAA
76651 AAACAAAAAA AAACAAAAAA AAACAAAAAA AAAAAAAGAA CAAAGATTTC
76701 TTCCAAGTCA ATAATAAAAA CAGAAAATGC AATTTAAAAA TGGATAAAGA
76751 ATCTGAGTAG TTTTACATTA AAAGATAAAT AAATGGTCAG TGAGCACTTC
76801 AAAAGATCCT GAGCATTACT AAACATTAGA GAAATGCAAA TCAAAATCAC
76851 AATGAGATGT CATTTCATAC CTATTGCTTT CTTTTTCTTT TTTTTTTTTT
76901 TTGAGACAGA ATCTTGCTCT ATCTTCCAGG CTGGAGTGCA GTGTGTGTGA
76951 TCATGAAAAT GGCTCACTGC AGCCTCAACA TCCTGGGCTC AAGTCATCCT
77001 CCTGCCTCAG CCTCTTGAGT AGCTGGGACT GCAGGCATGT GCCACCGCAC
77051 CAGACAATTT TTTTTTTCTT TTGTAGACAC AGTGTCTCAC TATGTTGCCC
77101 AGGCTGGTCT GAAACTCCTG GGTTGAAGCA ATCTTTCTGC CTCAGCCCCC
77151 CAAAGTGCTG TAAGTATAGG TGTGAGCCAC CACACTGGGC CAGTACTATT
77201 CTTTAAAAAA TGGGAAATAA CAAGTGTTGG AGAGGATGTA GAGAAACTGG
77251 AGCCTTTGTA CATTGATAGT GGGAATGTAA TGTGGTACAG CCACTGAAGA
77301 AAACAGTTGG ACAGTTCTTC AAAAAGTTAA ACATAGAGTT TCCATTTGAT
77351 CCAACAATTC CGTTACTCAA TATTTACTCA AAATAATTGA AAGCAGGGAC
77401 TCAAATAGAT ACTTGCACAC CAGTGTTCAC AGCAGCATTA TTCATAATAG
77451 TCAAAAGGTA GAAATAACCC GAATGTCCAT CAACAGATGA ATGGATAAAC

FIGURE 3Y

77501 ACCACATAGT ATGTGCCTAT GATGGAATAT TACTCAGCCT TATAAAGGAG
77551 TAAAATTCTG ATATACACTA CAACATGGAT GAACCTTGAA ATCTTATAAT
77601 AAATGAAATA ATCCAGACAC AAAAGGACCA ATATTATATG ATTCCACTTA
77651 GATGAGATGC CTAGAACAGA CAAATTCATA GAAACAGAAA ATAAAATAGA
77701 GGTTACCAGG AGTTGGAGAG GAGGAATAAG GAGTTATTAT TAAATGGGTA
77751 TAGAGTTTCT GTTAGCAATG ATGAAAATGT TCTAAAAATG GACAGTGGTG
77801 ATGGTTGTAG AACATTCTGA ACGTACATAG TGCCACTGAA TTGTACTTAA
77851 AGTGGTTAAA ATGATAAATT ATATGATATG TATATTTTAC CACAATAGAA
77901 AAAAATACAA GAAGTTACCA GTGGGGAAAA GGAGGGATTA CAGAAGACAG
77951 GGATAACAGC ACGACTTTTC TCAGTATACC TTGTTTTTCG TATTTGACTT
78001 TGAAAATATG TACATACTTT ATATAACTAG AAAACAAAAT TAAATCTTAA
78051 AACAATCCCA AAAATGGAAT GTAAAAAAAA TGAAACCAAT TAATCTAAGT
78101 ATATATCCAG TTTGTGGCAT AACCACACAA AAATGAACTA TTCCAAGTGA
78151 CTTTTGAACA GAAAATTACT ATATACCATC AGTAGAATAT ATCCTAATAA
78201 CAAGAAAGAA CAGCAAAAAT ATCTTAAAGT GTTTTCAGTA ATGGCATTGT
78251 TGGGGGTAAT GTTGATACTG TTATTTTGAA AGTGTTGAGT GTATACAGTG
78301 GGATAGAACC AACAAGTATT TATAATGATA TCATTGAGAA CCAAGATTTT
78351 CATTGAGGGA GAAGACTGAT GAAGTTAAGA ATTTCTGTAA TCTTGAATGT
78401 AAACTGAAAG CATTATTATG AAATGTGTGA TGTGTTTATC TTAGTTTACC
78451 TTTGAATATG TGTATATTTA TAACTATACA TCTATAGCAG CAGACACTTC
78501 TGTCACCCAG ATTGTCTGAA ACAGGAAATA TACAAGATAG CCAGCAATAT
78551 GTTTTCATAT TCTACAGTTA CAAAGCTGTC AAAACTTACT AGGGTTATGT
78601 CAAACAAAAC ATGATCTAAC ATGACTATGT TCCTACTGGC TGAAGAATGA
78651 ACATTATGAA CTGAACATCA ATAAGAATAA TGACATCAAA CCCAGGAGTT
78701 CATTATAATA TATTTTTAAG TATATTGATT GCTTTTGGAG GGTTCTAGGA
78751 AACAAACAAA TCATTTTGAA AAGTGGTAAA TAAAGGAAAG ACTTCAGTTC
78801 AAGACCAGTC TGAGCAACAT AGTAAGACCC CATCTCTACA AAAAATTAAA
78851 ATATCAGCTG AGCATTGTGG TGTACATCTT TAGTCCTAGC CACTTGAAGG
78901 CTGAGGCTGG AGGATTGCCT GAGCCCAGGA GTTCAAGGCT GCAGTGAACT
78951 ATGATGGCAC CACTGTGGTC CAGCCAGGGT TAAATAGCAA GACCCTGTTT
79001 CTGGCGAAAA AAAAAAAAAA AAAAAAAAGG AAGACTTAAA CATACCTTTC
79051 CTATATGAAC TGTGCCTCGG AGTAACTAAA TAATTGATTA AAGCAAGTTT
79101 CTCTGTATAA AAGTACTCCA GCTAAAACAT TAAGGAGAAA TGATAGAATT
79151 CAAATATCAC AACCCCTAAG GAATTTTTGC ATCAAGACAA CAATAATTAA
79201 TGACTGATAA CACCACACAC AGAATACAGA CTTATTAATT GTATAACTCC
79251 TGATCAAGTG CATACCACTA TCTGTGAAAT AGTTTTGCCA AAAAAAAAAA
79301 AAAAAATCTA ACCTAAACTT GAACAAGCCT CTAGATCTAA CCACCAATTT
79351 TTACAAACTA CAAAGAATTG TGGAATGTAT AGATTGACGT GACATGAAGG
79401 CAATCGGCAA AGTCCAGACT GTGAAAATAC TACAGCAAAC ATTTAGGGTC
79451 TTTTTTTCTT TTTCTTTCTT TTTTTTTTTT TTTTTTTTTT TTTTGAGAGA
79501 GTCTCCCTCT GTTTCCCAGG CTAGAGTGCA GTGGTGTGAT CTCGGCTCAC
79551 TGCAACCTCC GCCGCCCAGG TTCAAGTGAT TCTCCTACCT CAGCCTCCTG
79601 AGTAGCTGAG ATTATAGGTG CGCGCCACCA TGCCCAGCTA ATTTTTGTAT
79651 TTTTAGTAGA GACGGGTTTC ACCATGTTGG TAAGCCTGGT CTCAAACTCC
79701 TGACCTCGTG ATCCACCCGC TTCAGCCTCC CAAAGTGCTG GGATTGCAGG
79751 CGTGAGCCAC TGCACCCAGC CCACCCTTGG TTTTTTTCAA CAAAAAATTA
79801 CTAGAAATAA AAGAATAATA GTTGGTCAAG GAAGCTGTAG AATAAGAAAG
79851 ACTGCCACAT ACATCAATGG CAGTGGGCGG GCTTTGTTTG AATCCAACTC
79901 TAGCATGCAA ACATTTGATA AAAATTTCTT TATTTAAAAA GAAAAGTTTA
79951 CAAAACAATC AGAAAAAATA AAAAAGATTG AGGATCTCAG GACAACTACT
80001 AGCCTAGATA ATTTATAAAG ATTAGATAAC TGACTCATTT TTATTAGTTT
80051 CTTTCCTAAT AAGGCAATAT GTATTAGATA TATCAGAGTA GAAGGAAATA
80101 TTTTTCTTAC ATCTATTTGG CTTTTTAAAT ATAAACATAT ATAAGTAAAA
80151 ACCAAAATGA TTTATAATCC CACCATTTAT GTAACTATCT TATTTTCAAA
80201 AAAAATTATG CAAATACTAG CATTTGTGTG CTTTTTTTCC TTTTGTGTTT
80251 GTGTGTTTAT ATCCTTTTTA AATATATCCT TTTTATGTAC CTAAGCAGCT
80301 GTATACTATA CTGCATACTA TAGTGTGAAC TTTGTTCTTT TCCTTCGTCT
80351 TTACAACATA TTGTGGAAAA CGTTCCATAT CAGAATATAG ATATGCCTTT
80401 TTGTAGCCAT TGAAATGCAA AGAAAAAAAG AATATAGATC TGTCTCATTT
80451 TTTAAAAATG CTGTATAATC TGTAGCACGA ATTTACTATA ATTTATTCGC
80501 ATGCTCCCTT ATCGATGGGC ATGTAAATTG TGTTAATTTT ATATGATATA
80551 ATGAGTATCC TTATATGTAT ATCTTGGCAC AGTTTTTCGA GTGTATCCAT

FIGURE 3Z

80601 AAAGTTTCTT GCAATGAAAT TATAGGGCAA CAAGGGTGTG GTGGCTCTTG
80651 TCTGTAATTT CAACACTTTG AGAGGCTACG GCAGGAGGAT TACTTGAGGC
80701 CAGGAGTTTG AGACCAGCGT GGACAACATA GTGAGCCCTC ACCTCTACTA
80751 AAAATTAAAA AAAAAAAAAA GAAAAAGTTT GGTATGGTGA TATGTACCTG
80801 TAGTCCCAGA TACCCAGGAG GCTGAGGTGG GAGGATCATT TGAACCTGGG
80851 ATGTCAAGGC TACAGTGAGC TATGACTGTG CCACTGCACT GCAGCCTGGA
80901 TGACACAGTG AGACCCTGTC TCAAAAAAAA AAAAAAAAAT TACAGGCCAA
80951 ATCCATATGC TTTTAAAGGA TATTTTTGAA TTGTTCTCAA AAAGAGGCTT
81001 CACCAAATTA CCATCCAGGG TATACAAGAT ACCCATTTCT CCATGTCCTT
81051 ACCAACAGTG GCTCTCATCA AGCCTTGGTG GAAATGCTCT CATACTGATA
81101 CTTTAACGAC TAAAAGTCAT GACATATCTG CTTAGGTTGT AAATTGCCTC
81151 CCTCTAAACT TATACAGAGA GAATTTAGAG TGTTGTCTCA GCTTGGTTCC
81201 AGTGTTATCC AAGCCATTAA CCTTTGTTTT GCCTTAGATT GTCACATTGT
81251 GGTATTTCAG TTAAAAAACA AAAACACAAC TGGTACTTTT TTTTTTTTTT
81301 TTTTTTTGAG ACGGAGTCTC GCTGTGTCGC CCAGGCTGGA GTGCAGTGGC
81351 GTGATCTTGG CTCACTGCAA GCTCCGCCTC CTGGGTTCAA GCCATTCTCC
81401 TGCCTCAGCC TCCCGAGTAG CTGGACCTAC GGGTGCATGC CACCACCCCC
81451 GGCTAATTTT TTGTATTTTT AGTAGAGACA GGGTTTCACC ATGTTAGCCA
81501 GGATGGTCTC GGTCTCCTGA CCTCGTGATC CGCCCGCCTC GGCCTCCCAA
81551 AGTGCTGGGA TTACAGGCAT GAGCCACTGT GCCTGGCCAC AATGGGGTAT
81601 TGTTTTTATA GACTGTTGAA ATCTGCCTTT GGAAACCATG GGTTTGCTGT
81651 GTTGTTATGG TGAATGAATT AGGTGCACAA TACTAGTTTT TAAAAAATGA
81701 ACTTCACACT AGGTACACCT TGAAAAATTA TTCCAGAGCT ATAAGAAGAG
81751 CTATAAGAAG AAAAATATGA TGGGTCATTG CTCCAAAGAA AGGTTTTAAA
81801 ATGTAAATTT GTACTTAATG AATAGGACAG TGTACCCTAA CCTCCTCCTT
81851 GCTATTCTTC AGGGATCTCT TCTAACAAGG GCTAATGCTT CACCTAAGCT
81901 GTGAAAAGCC TGCTGTGAGC ACTCCCTGTT CAGGGTCAGA AAAACACAAT
81951 GAACTGTTCT ATCATTTTAG GTTCTAGGAC AATGTTCTCT TGCTTTTCCT
82001 TGCTCAGAAT GGACCCTTGC TGGGGTAGCA TCAGAATGAG GATCTGGTGC
82051 AACAGTTCTG CAATAGGAAG TAGGTTCCCC TACTATCATG GTTTTCAAGC
82101 TTTTTTGACT GCAGCCCATA ACGAGAAATA ATGTTTTTCA TCATAACCCA
82151 GTAGATATAC TCACAGAGAC ACAGTATATT CATAAAAAAA ATCATAACGT
82201 TTAACCTTAT GTTAATAGCA TTTATCCTAT GTTATTCAAT CTATTTTATT
82251 TCTTTTTAAA AAATGCTCAT CACAGTTAAC TAAACTGATT TCACAACTCC
82301 TTAAAGGAAT TTGACTCACA ATTTGAAAAA CACTGCATTG TAGAATATTT
82351 TAGAGTCTCT TCCCAACCCT CAGAGTCAGA TTTATTTCAA GATGGCCCCT
82401 GTAAGACAGC TTCAAGCTTG TGAGTGACTT TCTTTTTTCT TTTTACTTCT
82451 TTACCATTTA CCATGACTCC CAAATAAGTG ACTCTTTTGG CTTATTTGGT
82501 AACCATGCTA ATTTCTACAC ATAGAACCTA GAGCATTTAC ATAAGACCCA
82551 CCCAAAGCTT GTGTTTTAAC CTTGCTTCTC TCCTTTCTTT CTTTGATTCA
82601 TTGATTATGT TTTCTATTGC TATCTGTTCA ATCTGTGTTT CAGGCAGTGT
82651 ACAGGTACTG AGGCAACAAT GGTGAGTAAA AGCAAGCATG CATCCTGAGA
82701 TATACTGGGA ATGAAAGAAG CTAATCCAAA AGCATACAGG AAAATATTTT
82751 CAAACTTTGA TAAATTCTGT GTAAGCATAT GGCATTGCAC GTAACAGGGG
82801 AACCGCATTT AATATGGAGT GTTGGAAAAG GCTTCTGTGA GAAGTGACAC
82851 TTGAGCTAAG ACTAGAAAAG TGAAAAGAAT ATAACCAGGT ACTGGACAGC
82901 ATCATGAGTG CAGGCACAGG TGACATCGTA TCACAAGCTT CTAAGGCTGA
82951 AGGGGGCGTG AATTGCTAGC TGGAGAGTGG AAGGAAAAGA TCTTCAAGAT
83001 AAAGCTGGAA AAATAAACAG GGCCAGGCCT CATAGGTTTC TGTAGACCAT
83051 GGAAAGAGGT GAAGGTTATT TTGAGCCTGG ATGACATGAT AAAACTCACA
83101 TTGTAAAAAT ATAACTGCAA GGTAGAGAAT GGATTGAAGA GGTCCAAGAT
83151 TACGCAGACA GAGCTATGAA CAGCCTATTG CAATGGTCTG GGTCAAGCAT
83201 GATGGAGTAG GGTTGGAATA GGGTGGTGAA CTTTTATTAG TTATCTTCCT
83251 TACTGAGCAC ACTTTGCAAT GAATTTCAAA TGCACTGGGA CCAGACTTGT
83301 TAATTTTGGA GCTGTCGACT AACAAATAAG TAAGCCATGA TAACCCACCA
83351 AAGAAAGTTG CAGAAATGCA AGAGCAAGGC TGTGATGAAT GGTTGAGGTA
83401 CAAGGAAGCT CTTACTCACT CATTTTAAAA AATCAGATGA TATGAAGTTG
83451 AATATTCAAG ATATTGCCCA ATTGTGTTAT GTTCACATAT TTTACTGGGC
83501 ATAGTTCTGG ATAATAAAAT ATTTATCTTC TCTCCCTCTG AGAATTAAAA
83551 ATCTGAGATG GAGGCCTCTG ATGTGCCAAA GGAGAAAGAT GATTTTTAAG
83601 AGCCAAACGT GCCTCCATGA TTAAATACAT TTATATTTCT ACTGGCCAAG
83651 GAAAGCATGT TGCCTCTTGC CTGGGCCTCT TCTGTCTTTG ATTAATAATC

FIGURE 3AA

83701 CCCTGCACAT TCGAACACTG TTATTAACTT GCCACATTGG CACCTTTATC
83751 ACTTTGTTCT TTGAATAAAA AGAGCTTAAC CCAAGTCCCA GTAAAAATGT
83801 TCATTCAGGC TGAATTTAAG AAATATATTC TGCTCCCTTG GAGTTAAATG
83851 GAATAATAGG AGAAGAGTCC ACTTGACTGT TACCAGGTTT CTGAACTACA
83901 CCTGGCAGCC TAACATAGTC AACAGCAGGG AGTGAATCAC ATCTGCTCTG
83951 TATGCTAACC CGGTCTGAGT AGGTGGTTTG CATTGGCATC TAATTATTTT
84001 TATGGTTAGT ACTCTCTTCT CCTGACTTTT GGTACCAAAC CCTCACACAC
84051 CTCATTATCC CTATTGCATC TGCCACTCAT CCTAAAAGGC CTTGCTTACA
84101 TCCCACAATC AATCATTCTT TCTCTTACCT TAGCGGAGAA CAGCCTGAGG
84151 TGCAGCAGGT CCCAGATATG ATTACAGTTT CACCAGTTCA ATATTGTTTA
84201 CTGAATGGCC TGTAAAACAC AGTGAATATA ATTTGTGTTG CTGCAGTTGG
84251 AAGGCTTACA TACCACATTG CCTAGAACCA AAGACCTTTC CTCATGCCCA
84301 ATACACCAAT GGCAGAGATG ACCAGCCAGT CACTGCATCG AGATGAAGAA
84351 TAGTATCTCC CAAAAGGCAA TACCAAGCAT ATGTTTCTCA GGCTTTTACA
84401 AAACACTTTT TAAGTTTCTG TCTAAACTCC TCTAAGAGCT AAATTTTTCC
84451 AAGACGTATT CTGTGTAAAT CAGTCTTCAG TGATAAACAA AATTTTATTT
84501 ATTGAACTAT CAGGTGCTAT TAATGCTAAT TAGAATGTTA CCACCTCAGA
84551 TTAATGCTTC GTTGAATTTC TTTTTTTTCT GGTGTTTGTA AGTATTCCTT
84601 TTCTCCTTCA GCACAATGAT AATTATAAAG AAGAAAATGT ACTAAGTGCA
84651 TTTCTCCCAT CATTTGATAT TTTACATTTA TTTCCTCAGC AAATAATTTG
84701 TCACAAGGAA GTAATGTGCA TCCCTGGGCA CTGCTTGCAG GCACTTAATT
84751 CTTGATTCAA ATGAAACTTT AAAATGTTTT ATCCATGATG TTATGTCTAA
84801 AGAAACATGT CAAAGAAACA TGTCAGAGAA CTTGACTTTG AATAGAAATC
84851 ATGGCTGTGC TTTGAGGGAA ACAAAATAAA TCACAGAGGT AGGAATGCAT
84901 AGTTACAAGC TACTGTTTGT ACACAGCAGA GACCAATTCT ACTCTCTGTT
84951 CTCATTTCCT CTTCTAATTC CTCATCCCTA CACTCCTTCC TGTGTGAAGC
85001 CCATGTCTGA TCCTGCCTAA TTCAGTGACT GGGGGTCACT GCAGATGCGT
85051 GCACAGGGTC CTGTTATGGG ATCCGGATTC TGCCGCCTTC TCCAGACACA
85101 AGTTTCCCCT CATACCTGTT GTTCCAGCAA ATCCAAGCTA TTCTCCTTTC
85151 CCCACTTGCA CTAGGTTCTT TCCCTAGTCT GTGCTTGCAT GCATCCTATT
85201 TTTCTCTGGT ATTTTTCAAA TTTTACTTTG GCACCTGGAG AACGTTTTGG
85251 CACCACCATT TGTCAGGTGT TTAACTTTGT GCATTTCCTC GTGTGAATGG
85301 GAGCGTAGGT CCAGCATCGT GAGGAAGGAC TGGGGTCACA CTCACAGAGT
85351 GTGTCAGAGC CCACAAAGTC ACTCAGTAGA AACATCAGGA GATGTTAGCG
85401 TTATTTTTCA GTTATTACTA TGATCACCAT TCCTCAAAAT TGAGCTCTGG
85451 TTTTACCTCT CCTGACAAGC TTTCCTTTAC TTCCCCATCC CAAAGACAGA
85501 GTGAATTACT TCCTTGTACT GTGTGCTTAG TTCTTCATTG CCCTTCTTAT
85551 GTGTTTTCCT TATCATTAAT GTGGGACATG ATCTGTTATA ATGTTGCTGG
85601 GCAATGATGT TGTTAGTATA GAAAAATGGG CATGAGGATA GTTCAAGGAG
85651 TTCCCATAAC TCATATTTTA TGGGCCTTCT GCAATATATG GTTAGGATAC
85701 AACCATTAGC AATAAATGGA TAACTTGGGT TCTCTTCATT TTCTGTGTTT
85751 TATTGCTACA TGAATAAACA GTTATTGAGT GCTTACTGTA TGTCAAGCAT
85801 GACAATAAGT ATTATAATTA CCCTGTTTAT TCATCAGTAT GATCAAATGT
85851 GGTTATTATT CCCATGTGAC CCATGAGGAA ACTAAAGGCC TAAGGTGATA
85901 GAGCTAGTGA TAGACCACCT ACTCCCAAAG TCTGAGCTCT TAGCTCAAGA
85951 ACACTCTGCT CTGATCTGTA GGGTCTCATT TGTCTCTGAG ACTCTTTAAT
86001 GTGTAAATAT ATTTGATAAG TTTTCTCTTC TAATGTAATT CCAGGTATTC
86051 CTTCCAAGAT GAGGAAGACA TGTTCATGGT GGTGGACCTC CTGCTGGGTG
86101 GAGACCTGCG TTATCACCTG CAACAGAACG TCCACTTCAA GGAAGAAACA
86151 GTGAAGCTCT TCATCTGTGA GCTGGTCATG GCCCTGGACT ACCTGCAGAA
86201 CCAGCGCATC ATTCACAGGT CAGTCAAGTC CAAGGAGATG GCCATGAACG
86251 TAACGCAAGG AGAGAATCCA CAACTGGCTA CCTTCAATAA ATTCTTATTG
86301 AACATGACAT TTAATCCCCG TTTAATTCTT GAAACAGTAC CCTGAGGTAG
86351 GTTGATTGTC TTCATTTTGC AGATTTTGTA AAAGACTGAA CACATAGAGC
86401 TTAATTTGCC AAAGGTCACA GTAAACAACA AGATCACAAT CAATGAATTT
86451 TGGTACTATT TTATAACTAA GCTTAGACAA AAAGGAGAAA AGGTGACATA
86501 TAGAAACCTA ATAAATATTA AGTAAATAAT TAAATGGAGG TAGCACATGG
86551 AGGGAAAGAA ATAGAATGAA AAGAAAGAAA GTTCTTTGGG AAAAAAGCTT
86601 GAGTCTTTCT AATATTTGCT GTCCTGCAGT CTATATTAAA TTAATCCCTA
86651 ATGTATGTAC TGCAAATGGA GGTAGAAAAA GCAATAGCAA TGTCTTCTGC
86701 ATTTAGAGCA TTAGTAGTAA ATAAAGACAT ACAAATAACA TAAGAAACCA
86751 TAAAGCTATA GAGATAATAC AGAGAAAAGG ATAATACTTT ATAGTAAAGA

FIGURE 3BB

86801 AATTTGTAGT TTCAATGATG ATTTTATATA TAGTATCTCA TTTGATCTCT
86851 GAAATAACCT GAGATAAATG ATCAGAGCAG ATATAATTAG ACTAGAATTA
86901 CATATGAAAA AATCATGGCT TGTATACATT AAATTATCAC CCAGTTTACT
86951 TATATGAATT GTAAACATAT CAAACATCAA AACATCTACT AATCAACATC
87001 AAAACAACTA GTGTTTACTG GTTGATGACT TACTATGTGC CAGGCACTCC
87051 TAGGTACTTT ATGTACATTA GTTTATTAAA TCCTCAAAAC TCAGCAAAGA
87101 TTCCACATTT CATTATAATA TTCCCATTAC ACAGATAAAG AAACTGTCTC
87151 AAAGGTTTGC CAAGGACAAA CAGCTAACAA ATAGCGTAGC CAGGATTTAA
87201 ACCTAGATCT CTCTGACCTC AAAGTCAGAA TTCTATGATA CCAATTCACA
87251 TTACTTACAC ATATGAAATA TATGCATTAA TTGATTATAC ATCATTAAAT
87301 GAAAAATCAG TACATGTGAC TCTGCTGCTG TCATCTCTAA TCCTTGAAGA
87351 ATTTGCTGAG ATTTTAAGTA CAATTATGTC TCAATTAGTA AAAAGTTGGC
87401 TAGATAAAAT ATTTGACCAC CACCAGTTGA CATTGACCTG TAATTTATTT
87451 TTTAAACCTT TATATATATA TATATATTTA GAGAGATGGG GTTTCACCAT
87501 GTTGCCCAGT CTGGTCTCCA ACTTTTGGCC TCAAGTTGTC CTCCTGCCTC
87551 AGCCTCCCAA AATGCTGGGA TTACAGGAGT GAGCCACTGT ACTCAGCCTA
87601 TAATTTATCT TGATGAGTAC AGAGCCTATA GATGAAGGTG AAGCATCAGA
87651 ATTTATAGAT TCTCTGTGCA GGTACCACAG GCCAGTTCTT TTATTTATTT
87701 TTATTTTTTT GGGCCTTGGC CCTCTACATT TAGTTTTTAT TTAATGTTCC
87751 TTCTTTGGAA GGGCCTGCTT GTATTGGAAG TGTGCTCTTC AGGCACCAGA
87801 TAAATGAAAG CAGACCAGTT AATTACGTAG GATCTCAGAA GTGAATTTGC
87851 ACACCTGGTG TTTTTTTCAA TAACTAGAAA TCCTGTTCTC AAGCACTCAT
87901 CTTCCCATAC TGGTTTTCTG GTCCCTCATA GCTCTTTCTG AAGAGAGACT
87951 GTTCATACTT GTTAGTCTAT GGAGTCCCTC TCAAAACTTT CCTGCTCGTT
88001 CATTCTCCCA AAAATTGCCA ACCACAGCCT ATCTTGGTTG TGACATCACA
88051 GATATCAGAA AGAAGGCAGT GACCTTGAGA AACCAGCATG GCCTCAGAGC
88101 CTTTTCACTC TCTCTCCTTT TCCTGTTTGA AATTGGGTTC TGTCCCTTCT
88151 TTCTTTAGGC TTCATGTTCT TGGTCATCAA AAGACCAATT CTCTGAGCAT
88201 TTTCTCCATG TACTTAGAAC TGTGTTCCAA GAGGAATTCA GGAGGGAAAA
88251 ACAACAACAA AAATATTGAT ACAATTTTTC CCCAAGGAGC TTACTAACAC
88301 CCAATACTGT TTTTCTGTTC TTTCCCTCTC TTTTTTTCTC ACCGTTATCA
88351 TCATTTTGCC ACTTAAATCA TAAACCAAGG ATTAACTTTC TGGTTTTTTG
88401 CCCTTCAATC ACATCCACAG TTATTACTTA GTGCCCGTTC TCAGAAGGGC
88451 CTTTTTGTAC TGAAATGTCT CCTCACCATG GTAAAGGTAT GGAAGGCAAA
88501 CAGGATGACA TTTTGAGTGC AGTGTTAAAT TGAGGTGACA TCCTTCTGGT
88551 GTCAAAAACT ATTCAGGTGC ATTTCTGTAA CCTCTATGCA CCTCTCCCCC
88601 CACCTCCCAG GTGTTATATT TTACAGGCTG TCATACCCTT TTGTACCTCT
88651 CCTGAGGAGT TGTGACATTT GGTGTATAAT TAATTCATTT GTCTCCTTTA
88701 TAAAATTGTG AACTCTGCAT GTTTTGCTTT TCATTGTATA ACCAGTATGT
88751 GAAAAAAATA TGAGCCACAT GAATGAATGA TTGACCAGAA GTTCAGGCTT
88801 ACAAGTAGGA AATATTCAAA TATAGGACAT TAAATCCAAA GGCCTCAGAC
88851 CTACTTGTAC CTTGGTCTTT ACATTAATCA TGTTATTTAT CATCCAAACC
88901 AGGATACTCT GAGAGCTAAA GAGGATGCTA TTAATATTAA TAGCACTGGG
88951 AAGAGTCAAA AGCCATAAAT AATCTAGGCA ATTCAGGACC TATGTCAACA
89001 TCATTAAGGC TTTTCAAGGC AGTGTTTTTT GGTTTTTTAT TTTTTGTAGA
89051 GACAGGGTCT CCCTATGTTG CCTAGGCTGG CCTTGAACTC CTGGGCTCAA
89101 GCAATCCTCC TGCCTCAGCC TCCCAAAACT CTGGGATTAC AGGTGTGAGT
89151 CACCATGCCC AGCTTCAAAT AGACATTTTA ATTCTGACAG TGTTCTGATA
89201 ACCAGGATTT TCTGCTCTCA GAATACCAGA TATCAATTTG AAATGGTGTC
89251 AAATAGCTTT TTAAAAAGTG TACATGGTAA AAGAAGCAGT GATCCCTTTG
89301 TTTAAGGAAT TTAAATGATA ATAACTTTGT CAATCTGAGA CTAAGAACTC
89351 CTGGGCCAGA GAGTGCAAAA AGCAATACAG AAGAGATACA GGCTTCTGAA
89401 TACTGTAATT CTTTTTTAAA CCTCCTTCTT CAAAAGAATC AGCCCGATTC
89451 ATGTTGTACT TGAATTCAAG ATAACAAAAC ACCTTTTAGT TACTTAGAAA
89501 GATTAGATTG TAAAATATGT GCTGAGTTCC TAGAAATTAA AAGTGAGAAT
89551 GAAAAAAAGA ATCAATGAAA GTACAGTAGA TCTCCCGGAC AAGGAGAGAC
89601 CATCTGCATA AAACTGAAGA TATAAAATAT GTGACTTCCT ACTTTTAGAT
89651 TAAAATCTAC ATTTTGCCTT TGGACATGGT AGAAGATTCA AAATTACCCG
89701 TAAACAGTCA GCACTACGTG GAAGTAGGAG CAGCAGTAGG CTGCTGTTTG
89751 CTTAGGGTTT CCTGGGTACC AGGCTGCCTG CTAAGCACTT GTGAGTTATT
89801 TCACTCAGTC TTCCCATAGC TCCAGGAGGT TTATGGCACT TTGTCCCCAT
89851 TTCACCTTCG ATGAAACTCT GGTTCTGAAA AATTACTTGC CCAAGTTTGC

FIGURE 3CC

89901 ATGGCTATTA AGTAGGGAAA GCATCATGTT TAGGAAATGC AGAGCTCTTC
89951 ACCACTCTCC AGCCTGCAGA TGCTCAGCAT GGCTGCAGCT CTGAGGGGAG
90001 CGCGGGACAC CTATGCATGG CCACCTGCCT CAGGCACCCA CAGACGAAAG
90051 TGGTACATGT GGAACGGACA GACAGAGAAC AGCCTAAAAT TGGAAGCTAA
90101 ATTGTGTGAG AAAGACAAGT ACTTCAGAGA AGATAGTGTG GAGTCGCAAA
90151 ATAAGTTTCA TGAGAGCTCA TACAGAAAAC AGCCTAAAAC TAGAAGCTAA
90201 ATTGCGTAAG AAAGACAAGT ACTTCAGAGA AGTTGGTTGG GAGTAAGAAA
90251 GCAAGTCTCA TGAGAGCTCT GAGGGGTGTA AATGGGACTT TTAACAGCCA
90301 AAGCACACAG CAAGTCTAGC CTAGCAAGAG GAGCTCAATG GATGGAAGTC
90351 CTCACTTGTT TCCCTGTGTT AACATAGAAG GGGGTCTTTT TAAAATTTTG
90401 TTTTCACTTC AGCTTTTCTG CCAGAAATGT CTAGTGTAGT GATGTTTTAA
90451 AAAAAACCTA AGTATCTGTT TCCGCCACAA ATCCCCATTA AGACATAAAT
90501 GGAGTTTTAT TTTGTGGATG TTTAAAAATC CATGGACTTG AACTTTTGGT
90551 AGTTTCCCAA ATATGTAGAA TATTCAGCTA GTTTTCTTCA ATTTCAGAAT
90601 CTTTCTTTTC TATCATTGTT AAAGACACAG GGTTGCATAA TAACCATTAA
90651 GTTTGAATTG TGCAATTAGA CAACTTTCTT ATTAGTCAAG AAGTCAAACT
90701 TTTTGTGTGA GTACAGCTTG AAAATCAGCT TTAGTTTCCA AAGAATGGCC
90751 AGTTTGAAGT ATAATATTCT CTTTTGCTTA CTTGAAATCT GCAAATAAAT
90801 GCTTTAAATT AGGGACAAAG TGATTATTTG CTTTTATTTA AAAAATAAGG
90851 GAAACAAAAC TCATTACAAT CTCTTCTACA GGGTTAGTAC TATTCTATTT
90901 GTTGATTGCC TCAGCCTCTC CAATGAACAA TCTGGTGGAA AGTAATTATT
90951 TAATATTATA ATCCAAAGAC AAATTTCTGT TTACTCCCTT GTCAGATCTT
91001 AAAGTAGACT CAATTATGAA TTTAAGCTAA TGAGATGGAT TGTATGGGAC
91051 AATTAAATAG TAAGTCATTT TGGGTCAAAA TACCATTTGA GAGGATGGTT
91101 GATTGTTTTT TCCCTCTGAG AATTACCCCC CACTATAACG AGGTTATAAC
91151 TCACTGTTTG CTAAATTTTT ATAGGAATGA GATAAAAAAT CTGATTAGAG
91201 TAATTTGTGC AAGTAATTAC AGTACAACAG AGAGAGTTGC AAAAATTTCA
91251 TTTCCCATTG AGTACCGAAA TGTTGAAGAG AAATAAAAGA AGATTTATGG
91301 CTGTGTAGAA AAACACAGGA TGGTATTTTT ATTTATCACC TTTGCCTTCT
91351 TTGCTGTTCT CATTGGAACC AATAACTGAT TCCAGATTCA TCTTAGGGAC
91401 TGTATAAGAT GCAGATAGAA ATTATTTCTC ACACATGACC TCTTGGGCTG
91451 GAGTAGCTGC TTATGAGATG TTCCTATCAT TCTTCTAGAA ATCAGTACCT
91501 TGACAGTGAA GAAAAAAATC TTAGGAATAA TGCTTCTAGT CCAAATATTT
91551 ATTCAAAAAT TATTTACTGG GTACCTATTT GCCAGTGTTC TGAATGCCAG
91601 GCTCCCATGG GGAAGAAGAC AATCCCCCTG TCATAAGAAG TTGTTAATAT
91651 TATAGTGTGA AAAATAGTCA AGTAAACACT TCAACATTAA TATCAAAAGG
91701 CTTTTAAATG TTGTGGCATG TGCCATAAAG AATGAAAGCT GTTATGTGCA
91751 TATCCTGAGC GATGCATGTG TGCCTGCATG CACGTGCACG CACGCACACA
91801 CACACACAAT ATGCTTAGTT GCGTCTTCCC AATGCTCATG GTTATACCTC
91851 TAATTGTAGC CTCTGGACCA TGATATTCTA TATAAAAAGC TGTCTCCCCT
91901 CTCCAATCTT AAGCCCTCAT AAGTGGATAC TACACCTCAC TTATGTTTTA
91951 ATCTCCAGCA ACTTGCACTG GATCTAAACT AGAGTGCTTG CTGGATAATT
92001 CAATGACTGA ACAAATGAAT GAGGACAGTA TGTATATGTA ACCATTGGGT
92051 GAGTGCAGAA GGTAAAAGTT GCTGTGGAGG ATGTCGTCTT CAGCAAATTC
92101 TCAAATTTAT TCCACACATT CCTCTGTGCA TCCACAACAT GTGGGGTTCT
92151 GGTCTGCCTT TCCACTATGC TGGATTAGTT TTGTATGCTG TGTAACAAAT
92201 TCCTACAGTC CCAGTGACCA GAAAGAACAT ACCTTTATCA GCTCGCAGTT
92251 TCTTTGGGAC AGGTGTCTGG GCACAGTCTA GTTGAGTTCT CGGCACAGCT
92301 GCCATTAAGA TGTCAGCCAG AACTGGGTTC TCTTCTGGAG GCTGAACTGG
92351 GCAAGAATCC ACTTCCAAGC TCAGTCAGAA TGTTGGCAGG AGGTATTTCC
92401 TTGTGGCTGT AGGACCCATG GTGGCTACTT TCTTTAAATT TAACAAGGAG
92451 AAGAATACCG TAGAGTAAGT TGGCTAGAAA GAAAACAGAG TACACATACT
92501 TGAATGATGA TATATAACAT TGTAACATAA CTCAGTCACA GAAGTAAGAC
92551 CATCACATCT GCCATGTAAT GTCGGTTAGA AACAAACCAT GGAACCAGCC
92601 CATGCTGAGG GGCTGGAAAT TATGCAAGGG TGTGAACACC AAAAGCTGGG
92651 AATCCTGGGG GTCACCGTAC ACAGTCTGTT CACATTTCCT CTAAAGAAGT
92701 TGCACTGCAT CACAGTTCCA TACCAATTTC TGCTATGACC TTAAATATAG
92751 CCCTGAACTT CCCTGTCAAG GAAGAAGTGA GGAGGTTTCA ACAAGTGATC
92801 AGTAATGATT CTTTTATGTC TAAGATTCTA GGATGATTTC CTCTCTGCCC
92851 TGGTAGGCTG CTCTTCAAAG TATGACCTCC TCATTGTTTC TCTGCTCTAC
92901 CACACACTCA TTCCCCTCCA AGAAGGCTGC CCACCTGTAA TGACCTGTCT
92951 ACAGAGCCTG TGATAGTGAC TTGTGATAAA TGGCTATTAG CACATTTACC

FIGURE 3DD

93001 AATCAAGGTC CTGTTTGCAA TTCGGTTGTG GGTCAAAATT ATGTTTGTTT
93051 TAACTGAGGT CTTTAGTTTA TTTCAGGCAG AGATCTGGGC TGGAGTGTCA
93101 CCTTTGTGTC TAATTCTCAC ACACTGTACT ATCTTAGCAG TCACATTTTA
93151 TTTTCTTGAG ATGATAATTT ATAGGAAAAA ATAAGACATT TCTGCAGCTA
93201 ATCATTTTAG TCAATGATCA TTGAGTGACA GGTGAGCTCC TAATAAATAA
93251 ATTTGCCAAC ACAGTGACAC CTCAGGTTTC TGAAGCCTGT GGGAATGAGT
93301 CATCTGGAAA GATGTTTTTC TAATTCCTGG AAGTATTTCA GAGATTTTTA
93351 ACTATTTAAT TTATACTACA AAGCACCTAT GTCACTTTTT TAATGACTTA
93401 ATAGGAGCTA TCACTTATTG TTTACACCAA GAACTGCGTA CTGTGCTAAT
93451 TGGCAGGTTC CACACACCAC CTAACTTGAT AATCAACAAT TCTCTGAGGG
93501 GATTAAGCAA CTTGCCAATA TACAGTCAGT ATATGGGGAC CAGATTCAAA
93551 TGTAGAATTA CCTTCTTCAA AGGCCCTGTT CTAGGTATAG ACGCTCTTAC
93601 TTTCACTCTT ATAATAATAA GATATCCTCA AGGTCAGATG AGCTGTTCAG
93651 TGCTGTTTAC CAAATAGCAT AAAACTTCAG TTTAGATACA TATTTTAGTG
93701 GGTAGGTACT ATATGTTAAT TTGTGCTCCC TCAGAAAGAT TTGTTGAAGT
93751 CCTAACCTCC AGTGCCTCAG ACTGTCATCT TTTTTGGAAA GAGGGTTTTT
93801 ACCCAGATAA TCAAGTTAGA ATGAGGCCAT TAGTGTAGGC CCTAATCCAG
93851 TATGACTGGT GTCCTTATGA AAAGAGGAAC TTTGGACACA GAGGAACATA
93901 CAAAGAGTGA AGATGATGTG GATGTAGAGA GACACAGGGA GGATGACAGG
93951 TGAAGATGGG GGATTGATGT GATGGGTCCA CCAGCCAAGG AATGCCAGAG
94001 ATTGCCAGCA AACCCACAGA AGCTGGAAGA GGCCTGGGAG GAGTCTCCCT
94051 GAGAAGTTTC AGAGGGAGCA TGGGCCCTGC TGGCATCTTG ATTTTGGACT
94101 TTCTACCTTC AGAACTGTGA GAAAATTAAT TTCTGTGTTC TTCAAGCCAC
94151 TGTTTGTGGT ACTTTGTGAC AGCAGCTCTA ACAAATGAAT GTAGTAAATA
94201 TGTTTCTATT GTTTTCTTTG CTGCTAATTT TTTAATCTTT GCTTCTCTAG
94251 TAGGTGCTAC TCAGAGCACC TTCTGTCCTC ACTCCTAACA TGCTGCTTAC
94301 AATACATTAT GGGATAGAAG ACCAAGTGAC AAAACTTGTT TGTATTGTTT
94351 GTAAAATTAA ACTAAACCAA GAGAATATTC AGTAAGTCAA GTCCATTGGC
94401 TTTAGTATAG GGTAACCTAT TTTAATGTTG CCAGAGACTG TCTTTGCTTA
94451 CTTTTGTATT TCAGGTTTGG GAAGATATTT TCAGTATCTG TAGGCTTTTT
94501 TTTTTTTTAT ACCACTTCTC CTGTCCAAGG TGTGTTGTTT TGCTTTTATA
94551 TATCTATTAG GAAAGTTAAA TCTTTTCCAT TTTACCAAAG CTACATGTCC
94601 AGTATGAGAA CATTTAAAGT CTAAAAATTA TCTGATTACT TATATTGTAT
94651 GTGTTCTGCT TGATGCTGGC TTTCTTTCAG TGTATTGATA AAAGTTTCTA
94701 TTTGTTGCAG TGGAATAATA GACTTTGGTT TTAGGCTATC ATCTGTGGAG
94751 TGCTTAAGAA AATGCCCTTT CTTTTTGTTT TGGTAAATCT TCTTTTCAGT
94801 AGACCACAAG CCCTTGCAAA TGTTCTCTTT TTCTAACTCT GGTAGCAGAA
94851 GGACCACTTG AGCCTCAAAA CAAAACGGCA GTGCAGTAAT GAGGGTATTA
94901 GGTTGATGTG TTCTATTCAG CACCTGCTCC CGAGCTACCG AATAATGAAT
94951 GAGCATGAAT TACACATTGT GAAAACAGGA GAATCTGCCT TCTTTGTGTT
95001 GTATGCATCA AGCAGTTTCA AAAGGGCTTT GCAATTGTGT TTCTCACACA
95051 AAGCCACCCA TTTGTGAAAA CCCATGTGTA AAGGCAAAGA GAACTGTCTG
95101 TGTACAGGTT AACATTTAAC TAGACTGGCA GAGCTTTTAA TAATTTCTAT
95151 AAGGTTAATG GCTTCGTTAA TATGCAACCT GTGATTTGGT CCAAGTTAAA
95201 TTTTACTTTG CCCAGAATAC ATTATAATAT AAAGCTTAAG CTTTATTCTT
95251 TCAGGTTTAG TCATTTAACA CATAATATTG ATCAATTATG CATGTTGGAC
95301 ACAGAGCTCT GAATAGAGCT TTGAAATATA AAACTATGGT TTTAGTCCTC
95351 TTAGAGCTAT GATGTTTGGT AGGTTAGGTG AAGTAGACAC ATTTTTGACT
95401 TATAAATTTT CAGCTTACAA TGGGTTTATC AGGGCGTAAC CCATTGCAAG
95451 TTGGGAGCAT CTGTACGATG GTATAGATAT ATATAATGCA TATAGTTTTA
95501 TATCCTTTTA AGACAAAATA TGAAGATATT TTATTTGCTC AAATCTTGTT
95551 ACACAGTTTT CCACTGTGAT ATTCACATGC TGACAGAGAG GCTATTTGCA
95601 TGGTGTTTGT CACCAGCAAT GAACAGCAGC ATTTGAGTTA TGTAGTGGCT
95651 CTGCCAGTTA CCAGTGGGGC AACTTGGGCA AGACACTAAG CACCTCTGAA
95701 CCTCATTTGT TTTATCAGTA AAATGAAGAT AGCTATACAT ACTTCACAGG
95751 CTGTGGTGAT GATATATTCT AATGAATATA CAGTCTTAAA TAAAAACATT
95801 CAATAAATTC TAGCTACTCA TTTATATTAA TTTATTATAC CCATTTGCTT
95851 TGAGTTATCT TCTTTGCAAT AAGCTGTGGG AAAAACTTAC TGTTCCTTCT
95901 CATACTCCAG GATACATCAT CACCCAAATC ATTACACATT CTTATATAAC
95951 GCAAACATTA AGAAAGAACA ATAATCTTAC TAAAAAGCAG AGTGTGGTAT
96001 GGTAGAGAGA TTAAGAGGCT TTGGAATAGT TACATCAGGG ATCAATTAGT
96051 GAGCTGTGTG ACTTTAGGCA AATTAATAAA CTGAATTTCT TTAAATTTTG

FIGURE 3EE

96101 TTAAATAGGT ATAATAACAT TATATATAAG AAAGCAGGAA AAATATGAAC
96151 AGCTCCTATT ATAATGCTTG CAAAATCAGG AGTGCTTAAT AAATGGAAGC
96201 CACACTGCGA TTTTCCAGAT AATTGTGAAA CAACTACGGG CCATTACAAA
96251 ACCATAGGAA ATTAGAAGTG AGGAGTAATT TGGAGACTGA CAAGCTCTAC
96301 CTTCATCTAA AGGCAGAATT TCTTCTGCAG TCTCCCTAAC AAGGAATCGT
96351 TATACCTCAG GGATGGGATA GTCACTACCA CATAAAGTAG TTCATTTTCA
96401 GACATGCATA ACCTTAGAAA GTTCTTCTCT TGATTTACAA TTAGCCTCAT
96451 AGTTCTGTTG CTGCCTATTG GAGTTTTACT ACGTGTACAG TCAGGCAGGG
96501 CTTCCATTCA GTCACCACCC ATTAGTACTG TTGTACTAGT AATTTATGGA
96551 TGGCGTCCAT TCTTACTGGT CCATGTCCCA TTCTGATTTG TGTTTGTGCC
96601 ATTTTTAAGT GTTTTGAATA TTAACCCTGG TATCAGATAA ACATGGAGTC
96651 CTGACTTTTT CCATAATCAT GAATAACAGT GGAATAGTTA CATCAGATTT
96701 GTGTGCCACT GTGGTCCCAT CTATGAAATA GGGATAATAA TTGTACCTAG
96751 TTCATAAGGT TGTTTGAGGA TAGTGTGGAA TAAAGTATAA AAAGGGCTTA
96801 GCCTGGTTTC TCAAATATTG CAATAAATGA AACTTAGCAT CATGATGCTG
96851 TCACAATGGT TCAATGATAA TTGAAAACAT CGATTCATCA TTTAGCATCC
96901 TCAGCTTATC AGTTTCTCAC TATCTAGCTC TTCTTACACT GGACACTTCC
96951 TAATTATTCT TTCAATGTTT TCTGGAAGTT AGTTGAATAA TTACTGTGCA
97001 CCAGATACTA CACAGTAGTC CCCCTTGATG CATGAGGGAT ACATTCAAGA
97051 CCCCCAGTGG ATACCTGAAT ACGCAGATAT TTCCAAACCC ATATATACTA
97101 TGTTTTTTCC CTTTTGTACA TACCTATGGT AAAGTTTGAT TCATAGAGTA
97151 AGAGATTAAC AATAACTAAT AATAGAACAA TTATAACAAT ATGCAGAGTA
97201 AAAGTATGTG AATGCAGTCC CTCTCTCAAA GCATCTGATT GTACCGTACT
97251 TACCTATTTT TGAACCACAG TTGACTGTGG GTAAAAAGGA AAACTGCAGA
97301 TAAGGGGGGA TTACTATACT ACGAGTTTTA CATGTACCAT TTAACTAAAT
97351 CATTACGACT CTATAAAGTA GATATGATTA TTGTCCTCAG TTACAAATGT
97401 GGAGGGCTGA GTCTCAGAAC GTTCTATTAC CGACATGGTT TTGGTCCCAA
97451 CAGAAAACCT CATAATGGTT TAAACAATAA AAGAGATTTA TTATCTTATA
97501 AAATCAGAAA ATCCAGATGT GTGCTGGACT TGGAGGGTAT CTTGATTCAA
97551 CAATTCAGCA GTATCACCAA CTAGCTGGTT TCTTTCACTC TCTTCTCTCT
97601 TTTCCATGTG GCCACTTCAT CCTCAGCTTG TTCCTCCATG TGATTGCAAG
97651 AAAGCTGCCT GCTGCCCAGG GCTCCATGCT AAATTCTTTA AATCTAAAGA
97701 ATCACACTCC TTCTCAAAAC TTTCCCCAGG ACAGCAAGGA AGCTTTTTCC
97751 TCAGAAGCCC AGAACATAAT TCTTTCTGAT ACTCAGTGGC TTAAATTGGG
97801 TCACCAGCCC ATCCCTGAAC CAATAACAGG GCCTGTGGGA TGGGATAACT
97851 CCTACTTAGG CCTGACTCAC ATAATCCTTC CCTACAGTCA GGGTGGAGTA
97901 GGTTTCCCAA AGCACACAAA ATACAGTGTG TGTGTGTATG TGTGTGTGTG
97951 TGCGCACGTG CATGCGTGCG CGTGTGTGCG CGCATGTGTG CATGAATGTG
98001 TGTGTTACAG AGAAGTGAAA ATACCCAGTT GAAAACTGAA ATGATGATTA
98051 AGAGAATGAA GAATGCGTAT TAGAAAGGCA ATCAAAATGA CCATTAGTAA
98101 GCTGCACAGT CGAGATCTGA GCCTTGGTCA TTTGACTACA GAATTAATAC
98151 TCTTAAACCT CCACTATCTA CTGCTTCCCA AATCAACCTA GAAATCCCTG
98201 GGGTTGGATA GGACCATTTG TGTTTGAGAC TATTACCAAC ATTACTAAGT
98251 ACTATACTAA TATACTCATG CAACCTAAAG CATATATATG TGAAGTGTGT
98301 ATATGTACCC ATATATATAC ATACACACTC ATATACTACA CACAGTATAG
98351 CCTATACAGG GCTCATGTTT AATCAGCATA CACTGGTCTG GCCCTATCAG
98401 TTGTATTTCA GTGTATTGGC TGATGAAGAG GTCATGCCTA AGCTTTGCTG
98451 CTACTCCAGC CCCTTTTCCA ATCTCCCCCT CATCCCCCAC CCCTTCCCTC
98501 CCTTGACCCA GCAACTGAAG TGCTAACTCC TGGCCCAGGA GAGGTCCTTC
98551 AGGGCACTGC TCCTGGGCTT CCATCAGCAT CCCTTCTGAT GAAAGGATGA
98601 CTGTGCTGTT CTGGTTGTTA AATATTTTGT CCATCACCTC TGGCTATTTG
98651 TAAATATATA TACTTACATG GAATACTATA TATGCCCACT ATATTTCAGT
98701 AAACTTTACT ATGCTAAGCT CTAGAGAGTT TAGATCATTT GTCCAAGATT
98751 ACATAATGAG TGACTGGGAT TACAACCAAA GATTGTGAAG TACAATCTTA
98801 GGAGGATGAT ACCTAGTCTT TAATCATCTA ACCCTGACAG CCTTTCACTT
98851 CTGCCCCCTA TTCCAAACTG TTTTTCCTTA TAATTTTCCC TCACTCGCTC
98901 TTAACATGGG TCTGTTTTTT GAGACCAATA GCCCATCTGT GACACCCTAA
98951 ATAATATGTT ACAGAATTAT ATGTATAATA TTTTTCCCCT CTCCAGAACT
99001 TGGCGATGGC CCAATCTGAG AGACTGTTAT GTGGCAAATA ATTAAATACA
99051 AACTATGGAC CATCAAAAGG CCATGGGACA CTGAAGGAGT TGATTTTGGT
99101 TTCGATATAC CGATTTCCTT GTTTGCTATT TTCATGTACA TGTACCGGTA
99151 TAGGATTGCA GGGTGAGCAA CTTGACTCCA GGGGAGGCGC AATGAAGGGA

FIGURE 3FF

99201 TGTAATTAGC CTGTTAACCC TGCTAATGTC TTGTAAAGTC ATTCAAGTGA
99251 GAAGAGTAGA TACATCAATT CTTCCTTGGA TCCTGCCACA AGGAGCATTG
99301 TATTTCCACT CTGCTATTTA TAGTTCTCAC AGCTGGAATC AGCTGGTTCA
99351 GCAGGACATG GCTCTTTTTT ATTTAATCAA ACCAAGATGC AATGAAGAAT
99401 TTCCAAAGTA TGCATCCTAG AATTTCCCTT TATCACCCCC AAAATTCCAT
99451 AGTCCCTCTG AAATCATAGG CTCGTAACAG GCATAAATCA CTTCTTATTT
99501 ATTACTCTTA CTCTAATACA TACACATACA CTTACTGGAA AGTCAAGTTT
99551 CTTAGTTGGC CAATGGTAAA TGTGGCGCAT CTGGCACACA GGGTTTGTTT
99601 GGGTTGTTTT GGGGGTGGGG ATTGGTTGTT TTGCTTTGTT TTGTTTTCTC
99651 TTCTCTTCTT AGGGGAAAAA GACATGCAGG GCTTAGTATT CCAACAATTT
99701 GAGAAACCAG GGGGCTGGGA TTCATTCATT TTTATGACAA ATAGTTACTC
99751 GAGCACCTAC TTTATTCTTG GGTACTTTTA TGAGTCCAGG GGCTGCTGCA
99801 TTGAACAATA CAGAAAAGAA GTCCTTTCAC TTAGAACTTA CGTCCTAGTG
99851 GGGGTTGGGG GTTGGGGGTT GAGAGAATGA AGCATTCTTA CAAAGAATGT
99901 TAAAAGCGAA CTATGGGCAG GAATTGAGGA TATGAGTTTT GATGTATAAA
99951 GAAAAAGTGA CAAGGTCAAT AATTGGTGGT CTTAGTGTGA TAGATATGCC
100001 AGTTTGGAAA TTGTATTGAA TAAATGCTAG TCAGGGGCTA GGCTGTAGTT
100051 ATGAAAAGGA GATGATTAAG GAAGTGAGAA TAAGGAAACT ATTGGTGTGG
100101 GACGGATGAA AAGATTATTG GAGGCAAGTC AAGGAACTGA GAGGCCAGGG
100151 TGTTAGATGG AGCATTCATG TAGACACTGA AGTCACCAAG AATAATAAAT
100201 AACAAGTAAG AGGGAATTCA TCATTAGCTA TCTGCTTATG ATATGGATGT
100251 GTTTTTGCTG TGTCCCCATC CAAATCTCAT CTTGAATTGT AGTTCCCATA
100301 ATCTCCATTT GTCATAGGAA GAATGCAGTA GGAGTTAATT GAGTCATGGG
100351 GGTGGGTTTT TCCAATGCTG TTCTTGTGAT AGTGGGTGAG TCTCATGAGA
100401 TATGATGGTT TTATAAAGGG CAATTCCCCT GCACATGGTC TCTTGCCTGC
100451 CTCCACGTAA GAGGTGCCTT TGCTTCTCCA TCACCTTCTG CCATGATTGT
100501 GAGGGCTCCC CAGCCATGTG GAACTGTGAG TCTGTTAAAC CTCTTTTTCT
100551 TTATAAATTA CCCAGTCTTG GGTATGTCTT TATTAGCAGT GTGAGAATAG
100601 ACTAATAAAG CCAATTGGTA TGAGGAGTGG GGCACTGCTG TAAAGATACC
100651 CAAAAATGTG GAAGCAACTT TGGAACTGGG TAACAGGCAG GGGTTGGAAC
100701 AGTTTGGAGG GCTCAGAAGA AGATAGGAAA ATGTGGGAAA GTGTGGAACT
100751 TCCTAGAGAC TTGTTGAATG GCTTTGACCA AAATGCTGAT AGTGATATGA
100801 ATGAAAAAGT CCAGGCTGAG GTGGCCTCAT GTGGAGATAA GGAACTTACC
100851 AGGAACTAGA GCAAAAGTGA TTCCTGCTGT GCTTTAGCAA AGAGACTGGT
100901 GACATTTTTC CCCTGCCATA GAGATCTGTG TAACTTTGAA CTTGAGAGAG
100951 ATAATTTAGG GTATCTGATG GAAGAAATTT CTAAACAGCA AAGCATTCAA
101001 GAGGTGACGT GGGTGCTCTT AAAAACATTA AGTTTTATTC ATTCACAAAG
101051 ATATGGTTTG GAATTAGAAC TCATGTTTTA AAGAAAAGCA GGGAATAAAA
101101 GTTCAGAAAA TTTATAGCCT GATGATGGAA TAGAAAAGAA AAACCTATTT
101151 TCTGAGGAGA AATTCAAACT GGCTGCGGAA ATTTGCATCA GTAATGAGGA
101201 GCAAAATGTT AATGGCCAAG ACGATGGGGA AAATGTCTCC AGGGCATGTC
101251 AGAGGTAGCC CCTCCTATCA CAAGCCCTGA GTCCTGGGAG GAAAAATGGT
101301 TTCATGGGCT GGGCCCAGGG CCTTGCTGCT TTCGTAGTCT CAGGACTTGC
101351 TGCCCTGCAT CCCAGCTGTT TCTAAAGGGG CCAACATACA GTTCAGACCA
101401 TTGCTTCAGA GGGTGTAAGC AGCAAGCCTT GGTGGCTTAC GCATGGTGTT
101451 GGGCCTGTGG ATGCACAGAA GTCAAGAATT GAGGTTTGGG AACCTCTGCC
101501 TGGATTTCAG AGGATGTATG GAAATGCCTA GATGTCCCGA CAGAGTTGTG
101551 CTACATGGGC AGAGCCCTTA TGGAGAACCT CTGCTAGGGC AGCGTGGAAG
101601 GGAAATATGG GGTGGGAACC CACACACAGA GTTCCCACTA GGGCACCACC
101651 TAGTGGAGCT GTGAGAAGAA GGTCACCATC TTCCAGACAC CAGAATGGTA
101701 GCTCCACCAA CAGTTTGCAC CATGTGCCTG GAAAAGCTGC AGACATACAA
101751 TGCCAGCCAA TGAACGCAGC CAGGAAGGGG GCTGCACCCT GGAAAGCCAC
101801 AGAGGTGGAG CTGCCCAAGG TTGTGGGAGC CCACATGTTA CATCAGCGTG
101851 ACCTGGATGT GAGACATGGA GTCAAAGATT ATTTTGGAGC TTTAAGATTA
101901 TACTGCCCTG CTGGATTTCA GACTTGCATG AGGCCTGTAG CCACTTTGTT
101951 TTGGCCAATT CCTCTTATTT GGAATGAGTG TATTTACCCA CTGCCTGTAA
102001 CCCCATTGTA TCTAAGAAGT AACTAACTTA CTTTTGATTT TACAGGCTCA
102051 TAGGCAGAAG GGACTTGCCT TGTCTTAGAT GAGACATTGG ACTGTGGACT
102101 TTTGAGTTAT TGCTGAAATG AGTTAAGACT TTGGGGAATT CCCAGAACTG
102151 AGGGTTCCTC CCCATTGTAG ACCATATAGG TAGCTTCCAG ACGTTGCCAA
102201 GGCATTTGTA AACTGTCATG GTGCTAGTGA GAGTGTCTTT TAGCATGCTC
102251 ATGTATTATA ATTAGTGTAT AATGAGCAGT GAGGATGACC AGAGATCACT

FIGURE 3GG

102301 TTTGTCACCA TCTTGGTTTT GGCCAGCTTC TTCACTGCAT CTTATTTCTA
102351 TCAGTGGGGT CTTTGTGACC TGTACCTTGC AAAAACAGTC CTGCTGATTA
102401 CTAAATTCCT ATCTCACCTA TTCAAGATGG AGTCACTCTG GTCTGAATGC
102451 CCCTGATAAG AGAATCCACA GTGTTCAATT CTCCCCAGTT GATTCTGAAG
102501 CATATCCAGG TTTATTAGCC ACTAAGTAAA AATATATTAT AGACTACTGT
102551 CAATGAAAGA AACATTTTGT AAGTTATTTC ATATTTATTT TTACTTGAGA
102601 AGACTGAAAA GGTAAAGAAG TGATGCTAAA ATTTAGAACT AGAAAATCTC
102651 AACTTGCTCT AGTAGGAATT TTAATAGAGC ACACTAAGTT TCTTTTCATT
102701 TTCTCTCTCC TGGTATGTGA ATAAACAACC TTCCATACTG CAATTTACCC
102751 TGTAGTGAAT TAGATGTTAC CCTATTATAT TTTGGAGAAA CTATATAGTT
102801 AGAATCTAAG CTTAGATAAC TTATTTTTAT GTTTACAAAT CCACTTTCTC
102851 TTATACATTT TTCTTAAATT TTTCTCATAT TCTTTCTCTG AATTTGTGGT
102901 AAAAATACCC CTTTCCCATT CTATGTCATG GTTCTTTACG AAGCTTTCTC
102951 ATCCTCTCCA TCCCGAGGGA ACTATGTCTC ATTTATCTTT AGGTTTTCTG
103001 TATCTTACTA CAGTGACTTA CCAGAGTAGG TAAATATCTG ATGAATAAAT
103051 GAATACAAGA TTTAATTAAG AAGTAATCAC ATTAAACTAA TTGTTCCCTC
103101 TCTGATCTCT GTAATATTAA GTTTCAAAGT AGTTTCTGGG AAAAGTAGTT
103151 AACACAATGA TGTATGGATT CAATAAATAA GAAAAATGGT GCTCAGGGAT
103201 TTAACAGAAA GCTCATAAAA TGTCAAATCC ACAGCAATTA ATTTCTCCCA
103251 GTAAGTCCTC ATAAATTCAG GCCAAGAAAT TTGATACTGA TCTTGCCTCT
103301 CTCAACTCTC ATCCATCTTT GGTAGGGCTC CTCTGGGCCT CTTTTTCACC
103351 TGGCAAACAG TACCTGATAC TCATTGGATG CAGATCTGAA AGAGGTGGAA
103401 AGAGCCCGAC ACCTGGTTTA TCTCTAGCTT TATGGTGCAG AGAGTATTTG
103451 ATGGTGTGCA CAGTGCTCTG TATATACTGT TAGGATCAGC CTTCTTGAGT
103501 GCACTGGAAT TTCTCTGGGT GTCATTAAGT TCTTCATTTA CTGACCATGA
103551 GGCACTGGGA TAGAATATGA TATTAATCAA GAAACCATCC CTGACATCAT
103601 GATCCACTTG GAAAACTTGC AGAAATTAGA AAAATTTTTT GAGTAGGCAT
103651 TTTGCTTTGT TGCCCAGGCT GGAGTGCAAT GGCTAGTCAG GGCACAGTTG
103701 TGCAATGCAG CCTCAAACTC CTGGGCTCAG GTGATATCCC TCTTCCACCT
103751 CCTGAGTGGC TGGGACTATA AGTACACACC ACTGTGCCTG GCAAGAATTT
103801 TTTTTTTTAG GATGTTATAA GGCCTATAGT TATTTAATTA TTAATCCTGG
103851 GGTAGTTAGT GAAAAGATTT GGACCAGTCT TTTACACACT GATGTACAGC
103901 AAGATAACTA TAGTTAGTAA CATTGTATTA TATACCAGAA ATTTGCTATA
103951 TCAAAGTATC ATGTTGGCCA CTTCAAACAC ACAATTTTTG GTTTAAAATG
104001 ACTAAAAAAA TTAAAATAGC AAAGTAAAAA AAATTCACAG GAGAGCACAA
104051 AACCCACCTT CTTCCAATGA AGGGAGTAGT CTGGTGGTTA ATACTTGGAG
104101 GATAGAATGA TAGAGTTTGC AAAGCCTTGG TGAATATTAT AGTAAGGAAC
104151 ACTCCTGAAT CAAAAAATCG CATTGTACTT TATAACAGCC CTCACTTTTC
104201 CACTCTCAGA TTTTTACTGC CTTTCCCTAA TGTACCATTA AAGCCCTTCA
104251 GCCTAAATTC ATAGACTCCA TTAGAGAAGA AATTCTGAAA CAGGTTTTGG
104301 GAACACATTC TCAGCCTAGT CAAATAGCTT TCATGCTGCT AGAATAAAAA
104351 TACCTTAATC TTTGACAGAC CAAGTCTGTC AGCTTACTCT TTACTTAAAA
104401 ATATTAATGA GTAACAAGTC CCATATCCAT AAACAGAACC AAGTGTGTGA
104451 TAAACTGTGA TAAATGTTAT GGTGGAAGAA GTATCCCATG TGGTCAGAAT
104501 ATATGGGATT AGGGGGGATT TGACCCAGAA ATGAAAAATC AGGAAGGCTT
104551 CCTGCAGGAA ATGGCATCTG AGCTGTGGGG TTAAGGGTGA ATCTGTGTTG
104601 TCTGAGTGCA CTGGTGAGAG GACTCTAATT TAGGCAAAGC AACAGCAGGT
104651 GTGGATGTGA GGAGGCAAAA GGAGACAGGG GGTGGTTATA TAACTACATT
104701 ATCAACCATA TTTTTCCCAT TTATAGTCTT TAAGCTCACA TCATCTGTGC
104751 AATTCTAGAG TTACACAAGA AAATGATGCT TAATACTACT AACATTACTT
104801 TATGGCAATG TAAATGCTTT ATATGATCCA ATGGACCAAT ATCTACATGC
104851 TTAGATACAA CATGCTATAG GAAGTTTAGA GTCTGAGTTT TTGAATGAGA
104901 GAGGCCTTGG TTCAGAGCCC ATTTCTTCCA TTTACTAGCC TGTGACCTTG
104951 GGTTAAGCTT CAGTTTTCTG ATTTAAAAAT TGGGGATTTT CTGTCTCATA
105001 AATTTACTGT GAGAATTGAA TGAGAAGATG AGTATTGAGA AGCTAGTACA
105051 CTGTTTCAAC TCCAGTTAGC TTTCTTAAGC CTTTTTGCCC CTACCCCTTA
105101 GTTCTGTTCG TTTTATTGTG AGCAACTTTC TTTTTTCTTT TTACTCCTCT
105151 AGGGATATGA AGCCTGACAA TATTTTACTT GACGAACATG GTAAGTGAGT
105201 GATTTGTTTG CAATCAAGTA CATGACATGC ATGTAGAAAA GTTGATTGTT
105251 CCCAGCAGAG GGGTATTACA CATGAAAAAG GTATTTTGTT CTATTCATTC
105301 GAGCTCTACT TACAAACTCC TCATAGACAA TATGGGGGAA CTTTATTACT
105351 TATGGCAGGT TATAGTACAA CAATACACCC TTAAATCACA TTGAATTTAC

FIGURE 3HH

105401 CTAATGAGAA AATCATAGTC TACTCAATTT TCTTCCACTA CTATATTTCT
105451 TCAAGAAAAC CATCACAACT TTTCAGTGTT AGCTGGCCTT AATATAACAC
105501 GCAATCACCT ATTTTTTATA ATGATACAGA AGGCCTCAAG CTGAGAGCAT
105551 TTGGCCAGCA ATAGCATCTA CCTAGACATT AATGACATTA TTTTGTTCTC
105601 ATTGCATCTA CTTTTTTGCA TTCCTTCTTA TAAAAGGCAA ATTGGTTTTA
105651 CATTTGCAAA TTGGTTTTTA CATTTACTTA ATATCACAGA AGAATTCTTA
105701 CATTTTAGGG TCATTGTAAA GACTGACCTA ATACATGTAA ACTACTTGAT
105751 GCAGTGACTG TCACGAAGAA ATCACTCAAT AGAAGTCTAA TATTGGTACA
105801 ATTTTTATGA GGTGGTCATG GGTTTCTCCC CTTGGAAAGG AAGCTGGAAC
105851 TGCTTCATCT TGTTTTATGC GGCTTTGTCT ATGCTGGCAC ATAACTAGTA
105901 TGTACCAATG TATCTCAGAA AAGATATCAA GTTTTCTGTT TAAAAATTTC
105951 AGTTTGAGAA AAATCAGTTA AAGAAAAACA TAAAAAAGAT AAAAGTATAT
106001 GTGTTATCTA GATTTGTGAT ATAGGGATAT GGCAATAATC AAGATGGTGA
106051 TAAGTGAATG CTGAATTTCA AGAACTACTG ATTACACCCT CTAGAATAAG
106101 CTTTTGCCCG TGATGATTAA ATGTGTACGA TTTCTTCCTA ATATTTATTT
106151 TTGTGTATAT TGGGATTTAT TAGAATATCA GGGAAGATCT GCAGGGCACA
106201 AAAACTGTAT GTTATAAATG TTAACAGTGT CAATAAGATC TTTGTTATGT
106251 CTTTAGAAGG CTGCTAGATG AGGAGAGTCC TAGATCTTAA AGGCTCCTTA
106301 TTCAATTTTT ACAAAAAGGA TTTGCAAGTG GAACTGAAAC TCCAAGTACC
106351 ATCTATTGCT CATTATTTAT TTACCTATTT TTGAGCCTGA TTTTCCTGAT
106401 CCCACCTGTG CTCAGGGGGC TAAGAAACAC TGGTAATGAC CTCTAATTTC
106451 AAAGCTCACT GTCATTACTT ATTTATGGAC TGTCCAAAAA GATTTTTTCC
106501 ACTTTCTTCC AATGCCTTAT TTCTTCCTTA CCTTTACTGC TTCTGACATT
106551 TGAAAACAGG GTCTCTGATT CTCAGAAATG TGAGCAATGG TGAGATTTAG
106601 CATGAAGGTG ACTTTCTTTA AAATACCAGC TATCCAGAGC TAGGTACAGT
106651 GGCAGGCACC TGTAGTATCA GCTACTTGGG AGGCTGAGGC AGGAGGATCG
106701 CTTGAGCCCA GGAGTTTGAA TCCAGCCTGG GCAGCACAGA GAGACCCTGT
106751 TTCTTGTTGG GGGAAAAACA ATTACCACTG GCTTCTCTTC TAGCCTATAG
106801 AGGCCACCTT TGTGCAACTT AGGGAGAAGT GCTCCCCCTG CCCACCACAG
106851 CTTCCTGACA GCACATGGCC CACCAAGGAG AACCCAAGTT AGGATTGAGT
106901 CCTCACTTGC TCCCTCAGCT GGGTGCCTTT GTGCATGATT TCTGCTGTTC
106951 CACCATTTAT AGAGGCCTTA AATGAAGGCA TATAGGTCCT ATCAATCCAA
107001 CACTTTCCCA GCTTTATCCT CCCTTCAGAG AACAGTGTTT TCATCCCAGG
107051 TCTCATCCAT GGCTTCACCC TACTTCTATC ATTAAGGCAT CCTATTCTCC
107101 TTCAGTCAAC TTCTTCCTCC TCCTCATTTT CTTGGTGACT TGGTCATTGC
107151 AGATGAGGAA AAACATGAAG AAATCAATTA ATCTTCAAGT TTAACCACCT
107201 TTAGAGACTA CCCTTGTGAA AGATTAATTG TGTAACAGTG TGGTTAAGAA
107251 TGTGACTTCT GGAGCCAGAT TGCCTTCATT CAAAACACAC TTCACTCATT
107301 TCCTAGCCCC GAGAGCTTTG ACAAGTTGCC TAAACTTTGT CTTAGTTTTT
107351 CCAGGGATCA AAAGAATACT TACTTAGAAA AAAAATCTTA CTTACAAAAG
107401 AAATCTTACA GGGATCAAAA GAATACTTAA TTAGGGTCAT TGTAAAGACT
107451 GACCTGATAC GTGTGAAGTA CTTGATGCAA TGACTGTCAC AAAGAAATCA
107501 CTCAATAAAA GTCTAATATT AGTACAATTC TTCTGAGGCA GTCATGGCTT
107551 TCTTTCCTTG GAAAGGAAGC TGGGACTGCT TCATCTTGTT TTATGTTTCT
107601 TTGTCTATGC TAACACATAC CTAATACGTA CCAAATCTCT ACCAGATAGA
107651 ATCTGTAAAA GTTGTCCTTC CCAAATAATT ATTTTGATTT AAGAAGTGAT
107701 ATACCAAATA TTCTGCTTGT CTACTTCTTA GATCTTGTGT TTAAACCATT
107751 TTGTTTATCC CTTCATCCTC AGGTAACTAC ACTTTCCGTG TACATTCTGC
107801 TGTCTTTCAT GTGTGCAGGG GGCAAGGGTG CAGTCATGAC ATTTTATTCT
107851 TGGTGGAGCT GGGGCTCTGT TGCCTACAGA ATACAAGCCA TCATTCCAGT
107901 GTGCCAGAGA GAGAGTCTCA GTCTGCCCCT ATTACCTGGT GTCTTATTTA
107951 CAATGACTGC TTTCATTCTC AAGGCTTTTT AAAATTTGGT CAGTGAATTA
108001 AGAAGAGGCT TTTCTGTATT ATATTCCTAC CCTGAACTCA ACTTGAAAAT
108051 CAATTGCTTT GGGAAGGATT GTATATGAAT GGTACAGAAG TGAGCAAACA
108101 AAAAAGACTG AGAGCCATTT TCTAAACATT GCCTTAGGGA TCTCTTTCTG
108151 GAGATAATAA TTTTTTTGAA GTTATTTACT TCGTTTGTTC AGATTCTGAA
108201 AAAGTAGGAC TCTCAGACAT TACTCAAGGA ACATAATTAA CCACTTTTCC
108251 ATGAACAAAT TCCTGTTGTT CACCTCTCCC CAGCTCGTTA TGTAGAGCTG
108301 ATCTTGTGAG AATCAGCTGA ATCACAAATC AATGCCTGCC TTTTAGAGTG
108351 TCTGCTGGTG TGACTTTCCA TGTGGAGCTC ATATTTGAAG ACCTCATTTG
108401 CCTTCTCCAT CTCCATTTAT AATATTTCAT CCCTGATGGG CTGTCGCTTG
108451 GGCCTCATGT GGAAATTGTA GCCACTGTGA AGGGTAACCA CCTATCTCTC

FIGURE 3II

108501 TGGTGCCCCC TATGCGCATC CCTACAAGTG AGCTGTGTAT CACACCATGC
108551 TGCTTACATT TTTATGCAAC ACGATTCAGT AACAGGCAGA AACTTTTATT
108601 CTTACTGACT CATATTCTTT ATATTCATCT GAAAAGATTG ACATTTAAAG
108651 GAGCCAATTG TACAATGGGA AATCCACTGT GTGAATATTT CTTGTACATC
108701 AGAATTTGCC TTAAAAATGT TTTTAACTTA GAGCACATCT GTACTGTTCT
108751 CCCCAAATGT CCCATTTACT AGTTCAGAGC AAGATGACAT TAGGTCTTGG
108801 GTGACTCCTG ACCCACTATC CTAATGTATA TTTTCATTTC CTACCAATGT
108851 AAGTACCCCA TCCAATTCTA TCAATACCAT AGTGTCTAAA ATTCTTGTAT
108901 TTTTCTTATT CAGGAAATGC TACAACCAGA GGAACAGTAA TGTCTGCCTG
108951 ACATATCAGA GAAAATGACA ATTATGTCAT CATCTGTCAC TTAGGTTTCT
109001 TAATACCATC CTGTTACAAG GAATAGAGGC AAAAACTCAG CGTAGGAGGT
109051 GAGAAAAAAC TGAGGCTGCC ATCTTAACAG CCTTTTCATT GCAGAGTCTC
109101 AAAATGTACC AAAAGATGAA GTGGACAGTG TCCTTTTAAA ACAACATACA
109151 GTGTAGAATA CAGTAACTTA TCCCCATTTA ATTACTCCCT AGGTAGTGCC
109201 TAAGGATATA CATTTTCAGC AAGGATCTCA GAAAAATGTG GGGCACATAT
109251 TCTAAACACC TGCGAGTAGC AGAGACTTAA AAGTTGGGAG CAGTGCCAAC
109301 TGATTGGTTA TGGTGCCCTA GAGCACTGCG TTGATGAAAG AGATCCTCAG
109351 GCTGTGCACA GGAGCAGCAA GAAAGAGTGT AAATGATGAC AACAATGATG
109401 GCTGAATTCA ATGGCATCAT AAAATGAATT CAGATTTTTT ATATGATCCT
109451 CTATCCCAAG CAATAGAGGC AAAAAAAAAA AGGCAGAAAC CCTCTCCTAG
109501 AGTGGTAAAT TAGGAAGTTC TGAGGCTTGC ACCTGAAAAA CTTTTCACTA
109551 AAGTAGTGAT TCTCAACTGG GCGTAATTTT GCTCTACTCC TTCTCCCTGC
109601 AGAGGACATT TGGTAATTTC TGGAGACATT TTTGATTATC AGGATTCCAG
109651 CCAGGGTTGG GAGGTGATAT CAGCAGCTAG TGGGTAGAGG CCGGGATGCT
109701 AGCATGCATC CTGCAATGCA CAGGACAGTT CGCACTACAA AAAATTATCA
109751 GGTCCAATAT TTCAATGGTG CTGAGGTTGA GAAACTCTGC TCTAAGGCTC
109801 ACTCAAGGCC TGGGCTAATG AAAAAAGCCA GAGAAGTCCT TCATTCCCAA
109851 GGCAATTCCT GTGTCCTTCA GTCAGCAGGA GACTGAACCC TTTCCTGTGA
109901 TCCAGCAGTC AAATTTCATT TTCAAAACAC AGAAGGGAAC CTGGCAGATA
109951 GGTCACCATG GTAAGGAGAA GCAAGTCATG GCTGTAGCCG GACCTGGGAC
110001 TAAGGCTTAG GGCCAGCACT CTGTGAAGTT CTGCCTTCAT TGTTTAGCTC
110051 AGAAGCACCA GGTTACAAGA TCCAGTAGAA CCTGACCCTC AAATAATTTC
110101 TCCCTCTCCT TAAATAGGCA TCCTGGAAGT GGACTAGAAC TCTGAGCCAA
110151 TCAGAAATTA ACTGTTTTAG GTTATTCAGT TCTTTGATCT TGTGATACAG
110201 CACACAAAGT TTTTGGTAGA TTCATAGTCT GACAAAGGGA TTCTAGACAA
110251 AATTCTAGGT CTTAACTCCA GCTCTGTAAC TTTTGAGTCT TTTGAACCTA
110301 GCCATAAATG ACTCATATAT AAAATAGGGC CTACCTCACT AGGCTAAAGG
110351 AGAAATTTTG TGCAACAACA TTTTGAAAAC TGAATCATGC AAGTGTAAAC
110401 AGCATTTAAA AGGAAAATAC TCAACATTCT TTCAACTGAC GTGTAATGAG
110451 TACTCACCAG AGTTGAGATG TTCTGCTAAG CCAGGCCCTC TTTTAAAAAT
110501 GTAATCTCAA ACTTTATTAG GTCTCATAAT CACCTGGAAG GCTTATTTAA
110551 ATATTGGCGC CCAACCCACA GAGTTTCTGA TTTGTTATAA TAGAGTTGAG
110601 GGGGGACGGG GCGTAAGAAT CTGCATATCT AACAAGTTCC CAGGTGATGC
110651 TGATGCTGCT GATCTGGGCA CTACATTGTA GGAATCAATT GGCTCTAAAA
110701 CCTTCTCTAC CTTCCACTTC TACATGAGCA TACATAATCT TGTAGCTGAG
110751 TCAGCTTGGA AATCTATGCA GACTAAAGTA GACAGTTGCA TGTCTGGCTG
110801 CTCATCTGAA TCACCTGTGG AATTTGTTGT TTTTAATACA GATACCTGGC
110851 TCTCCTACAA GTCCCACTGA ATTGGAGTTT CAGGAGACCG AAGCCCAGGC
110901 ACATGTATTT TGCAAAACTA CACTGAAGTT TCTGATAATG ACGGATATCA
110951 ACAATTAAAC GCTTACTTCT TGCCAAATGC TGTGCTAAGT CTCCTGTAAT
111001 CATTCTTTCA TTTAATATTT CTAATAACCT CTTGAGAAGA CTATGATTAT
111051 CTTTCCAACT TTACAGAGAG GATAAGTGAC GTTTTCAAGG TAACACAGCT
111101 AGTTAGTGGT AGAACCTAGA CTTGAAGCCA AGCAGTCTGA CTCCAAGAAA
111151 CAGGCTCTTC ACCACAGTCT CCAGACTCAC CTGATTTGTA TTAAACTTTG
111201 TGAATCACTG ATCCAACACT ATGAGCAGGA CCCATGGGGA GAAAGAGAAA
111251 AAGAAAAAAC AGAGACAACC TACGCTATGA TAAAGTTATT GAAATCAGGC
111301 ATTGGTGCCA CTCCAGCAAG AATGAGTGGC TACCTTTTTT TTAGATGAGT
111351 GCTACCTTTA CTTTACTGAA ATATCATGAC ATAAACAAAG CCAAAACACT
111401 TTCTGCACAA AATAAAATCC TGGTGATAAA GGCAGTGGGA TTTATGCTTA
111451 GCAGCAGGCT GGATACTATC AGGGAGCAGA CAAAGAAGTT TGATACAGGG
111501 CTTGTGGACT GTGGGCCCTG GAAGAATCTG ATGACATGCC CTCCAATTAC
111551 AGCTGTATCT CATCAAAACC ACAGACACAT GTAAATGGAA ATGCCAACAC

FIGURE 3JJ

111601 TTCAAGATTC TCTGAAAGCA GTTGACTGTC ATGCCAACAG CTAACATAAT
111651 AGGCTTGTTT GCCTGAGCTT TTGGCACGGC CCTTTTGTTC CCTTTAGCTG
111701 TAAATGCAGG GACCCTAGAG CACCTCATAG AGTGTGTTCC CTGCCACGTA
111751 TAAGTATTAG ACCCACACTA TATTGCTTTG AGTGTTAAAG CTGAAAGAGA
111801 CCCTAGAGAT CATTTAGTCT ACTCCTTCTT TTTTTATGTG AAGGAAAATT
111851 TAGATCCACC TTGGAAAAGG ACTTAGAGTC TACTATGTGT TAGAGGCTGA
111901 GTTCAAGGCA GAACCCAGGC CTCCTGGCTC CCAGTCTAGT GCTCTTTATA
111951 GAATCCCTTT AAAAATGAAG TTGACTGGCC GGGCGCAGTG GCTCACGCCT
112001 GTAATCCCAA CACTTTCAGA GGCCGAGGCA AGCAGATCAC GAGGTCAAGA
112051 GATCGTAGAA CACCCTGACC AACATGGTGA AATCCCATCT CTACTAAAAA
112101 TACAAAAATT AGCTGAGCAT GGTTGTGCAT GCCTGTAATC CCAGCAACTC
112151 GGGAGGCTGA GGCAGGAGAA TCACTTGAAC CCGGGAGGCG GAGATTGCAG
112201 TGAGCCGAGA GCACACCATA ACACTCCAGC CTGGCAACAG AGTGAGACTC
112251 CACTTCAAAA AAAAAAAATT AAATTAAATT TAAAAAAAAC CTAAAGTTAA
112301 ACCCCGCCCC CCACCCACCG CCCCCCGCTA TCCCTTGATA ACAGTTATTT
112351 TGCTGGGAAC TGATGAGGCC AACCTGAATT ATCAGACAAA AAATATGTAC
112401 AAAAATATTT TAGAAAAACT GAAGAAAAGG GATGCTTTCT TGGCTAGGAA
112451 ATAAATATTT GTATCCATAT TCATGCCAGT TTTGTAGTAA TAATATTTGC
112501 CTCTTACTTT TCTTTTCTTT TTTTTTTGAG ATAGTCTCAC TCTGTCACCC
112551 AGGCTGGAGT GCAGTGGTGT GATCTCAGCT CACTGCAACC TCTGCCTCCC
112601 AGGTTCATGT GATTCTCCTG CCTCAGCCTC CCAAGTAGCT GGGATTACAG
112651 GCACCCATCA CCACGCCCAG CTAATTTTTT ATTTTTTATT TTTAGTAGAG
112701 ACAGGGTTTC ACCATTTTGG CCAGGCTGGT CTCGAACTCC TGACCTCAAG
112751 TGATCTGCCC ACCTCAGCCT TCCAAAGTGC TAGGATTACA GGGGTGAGCC
112801 ACCACGCCCA GCCTATTTGC CTCTTTAAAA AAAATAATCC CATAAGGGAT
112851 GTTTGGAAAC GTGATACTTT GAGTATCTCT TGGCTGTCTC CTTCATAGTA
112901 TTCATAGGCT AAAGTAACTT AAAATGTCAC CAACAGACAA AAGATGCCTA
112951 ACTAGAATTA CCTGACCACA AATTCTTAAC TACTAAGGGT AAAACTTTTC
113001 TGAGGCTGAA CTACAGGCTT ACAATCAGAG ACTAATCATT GCATATCATG
113051 AAATGGAGAA TTGTTGGTTT AAGACCATAT CGGCCTTGAG GATGGACTGC
113101 AACTGGCCTA CAAGAATTAA CAGACTAATT GGGTGTTTTC AGTTAAAAGC
113151 ATGATTGTGC CACTGGGTTG AATGGGACTT AACTTTCTGT GTGGTTCTTC
113201 TCTCTCTGCA GGGCACGTGC ACATCACAGA TTTCAACATT GCTGCGATGC
113251 TGCCCAGGGA GACACAGATT ACCACCATGG CTGGCACCAA GCCTTACATG
113301 GGTATGGGTT TCATGAGTGT CTTTTTTTTT TCTTTCCTGT AAATACCATT
113351 TATTACAGGT GGAATCATCT GTGGGGATTT GCAGCTAGAA CTGGTAAGTT
113401 CCTCTCTGAC TTTACCTGTG GAGCTTCTGA TTTCATGGGT CTTCTCCACT
113451 AGCAAGCACC CAAGATGACT TTGATAGGAA AGGACCATTG ATTACATTTT
113501 GAAAACTTAC TTCGTGTGTC AAGGAAGACC GTTTGTACCC ACTTCCTAAC
113551 AAAAATATTA ACTAATTCAA TAAATACCTA CTAACTGTCT CTGTGTGCTT
113601 AGCACTGTTT CAGATGCCGG TGACCCTGTA GAAAGCAACA CAGACAAGGT
113651 CTTCAGATCC TGGAGCTTAC ATTCTAGTGG GAGCAGATTT ATAAAAAAAA
113701 AAGAACCAAA CAAGGCCGGG CATGGTGGCT CACGCCTGTA ATCCCAGCAC
113751 TTTGGGAGGC TGAAGTAGGC AGATCATGAG GTCAAAAGAT TGAGACCATC
113801 CTGGCCAACA TGGTGAAACC CTGTCTCTAC TAAAAATACA AAAATTAGCT
113851 GGGTGTGGTA GCATGCGCCT GTAGTCCCAG CTACTCGGGG GGCTGAGGCA
113901 GGAGAATCGC TTGAATCTGG GAGGCGGAGG TTGCAGTGAG TCGAGATCGC
113951 GCCATTGCAC TCCAGCCTGG CGACAAAGCG AGATTTCGTC TCAAAACAAA
114001 CAAACAAACA AACAAACAAA GAAGTAGGAA ACAGTAATAA GCAAAATGAT
114051 AATAAGTGGC AAAGTATTAT TTTAACCATT ATTTACATAA TACTGCATTA
114101 CATACATAGA GCTATAAACT TTACAAAATA CATTCCCAGC TATAATTTTA
114151 GATTTACTTG TAGTGCCACA ACAATCCCAT GAATTCTTCT GTTTAAAGAT
114201 AAGGAAATTC TGGAGCTGGA TGGTGGCATG CATCTGTGGT CCCAGCTGCT
114251 TTGGAAGCCA AGGCAGGAGC ATTGCTCGAG TCCAGGAGTT GGAGGCTGCA
114301 GTGAGCTATG ATCATGCCAC TGTACTCCAG CCTGAGTGAT AAAGTGAGAC
114351 TCTGTCTCTA AAAACAAATA AATTATTTTT AAAAATAAAT AAAGGTGAGG
114401 AAATTCTGCC TCAGAAAGTT TAAATGTCTT TGCATTATTT TGTGTGTAGC
114451 GAGGTGAGGA ACTGGTTTTT GCCTTGACAA TTCAGCATTT ACTAAGGGGT
114501 GACCAAAAAG AGAGTGTTAG ATGCAAAATT GTCAGTTGGT TTCACGTATA
114551 GTTGTGGTAA CAAATCAACT ACAAAAACTC TAAGTTCACC TGTTGGGAGC
114601 AGCCATCTAT ATAGACACCA GAACTAGTTG TTAGCAGAAC CAGCTTTACT
114651 TCCCGTCCAG CCTCAACAAT GCAAGGAGAG AGCTAGTGTC CTCGAGGGGG

FIGURE 3KK

114701 CACACAGTAT TCAGAAAGAG GGAGTTCTCC CTCCCTTTTC CCTGTGGTTG
114751 CTCCTAAGGC AAGTGAGTCA GATCTCAAGA GAATTATCTG TAAACTCTTA
114801 GAGTGACTGC AAGAAAAGAT ACCTGGAATT TAATTCTTGA TTAGATATCT
114851 GTGTAGTTAC TGGACTTGTG ACTGGTCCTG GAGTTAACAC AGCCTGGTTG
114901 GCCATGGAAG TTTGATGAGT TTGGGGGCTA GTCTTTCTGG GGATCATAGC
114951 AGCAGGAGAC AGGTATGCAG TGAATGTGAT TTGTCTTGGG GAGAAGGGAG
115001 GTGGATTAGC TACAGGCTGT GATCCACCTT CACATGGGAC CCTCCAATGA
115051 CCAAGAATAT AGCCTGGAAG GGAGGGAGGC TCCTGTCAGT GTGACTTCCT
115101 GAAAACACCA CAAGTCCCAA TAGAGCTCAA CATATCAGAA TCACTGAGAG
115151 TGGAGTCTAG GCATAGTGTG ATTTAAAGCT CTTAGCGTAA TTCCTCCGTG
115201 TAGCTAGGAG TCACAACTTC CACCACAGAC CCCTAAAGAG AGATTACTCT
115251 GCAGGGTAGC ACATGTGTGA GGACCCCTCT GCCTCGACTA CCCTTCTTTC
115301 ATGTCCTAAA ACAAATAGTG CTTTCTAGGA AAAGATAGAA GGACGTGTGT
115351 GAGAGCCAGA TCAATCCTCC ACCTCCATAC CGGGGTGGCT GAAACCAGCC
115401 CAGCAGGGTG AGTGAAGGAG CTTTGAATCA GATATAAGAA TAGTTTTAAA
115451 ATTCACAGAA CTGAATTGTA AAGCATCTAA AGTAAATGTA ATAAGCAAAT
115501 AGGACTAAAA CTTATTAGGC AACAGACTGA GATATCATTA GGCGAGCTCC
115551 TTATCCAGCA AAAACAGGAA GTTAGACACT GCACAGTTGC TGTCAAATGA
115601 CAGAAGACTA AAAACTACTC ATGCTTGGCG GGGTGCGGTG GCTCACACCT
115651 GTAATCCCAG CACTTTGGGA GACCGAGGCA GGCGGATCAC AAGATCAAGA
115701 GATCGAGACC AGCCTGGCCA ACATGGTGAA ACCCCATCTC TACTAAAAAT
115751 ACAAAAATTA GCTGGGCATG GTGGCGTGCA TCTGTAGTCA TAGCTACTCG
115801 GGAGGCTGAG GCAGGAAAAT CACTTGAACC TGGGAGGCGG AGGTTGCAGT
115851 GAGCCGAGAC TGTGTCACTG CACTCCAGCC TGGCGACAGA GTGAGACTCC
115901 ATCTCAAAAG AAAAAACAAA CAACAACAAC AACAAAAAAC CTACTCATGC
115951 TTTACCCTAA TTAGTTAAGA TGCTTAAAGC AGGTGATGTG GTGATGTTGC
116001 TGTTTAAACT GGTGGGATTA AGTCGGGTGG AATGAATTGT TTCAGCTAGA
116051 TATGGTCAGA GTAATTCAAA GGTAAAATAT TTCAACTTGA AATCAAGGAC
116101 AAGAGCAATG CCATTTTCTT TTAATATTTC ATTCTCTTCC CCCATGTAAC
116151 TAGAGAGAGA GAGAGAGAGA GGAAAAGAGA ACCCCCTACA TGCAGAGCCA
116201 CCTCACTTTC CAACAGAAAT CTTCTATGAG AAAAAAAAAT GAGCCTTATT
116251 TTCTATGATA TTTGAACAAC TGCAAATTTC ATGGCTTTCA ATTACCAGTG
116301 GGGGGAATAA ATCTCTTTTG TCACTTCTAA AATAATGGAC ATATATAATT
116351 CAGCCTATTT TCTGCCTAAA ACCTATGGTA CTCAAATGAT AAAAAAGCAT
116401 ATCCAAGCCT GCTGCTCTGA TGAGTTTATT CTCCAGGTTT CCTGGGTTTC
116451 CATATTAAGG GCTATTTTCT TGGAACCAAA TCAGAAAATG TGCATCTGGG
116501 TTTCCAGGGT TGGTTTCCAT GGTGAGAGAA GTACGGGGAG GCCACCTTTC
116551 TTTCCTCTCC CCAGTGGTTT TAAGTACAAT ATCTGTATAA TGTAATTTTT
116601 TCAAAGTTGG CATTTCTAGT CTTCTCACAA GATAGAACTG GGAAATTGGA
116651 ACCTAGGAAA AATTCTGTGC ACCTTCCACT TTTACCCTTG TAATTAACAA
116701 TGACTAATAT TTCTTGAAAT CTTTCCCTGG ACCAGACAAG GTGTTAAATG
116751 TTTTACATTC ATTTATTTGT TTATTTTTCT CAGCAGCCCC ATGGGGTGGA
116801 CTATACTTAT CACTACTTTA TAATGAGAAA AATCAGAAGC TAAATAATTT
116851 GGCCGAGATC ACATGGCTAA TAATTGAAAA GTCTAGATTT AAATCAAGCT
116901 CTGTCTGATT TCAGAAATCA AGCTTTTTCT TAAAAGGAAG ATTAATGAGA
116951 AATAAAAATA TATATTTGTA AATATTTTTA TCTGTGGTTT TTAAATGGTT
117001 CTAAGTCAAC TTAGTTAGGC TAACATATTC GAAATGTTTC TTGCCTTATT
117051 CCAAAATGAT TATGTGATTG CCACACTCCT CCTTTTGGAT AGGAGTCTTT
117101 CCCAGACGTA TTGTGGGTAG AAGTCTGCTG TCTCTTTTTA AAAATTATGC
117151 TCCCAATGGT TTGGTAAAAT CTACCAAATC TATCAGCACC CATTTTATAG
117201 TGCTTTCATA GGATACTAAG TAGCAATTCA CCAGAAAGAA CAAAAAGAAT
117251 TCTAAAAAGA AAGAAAACTA ACCAAAATAC TGAATGAAGA TTGGAGAAAT
117301 ATTCATCTAC TAATACAAGA TGCTGAGCAT ATTTTAAATC AGTTCCATAG
117351 CTCTGTAAAT AATAAGACAG TATGCCAGTT CTTCACCACC TTCCATCAAG
117401 CAAGGAAAGT TTTGCTTTTT ACAATTTATT GTCCTCTACC TCTGTGCTCC
117451 CTCTGGTCCC TCCATTATTC CTTCTCTCTT CTCCTTTGTC TGTATGAATA
117501 TAATCCAGAT TACTTAGAGT TAACCAATTA AAACCTTCTC CGCCGGGCGC
117551 GGTGGCTCAC CCTGTAATCC CAGCACTTTG GGAGGCCGAG GCGGGCAGAT
117601 CACAAGGTCA GGAAATCGAG ATCATCCTGG CTAACACGGT GAAACCCCGT
117651 CTCTACTAAA AAAAATACAC AAAAAAATTA GCCGGGCGTG GTGGCAGGTG
117701 CCTGTAGTTC CAGCTACTCG GGAGGCTGAG GCAGGAGAAT GGCGCGAACC
117751 CGGGAGGCGG AGCTCGCAGT GAGCAGAGAT CGCGCCACTG CACTCCAGGC

FIGURE 3LL

117801 TGGGCGACAG AGCGAGATTC CGTCTCAAAA AAAATAAAAT GAATAAAATA
117851 AAAAATAAAA ATAAAAATAA AACATTCTCC TCCAAATTAT ATATGTATGT
117901 ATGTGTATAT ATGTATATGT ATGTGTGTGA GTGTGTGTGT GTATATATAT
117951 ATATATATAT AAATAAGTTC ACTATGGACT AGCAAGCAAA AGGAAAGTAA
118001 TAATCCCTTT GCCAATAGAT ATTTATGGTT TATTTCCAGA CATTTTTTCC
118051 TAAGCACAAA CACATACTGT TTACATTTTT TAAATATTCG ATCATGCTAA
118101 ATGTAACCTA AATTTTCATT TTATAATGTA ACAATAATGA TAGCATCATA
118151 TAGTGAACAT TTATTGTTCC AAGCACTTTG CTAAGTTTTT AACATTTATT
118201 ATTAAACTCT CAACCCCATA AAATAGGTTT TACTATTGTT TAGATTTTAC
118251 AAGTTAAAAA AAAATCAGGC CCAGAGAGAG AGAAAGTGAT GTGTTCATAA
118301 TCACACAGCC AGTGATTGGC AGAGCATGAA ATTAAACCCA AGTCTAGAAA
118351 CATGCCGTGC CTGAGACATG GACGATGATG TGACAATGAT GAAGGTAGAA
118401 TGTCTGACAT TGCTAAGCTC TTCCTAAATG TTAAGCACTG TTGTAACTGC
118451 ATGCATTGTC ATTTAAACTA AAAACAGTTC TGTGAGGCCA CTACTATCGT
118501 TACAGTTTTA TTATTGCATA ATATATTAAC ATATAATTAA TGTAGTATAT
118551 TGTATATATA GTACTATTGT TATAGTATAT ATTGTTCTCA CTTCAGAAAT
118601 TAGCAGACTG AAAGGTTAAG AAACTTGTTG ACTGTGAAGC TGGAGACAGT
118651 CATAGGGGTC TGATGCCAGA GCCCTAACTC TTAACATGCT GCAGTACTGT
118701 CCCTTTGTTC ATGTCAATAA ACATGCCTCT GCTAAAATAG AAACCCACTT
118751 CTCTTAATCA ATTTTTTATT GTTGAATGTT AGGTTGTTTC TCATTTTGAA
118801 ATACAGATAG AGCATCCCAA ATCCAAAATG CTCCAAAATC CAAAACATTT
118851 TGAACACCAA CATGACACTC AAAGGAAATG CTCATTGAAG TATTTTGGAT
118901 TGATTTGGGG ATTTGGGATG GCCAACCAGT ATAGTGCAAA TATTTCAAAA
118951 TCTGAAAAAA AAAATTGAAA TGCAGAACAC TTCTGGTCCC AAGTATTTCA
119001 AATAGGGGAT ACTCAACCTG TACATTTAAA TTTGTAGTAA AAATCCTGTT
119051 AGCAGAATTA TGTCCTGGAA CTTAGTTATT TCTTTGTGAT AAATTTTCAT
119101 TCAATAATAA TAGTGTATTC TCTTACTGAA AATCACTCAA AGAAAATTTT
119151 GTGTTCTCAC CACAGAAAAC AGTAATGTGG GTAATGTGAG GTAAGGCACA
119201 TGTTAATTAG CTCTATTCAG CCATTCTAAA ATGTATTTAT TTCAAAAAAT
119251 AGTGTCATAT ACAATATATG CAATTTTTAC TTCTTAATTA AAATTAATTA
119301 ATTTGATTAA TTAAAAGAGC AAAAGAATTT CTGGTCAAAG CCTTTACATG
119351 TTAATAGATT TCTGTTCTGA AAATTCATAT TAACTTGTAC TTGCTCTGGA
119401 AGTGTCTGAA GATATTCATT TCCCTGCATT CTTATCAGTG CTACACTATC
119451 AATATCTTTA ATTGTCCCAA AAAAGGTAGG TAAAAATGAT ATGACATTAT
119501 GATATTACCA CAGTATTTCT TTGACTTCTT TTGTCAATTG CCTGTTCAAA
119551 TTCTTTGCTC ATTTTCTATT AAGGTGTTAA TACTTTTATC CTATTCCAAT
119601 AGTTCTTATT GATTATATAA ATAATTCTTG CCTTTTATAT ATTTGGAATA
119651 TGAAATCCTA GGGTATCATA TTTGTTGTAC ATTTCATTAC AAATATAATT
119701 TCTCATTTTT AATTTGTTGC TGTTTTATGG CCTAGTTTTG ACATGAAAAG
119751 CTTGCTAAAA ATATTATCAA GCCACTCATC TTTTTACTTT GCTTTCTAAC
119801 TTTGATGCTT TTCTTAGCAA GACCTTCTTA CCAGATTTTA GATGTGTTTG
119851 CTTAATATTT TTATTCTGAT TATGGTTTCA TTTTTTTACT TAACTCAGTT
119901 GTATATTATT TTGACTGAAC GGATGTGGCA AGGATCTGAC TTTATTTTTG
119951 TATGATTATT AAATAATTGT TTTGAGACTA TGTATTAAAT AAGTCCCTTT
120001 CCATGCTGAT TTGAAATATG TTCATCATAA ACTAAATACA TTTTTGTGCT
120051 AATATCTATA TTCTGTAGAT TTCAAATCTT GTAGCTTTAT AGGTTAATAC
120101 ATGGGATGCG GGACTCTTTC TTTATTCTTT TCCAAAAATA TTACTTCCAC
120151 AATTTTTTTC TTGTAGATGA AATTTAGAAT CATTTTTGTA AAGTTCCATG
120201 AATTAATCCC ATTAAATGTA TAGATTAGTG TTGGGTCCCT TTCTTTATGT
120251 CCTGACCAAA ATTTAATACC CACGTTTAAA AAAATCTGAA AACCAAATGA
120301 TGGAAATCCA AATATTTAAT AAATATATTA AAATGTAGTC AAGCTTATTA
120351 GTAAACAAGA CAATGCCAAT TTAAACCACA GTGAAATACT ATTACACACT
120401 CACCAGATTG GCAATAAAGG GTCAGTTATT GCCAAGTGTG GGTAAGGATG
120451 TTCAACAAAA GGAACCCTGA TCTAATACTG GTCATAGTGT GAATTTATAC
120501 AACACTTTGG TAAATAGTTT GGAGTTACTG TGGTACACAG AAAAGTTACA
120551 CATTCTTATC ACCAACAGTT CCCCTGCCAG GAATACACTC TAAAGAGATA
120601 TGCACTTATA GGAATACTCA CATGTATAGG AACGTTCATG ACAGCATTGT
120651 TCACAATAGT CCCAAACTGA AAATAACCCA AATGGCTATC AACAATGGGA
120701 TAGGTAGGTA AATTACAGTA TATTCATATA GCACTAAAAG TGAACAAACT
120751 TAACTACATG TAGCAACTTG GATAAATCTT ATACACATAC CATTGAGTAA
120801 GAAAAGTAAG ACACCAAAGA ATACAAGGAA TACGATTTGA TTTAATAGGA
120851 TTTAATTTAA TGGAATTTAA TAGAATACAA GGCATAGATT TTTTTTTGCT

FIGURE 3MM

120901 TTGTTAGTGT TTCCTTTATT ATAAAGCACT GAAATAAATA AATAGGTAGC
120951 TAGCCAATTT ATCCACAGTT TCTGGGAGCT ATATAAGATA GGCAAAGCTA
121001 AACTATTGTC TAAAAATATG TACATAGATA TTGATCTATA TAGAAAAACA
121051 AGAAAATTAT TAACATAAAA TTTAGCACAG TGACTTCTAG GGTTATGAAC
121101 AGAACAGGAC ACAGTGATGG GGACAAGATT CTATTTCTTG ACCTGTATCA
121151 TGTTTATGTG GACATTTGCT TATAACTGTT TGCTAATTCT GCAGTGTTTT
121201 ATTTACTTTT CTGAATATAT GTATAGAAAT ACATAATGAG CAATACCAAA
121251 CAAAATACTC AGTGGCTTTT TTGAAGGACA CTTAGCCCTT CTCTGACTCT
121301 CTTAGTACTC TCTTAGGTGC AGGGAATCTT CTGGAAGGGT TGGTGAAAGC
121351 CCTTCAATAT CTTCCTGCTC TGGTTTCTCA GCTATTTGAG GGCTCAAATA
121401 ATTACTCGTC TGTTATGTTT TTGTATGTTG TCATAAGGTT TCTTCTTAAT
121451 GTTCCACCAA AATGCTTCAG TGCCTTGCAT ACCATGAATA TTTTCTGAAT
121501 GAATAAATGT GTATTAAAAT GTTTTAATGC CTGAAAATAG ACCAGGTAGA
121551 AGAGGATGAA AAAGAATACT GGATAAATAA AGCTGGAAGA AAGAAAGAAA
121601 GTGAAAAGAA TACTCATGTA AACCCCAAGG ATAATCCAAT ATGACAGATA
121651 CATAACTTGT ATAGAGTAAT GTTTATTCTA TTAGGCATTT TCTTAGCACA
121701 GTGGCTCTGA TTATCCCTCA AAGTTCTTTG TAGCTTCTCT GAGTGACGTG
121751 TCTGTCACCC ATCACCTGGG GACTATCTGA TATGACTTGT TGTGAGATAC
121801 TGAGAAGGGA GAGCAGAAAT ATAGTCCATC CTGTCTGTGG GAGTAGTGTG
121851 GGGTCAGGGC CATTACCTCC CAAATTGCAC TGGGGGCTGT GACTTGCAGA
121901 AAGGATGCAG TGATTCATGA AAGGTGAATG CACTAGGGAA ATAGCCCTCC
121951 TTATTCCTGC TGCATCAAGC TCTTATAGTC AGGGCCAGTC CCGGGCATTG
122001 GGATGTAAAC ACTCTACCTC TCTAGTTGGA TGTTGTTCAC AGGATTTTAC
122051 TTAAAAAGAA CATGAGTGCA CTGGGTAGGG AAAACCTGTG TGTGCAGGAC
122101 CCATGTCATA CCAGTTTCCT TTGCCCAGAG CCAGCACTTT ATACAGGAGG
122151 CTTGGGATCA ACCATACAAA TCTTTCAACT AGGTCAATTA TTATGAATGT
122201 TTGCCTCTCT AGAAGCCTAC CCAATGTTTC TGAGCACTTT ATAAGTGCTA
122251 GGCACCATAC TGAGATTTTG ACATGGATTA TCACTGTTAA TTTCTAACTC
122301 TATAAAGATT GCCTTATTGG CTGGGTGCAG TGACTCACAC CTGTAATCCC
122351 AGTACTTTAG GAGGCCAAAG CAGGTGGATC ACCTAAGCCC AGGAGTTCAA
122401 GACCAGTCTG GGCAACATGG CAAGACCCTA TCTCTACAAA AAGCACAAAA
122451 ATTTTACCAA ATGTGGTGGT ACCCACCTGT AGTCCCAGCT ACTTGGGAGG
122501 CCAAGGTTGG AGGATCACTT GAGTCTGGGA GGTCGAGGCT GCAGTGAGCC
122551 ATGATTGTAT CACTGCAATC CAGCCTGGGC AATGGAGTGA GATTCTGTCT
122601 CAAAAAAAAA AAAAAAAAGA AAAAAAAAAG AAAGAAAGAA AGAAAGAAAA
122651 AAAAGGAAAA GAAAAGGGAA AGATTGCCTT ATTGTTCTGC TTTTGCTGTT
122701 TCTCAGGCTC TGCCAACTTG CTCAAGGTCA CAGTAAGTGG TGAAGGTAGA
122751 ATTTGAACCC AGAGAGCACA GCTCCAGAGC TAATGATCAC AACTATTGCT
122801 TGAGCAATTG ATTTGTTCAT TCATTCAACA AATTTCTCTC CAGTGATTCT
122851 GAATGCCAGA TTCTGTATTA GACAGTAGGA ATATGGTGGT GAGCATGCAG
122901 AAGCATTCCC TGCCTTTGCT TTGTGCTTCA TTCTCCCTAT TACATCCCTC
122951 AGGAGTTAGG TTTATTCTTA GAAGGGTAAG TAAAAGGTTC ATAGTGTGTC
123001 AAAGTGCTTA GAGAATGCAT AACTTGGGGT CCTCTCTGGG GGTAAAATTG
123051 ACTGTAGCTC TGCCTTCCAC TGGAATCAAT TGAAAGAACT ACAGTTACAA
123101 AGTGTAAAGA ACCCACAGCT GTTGTAAAAC CTTACACTCT CCAGAATGCT
123151 TGCTCCCTCT TTTCTCCCTC CCTCATCCCC AACAGATGGC TGCAAGTGCT
123201 TCCCTTGCTG CTTCCAGGTG ACTCTGAGAT AGAGAGATTA TCCAATGTAT
123251 GCTGTACCAA ATTCTGCACG TTGTCTGCGA CTGTTATAGA AATTTAGATC
123301 CTTTAGTTGA AACCTTCCCA ATCAAAACAA ATAACATCTT CTTAGCCTTC
123351 TTGATTTCAG GGTGAGCCAC ATATTTGAGG CCCAATAGGA CCCAAATTTT
123401 AATCGGTGCA TGATCTAAAT AAGCGAAGAG TTTATCCATG AAGGCCTATG
123451 CATGCCTGTG TGTGTTGACT GATGAATGAG GCTACTGAGA GAGATTAGAA
123501 AATTAGAAAT GTTTGCCTGC TGTGAGCAAT CTAGCAACGG ATGATAAACA
123551 TCCATAAAAG TGTTTATATT TTTGATCCTG GTAATTCTCC TTTGGAGGAA
123601 CATGTTGAGA AAATATAATA CTAATGTCTC AGGGAATCAA ACTGGTTTAA
123651 TTTTTCGTGT TTTTCAGCAC CTGAGATGTT CAGCTCCAGA AAAGGAGCAG
123701 GCTATTCCTT TGCTGTTGAC TGGTGGTCCC TGGGAGTGAC GGCATATGAA
123751 CTGCTGAGAG GCCGGGTACT GTAGTAGCAT TTCCTCTTTG GTTATTTTTC
123801 CAGCAAGTTC TATTTTAGAA TGAAAGAATG TATTGTTTGC TAAGATCCAA
123851 GCAGTTCACT TGAAAGCTGA AATCAGCTAT GCCATGTGAT GTTGATAACA
123901 CCCCTTGAGA TTTCTGCATA GGTTAATTCA TTTGTCCCGC ATATGGGACC
123951 AACCATGTCA ATTACCATTA AATTACACAG TTAAAAGTAA AGGAATAATA

FIGURE 3NN

124001 TGGATATTAT AAACTCCCAA AGAGGGGAAA TCAATACACC TCACTAAATA
124051 TCTTGTGTAA ATATCTGTGT TTGTTTAAAG AAAGTCATTT TGCAGTCATA
124101 GTACAGGACT CTAATTCAGA CATACCTCAC CAAGGCTAGT GTGAATTATT
124151 AATACAACAC AATTCATGCT CTGTCTTGTT GGATTTCTAT CACTTGGCTC
124201 CTGGGTTCTG GGTTCAGTGA CAAATTAGAG TCATTTCCTT TTAAAGGAAA
124251 CATTTCTTAA ACTAAGAATC TCTTTCCCAG AAAAAAGAGA TGAAAAGAAA
124301 GCAAATATGC TGAAACATAT TTTATACAAT TTGTGCAAAC TATTACATAA
124351 TAGAAATACA CTCCTTAGGT TATATCTCAG TCAGCTCTGC TTACCATAAT
124401 AAAATACTGC AGACAGGATG GCTTAAATAA CAGACATCTA TTTTCTTGGT
124451 TATGGAGGTT GGAAGTCTGA GATTAAGATG CCAGAATGGT TGGGTTATGG
124501 TGAAATCTCT TTTTGGCTTG CAGATAGCAG CCTTTTTTCT GTGTCCTCAC
124551 ATGGCAGAGA GAGATCTTTG TCTTCTTATA AGTCTACTAA TCCCATCACG
124601 AGGGACCTAC CCCCATAAAC TAACCTAACC CTTATTCCCT CTCAGAGGCT
124651 CCATTTCCAA ATACCATCAA ATTGAGGGTT AAGGCTTCAA CATCTGAATT
124701 TTGAGTGGGA CACAAACATT CAGTCCATGA CATTCTATCC TTGACCCCTC
124751 CAATATTCAT GTCCTTCTCA TATGCAAAAT ACATACATTC AACAGTCCCA
124801 AAAGTCTTAA CTTATTCCCA TATCAACTCT AAAGTCTGAA GTCCAAAATC
124851 TCATCTAAAC ATCATAGAAA TTGTGTATGG GTGAGACTCG AGGTATGATT
124901 CATCCTAAGG CAAAATTTCT CCTCAGCTAT GTACCTATAA AAGCAGACAA
124951 GTGGCCAGGC ACTGGCTCAT GCCTGTAATC CCAACACTTT AAGAGGTAGG
125001 AGGCAGGAGG ATTCCTTGAG CCCAGGAGTG TGAGACCAGC CTGGGCCACA
125051 TGGGAGACCC TGTGTCTACA ACACCTTTTT TTTTTAATTA GCCAGGCATG
125101 GTGGGGCAAG CCAGTGGTCC CAACTACTCA GGTGGTTGAG GTGGGAGAAT
125151 CACTTGAGCC CAGGAGGTAG AGGCTGTAGT GAGCCAAGAT CATGCCACTG
125201 CACTCCAGCC TGAGCTACAG AGTGAGACCC CATCATTAAA CAAAACAAAA
125251 CAAAAAACAA ACAAACAAAA AACAAGCAAG TTATGTGCTT CCAAAATACA
125301 ATGATACCAT AGCTGTGGGA TAGAGAATCC CATTCCAACA TTTCAAAAGA
125351 GAAATGGGAA AGAAGGAAGG GGCATCAGCT CCTAAACAAG TCCAGAACAT
125401 ATCAAAGCAA ATTCTATTAT ATCTTAAAAC TCGAGAATAA TCTTCTTTGA
125451 GTTGTTGGTT TGCCCTCTAG ATCTACACAG GCATGGGAGC AATCACTCTC
125501 ATGGCTGGGG ATGGGGAGAG GGGACTTGCT TAAGTGGCTC TCTACAAAGG
125551 CACTACCCAC ATGGCTCTCT GTGAAGGCTC TGTCTACACA GCTCTGTTGA
125601 GTGGTGGTCC TGCCCTTCGA AACAGAGGTG GAGGCAACCC TGCTCCCCAA
125651 GCCAGTGCAC TCTGGACCTG TAGTGGGAAT GGCAGCCCTG ATGATCTGTG
125701 AATCGCCCTC ATGATCCTTC TTCCTTTTAC TTGAAGGATA GCACATGTTC
125751 ACAGCTGGAT AGCATTACGG TCCCAGCCTG TAAAATCCAA GAAGTCTGAC
125801 AGCCTTTCTT CATAAATTCA AACTGGCAGC ATCTGCTAGT ATAATCCCAT
125851 CTTTATTTCT AGCTTCTGTT GTGATAACTA CTTGATTGTT CAGCTACACT
125901 CTAGTGTGCT CTTCAGAACA GGCTTGCTCA TTTTCTGCAA TATGGATAGA
125951 AATCTTCAAT TTCTGGTTGC TTTTTGCTTA ATTATTTTTT CTTCAATTCA
126001 AACATTCCCT TTAACATTTT ACTATAAGCA GACAGAAGGA ACCAAGTTAC
126051 TCCTTCAAAG TTTTGCTTAG AAATCTCCTC GGCTGGCCTG GTGCAGTGGC
126101 TCATGCCTAT AATCCCAGCA CTTTAGAAGG CTGAGGCGGG CAGATCACCT
126151 GAGGTCAGTA ATTCGAGTCC AACCTGATCA ACATGGAGAA ACCCCATCTG
126201 TACTAAAAAT ACAAAATTAG CCGGGCATGG TGGTGGATGC CTGTAATCCC
126251 AGCTACTCAG GAGGCTGAGG CAGGAGAATC ACTTGAACCT GGGAGGTAGA
126301 TGTTGCAGTG AGCTGAGAAC ACAACATTGT ACTCCAGCCT GGGCAATGAG
126351 AGCGAAACTC CATCTCAAAA AAAAAAAAAA AAAAAAGAAA TCTCCTCAGC
126401 TAAATATCTC ATTTCATCAC TCACAATTTC TACCTTCTGC AAAATAGTAG
126451 AACACAGTTC AGACAAGCTC CTTGCCACTT TATAACAAGA ATCACCTTTC
126501 CTCCAGTTTC CAATAACATG TTCCTCATTT CTGTCAGACC TCACCAGAAT
126551 CACCCTTAAT ATCCATATTT CTAGTGCATA CATCCACAGT CTTCCAGCTC
126601 AATAACTAGT TCCAAAGTCA CTTCCACATT TTAAGGCATT TGTTCCAGCA
126651 GCATTCCAAT TCTCAATACC AAAATTTTAG TCTGCAATAT CTGCCTTCAC
126701 AAAATACCAC AGAATTGGTG GCTTAGGCAA CAGAAATTTA TTTTCTCAGT
126751 TATGGAGTCT AGAATTCTGA GATTAACGTG CCATCATGGT TGGGTTCTGG
126801 TGAGGGCTTT CTTCCTGACT TGCAGACAGC TTCTTTCTTG CCCTCACATG
126851 ACGGAGAGAG AGATAATCTC TTTCTCTTCT TTTTGTAATA AGGCCACTAA
126901 TCCTATCCTG AGGGCTCCAC CCTTATGACC TAATCTAACC CTAATTACCT
126951 CCCAAGGGCT TCATCTCCAA ATACCATCAT ATTGAAGGTT AGGGATTAAA
127001 TTTAGAAATT TTGGGGGGAT ACATTCAGTC TGTAACAGGT TGTATACTCT
127051 CAAGGTCCCA GTGATGGATG CAATCAGTGA TTCCTCTAAG ACCAAAGAGT

FIGURE 3OO

127101 TGAAGACCTG ACTTTAGGAG CTTGTTTATC CCACAGAACT AAAGAATTGG
127151 GTATCTCAAG TCATCATCCA GATACTGCAG CTCTCCTCTC CTAACTTTTT
127201 GGAGTCATTC TTTCTGCTGC TGTCAATAGC CCTCTTCTTT GGTCCCACAA
127251 CACACCATCA TGATTTCTGC ATTAAAAATG CCATCTCCCA AGTAATTAAC
127301 CTATTCACAG TAAGAACAGT TGTTAGAAGT TGGGGTTATT TCATCATGGT
127351 CCAATGGCTT TATCTTGCTC AGGAAATCAA AGATGAGTGT TTCTAAAGCA
127401 AAAAAAAGGA GGATCTCACA ATTGTATCTG TTTCATTCAC TCTGCAGGGT
127451 CCATTTTACA CCCAAACATT CATTAGTTCA TTGTTTGTAC TCCTGCCTTT
127501 CCTGAGGAAG TCATTGTAGC ACTATTTCTT AAGTATATTC AAATTTGGAT
127551 AAGTTAGTCA AATTGATGTG AAAGGACCAC CCTTGTAAGC CAAATGTGTA
127601 AGTCCTACAT AGGGATATTA CCTGTTTTTA TCTCCTGATG GGCTTTTTTT
127651 TTTTCAAGTT TCTAAATAAA TCCAGTGAAC AAGTAGATAC GCTACTCATG
127701 ATTATATAGG AAAACAGAGA AGAGAAACAT ACACTTACTT AAAAGTAGAA
127751 ACATATCTGC TCTTTCCCAC TTCACCCTTA ATTTTTTTCT CCCCAGCCAA
127801 TTTACTCACC TTCTGTGGCT GTGCTTCTGT GTTAGACCCT TGCTAGCTGC
127851 TTCTGGGGTT CAGAGCAATT GTGCTCTGCC CTCATCTTTT ATGACACACC
127901 TAGCAAAACA GAAGCAGAGG AGCGAGTTGA AACAGACAAA CGACTATCTG
127951 TTATTCTTCA AACATGCCTA GGATTGTATT TAACTATCAC CTATCTAAAA
128001 GAGGTATTCT CGCCTGCCTG GAAAGAATTT TGCTAAGAAA ATTGTTTCTC
128051 TTCTTCCCAT ATTATTTTAC CTCTATGCTA GTTCCCTGTG ATTTGATATG
128101 TCAACTTTGA CAAATTCATT TTTCTAAAGC ACAGATATGA CCTTTTTTGT
128151 TAAGAAAAAG AAACTACTGT TGCTCCCCAG TGCTACACAC ACACACACAC
128201 ACACATACAC ATACACACCC TTCACAAGCC TTATCTGCAC CCCCGCCCAC
128251 TCCCCACAAC AAACTTCAGA TGTCTTAGCT TGGCATTCTT CGGAATTAGG
128301 TCAACGTTTC AGATTTTGCT TCCATTTGTG TATTTCTGAC CCTTCATGAA
128351 CTCATTTTGG CCTCTTAGAA CTTCTTCCTC TTCTCAAAGC ATCTCTTGGG
128401 TTTTTTAACC TCTTGTTCCT TCGCCTATAA AGAGAGTTTC CAAGGCAAAC
128451 CTTGGTCTTC TTTAAAAATC ACTCTGCGTA AGATTTGAAA TCACTAAATG
128501 AAGTTTTAAT AAAGGATATA TCTTCATTGC AGGGCTTTTC AAAATCTTTA
128551 TAGCCAAGTA TTTTGGTCAT TTCTAAGAAA GGACACACTA TTAAACTATT
128601 CCAGTTCGTG TTGGGGAGGT TTTTCTAGAT CTCTTTATAT TCAAATTCTA
128651 TTCATACTTT ATCACCTATG ACAAAATAGC ACTTTCTCTA AAGAAACATT
128701 CTCTGACCTC CCTATCTAAA GTGATCCGAA TCTCTTCCAA ACATTTATTT
128751 ACTTTATGTA TCCTGTGAAT CTTTGGAATC TAAGCTTATT AGAAAATATA
128801 GAAAACCACG AAAATGAAAG CAAAAATCAG CTGTAGTCTC TAAGGCAAAG
128851 AACATTTCCA ATTAAGAAAT TAAACTCCCT TTGACTTTTA AACCCCATCT
128901 TAGCAGTTTG TTGCATTCAC TTCCAACTTG TTTCTGTTCT CATAAGGATA
128951 CTCTATCTTC AGATAGATAG ATATAGATAG ATGTGTTGTT TTAGCAAAAA
129001 TAGAAGTATG TTTTACCTTG TTGAGCCTTT TTTTTTTTCA TTTCATAAGA
129051 TAAAATGTAC AGCTTTCTAG ATCAGAACAC CTAAATCTAT TTTCTTTTTA
129101 AGGATTAAAT CTATAGGCAT ATCAATTTTT ATTTTTTATC TCTTGTATAT
129151 TATTAGGTTG TTAATTCATT AAAGGTAAAG TATGTATCTT ATATAGGTTA
129201 GTATTATTCA CAGTATTTAA CTGTTTTTTT TTTCCTCAGG AGAGTCTTGC
129251 TCTGTCCCCC AGGCTGGAGT GCAATGGCCC AATCTCGGCT CACTGCAACC
129301 ACCCCCTCCT CTGTCCAATC AACCCTCCCG CCTGAGCCTC CCAAGTAGCT
129351 GGGACTACAG GCATATGCCA CCATGCCTGG AAATTTTTTG TATTTTTTGT
129401 AGAGTTGGGG TCTTACCATG TTGCCCAGGC TAGTCTTGAA CTCCTGGGCT
129451 CAAGCAATCC ACCTGCCTTG GCCCTGCAAA GTGGTGGGAT TACAGGTGTG
129501 AGCCGCCGCA CCTGGTCACA ATATTTAACT TTAAATAGGT ATATAATACA
129551 TGGTTATTTT CACTCACATC CATGTGAAGA GACCACCAAA CAGGCTTTGT
129601 GTGAGCAACA AGGCTATTTC ACCTGGGTTT CAGGTGGGCT GAGTCCGAAA
129651 AGAGAATCAG CGAAGGGAGA TAGGAGTGGG GCCGTTTTAT AAGATTTGGG
129701 TAGGTAAAGG AAAAAGGGGG GTTGTTCTCT GGTGGGCAGG GGTGAGGATC
129751 ACAAGGTGCT CAGCGGGGGA CGTTTTGAGC CAGGATGAGC CAGGAGAAGG
129801 AATTTCACAA GGTAGTGTCA TCAGTTAAGG CAGGAACCGG CCATTTTCAC
129851 TTCTTTTGTG GTGGAATATC ATCAGTTAAG GCAGGAACCA GCCATCTGGA
129901 TGTGTATGTG CAGGTCACAG GGGATATGAT GGCTTAGCTT GGGCTCAGAG
129951 GCCTGACAGT TATTGAATGA ATGGAGAAAC AAATCACTTA GACACCTTCT
130001 AGGAAAAAAT GACCAACTAT GCTACCTGCA ATTACGTTTC AAAATGTAGC
130051 TTATCTGAAG AAAAGGAAGT AACATTTAAT TACAAGCATC AATACAACTC
130101 AAGCACAGAG GAAGTGTGCT AAACAATTTC CTCCATACGT ACAAATTTTT
130151 ATTTACAGAA AAGTATATGT CTTAATGAGA AAATGTGCTC GAAAACATTC

FIGURE 3PP

130201 TCATCATTTC TGAGTTTGGT TTCAGTCTTA ATGAATGTGT CCCTTAACTA
130251 TTAATCTGCT TTGTCATCTC TCTAACTCCC TACTATCTCA TTGCCATTGC
130301 AAAGGCAAAG GTCCACATCT TTTATAGTTT CATATTATCC AAAAGTGTTA
130351 ACTTAGGATA GATGTGTACA TAGTTTTGTA CTCATTGTAC ATGCTTAGCT
130401 GCAATTCTTT TGCCTTTGCA CTTCTGAAAT ACAACCATAT TCACAACACA
130451 TCATTTGTTC CCTTATAACA TTTCACCTTT TCCACTTTGT TTATTCTCTA
130501 TATGCTCACT GTTAGTTTAG ATGCTGCCTT AGGCTTTTAT GATATATACT
130551 GTGACTGCAT ACTGTAATTT TTCTCTATAG CATGTATCCC ATTTATTTAA
130601 GTGTGTGTGT GTGTGTGTAT ACAGTCTATA TAATAAATTT ACATGCTTCC
130651 TTAAGTAGAC TGTAGGCCCC ACCAACATAG AAACCATATG TGTCTTGTTC
130701 TTCATTGTAC CCTCAATGCC TAAGAAAGGT GCTGGAACAT GGTAGGCATT
130751 CAATAAATAA TTGGTAAATA AATAAATATA CAATTCTGGT AGTTGATTAA
130801 TTCAAATTAA TTTTAAAATT TAGAACTGTA AAAGTAAATT AAAAAATAAG
130851 ATAAAGACAA TGTGATTATT TTTTAATAAA CCAACAGGTC ATGGAGATTT
130901 TAAAAATTAA ATTCAGTCAT ATGGCCTTGT AAAGTAACTA GAGAAAAATG
130951 TACACACTTA AACCAGCTGC TTGTGGCATT CATCAGTTAA TTCATTTGTT
131001 TATAAAATCA TTTTATTTTC TAGGTGGCCC AGAAACAGTA GGTTGAGAAG
131051 CAGCAATGAA TTAAAATCAA GAAGAAACAC AGAAAAAAGT AAAAACACAT
131101 GTGCATACAC ATATAAGCCT AGAAGCTTGA GTATACTAAG CCTAATCTGA
131151 TTCTTAATGA TAAACATGGT CTGAATCATA TGGAGTAACC TAACCCTTTG
131201 GCTACTAAAT TACCAATAAA CATTGATAAT GGTGATAAAG CATCTAGCAC
131251 TCCTTTACTG ATATTGAGTT AATGAGTTAT TTCTACTATA TAATTACCAA
131301 GACATATGAT ATAGCTATGG TCCTTTATTT AGTGTTGAGG GGGTAAATAT
131351 GGCAGTTGTT TTTAGATCTT ACTTAAAAAG CAAAAATGTT TGAATTAATC
131401 TCCCTTTCAA GGGCCACCTC CTGGCACTTC ATGGTTCCAT GAATAGCTGA
131451 CATTGACTTG CCATGTGTAA AATTAAGCTT TTCTTCCCAT CACTTTTCTT
131501 GAGGACTCAT TTTGCTGTTC ACTATTCATT CACATTTACA TATGCCCATT
131551 TTTACCTTTG TGTCAATAAT GATAAAAATC TCTCTCTTAT ATTGTGTCTA
131601 ATACTATTAG CCACTCACTC TGTTGAGAAA TTTACACATA TTATCTCCTT
131651 TAATTTTTCC AGCAATCTCA TGAGGTAGCT CATTTTACAG ATGAAGTAAC
131701 AAGCTCAGAA ATTGAGTGGA GAAGTTTAGC ACCAAATCCT TTTAACCTCA
131751 AACACATGAT TATTTTATAT TACCTCTTAA CACTGATTTA CTACAGGGAA
131801 AAACTTAAAC CCTTTCATTT CCCCCAATTT AGGTCATCCA TCAACAGTCA
131851 TTTATTAAAT ATCTTAAAAG GGCCAGGCAT GTGATCAATG TGTATATCCA
131901 TATTAACTGT GCTGTGGCTA GTTAATCGAA TATGGAAATT TTGTTCATTA
131951 AATAAACATG TATTGTGCAC CTACTGAATG CTTGGTCTCA TGAACAAGAA
132001 TGATATAATC TCTGGCTGTG AGTATCTTAC AGTTCACATA AGAGACATGA
132051 AATTTCAGTG TTGGTGAGTC CCCTACAAAA TAATATAGAT AAAGGCTGTC
132101 CTCTAGTGTA AAGCTGTGAA AACTACAGCT AATCCACAGT TTTCTTTTGT
132151 TTAATTTCTT TTCTTTTTAA ATTACTTTTC TTCAAAATTA AAACTGTAGA
132201 AGAACCTGGT TCTTCCCCCA AAATTTTTTT TAAAAGCTTC TGCCTCATCA
132251 CAAAATTCTC CACCCTGCCA TACTCTGTGG AACCAGGGAC TCATAGCATT
132301 TGTGGGACTG GAGTTGATGT TTTCTGAGCA GTTTTCTGTC CTGAGCTTCC
132351 TCATTATGTT GCAGTGAAAG GGATGGTATG GTAAAATTCT GGATTTACTT
132401 GCAATCAACC CTTACATAAT AATTTTTTAG ACTTCCATTT ATTGAGGACT
132451 TGTCCAGTAT TTCGTGTTAA TACTTATATA ATACCTTATA AAACAATTTC
132501 AAATCAGCAT CTCAGAGGCT GATTCAGTCC ACTTGAATGT TTTGTTTGGC
132551 TCAGTGGAGT GTTCAACTTT AAAATTTATG GTATTTTAGA AGCGACCATA
132601 AATTCCTAGT GTCTCTTTAA GAAAAAGTAG GGGGTCTGGC AACACAGGAC
132651 CACCTACACA TATGGCAACG CAAGAGTCAG CTGGACAGGG TTAGAAATTG
132701 ATATAGATAT TTTATCGGTT GAAAGTTTAG CTTGGAAACA TTTGGAAATT
132751 TTTTTTTTCT TTTGTCCTAT ACAAATGAAG ACTTTTACTT CTTTTCTCCC
132801 TTAAGAGACC GTATCATATT CGCTCCAGTA CTTCCAGCAA GGAAATTGTA
132851 CACACGTTTG AGACGACTGT TGTAACTTAC CCTTCTGCCT GGTCACAGGA
132901 AATGGTGTCA CTTCTTAAAA AGGTAAGAAG GAAGACTGCA TGTCCAAACG
132951 AAGTAACAAA AGGAAGCAGG CTCTCTGGCT TAAGTTTAGA AGTTAGTATA
133001 CAATATTGGG GACAGTCATG ATAGTATACA TTTGTAGAGT GTATTTTCTA
133051 GCTGTTAGCT TTCAAATACA TGGCTTCATT AACTCAACTC AGATTCCCCT
133101 TGGATGTCCC AAAGCCATCT TAAACTCAAA GGACTTCTTT ATGCTTTGTC
133151 TTTCCTGAAT ATCTTCTCAG GAAATTACTC TCAGTGACTG GCTTCTCTAT
133201 CCAAATCCAC TTACGCCAGC CAGCAACCAG GACTCATCTT GTCATACTGC
133251 GTATTCAATT NNNNNNNNNN NNNNNNNNNN NNNNNNNNNN NNNNNNNNNN

FIGURE 3QQ

133301 NNNNNNNNNN NNNNNNNNNN NNNNNNNNNN NNNNNNNNNN NNNNNNNNNN
133351 NNNNNNNNNN NNNNNNNNNN NNNNNNNNNN NNNNNNNNNN NNNNNNNNNN
133401 NNNNNNNNNN NNNNNNNNNN NNNNNCTAGC CTTATAACGG GTTTGTCCAC
133451 ATACACTTTT ACCACTCCAT TCTATTCCCC ATGCAGCCCC ACAGTGGTCT
133501 GTTAAAGGAC AGTCCAGGAT ATTTTCCTTA TTCTTAGAAT AAAGATTAAA
133551 ATAATTTTGT GGTACAAAAG TTCAAAATAC CTCTCAAGCC TTGTTTTGGA
133601 CTTTTGGACT TTTGTCCCCC CTTTGACTAC ACATAAACTG CTTTGGCCTT
133651 TTTCTTCTTC TTTTCTTTCT TTTCTCCTTC TTCACTTTTA CATACCAGTC
133701 TTCCTCTCAC CACAGGACCT TTGCACATGC CAGTACCTAT TCCTGGAACA
133751 GTGCCTCCAA TCCTAGTTCC TCCAGTTCCT CCTTGAGAGC AGTACTACTC
133801 AATGTGGTTC ACTGGTTCTA GTCCATGAAT TTTTTCTGCA GGTCTATTGT
133851 AAGTAAAGAA CTTGAGAGAA GCATTTAGAA ACTTTTATAG CAATTGGACA
133901 CTGCTGTAGC ATCTAAACAC ATGATCAATG GACTTATCTT ATTGAAGAGG
133951 GTCCAAGCTT GTTTGACGGT TGTTGAACTC AAGTCACAAG GTGTCTATGT
134001 GGGGTGCTGC ATACTGGCAA TGCATAATAA GACCACATAC TGATTTCAGT
134051 GGATTGGAAA TTGAAACAGT ACAAAAACAA ACAAAAATAA CTGACCCTTC
134101 TACATAGTTT GGGAAGCACA ACTTTAGCTC TTAGCTCAAA TATCACCTTC
134151 TTGGTGTAAG TTCACATAAC ACTATCTTTC CTTCATAGCA TTTTTCAGTT
134201 TAAAATTATA CCCAGCATTT GTGTGATCCT TGGTTACGTA CCATTTTCTT
134251 CTTAGCTTCA TGAGGGTAGG GACCATGTCT GACATGTGTT ACCATTGTAT
134301 TCTCAGCATC TAACACAAAG CCTGAGAAGT GAAATTTGAC AAGTATTCAA
134351 ATAAATGAGG TCCACAGCTT TCATCAGATT TTCAAGGTAC CCATCTTCAT
134401 CAAACAGATG AAGAACAGTT ATAGCGGGAG GTCAAAAGTG TATATTGAGT
134451 GATGATACAA AACAAGAATG AGGGGCCCAA GAGGAATGGG CTTGGCCTTT
134501 TTTTTTTTTT TTTTTTTTTT TTTTTTTGAG GAGAAAATTG CACCAGTTGT
134551 GGCTGGTAAT GGAAAATAGC TTTAGTGGCT AAGGAGTCAT CATTTGTGTC
134601 TCTTGTTTTT GGAGTCAAGT TCCTTATTTT GGAATAGGGA CATTGCATCA
134651 GTAATGTCAA AGACATAGAA TGGGGGATCA TTTTTCATAA GCAAATTCTG
134701 CTTAGTTCCA AGACAGCCCT GCTTCACTCC ACAAATTACA CCCTGAGGTT
134751 GCATGGTTGT CATCTTCAGA AGCATTCTCA AGTGGGACTG ACAATGCCTA
134801 TTTGAGCCAC ACAATTGCTG TGATGTTGGC TCAGGAATGG TTAAGGGGGC
134851 AAAAATCTTT TATCTCAATT AGTAAAATCT AGAACTATAA CAGTTACTTT
134901 AGTTACACCT TATCTATGCC GCCCCCAATG TATTTTAATT AGTTGTAAAA
134951 ACAGCTACAA TTCTTAGTAG GAAATGAGTT CTACTTGTGA AATGTATCAA
135001 CATTTGTCAC CATAGGTTTT CTACTAGGTA CTTTGTATAA ATAGCCTCCC
135051 ACTAATCCTG ATTACAATCG TATGAAATAC ATTATTACCA CTTTTTTTAA
135101 ACACATGGGT AAACTANNNN NNNNNNNNNN NNNNNNNNNN NNNNNNNNNN
135151 NNNNNNNNNN NNNNNNNNNN NNNNNNNNNN NNNNNNNNNN NNNNNNNNNN
135201 NNNNNNNNNN NNNNNNNNNN NNNNNNNNNN NNNNNNNNNN NNNNNNNNNN
135251 NNNNNNNNNN NNNNNNNNNN NNNNNNNNNN NNNNNNNNNN NNNNNNNNNN
135301 NNNNNNNNNN NNNNNNNNNN NNNNNNNNNN NNNNNNNNNN NNNNNNNNNN
135351 NNNNNNNNNN NNNNNNNNNN NNNNNNNNNN NNNNNNNNNN NNNNNNNNNN
135401 NNNNNNNNNN NNNNNNNNNN NNNNNNNNNN NNNNNNNNNN NNNNNNNNNN
135451 NNNNNNNNNN NNNNNNNNNN NNNNNNNNNN NNNNNNNNNN NNNNNNNNNN
135501 NNNNNNNNNN NNNNNNNNNN NNNNNNNNNN NNNNNNNNNN NNNNNNNNNN
135551 NNNNNNNNNN NNNNNNNNNN NNNNNNNNNN CATTCCAGGT TTATTCCTAA
135601 TGTGAGTCAA TCCTAACAAA GCCAAATAAC TCCCATTCAG TGCGCATTAC
135651 CCGGTGTGCC AGATTCACAC ATTGTCTCAT TAGATAATCA CACCAGTGTT
135701 GTTAAGAGAG CCCCAATTCC CATTTTACAG TATGAGAGAA TTGAGACATG
135751 CACAGGGTAA GTTTGTCACC AAAGGTCACA AAGCTAGCAA GTAGTCAAGC
135801 TGGGATTCTA ATCCAGGTGT ATTTGCGACT GAAGTTCTAG CTTTTAACCA
135851 CTTTTTATGG TCTGTTTTTA TTGAAAGGAA GTCCTAGTTC CCCAAATAGT
135901 CATTCTCATG AATCTGCTGG GGTTTTTTTT AAGTTTTCTT TGATTCTAAA
135951 GATGCAGAAG TTTGTGTCCC TAGAGATCTG AGTCAAAGAA TTGAAAATTG
136001 TTGGAGTTGG GGTGAGGAAT TTATTTTAGC ATTTGCCCCT CATCCTTTGT
136051 TTGTTCTGTC TCAGGGATTT ATATTTGTAA GGACTGATAA CCAAAGACAT
136101 ATAATTCCCA TTGGATGGAT AGCCAAACCA ATGGACTTCT GTGGTCTACT
136151 GCATTATGCT GGTAAGAGCC AGAGTCCAGA AGCTTAGGCC AAAGGTCCCA
136201 AGTGAGGCCA CTAGCTCCTT CTCTCTGCCT AGAACTGAAA TTATATGTTC
136251 AGTTGTAGGT ATATTGGGCA GAATAAGAGG CTTCTAAAGG GGCCTGTAGA
136301 ACCAATTCAG TTTTCTGTTT TGGCTGTCAT GGCAGCTCAG GCCTGCAATC
136351 TCAGCACTTT AGGAGGCCGA GGCAGGAGGA TCAGGGGTTC AAGATCAGCC

FIGURE 3RR

136401 TTGGCAACAT GGCAAGACCG TGTCTCTACA GAAAAAGAAA AAAAAATTAG
136451 GCAGGCGTGG TGGTACTTGG GTGTAGTCTC AGCTACCTAG GAGGCTGAGG
136501 TAGAAAGATC ACTTAAGCCC AGGAGTTTGA GGCTGCATGA GCAGTGATTG
136551 TGCCACTGCA CTCTAGCCTG GGTAACAGAG TGAGACCCTG TCTCAAAAAA
136601 AAAAAAAAAT TACTCTTAAG CCCATATGAG GCATTTGCTG TGGGAATGTG
136651 AGAGTGTGAT CCTTCATGTA CACACAGCAG GAGGCATGCT CCAATGAGAG
136701 GGTAAGGAGA AAGTACAAAG TGAGAGAAAG GAGAAAGCAG GGTGGTGGAA
136751 TTGTACCTTA TGGAGCAACA GGAGGGTAGG TCTGAGTTCT TACCTCTCCG
136801 CTTTGTGGGG TCCATTAGGG GCAACTTGTA CCATAATTGA CACATGACAC
136851 AATGAAGGTC TAGGCACCCC AACTCTTGCT TCCCCCTCCT TCTATGTGTT
136901 GCGTCCCTGC AATTAGCCAT CAATGCTGGC TCAAAAGAAG TTCTACGTTA
136951 TGCTTCTCTG ACTTTAGTGT GAATCGGAAT CATCTGGGAA GCTCATTAAA
137001 GTGCAAGTTC TTGGACCTCA CATTCTGAAA TTCTGATTTG GGAAGTCTGG
137051 TTGGAGAACT GGGAAGCTGA GCAAGCAACT TAGGTGATTC TGAGTTACAT
137101 GATTATTAGA GCGCACTTTC GGAAACATAA CCCAAAATTT ATTTTCCACT
137151 TTAGAAAAAT AACTGTAAGT CGGCTTTTGT TTTTACTCAT TGAGGCCTAA
137201 TTGAGAGTTT AGAAAAATAA ACGAAGAATA TGAAAAACGA TGCTGGCAAT
137251 AAATAACGTA AAACTTAGAG TGGGAATCCC AGTGTATTAT TCATGGACTG
137301 CTCCGTTAAG ACTAAGTATT ATTTTCCGTA TTAGGTCTGC TGTGTTTTTC
137351 AGAATGATAC AGTAATCTGA GGATTGAGCC AACTGTCTTC CTTGCAGAAA
137401 GGCAGGCTGA ATTGTGATCC TACCTTTGAA CTTGAGGAAA TGATTTTGGA
137451 GTCCAAACCT CTACATAAGA AAAAAAAGCG TCTGGCAAAG AAGGAGAAGG
137501 ATATGAGGAA ATGCGATTCT TCTCAGGTAA GCAGGTCCCC ACCAAACTCA
137551 GGGTCATGGG TATCCCCATG ATGGCTGCAA TATCTTCGAG AGCTTCTACT
137601 GGGAGGTCAT TTCAGCTTCC TGCTTTTGCT GCTTAGTGAA ATAGGAGAAG
137651 TAGATCAGCC GGGTTTCTAA AAGGGCAGAC CAGAGCTCCT CTGAGGATCC
137701 TAGCAGCAAC ATTTTACTTG TAGGCTTTCC GTCTAGAGTT CTGCCATTAA
137751 CTTGACTCAG TTATTTCTCT CTTCCAGTTC TCAATTCAAA ATTTACAAAT
137801 TTCCTGGGAG AGGAACTGTC ATTGGCCAAG CTTAGGTCAG GGGATGATTC
137851 ATAAAATTAT GGTAAAGGGG CAGGTTTCAA AGTACACACA TGGTTGTTTT
137901 GGACCTCACT CCTGCTTTGA GGAGTTTCTG GGAGCAGCCA ACCCTAGAGA
137951 TGATGTCTGT TCTTTGCCAC AAGCAGAATT TTATGATATC AAGCCTCACA
138001 GAAGAGTGTC TGTTCACAGG AATGACGGAA TTCTAACATG GTGGAGCACT
138051 ATTGCTGGAT TTCAGGCTGA GTTAAATTAA CTTTGTAACT AAGTATATTA
138101 TTCTCTGTCA GAGTCAGAGC TCAGATTTCA GTGAAGTAAC TTGCAAACAC
138151 TCAGTAGGAT TTTATACTCA CATGTGGCTC TATGAATTAT AATGATGATG
138201 AAGTAATAAA GTTACTTTGC CTCTAAAGGT CATCTATCTA TCCACACGAC
138251 CATTTCCATT CCTCCATCAA TCCCTGCCTC CCTCCATCCA TTCATTTAGG
138301 CTACTTTTTT TTAGTAGCTA TGATCTGCCA GGTCCTGTGC TAAAGACTGG
138351 AGTGAGAAAT GATTGAGATA TAATTTCTAT ACTCAGTGCT GTCCCTTTTC
138401 TCAAAGATTG TGTAGTCTTG TGGTAAAGAT GGCTCTGCAA ACAAATAAGT
138451 ATCCTCCATC TCCTTAATTT CTCTAGTAGT CAGGGGCCAC TATATATTTC
138501 AATGGACAAT TAACCAACGT TCACATCTCT GTCCTGTTTG ATCACAGAAC
138551 TGGCTTCTCG TCAGATTCCC TTCAGGAAAT ATTTTCTAGG ACCCTCCAAG
138601 GAATGCTTAG CTGTGCTGCT AACCCGTCTT GCATATTGCT TGTCTCTGAA
138651 CTGTCTTCTT CCCAATGGTC TGTTCCTCAT GATCATGTCA TAACCAACCC
138701 GCTTCTCCAG ACTTGCTCCT TCCCCTGACC TAGCAGAACT TGGCTCAAGG
138751 TGGATACAGG CCTCTCTGAT AACAGGACCT AACATGTGAT AAAAACCAAG
138801 AGATCCTTTT TATTACAAGT TTTTAAAGTT TTAGAAATAA CTGAGCAATT
138851 TAGGAATAAC TTTTGACCAT ACGTACCATG CTCAACATGA TCTGCCCATC
138901 TTTCCTGCCA CATCCTTGTA CTATCCCACT CTGACCCTCA CTTAAAACCC
138951 TCCAACCTCA CAGGCCCTGC AAGTGTCTCA CTCTCAAGCA CTGAACCTTT
139001 TGTTCTTCTT CAAGGCCTTT GCCCTTGCTC TTCCCTGTTC CTAGAATGGT
139051 CTTCCCTTTC ATCTTCACAT AGGGGGCTTC CTCTCATTCT TTATACCTTA
139101 AATATCACCT TGTCATTTCT GTTGTTGAAT TATAGGATGT TTTTTACATA
139151 TTCTGGATAT TGGACCCTTA TCAAATATGT GAACTGCAAA TAGTTTCTCC
139201 CTTAGTCATT CTACGAAGCC AGCATTACCC TGATACCAAA CTGGACAAAG
139251 ACATCACAAA AAATGATAAT TACAAACTGA CATCTGTTAT GAATATAGAT
139301 GCAAAAAATCC TTAACATATT AGCAAGGTGT TCAGTTAGGC TTTTGACTTA
139351 AGATGTTTCT TCTTTTTTAA TATTGGTGTT TATAGCTATA AAGTTCCTTC
139401 TGAGCACTGC CTTCACCTAT CCCATAAGTT TTGGGATGCT GTGGTTTGTT
139451 TTTAATTCAT CTCTAAGTAT ATTCTGATAT CTCATGTGAT TTCTCTTTTT

FIGURE 3SS

139501 GACTCTTTTT TTAAGAGTTT GTTGTTTAAT TTCCACATTT TTGTGAATTT
139551 TCCAGTTTTC CTTCTGTTAT TGATTCCTAC CTTCATTCCA ATTATTTCAG
139601 TCTTTTTAAA TTTTTTGATA CCTGTTTTGT GGTTTCCTTC CATGGTTTCC
139651 TTTAACTCTG AGCATATTCA AGACGGTTGT TTTAAAATCT CACTCTAGAA
139701 AGCTCAATGT TTGAGCTTCC TCAGGACAAT TTCTATCCGT TGATTTTAAG
139751 TCTTTGAATG GCAATATTTT CCTGTTTCTT TGTGTGCCTT GTGATTTTTT
139801 TTCTGTTGCT ATTGAAAACT CGACATTTAA ATATGATAAT GTGGTAACTC
139851 TGGAAATCAG GTTCCTCCTT TCTTCATGGT TTGCTATTTT TTGATTGTTG
139901 AAGGCTGTAG TTATCCATTG TTTAGCGACT TCTCCAAACA ATGTTTGCAG
139951 AGATTGTCTG CTTTGTTGTG TCATCACTGA AGTTTCTGTT ACTTTAGCCT
140001 GTGCTCAGCT AATGTTTTGA CTGAGATTTA ACACCAAGAG CATTTTTAAG
140051 TTGTTTTTCT TTTCTTAATT TAGTGTTCAC TTGGTTCCAG TAAACCTTTG
140101 AGTGCTTTCC GGAGTTTTGA CAAAGTTGGT TTTGACAGTA TCTGCTTGTT
140151 TTTTTGATGT TTCTGTTCAG AGATGGGGCT TGGAACTGCT TACATCAGCA
140201 TTTTTCTCTA GATTCTTCTA ATCTTGTACC CCAGGTTCAA AAATAAAAGG
140251 TACTTTGCTT CAAAACAAAG AATAGTCTTT CTTCCAAGAA GAATCAGAAA
140301 GATTATGAAC TATTTTTCTG ATTCTTCACT CTATTTTCTC TCTTTTACAT
140351 TAAGGCTTTT AAAACATGAG TCAATCTTAC CTTATTATAT TATTAACATG
140401 CTCGTTCATT CATTCATTCA TTTATTCAGA TGACTGTAAA ATTCCTGCTT
140451 TGTTAGGAAA TATTTCTGAC TAGGTGGTTA ATGCTATGGT TAGATACACA
140501 AAGTGCTGTG GGAATTGCTC ACTGGACCTG AGTGAAGGGT TAGGATAGGC
140551 TTTCCAGAGG AGGCAACATT TGATCTGGTT CCTCCAGATT GAGCAGAGGT
140601 AGGTGAGCAT ACAGGAAAGG ACAAGAGCAT TTCAAGGCTG GCACATCTCA
140651 GGGCACAGGC AGATCTTAAT GTTACAGAGG AAATAAAATG ACAGGTGGTT
140701 TCTGATCATA GGAATTACCC ATGCTGTGTT CAAAAGGCTT GTGACATTAC
140751 TCATCCTCCC TGCCTTTAGT CTTATCTAGA GCCATTCACT GAAGGCATTC
140801 CTTCAGCAAA ATCTAACAAG AACATACACC ATATCAGTAT CATATTAGCT
140851 ATAGCTTAGC CCCATTTCTG CCCCACTGTG TGTAGCTCAG AGTCACCTTG
140901 TTACTCTAGA GCCAAATTCA TCACTGTTTA GGTACCCACA TTAGAAAAGA
140951 GTCAAGTGTT GGCAAGGGAA TTCCAATCAA GCCACAAGCC TGGAAAAGGA
141001 GCTCTCTATT CTGAGCTCTC TGAGTTCTCT ATTCTGTTTA ATTGGTCTAT
141051 GCGTCTGTCG TTGTACCAGT ACCATGCTGT TTTGGTTACT GTAGCTTTGT
141101 AGTATAGTTT GAAGTCAGGT AGTGTAGTAG TGTAATAATG CCTCCAGTCT
141151 TTTTTTTTTT TTTTTTTTTT TTTTTTTTTT TTTTTTTTTT GCTTAGGATT
141201 GTCTTGACTA TTCAAGCCCT TATTTGGTTC CATATACATT TGAAAATAGT
141251 TTTTTTTTCT AATTCTGTGA AGAATGCCAA CAGTCATTTA ATGGGAATAG
141301 CATTGAATCT ATAAATTACT TTAGGCAGTA TGGCCATTTT TATGATATTG
141351 ATTCTATCTG GGAACCTGGA ATGTTTTTCC ATTTGTTTGT GTCCTCTCTG
141401 ATTTCCTTGA GCAGTGGTTT GTATTTCTCC TTGAAGAGGT CCTTCATTTC
141451 CCTTGTTAGC TATATTCCTA GGTGTTTTAT TGTTTTGTAG CAGTTGTGAA
141501 TGGGAGTTCA TTCATGATTT GTCTCTCTGC TTGCCTGTTG TTGGTGTATA
141551 GGAATGCTAG CAATCTTTGC ACATTCATTT TATATCCTGG GTTTCAGTAT
141601 TTTAAAAACT TACTTCAGGT GATTCTATGT GTGCAACCAT GATTGAGATA
141651 CACTGTTATA GAATCTAGGA TGTGATAAAC TAGAAGAACA TAACTAAAGT
141701 TTTGCATTTT TCGGGTGTCT CAGTTTCCTC ATTTATAGAT GGAGTTGGTA
141751 TGTGTACCAA GTTCATAGGC TTGTTCTGAG TAAATTAGTG CATGTAAAGT
141801 GCTCCACAGA ATGTTAGCTG TTGTGATGCT TTACTTTCCA TTGCACTTCC
141851 TGACTCCTAG CCTTTCTTTT CCTTGGCTCT TTTTATGCTC ATGTCAGATG
141901 CCTCTATTGT TTCTTTCCCC CCAGAATATC CTCCACTTTA TCTTGCTCTG
141951 CTCAACATCT TTAAAGTATA GAATCAACAG ACTGCCATGC CACCCAGTCT
142001 GTCTGACAAT TGAGGCAAAT TCCCTAAGTC CTCTTGTTCT CCTTCTGAGA
142051 TTTCCACCTG CTCTAACCCC TTCCAATATT TCAGATGCCG TCTCCAGCTA
142101 TGATAATTTA ATCAGTGTTT GCTCTGCTCA TCCTTGATAT GTGAGTCCTA
142151 AGATTTTAAG CGATCATTTC CCTTCTAAGT CATGTATGAC CCATTAGTCC
142201 CTCCATTCTT TTTTCTTACC CCTCATTTCA TATTCTCTTT ATGGCTACTC
142251 CTGTTGATGT ATCCATTTGG CCACACTTCT TAAACTTCTC CACCTAAAGC
142301 AGAGGAAAAA GAACAAGTTG AACATGAACC CTTTAAGGGT AATGGGGTCT
142351 GAAGTGTCAC ACTAAAAGGT CATCTGCAAG TATGTATTTC ATATCTTTGT
142401 TTAAATAAAA TAGTTACATA GTAGAGGGAA AAAAAATCCA TGTGGATTTT
142451 GCATTTCACT CAATTATAAC CTTGATTTTT AATGCTAAAA ATTATTTTTC
142501 CTAAAATCTT GGGGTAAAAG TGTTGCTCCA AAGAGCTTTT ATCAGATTAT
142551 GTTTATCCTG TAGCTGCCTG TCCCCTGTGA CCGATACTGG AAACCCTCAG

FIGURE 3TT

142601 GATTACAAAT GCCTCCGTTT GCAAGTAAGA GTGAAATACA GCAGAACTGT
142651 GTCTTCTCCT TTGTCTTGTT CCCCATCTCT CTTCTGTGCT TTGTATTGTT
142701 TCCTCTCCTG TCACCTAAAC AGGCACTCTG AAAGAAAACT CTCCAGTACT
142751 GGAGAACTTA GCATATTCTA ATTCCTAGGT TAAAAAAAAA TAATAAATGA
142801 CTGAATGATT TTTTTTAAAG AATATTTTCC ATCAGAAGAA ATTTGGAAGT
142851 ATTTTGTTGC AGAATTTTAA AACATTTGAT CTGGGTCTAA TTCTGTCCTG
142901 GGACTGGTAA TCATCTTTTT TTGAGGCTAA ATTTTCTCAT TTTGATGAAA
142951 AAGTCATCAA TAGATGTTGA AAGCTGGACA GTGCAGTGTC AAAGCAAATG
143001 CTTTGCATGT CTGCAAGAAA GTCACAAATA AAGAAGGCTC TGCTGACTAA
143051 AAGAGAAAGA TACTTAATCA ACTCCAGTAC CATTGTTGAG GGGAACATTC
143101 TATCAGGATT CAGTATAGAG AGATATTTTT AGGCTATTCA CAAAATCCAG
143151 GTAGAACCTC CAAGCTACAT TTACAATAAT ACTAGCTTTT AGATTAATTG
143201 TTGTTTTTTA AATATGTATT AGCCTCTTAT ACAAATATAA GGAGTTACAA
143251 ATTATTATTA CAATAATCTT GGCTTTCGTG ATTGTCCAAT GTATTTACAC
143301 GTACCGAGAG CTTTATTTCT CCGTATAGTT TCAAGTTACT GTCTCGTGTC
143351 CTTTCATTTC ACCTTGCAGG ACTCCTTTGA GCATTTCTTA CAGGGAAGTT
143401 CTAGTGGTAA TAAACTCCCT CCACTTTTAT CTGGAAACAT CTTAGTTTCT
143451 CTCTCACTTT TCAAGAACAG TTCTGCCAGA TAGAGGACCC TTGGTTGATA
143501 GGTTTTTTTC TTTTAGCACT TTGAATATAT CAGCCCACTG CCTTCTGGCC
143551 TCCAAAGTTT CTGATAAGAA ATCTGCCCGT CATCTTATGA TGTACTTGAC
143601 AAATTTTTTC TCTCTTGCTG CTTTCAAGAT TCTCTCCTTG TCTTTGGCTT
143651 TAGAAAGTTT GCTTATATTG GCTGGACATG GTGGCTCACA CCTGTAATCC
143701 CAGCACTTTG GGAGGCTGAG GCAGGCGGAT CACTTGAGGC CAGGAGTTTG
143751 AGATCAGCCT GGCCAACATG ATGAAACCCC TGCCTCTACT TAAAATTCAA
143801 AAATTAGCTA AGTGTAGTGG TGCACACCTG TAATCCCAGC TACTTGGGTG
143851 GCTAAGGCAA GAGAATCTCT TGAACCCAAG AGGAGGAGGT TGCAGTGAGC
143901 TGAGAGCATG CCACTTCACT CCAGTCTGGG CAACAGAGCA AAAGTCTGTC
143951 AGAAAAAAAA AAAAAGGAAA GTTTGATTAT ATTATGTGTC AATGTGGGTC
144001 TTTTTGAATT CATCTTACTT GGGATACACT GTGCCTTTTT GGATTTGGGG
144051 GCTCATGCCT TTCAGCTATG ATTTCTTTAA GTATTCTGTT TTCCTTTTTC
144101 TCTCTCTTCT CCTCCTGGGA CTTCCACAGT ACGTACACTG GTTTGCTTGA
144151 TGGTGTTCCA TACATTCCTG TAGGCCAGGG ATGTCCAATC TTTTGGCTTC
144201 CCTGGGCCAC GTTGGAAGAA GAGGAATTGT CTTAGGCCAC ACATAAAATA
144251 CACTAACACT AACGATAGCT GATGAGCTAA AGAAAAATCA CCCTCAAAAA
144301 AATCTCCTAA TGTTTTAAGA AAGTTTACAA ATTTGTGTTG GGCCACATTC
144351 AAAGCCATCC TGAGGCACAT GTGGCCCATG GGCTGTGGGT TGGACAAGCT
144401 TGCTATAGGC TCTGTTCATT ATTCTTCAAT CTTTTTTCTT TCTGTTCCTC
144451 AGACTCAGTA ATTTCCACTG TCCTGTCATC AAGTTTGATA CTGATTCCTT
144501 CCTTGCCTGC TCAATTTTGC CGTTGAAACC CTGTAGCAAA TTTTTAAATT
144551 TTAGTTATTG CACTTTTCAG CTCAAGAATT CCTTTTTAGT TTCTTTTTAG
144601 GTTTTCTATA TTTTTATTAA TACTTTAGTT TTGTTTGCAC ATCATTTTCT
144651 TGATTTTCTC TATATCTTCC TTTAGCTCTT TGAGCATCTT TAAGATAGTT
144701 GTTTTGATGT CTTTATCTAG TAGATCTACT GTTAGGTCTT TTTAAGGGAT
144751 AGGTTTTTTG GTTTATGTTT TTTACTGTGA ATGAGCCATA CTTCTCTATT
144801 TCCTGGCATG CCTTGTTATT TTTTGTATTG GACACTTGAA TCTAATAATG
144851 TGATAAATCT AGGAAAATCA GATTTCTCCC ATCCCCAGGG TTTGCTGTTT
144901 TTTGTTATTG TTTTTATTTT TATTTTTTAT TATTGTTGTA AGCTGTCTCC
144951 ATGCCAAGGA TCAGCTGAGG TGTAAACATA AGATCTTCTT AGGTCTTTTC
145001 TGAGCCTGCA CCCTTCCCTG GTCATGTGCA GTCACTTTCT AATTTTCCCT
145051 ACACATGCAG TTGTTTTTGA ATGTCCCAGC CTTTCACGTG TGGCTCCCAA
145101 AAGGAGGAAA GGAGAAAAAT GAAGAGGGTG AAAAGGTGCT GGCCCTTTAA
145151 TTCTCCCAGA AGTCACTTCA GCCTGAGGGA GAGTGGCTGG CAACATTGTG
145201 GGGGAGGTGC AACAACAATG GCCATCAAGC ATTTTGTTTG CACCTCTGTG
145251 ATCAGAAGCA GCAGTGTCGG AAGCACAGAT CCTCAGAATT TGGAGAACAC
145301 AGTTCTTGCT TTCCACCCTG ACTCTCACAG GCTGTGTGCA AACTGCTCCG
145351 GAACATGTGT GTGCTCAGCT CCCTCCCATG GGGCTGGAGG ATGAGGGATG
145401 GGTAGCTGCT GCTGTGCTAA GAGCTTAAGT TGGTCATAAT TAACTGCGCT
145451 TTGCCACCCA AGCCTTCCCT GAAAGTTGCA AGCTTTCAAT AGACTCCAGA
145501 GTTCTAAAAT AGTGACATTA GACAGATTCT GCCAGTGCAA TCGCTGTCTA
145551 GGAGGGGAGA CAGATTCCTG GTGCTTCCTG TTTTGCCAGC TTCCCGGAAT
145601 CTTCTTCACA TAGCATCCAT TTTGAAGATA CTACTTACTT CTCAATTTGG
145651 GGCTATTCAT TGAATAGACT GTCACCAGGT TATTGGCTGT TTGAAGATTC

FIGURE 3UU

145701 TCATTTGTCT GCTAACTATA CCTCTATTTT TTTTCTACGT TCACCTGGAA
145751 GACATGTCTT CTTCAAGAGC ACCTTGACTC TGTCCAGAAG GAGTTCATAA
145801 TTTTCAACAG AGAAAAGTAA GTAATTCCTG GGAGAACAAC AGCCCCAGAA
145851 ATGGTGGCAT GTTTCAGCCA GACTTTACTT GCAGAGAAAA TATATTTTTA
145901 ACATTTTAAA AATTATTTTC TAATTGGGAA AATGATGCAA TCTATTATAG
145951 AAAATGTAGA AACCTTTTTT GTAAGGTATT TAACATTTTT TAATTGATAA
146001 ATTAGCCTAG CATCAAGTTT TTGTTTGTGA GAAGGGAAGA GGAATTAGGA
146051 TTTAAACACT TAAAAATCAA AGCCTTTTAA AAGATTTCCT TGGCTCATGC
146101 TTATTTATAA ATTATTGGGC TTAATATTAT TTCAAAAGCT TAAACCTTTC
146151 ATTTTATTTT TCAAAGAATA AAACATCTTT TTTTTTCTTT TCTTTTTAAG
146201 AGTAAACAGG GACTTTAACA AAAGACAACC AAATCTAGCC TTGGAACAAA
146251 CCAAAGACCC ACAAGGTGAG GATGGTCAGA ATAACAACTT GTAAAGGCCT
146301 CATGTCTTCT TCTTGGGACA ATCTCATGCC AGAAACTTCT AATTACATAT
146351 GTCAAGAAAA GCTGACAGTA GTTCTTGCCA CTCCACACAC CATGACTTAG
146401 AAAATGTGAA TGAATATATT TCAAAAAAGG CAGCACAACA CAGTGAAGGG
146451 TCCTGGGCCT GAGCTCCTGG GATGTCATTT CACATCAATC AACTGTGTGA
146501 TCTAGAGCAA GTCACTTAGC CACTTTCTGT GCTTTACTTT ATTTATCTAA
146551 AATGAGAGGG TTATACTAGA CGAGCCATAC CCTGCCTTTT TAGTGCTATA
146601 GTTGTTATTC TAAACCGCCT TTATTTTTAT TTTAAAATTA ATATATGAAT
146651 ATAGATTTAT TTTTCCACTC CTTCTAATTA TGCAGTGACA AATGGACAAA
146701 TGGACACAGG ACTCAGTGAG ACTTTTCAGA CCTCGAAAGT TTCATAAAGT
146751 GGTCAGAATG CCCCAGGCTA CTTGGATAAA GATAAGGAAT TCTATCAGGG
146801 AGGCATGAAT GGAATCAGAT TAAAAGTAAC AGAGATGGAT GAGGGCCTTC
146851 CAGTGATATG CGTGAATCAG CATTAGATCC GCTTATCTCA GCTGGCAGGA
146901 GCCTGCTGTG CACACCACTT CCCAGCTCCC TCTTCAACAA TGTGAAAGTG
146951 GTAACTTGAA ATTGGTAATA ATGGGAGCAT TTACACCACG GAAACTGGTA
147001 AATGCTCGTT TTTTCCCTCC TAACAAGTGA ATTGCTAAAT ATTAGCCCAC
147051 CACTCCTTCC AAGAAGCATG TTCCTTGAGG GCTAATTGTC CTCTGAAGAT
147101 TAGCAGAGAC CTGTATCTGG AGAGGATCAG AAAAGAATGT CATCACACTG
147151 AAAGTATGTC CACCTTGCAG TTCAGAAAAG TTGCATCTTA TATGGGGTTT
147201 ATTGTCTAAG TTAGAAATGA ATTTAGAAGA TAGTAAAATT TACCGTTGAA
147251 AAACCCCTTA AATTACCCAT AAAGTATATG GGAAGTATCT TTTCTCAGTA
147301 AAGCCCAATA CAGTGTCACC TTTCACTAAT GAAACAAGCC ATTGCTTTTG
147351 TTTTGTTTTG ACTTAGTTAT TTTTATTTTT GGTCTCATTT TGGCTAATAC
147401 CAGATGAGCT AAAATGTTGA ACAAATTATA CTTGTTTTTA TAGACTAGAA
147451 TTACTCTTTT TTTTCTTTTC AGGCAGAGTC TCACTCTGTC ACCCAGGCTG
147501 GAGTGCAGTG GCATGATCTC TGCTCACTAC ATCTGCCTCC CGGGTTCAAG
147551 TGATTCTTGT GTCTCAGCCT CCTAAGTAGC TGGGATCGCA TGTGTGTGCC
147601 ACCATGTGTA GCTAATTTTT TGTATTTTTA GTAGAGATAG GATTTTGCTA
147651 AGCTGGCCAG GTTGGTTTCA AACTCCTGGT CTCAAGTGAT CCGCCCACCT
147701 TGGCCTCCCA AAGTGCTGGG ATTACAGGCG TGAGCCACCA AACCTGGCCT
147751 TAGAATTACT CTTAGAACAG TGGAATGCCC ACACATCCAA GACAGGCAAG
147801 TTCATGGAGA CTAAGGGAAC AGTGGTATCA TGTCTCCCTT CTCCCTTGTG
147851 CTTACTACAA GAATGGCAGG CAGAATTCCC TACTTATTTA AAATATCACT
147901 GATGTCTCAC TCTTTTTCTT TATATTTTAT TTATTGATTT GCCACAAAGT
147951 TTAATTCACC TAAGTGAGAC GTGCATATGA TGTAACTCCA CTGTACAGAT
148001 ACACAGATCT TTACAGAAGA ACTATTTTTG GCAACCCCTA TGCCCCTGGG
148051 TAGGGTCCAG AAGTGAACAG GCTTGGTGGG GGATTGTTTT CACCTCTTGG
148101 CTACTCAGAG TACCTAAACC TGTCCTTACT TATGGAGAGC ATGTGTCACA
148151 CCAAGATGGC AGTAAGCTGG CAACTGCGAA GACCTGACTG ATGCCCATTT
148201 GGGAAGCCAG GCAAGTGAAA ATGGACCGAA GAAACAGAGA TGGCTGTCTT
148251 TTATGCAGGG CTTTTCCATA AAGAGGTTAC ACTGGGGCAA CCAAGTATGT
148301 GTAGAAAGCC AGAGCTAAAC TTCAGCTTGG CATTCACAGT TTTCTCTTCA
148351 CTGAGCTAAT AGGCCCAGAG TTTCGGGCAG AGCTGTGAAA TAGTGCTTCT
148401 CTAATAGCAA CCATATTATT GTTACATAAT TAAAAGCCAG CTCTTTTGTT
148451 GTTTGTTTGA TTCCTTTTCC CTACAGTTCC CACATCATTT GTCTGTGCTA
148501 TTCTGTTTTT CTCCAAACAC TATAAACTTG AAGCAATTGC CCTGACTCGA
148551 TTTCAGAGAA GGGGATG
(SEQ ID NO: 3)
FEATURES:
Start: 2003
Exon: 2003-2054

FIGURE 3VV

| | |
|---|---|
| Intron: | 2055-22564 |
| Exon: | 22565-22567 |
| Intron: | 22568-39943 |
| Exon: | 39944-39999 |
| Intron: | 40000-41067 |
| Exon: | 41068-41219 |
| Intron: | 41220-79497 |
| Exon: | 79498-79500 |
| Intron: | 79501-86044 |
| Exon: | 86045-86218 |
| Intron: | 86219-105152 |
| Exon: | 105153-105190 |
| Intron: | 105191-113211 |
| Exon: | 113212-113301 |
| Intron: | 113302-123667 |
| Exon: | 123668-123765 |
| Intron: | 123766-132805 |
| Exon: | 132806-132922 |
| Intron: | 132923-133775 |
| Exon: | 133776-133848 |
| Intron: | 133849-134127 |
| Exon: | 134128-134155 |
| Intron: | 134156-134530 |
| Exon: | 134531-134545 |
| Intron: | 134546-135588 |
| Exon: | 135589-135601 |
| Intron: | 135602-137397 |
| Exon: | 137398-137526 |
| Intron: | 137527-145751 |
| Exon: | 145752-145816 |
| Intron: | 145817-146200 |
| Exon: | 146201-146291 |
| Stop: | 146292 |

SNPs:

| DNA Position Minor | Major | Minor | Domain | Protein Position | Major | |
|---|---|---|---|---|---|---|
| 210 | G | A | Beyond ORF(5') | | | |
| 332 | T | A | Beyond ORF(5') | | | |
| 1131 | T | A | Beyond ORF(5') | | | |
| 1221 | C | T | Beyond ORF(5') | | | |
| 2011 | G | C | Exon | 3 | A | A |
| 4309 | A | C | Intron | | | |
| 4345 | C | T | Intron | | | |
| 4651 | T | C | Intron | | | |
| 5037 | A | G | Intron | | | |
| 5126 | C | T | Intron | | | |
| 6048 | G | T | Intron | | | |
| 6229 | - | T | Intron | | | |
| 6328 | G | A | Intron | | | |
| 6350 | C | T | Intron | | | |
| 6382 | G | T | Intron | | | |
| 6434 | A | - | Intron | | | |
| 6722 | A | G | Intron | | | |
| 6751 | C | T | Intron | | | |
| 6752 | A | T | Intron | | | |
| 7070 | T | C | Intron | | | |
| 7306 | T | C | Intron | | | |

FIGURE 3WW

| | | | |
|---|---|---|---|
| 7339 | A | G | Intron |
| 7531 | G | A | Intron |
| 8902 | A | G | Intron |
| 9471 | G | A | Intron |
| 10023 | C | T | Intron |
| 10594 | C | G | Intron |
| 11233 | C | T | Intron |
| 11295 | - | A T | Intron |
| 11534 | - | T | Intron |
| 11757 | T | C | Intron |
| 11951 | G | A | Intron |
| 12901 | C | A | Intron |
| 13040 | C | T | Intron |
| 13081 | A | G | Intron |
| 13173 | G | T | Intron |
| 13272 | C | T | Intron |
| 13333 | A | - G | Intron |
| 13485 | C | A | Intron |
| 13933 | A | T | Intron |
| 14086 | G | A | Intron |
| 14094 | C | T | Intron |
| 14141 | G | - | Intron |
| 14831 | T | C | Intron |
| 15319 | T | C | Intron |
| 15321 | T | C | Intron |
| 15335 | A | G | Intron |
| 15477 | G | A | Intron |
| 15650 | T | C | Intron |
| 15880 | C | T | Intron |
| 16944 | G | A | Intron |
| 17061 | C | T | Intron |
| 17494 | G | C | Intron |
| 17642 | T | A | Intron |
| 17737 | A | C | Intron |
| 18068 | A | G | Intron |
| 18339 | C | T | Intron |
| 18361 | C | T | Intron |
| 19218 | A | G T | Intron |
| 19298 | C | A | Intron |
| 19629 | C | T | Intron |
| 19679 | G | A | Intron |
| 19981 | A | G | Intron |
| 20014 | C | T | Intron |
| 20280 | C | T | Intron |
| 20612 | A | C | Intron |
| 21966 | C | T | Intron |
| 22017 | T | C | Intron |
| 28009 | G | A | Intron |
| 28059 | T | A | Intron |
| 28580 | T | C | Intron |
| 28595 | A | C | Intron |
| 28823 | - | A C | Intron |
| 28827 | C | G | Intron |
| 28842 | G | T | Intron |
| 30128 | T | A | Intron |
| 30150 | T | G | Intron |
| 30188 | C | T | Intron |
| 30453 | T | C | Intron |
| 34990 | A | G | Intron |
| 35203 | G | A | Intron |
| 36206 | G | A | Intron |
| 39692 | C | T | Intron |

FIGURE 3XX

| | | | |
|---|---|---|---|
| 40095 | A | G | Intron |
| 40191 | T | C | Intron |
| 40287 | G | A | Intron |
| 40384 | T | C | Intron |
| 40510 | G | A | Intron |
| 41664 | C | T | Intron |
| 48324 | T | G | Intron |
| 48423 | C | T | Intron |
| 50015 | A | C | Intron |
| 50095 | T | G | Intron |
| 52300 | A | G | Intron |
| 52623 | C | G | Intron |
| 52773 | G | A | Intron |
| 53140 | G | A | Intron |
| 53848 | A | T | Intron |
| 57636 | - | A | Intron |
| 57693 | A | T | Intron |
| 58585 | T | C | Intron |
| 58649 | T | C | Intron |
| 62188 | A | T | Intron |
| 63478 | G | A | Intron |
| 65457 | C | A | Intron |
| 69947 | A | G | Intron |
| 69981 | C | T | Intron |
| 71165 | G | A | Intron |
| 71347 | A | G | Intron |
| 71903 | A | G | Intron |
| 71908 | C | T | Intron |
| 71994 | G | A | Intron |
| 72010 | T | C | Intron |
| 72612 | G | A | Intron |
| 73294 | A | G | Intron |
| 73385 | C | G | Intron |
| 74121 | G | A | Intron |
| 75646 | A | G | Intron |
| 75698 | C | T | Intron |
| 79007 | - | A | Intron |
| 80043 | A | G | Intron |
| 80499 | G | C | Intron |
| 80940 | A | - T | Intron |
| 81615 | G | T | Intron |
| 82599 | C | - | Intron |
| 82952 | - | G | Intron |
| 85020 | A | T | Intron |
| 88843 | C | T | Intron |
| 89700 | G | A | Intron |
| 90002 | G | A | Intron |
| 90615 | A | G | Intron |
| 92506 | A | G | Intron |
| 92558 | T | C | Intron |
| 92667 | G | A | Intron |
| 92803 | A | T | Intron |
| 95079 | T | A | Intron |
| 95089 | G | A | Intron |
| 96495 | G | A | Intron |
| 97070 | T | A | Intron |
| 99913 | A | C | Intron |
| 102375 | C | T | Intron |
| 102686 | - | A | Intron |
| 102687 | A | C | Intron |
| 102939 | C | T | Intron |
| 106162 | G | T | Intron |

FIGURE 3YY

| | | | |
|---|---|---|---|
| 106378 | T | G | Intron |
| 107310 | C | T | Intron |
| 108663 | C | A | Intron |
| 108876 | A | T | Intron |
| 110733 | C | G | Intron |
| 111546 | A | G | Intron |
| 116728 | T | C | Intron |
| 118403 | G | T | Intron |
| 118491 | C | G | Intron |
| 118888 | A | G | Intron |
| 125444 | - | A T | Intron |
| 125810 | T | C | Intron |
| 126092 | T | C | Intron |
| 127506 | G | A | Intron |
| 127878 | G | T | Intron |
| 139738 | T | C | Intron |
| 140261 | C | T | Intron |
| 141590 | T | G | Intron |
| 142613 | C | T | Intron |
| 142774 | C | A | Intron |
| 143288 | G | A | Intron |
| 145610 | A | C | Intron |
| 148360 | T | C | Beyond ORF(3') |

Context:

DNA Position

210

TCCCTCTCTCATACCATTTAATTGGTTGCTTCCTAATTAATGACTCTCTTTGCTCTCTAT
TTAATGATTCTTGCTAAAGTCCATAAGGCACTTTGCCAGCAGTTGGTTTTTAGTATGAAA
AGTAGCATTTCCTTAATGAGTCTGAGTCTGCCTTCCAAATGAAGGGTTTACTTACATTTT
CCTAATGGGAAAACGAGCTTTTCTTCTAC
[G,A]
CTTCCTTAGGGGTTTCATAAGTTCTTTTTCAATAACTCATCCTTAACACTTTCTCCAATT
CTGCCTGTAATCAATATTCCCTTCACATGTAAAGAGCTCAGGAGGAAATCAACTATTTTT
TTAAAAATACGCAATAAGGAAATTCTGCTACTCTTAGAAATAGCAGGAGCTAACATTCAT
TCTTTGCATATCATGTGCTAGGCATTGTGCCAATTACCTTATATACATTGTCTCATTATA
TGTATCCATGACCATATATGTGCTAAGCATGAAATTTTCTTAAGCCAGATAGCTGAGTAG

332

CCTAATTAATGACTCTCTTTGCTCTCTATTTAATGATTCTTGCTAAAGTCCATAAGGCAC
TTTGCCAGCAGTTGGTTTTTAGTATGAAAAGTAGCATTTCCTTAATGAGTCTGAGTCTGC
CTTCCAAATGAAGGGTTTACTTACATTTTCCTAATGGGAAAACGAGCTTTTCTTCTACGC
TTCCTTAGGGGTTTCATAAGTTCTTTTTCAATAACTCATCCTTAACACTTTCTCCAATTC
TGCCTGTAATCAATATTCCCTTCACATGTAAAGAGCTCAGGAGGAAATCAACTATTTTTT
[T,A]
AAAAATACGCAATAAGGAAATTCTGCTACTCTTAGAAATAGCAGGAGCTAACATTCATTC
TTTGCATATCATGTGCTAGGCATTGTGCCAATTACCTTATATACATTGTCTCATTATATG
TATCCATGACCATATATGTGCTAAGCATGAAATTTTCTTAAGCCAGATAGCTGAGTAGAA
TTTTAAAATATTATTTTGTACAAAATCTAGACCTTTACCCCATTTGGGGGATAGATCTGA
AGATCTGGGCTCATGTTTCCATGTGGTGACAATCTGTTTGATCTGAGCACAATTACTTTA

1131

AGGACTGGAACACAGGATGCTGCCTCTCTTTACCATTATGTTTTAAAGTGGAGCAAAGCC
GTAGTTTTCAGGATCTTTTCTTGTTCACACATATCATTTAATTTGAGCCTCAGAGCGGCT
AACAGTTTTGAGCACTTATGCTATGAAAATGTTTTGTGTATTCAGTTAAATGTATGCATA
TCATACATTTATGTAACTCAATACATATATATAAATGTGATATAACATACGTATGATATA
ACAGAGTTATATATATGTGTATTATTTAACTTAATATATAATGAGTTAAGTGTATGCATA
[T,A]
CATAGATTTATGTAACTCAATATATAAAGAGTTATATAATACAACAGAGTTGATATATAT
ATAAATGTTGTATATAAACATAATATATACGTTAATATATATTAACAAAGAGTTGTATAA
TACAACACAGAGTTAATAATATATAAATACAACACAAAGAGTTATATATGTGTGTATTAT
ACATTTAACTTAATATATAATGAGTTAAATGTATGTCTGTCCCATTCAACTCTCCATTGA

FIGURE 3ZZ

GGAAAGTACCATTATCTTCCCCAAGTTCAGAAGAAGAAAACAGAGAAATATATTGAAATT

1221 ATATCATTTAATTTGAGCCTCAGAGCGGCTAACAGTTTTGAGCACTTATGCTATGAAAAT
GTTTTGTGTATTCAGTTAAATGTATGCATATCATACATTTATGTAACTCAATACATATAT
ATAAATGTGATATAACATACGTATGATATAACAGAGTTATATATATGTGTATTATTTAAC
TTAATATATAATGAGTTAAGTGTATGCATATCATAGATTTATGTAACTCAATATATAAAG
AGTTATATAATACAACAGAGTTGATATATATATAAATGTTGTATATAAACATAATATATA
[C,T]
GTTAATATATATTAACAAAGAGTTGTATAATACAACACAGAGTTAATAATATATAAATAC
AACACAAAGAGTTATATATGTGTGTATTATACATTTAACTTAATATATAATGAGTTAAAT
GTATGTCTGTCCCATTCAACTCTCCATTGAGGAAAGTACCATTATCTTCCCCAAGTTCAG
AAGAAGAAAACAGAGAAATATATTGAAATTCAGCAATTTGCTGGTGTGGTCAAGTCCAAC
CCAGAACTTGCTTCTTTTACATTGTAGTACCCTCCAGGGTATGCAGAAACAGATAGCTAG

2011 TAGGTCTGCTATTGATGAGCCATGCAGTGTTTTCTCCTGTTGCTTGATGTTTTTATTCTG
AAATCATGGTTGGTTTTCAAACACAAAAGTTTTCACTACAGTGATACAGATGAGGTTTAT
GTTTCCGCCACAGTCTATACTCAGGGTGCCTAGAGTATAGCATATTATTAGGGTACTATT
TCTTTTCCTATCCTAGATATCCAACTAAGGCTTCGGGACATGTTTTGAGCGAAGATGGGT
GTTTCTGCCCGGATAGTATAAATCGAGGATCCAGGTCTGGGCAGATTCAACCATGGGAGC
[G,C]
AACACTTCAAGAAAACCACCAGTGTTTGATGAAAATGAAGATGGTAAGAAATATGGGATA
GTGGCATATAAAAAATAGAATTTTGCAAAATTCAAGTATATGCTTCTAGTTTCATAAGTT
AAGCATAAGCATGGTCTGTAGGGCCTTGAAGGAAAAAGGCAAAGCTGCATGAGTGAGTCT
GAGGACTTTGTAGGCTCATAGCTAGGTTTTACCTTCCACTTTCCATGGGACCTTTGGCAG
CTTTCCTAATCTCCACTATACCAATGTCCTTTGTCCAAAGGGAGCTGCAGTTGGGCATGT

4309 GAAAACTTTTTTTTCATGGCTATTGTGATTGCCTTGCTTTAACTTATCAAATAGTAAAAG
CAAAGATCTAGAGACTAGTGATATTACTTAATTTTTCTGTCTCTAAAATGGAAAGACAAA
TAGGCTTGCTTTTCATTTAGTTGGTTTCCTCTGCTTCCTCTGGACTCAGAGCTAATGTTG
TACATGAGGCTGGTCGTCAGAGAATAGGGTGGAAAAGAGAGGCCAGCTGCATACTTTTAA
CTTGCTGGGCTACATTTGAAGGTAGTAGAATAGCATTATGATGAGAAAACACAGAAATGC
[A,C]
TAACTCTTCCTTGATTCAGCCAGGCTTTGTTCTTGCGGGATGCCCAAGAAAGCTACATAA
CCAAAGAATTGTGACAATTGGGAAATAAGATACCCCTTTTTAGTTACTTTAAAGGACTCT
AGAAAAACTAGGTTGAAGGAGAGTTAGGCTTAGGGACCAGACAGGTCTTTCTTAACACCC
TCTAGGTCACCACCTTTTCTGTTGTCTGGCTTCTCAGCCCAATGAGATGAACCCACTGCA
GCACCCATAAAGGAAAGATCTGAGCATAGCAACAAGTCTGTGCCTCCCAAAGGTGCTAGG

4345 CTTTAACTTATCAAATAGTAAAAGCAAAGATCTAGAGACTAGTGATATTACTTAATTTTT
CTGTCTCTAAAATGGAAAGACAAATAGGCTTGCTTTTCATTTAGTTGGTTTCCTCTGCTT
CCTCTGGACTCAGAGCTAATGTTGTACATGAGGCTGGTCGTCAGAGAATAGGGTGGAAAA
GAGAGGCCAGCTGCATACTTTTAACTTGCTGGGCTACATTTGAAGGTAGTAGAATAGCAT
TATGATGAGAAAACACAGAAATGCATAACTCTTCCTTGATTCAGCCAGGCTTTGTTCTTG
[C,T]
GGGATGCCCAAGAAAGCTACATAACCAAAGAATTGTGACAATTGGGAAATAAGATACCCC
TTTTTAGTTACTTTAAAGGACTCTAGAAAAACTAGGTTGAAGGAGAGTTAGGCTTAGGGA
CCAGACAGGTCTTTCTTAACACCCTCTAGGTCACCACCTTTTCTGTTGTCTGGCTTCTCA
GCCCAATGAGATGAACCCACTGCAGCACCCATAAAGGAAAGATCTGAGCATAGCAACAAG
TCTGTGCCTCCCAAAGGTGCTAGGCTCTCTGTCTGTTTATGCAGACAGTTGCAAGGCAAA

4651 GCCCAAGAAAGCTACATAACCAAAGAATTGTGACAATTGGGAAATAAGATACCCCTTTTT
AGTTACTTTAAAGGACTCTAGAAAAACTAGGTTGAAGGAGAGTTAGGCTTAGGGACCAGA
CAGGTCTTTCTTAACACCCTCTAGGTCACCACCTTTTCTGTTGTCTGGCTTCTCAGCCCA
ATGAGATGAACCCACTGCAGCACCCATAAAGGAAAGATCTGAGCATAGCAACAAGTCTGT
GCCTCCCAAAGGTGCTAGGCTCTCTGTCTGTTTATGCAGACAGTTGCAAGGCAAAGGAAG
[T,C]
AGGAGGGCAAGTCCACCTACTATAAACCTGTCACTCTCTAGACATGAAGAATAGAGGAGG
AAACAAGTTGGTCCTTGCTCTGTCATTGTGAACCCCATGTTCTGATGATGGAAGGCTGAC
AATAAAAAGGTAAATAATACATAAACCAGATAATTTCACAGTGCCTTAAAGTGCCACCAA
GGAAATGACTCCTAGTGATCTTACAGACAGTGACAGTGATGGTGAGGAGGCCACTTTAGA
TAGGGTGGCTGCGGTTGTCTTTCTAAGGAGGTGACATTTGGGCTGAAGCCTGAAAGATGA

FIGURE 3AAA

5037 TTGTGAACCCCATGTTCTGATGATGGAAGGCTGACAATAAAAAGGTAAATAATACATAAA
CCAGATAATTTCACAGTGCCTTAAAGTGCCACCAAGGAAATGACTCCTAGTGATCTTACA
GACAGTGACAGTGATGGTGAGGAGGCCACTTTAGATAGGGTGGCTGCGGTTGTCTTTCTA
AGGAGGTGACATTTGGGCTGAAGCCTGAAAGATGAGAAGAAGCCATCTATGAAATGACAT
GAAAAGAATAGTTCAAGAACAGGAAAAACAAGTCCAAAATCCAAATAATGACAAAATCAG
[A,G]
ATTGAATAGTTGCCTATATCTTAACGTTCTCTCATGAGCACTAGTTTGCCAAAGAGACTG
CATTTATTGCCATGTTAACTTATTTCTTCAAAAGATGATTGATTTGAGGAGAAAAAGTAT
GCCATTCTAGGGAATTTACTTTGCTTTAAAATTCAGTACATTTTGTAAAGTTCATTTGAC
TCTTCACATAAATCTGGATTGAGCACAAGGTAAAATTGTATCTGATTGCTGTGAAGCTCC
TGACCAAGAAAAAGCAACCAAAAAGCACTGATTAACCAAACAACATTAATGCTTATGTCA

5126 CACCAAGGAAATGACTCCTAGTGATCTTACAGACAGTGACAGTGATGGTGAGGAGGCCAC
TTTAGATAGGGTGGCTGCGGTTGTCTTTCTAAGGAGGTGACATTTGGGCTGAAGCCTGAA
AGATGAGAAGAAGCCATCTATGAAATGACATGAAAAGAATAGTTCAAGAACAGGAAAAAC
AAGTCCAAAATCCAAATAATGACAAAATCAGGATTGAATAGTTGCCTATATCTTAACGTT
CTCTCATGAGCACTAGTTTGCCAAAGAGACTGCATTTATTGCCATGTTAACTTATTTCTT
[C,T]
AAAAGATGATTGATTTGAGGAGAAAAAGTATGCCATTCTAGGGAATTTACTTTGCTTTAA
AATTCAGTACATTTTGTAAAGTTCATTTGACTCTTCACATAAATCTGGATTGAGCACAAG
GTAAAATTGTATCTGATTGCTGTGAAGCTCCTGACCAAGAAAAAGCAACCAAAAAGCACT
GATTAACCAAACAACATTAATGCTTATGTCATTTTTGATATCCATATTTTTATATACATA
ATCATAATGTATAATCAAACTGGGCCAGTATCAAGGGCACTAAAATGAGCCAACTTAATT

6048 ATCTGATCTTGAACACATAATTTTATTAGTTACTTATGTTGATCTTTATTCAGCAAAAAC
AAAGTAGGAGATTTTCAGGCTAGGCATGGTTGCTTACGCCTGTAATCCCAGCACTTCAGG
AGGCCGAGGCGGGCAGATCACGAGGTCAAGAGATCGAAACCATCCTGGCCAACATGGTGA
AACCCCATCTCTACTAAAAAATACAAAAAAAATTAGCTGGGCATGCCAGTGTGCGCCTGT
AGTCCCAGCTATTCAGGAGGCTGAGGCAGGAGAATCTCTTGAACCTGGGAGGTGAAGTTT
[G,T]
CAGTGAGCTGAGATTGCTCCACTGCACTCCAGCCTGGCAACAGAGCAAGACTCTGTCCAA
AAAAAAACGGCTTGCTTATTTGATTATATAAGATATCTTTCATAAATTAGATCTCAAATT
ATACTATTGTTTTGCAGTTTTAGCTTTTATGTTTTAGGGCAAATCTTAAGTCCTAATTAC
TTTTTTTTTATTATTGTGGTAAAATGTATATAACAAAATGTACCATTTAATCATTTTAGA
ATATACGGTTTATGACATTAAGCACATTCACGTTATCATGCAACCATCACCACTACCCAT

6229 ACCCCATCTCTACTAAAAAATACAAAAAAAATTAGCTGGGCATGCCAGTGTGCGCCTGTA
GTCCCAGCTATTCAGGAGGCTGAGGCAGGAGAATCTCTTGAACCTGGGAGGTGAAGTTTG
CAGTGAGCTGAGATTGCTCCACTGCACTCCAGCCTGGCAACAGAGCAAGACTCTGTCCAA
AAAAAAACGGCTTGCTTATTTGATTATATAAGATATCTTTCATAAATTAGATCTCAAATT
ATACTATTGTTTTGCAGTTTTAGCTTTTATGTTTTAGGGCAAATCTTAAGTCCTAATTAC
[-,T]
TTTTTTTTATTATTGTGGTAAAATGTATATAACAAAATGTACCATTTAATCATTTTAGAA
TATACGGTTTATGACATTAAGCACATTCACGTTATCATGCAACCATCACCACTACCCATC
CTCAGAACATTTCTCTTCTCGAATTGAAACTTGGTACCTCTGAAACAATAACATCCACAT
TCCATCCCCTCCCCAGTCCCTGTTAAACAACCATTTGACTTTATGTCTCTATGAATTTAA
CTACTCTATGTACCTCATATAAATGGAACATATAAGATTTGTTCTTTTGCATCTGGTTTA

6328 GAACCTGGGAGGTGAAGTTTGCAGTGAGCTGAGATTGCTCCACTGCACTCCAGCCTGGCA
ACAGAGCAAGACTCTGTCCAAAAAAAAAACGGCTTGCTTATTTGATTATATAAGATATCTT
TCATAAATTAGATCTCAAATTATACTATTGTTTTGCAGTTTTAGCTTTTATGTTTTAGGG
CAAATCTTAAGTCCTAATTACTTTTTTTTTATTATTGTGGTAAAATGTATATAACAAAAT
GTACCATTTAATCATTTTAGAATATACGGTTTATGACATTAAGCACATTCACGTTATCAT
[G,A]
CAACCATCACCACTACCCATCCTCAGAACATTTCTCTTCTCGAATTGAAACTTGGTACCT
CTGAAACAATAACATCCACATTCCATCCCCTCCCCAGTCCCTGTTAAACAACCATTTGAC
TTTATGTCTCTATGAATTTAACTACTCTATGTACCTCATATAAATGGAACATATAAGATT
TGTTCTTTTGCATCTGGTTTATTTCATTTAGCATATATTTTTAAGGTTCATCCATGTTGC
AGCATGTGTCAAGATTCTCTTTCTTTTTAAGTCTGAGTCGTATTCCATTGTATGGATATA

6350 AGTGAGCTGAGATTGCTCCACTGCACTCCAGCCTGGCAACAGAGCAAGACTCTGTCCAAA
AAAAAACGGCTTGCTTATTTGATTATATAAGATATCTTTCATAAATTAGATCTCAAATTA

FIGURE 3BBB

TACTATTGTTTTGCAGTTTTAGCTTTTATGTTTTAGGGCAAATCTTAAGTCCTAATTACT
TTTTTTTTATTATTGTGGTAAAATGTATATAACAAAATGTACCATTTAATCATTTTAGAA
TATACGGTTTATGACATTAAGCACATTCACGTTATCATGCAACCATCACCACTACCCATC
[C,T]
TCAGAACATTTCTCTTCTCGAATTGAAACTTGGTACCTCTGAAACAATAACATCCACATT
CCATCCCCTCCCCAGTCCCTGTTAAACAACCATTTGACTTTATGTCTCTATGAATTTAAC
TACTCTATGTACCTCATATAAATGGAACATATAAGATTTGTTCTTTTGCATCTGGTTTAT
TTCATTTAGCATATATTTTTAAGGTTCATCCATGTTGCAGCATGTGTCAAGATTCTCTTT
CTTTTTAAGTCTGAGTCGTATTCCATTGTATGGATATACCACATTTTGTTTATCTTTTCA

6382 CTGGCAACAGAGCAAGACTCTGTCCAAAAAAAAACGGCTTGCTTATTTGATTATATAAGA
TATCTTTCATAAATTAGATCTCAAATTATACTATTGTTTTGCAGTTTTAGCTTTTATGTT
TTAGGGCAAATCTTAAGTCCTAATTACTTTTTTTTTATTATTGTGGTAAAATGTATATAA
CAAAATGTACCATTTAATCATTTTAGAATATACGGTTTATGACATTAAGCACATTCACGT
TATCATGCAACCATCACCACTACCCATCCTCAGAACATTTCTCTTCTCGAATTGAAACTT
[G,T]
GTACCTCTGAAACAATAACATCCACATTCCATCCCCTCCCCAGTCCCTGTTAAACAACCA
TTTGACTTTATGTCTCTATGAATTTAACTACTCTATGTACCTCATATAAATGGAACATAT
AAGATTTGTTCTTTTGCATCTGGTTTATTTCATTTAGCATATATTTTTAAGGTTCATCCA
TGTTGCAGCATGTGTCAAGATTCTCTTTCTTTTTAAGTCTGAGTCGTATTCCATTGTATG
GATATACCACATTTTGTTTATCTTTTCATTAGTTGACATTGATTGTCCTCACCTTTTGAT

6434 ATATAAGATATCTTTCATAAATTAGATCTCAAATTATACTATTGTTTTGCAGTTTTAGCT
TTTATGTTTTAGGGCAAATCTTAAGTCCTAATTACTTTTTTTTTATTATTGTGGTAAAAT
GTATATAACAAAATGTACCATTTAATCATTTTAGAATATACGGTTTATGACATTAAGCAC
ATTCACGTTATCATGCAACCATCACCACTACCCATCCTCAGAACATTTCTCTTCTCGAAT
TGAAACTTGGTACCTCTGAAACAATAACATCCACATTCCATCCCCTCCCCAGTCCCTGTT
[A,-]
AACAACCATTTGACTTTATGTCTCTATGAATTTAACTACTCTATGTACCTCATATAAATG
GAACATATAAGATTTGTTCTTTTGCATCTGGTTTATTTCATTTAGCATATATTTTTAAGG
TTCATCCATGTTGCAGCATGTGTCAAGATTCTCTTTCTTTTTAAGTCTGAGTCGTATTCC
ATTGTATGGATATACCACATTTTGTTTATCTTTTCATTAGTTGACATTGATTGTCCTCAC
CTTTTGATTTTTGTGAATAAGGCTGCTATAAACATTGGTGTGCAAATATCTGTTCAAGTC

6722 CCAGTCCCTGTTAAACAACCATTTGACTTTATGTCTCTATGAATTTAACTACTCTATGTA
CCTCATATAAATGGAACATATAAGATTTGTTCTTTTGCATCTGGTTTATTTCATTTAGCA
TATATTTTTAAGGTTCATCCATGTTGCAGCATGTGTCAAGATTCTCTTTCTTTTTAAGTC
TGAGTCGTATTCCATTGTATGGATATACCACATTTTGTTTATCTTTTCATTAGTTGACAT
TGATTGTCCTCACCTTTTGATTTTTGTGAATAAGGCTGCTATAAACATTGGTGTGCAAAT
[A,G]
TCTGTTCAAGTCCCTGTTTTCAATTCTTCAGGGTATATACCTAGAAGTGGAAGCACTGGA
TCATATAATTCCTTGTTTGACTCTCTGAGGAACCATCATACTGTCTTCTACCTAATTATG
CTTTGTGTTTTAGTAATGGGACACAGCCTGGCATGATGGGCTAGAGTATTGGAAAGGCAT
GCACAGGTTCAAGTCTCAGCTGTGCCACGTGCCAGTAATCTACATGTTTCTATGAGAAGA
GTCAAAGAGGATATAGCCTGGTCAACCATTATCAGACACTGGAGTCAGTTTGACTAATTA

6751 TATGTCTCTATGAATTTAACTACTCTATGTACCTCATATAAATGGAACATATAAGATTTG
TTCTTTTGCATCTGGTTTATTTCATTTAGCATATATTTTTAAGGTTCATCCATGTTGCAG
CATGTGTCAAGATTCTCTTTCTTTTTAAGTCTGAGTCGTATTCCATTGTATGGATATACC
ACATTTTGTTTATCTTTTCATTAGTTGACATTGATTGTCCTCACCTTTTGATTTTTGTGA
ATAAGGCTGCTATAAACATTGGTGTGCAAATATCTGTTCAAGTCCCTGTTTTCAATTCTT
[C,T]
AGGGTATATACCTAGAAGTGGAAGCACTGGATCATATAATTCCTTGTTTGACTCTCTGAG
GAACCATCATACTGTCTTCTACCTAATTATGCTTTGTGTTTTAGTAATGGGACACAGCCT
GGCATGATGGGCTAGAGTATTGGAAAGGCATGCACAGGTTCAAGTCTCAGCTGTGCCACG
TGCCAGTAATCTACATGTTTCTATGAGAAGAGTCAAAGAGGATATAGCCTGGTCAACCAT
TATCAGACACTGGAGTCAGTTTGACTAATTATATGGTGTTCTAAGGAAACTTGAGGTACC

6752 ATGTCTCTATGAATTTAACTACTCTATGTACCTCATATAAATGGAACATATAAGATTTGT
TCTTTTGCATCTGGTTTATTTCATTTAGCATATATTTTTAAGGTTCATCCATGTTGCAGC
ATGTGTCAAGATTCTCTTTCTTTTTAAGTCTGAGTCGTATTCCATTGTATGGATATACCA
CATTTTGTTTATCTTTTCATTAGTTGACATTGATTGTCCTCACCTTTTGATTTTTGTGAA

FIGURE 3CCC

```
        TAAGGCTGCTATAAACATTGGTGTGCAAATATCTGTTCAAGTCCCTGTTTTCAATTCTTC
        [A,T]
        GGGTATATACCTAGAAGTGGAAGCACTGGATCATATAATTCCTTGTTTGACTCTCTGAGG
        AACCATCATACTGTCTTCTACCTAATTATGCTTTGTGTTTTAGTAATGGGACACAGCCTG
        GCATGATGGGCTAGAGTATTGGAAAGGCATGCACAGGTTCAAGTCTCAGCTGTGCCACGT
        GCCAGTAATCTACATGTTTCTATGAGAAGAGTCAAAGAGGATATAGCCTGGTCAACCATT
        ATCAGACACTGGAGTCAGTTTGACTAATTATATGGTGTTCTAAGGAAACTTGAGGTACCA

7070    TGGAAGCACTGGATCATATAATTCCTTGTTTGACTCTCTGAGGAACCATCATACTGTCTT
        CTACCTAATTATGCTTTGTGTTTTAGTAATGGGACACAGCCTGGCATGATGGGCTAGAGT
        ATTGGAAAGGCATGCACAGGTTCAAGTCTCAGCTGTGCCACGTGCCAGTAATCTACATGT
        TTCTATGAGAAGAGTCAAAGAGGATATAGCCTGGTCAACCATTATCAGACACTGGAGTCA
        GTTTGACTAATTATATGGTGTTCTAAGGAAACTTGAGGTACCACAAGAAAAGTCTCCAAA
        [T,C]
        CTAAATAATTACTAATGAATTAATTGAGGGGGAAACTTATTTAACCTTTGTAAGCCTCAG
        TTTCTTTGTATGTAAAATGCAGGTAATAATTGGGCATACTTCATTAGGTCTTTGTGAGGA
        TTGAATAAATAATGCAAGTAAAACACTTAGCAAAGTATTTCCCATAAAGTAACCACTCAA
        TTAATGCTAATTAAGTGTTATTTACTAACATCAGAGTTTCCTAGTGTGAACTCTTTGAAG
        TACTTTAAGTTCTGAGAAAAACAAAATTAATTAAATGCAACTCTGTCGATTCCACAGTTA

7306    GTCAGTTTGACTAATTATATGGTGTTCTAAGGAAACTTGAGGTACCACAAGAAAAGTCTC
        CAAATCTAAATAATTACTAATGAATTAATTGAGGGGGAAACTTATTTAACCTTTGTAAGC
        CTCAGTTTCTTTGTATGTAAAATGCAGGTAATAATTGGGCATACTTCATTAGGTCTTTGT
        GAGGATTGAATAAATAATGCAAGTAAAACACTTAGCAAAGTATTTCCCATAAAGTAACCA
        CTCAATTAATGCTAATTAAGTGTTATTTACTAACATCAGAGTTTCCTAGTGTGAACTCTT
        [T,C]
        GAAGTACTTTAAGTTCTGAGAAAAACAAAATTAATTAAATGCAACTCTGTCGATTCCACA
        GTTAATTAGACCTATTCATGTTTCTATTGACTGGATTAACAGAACGGCAGATTTTATGGA
        TTCTGTTAAAACCTATATAAAAACACTTTAAAAGAAGCCAAGTTATTGACTGCACAAAAA
        CATAATCTCATCTGATATCTTTTTTATCCCCCTGAGGTTATTGTGTTTTTGTTTAAGGCA
        AAATCAAGAACTAATTGGGATGAAAATAACTAAAGTTTACTTTGTCTGATTTAAGTCCCA

7339    AACTTGAGGTACCACAAGAAAAGTCTCCAAATCTAAATAATTACTAATGAATTAATTGAG
        GGGGAAACTTATTTAACCTTTGTAAGCCTCAGTTTCTTTGTATGTAAAATGCAGGTAATA
        ATTGGGCATACTTCATTAGGTCTTTGTGAGGATTGAATAAATAATGCAAGTAAAACACTT
        AGCAAAGTATTTCCCATAAAGTAACCACTCAATTAATGCTAATTAAGTGTTATTTACTAA
        CATCAGAGTTTCCTAGTGTGAACTCTTTGAAGTACTTTAAGTTCTGAGAAAAACAAAATT
        [A,G]
        ATTAAATGCAACTCTGTCGATTCCACAGTTAATTAGACCTATTCATGTTTCTATTGACTG
        GATTAACAGAACGGCAGATTTTATGGATTCTGTTAAAACCTATATAAAAACACTTTAAAA
        GAAGCCAAGTTATTGACTGCACAAAAACATAATCTCATCTGATATCTTTTTTATCCCCCT
        GAGGTTATTGTGTTTTTGTTTAAGGCAAAATCAAGAACTAATTGGGATGAAAATAACTAA
        AGTTTACTTTGTCTGATTTAAGTCCCAAACTGACTAATAAGTAATCCCATTTGATCAACA

7531    CCCATAAAGTAACCACTCAATTAATGCTAATTAAGTGTTATTTACTAACATCAGAGTTTC
        CTAGTGTGAACTCTTTGAAGTACTTTAAGTTCTGAGAAAAACAAAATTAATTAAATGCAA
        CTCTGTCGATTCCACAGTTAATTAGACCTATTCATGTTTCTATTGACTGGATTAACAGAA
        CGGCAGATTTTATGGATTCTGTTAAAACCTATATAAAAACACTTTAAAAGAAGCCAAGTT
        ATTGACTGCACAAAAACATAATCTCATCTGATATCTTTTTTATCCCCCTGAGGTTATTGT
        [G,A]
        TTTTTGTTTAAGGCAAAATCAAGAACTAATTGGGATGAAAATAACTAAAGTTTACTTTGT
        CTGATTTAAGTCCCAAACTGACTAATAAGTAATCCCATTTGATCAACAGATTCAGTGAAA
        ACTGTCCCCCATTCTCAACTACCATATGGATATTCTGAGAAATAATTAATGATGCAGAAA
        AACATTTTTTGTTTTCTGAAATAAAAGAATAGACGTGCAAGTGACACTTCTTTTTAATGC
        TTACAACCTTTTTTTAAAAATCTACTTTATTTTCTCTATCTGAATGCACTAGATTTTGTT

8902    AAGTCCAATTTATGGCAAGGGTTTTAATTTGTAAGGGCTTTATTTCTCCATACAAAGGGA
        TTGGAGAAACAAACTAGAAAGCCAGAAAACAGACCACAAACACTGAGCTAGTGGTTCCAA
        CTGGAGTGTTCCCTGAGCAGTGACTTATGAATACTTGTTTAGAAGAATCAACTCAAACAA
        ATTTAGGAAAGTCACATCCTGCCTTTAGAGCTTCCAGTGTTTGTTAGCATATTAAAGTCT
        CTGAAATGACCTACAATATTGAAATCTCAGTCTTCTGCTATTTTTAATATTTATTTCAAA
        [A,G]
```

FIGURE 3DDD

TGAAATAATTTTTGTGAAAAACATTTTAATGTCTGTGGCTCATAATATTCTGTGGATCTC
AGTTTGGGAAATGAAAGATTATAATCGTATCTACTCTTTATCTGTTGGAAACATCTTTCC
ATTTATTTTTCCTGCTGGTTTAATGGCAACAAATTTTTACATGTGAAATATTTGTAATGT
GATTTATATGAAAAAATGTAATTTTCTTATTACACGATCAAAAGTGGTTATGCTCCTCTG
TAAGTTTTTCCTTACAAGTTTTTATGTTGCATAATTTATATCTATTTGGTTTAATGAGTA

9471 GCATAATTTATATCTATTTGGTTTAATGAGTACAACACAAGATAGCTCAGTTTAATTCTG
GGATGTTGGATGTTTCTAGTTAAAGTACAAGTTGGATTTGATGAAAATTCATTGCTTCTT
TATGATTTTTTAAAACTCAAGAACATGTTAGTTAAAGAGTGTCTTCTGAACAAATTCTTG
TGAAGTAGTTGCTGATTATTAAGTAACACTCATGCTACCGTAACTTTTTATACTATCCAA
AGCTATAGACATTTTTAATTTTCAACTTGCAACTACCTAGGTTGAAAAATTAAATCTGCA
[G,A]
GCCAGTTTCATTATTCAGACAATTTGGTTATCACTTCAAGCCTACTATCTTCAAAGAAAA
TGGGAGTGCAGGCCTTCATGGGAGCTGACTTCTGCTGTATGGCCTTGCAAATGTCAACTC
GATTAGAGTGACCAGTGTTAGCCCTCAATTCACAAACTCAGGTCCCATGAAATATACACG
GATTTCTACTATGCATTACTATGTGACCATTCATGGAAGTTTCGTTTGGAAACACAGACA
TTAAAAAGCCAGTCATGGAATAACATTCTTGTTAAAACAGGACATTGGCAAAAAGGACTA

10023 GTCATGGAATAACATTCTTGTTAAAACAGGACATTGGCAAAAAGGACTAGAAAACTTCTG
GCTATAGATTTTGAATCCAATAGCCTTGCATAGGCTTTTCTGTTTCCTCCTAAACTATGT
CTTCTGTCCTTTCTGGAGGCATATTTATAGTAAAATAAACAAAATTAACCTTGTTTTACA
CTTGAGTAACCTATACCTTTGGTTATTTACGAGAATTACTTAAAGCAGAGTTGGCAACTT
TTTCTGTGATGGGCCTGATACTAAATATTTTACACTTTCCAAGTAATACAGTCTCTGTCA
[C,T]
AACTACTCAACTCTGCCACTGTAGCATAAAAGCACACTTAGACAATGCAGAAACAAATGA
ACATGGCTTTGTTCCAATAAAACTTTATTTATGGACACTGAAATGTGAATTTCAAAAATA
TTTTTTGCATAAGATCAAATATTATTCTTTTGATTTTTTTCCAATCAATAAAAAGTGTAA
AAATTGGCCGGGCATGGTGGCTCATGCCTGTAATCCCAGCACTTTGGGAGGCCGAGGTGG
GCAGATCACCTGAGGTCACGAGTTCGAGACCAGCCTGACCAACATGGAGAAACCCTGTCT

10594 CAGCCTGACCAACATGGAGAAACCCTGTCTATATTAAAAATACAAAATTAGCTGGGTGTG
GTGGGGCCTACCTGTAATCCCAGCTACTCGGGAGGCTGAGGCAGGAGAATCGCTTGAATG
CAGGAGGCAGAGGTTGCGGTGAGCCCAGATTGCACCATTGCACTCCAGCCGGGGCAACAA
GAGCAAAACTCCGTCTCAAAAAAAAAAAAAAAAAAAAGTGTAAAAACCATTCTTAGTTCA
TGAGCTATACAAAAATAGATAGTGAGTTAGATTTGGCCCATGGGGCTTATTTTGCTGACT
[C,G]
CTGCTCTAAGCATCTTGCAGACATTTCTTCATATGCCCTAGGAGATTTCTGATATCCCCT
CATAATACCCTGGCCTTACACCAAGACTACAATCTGTTCTTTGCAGATGCTTAATAAATT
CATTCTTCCCTGTCATTCAGTTGATCTGTGTGAGCCAGTGGAAATACTTGGGCCAATAAA
TCTAGTGTGTTTGAGGGTAAAATATGCTATTTTTGTAAGATATATTATTTAATGGCCACA
CAACCTAAATTCAATTAAATGGTTACAACCTGTAACGCATTTAAAATATGACTAGGCAGA

11233 CATCCAACAGTTGATGTTGATCCCCCCATCCTGCCCCACTGTTCTACTTTGCAATTTGTT
TGAAAGAAATTGTCAATATATTTCTGACTTCTGAGCAAATCCATGAATCGGGATCCAGCA
ACAGGAAAAGAAGCTGTTGCTGCCCATTGCTTGGTTTTGGCACCAGGAATGGATAAATCC
CAGACTTCCTGGGGCACGTGTTTTATAAAAGGGAAGTGCTGACAGTGCAAACAGCTGCCA
TCAATTGGCCTTGGAGACTACTTCCCTGGAGAAGCTCCAATTATATTCTTAAAGGACCCA
[C,T]
CAAGCTCTTCAAGTGTTAGTGGCAACCATTTGCTGCCAACCATTTGAAATGATGAAGTAA
TTTTTTTTTTATTAGTGGATCCTAAGTGATAGGCTCTAGAACTGATCTTCAACCTTAACTA
ATATCATGGCATCAGAGGGCTACAGATTAAATCAGTGGTTCCCAGTCACTCTCTGTGGAC
AAGTAGCAACTACGACAAAGCTTTTCTTAGTCTATGGTGGAAGAGAAAAATTAGGACAAT
GTAATAAGCATCCCATAAACTTATTAAACCTATTAAAATTTAATTTTAAGATTATGTCAT

11295 AAAGAAATTGTCAATATATTTCTGACTTCTGAGCAAATCCATGAATCGGGATCCAGCAAC
AGGAAAAGAAGCTGTTGCTGCCCATTGCTTGGTTTTGGCACCAGGAATGGATAAATCCCA
GACTTCCTGGGGCACGTGTTTTATAAAAGGGAAGTGCTGACAGTGCAAACAGCTGCCATC
AATTGGCCTTGGAGACTACTTCCCTGGAGAAGCTCCAATTATATTCTTAAAGGACCCACC
AAGCTCTTCAAGTGTTAGTGGCAACCATTTGCTGCCAACCATTTGAAATGATGAAGTAAT
[-,A,T]
TTTTTTTATTAGTGGATCCTAAGTGATAGGCTCTAGAACTGATCTTCAACCTTAACTAAT
ATCATGGCATCAGAGGGCTACAGATTAAATCAGTGGTTCCCAGTCACTCTCTGTGGACAA

FIGURE 3EEE

GTAGCAACTACGACAAAGCTTTTCTTAGTCTATGGTGGAAGAGAAAAATTAGGACAATGT
AATAAGCATCCCATAAACTTATTAAACCTATTAAAATTTAATTTTAAGATTATGTCATTT
TTTGTATGTGTGTATGCTTAGTATTTATGGATTGTGGAAATAGAATTTTTTTTTTATAGT

11534 CAAGCTCTTCAAGTGTTAGTGGCAACCATTTGCTGCCAACCATTTGAAATGATGAAGTAA
TTTTTTTTTATTAGTGGATCCTAAGTGATAGGCTCTAGAACTGATCTTCAACCTTAACTA
ATATCATGGCATCAGAGGGCTACAGATTAAATCAGTGGTTCCCAGTCACTCTCTGTGGAC
AAGTAGCAACTACGACAAAGCTTTTCTTAGTCTATGGTGGAAGAGAAAAATTAGGACAAT
GTAATAAGCATCCCATAAACTTATTAAACCTATTAAAATTTAATTTTAAGATTATGTCAT
[-,T]
TTTTGTATGTGTGTATGCTTAGTATTTATGGATTGTGGAAATAGAATTTTTTTTTTATAG
TGAGAACCTAGGTAAGTGACTTACCTCTCTGATCCCCCATTTTCTCATATGTAGAAGGGG
GCTAATAATAGTATCTGTCTCATAGTTTTTGTGAGAATAAAAAAATTGTCCAGGTAAAAT
GCTTAGCTGGTGACTGGCACACAGTAATTGCTCAATAAATGTTAGCTATTATTGCTATCA
TTATATAATCATCATGGTTTCCAATGCCTTTACTTGGCAAATAAAAGAACAAAAGTCACC

11757 AGAAAAATTAGGACAATGTAATAAGCATCCCATAAACTTATTAAACCTATTAAAATTTAA
TTTTAAGATTATGTCATTTTTTGTATGTGTGTATGCTTAGTATTTATGGATTGTGGAAAT
AGAATTTTTTTTTTATAGTGAGAACCTAGGTAAGTGACTTACCTCTCTGATCCCCCATTT
TCTCATATGTAGAAGGGGGCTAATAATAGTATCTGTCTCATAGTTTTTGTGAGAATAAAA
AAATTGTCCAGGTAAAATGCTTAGCTGGTGACTGGCACACAGTAATTGCTCAATAAATGT
[T,C]
AGCTATTATTGCTATCATTATATAATCATCATGGTTTCCAATGCCTTTACTTGGCAAATA
AAAGAACAAAAGTCACCCGATATTGATCTCCCTTTTCTTCCCTAGTTTTCTGGGGGGTGG
GAGGCAGAGACCGAATTTTCTGATCTGTGAAATCTGAATTTATCATTGTAATTTTCCATA
AGTGCTATGTAGAGAACTCATTTAAGTTGCTGGGATGAAAAAAAATCAAAAGTGGCCTAT
TGTGCTGGGTGCAGTGGTTCACGCCTGCAATCCCAGCACTTTGGGAGGCTGAGGGGGGTG

11951 GGGGGCTAATAATAGTATCTGTCTCATAGTTTTTGTGAGAATAAAAAAATTGTCCAGGTA
AAATGCTTAGCTGGTGACTGGCACACAGTAATTGCTCAATAAATGTTAGCTATTATTGCT
ATCATTATATAATCATCATGGTTTCCAATGCCTTTACTTGGCAAATAAAAGAACAAAAGT
CACCCGATATTGATCTCCCTTTTCTTCCCTAGTTTTCTGGGGGGTGGGAGGCAGAGACCG
AATTTTCTGATCTGTGAAATCTGAATTTATCATTGTAATTTTCCATAAGTGCTATGTAGA
[G,A]
AACTCATTTAAGTTGCTGGGATGAAAAAAAATCAAAAGTGGCCTATTGTGCTGGGTGCAG
TGGTTCACGCCTGCAATCCCAGCACTTTGGGAGGCTGAGGGGGGTGGATCGCCTGAGGTC
AGGAGTTCAAGACCAGCCTGGCCAACATGGTGAAACCTTGACTCTACTAAAAATACAAAA
ATTAGCCTGGCATGATGGTGGGCACCTGTAATCCCAGCTACTCAGGAGGCTGAGGCAGGA
GAATCCCTTGAACCCAGGAGGTGGAGGATTCAGTGAGCCGAGATCTACTGCACTCCAGCC

12901 AGTGATTATGGGACAGCTAAATGATGGTGCCAAGTAGGAGCTGGAGTAGAGTATCCAGCA
ATGAGTGGAAACATCTGGGATGGAGACAGAAAGACACGGGTATTAATTCTACGGGGATGG
CTAAGTCTGCTCTGAGAGACAGTGTGGAGACCAAGGAGAAGAGGAATCCTAATATTTAGA
AACAAGGCAGTGGATAGCAATCTAGCTATGGAAAGTGGAAGGAAAGAGATAGTTGATCAT
CCAGTTCAACACTACTCTTGTTGTAGTTCACTTATGTTGAATGCTTCTGTGTGACTAAGT
[C,A]
GGTGAGAAAAATCTATGGGAGTAGGCAACATGGAGGATGTTGGTATTCACAAAAGCAGTT
TAGTGGAGTGTGGAGGCCTGAGCCAGACTAGAATGAGTTAGGAGTAGATGGAAGATAAGA
ATGCAGATATGGGCCCAGCGCGGTGGCTCACGCCTGTAATCCCAGCACTTTGGGAGGCCA
AGGTGAGCAGATCACAAGGTCAGGAGATCGAGACCATCCTGGCTAACACCGTGAAACCCC
ATCTCTACTAAAAATACAAAAAATTAGCCGGGCCTGGTGGCGGGTGCCTGTAGTCCCAGC

13040 CAGTGTGGAGACCAAGGAGAAGAGGAATCCTAATATTTAGAAACAAGGCAGTGGATAGCA
ATCTAGCTATGGAAAGTGGAAGGAAAGAGATAGTTGATCATCCAGTTCAACACTACTCTT
GTTGTAGTTCACTTATGTTGAATGCTTCTGTGTGACTAAGTCGGTGAGAAAAATCTATGG
GAGTAGGCAACATGGAGGATGTTGGTATTCACAAAAGCAGTTTAGTGGAGTGTGGAGGCC
TGAGCCAGACTAGAATGAGTTAGGAGTAGATGGAAGATAAGAATGCAGATATGGGCCCAG
[C,T]
GCGGTGGCTCACGCCTGTAATCCCAGCACTTTGGGAGGCCAAGGTGAGCAGATCACAAGG
TCAGGAGATCGAGACCATCCTGGCTAACACCGTGAAACCCCATCTCTACTAAAAATACAA
AAAATTAGCCGGGCCTGGTGGCGGGTGCCTGTAGTCCCAGCTACTCGGGAGGCTGAGGCA
GGAGAATGGCGTGAACCCGGGAGGTGGAGCTGGCAGTGAGCCGAGATGGTGCCACTGCAC

FIGURE 3FFF

TCCAGCCTGGGCAACAGAGCAAGACTCCATCTCAAAAAAAAAAAAAAAAAAAAGAATGCAG

13081 AACAAGGCAGTGGATAGCAATCTAGCTATGGAAAGTGGAAGGAAAGAGATAGTTGATCAT
CCAGTTCAACACTACTCTTGTTGTAGTTCACTTATGTTGAATGCTTCTGTGTGACTAAGT
CGGTGAGAAAAATCTATGGGAGTAGGCAACATGGAGGATGTTGGTATTCACAAAAGCAGT
TTAGTGGAGTGTGGAGGCCTGAGCCAGACTAGAATGAGTTAGGAGTAGATGGAAGATAAG
AATGCAGATATGGGCCCAGCGCGGTGGCTCACGCCTGTAATCCCAGCACTTTGGGAGGCC
[A,G]
AGGTGAGCAGATCACAAGGTCAGGAGATCGAGACCATCCTGGCTAACACCGTGAAACCCC
ATCTCTACTAAAAATACAAAAAATTAGCCGGGCCTGGTGGCGGGTGCCTGTAGTCCCAGC
TACTCGGGAGGCTGAGGCAGGAGAATGGCGTGAACCCGGGAGGTGGAGCTGGCAGTGAGC
CGAGATGGTGCCACTGCACTCCAGCCTGGGCAACAGAGCAAGACTCCATCTCAAAAAAAA
AAAAAAAAAAAAGAATGCAGATATGGCAAGTATAGACAAGCTTCAAGAAGTTTGGTCTAAA

13173 TATGTTGAATGCTTCTGTGTGACTAAGTCGGTGAGAAAAATCTATGGGAGTAGGCAACAT
GGAGGATGTTGGTATTCACAAAAGCAGTTTAGTGGAGTGTGGAGGCCTGAGCCAGACTAG
AATGAGTTAGGAGTAGATGGAAGATAAGAATGCAGATATGGGCCCAGCGCGGTGGCTCAC
GCCTGTAATCCCAGCACTTTGGGAGGCCAAGGTGAGCAGATCACAAGGTCAGGAGATCGA
GACCATCCTGGCTAACACCGTGAAACCCCATCTCTACTAAAAATACAAAAAATTAGCCGG
[G,T]
CCTGGTGGCGGGTGCCTGTAGTCCCAGCTACTCGGGAGGCTGAGGCAGGAGAATGGCGTG
AACCCGGGAGGTGGAGCTGGCAGTGAGCCGAGATGGTGCCACTGCACTCCAGCCTGGGCA
ACAGAGCAAGACTCCATCTCAAAAAAAAAAAAAAAAAAAAGAATGCAGATATGGCAAGTAT
AGACAAGCTTCAAGAAGTTTGGTCTAAAAGGAAGCGGAGAAATAAACAAAGAGATGATGC
CTAATATAATTCAGCTAAATGTAATATAATGGATTTTTTTAAGATGAGGTACTAGAGCAT

13272 TGGAGGCCTGAGCCAGACTAGAATGAGTTAGGAGTAGATGGAAGATAAGAATGCAGATAT
GGGCCCAGCGCGGTGGCTCACGCCTGTAATCCCAGCACTTTGGGAGGCCAAGGTGAGCAG
ATCACAAGGTCAGGAGATCGAGACCATCCTGGCTAACACCGTGAAACCCCATCTCTACTA
AAAATACAAAAAATTAGCCGGGCCTGGTGGCGGGTGCCTGTAGTCCCAGCTACTCGGGAG
GCTGAGGCAGGAGAATGGCGTGAACCCGGGAGGTGGAGCTGGCAGTGAGCCGAGATGGTG
[C,T]
CACTGCACTCCAGCCTGGGCAACAGAGCAAGACTCCATCTCAAAAAAAAAAAAAAAAAAA
GAATGCAGATATGGCAAGTATAGACAAGCTTCAAGAAGTTTGGTCTAAAAGGAAGCGGAG
AAATAAACAAAGAGATGATGCCTAATATAATTCAGCTAAATGTAATATAATGGATTTTTT
TAAGATGAGGTACTAGAGCATGTAATATAAATCTATTAAATTGGGTGGCCAGGAACCAGG
ACTGGCTCATCAGCATGGACCAGGCTAGACGCACAGGGCCTTATATCCAGAAGGACATCA

13333 GGCCCAGCGCGGTGGCTCACGCCTGTAATCCCAGCACTTTGGGAGGCCAAGGTGAGCAGA
TCACAAGGTCAGGAGATCGAGACCATCCTGGCTAACACCGTGAAACCCCATCTCTACTAA
AAATACAAAAAATTAGCCGGGCCTGGTGGCGGGTGCCTGTAGTCCCAGCTACTCGGGAGG
CTGAGGCAGGAGAATGGCGTGAACCCGGGAGGTGGAGCTGGCAGTGAGCCGAGATGGTGC
CACTGCACTCCAGCCTGGGCAACAGAGCAAGACTCCATCTCAAAAAAAAAAAAAAAAAA
[A,-,G]
AATGCAGATATGGCAAGTATAGACAAGCTTCAAGAAGTTTGGTCTAAAAGGAAGCGGAGA
AATAAACAAAGAGATGATGCCTAATATAATTCAGCTAAATGTAATATAATGGATTTTTTT
AAGATGAGGTACTAGAGCATGTAATATAAATCTATTAAATTGGGTGGCCAGGAACCAGGA
CTGGCTCATCAGCATGGACCAGGCTAGACGCACAGGGCCTTATATCCAGAAGGACATCAC
CTTTGGGTTTTAATGCTCTGCACTTGCTGTCTCCAAATTCTAACTGTCTCTTAGGCTCTC

13485 GTGCCTGTAGTCCCAGCTACTCGGGAGGCTGAGGCAGGAGAATGGCGTGAACCCGGGAGG
TGGAGCTGGCAGTGAGCCGAGATGGTGCCACTGCACTCCAGCCTGGGCAACAGAGCAAGA
CTCCATCTCAAAAAAAAAAAAAAAAAAAAGAATGCAGATATGGCAAGTATAGACAAGCTTC
AAGAAGTTTGGTCTAAAAGGAAGCGGAGAAATAAACAAAGAGATGATGCCTAATATAATT
CAGCTAAATGTAATATAATGGATTTTTTTAAGATGAGGTACTAGAGCATGTAATATAAAT
[C,A]
TATTAAATTGGGTGGCCAGGAACCAGGACTGGCTCATCAGCATGGACCAGGCTAGACGCA
CAGGGCCTTATATCCAGAAGGACATCACCTTTGGGTTTTAATGCTCTGCACTTGCTGTCT
CCAAATTCTAACTGTCTCTTAGGCTCTCATCAACACCCACCTCCATATCCAGATATTGAG
TACCTCAGGGAGTTCAATTTGGAAGCAAATGATGTGAAAATGTACTTTACTATCCAGTAA
CATTCTTGTTAGGGAGTGTTGGCAGAGATTGTCGAACAACCATAATGCATTTTATCATTC

FIGURE 3GGG

13933 CATCAACACCCACCTCCATATCCAGATATTGAGTACCTCAGGGAGTTCAATTTGGAAGCA
AATGATGTGAAAATGTACTTTACTATCCAGTAACATTCTTGTTAGGGAGTGTTGGCAGAG
ATTGTCGAACAACCATAATGCATTTTATCATTCGATCAGTCTACAATTTAAACATAGCAG
GACTGGACAGAGGCACAGGAAGATTAAGCCACTGACCTTAAGTCAGACAGTCACATGGGT
AGATCCGGAATCTTGATCTAAAATGAATACCATTTTTTCAGTTATAGCTATCTTCCCAGG
[A,T]
TGGCCAACCAGAATGCATATATAAAATTTCAAAAACAAACATTGGGAATTGCTCTTCAGC
AAGAATACATCAAACACCCATTATGTGCCTAACTCTAAATCTTACTTTCAGAGAGCTAAA
AACAATTTCATTTCACAGTGACATTCATCTTCGCTTCTGCCGTAACTCACATGCATATGC
CTTAGACCACATTATTAATGAAGTATTGGGGGGTTCCATCTAGAGCACCTTTTCTTCCCT
GGAGTTAATCATCCAGTTCAGCACCACTCTTGAGCTTTGCTTAGCTTCTTCTACCCATTT

14086 GATCAGTCTACAATTTAAACATAGCAGGACTGGACAGAGGCACAGGAAGATTAAGCCACT
GACCTTAAGTCAGACAGTCACATGGGTAGATCCGGAATCTTGATCTAAAATGAATACCAT
TTTTTCAGTTATAGCTATCTTCCCAGGATGGCCAACCAGAATGCATATATAAAATTTCAA
AAACAAACATTGGGAATTGCTCTTCAGCAAGAATACATCAAACACCCATTATGTGCCTAA
CTCTAAATCTTACTTTCAGAGAGCTAAAAACAATTTCATTTCACAGTGACATTCATCTTC
[G,A]
CTTCTGCCGTAACTCACATGCATATGCCTTAGACCACATTATTAATGAAGTATTGGGGGG
TTCCATCTAGAGCACCTTTTCTTCCCTGGAGTTAATCATCCAGTTCAGCACCACTCTTGA
GCTTTGCTTAGCTTCTTCTACCCATTTGGATTTTAAGGACAACAATTCCAATGGCCTTTA
TCCATGTATTTAACAATTCATTATGAGCCAGGTGAAGTGGATCACACCTCTAATCCCAAC
ACTTTGGGAGGCTGAGGCAGGTGGATCGCTGGAGCCCAGGAGTTCACAACCAGCCTGGGC

14094 TACAATTTAAACATAGCAGGACTGGACAGAGGCACAGGAAGATTAAGCCACTGACCTTAA
GTCAGACAGTCACATGGGTAGATCCGGAATCTTGATCTAAAATGAATACCATTTTTTCAG
TTATAGCTATCTTCCCAGGATGGCCAACCAGAATGCATATATAAAATTTCAAAAACAAAC
ATTGGGAATTGCTCTTCAGCAAGAATACATCAAACACCCATTATGTGCCTAACTCTAAAT
CTTACTTTCAGAGAGCTAAAAACAATTTCATTTCACAGTGACATTCATCTTCGCTTCTGC
[C,T]
GTAACTCACATGCATATGCCTTAGACCACATTATTAATGAAGTATTGGGGGGTTCCATCT
AGAGCACCTTTTCTTCCCTGGAGTTAATCATCCAGTTCAGCACCACTCTTGAGCTTTGCT
TAGCTTCTTCTACCCATTTGGATTTTAAGGACAACAATTCCAATGGCCTTTATCCATGTA
TTTAACAATTCATTATGAGCCAGGTGAAGTGGATCACACCTCTAATCCCAACACTTTGGG
AGGCTGAGGCAGGTGGATCGCTGGAGCCCAGGAGTTCACAACCAGCCTGGGCAACATGGT

14141 CCACTGACCTTAAGTCAGACAGTCACATGGGTAGATCCGGAATCTTGATCTAAAATGAAT
ACCATTTTTTCAGTTATAGCTATCTTCCCAGGATGGCCAACCAGAATGCATATATAAAAT
TTCAAAAACAAACATTGGGAATTGCTCTTCAGCAAGAATACATCAAACACCCATTATGTG
CCTAACTCTAAATCTTACTTTCAGAGAGCTAAAAACAATTTCATTTCACAGTGACATTCA
TCTTCGCTTCTGCCGTAACTCACATGCATATGCCTTAGACCACATTATTAATGAAGTATT
[G,-]
GGGGGTTCCATCTAGAGCACCTTTTCTTCCCTGGAGTTAATCATCCAGTTCAGCACCACT
CTTGAGCTTTGCTTAGCTTCTTCTACCCATTTGGATTTTAAGGACAACAATTCCAATGGC
CTTTATCCATGTATTTAACAATTCATTATGAGCCAGGTGAAGTGGATCACACCTCTAATC
CCAACACTTTGGGAGGCTGAGGCAGGTGGATCGCTGGAGCCCAGGAGTTCACAACCAGCC
TGGGCAACATGGTGAGACTCCATCTCTACCATTTTTTTTTTTAATTAGTTGGGTATGGTGG

14831 ACAATTTATTTCATCATCATTGTCATCATCATTGTCACTGCTCACTCTTCAACATTTTTT
AGGTCAACTTAATTAATATGATACCTTGTGGGATAATTTTTTATTTATTTTTATAAAATAT
TGAAGTTTTTGCCACTTTGATAACTTCTTCATTTTCTGTCCAGAGTATAACATACCAGGG
AAAAGGCTCTAAAATAAGGCTTGAGGTATTAAAAAGATCTTCTGTTTAAGTCTTATGTTC
CTAATCAATAACTAGAATTGGCCTGATTGCTTTCCTCAGTGGGTTTTCTGGTAGTCCTGA
[T,C]
ATGATATCGAGGCTGTCATATAGTCCTGAAATATCCTATCATTAACATTTGTGGTGGTAT
CTGATATAAAGGTAGATGAACTTCATTGCAGCTATTCTTAGGAAATGCGTATTTAAATGC
ATAGTTAAAAGCAAGATTTACAATTATAGAAGGAATGCAAATGAGTTGTAGAAAGCTCAT
AAAATAAAAATCAAGAAGAAAGAATTACCCATCATGCCTCAGCCCAGTGATAACCACTGC
TAATATTTTTGGCTGTTTTCATTTGCAACCCCATCTCCATTCTAGCAGCCCTCATCCCTC

15319 AAATCAAGAAGAAAGAATTACCCATCATGCCTCAGCCCAGTGATAACCACTGCTAATATT
TTTGGCTGTTTTCATTTGCAACCCCATCTCCATTCTAGCAGCCCTCATCCCTCCTACCCA

FIGURE 3HHH

```
              CTATGTTTTTCACTATATTTCTTGTTTAAATTTACTTAATTATTTGTTAATTATGTTTTT
              CCTCTCACTAGAAAGTGAACTCCATGAGGGCCAGGGATTTTTGCTATTTTGTTCACTTTT
              GTATCCTTAGCACCTACTTTGTTGATTAAGTGAATGCATTAATGATCTATTTTTAATCTG
              [T,C]
              GTATGTGTATAAAAGACACTTGATATATCTGGGATGATATTCAATATACTTTTGTATCCT
              CATTTTCACCATAGGTAGTTTATGTCAATTCCTTGAAATTTGTTGATTTTCTTGAATAAT
              TTAGCAGTTGTACAATTCTAAAACATAAATATAATTTGCTTAAATATACATACCATTTTA
              AACATATTTAAATGTGAAAATACAGTTGAGTTCTCTTAGATTGCAATTTTGTAACTTTTG
              ATAATCCTTTGATCCTGAAAAAAATTTTTTGGCATGAGGGAAGAGATGAATATTTCTTTT

     15321    ATCAAGAAGAAAGAATTACCCATCATGCCTCAGCCCAGTGATAACCACTGCTAATATTTT
              TGGCTGTTTTTCATTTGCAACCCCATCTCCATTCTAGCAGCCCTCATCCCTCCTACCCACT
              ATGTTTTTCACTATATTTCTTGTTTAAATTTACTTAATTATTTGTTAATTATGTTTTTCC
              TCTCACTAGAAAGTGAACTCCATGAGGGCCAGGGATTTTTGCTATTTTGTTCACTTTTGT
              ATCCTTAGCACCTACTTTGTTGATTAAGTGAATGCATTAATGATCTATTTTTAATCTGTG
              [T,C]
              ATGTGTATAAAAGACACTTGATATATCTGGGATGATATTCAATATACTTTTGTATCCTCA
              TTTTCACCATAGGTAGTTTATGTCAATTCCTTGAAATTTGTTGATTTTCTTGAATAATTT
              AGCAGTTGTACAATTCTAAAACATAAATATAATTTGCTTAAATATACATACCATTTTAAA
              CATATTTAAATGTGAAAATACAGTTGAGTTCTCTTAGATTGCAATTTTGTAACTTTTGAT
              AATCCTTTGATCCTGAAAAAAATTTTTTGGCATGAGGGAAGAGATGAATATTTCTTTTGG

     15335    ATTACCCATCATGCCTCAGCCCAGTGATAACCACTGCTAATATTTTTGGCTGTTTTCATT
              TGCAACCCCATCTCCATTCTAGCAGCCCTCATCCCTCCTACCCACTATGTTTTTCACTAT
              ATTTCTTGTTTAAATTTACTTAATTATTTGTTAATTATGTTTTTCCTCTCACTAGAAAGT
              GAACTCCATGAGGGCCAGGGATTTTTGCTATTTTGTTCACTTTTGTATCCTTAGCACCTA
              CTTTGTTGATTAAGTGAATGCATTAATGATCTATTTTTAATCTGTGTATGTGTATAAAAG
              [A,G]
              CACTTGATATATCTGGGATGATATTCAATATACTTTTGTATCCTCATTTTCACCATAGGT
              AGTTTATGTCAATTCCTTGAAATTTGTTGATTTTCTTGAATAATTTAGCAGTTGTACAAT
              TCTAAAACATAAATATAATTTGCTTAAATATACATACCATTTTAAACATATTTAAATGTG
              AAAATACAGTTGAGTTCTCTTAGATTGCAATTTTGTAACTTTTGATAATCCTTTGATCCT
              GAAAAAAATTTTTTGGCATGAGGGAAGAGATGAATATTTCTTTTGGAGTATTTAAATCAT

     15477    ATTATTTGTTAATTATGTTTTTCCTCTCACTAGAAAGTGAACTCCATGAGGGCCAGGGAT
              TTTTGCTATTTTGTTCACTTTTGTATCCTTAGCACCTACTTTGTTGATTAAGTGAATGCA
              TTAATGATCTATTTTTAATCTGTGTATGTGTATAAAAGACACTTGATATATCTGGGATGA
              TATTCAATATACTTTTGTATCCTCATTTTCACCATAGGTAGTTTATGTCAATTCCTTGAA
              ATTTGTTGATTTTCTTGAATAATTTAGCAGTTGTACAATTCTAAAACATAAATATAATTT
              [G,A]
              CTTAAATATACATACCATTTTAAACATATTTAAATGTGAAAATACAGTTGAGTTCTCTTA
              GATTGCAATTTTGTAACTTTTGATAATCCTTTGATCCTGAAAAAAATTTTTTGGCATGAG
              GGAAGAGATGAATATTTCTTTTGGAGTATTTAAATCATCTCTGCAATAATCCTTTGATCC
              TGAAAAAAAATTTGTGGCATGAGGGAAGAGAAGAATATTTCTTTTGGAGTGTTTAAATCA
              TCTCTACAATTAATAATATCTAAAGCAGTTTGGTTGGTTTATTTAGGTAGGATTAATTTT

     15650    GGGATGATATTCAATATACTTTTGTATCCTCATTTTCACCATAGGTAGTTTATGTCAATT
              CCTTGAAATTTGTTGATTTTCTTGAATAATTTAGCAGTTGTACAATTCTAAAACATAAAT
              ATAATTTGCTTAAATATACATACCATTTTAAACATATTTAAATGTGAAAATACAGTTGAG
              TTCTCTTAGATTGCAATTTTGTAACTTTTGATAATCCTTTGATCCTGAAAAAAATTTTTT
              GGCATGAGGGAAGAGATGAATATTTCTTTTGGAGTATTTAAATCATCTCTGCAATAATCC
              [T,C]
              TTGATCCTGAAAAAAAATTTGTGGCATGAGGGAAGAGAAGAATATTTCTTTTGGAGTGTT
              TAAATCATCTCTACAATTAATAATATCTAAAGCAGTTTGGTTGGTTTATTTAGGTAGGAT
              TAATTTTCAGTATGAATATTATTTAAAAAACAAATATAGTCAGTTGAATTGCTGTGGAGG
              TTTCTGTACGATTTACTCAAAGCTGGCTCTTTTTCTGTACGCACTACCACGCCCGGCTAA
              TTTTTGCATTTTTTTGGTAGAGATGGGGGTTTCACCATGTTGGCCAGGCTGGTCTTGAAC

     15880    AAAATTTTTTGGCATGAGGGAAGAGATGAATATTTCTTTTGGAGTATTTAAATCATCTCT
              GCAATAATCCTTTGATCCTGAAAAAAAATTTGTGGCATGAGGGAAGAGAAGAATATTTCT
              TTTGGAGTGTTTAAATCATCTCTACAATTAATAATATCTAAAGCAGTTTGGTTGGTTTAT
              TTAGGTAGGATTAATTTTCAGTATGAATATTATTTAAAAAACAAATATAGTCAGTTGAAT
```

FIGURE 3III

```
        TGCTGTGGAGGTTTCTGTACGATTTACTCAAAGCTGGCTCTTTTTCTGTACGCACTACCA
        [C,T]
        GCCCGGCTAATTTTTGCATTTTTTTGGTAGAGATGGGGGTTTCACCATGTTGGCCAGGCT
        GGTCTTGAACTCCTGATCTCAAGTGATCCACCCACCTCAGCCTCTCAAGGTGCTGGGATT
        ACAGGCATAAGCCACCATGCCCAGCCTGCATTTATCCTTACATGATGGTGAAAAATAATG
        TTTGTACTTCCTTCAGAATAATTTCAAGAAGGATCCCTGGAGTCAGCTAATGATTAGAGT
        CAGGACTGTGCCTTAGTTGATGGCCCATATAGCACTACTGAACATGCCAGAGCTTTTGCT

16944   TTCAACTCTTACCAGCTCTATGAGCTTGAGCAGGTTACATACTCTTTTCAAGTCTTAGTG
        CTTCACTTGTATTTTGGGGCTAATAAGGATTATACGAAATAATGCAGGTTAAATGCCTAG
        CACTTTGCTTTACATACTAAGGGTTCCCAAGTGCTTTATTATTAGGTTTCTGAATGTTAT
        ATATAAAGTTTCAGTGCTGCAAAAGGAATAGCACTCGAATATAACATTTTCTTTTTAATT
        CTCAGCAAGGCAACGTACTTCTATATAGAAGGGTGCACCCTTACAGATAGAATAATGGTG
        [G,A]
        GCGCACACTTGGACAAGGGAGGAGAAGGGGTTCTTATCCCCCACGCACGTGGCCCCTGCT
        CCTGTGTCGTTCCCCTATTGGCTAGGGTTAGACCACACAGGCTAACCTAATTCTGATTGG
        CTAATTTAAAGAGAATGACGGGGTGAGGGCTTTGGCAGAGTCAGGGCAGAGCAGATAGCA
        GGTAATCGGACTGAGTTAGGGTGGAGCAGGTGATCTGAATGAGTCAGGGTGGAGCAATCA
        AAAAGGTTGCTTTATGAGGAAGTTACGTTTAAAAGTAGAAGGCAGGCTGGGCGCGGTGGC

17061   TAGCACTTTGCTTTACATACTAAGGGTTCCCAAGTGCTTTATTATTAGGTTTCTGAATGT
        TATATATAAAGTTTCAGTGCTGCAAAAGGAATAGCACTCGAATATAACATTTTCTTTTTA
        ATTCTCAGCAAGGCAACGTACTTCTATATAGAAGGGTGCACCCTTACAGATAGAATAATG
        GTGGGCGCACACTTGGACAAGGGAGGAGAAGGGGTTCTTATCCCCCACGCACGTGGCCCC
        TGCTCCTGTGTCGTTCCCCTATTGGCTAGGGTTAGACCACACAGGCTAACCTAATTCTGA
        [C,T]
        TGGCTAATTTAAAGAGAATGACGGGGTGAGGGCTTTGGCAGAGTCAGGGCAGAGCAGATA
        GCAGGTAATCGGACTGAGTTAGGGTGGAGCAGGTGATCTGAATGAGTCAGGGTGGAGCAA
        TCAAAAAGGTTGCTTTATGAGGAAGTTACGTTTAAAAGTAGAAGGCAGGCTGGGCGCGGT
        GGCTCACGCCTGTAATCCCAGCACTTTGGGAGGCAGAGGTGGGCGGATCACGAGGTCAGG
        AGATGCAGACCATCCTGGCTAACACGGTGAAACCCCGTCTCTACTAAAAATACAAAAAAA

17494   CTTTATGAGGAAGTTACGTTTAAAAGTAGAAGGCAGGCTGGGCGCGGTGGCTCACGCCTG
        TAATCCCAGCACTTTGGGAGGCAGAGGTGGGCGGATCACGAGGTCAGGAGATGCAGACCA
        TCCTGGCTAACACGGTGAAACCCCGTCTCTACTAAAAATACAAAAAAATTAGCTGGGCGT
        GGTGGCAGGCACCTGTAGTCCCAGCTACTCAGGAGGCTGAGGCGGGAGAATGGCATGAAC
        CCAGGAGGCGGAGCTTGCAGTGAGGCGAGATCCTGCCATTGCACGCCAGCCTGGGCGACA
        [G,C]
        AGACTCCACCTCAAAAACAAAACAAAAAAGTAGAAGGCAAAGAATTGAACATACTGACAT
        ATTAAGTCTTTGAAAAGAAATTTAGAACTCATATCTAACAATCCCTCCCCTTGTATTTCC
        TTACAGCTTTCTTTTCAAACTTTTTTTTAATATGCCTTGGCTTAGTAGTTTTGCTTCATT
        TTCCAAAAGAAGAAGCTTCTCTGGATAAGGTGGAGGTTAGTTAAGGGAGGTTTCAGTAAG
        TGACATTTTTATGAGCCTCTGCATCTACTTACGGATGCACAGTATGACACAGCACCCGAC

17642   CTACTAAAAATACAAAAAAATTAGCTGGGCGTGGTGGCAGGCACCTGTAGTCCCAGCTAC
        TCAGGAGGCTGAGGCGGGAGAATGGCATGAACCCAGGAGGCGGAGCTTGCAGTGAGGCGA
        GATCCTGCCATTGCACGCCAGCCTGGGCGACAGAGACTCCACCTCAAAAACAAAACAAAA
        AAGTAGAAGGCAAAGAATTGAACATACTGACATATTAAGTCTTTGAAAAGAAATTTAGAA
        CTCATATCTAACAATCCCTCCCCTTGTATTTCCTTACAGCTTTCTTTTCAAACTTTTTTT
        [T,A]
        AATATGCCTTGGCTTAGTAGTTTTGCTTCATTTTCCAAAAGAAGAAGCTTCTCTGGATAA
        GGTGGAGGTTAGTTAAGGGAGGTTTCAGTAAGTGACATTTTTATGAGCCTCTGCATCTAC
        TTACGGATGCACAGTATGACACAGCACCCGACAAGAATAAGTCCACCTATTACGGCTGCG
        AGGGAAGTAAGAATTGAGGCTATTATTCCTTCTCATTTACCAAACTACTTTTCTAGCCAT
        CTTATAAAGGGGTCATTTACCCCTGAGTTGCTGGCTAACTTATTGGATAGAGCAGTCAGA

17737   GGAGGCGGAGCTTGCAGTGAGGCGAGATCCTGCCATTGCACGCCAGCCTGGGCGACAGAG
        ACTCCACCTCAAAAACAAAACAAAAAAGTAGAAGGCAAAGAATTGAACATACTGACATAT
        TAAGTCTTTGAAAAGAAATTTAGAACTCATATCTAACAATCCCTCCCCTTGTATTTCCTT
        ACAGCTTTCTTTTCAAACTTTTTTTTAATATGCCTTGGCTTAGTAGTTTTGCTTCATTTT
        CCAAAAGAAGAAGCTTCTCTGGATAAGGTGGAGGTTAGTTAAGGGAGGTTTCAGTAAGTG
        [A,C]
```

FIGURE 3JJJ

CATTTTTATGAGCCTCTGCATCTACTTACGGATGCACAGTATGACACAGCACCCGACAAG
AATAAGTCCACCTATTACGGCTGCGAGGGAAGTAAGAATTGAGGCTATTATTCCTTCTCA
TTTACCAAACTACTTTTCTAGCCATCTTATAAAGGGGTCATTTACCCCTGAGTTGCTGGC
TAACTTATTGGATAGAGCAGTCAGACCATGCAGTGCCTTTCTAATACTTCCATTAGGGGC
AGTGTTGTTTGGGATGAAGGTGCAACATTGAGTTTTAATTATGATGCAAACTACCCCTCT

18068 GATGCACAGTATGACACAGCACCCGACAAGAATAAGTCCACCTATTACGGCTGCGAGGGA
AGTAAGAATTGAGGCTATTATTCCTTCTCATTTACCAAACTACTTTTCTAGCCATCTTAT
AAAGGGGTCATTTACCCCTGAGTTGCTGGCTAACTTATTGGATAGAGCAGTCAGACCATG
CAGTGCCTTTCTAATACTTCCATTAGGGGCAGTGTTGTTTGGGATGAAGGTGCAACATTG
AGTTTTAATTATGATGCAAACTACCCCTCTTTCTGCTACTATCATGTCTAAGGCTATTTT
[A,G]
TTTTGCCAAGCCATCTGGCTAGTAGCCCCTAATTGCTCAGCTATTCCATTAACAGCATCT
CTAGTGTAGTTAATAAATCACTGTTGGTTGTAGTAGCTGTAGTTTATCCAATCTACATTT
TTATTAATTGTCACTCACCAAAATATTGACTTAAATCCTGCGGCTATTTGATTTTGGGCT
TTAAATTGATCTGGTATTCCTCATGGGACCCTAATTGTGTCTAAATAGACGTGAGAGTTG
AAAGACCCATAAGGGGCTTCTCTCGCTTTACGATGTCTTATTTTTCCTTCCTCTGGTTGA

18339 TCTGCTACTATCATGTCTAAGGCTATTTTATTTTGCCAAGCCATCTGGCTAGTAGCCCCT
AATTGCTCAGCTATTCCATTAACAGCATCTCTAGTGTAGTTAATAAATCACTGTTGGTTG
TAGTAGCTGTAGTTTATCCAATCTACATTTTTATTAATTGTCACTCACCAAAATATTGAC
TTAAATCCTGCGGCTATTTGATTTTGGGCTTTAAATTGATCTGGTATTCCTCATGGGACC
CTAATTGTGTCTAAATAGACGTGAGAGTTGAAAGACCCATAAGGGGCTTCTCTCGCTTTA
[C,T]
GATGTCTTATTTTTCCTTCCTCTGGTTGATGAAATGCCAGGGTGAAAGGGATAGCCAATT
GGACTAAAGCACAAGTGCCACTCCAGTTATTTGGCAGAGTGTCCAGTAAAGGTCCACCAC
AATACCACCACACATCCACACATCCGCTCGGGGATGAATAAGGGCTGACTGATTGATAAG
CTCTTGAAAATTCTTAAGCTCACTGCATCCCTTCAGGTCTCCAAGGAACGCTAAGTTTCC
TCCCTGTCATGAGAGACACTAAGTGAACTAGTTTTGGGAGACAGAAGCTGGATGGCCCTT

18361 CTATTTTATTTTGCCAAGCCATCTGGCTAGTAGCCCCTAATTGCTCAGCTATTCCATTAA
CAGCATCTCTAGTGTAGTTAATAAATCACTGTTGGTTGTAGTAGCTGTAGTTTATCCAAT
CTACATTTTTATTAATTGTCACTCACCAAAATATTGACTTAAATCCTGCGGCTATTTGAT
TTTGGGCTTTAAATTGATCTGGTATTCCTCATGGGACCCTAATTGTGTCTAAATAGACGT
GAGAGTTGAAAGACCCATAAGGGGCTTCTCTCGCTTTACGATGTCTTATTTTTCCTTCCT
[C,T]
TGGTTGATGAAATGCCAGGGTGAAAGGGATAGCCAATTGGACTAAAGCACAAGTGCCACT
CCAGTTATTTGGCAGAGTGTCCAGTAAAGGTCCACCACAATACCACCACACATCCACACA
TCCGCTCGGGGATGAATAAGGGCTGACTGATTGATAAGCTCTTGAAAATTCTTAAGCTCA
CTGCATCCCTTCAGGTCTCCAAGGAACGCTAAGTTTCCTCCCTGTCATGAGAGACACTAA
GTGAACTAGTTTTGGGAGACAGAAGCTGGATGGCCCTTGGGGGCTGACCTGCAGGGTACC

19218 CTTGTTGCCCAGGCTGGAGTGCAATGGCGCAATCTTGGCTCACTGCAACCTCTGCTTCCC
AGGTTCAAGCAATTCTCCTGTCTCAGCCTCCCGAGTAGCTGGGATTACAGGCATGCACCA
CCATGCCTGGCTAAGTTTGTATTTTTAGTAGAGACGGTGGTTTCTCCATGTTGGTCAGGC
TGGTCTTGAACTCCCAACCTCAGGTGATCCCCCTGCCTCGGCCTCCCAAAGTGCTGGGAT
TACAGGCGTGAGCCACCGAGCCTGACCTGTTTTAAGTCTTTAGTTTTTACAATAGCTATC
[A,G,T]
TGGTCTTGTTGTTAGATGGAGGAGGAGCAACTGTTCCGTTGTGAGAGGTTTTGGAAGAAG
GCTTACAGGAAGGTGCAGGCGGTGGGGATCAAAGAAATGCATTTTAAATAATCTAATAGG
GTTTGTCCCTGAAACCTCAGCCCCTATAGCATAAAACTGACTTAAAGAAGGGAACTGGCT
TAGAAAAGGGGAAGAAATTTGAGAGTTTGAGATAATAACCTGTAGAGAATTATAGATAAT
AACCTGTATAGGTTTAGCTGACAGCTGGGGGGAGGGCTGTCTCTTTAGTAAAATGAGTGT

19298 TCTCAGCCTCCCGAGTAGCTGGGATTACAGGCATGCACCACCATGCCTGGCTAAGTTTGT
ATTTTTAGTAGAGACGGTGGTTTCTCCATGTTGGTCAGGCTGGTCTTGAACTCCCAACCT
CAGGTGATCCCCCTGCCTCGGCCTCCCAAAGTGCTGGGATTACAGGCGTGAGCCACCGAG
CCTGACCTGTTTTAAGTCTTTAGTTTTTACAATAGCTATCTTGGTCTTGTTGTTAGATGG
AGGAGGAGCAACTGTTCCGTTGTGAGAGGTTTTGGAAGAAGGCTTACAGGAAGGTGCAGG
[C,A]
GGTGGGGATCAAAGAAATGCATTTTAAATAATCTAATAGGGTTTGTCCCTGAAACCTCAG
CCCCTATAGCATAAAACTGACTTAAAGAAGGGAACTGGCTTAGAAAAGGGGAAGAAATTT

FIGURE 3KKK

GAGAGTTTGAGATAATAACCTGTAGAGAATTATAGATAATAACCTGTATAGGTTTAGCTG
ACAGCTGGGGGGAGGGCTGTCTCTTTAGTAAAATGAGTGTATGGTTTTAGTAAATTACAA
AAACTGGTTGGGGCAATCCCTTCTTGCTATTTAGTGGTCCACAGAACATTGGACCAACTA

19629 ATCTAATAGGGTTTGTCCCTGAAACCTCAGCCCCTATAGCATAAAACTGACTTAAAGAAG
GGAACTGGCTTAGAAAAGGGGAAGAAATTTGAGAGTTTGAGATAATAACCTGTAGAGAAT
TATAGATAATAACCTGTATAGGTTTAGCTGACAGCTGGGGGGAGGGCTGTCTCTTTAGTA
AAATGAGTGTATGGTTTTAGTAAATTACAAAAACTGGTTGGGGCAATCCCTTCTTGCTAT
TTAGTGGTCCACAGAACATTGGACCAACTACAGCATAAAAGCTCTACGTCGGGGGCGGGG
[C,T]
GGGGGGTAGGACTCTGGGTTGACATTGGGGTCTTTATTGAAATTTCCCCGGATTAAATGG
TCCCAATTCACTAATGCCCAGTCTGATGACAGTCAGGAGGCACAGAGGTATTTTTTCTGA
AATAGAGAGGTGTCTTTGACTTGGCAAATCCCCACAGGGTATAACAAGGCAAGCATTAAG
TGCAATAGTTTGAGGCAAAATTGACTTGGTTATGTTAATAACTAGATGGTCAGCAATAGA
GCCAGTAAAGAAGAAAGAGTAATAGAATAGATAAAAGAGAGTTAAATTTTTCTTAGCTTT

19679 CTTAAAGAAGGGAACTGGCTTAGAAAAGGGGAAGAAATTTGAGAGTTTGAGATAATAACC
TGTAGAGAATTATAGATAATAACCTGTATAGGTTTAGCTGACAGCTGGGGGGAGGGCTGT
CTCTTTAGTAAAATGAGTGTATGGTTTTAGTAAATTACAAAAACTGGTTGGGGCAATCCC
TTCTTGCTATTTAGTGGTCCACAGAACATTGGACCAACTACAGCATAAAAGCTCTACGTC
GGGGGCGGGGCGGGGGGTAGGACTCTGGGTTGACATTGGGGTCTTTATTGAAATTTCCCC
[G,A]
GATTAAATGGTCCCAATTCACTAATGCCCAGTCTGATGACAGTCAGGAGGCACAGAGGTA
TTTTTTCTGAAATAGAGAGGTGTCTTTGACTTGGCAAATCCCCACAGGGTATAACAAGGC
AAGCATTAAGTGCAATAGTTTGAGGCAAAATTGACTTGGTTATGTTAATAACTAGATGGT
CAGCAATAGAGCCAGTAAAGAAGAAAGAGTAATAGAATAGATAAAAGAGAGTTAAATTTT
TCTTAGCTTTAGTTTGGCAGGGCTTTCCCCTGGGGCTGTGGCCCACAACTCTGGAGGGGG

19981 ATTAAATGGTCCCAATTCACTAATGCCCAGTCTGATGACAGTCAGGAGGCACAGAGGTAT
TTTTTCTGAAATAGAGAGGTGTCTTTGACTTGGCAAATCCCCACAGGGTATAACAAGGCA
AGCATTAAGTGCAATAGTTTGAGGCAAAATTGACTTGGTTATGTTAATAACTAGATGGTC
AGCAATAGAGCCAGTAAAGAAGAAAGAGTAATAGAATAGATAAAAGAGAGTTAAATTTTT
CTTAGCTTTAGTTTGGCAGGGCTTTCCCCTGGGGCTGTGGCCCACAACTCTGGAGGGGGC
[A,G]
GCGCTTTCTTGACTCGGGTGTGATGAGTCCATCCCTTTTTCACTGTAGAAACAGCAGTCT
TGGTGGTGAGCAGCACAAGGTAGGGTCCTTCCCAGGCTGGCTCGAGTTTTCCTTCTTTCC
ACCCTTTGATAAGAACGTGATCTTCAGGCTGGTGTTGGTTTACCGGAAATTCTAGGGGTG
GTACCTGTGCTAAAAGACTTTTAGTTTTGAGGGAAAGGAAAATGGAAGATAAACCAAGTA
TATAATTTCTAAGAAATGGACCTTTTGTTTTAAATGTGGGGACATCAGCAGTGGACTTTA

20014 GATGACAGTCAGGAGGCACAGAGGTATTTTTTCTGAAATAGAGAGGTGTCTTTGACTTGG
CAAATCCCCACAGGGTATAACAAGGCAAGCATTAAGTGCAATAGTTTGAGGCAAAATTGA
CTTGGTTATGTTAATAACTAGATGGTCAGCAATAGAGCCAGTAAAGAAGAAAGAGTAATA
GAATAGATAAAAGAGAGTTAAATTTTTCTTAGCTTTAGTTTGGCAGGGCTTTCCCCTGGG
GCTGTGGCCCACAACTCTGGAGGGGGCGGCGCTTTCTTGACTCGGGTGTGATGAGTCCAT
[C,T]
CCTTTTTCACTGTAGAAACAGCAGTCTTGGTGGTGAGCAGCACAAGGTAGGGTCCTTCCC
AGGCTGGCTCGAGTTTTCCTTCTTTCCACCCTTTGATAAGAACGTGATCTTCAGGCTGGT
GTTGGTTTACCGGAAATTCTAGGGGTGGTACCTGTGCTAAAAGACTTTTAGTTTTGAGGG
AAAGGAAAATGGAAGATAAACCAAGTATATAATTTCTAAGAAATGGACCTTTTGTTTTAA
ATGTGGGGACATCAGCAGTGGACTTTATAGTCCTTGGTGCCTTTTTACTGAGAAATTTCC

20280 CGGCGCTTTCTTGACTCGGGTGTGATGAGTCCATCCCTTTTTCACTGTAGAAACAGCAGT
CTTGGTGGTGAGCAGCACAAGGTAGGGTCCTTCCCAGGCTGGCTCGAGTTTTCCTTCTTT
CCACCCTTTGATAAGAACGTGATCTTCAGGCTGGTGTTGGTTTACCGGAAATTCTAGGGG
TGGTACCTGTGCTAAAAGACTTTTAGTTTTGAGGGAAAGGAAAATGGAAGATAAACCAAG
TATATAATTTCTAAGAAATGGACCTTTTGTTTTAAATGTGGGGACATCAGCAGTGGACTT
[C,T]
ATAGTCCTTGGTGCCTTTTTACTGAGAAATTTCCTTTAGCACCTATTTTTATTAGATTTT
AGACCAAAGAAGGCCAAACACCATTTTATATTTAACAGTGCTTCCTGTATGATTCTTATA
CCAGATAAGCTAAGTTTCACCTTTATATTAGCAAGTTGTTAAACTTAATTTTAATAAAAC
TTTGTAGACATATTTATCCAATTTTTAATGTCTGACCATAATGTATGATTCTTATAGACT

FIGURE 3LLL

CTTTTTAACCTTTTATAATTTTTGTTAAAGAGCAGGTTAGTGCTTTAAGAAATACCTGTT

20612 TCCTTTAGCACCTATTTTTATTAGATTTTAGACCAAAGAAGGCCAAACACCATTTTATAT
TTAACAGTGCTTCCTGTATGATTCTTATACCAGATAAGCTAAGTTTCACCTTTATATTAG
CAAGTTGTTAAACTTAATTTTAATAAAACTTTGTAGACATATTTATCCAATTTTTAATGT
CTGACCATAATGTATGATTCTTATAGACTCTTTTTAACCTTTTATAATTTTTGTTAAAGA
GCAGGTTAGTGCTTTAAGAAATACCTGTTGTGCTTTTATTTTAATGTCCAGTTCACAGAA
[A,C]
AACTGTATGATACCCCTTAAACTTTAGCCAATATGTTTACACACAGAATTTCCTTTATAA
TTAACATTTCAAAACTTGCTTAAACCTTTAAAACAAAATATTTGTTTATTTTTAAACTTT
TAATGTAGGTAAAAATCCACATTCTTATGGCTCCTTATAATCCTTTTACCAAAGGCATAT
TTTACTTTCCTTATACACCTTGCACATAAACTGTTTCTTCAATAGCTTTACATTCAGGAG
GCTTAATTACTTTTAAATTATACAACATTTCTTACATAAATTCCCTTTTAAAACTTTTTT

21966 GGTTTCCTCTAAAAGTTACTTTTCTACTTCCTTCTGTTAGCAAAGCAGTTGCGGCTACAG
ATTGAATGTATTCAGGCCATCCGCGGGTTACTGGGTTAAGGATTTTTGATAGGAAGGCTA
CTGGTTGTCAGTGGCCTCAGTGCTTTCAGGCTATGCCCTTGTTTATACTTACAACAAGGT
GGTACTGGAGTGTTATAGGGTCACCGAGAAGACCTTCGATTATCAGTTATAGGTTTTAAA
TTTACCCTGGCTTTTTTTTTTTTTATTATTATACTTTAAGTCCTAGGGTACATGTGCACAA
[C,T]
GTGCAGGTTTGTTACATATTTATACATGTGCCACGTTGGTGTGCTGCACCTATTAACTAA
GGAATAGGGTACACTGTTTTTTCTTTACTACTTCTATCTCTTTCTTTCCCTCTCTGACTT
TCTGTCTCTTTCTTTCTGACTCCCTCTTTGTAGCTCTGCCTCTCTTTCTCTCTCTCTGCC
TCTCTCCTCTCTGTCTCTCTCTTCTCTGTCTCTGTCCTGTTTCTCTCTCTCTCTTGTTTC
TCTCTCCTCTGTCTCTCTCCTCTCTCCCTCTCTTCTGTCTCTCTCTCCTGTCTCTCTCTT

22017 CGGCTACAGATTGAATGTATTCAGGCCATCCGCGGGTTACTGGGTTAAGGATTTTTGATA
GGAAGGCTACTGGTTGTCAGTGGCCTCAGTGCTTTCAGGCTATGCCCTTGTTTATACTTA
CAACAAGGTGGTACTGGAGTGTTATAGGGTCACCGAGAAGACCTTCGATTATCAGTTATA
GGTTTTAAATTTACCCTGGCTTTTTTTTTTTTTATTATTATACTTTAAGTCCTAGGGTACA
TGTGCACAACGTGCAGGTTTGTTACATATTTATACATGTGCCACGTTGGTGTGCTGCACC
[T,C]
ATTAACTAAGGAATAGGGTACACTGTTTTTTCTTTACTACTTCTATCTCTTTCTTTCCCT
CTCTGACTTTCTGTCTCTTTCTTTCTGACTCCCTCTTTGTAGCTCTGCCTCTCTTTCTCT
CTCTCTGCCTCTCTCCTCTCTGTCTCTCTCTTCTCTGTCTCTGTCCTGTTTCTCTCTCTC
TCTTGTTTCTCTCTCCTCTGTCTCTCTCCTCTCTCCCTCTCTTCTGTCTCTCTCTCCTGT
CTCTCTCTTTCTCTCTCCTCTCTCTCTCTCCCCTCTTGTCTCTCACTCCTGGCTGTCTCT

28009 AATTTGTCCTTTTTCACCCTTCCTTGGCAAATCACGCAATATTCCTTCTTAAAAATGGGT
AAAGTGCCAGCCGAACTTAGAAGAGGGACTGATTCTATCTCTATTCTGACCAGGTATACG
GTAGACTGTAATTTAATGTCAGCACCTTTCTGTTGCCATAATGAGGTATATTTATTTCTG
TTCAAAGATCATGCAGCCCTGACAAAGCAAATACCCTCTGACTCCCACTGTTAATTATCC
TTCAGTTGCTACAGGGTTTTCATCCATGTCCTCACTTAGGAGAGTTGGCGGTTGTGAAGC
[G,A]
GATGGAGTCCACAATCTCAGTGGCAGTTCTTAATGCTTTGAGCTCAAAGTGTGAGTAAGT
CGATGAGTGAGGCTTTTAAGATGTAAATCCAATATCTGCAGAGAAATCTGAAGCTGTAAT
ATTAGAACAACATTCAAATGAGGACTTCATTGACTAGCTCATTAAGAAGTCCTTTGATAA
TAGCATGTTGGTAAGACTTTTCTTAGAAGGTACATATTATAAATGATGATGTGCTAAGAA
ATCAACATAAAGGAAAATAGAAAAATTTTCCCCAAATCCATCCTTTTTCTGTAGAACTTT

28059 AAAAATGGGTAAAGTGCCAGCCGAACTTAGAAGAGGGACTGATTCTATCTCTATTCTGAC
CAGGTATACGGTAGACTGTAATTTAATGTCAGCACCTTTCTGTTGCCATAATGAGGTATA
TTTATTTCTGTTCAAAGATCATGCAGCCCTGACAAAGCAAATACCCTCTGACTCCCACTG
TTAATTATCCTTCAGTTGCTACAGGGTTTTCATCCATGTCCTCACTTAGGAGAGTTGGCG
GTTGTGAAGCAGATGGAGTCCACAATCTCAGTGGCAGTTCTTAATGCTTTGAGCTCAAAG
[T,A]
GTGAGTAAGTCGATGAGTGAGGCTTTTAAGATGTAAATCCAATATCTGCAGAGAAATCTG
AAGCTGTAATATTAGAACAACATTCAAATGAGGACTTCATTGACTAGCTCATTAAGAAGT
CCTTTGATAATAGCATGTTGGTAAGACTTTTCTTAGAAGGTACATATTATAAATGATGAT
GTGCTAAGAAATCAACATAAAGGAAAATAGAAAAATTTTCCCCAAATCCATCCTTTTTCT
GTAGAACTTTAATGATGATACCTCATTCCTTTGTAACTTAATTTTAAAAAGTTAATTATG

FIGURE 3MMM

28580 CCCAAATCCATCCTTTTTCTGTAGAACTTTAATGATGATACCTCATTCCTTTGTAACTTA
ATTTTAAAAAGTTAATTATGCACCTACTATGATACGTCCAAAATGTTTTTAGGTGATGTG
GATATAGCGAAGAACAAGACACACCCAGTGTCTTCCTTCATGGAGTCTATATTCTTGGCA
CTGTTGGTCCTGTGTGAAGTCCTAACATTATTTTGCTTAATGTTTTGGCAAGAGAGGCAA
CATTGGCTGGGCGTGATGGCTCATACCTGTAATCCCAGCACTTTGGGAGGCTGAGGTGGA
[T,C]
GGATCACCTGAGGTAGGGAGTTCAAGACCAGCCTGATAACATAGAGAAACCCTGCCTCTC
CTAAAAATACAAAATTAGCCAGGCATGGTGGTGCGTGTCTGTAATCCCAGCTACTCTGGA
GGCTGAGGCAGGAGAATCACTTAAACCTGGGAGGCAGAGGTTGTGGTGAGCCGAGATTGT
GCCATTGCACTTGTACTCCAGCCTGGGCAACAAGATTGAAACTCCATCTCAAAAAAAAAA
AACCAACAGGCAACATTCTGGGCTGAAACAAAGGTAATTCATCTGGTAACAATAGCAATA

28595 TTTCTGTAGAACTTTAATGATGATACCTCATTCCTTTGTAACTTAATTTTAAAAAGTTAA
TTATGCACCTACTATGATACGTCCAAAATGTTTTTAGGTGATGTGGATATAGCGAAGAAC
AAGACACACCCAGTGTCTTCCTTCATGGAGTCTATATTCTTGGCACTGTTGGTCCTGTGT
GAAGTCCTAACATTATTTTGCTTAATGTTTTGGCAAGAGAGGCAACATTGGCTGGGCGTG
ATGGCTCATACCTGTAATCCCAGCACTTTGGGAGGCTGAGGTGGATGGATCACCTGAGGT
[A,C]
GGGAGTTCAAGACCAGCCTGATAACATAGAGAAACCCTGCCTCTCCTAAAAATACAAAAT
TAGCCAGGCATGGTGGTGCGTGTCTGTAATCCCAGCTACTCTGGAGGCTGAGGCAGGAGA
ATCACTTAAACCTGGGAGGCAGAGGTTGTGGTGAGCCGAGATTGTGCCATTGCACTTGTA
CTCCAGCCTGGGCAACAAGATTGAAACTCCATCTCAAAAAAAAAAAACCAACAGGCAACA
TTCTGGGCTGAAACAAAGGTAATTCATCTGGTAACAATAGCAATAACATAAATAGCAGTA

28823 TGGCTGGGCGTGATGGCTCATACCTGTAATCCCAGCACTTTGGGAGGCTGAGGTGGATGG
ATCACCTGAGGTAGGGAGTTCAAGACCAGCCTGATAACATAGAGAAACCCTGCCTCTCCT
AAAAATACAAAATTAGCCAGGCATGGTGGTGCGTGTCTGTAATCCCAGCTACTCTGGAGG
CTGAGGCAGGAGAATCACTTAAACCTGGGAGGCAGAGGTTGTGGTGAGCCGAGATTGTGC
CATTGCACTTGTACTCCAGCCTGGGCAACAAGATTGAAACTCCATCTCAAAAAAAAAAAA
[-,A,C]
CAACAGGCAACATTCTGGGCTGAAACAAAGGTAATTCATCTGGTAACAATAGCAATAACA
TAAATAGCAGTAATAATTATACATTATTGAGTTCCTATTCTCTGCCAAAAATGGTTGATA
AGCACCTTTGATATGGCTTATTTTACCTAGTCCTCATTATAACCTTAGAAGGTATATTGT
ATCTGGTCAAAATTGAAAGAAGAAATTGAAACTCACAGAGGGTAAATAATTAAAGTTCAT
AGCTAGTAAGTAGTACAGACAAACCCAAAAGCAGAGTTTCATGCTCATAGTCACCATAAT

28827 TGGGCGTGATGGCTCATACCTGTAATCCCAGCACTTTGGGAGGCTGAGGTGGATGGATCA
CCTGAGGTAGGGAGTTCAAGACCAGCCTGATAACATAGAGAAACCCTGCCTCTCCTAAAA
ATACAAAATTAGCCAGGCATGGTGGTGCGTGTCTGTAATCCCAGCTACTCTGGAGGCTGA
GGCAGGAGAATCACTTAAACCTGGGAGGCAGAGGTTGTGGTGAGCCGAGATTGTGCCATT
GCACTTGTACTCCAGCCTGGGCAACAAGATTGAAACTCCATCTCAAAAAAAAAAAACCAA
[C,G]
AGGCAACATTCTGGGCTGAAACAAAGGTAATTCATCTGGTAACAATAGCAATAACATAAA
TAGCAGTAATAATTATACATTATTGAGTTCCTATTCTCTGCCAAAAATGGTTGATAAGCA
CCTTTGATATGGCTTATTTTACCTAGTCCTCATTATAACCTTAGAAGGTATATTGTATCT
GGTCAAAATTGAAAGAAGAAATTGAAACTCACAGAGGGTAAATAATTAAAGTTCATAGCT
AGTAAGTAGTACAGACAAACCCAAAAGCAGAGTTTCATGCTCATAGTCACCATAATGTAT

28842 ATACCTGTAATCCCAGCACTTTGGGAGGCTGAGGTGGATGGATCACCTGAGGTAGGGAGT
TCAAGACCAGCCTGATAACATAGAGAAACCCTGCCTCTCCTAAAAATACAAAATTAGCCA
GGCATGGTGGTGCGTGTCTGTAATCCCAGCTACTCTGGAGGCTGAGGCAGGAGAATCACT
TAAACCTGGGAGGCAGAGGTTGTGGTGAGCCGAGATTGTGCCATTGCACTTGTACTCCAG
CCTGGGCAACAAGATTGAAACTCCATCTCAAAAAAAAAAAACCAACAGGCAACATTCTGG
[G,T]
CTGAAACAAAGGTAATTCATCTGGTAACAATAGCAATAACATAAATAGCAGTAATAATTA
TACATTATTGAGTTCCTATTCTCTGCCAAAAATGGTTGATAAGCACCTTTGATATGGCTT
ATTTTACCTAGTCCTCATTATAACCTTAGAAGGTATATTGTATCTGGTCAAAATTGAAAG
AAGAAATTGAAACTCACAGAGGGTAAATAATTAAAGTTCATAGCTAGTAAGTAGTACAGA
CAAACCCAAAAGCAGAGTTTCATGCTCATAGTCACCATAATGTATTCAGAAACTTTTAGG

30128 GGCCAATGAATCTGAATTTAAAAACATGTATTTGTGTGATTTTGATGGGTGGACACACTT
GAGAATCACGTCAGGACCATTTATGTGGCTCTCAATTACATATACACTACTTTATATTGC

FIGURE 3NNN

AGTTGTTTATTTATGTTATATTGCAGTTATTTATTTATGTTTCATCTCTTTTCCTGAGAA
ATTACCTTCCTGATAATCCAATGCAGAGATAAATTAAGAAAATCTGTAGGAAAGAATAGA
TCATCAAGTCCCTTGCAACATTCTTCTGAGGTTGTAATAATCTCCTCTAGGATGCTTTGC
[T,A]
GGATTTCCCTGGACTAGGTTGTCTTTTCCTGCTACTTTCTCCCATTACAGGTCTCCCTAC
GGCAGCACTGCTTATATCACTTGGAACTTGAATCTATTTTGGTAAAAAAAAAGTTAAAAA
TTAAATTATCAGAAGGATATTGGGGATGCCTGCAGAGTAATCAAAATAGGATCTATATTG
TTATAGAGCCAGGCACATTAATGCCATCAGCTTTAGCCCTTTATGTTGTGATTTTACTTT
ATTCCAAATGTCAGCTTTATCCTGTTGGATGTGCTGATCTTTTTTCTCTACATTCAGCCA

30150 AACATGTATTTGTGTGATTTTGATGGGTGGACACACTTGAGAATCACGTCAGGACCATTT
ATGTGGCTCTCAATTACATATACACTACTTTATATTGCAGTTGTTTATTTATGTTATATT
GCAGTTATTTATTTATGTTTCATCTCTTTTCCTGAGAAATTACCTTCCTGATAATCCAAT
GCAGAGATAAATTAAGAAAATCTGTAGGAAAGAATAGATCATCAAGTCCCTTGCAACATT
CTTCTGAGGTTGTAATAATCTCCTCTAGGATGCTTTGCTGGATTTCCCTGGACTAGGTTG
[T,G]
CTTTTCCTGCTACTTTCTCCCATTACAGGTCTCCCTACGGCAGCACTGCTTATATCACTT
GGAACTTGAATCTATTTTGGTAAAAAAAAAGTTAAAAATTAAATTATCAGAAGGATATTG
GGGATGCCTGCAGAGTAATCAAAATAGGATCTATATTGTTATAGAGCCAGGCACATTAAT
GCCATCAGCTTTAGCCCTTTATGTTGTGATTTTACTTTATTCCAAATGTCAGCTTTATCC
TGTTGGATGTGCTGATCTTTTTTCTCTACATTCAGCCAGTTCCATTCTCATGTTCTGGAA

30188 GAGAATCACGTCAGGACCATTTATGTGGCTCTCAATTACATATACACTACTTTATATTGC
AGTTGTTTATTTATGTTATATTGCAGTTATTTATTTATGTTTCATCTCTTTTCCTGAGAA
ATTACCTTCCTGATAATCCAATGCAGAGATAAATTAAGAAAATCTGTAGGAAAGAATAGA
TCATCAAGTCCCTTGCAACATTCTTCTGAGGTTGTAATAATCTCCTCTAGGATGCTTTGC
TGGATTTCCCTGGACTAGGTTGTCTTTTCCTGCTACTTTCTCCCATTACAGGTCTCCCTA
[C,T]
GGCAGCACTGCTTATATCACTTGGAACTTGAATCTATTTTGGTAAAAAAAAAGTTAAAAA
TTAAATTATCAGAAGGATATTGGGGATGCCTGCAGAGTAATCAAAATAGGATCTATATTG
TTATAGAGCCAGGCACATTAATGCCATCAGCTTTAGCCCTTTATGTTGTGATTTTACTTT
ATTCCAAATGTCAGCTTTATCCTGTTGGATGTGCTGATCTTTTTTCTCTACATTCAGCCA
GTTCCATTCTCATGTTCTGGAAGCTTGTGACAGAGGGGGAATATGCATTTCAAGATCAGA

30453 TTTCCTGCTACTTTCTCCCATTACAGGTCTCCCTACGGCAGCACTGCTTATATCACTTGG
AACTTGAATCTATTTTGGTAAAAAAAAAGTTAAAAATTAAATTATCAGAAGGATATTGGG
GATGCCTGCAGAGTAATCAAAATAGGATCTATATTGTTATAGAGCCAGGCACATTAATGC
CATCAGCTTTAGCCCTTTATGTTGTGATTTTACTTTATTCCAAATGTCAGCTTTATCCTG
TTGGATGTGCTGATCTTTTTTCTCTACATTCAGCCAGTTCCATTCTCATGTTCTGGAAGC
[T,C]
TGTGACAGAGGGGGAATATGCATTTCAAGATCAGAAGATCCAGAGTGAAAATGATTGGAA
TGGCCTGAGTCACAGTTCCAATCCTAGAACAAGGCATCTTGCTAGGGATGTGAGAGATGA
TAAGTGACAGATACAGTGACAGCAAGTGGTTGATGGGATCTGAGTTGTGAGAGAGGGTCT
GTGAAAAATGAAAGACCTGCATAAGAAGAGGAGAAGCAGAAATATGAACATTGTTGTGAG
TCAGGTCTTTACCCAACTCTGTGCTGCTTATTCTACTTTTTTGTGCAAGATTGATTATGT

34990 GGTTACACAGCTGGTGTCCTCGTTGCCTGTTCAGTAGAAAGGTTTACATAAACAGCAAGG
TGTGCTGTTCTCAATAGACTCACTTATGTTCATGATTTGGTACTTGCTCAAGCTGGAATC
AATTTTTAGAAAAAATAAAATCTTTTGCAAAGATTTTTACCTCAAAAATAGAAAAAAAGG
GCATTCCTGCCTTACCTTCTACAAGGGTCTTCTCTGAAATTCCAAGCATCAGGGTGTTAT
AACAGACTCTAAAAAGGGTTTCCTTTTTTCTTTCCTTTAACATTGCTTATTGCACAGCAT
[A,G]
TTGAGACAGAGAAGATGGTAAGTGAAATAAAACAAAGGAAATAAAAAGTATCATCACTGG
GTTTCAGAATCAGCATGGTTTATGCTAAGGGAAAGACTTGGAAACCTTGATTCAACATAT
AATTCTAAAAAGAGACAGGAAGAAATCCCACCTTGTTTCCTCTGATTCTACCTTTGGGAT
GGGTAGGTATGTTATACAATAAGAATAACATTGAGATGACTGCTATAAAAATAGTGGTTA
AGAGCCTGGGTCCAGAATGAGAAAGGTGGATATTGAATTTACCTGAGTGCAACTAGGCAG

35203 CTGAAATTCCAAGCATCAGGGTGTTATAACAGACTCTAAAAAGGGTTTCCTTTTTTCTTT
CCTTTAACATTGCTTATTGCACAGCATATTGAGACAGAGAAGATGGTAAGTGAAATAAAA
CAAAGGAAATAAAAAGTATCATCACTGGGTTTCAGAATCAGCATGGTTTATGCTAAGGGA
AAGACTTGGAAACCTTGATTCAACATATAATTCTAAAAAGAGACAGGAAGAAATCCCACC

FIGURE 3OOO

TTGTTTCCTCTGATTCTACCTTTGGGATGGGTAGGTATGTTATACAATAAGAATAACATT
[G,A]
AGATGACTGCTATAAAAATAGTGGTTAAGAGCCTGGGTCCAGAATGAGAAAGGTGGATAT
TGAATTTACCTGAGTGCAACTAGGCAGACTCAAGTGAGTTGATTTTACCCACTCCTCCAC
TCAAATACTGGGTATGGCTTTGCAAAAACATTCAACCAGTTATCCACATAGTTGGTCTTA
ACTTTCCATGTGACTATAATGAATATAAACTTGCTAATGAGCAGAGTGTGATTTTAGTGT
TTAAACTATTTTTTCCCGAATAATAGTTCCTAGATGCAGTTAATGAGCCTTATTGGGTAC

36206 TCCAAGTAATTATCACAACATTAAGGTGCATTCAGCTTTGTGTGTTAACGTGGTATACCT
CCAGGCAACTTTTAGGATACTGTACAGATACAATGGCTGTGAAGGCTGGGATGAAAAGAC
CTGTGCGAAGCAGGACTGAGGCACTTAAGGAAGGCCTCAGAGTTACATCTCCTTTGCCTG
TTTTCTTGCAGGCCACATACCCTAGCCCAGCCCTGTCAGCATGAGTGAGAACCAGGCTCT
GCCTTTGCCCACACTAAACCACTACCTTCAAGGCCCCACAAAGACCCAGTGTCTCCAGAC
[G,A]
GTCTTTCTGTCTTCTTAACACTCAGAGCTCCATGAACCAGAATGAAAGTTTTGGAACATG
ATCCAAGTAAAAGACTCAAGAAGTAAACACCACTAAGGTTAACTTTGCTTTAGAGGTTAG
AGAAAACACTGCAAGGACACCACACCAGAGACTATGAAAACCCCAAATGTATTGAAATGA
TGCTGATTCCATTTACCTCCATATTGCCTGATAATACCCAGGTGCTACCATGGCAGCTTA
AGGTGGTATTTGCTGGGAGCTATGATACTCTTTAAGAAGTAATAGCACTACTAGTAAAAG

39692 AAAATTGAAATTACTTAGATACAAAAGAGTGGTTGTAGTAAGAAAATAGGCAAGGAGAAC
ATTTTAAAGTGCTGATCCTCGGTAAAGCCATACATAGGATGCACCTGGGAGCAGATCTTT
CTGAAGTCATTCTGTGCTCAGAGATGTTTCTCCTTACCTTGCTGCCTATGTCAAATTCTC
TGTGATATGTTCTTAGAGCCCCATGACCTCTCTTCTTAACTTGCAGTGGGAGCTTGAATT
TTCCATTTATTTTTGTGACCATTTAGTCTATAAGAGTCTCCGTCTTTACAGGGCCCTCAC
[C,T]
TGACTACAGACTCCATAAAGGCAGAGATTCTATTTTTACTCTATTATTACTGTATTCCCA
GCACTAAGCACTAGGATTAATACATAGTAAGTGTTCAACAGATGTTTACTGGATGATTAG
ATTGGCATTTTAAGGTAGTCTGAGATCACGTTTTAGACAAGATACTTCAGTTTAGTCCAA
TCTTTATTATTTATTAGCTACTAAAGAGAAATTGATAATTACTCATGATATTCTTCTTTT
TTGTTTTACAGTCAACTTTGACCACTTTGAAATTTTGCGAGCCATTGGGAAAGGCAGTTT

40095 TGTTTACTGGATGATTAGATTGGCATTTTAAGGTAGTCTGAGATCACGTTTTAGACAAGA
TACTTCAGTTTAGTCCAATCTTTATTATTTATTAGCTACTAAAGAGAAATTGATAATTAC
TCATGATATTCTTCTTTTTTGTTTTACAGTCAACTTTGACCACTTTGAAATTTTGCGAGC
CATTGGGAAAGGCAGTTTTGGGAAGGTGAGAACAAATTGAAATGATTAACCACCAGCAGG
GTTATGTAGCCCAGGGAACAGAGGGTCCAGAAATGTTCACATTATTGAGTTGCTGGGACC
[A,G]
CAAGGAAAGATAATTAAGTGAAAATGTTTTTGTAATGGATTTTTATAAAATTGTCACCAC
AGTTTAAGAAAAGCGTGTGACAGGCAGCTACATAATGAACATATACTGTTGTCAGAATAA
TCTCATTAAACTCAAATCTGTTTACTCTCAGTAAACTTTAAGGCTTTTCTCTCTACCCTA
AAGGAGATGAAGATTTCAGAATCATTTTCAGATTCTACCAGCTGTATGCCCAGTAATAGT
TATCTTGTTTATGGAAGAGTTACTTATTTTCATGTGGGAAAGAAGTCATCCGATTTCTAT

40191 TACTAAAGAGAAATTGATAATTACTCATGATATTCTTCTTTTTTGTTTTACAGTCAACTT
TGACCACTTTGAAATTTTGCGAGCCATTGGGAAAGGCAGTTTTGGGAAGGTGAGAACAAA
TTGAAATGATTAACCACCAGCAGGGTTATGTAGCCCAGGGAACAGAGGGTCCAGAAATGT
TCACATTATTGAGTTGCTGGGACCACAAGGAAAGATAATTAAGTGAAAATGTTTTTGTAA
TGGATTTTTATAAAATTGTCACCACAGTTTAAGAAAAGCGTGTGACAGGCAGCTACATAA
[T,C]
GAACATATACTGTTGTCAGAATAATCTCATTAAACTCAAATCTGTTTACTCTCAGTAAAC
TTTAAGGCTTTTCTCTCTACCCTAAAGGAGATGAAGATTTCAGAATCATTTTCAGATTCT
ACCAGCTGTATGCCCAGTAATAGTTATCTTGTTTATGGAAGAGTTACTTATTTTCATGTG
GGAAAGAAGTCATCCGATTTCTATTTGTTTCCTCATTTGTCTAATGTTTTTATCTTAAGA
AAAATACATATTCAGTTTAATTTTTTTTTGCAAGAAACTTCTGTATTCAAACCCTGATTAC

40287 CAGTTTTGGGAAGGTGAGAACAAATTGAAATGATTAACCACCAGCAGGGTTATGTAGCCC
AGGGAACAGAGGGTCCAGAAATGTTCACATTATTGAGTTGCTGGGACCACAAGGAAAGAT
AATTAAGTGAAAATGTTTTTGTAATGGATTTTTATAAAATTGTCACCACAGTTTAAGAAA
AGCGTGTGACAGGCAGCTACATAATGAACATATACTGTTGTCAGAATAATCTCATTAAAC
TCAAATCTGTTTACTCTCAGTAAACTTTAAGGCTTTTCTCTCTACCCTAAAGGAGATGAA
[G,A]

FIGURE 3PPP

```
            ATTTCAGAATCATTTTCAGATTCTACCAGCTGTATGCCCAGTAATAGTTATCTTGTTTAT
            GGAAGAGTTACTTATTTTCATGTGGGAAAGAAGTCATCCGATTTCTATTTGTTTCCTCAT
            TTGTCTAATGTTTTTATCTTAAGAAAAATACATATTCAGTTTAATTTTTTTTGCAAGAAA
            CTTCTGTATTCAAACCCTGATTACTAGTTTCTCAATGGAGACGTACTTTAAGAGAATAAT
            ATTTCATATAAAACTTGCATTTTAAAATCATTTTCTGTTTACTTTTTCAGGCATTATACA

40384       TTGCTGGGACCACAAGGAAAGATAATTAAGTGAAAATGTTTTTTGTAATGGATTTTTATAA
            AATTGTCACCACAGTTTAAGAAAAGCGTGTGACAGGCAGCTACATAATGAACATATACTG
            TTGTCAGAATAATCTCATTAAACTCAAATCTGTTTACTCTCAGTAAACTTTAAGGCTTTT
            CTCTCTACCCTAAAGGAGATGAAGATTTCAGAATCATTTTCAGATTCTACCAGCTGTATG
            CCCAGTAATAGTTATCTTGTTTATGGAAGAGTTACTTATTTTCATGTGGGAAAGAAGTCA
            [T,C]
            CCGATTTCTATTTGTTTCCTCATTTGTCTAATGTTTTTATCTTAAGAAAAATACATATTC
            AGTTTAATTTTTTTTGCAAGAAACTTCTGTATTCAAACCCTGATTACTAGTTTCTCAATG
            GAGACGTACTTTAAGAGAATAATATTTCATATAAAACTTGCATTTTAAAATCATTTTCTG
            TTTACTTTTTCAGGCATTATACAGACCTCTAAAGAAATTTCAAAAACATGGACATCATAT
            TTAGTGTTTTTCCAGTCCTTAAAGTCCTTTTTGGTTATATCATGTATGGGTTGTAAACAG

40510       GAATAATCTCATTAAACTCAAATCTGTTTACTCTCAGTAAACTTTAAGGCTTTTCTCTCT
            ACCCTAAAGGAGATGAAGATTTCAGAATCATTTTCAGATTCTACCAGCTGTATGCCCAGT
            AATAGTTATCTTGTTTATGGAAGAGTTACTTATTTTCATGTGGGAAAGAAGTCATCCGAT
            TTCTATTTGTTTCCTCATTTGTCTAATGTTTTTATCTTAAGAAAAATACATATTCAGTTT
            AATTTTTTTTGCAAGAAACTTCTGTATTCAAACCCTGATTACTAGTTTCTCAATGGAGAC
            [G,A]
            TACTTTAAGAGAATAATATTTCATATAAAACTTGCATTTTAAAATCATTTTCTGTTTACT
            TTTTCAGGCATTATACAGACCTCTAAAGAAATTTCAAAAACATGGACATCATATTTAGTG
            TTTTTCCAGTCCTTAAAGTCCTTTTTGGTTATATCATGTATGGGTTGTAAACAGAAATTC
            TTTGCACAGTATTATTCAGCTTGACAGTTCAGTCATGTCTATTTCAGTCACTCAAAGCAG
            GATTAAGGATGTTACTTGTTATTGGAATATTCCTGACATGGAGGCAGCTATTTTCACCAA

41664       GAAAACAGTGAAAGTACAGAGATTTATTGCAAAGTGGAAAAGTACACACTCAAGAGAGGG
            GAGCATGGGTGAACTCCAGCGAATGTCATGTAAGGGGGGGTTTGAGGCTGCTGCCATAAT
            GGGTTTCTTTAACCAAGGGGTGAAACATTCATGATGATTCCTGAAAAAAGATGGAGATTT
            CTTGGAACTGTGGTGCCAGCTATTTTTACACCAAATATGAATGTTCCTGGAACTGTCATG
            GTGCTGGTGGGTGTATGATTTAGTATGTTAATGAGTGTATGATGAGGTCCTAGGTGAAAC
            [C,T]
            TAGGTCAAATCCAGCACAATGGAGAGGACCCACAGACTCTCTGAAGGAAACGACTGCTCC
            TGCAGGACCCAGGCAACTCCCCCAAAACTGTGAGTACCCCAACTGTGGAGGTGGGAAAGA
            GAGACCCTCCTCTCCCAAACACACACCCCACTGGAGAAGCTGAAGGTCTGTTTGCTGGA
            GAAGTTTCTGACTTTACCTGGAGCTGAGTGGACTTGAAGAGCCCAGTGAAATACACGGGG
            AGAAGAAGCAGCAGAAAGGCCCTGGGAGCTTGCTGGGTCCACAAGCAGGCCATTCCTGCC

48324       CACTGATATGTGGAAGCTAAGCTATGAGGATGCAAAGCAATGAGAATGATACAATGGACT
            TTGGAGACTTAGGGGGAAGAGTGGGAGGGGGGCGAGGGATACAAGACTACAAATGTGGTG
            TAGTGTATACTGCTCAGGTGATGGGTGCAACAAAATCTCACAATCACCACTAAAGAACTT
            ACCCATGTAACCAAAACCACCTTTACCCCAATAACTTATGGAAAAATAATCCAGCACCAC
            ATTAGGTTTAGTCGGACTTAGCCAGCTTGGCTTACACCCTGGTTTTTCAGGTTCTTATCA
            [T,G]
            TCCCAGTTTATGCAGCTGTTTCAACATTTTCCTTTTGCTAGTCATGTGAAACTGCTGTCT
            GGAATTTTCTTTTCTCCTGCTACCACCCTTTATTATTCCTGTCTCACTTTCATCTTCATC
            CCTACTGTTACATAAATGCATCTTGATTTCTAGGCAAGCATTTGTCAAATTCTCATTAGG
            ATCTTCCTCAGGGTCTTTTGTTCTCCTTAGTTTCTTTGGCTTTATAGTGAAAGAACATTT
            TTCTTTTATTGTCACTAACAAATACTTCTTGGTCAGTTGTCACAGTTCCCCTTGTCCTTG

48423       TACAAGACTACAAATGTGGTGTAGTGTATACTGCTCAGGTGATGGGTGCAACAAAATCTC
            ACAATCACCACTAAAGAACTTACCCATGTAACCAAAACCACCTTTACCCCAATAACTTAT
            GGAAAAATAATCCAGCACCACATTAGGTTTAGTCGGACTTAGCCAGCTTGGCTTACACCC
            TGGTTTTTCAGGTTCTTATCATTCCCAGTTTATGCAGCTGTTTCAACATTTTCCTTTTGC
            TAGTCATGTGAAACTGCTGTCTGGAATTTTCTTTTCTCCTGCTACCACCCTTTATTATTC
            [C,T]
            TGTCTCACTTTCATCTTCATCCCTACTGTTACATAAATGCATCTTGATTTCTAGGCAAGC
            ATTTGTCAAATTCTCATTAGGATCTTCCTCAGGGTCTTTTGTTCTCCTTAGTTTCTTTGG
```

FIGURE 3QQQ

```
        CTTTATAGTGAAAGAACATTTTTCTTTTATTGTCACTAACAAATACTTCTTGGTCAGTTG
        TCACAGTTCCCCTTGTCCTTGAGGTCAATATATATATATTTTTAAACATTGTAATTAAAT
        ATGCTGACTGGGAAGGAGTTCAGATGTCTTACTAGTTATTAGATACTTTCTTTCCCCATG

50015   GCCTTAGCATTTTACCTTCTCATATTTGTCTTTCATCGCTGTGTGGGCAAAGTTGATTTC
        ATTCTGTTCCTTTTTTTAAGAAAATGGGTATTGTGAGGCTTTAAGCTGGCCAAAGATGAT
        AGATTTTGCTGTTTGCTAATTTGGTGTCATTCCAGACAACATTCTGTTCTCCATGCATAC
        TGACCTGGTGATAACATGACATATAACCTATTCTTTCCTTCTCACTTCTCACATTGAACC
        TCACAGTGGAACACTAGGCATCATTAACAATGATAGAAGAAAGAGAGGAGACTTACCTCC
        [A,C]
        CCCAGTGATTCTGGTACTACATTCAAAACTAGAAACTAACTGGGAGGGGGAATTCTTAAA
        GTACAACAGCAACTCCCTTTGTCTTCCAAACCATGAGAAAAATCTTCACAAATCTGTATC
        ATTCTTCCTAATAAATGCTTTTTGTTTTAGTAAGTACAATATATTCAATGTAAGTTTATC
        TTTCCACATTTATAAACCATCTTGCAGTGCTTTTGAAGGTGTGATTGTGAGTGTATTAGT
        CAGTTCTCACATTGCTATAAAGAAATACCTGAGACTGGGTAATTTTTAAAGAAAAGAAGT

50095   AAAATGGGTATTGTGAGGCTTTAAGCTGGCCAAAGATGATAGATTTTGCTGTTTGCTAAT
        TTGGTGTCATTCCAGACAACATTCTGTTCTCCATGCATACTGACCTGGTGATAACATGAC
        ATATAACCTATTCTTTCCTTCTCACTTCTCACATTGAACCTCACAGTGGAACACTAGGCA
        TCATTAACAATGATAGAAGAAAGAGAGGAGACTTACCTCCACCCAGTGATTCTGGTACTA
        CATTCAAAACTAGAAACTAACTGGGAGGGGGAATTCTTAAAGTACAACAGCAACTCCCTT
        [T,G]
        GTCTTCCAAACCATGAGAAAAATCTTCACAAATCTGTATCATTCTTCCTAATAAATGCTT
        TTTGTTTTAGTAAGTACAATATATTCAATGTAAGTTTATCTTTCCACATTTATAAACCAT
        CTTGCAGTGCTTTTGAAGGTGTGATTGTGAGTGTATTAGTCAGTTCTCACATTGCTATAA
        AGAAATACCTGAGACTGGGTAATTTTTAAAGAAAAGAAGTTTAAGTGGCTCATGGTTCTG
        CAGGCTGTGCAGGAAGCATAGTGGCTTCTGCTTTGGGGAGGACTCAGGAAGCTTCCAATC

52300   GTATGAAGAACTGTGTGTGTGGTGTGTGGGTATGTATGTGTTGGGGTTTCAGAGAAAGAA
        GGTAAGTAGTCTGGGGGCAGGGACGTTAAGGAGGAAAGAACATTTGGAAATAAAATTCAA
        CCTGACTTGCCTCCAGGGACCTGGCTACACTCAGGAACAGTCTTCAAATGTAGGCCATGT
        TATCAAGTGAATGCTGCCAGACAGGGCTGGCATCCAGGAAAAGTAAATAAAATCTTCTTG
        TGCGTCTGTCTCTGAGGGCTCTTCACAAAGCCCTGGCAACCCACAGCCTGAAAACAAATA
        [A,G]
        GCCCCAGTCTTTCCCAGCATAGTTGATTCCCCAGGTGGCTTTTGTTAATTGAGATTAAAC
        CTGTAGCTGCACACAACTCCTCAGGGCCTCTATCTCTTTACTCATGTCTTTGTCCCTGTG
        GATAGAAGGGGTCCACATGTGGTTTCAGGAAATTAGGACACCAGATCATCTGTTTTAACT
        GGAAAGAACTACCTGTACTGAGAGTGTGACAAGGTCCTTTCAGACTCTGAACATAGCCCA
        ATAAATGGTATCAACCTTAAATAACGAGATTCTGAAAATATGATTAAGTATCGAGTTTGC

52623   TTGATTCCCCAGGTGGCTTTTGTTAATTGAGATTAAACCTGTAGCTGCACACAACTCCTC
        AGGGCCTCTATCTCTTTACTCATGTCTTTGTCCCTGTGGATAGAAGGGGTCCACATGTGG
        TTTCAGGAAATTAGGACACCAGATCATCTGTTTTAACTGGAAAGAACTACCTGTACTGAG
        AGTGTGACAAGGTCCTTTCAGACTCTGAACATAGCCCAATAAATGGTATCAACCTTAAAT
        AACGAGATTCTGAAAATATGATTAAGTATCGAGTTTGCTGGAGCCCAGAGCTTGAGGATG
        [C,G]
        CCACCTGGGAGCACAGATTCACTTTGCCCAGAATGTACACTCCAATTAGCAGCAGTTATA
        AGTGGGGTTTTAAGAAAAAAAGACAAGGCAGTTCCTAAGTTATTTACCAAAAATTTACAT
        TAAAATAATGTAAGCTATTGATGGACTATGCATTATTCTTTATATCACAAATTACAGGAA
        CACAAAGATAATGGGTGAGGCAGCTAGTCAGGAACAAAATGGCTTTAAAATACTGTCCTT
        GAGCATGGGTTTGAGGCTGTGACTGACATCCCATACTCATGTTTCTCTAAACCTAATAAA

52773   TTTTAACTGGAAAGAACTACCTGTACTGAGAGTGTGACAAGGTCCTTTCAGACTCTGAAC
        ATAGCCCAATAAATGGTATCAACCTTAAATAACGAGATTCTGAAAATATGATTAAGTATC
        GAGTTTGCTGGAGCCCAGAGCTTGAGGATGCCCACCTGGGAGCACAGATTCACTTTGCCC
        AGAATGTACACTCCAATTAGCAGCAGTTATAAGTGGGGTTTTAAGAAAAAAAGACAAGGC
        AGTTCCTAAGTTATTTACCAAAAATTTACATTAAAATAATGTAAGCTATTGATGGACTAT
        [G,A]
        CATTATTCTTTATATCACAAATTACAGGAACACAAAGATAATGGGTGAGGCAGCTAGTCA
        GGAACAAAATGGCTTTAAAATACTGTCCTTGAGCATGGGTTTGAGGCTGTGACTGACATC
        CCATACTCATGTTTCTCTAAACCTAATAAATTGTGCATATCTCATATAGCTCAGACTGCT
        CTGAGCTATTTTTGTTTTCTCATTTCCCCCCTTTTCATCAAGATTTTGCAAAGAAAGCAT
```

FIGURE 3RRR

TGTGGATGAACTTAAGCAGTTTTGGCTCCTTTTATGTTCAGGAACTTAGTCCTGCATTGC

53140 AAATGGCTTTAAAATACTGTCCTTGAGCATGGGTTTGAGGCTGTGACTGACATCCCATAC
TCATGTTTCTCTAAACCTAATAAATTGTGCATATCTCATATAGCTCAGACTGCTCTGAGC
TATTTTTGTTTTCTCATTTCCCCCCTTTTCATCAAGATTTTGCAAAGAAAGCATTGTGGA
TGAACTTAAGCAGTTTTGGCTCCTTTTATGTTCAGGAACTTAGTCCTGCATTGCTAGGAA
GTCTTATTCCCAGATGGTCCTGTCCCACATTTGGGGGAAGGGGAAAGGATGAGTCTTAGT
[G,A]
GGGATTTTAACACCATCAGAAGCAAAATTGGGATGGCATCGCAGGGTGCCACAAATGAGA
CCTCACCCAAGTCACTAATTTATGTAGCTACTGTTGCTTGTGGGATCATCTCCAGGCTTC
AGAATACCATGCAGTTAGTTTTCTCGGAATAAGTAAAACAATGAGCTATACATAGTAGAA
ATATAATACACATAACAATTACAATTAAAAAAAAAAAAGAATTTCTATGCCTGAATGAAA
AAAATATCTATTCCATTGGAAAGTCAACTAAAAACATCATGAAGAAAATTAAAATCCAGT

53848 GTGTGCTATAATTTTCTTCTGAACCATAATTTCTCTCTCTTCAGTTCACTATTTCTACCC
AAGATAAATGTTATCAGGACCAACATACTTGTAAAATAAGCTTTAGTATTATATTTGGCC
TAATTATTTGCATTAAGTGCAACAAAAATAATGAATGGCCATGTACGCATTTTTAAGTTG
GCTTTGCTGGAACTTTTTCATAAGGAATCTCAGATTAGACTTTTAAAAGCCTCTCTAAAC
TAGATATTGAAGCCAATAATTCACCATCAAACTGCCTGTAGCATCTACATAAATTGGGTG
[A,T]
ATTTCTCCCTTCTTCAGGTTCTGAAATATATTGAGGTTTCTAGGCCTGTCAAATGATGAC
ATTCTTTACTTACTGCAAGGTCAAAAAACTTGTGAGGGTACCATGTAGACAAGGTATCAG
GTCAGTTTTCCAAAAGGACTATTGATTTGGCTCTATAAAGTCAACTTCAATTCATCAAAG
CAGTTTGGTCATATCTGAAAGTATGTCATTTCACCCAAAGCCTTGGTAAAATGACCAGCC
TTAGTAAAATGACCAGTGTCTCCAACTGTGTACTGTTACAGAAGAAAACAGGTTCTTACT

57636 TATGTGAACTAAAAGGGATTTGAGTTATTTTCTATTTTTCTGATAAAATATTTAAGTGTT
TCCTTTCTCTTTTGGCCAATTAGAACTCATTCATATATTTTTGTAATAAATTTTACATAC
ACATGACACATATAAACATGCAGACACACACAGGCAGATTTTATAGCTTTGTAAGTTTCT
TCATTTGCCAGTTTTCAATAGTTTCTCTCCCACCTTTAGACTGTCAAGCCCTAAACAATT
GTTAGCTAGGCAACCTTAAATTTGTACTTCTAAAGGGATGACTCTTAGCTGAAACAAAGT
[-,A]
AAAAAAAATAAAAATTACACTTCAAAAACACAGAGCGGAGCTCAAACTAAGGGAGCAGGT
GTATATAGGTAAAGGTCCAGTTAAGACAAGATGGCCAAGGAAAGCATCTTAAGTAAAGGT
AGGACTTGTATAGATTTAAACCAATGTTAAATTTCTCATGACTCAGCTCTCCCTCTCCTC
CAGGTGCACAGAGGCAGAAACCCTTACAAATGGAGATTTCCTTTATCAATGTAAATTTCA
ATATAGCCAGCTAAATGCCAGCAAGGTATATTTTGGAGAACTGTTAGAGGCAGTGAATCT

57693 GTTTCCTTTCTCTTTTGGCCAATTAGAACTCATTCATATATTTTTGTAATAAATTTTACA
TACACATGACACATATAAACATGCAGACACACACAGGCAGATTTTATAGCTTTGTAAGTT
TCTTCATTTGCCAGTTTTCAATAGTTTCTCTCCCACCTTTAGACTGTCAAGCCCTAAACA
ATTGTTAGCTAGGCAACCTTAAATTTGTACTTCTAAAGGGATGACTCTTAGCTGAAACAA
AGTAAAAAAAAATAAAAATTACACTTCAAAAACACAGAGCGGAGCTCAAACTAAGGGAGC
[A,T]
GGTGTATATAGGTAAAGGTCCAGTTAAGACAAGATGGCCAAGGAAAGCATCTTAAGTAAA
GGTAGGACTTGTATAGATTTAAACCAATGTTAAATTTCTCATGACTCAGCTCTCCCTCTC
CTCCAGGTGCACAGAGGCAGAAACCCTTACAAATGGAGATTTCCTTTATCAATGTAAATT
TCAATATAGCCAGCTAAATGCCAGCAAGGTATATTTTGGAGAACTGTTAGAGGCAGTGAA
TCTGTATGTGTCTGCAGCAACTTCAATTCTTGCCTACTCTCAAAATAAAAAATTCAACTG

58585 GAAGTTATGTGCATGCTTACTTGAGGCATCTTTTTTTCCTTACCAGTTGACTGTTCCTAG
AGGAAGGTCATATACCAGTTAAACTCTACCATTTTTGCCTCTTAGTGTGCATGCTTGAGC
CTACTCGCCCACCTCCTGAGATCTTATCAGGAACCTACTGATCATCAGTTTCAGGGTTTT
TCTATCTACTGGGAGATTGCCTTTTCCTGGCGCCGGCTGCAACCAAATATTATTTGAGAG
AGACAGTTTAACAACCACCTGACCATCACCTAATGGTTGTCTGACATTCCTTGGTGGAGG
[T,C]
TGGGGGTGATCTCCTGCCTTGCCCATGTCTGCCTGCCTACTGTAACAGACCAACTTAGTT
AAATAGGTGGGCTTTTCAACTTAGTTTGTTTCTTGGTGAGATGACTGACATCATTGTGAA
GCTCTTTAATGAACAGGGCAAAGAAAGCCTTCTCTATGCCTGGACTCGGCATGGACAGCT
CTGGGAAAGAAGAAAGCCTATTTTACCTGAGGGCCTATCTTTTATAAATATTTTGTTCAA
ATTCTTTCTTTTAAAACAAAGGTTCTTTTTCAATGACTTACCAAACCAATACACCTTAAC

FIGURE 3SSS

58649 AGGTCATATACCAGTTAAACTCTACCATTTTTGCCTCTTAGTGTGCATGCTTGAGCCTAC
TCGCCCACCTCCTGAGATCTTATCAGGAACCTACTGATCATCAGTTTCAGGGTTTTTCTA
TCTACTGGGAGATTGCCTTTTCCTGGCGCCGGCTGCAACCAAATATTATTTGAGAGAGAC
AGTTTAACAACCACCTGACCATCACCTAATGGTTGTCTGACATTCCTTGGTGGAGGTTGG
GGGTGATCTCCTGCCTTGCCCATGTCTGCCTGCCTACTGTAACAGACCAACTTAGTTAAA
[T,C]
AGGTGGGCTTTTCAACTTAGTTTGTTTCTTGGTGAGATGACTGACATCATTGTGAAGCTC
TTTAATGAACAGGGCAAAGAAAGCCTTCTCTATGCCTGGACTCGGCATGGACAGCTCTGG
GAAAGAAGAAAGCCTATTTTACCTGAGGGCCTATCTTTTATAAATATTTTGTTCAAATTC
TTTCTTTTAAAACAAAGGTTCTTTTTCAATGACTTACCAAACCAATACACCTTAACCAAG
GTTATGTCTAAACCAAGGATCAACTAGGCATTTCCAAAGAGTGGCAAAGTAGTCCTCACA

62188 GGTGGCCTTCAGAGCCACAGCATCAACAATATTAACTTCCCTATTAGTAGTGTTCTATTA
CTTTGGGTTTTACATATATTATCTCATTTATTCATCATAACAACCTGGTTGATAGGGATT
ATTATTCCCATTCTATTCCTGAAGAAACTGAGGCTCAAAGGAGCTAAAATATTTTCCTAT
AGTCACACAGCTAGGAAGTGGCAGAGCGAGGACTCAAACCCAAGAATCCTGACTTCAAAG
CCTCTGCTCTTCCTGCTGCACTATACCATCCCTATACACATCTCTGAGACTCCTGTAAAA
[A,T]
TATGTAAGGAACAGGATTTATTTCATTTATTGTCTTTCATATCCCACAAGAATACAAACT
GTGTAAGGCAGGTATGTCTGTATGTTTTTTATCACTGCCTCATTCCCCATCTTCCACAAC
AGTGCCTACCGCACAGTAAGTGCTCGATAAATATCTTTTAAATGAGCATGTGAATGAATG
TGTGTTAGTGTTAGGGCTAAGGCCTTTGGCTTCTGGTTAATTGCCCTTTTTGCCATTATG
CCAATGTCATTTGCACACTCACAAACATACCCTCATATAATCATATGCACTTCAGTTTCT

63478 CATCTCAAGATATGTCAAATAAGTGTATTTGGGGTGAAATATTTTTGGTTTCCTTTGCTA
GAAATGAAATGTCCCTGCTTCCCCATAGCCAGAAAAGATTCTTGAGTGGACAACTGCACC
TAAACTTGAACCTGAGCACTAGAAAGTCTTTTGTTTTATTCTATGTTTTTATAAATTTAA
ATCTAATTTTTTGAATATAAAATAATACATATTTTGTAAATGTGGAAACACAGAAAGTTC
TAATGAAAAAATAAAAACCTGTATTTCATCACGCAGAAATATCTGCTGTATTAGTTTTCC
[G,A]
TTGCTGCGGTAACAAATTGCCACAAACCTGGTGGCTTGAGACATCATAGATTTAGTATCT
TACAATTCTGGAAGTCAGAAGTCCAAAATCAGTCTCCCTAGGCTAAAATCAATGTGTCAC
CAGGGCTGTGTTTCTTCCAGAGCCTCCAGGTGAGAATCTGTTTCATTATCTTTTCTAGCT
TCTTGAGGCTGCCTGTATTCTCGGCTTGTGGCCCCTTCCTTTATCTTCAAAGCCAGCAGC
ATACTATCTTCAAACCTCTCTCTGACTCTGACTTCATGTTCTCCTTATTCATCTTTTAAG

65457 AACCTTTTTCTTCTGCCATGAGACTAACCCTGGCTTCTTCACGTGCGGGTGGAAGGGTTC
CTAACAGCAACAGCTGACAAACTTAATGAGCAAGCACTTTTTCAGCCTCTGCCACAGTCA
CATTTTCTATCCTATTGGCTAAAGTAAATCACGAAGTCAGGCTCAGATTCAAGGGGTGTA
GAAATAGGCTCCACTTCTGATGAGTGGCACGGCAAAGTCAACATTGCAAAAAGCCAGGCA
GAGATATTACTGTGGCCAGTTTTGCAAACAATCCACCGTAATACATAAAATATGTTTAAG
[C,A]
AGTCCACAAAATGATCAAGGAAATGGTAGAAACTATAAACACTGCAAGAACTCAGAGCCA
CATGATGTTATTGAGTCCTTGTAGTGCTCTGAAAGGGTTCAAGGAAGAAGTTGTTTTGGC
ATATGACCCTGATGAACTTGCAAAAGTAGAGAAGAAGGGAGCACAGTTTCTGAAGAAGAA
CTTAGTAGAGAAGTGTTATTCTGTGGCCAGTACGCAGTAATTGTTCCACCTAGAGATGTT
GACTGACTGATGAACAGGAAGCTGAGTCTTTATAATGCAGATATTCACATATTCATTTAC

69947 CTGTAAATCCCAGCTACTTGGGAAGCTGAGGCATGAGAATCCCATGAATCCTAGAGGTGG
AGGTTGCAGTGTGCCGAGATCATGGCGCCAATGCACTCCAGGTTGGGCGACAGATCCAGA
CGCTGTCTCAAAAAAAAAAAAAAAAAAAAAAAAATCTTTGCCTATGCCAACGTGGAGCTA
TTCTATCCTGTTTCCTAGAAGCTTCACTGTTTTAGCTTTCACATTTAGATCTACAGTCTA
GGATCAAGTTTTATTTTGTCTTCATATAAATAAGTAATTGACCCTTAGCCATTTGTTGAT
[A,G]
AGCTTATACTTTCCTTACGTCACCACAGAACCACATTTGTTATTAATCAAGTCACCATCT
ATGTATGGGTTTCCTGACTCTGTTCCATTGATTCATTTGTATACTCTTGCATATTTATCA
CTCTGTTTTAATTACTGTAGTTTTATACTGGATTTTCAGTAATTCATCTTTGGATTATGT
TGGCTACAGTTGGTTCTTTAAAATTCCATATAAATTTCATAAGTAGCTTTTCAATTTGTA
TTTTAAAGCTGCTGGTATGTATATTGGGTACATGGAGTCTATAGATTAATTCAGGGATAA

69981 GAGAATCCCATGAATCCTAGAGGTGGAGGTTGCAGTGTGCCGAGATCATGGCGCCAATGC
ACTCCAGGTTGGGCGACAGATCCAGACGCTGTCTCAAAAAAAAAAAAAAAAAAAAAAAAA

FIGURE 3TTT

TCTTTGCCTATGCCAACGTGGAGCTATTCTATCCTGTTTCCTAGAAGCTTCACTGTTTTA
GCTTTCACATTTAGATCTACAGTCTAGGATCAAGTTTTATTTTGTCTTCATATAAATAAG
TAATTGACCCTTAGCCATTTGTTGATAAGCTTATACTTTCCTTACGTCACCACAGAACCA
[C,T]
ATTTGTTATTAATCAAGTCACCATCTATGTATGGGTTTCCTGACTCTGTTCCATTGATTC
ATTTGTATACTCTTGCATATTTATCACTCTGTTTTAATTACTGTAGTTTTATACTGGATT
TTCAGTAATTCATCTTTGGATTATGTTGGCTACAGTTGGTTCTTTAAAATTCCATATAAA
TTTCATAAGTAGCTTTTCAATTTGTATTTTAAAGCTGCTGGTATGTATATTGGGTACATG
GAGTCTATAGATTAATTCAGGGATAACTAACATCTTTTTAAAATATCAAATTTCCAATTC

71165 ACTAGAAGTTTTTTTTTTTTTTTTAACATGAATGAGTACAATATTTTATCAAATACTTTTGT
TTTACTGAGGTCATTTCTATTGTGAGTGAAGCAAGTTGATTTGTAAATATTAAAGCAATC
TTGATTTCCAAAAGTAAATGCTAGTTGGTCATGTTCTATTATCCTCTTGTGTATATTACT
GGCTACAATAAAAATATTTGTTTTTTATATTTTTTATATTATTATTCATACATTATTTATG
TATGTTATTTATTATTTATAAATATGTATTCTATTTATATATATTCCTACATATATTTTA
[G,A]
GATGTACATAGACAAGTTTGAATGGTAACAAGAATGAGCCAACTGAGAGGAAGAAATTGG
TAATGTAGTAAAGAGCGGGGATGATTGCCAAGTCAGGTCCTGCAGGTGGTGAGATGAATG
TGACTCAGGGCACAGGTGAATGAGCTGACCTTAGGTGGAAGTGGGGACCCTTCCTTCATG
TACTAGGAGAGAAAGCAGAGTTTGAAGTCTGTATGTGTGTGAGCTGCTGGGCTTCTCAGA
GGGCAGATGAAATAGTTCTTATGCCATTGCCTGTGTTTTCCCTGTGGTATATGAGGCCAT

71347 CTACAATAAAAATATTTGTTTTTTATATTTTTTATATTATTATTCATACATTATTTATGTA
TGTTATTTATTATTTATAAATATGTATTCTATTTATATATATTCCTACATATATTTTAGG
ATGTACATAGACAAGTTTGAATGGTAACAAGAATGAGCCAACTGAGAGGAAGAAATTGGT
AATGTAGTAAAGAGCGGGGATGATTGCCAAGTCAGGTCCTGCAGGTGGTGAGATGAATGT
GACTCAGGGCACAGGTGAATGAGCTGACCTTAGGTGGAAGTGGGGACCCTTCCTTCATGT
[A,G]
CTAGGAGAGAAAGCAGAGTTTGAAGTCTGTATGTGTGTGAGCTGCTGGGCTTCTCAGAGG
GCAGATGAAATAGTTCTTATGCCATTGCCTGTGTTTTCCCTGTGGTATATGAGGCCATCC
ACTGAGAATGAAGGTGGTCAGAGTATAGGAAATTTTGAGATGCCGAGAAGATCTGTGAAA
TTAGTAGAGAATTAGAATAGGATTTTCTAAGTATCCATTTGAGACTTGTAGTTATAATTA
AACAAGAATCTATCCTGCAGATTTGTATTTTTCTCCTTAGATTGCACTTAATAGATCACC

71903 TGCAGATTTGTATTTTTCTCCTTAGATTGCACTTAATAGATCACCAGTTCATTTTTGTTG
CTGTTTAAAAGCATATTGAGTTTAAGCAGGATTGGAGTTTAATTGGGTGAGGTATTCTCA
CTGTGACTAAGTTTGATGAATTGAAAAGCGTAGTTGTAGAAAGGAAACTCAAGAAGGAAA
TTCTTGGGGAAACTTAAAGAATCGTATATATGCAATGTCACTTTTTAAGACAACTAATAT
TTTTAAGAATTTACTACTTTTGAGGTGCTGTACTAATATATTACATGTATAATTTCATAT
[A,G]
TCTTCAACTACTAGTTCCTGTAAATAAGTATGCTGATGATGACACGTTCCATTTCTTTCG
ATAGCCACAAAAACAGGAAGTGATGACAAAGCTGGATTCTAACTCCTGACTCCCAAATTC
TCTAAGACCCTCAGCATTAACATATATTTTATTTTAATGTTATTATATATGTATCATTAC
TTTTACAACTCTTAAACCAAACATTTTAAAATTAGCTACAACTGCAAAATCAACTTAAAA
ATTTCAAAGAGCCATTTAACATGATAAATTAAAATATTTTAGTAAAACAAAATCACCACT

71908 ATTTGTATTTTTCTCCTTAGATTGCACTTAATAGATCACCAGTTCATTTTTGTTGCTGTT
TAAAAGCATATTGAGTTTAAGCAGGATTGGAGTTTAATTGGGTGAGGTATTCTCACTGTG
ACTAAGTTTGATGAATTGAAAAGCGTAGTTGTAGAAAGGAAACTCAAGAAGGAAATTCTT
GGGGAAACTTAAAGAATCGTATATATGCAATGTCACTTTTTAAGACAACTAATATTTTTA
AGAATTTACTACTTTTGAGGTGCTGTACTAATATATTACATGTATAATTTCATATATCTT
[C,T]
AACTACTAGTTCCTGTAAATAAGTATGCTGATGATGACACGTTCCATTTCTTTCGATAGC
CACAAAAACAGGAAGTGATGACAAAGCTGGATTCTAACTCCTGACTCCCAAATTCTCTAA
GACCCTCAGCATTAACATATATTTTATTTTAATGTTATTATATATGTATCATTACTTTTA
CAACTCTTAAACCAAACATTTTAAAATTAGCTACAACTGCAAAATCAACTTAAAAATTTC
AAAGAGCCATTTAACATGATAAATTAAAATATTTTAGTAAAACAAAATCACCACTGATAC

71994 TTGGAGTTTAATTGGGTGAGGTATTCTCACTGTGACTAAGTTTGATGAATTGAAAAGCGT
AGTTGTAGAAAGGAAACTCAAGAAGGAAATTCTTGGGGAAACTTAAAGAATCGTATATAT
GCAATGTCACTTTTTAAGACAACTAATATTTTTAAGAATTTACTACTTTTGAGGTGCTGT
ACTAATATATTACATGTATAATTTCATATATCTTCAACTACTAGTTCCTGTAAATAAGTA

FIGURE 3UUU

TGCTGATGATGACACGTTCCATTTCTTTCGATAGCCACAAAAACAGGAAGTGATGACAAA
[G,A]
CTGGATTCTAACTCCTGACTCCCAAATTCTCTAAGACCCTCAGCATTAACATATATTTTA
TTTTAATGTTATTATATATGTATCATTACTTTTACAACTCTTAAACCAAACATTTTAAAA
TTAGCTACAACTGCAAAATCAACTTAAAAATTTCAAAGAGCCATTTAACATGATAAATTA
AAATATTTTAGTAAAACAAAATCACCACTGATACTTTAATATTCTTAGGTCTGAGAAAAA
CCATTATGTCGTATTATTCCTGCGTTCCTGGTAGCGTTTCTACTGCTGGACATCAGAAAT

72010 TGAGGTATTCTCACTGTGACTAAGTTTGATGAATTGAAAAGCGTAGTTGTAGAAAGGAAA
CTCAAGAAGGAAATTCTTGGGGAAACTTAAAGAATCGTATATATGCAATGTCACTTTTTA
AGACAACTAATATTTTTAAGAATTTACTACTTTTGAGGTGCTGTACTAATATATTACATG
TATAATTTCATATATCTTCAACTACTAGTTCCTGTAAATAAGTATGCTGATGATGACACG
TTCCATTTCTTTCGATAGCCACAAAAACAGGAAGTGATGACAAAGCTGGATTCTAACTCC
[T,C]
GACTCCCAAATTCTCTAAGACCCTCAGCATTAACATATATTTTATTTTAATGTTATTATA
TATGTATCATTACTTTTACAACTCTTAAACCAAACATTTTAAAATTAGCTACAACTGCAA
AATCAACTTAAAAATTTCAAAGAGCCATTTAACATGATAAATTAAAATATTTTAGTAAAA
CAAAATCACCACTGATACTTTAATATTCTTAGGTCTGAGAAAAACCATTATGTCGTATTA
TTCCTGCGTTCCTGGTAGCGTTTCTACTGCTGGACATCAGAAATAGAGAATAGTAGAGCC

72612 CTGAGATAAGAGCAGAGACAGGGGAAAAGCAAAACATTTCTGAAGAGGCAGTTGGTCTAG
TTTGGCTATAATCACTAGACGGGTAAAGGAACATTGGGTGCATTAAAAGTAGAGAGCCTG
GGATGAAGGCGTGAAGGCTGAGTAAGAATCTCTTCACTTGGTAGTAATTCTAGTTCATCC
CCCTCTGACCTGCAATTCTGAACATGGTGTAGCTTGGTCAATAAGGAAATAAATTGCCTT
TCTGGCTGGAGAGGCAAAGGGTAGACAATACATTGTGCCAGCTGAACTTCCTGTCTCTCC
[G,A]
CTCTGGAGAAGAGCCAGTCACAATGTATGACTCAGCACGCCGGGCACCTCTCCCACGCCA
GCCAGGCCTGCCCAGCCACTTGCTGAATCACAAGTGGCCATTTCCAATCCCATCAGTGAC
CCAAGCTCTCCAACTTAGACTAGTTTCTCTGTGATCGGTCTATGATTGTCATGGAGCACA
AAAAGTATTAACTTCTAACATTTATTTTTCTTTCCTGGATGCTTGATGAACTTTATAAGC
AAGAGACTGATTTAATTGTTCCTCATTATCATCTGAGCATGCCGTCTTGGCTTGCCCTTT

73294 TCTGTAGAAAATAATAATAGCAAAATTTCTCCCTTGAGAAGCTTCATAAATTAAATCTCC
AGAGCCAGTATATGTAAGCCGACAGATTATGAAATATGATTTAATGCTCTGTCCAGAGAA
AGGTCAGGGCTTCAGAAAAATCATCATAATATCAAGAAAAACTAATCTGCAACCTGTTAT
ATGATTTTTAAAAATCACCCCCCATCTTTTTTACTGTGCAAACTGTAGATTTTTGTTTAT
TTTATTTGAGGCTATAGTTTATGTCTTGAATCACACACATATGAGTATTACTTTCTGTGA
[A,G]
GTTTTCATGACCCCTGCAATCAAACTTGGGTCCTTCTGTTAGTTTCTATCACAGTATCCT
TCACTTTTCTTTCACAATTCTTGCCATATTCTATAACTACATATTTGTTTGTTAAATATT
TGTTTATCTTTTATAGATGATTGGCTTCAGGAAGAGGGAAACCATGTCCTTTTGTTCAGT
CCTTTATTCTCAGCACCTTGCACAACATGAATATACAAAAAATATTTGTAAAATGACCAT
CGAATGAACAAGTGCTCATTAAGTACCAAGCTATATGCCAGGGGTTGCTGATGGTTAGAA

73385 AAATATGATTTAATGCTCTGTCCAGAGAAAGGTCAGGGCTTCAGAAAAATCATCATAATA
TCAAGAAAAACTAATCTGCAACCTGTTATATGATTTTTAAAAATCACCCCCCATCTTTTT
TACTGTGCAAACTGTAGATTTTTGTTTATTTTATTTGAGGCTATAGTTTATGTCTTGAAT
CACACACATATGAGTATTACTTTCTGTGAAGTTTTCATGACCCCTGCAATCAAACTTGGG
TCCTTCTGTTAGTTTCTATCACAGTATCCTTCACTTTTCTTTCACAATTCTTGCCATATT
[C,G]
TATAACTACATATTTGTTTGTTAAATATTTGTTTATCTTTTATAGATGATTGGCTTCAGG
AAGAGGGAAACCATGTCCTTTTGTTCAGTCCTTTATTCTCAGCACCTTGCACAACATGAA
TATACAAAAAATATTTGTAAAATGACCATCGAATGAACAAGTGCTCATTAAGTACCAAGC
TATATGCCAGGGGTTGCTGATGGTTAGAAATGAGCAGGGCACAAAATTCTTTGTTCAATT
AGTGAGCAATTCAGGCAAAAAGAAAATATTAATGGTGATTATACAATATAATGCAATGCA

74121 CTCTCACCTCAACCTCTTAAGTAGCTGGGACTACAGGTGCATGCCACTATACTGGCTAAT
TTAAAAACAGAAGCCAACAAACAAAAAACACACCTTTTTAAGACTGGGTCTCACTATGTT
GCCCAGGCTGGCCTTGAACTCCTGGCCTCAAGCGATCATCCTGCCTTCCAAAGTGCTACC
TTCTAGAGTATTGGGATTACAAGCGTGAGTCATCTGCACCAGGCCTGAAGCATTCTGTAA
TGGAGAAATACCTGGGTGCTATGGAAGGGCAGAGGGGGAAACACAGAGGAGTAACATCTA
[G,A]

FIGURE 3VVV

TTTACGTTTGTCAAGGAGAGGCCAGGAAAGACTAACTACAGGGGAGATAAACTCCAACCA
AGAGTCTTTAAGTCTTCCAAGACTTACGTACAAGTTTCTTATTGCTAAAATGGAAGTTTT
AATGAACATTTATTTATTTATTTGAGATGGGGTTTCACTCTTGTTGCCCAGGCTGGTGTG
CAATGGCACAATCTTGGCTTACTGCAACCTCTGCCCCCCAGGTTCAGGTGATTATCCTGC
CTCAGCCTCCAAAGTAGCTGGAATACAGGAGCCTGCCACCATGCCCAGCTAATTTTTTTT

75646 CACTCCAGCCTGTGCTACAGAGAGAGACTCCGTCTTAAAAAACAAAACAAAATAACAACA
ACAACAAACAAAGATAGATGCATAGAGTTTTTCACTGTTGCACTATTTATATTAGCCAAA
AACCGGGAAACAACCTGAATATTCATCAAGTGGGGACAGGTTGAGTAATCATGTGACATA
CATAAATTGCAGCACTGCACACTTGAGAAAAGAAGTGAGAAATGTCTCTATTTCCTAGTG
TGGTTTGCTCTCCAGAGTATACTGTTAAGTGAAAAAAGCACTGTGGCCTCAAATTTATCT
[A,G]
TAGATTCTATACAATCCCCATCAAAATCTCAGCTGGCTTCTTTGCAGAAATTCACAAGCT
GATCTTAAAATGTGTATAGAAATCCAAGGGACTCAAAATTCAATAAATTCAAAGACTAGC
CAAAACAATCTTGAAAAAGAAGAGCAAAGTTGGAGGGCTCATACTTTTCAGTTTCGAAAG
TTGTTATGAAGCTACAATAATCAAGATAGGGTGGTCCTGGCATAAGGATAAACATGGAAC
AGAATTGAGCATCTAAAAATAAAGCCTCATATTTCCAGTCAATTGACTTTTAACCAGGGT

75698 TAACAACAACAACAAACAAAGATAGATGCATAGAGTTTTTCACTGTTGCACTATTTATAT
TAGCCAAAAACCGGGAAACAACCTGAATATTCATCAAGTGGGGACAGGTTGAGTAATCAT
GTGACATACATAAATTGCAGCACTGCACACTTGAGAAAAGAAGTGAGAAATGTCTCTATT
TCCTAGTGTGGTTTGCTCTCCAGAGTATACTGTTAAGTGAAAAAAGCACTGTGGCCTCAA
ATTTATCTATAGATTCTATACAATCCCCATCAAAATCTCAGCTGGCTTCTTTGCAGAAAT
[C,T]
CACAAGCTGATCTTAAAATGTGTATAGAAATCCAAGGGACTCAAAATTCAATAAATTCAA
AGACTAGCCAAAACAATCTTGAAAAAGAAGAGCAAAGTTGGAGGGCTCATACTTTTCAGT
TTCGAAAGTTGTTATGAAGCTACAATAATCAAGATAGGGTGGTCCTGGCATAAGGATAAA
CATGGAACAGAATTGAGCATCTAAAAATAAAGCCTCATATTTCCAGTCAATTGACTTTTA
ACCAGGGTGCCAAGAAAATTCAATGGGGGAAGAATTTGTCTTTTCAACAACTGGTGCTGG

79007 AATATATTTTTAAGTATATTGATTGCTTTTGGAGGGTTCTAGGAAACAAACAAATCATTT
TGAAAAGTGGTAAATAAAGGAAAGACTTCAGTTCAAGACCAGTCTGAGCAACATAGTAAG
ACCCCATCTCTACAAAAAATTAAAATATCAGCTGAGCATTGTGGTGTACATCTTTAGTCC
TAGCCACTTGAAGGCTGAGGCTGGAGGATTGCCTGAGCCCAGGAGTTCAAGGCTGCAGTG
AACTATGATGGCACCACTGTGGTCCAGCCAGGGTTAAATAGCAAGACCCTGTTTCTGGCG
[-,A]
AAAAAAAAAAAAAAAAAAAAAGGAAGACTTAAACATACCTTTCCTATATGAACTGTGCCT
CGGAGTAACTAAATAATTGATTAAAGCAAGTTTCTCTGTATAAAAGTACTCCAGCTAAAA
CATTAAGGAGAAATGATAGAATTCAAATATCACAACCCCTAAGGAATTTTTGCATCAAGA
CAACAATAATTAATGACTGATAACACCACACACAGAATACAGACTTATTAATTGTATAAC
TCCTGATCAAGTGCATACCACTATCTGTGAAATAGTTTTGCCAAAAAAAAAAAAAAAAAT

80043 ATTGCAGGCGTGAGCCACTGCACCCAGCCCACCCTTGGTTTTTTTCAACAAAAAATTACT
AGAAATAAAAGAATAATAGTTGGTCAAGGAAGCTGTAGAATAAGAAAGACTGCCACATAC
ATCAATGGCAGTGGGCGGGCTTTGTTTGAATCCAACTCTAGCATGCAAACATTTGATAAA
AATTTCTTTATTTAAAAAGAAAAGTTTACAAAACAATCAGAAAAAATAAAAAAGATTGAG
GATCTCAGGACAACTACTAGCCTAGATAATTTATAAAGATTAGATAACTGACTCATTTTT
[A,G]
TTAGTTTCTTTCCTAATAAGGCAATATGTATTAGATATATCAGAGTAGAAGGAAATATTT
TTCTTACATCTATTTGGCTTTTTAAATATAAACATATATAAGTAAAAACCAAAATGATTT
ATAATCCCACCATTTATGTAACTATCTTATTTTCAAAAAAAATTATGCAAATACTAGCAT
TTGTGTGCTTTTTTTCCTTTTGTGTTTGTGTGTTTATATCCTTTTTAAATATATCCTTTT
TATGTACCTAAGCAGCTGTATACTATACTGCATACTATAGTGTGAACTTTGTTCTTTTCC

80499 AAAAAAATTATGCAAATACTAGCATTTGTGTGCTTTTTTTCCTTTTGTGTTTGTGTGTTT
ATATCCTTTTTAAATATATCCTTTTTATGTACCTAAGCAGCTGTATACTATACTGCATAC
TATAGTGTGAACTTTGTTCTTTTCCTTCGTCTTTACAACATATTGTGGAAAACGTTCCAT
ATCAGAATATAGATATGCCTTTTTGTAGCCATTGAAATGCAAAGAAAAAAAGAATATAGA
TCTGTCTCATTTTTTTAAAAATGCTGTATAATCTGTAGCACGAATTTACTATAATTTATTC
[G,C]
CATGCTCCCTTATCGATGGGCATGTAAATTGTGTTAATTTTATATGATATAATGAGTATC
CTTATATGTATATCTTGGCACAGTTTTTCGAGTGTATCCATAAAGTTTCTTGCAATGAAA

FIGURE 3WWW

TTATAGGGCAACAAGGGTGTGGTGGCTCTTGTCTGTAATTTCAACACTTTGAGAGGCTAC
GGCAGGAGGATTACTTGAGGCCAGGAGTTTGAGACCAGCGTGGACAACATAGTGAGCCCT
CACCTCTACTAAAAATTAAAAAAAAAAAAAAAGAAAAAGTTTGGTATGGTGATATGTACCT

80940 GGTGGCTCTTGTCTGTAATTTCAACACTTTGAGAGGCTACGGCAGGAGGATTACTTGAGG
CCAGGAGTTTGAGACCAGCGTGGACAACATAGTGAGCCCTCACCTCTACTAAAAATTAAA
AAAAAAAAAAAGAAAAAGTTTGGTATGGTGATATGTACCTGTAGTCCCAGATACCCAGGA
GGCTGAGGTGGGAGGATCATTTGAACCTGGGATGTCAAGGCTACAGTGAGCTATGACTGT
GCCACTGCACTGCAGCCTGGATGACACAGTGAGACCCTGTCTCAAAAAAAAAAAAAAAAA
[A,-,T]
TACAGGCCAAATCCATATGCTTTTAAAGGATATTTTTGAATTGTTCTCAAAAAGAGGCTT
CACCAAATTACCATCCAGGGTATACAAGATACCCATTTCTCCATGTCCTTACCAACAGTG
GCTCTCATCAAGCCTTGGTGGAAATGCTCTCATACTGATACTTTAACGACTAAAAGTCAT
GACATATCTGCTTAGGTTGTAAATTGCCTCCCTCTAAACTTATACAGAGAGAATTTAGAG
TGTTGTCTCAGCTTGGTTCCAGTGTTATCCAAGCCATTAACCTTTGTTTTGCCTTAGATT

81615 AGTCTCGCTGTGTCGCCCAGGCTGGAGTGCAGTGGCGTGATCTTGGCTCACTGCAAGCTC
CGCCTCCTGGGTTCAAGCCATTCTCCTGCCTCAGCCTCCCGAGTAGCTGGACCTACGGGT
GCATGCCACCACCCCCGGCTAATTTTTTGTATTTTTAGTAGAGACAGGGTTTCACCATGT
TAGCCAGGATGGTCTCGGTCTCCTGACCTCGTGATCCGCCCGCCTCGGCCTCCCAAAGTG
CTGGGATTACAGGCATGAGCCACTGTGCCTGGCCACAATGGGGTATTGTTTTTATAGACT
[G,T]
TTGAAATCTGCCTTTGGAAACCATGGGTTTGCTGTGTTGTTATGGTGAATGAATTAGGTG
CACAATACTAGTTTTTAAAAAATGAACTTCACACTAGGTACACCTTGAAAAATTATTCCA
GAGCTATAAGAAGAGCTATAAGAAGAAAAATATGATGGGTCATTGCTCCAAAGAAAGGTT
TTAAAATGTAAATTTGTACTTAATGAATAGGACAGTGTACCCTAACCTCCTCCTTGCTAT
TCTTCAGGGATCTCTTCTAACAAGGGCTAATGCTTCACCTAAGCTGTGAAAAGCCTGCTG

82599 CCTTAAAGGAATTTGACTCACAATTTGAAAAACACTGCATTGTAGAATATTTTAGAGTCT
CTTCCCAACCCTCAGAGTCAGATTTATTTCAAGATGGCCCCTGTAAGACAGCTTCAAGCT
TGTGAGTGACTTTCTTTTTTCTTTTTACTTCTTTACCATTTACCATGACTCCCAAATAAG
TGACTCTTTTGGCTTATTTGGTAACCATGCTAATTTCTACACATAGAACCTAGAGCATTT
ACATAAGACCCACCCAAAGCTTGTGTTTTAACCTTGCTTCTCTCCTTTCTTTCTTTGATT
[C,-]
ATTGATTATGTTTTCTATTGCTATCTGTTCAATCTGTGTTTCAGGCAGTGTACAGGTACT
GAGGCAACAATGGTGAGTAAAAGCAAGCATGCATCCTGAGATATACTGGGAATGAAAGAA
GCTAATCCAAAAGCATACAGGAAAATATTTTCAAACTTTGATAAATTCTGTGTAAGCATA
TGGCATTGCACGTAACAGGGGAACCGCATTTAATATGGAGTGTTGGAAAAGGCTTCTGTG
AGAAGTGACACTTGAGCTAAGACTAGAAAAGTGAAAAGAATATAACCAGGTACTGGACAG

82952 CAGGTACTGAGGCAACAATGGTGAGTAAAAGCAAGCATGCATCCTGAGATATACTGGGAA
TGAAAGAAGCTAATCCAAAAGCATACAGGAAAATATTTTCAAACTTTGATAAATTCTGTG
TAAGCATATGGCATTGCACGTAACAGGGGAACCGCATTTAATATGGAGTGTTGGAAAAGG
CTTCTGTGAGAAGTGACACTTGAGCTAAGACTAGAAAAGTGAAAAGAATATAACCAGGTA
CTGGACAGCATCATGAGTGCAGGCACAGGTGACATCGTATCACAAGCTTCTAAGGCTGAA
[-,G]
GGGGCGTGAATTGCTAGCTGGAGAGTGGAAGGAAAAGATCTTCAAGATAAAGCTGGAAAA
ATAAACAGGGCCAGGCCTCATAGGTTTCTGTAGACCATGGAAAGAGGTGAAGGTTATTTT
GAGCCTGGATGACATGATAAAACTCACATTGTAAAAATATAACTGCAAGGTAGAGAATGG
ATTGAAGAGGTCCAAGATTACGCAGACAGAGCTATGAACAGCCTATTGCAATGGTCTGGG
TCAAGCATGATGGAGTAGGGTTGGAATAGGGTGGTGAACTTTTATTAGTTATCTTCCTTA

85020 ATCCCTGGGCACTGCTTGCAGGCACTTAATTCTTGATTCAAATGAAACTTTAAAATGTTT
TATCCATGATGTTATGTCTAAAGAAACATGTCAAAGAAACATGTCAGAGAACTTGACTTT
GAATAGAAATCATGGCTGTGCTTTGAGGGAAACAAAATAAATCACAGAGGTAGGAATGCA
TAGTTACAAGCTACTGTTTGTACACAGCAGAGACCAATTCTACTCTCTGTTCTCATTTCC
TCTTCTAATTCCTCATCCCTACACTCCTTCCTGTGTGAAGCCCATGTCTGATCCTGCCTA
[A,T]
TTCAGTGACTGGGGGTCACTGCAGATGCGTGCACAGGGTCCTGTTATGGGATCCGGATTC
TGCCGCCTTCTCCAGACACAAGTTTCCCCTCATACCTGTTGTTCCAGCAAATCCAAGCTA
TTCTCCTTTCCCCACTTGCACTAGGTTCTTTCCCTAGTCTGTGCTTGCATGCATCCTATT
TTTCTCTGGTATTTTTCAAATTTTACTTTGGCACCTGGAGAACGTTTTGGCACCACCATT

FIGURE 3XXX

TGTCAGGTGTTTAACTTTGTGCATTTCCTCGTGTGAATGGGAGCGTAGGTCCAGCATCGT

88843 CTTCTGGTGTCAAAAACTATTCAGGTGCATTTCTGTAACCTCTATGCACCTCTCCCCCCA
CCTCCCAGGTGTTATATTTTACAGGCTGTCATACCCTTTTGTACCTCTCCTGAGGAGTTG
TGACATTTGGTGTATAATTAATTCATTTGTCTCCTTTATAAAATTGTGAACTCTGCATGT
TTTGCTTTTCATTGTATAACCAGTATGTGAAAAAAATATGAGCCACATGAATGAATGATT
GACCAGAAGTTCAGGCTTACAAGTAGGAAATATTCAAATATAGGACATTAAATCCAAAGG
[C,T]
CTCAGACCTACTTGTACCTTGGTCTTTACATTAATCATGTTATTTATCATCCAAACCAGG
ATACTCTGAGAGCTAAAGAGGATGCTATTAATATTAATAGCACTGGGAAGAGTCAAAAGC
CATAAATAATCTAGGCAATTCAGGACCTATGTCAACATCATTAAGGCTTTTCAAGGCAGT
GTTTTTTGGTTTTTTATTTTTTGTAGAGACAGGGTCTCCCTATGTTGCCTAGGCTGGCCT
TGAACTCCTGGGCTCAAGCAATCCTCCTGCCTCAGCCTCCCAAAACTCTGGGATTACAGG

89700 ATACTGTAATTCTTTTTTAAACCTCCTTCTTCAAAAGAATCAGCCCGATTCATGTTGTAC
TTGAATTCAAGATAACAAAACACCTTTTAGTTACTTAGAAAGATTAGATTGTAAAATATG
TGCTGAGTTCCTAGAAATTAAAAGTGAGAATGAAAAAAAGAATCAATGAAAGTACAGTAG
ATCTCCCGGACAAGGAGAGACCATCTGCATAAAACTGAAGATATAAAATATGTGACTTCC
TACTTTTAGATTAAAATCTACATTTTGCCTTTGGACATGGTAGAAGATTCAAAATTACCC
[G,A]
TAAACAGTCAGCACTACGTGGAAGTAGGAGCAGCAGTAGGCTGCTGTTTGCTTAGGGTTT
CCTGGGTACCAGGCTGCCTGCTAAGCACTTGTGAGTTATTTCACTCAGTCTTCCCATAGC
TCCAGGAGGTTTATGGCACTTTGTCCCCATTTCACCTTCGATGAAACTCTGGTTCTGAAA
AATTACTTGCCCAAGTTTGCATGGCTATTAAGTAGGGAAAGCATCATGTTTAGGAAATGC
AGAGCTCTTCACCACTCTCCAGCCTGCAGATGCTCAGCATGGCTGCAGCTCTGAGGGGAG

90002 AAACAGTCAGCACTACGTGGAAGTAGGAGCAGCAGTAGGCTGCTGTTTGCTTAGGGTTTC
CTGGGTACCAGGCTGCCTGCTAAGCACTTGTGAGTTATTTCACTCAGTCTTCCCATAGCT
CCAGGAGGTTTATGGCACTTTGTCCCCATTTCACCTTCGATGAAACTCTGGTTCTGAAAA
ATTACTTGCCCAAGTTTGCATGGCTATTAAGTAGGGAAAGCATCATGTTTAGGAAATGCA
GAGCTCTTCACCACTCTCCAGCCTGCAGATGCTCAGCATGGCTGCAGCTCTGAGGGGAGC
[G,A]
CGGGACACCTATGCATGGCCACCTGCCTCAGGCACCCACAGACGAAAGTGGTACATGTGG
AACGGACAGACAGAGAACAGCCTAAAATTGGAAGCTAAATTGTGTGAGAAAGACAAGTAC
TTCAGAGAAGATAGTGTGGAGTCGCAAAATAAGTTTCATGAGAGCTCATACAGAAAAACAG
CCTAAAACTAGAAGCTAAATTGCGTAAGAAAGACAAGTACTTCAGAGAAGTTGGTTGGGA
GTAAGAAAGCAAGTCTCATGAGAGCTCTGAGGGGTGTAAATGGGACTTTTAACAGCCAAA

90615 TCTAGCCTAGCAAGAGGAGCTCAATGGATGGAAGTCCTCACTTGTTTCCCTGTGTTAACA
TAGAAGGGGGTCTTTTTAAAATTTTGTTTTCACTTCAGCTTTTCTGCCAGAAATGTCTAG
TGTAGTGATGTTTTAAAAAAAACCTAAGTATCTGTTTCCGCCACAAATCCCCATTAAGAC
ATAAATGGAGTTTTATTTTGTGGATGTTTAAAAATCCATGGACTTGAACTTTTGGTAGTT
TCCCAAATATGTAGAATATTCAGCTAGTTTTCTTCAATTTCAGAATCTTTCTTTTCTATC
[A,G]
TTGTTAAAGACACAGGGTTGCATAATAACCATTAAGTTTGAATTGTGCAATTAGACAACT
TTCTTATTAGTCAAGAAGTCAAACTTTTTGTGTGAGTACAGCTTGAAAATCAGCTTTAGT
TTCCAAAGAATGGCCAGTTTGAAGTATAATATTCTCTTTTGCTTACTTGAAATCTGCAAA
TAAATGCTTTAAATTAGGGACAAAGTGATTATTTGCTTTTATTTAAAAAATAAGGGAAAC
AAAACTCATTACAATCTCTTCTACAGGGTTAGTACTATTCTATTTGTTGATTGCCTCAGC

92506 CAGTCCCAGTGACCAGAAAGAACATACCTTTATCAGCTCGCAGTTTCTTTGGGACAGGTG
TCTGGGCACAGTCTAGTTGAGTTCTCGGCACAGCTGCCATTAAGATGTCAGCCAGAACTG
GGTTCTCTTCTGGAGGCTGAACTGGGCAAGAATCCACTTCCAAGCTCAGTCAGAATGTTG
GCAGGAGGTATTTCCTTGTGGCTGTAGGACCCATGGTGGCTACTTTCTTTAAATTTAACA
AGGAGAAGAATACCGTAGAGTAAGTTGGCTAGAAAGAAAACAGAGTACACATACTTGAAT
[A,G]
ATGATATATAACATTGTAACATAACTCAGTCACAGAAGTAAGACCATCACATCTGCCATG
TAATGTCGGTTAGAAACAAACCATGGAACCAGCCCATGCTGAGGGGCTGGAAATTATGCA
AGGGTGTGAACACCAAAAGCTGGGAATCCTGGGGGTCACCGTACACAGTCTGTTCACATT
TCCTCTAAAGAAGTTGCACTGCATCACAGTTCCATACCAATTTCTGCTATGACCTTAAAT
ATAGCCCTGAACTTCCCTGTCAAGGAAGAAGTGAGGAGGTTTCAACAAGTGATCAGTAAT

FIGURE 3YYY

92558 GACAGGTGTCTGGGCACAGTCTAGTTGAGTTCTCGGCACAGCTGCCATTAAGATGTCAGC
CAGAACTGGGTTCTCTTCTGGAGGCTGAACTGGGCAAGAATCCACTTCCAAGCTCAGTCA
GAATGTTGGCAGGAGGTATTTCCTTGTGGCTGTAGGACCCATGGTGGCTACTTTCTTTAA
ATTTAACAAGGAGAAGAATACCGTAGAGTAAGTTGGCTAGAAAGAAAACAGAGTACACAT
ACTTGAATGATGATATATAACATTGTAACATAACTCAGTCACAGAAGTAAGACCATCACA
[T,C]
CTGCCATGTAATGTCGGTTAGAAACAAACCATGGAACCAGCCCATGCTGAGGGGCTGGAA
ATTATGCAAGGGTGTGAACACCAAAAGCTGGGAATCCTGGGGGTCACCGTACACAGTCTG
TTCACATTTCCTCTAAAGAAGTTGCACTGCATCACAGTTCCATACCAATTTCTGCTATGA
CCTTAAATATAGCCCTGAACTTCCCTGTCAAGGAAGAAGTGAGGAGGTTTCAACAAGTGA
TCAGTAATGATTCTTTTATGTCTAAGATTCTAGGATGATTTCCTCTCTGCCCTGGTAGGC

92667 AAGCTCAGTCAGAATGTTGGCAGGAGGTATTTCCTTGTGGCTGTAGGACCCATGGTGGCT
ACTTTCTTTAAATTTAACAAGGAGAAGAATACCGTAGAGTAAGTTGGCTAGAAAGAAAAC
AGAGTACACATACTTGAATGATGATATATAACATTGTAACATAACTCAGTCACAGAAGTA
AGACCATCACATCTGCCATGTAATGTCGGTTAGAAACAAACCATGGAACCAGCCCATGCT
GAGGGGCTGGAAATTATGCAAGGGTGTGAACACCAAAAGCTGGGAATCCTGGGGGTCACC
[G,A]
TACACAGTCTGTTCACATTTCCTCTAAAGAAGTTGCACTGCATCACAGTTCCATACCAAT
TTCTGCTATGACCTTAAATATAGCCCTGAACTTCCCTGTCAAGGAAGAAGTGAGGAGGTT
TCAACAAGTGATCAGTAATGATTCTTTTATGTCTAAGATTCTAGGATGATTTCCTCTCTG
CCCTGGTAGGCTGCTCTTCAAAGTATGACCTCCTCATTGTTTCTCTGCTCTACCACACAC
TCATTCCCCTCCAAGAAGGCTGCCCACCTGTAATGACCTGTCTACAGAGCCTGTGATAGT

92803 AATGATGATATATAACATTGTAACATAACTCAGTCACAGAAGTAAGACCATCACATCTGC
CATGTAATGTCGGTTAGAAACAAACCATGGAACCAGCCCATGCTGAGGGGCTGGAAATTA
TGCAAGGGTGTGAACACCAAAAGCTGGGAATCCTGGGGGTCACCGTACACAGTCTGTTCA
CATTTCCTCTAAAGAAGTTGCACTGCATCACAGTTCCATACCAATTTCTGCTATGACCTT
AAATATAGCCCTGAACTTCCCTGTCAAGGAAGAAGTGAGGAGGTTTCAACAAGTGATCAG
[A,T]
AATGATTCTTTTATGTCTAAGATTCTAGGATGATTTCCTCTCTGCCCTGGTAGGCTGCTC
TTCAAAGTATGACCTCCTCATTGTTTCTCTGCTCTACCACACACTCATTCCCCTCCAAGA
AGGCTGCCCACCTGTAATGACCTGTCTACAGAGCCTGTGATAGTGACTTGTGATAAATGG
CTATTAGCACATTTACCAATCAAGGTCCTGTTTGCAATTCGGTTGTGGGTCAAAATTATG
TTTGTTTTAACTGAGGTCTTTAGTTTATTTCAGGCAGAGATCTGGGCTGGAGTGTCACCT

95079 TTTGGTAAATCTTCTTTTCAGTAGACCACAAGCCCTTGCAAATGTTCTCTTTTTCTAACT
CTGGTAGCAGAAGGACCACTTGAGCCTCAAAACAAAACGGCAGTGCAGTAATGAGGGTAT
TAGGTTGATGTGTTCTATTCAGCACCTGCTCCCGAGCTACCGAATAATGAATGAGCATGA
ATTACACATTGTGAAAACAGGAGAATCTGCCTTCTTTGTGTTGTATGCATCAAGCAGTTT
CAAAAGGGCTTTGCAATTGTGTTTCTCACACAAAGCCACCCATTTGTGAAAACCCATGTG
[T,A]
AAAGGCAAAGAGAACTGTCTGTGTACAGGTTAACATTTAACTAGACTGGCAGAGCTTTTA
ATAATTTCTATAAGGTTAATGGCTTCGTTAATATGCAACCTGTGATTTGGTCCAAGTTAA
ATTTTACTTTGCCCAGAATACATTATAATATAAAGCTTAAGCTTTATTCTTTCAGGTTTA
GTCATTTAACACATAATATTGATCAATTATGCATGTTGGACACAGAGCTCTGAATAGAGC
TTTGAAATATAAAACTATGGTTTTAGTCCTCTTAGAGCTATGATGTTTGGTAGGTTAGGT

95089 CTTCTTTTCAGTAGACCACAAGCCCTTGCAAATGTTCTCTTTTTCTAACTCTGGTAGCAG
AAGGACCACTTGAGCCTCAAAACAAAACGGCAGTGCAGTAATGAGGGTATTAGGTTGATG
TGTTCTATTCAGCACCTGCTCCCGAGCTACCGAATAATGAATGAGCATGAATTACACATT
GTGAAAACAGGAGAATCTGCCTTCTTTGTGTTGTATGCATCAAGCAGTTTCAAAAGGGCT
TTGCAATTGTGTTTCTCACACAAAGCCACCCATTTGTGAAAACCCATGTGTAAAGGCAAA
[G,A]
AGAACTGTCTGTGTACAGGTTAACATTTAACTAGACTGGCAGAGCTTTTAATAATTTCTA
TAAGGTTAATGGCTTCGTTAATATGCAACCTGTGATTTGGTCCAAGTTAAATTTTACTTT
GCCCAGAATACATTATAATATAAAGCTTAAGCTTTATTCTTTCAGGTTTAGTCATTTAAC
ACATAATATTGATCAATTATGCATGTTGGACACAGAGCTCTGAATAGAGCTTTGAAATAT
AAAACTATGGTTTTAGTCCTCTTAGAGCTATGATGTTTGGTAGGTTAGGTGAAGTAGACA

96495 GGAAGCCACACTGCGATTTTCCAGATAATTGTGAAACAACTACGGGCCATTACAAAACCA
TAGGAAATTAGAAGTGAGGAGTAATTTGGAGACTGACAAGCTCTACCTTCATCTAAAGGC

FIGURE 3ZZZ

AGAATTTCTTCTGCAGTCTCCCTAACAAGGAATCGTTATACCTCAGGGATGGGATAGTCA
CTACCACATAAAGTAGTTCATTTTCAGACATGCATAACCTTAGAAAGTTCTTCTCTTGAT
TTACAATTAGCCTCATAGTTCTGTTGCTGCCTATTGGAGTTTTACTACGTGTACAGTCAG
[G,A]
CAGGGCTTCCATTCAGTCACCACCCATTAGTACTGTTGTACTAGTAATTTATGGATGGCG
TCCATTCTTACTGGTCCATGTCCCATTCTGATTTGTGTTTGTGCCATTTTTAAGTGTTTT
GAATATTAACCCTGGTATCAGATAAACATGGAGTCCTGACTTTTTCCATAATCATGAATA
ACAGTGGAATAGTTACATCAGATTTGTGTGCCACTGTGGTCCCATCTATGAAATAGGGAT
AATAATTGTACCTAGTTCATAAGGTTGTTTGAGGATAGTGTGGAATAAAGTATAAAAAGG

97070 ATAGTGTGGAATAAAGTATAAAAAGGGCTTAGCCTGGTTTCTCAAATATTGCAATAAATG
AAACTTAGCATCATGATGCTGTCACAATGGTTCAATGATAATTGAAAACATCGATTCATC
ATTTAGCATCCTCAGCTTATCAGTTTCTCACTATCTAGCTCTTCTTACACTGGACACTTC
CTAATTATTCTTTCAATGTTTTCTGGAAGTTAGTTGAATAATTACTGTGCACCAGATACT
ACACAGTAGTCCCCCTTGATGCATGAGGGATACATTCAAGACCCCCAGTGGATACCTGAA
[T,A]
ACGCAGATATTTCCAAACCCATATATACTATGTTTTTTCCCTTTTGTACATACCTATGGT
AAAGTTTGATTCATAGAGTAAGAGATTAACAATAACTAATAATAGAACAATTATAACAAT
ATGCAGAGTAAAAGTATGTGAATGCAGTCCCTCTCTCAAAGCATCTGATTGTACCGTACT
TACCTATTTTTGAACCACAGTTGACTGTGGGTAAAAAGGAAAACTGCAGATAAGGGGGGA
TTACTATACTACGAGTTTTACATGTACCATTTAACTAAATCATTACGACTCTATAAAGTA

99913 GGGTGGGGATTGGTTGTTTTGCTTTGTTTTGTTTTCTCTTCTCTTCTTAGGGGAAAAAGA
CATGCAGGGCTTAGTATTCCAACAATTTGAGAAACCAGGGGGCTGGGATTCATTCATTTT
TATGACAAATAGTTACTCGAGCACCTACTTTATTCTTGGGTACTTTTATGAGTCCAGGGG
CTGCTGCATTGAACAATACAGAAAAGAAGTCCTTTCACTTAGAACTTACGTCCTAGTGGG
GGTTGGGGGTTGGGGGTTGAGAGAATGAAGCATTCTTACAAAGAATGTTAAAAGCGAACT
[A,C]
TGGGCAGGAATTGAGGATATGAGTTTTGATGTATAAAGAAAAAGTGACAAGGTCAATAAT
TGGTGGTCTTAGTGTGATAGATATGCCAGTTTGGAAATTGTATTGAATAAATGCTAGTCA
GGGGCTAGGCTGTAGTTATGAAAAGGAGATGATTAAGGAAGTGAGAATAAGGAAACTATT
GGTGTGGGACGGATGAAAAGATTATTGGAGGCAAGTCAAGGAACTGAGAGGCCAGGGTGT
TAGATGGAGCATTCATGTAGACACTGAAGTCACCAAGAATAATAAATAACAAGTAAGAGG

102375 TTAGATGAGACATTGGACTGTGGACTTTTGAGTTATTGCTGAAATGAGTTAAGACTTTGG
GGAATTCCCAGAACTGAGGGTTCCTCCCCATTGTAGACCATATAGGTAGCTTCCAGACGT
TGCCAAGGCATTTGTAAACTGTCATGGTGCTAGTGAGAGTGTCTTTTAGCATGCTCATGT
ATTATAATTAGTGTATAATGAGCAGTGAGGATGACCAGAGATCACTTTTGTCACCATCTT
GGTTTTGGCCAGCTTCTTCACTGCATCTTATTTCTATCAGTGGGGTCTTTGTGACCTGTA
[C,T]
CTTGCAAAAACAGTCCTGCTGATTACTAAATTCCTATCTCACCTATTCAAGATGGAGTCA
CTCTGGTCTGAATGCCCCTGATAAGAGAATCCACAGTGTTCAATTCTCCCCAGTTGATTC
TGAAGCATATCCAGGTTTATTAGCCACTAAGTAAAAATATATTATAGACTACTGTCAATG
AAAGAAACATTTTGTAAGTTATTTCATATTTATTTTTACTTGAGAAGACTGAAAAGGTAA
AGAAGTGATGCTAAAATTTAGAACTAGAAAATCTCAACTTGCTCTAGTAGGAATTTTAAT

102686 CAGTCCTGCTGATTACTAAATTCCTATCTCACCTATTCAAGATGGAGTCACTCTGGTCTG
AATGCCCCTGATAAGAGAATCCACAGTGTTCAATTCTCCCCAGTTGATTCTGAAGCATAT
CCAGGTTTATTAGCCACTAAGTAAAAATATATTATAGACTACTGTCAATGAAAGAAACAT
TTTGTAAGTTATTTCATATTTATTTTTACTTGAGAAGACTGAAAAGGTAAAGAAGTGATG
CTAAAATTTAGAACTAGAAAATCTCAACTTGCTCTAGTAGGAATTTTAATAGAGCACACT
[-,A]
AGTTTCTTTTCATTTTCTCTCTCCTGGTATGTGAATAAACAACCTTCCATACTGCAATTT
ACCCTGTAGTGAATTAGATGTTACCCTATTATATTTTGGAGAAACTATATAGTTAGAATC
TAAGCTTAGATAACTTATTTTTATGTTTACAAATCCACTTTCTCTTATACATTTTTCTTA
AATTTTTCTCATATTCTTTCTCTGAATTTGTGGTAAAAATACCCCTTTCCCATTCTATGT
CATGGTTCTTTACGAAGCTTTCTCATCCTCTCCATCCCGAGGGAACTATGTCTCATTTAT

102687 AGTCCTGCTGATTACTAAATTCCTATCTCACCTATTCAAGATGGAGTCACTCTGGTCTGA
ATGCCCCTGATAAGAGAATCCACAGTGTTCAATTCTCCCCAGTTGATTCTGAAGCATATC
CAGGTTTATTAGCCACTAAGTAAAAATATATTATAGACTACTGTCAATGAAAGAAACATT
TTGTAAGTTATTTCATATTTATTTTTACTTGAGAAGACTGAAAAGGTAAAGAAGTGATGC

FIGURE 3AAAA

TAAAATTTAGAACTAGAAAATCTCAACTTGCTCTAGTAGGAATTTTAATAGAGCACACTA
[A,C]
GTTTCTTTTCATTTTCTCTCTCCTGGTATGTGAATAAACAACCTTCCATACTGCAATTTA
CCCTGTAGTGAATTAGATGTTACCCTATTATATTTTGGAGAAACTATATAGTTAGAATCT
AAGCTTAGATAACTTATTTTTATGTTTACAAATCCACTTTCTCTTATACATTTTTCTTAA
ATTTTTCTCATATTCTTTCTCTGAATTTGTGGTAAAAATACCCCTTTCCCATTCTATGTC
ATGGTTCTTTACGAAGCTTTCTCATCCTCTCCATCCCGAGGGAACTATGTCTCATTTATC

102939 CTAGAAAATCTCAACTTGCTCTAGTAGGAATTTTAATAGAGCACACTAAGTTTCTTTTCA
TTTTCTCTCTCCTGGTATGTGAATAAACAACCTTCCATACTGCAATTTACCCTGTAGTGA
ATTAGATGTTACCCTATTATATTTTGGAGAAACTATATAGTTAGAATCTAAGCTTAGATA
ACTTATTTTTATGTTTACAAATCCACTTTCTCTTATACATTTTTCTTAAATTTTTCTCAT
ATTCTTTCTCTGAATTTGTGGTAAAAATACCCCTTTCCCATTCTATGTCATGGTTCTTTA
[C,T]
GAAGCTTTCTCATCCTCTCCATCCCGAGGGAACTATGTCTCATTTATCTTTAGGTTTTCT
GTATCTTACTACAGTGACTTACCAGAGTAGGTAAATATCTGATGAATAAATGAATACAAG
ATTTAATTAAGAAGTAATCACATTAAACTAATTGTTCCCTCTCTGATCTCTGTAATATTA
AGTTTCAAAGTAGTTTCTGGGAAAAGTAGTTAACACAATGATGTATGGATTCAATAAATA
AGAAAAATGGTGCTCAGGGATTTAACAGAAAGCTCATAAAATGTCAAATCCACAGCAATT

106162 GTTTTATGCGGCTTTGTCTATGCTGGCACATAACTAGTATGTACCAATGTATCTCAGAAA
AGATATCAAGTTTTCTGTTTAAAAATTTCAGTTTGAGAAAAATCAGTTAAAGAAAAACAT
AAAAAAGATAAAAGTATATGTGTTATCTAGATTTGTGATATAGGGATATGGCAATAATCA
AGATGGTGATAAGTGAATGCTGAATTTCAAGAACTACTGATTACACCCTCTAGAATAAGC
TTTTGCCCGTGATGATTAAATGTGTACGATTTCTTCCTAATATTTATTTTTGTGTATATT
[G,T]
GGATTTATTAGAATATCAGGGAAGATCTGCAGGGCACAAAAACTGTATGTTATAAATGTT
AACAGTGTCAATAAGATCTTTGTTATGTCTTTAGAAGGCTGCTAGATGAGGAGAGTCCTA
GATCTTAAAGGCTCCTTATTCAATTTTTACAAAAAGGATTTGCAAGTGGAACTGAAACTC
CAAGTACCATCTATTGCTCATTATTTATTTACCTATTTTTGAGCCTGATTTTCCTGATCC
CACCTGTGCTCAGGGGGCTAAGAAACACTGGTAATGACCTCTAATTTCAAAGCTCACTGT

106378 CTGATTACACCCTCTAGAATAAGCTTTTGCCCGTGATGATTAAATGTGTACGATTTCTTC
CTAATATTTATTTTTGTGTATATTGGGATTTATTAGAATATCAGGGAAGATCTGCAGGGC
ACAAAAACTGTATGTTATAAATGTTAACAGTGTCAATAAGATCTTTGTTATGTCTTTAGA
AGGCTGCTAGATGAGGAGAGTCCTAGATCTTAAAGGCTCCTTATTCAATTTTTACAAAAA
GGATTTGCAAGTGGAACTGAAACTCCAAGTACCATCTATTGCTCATTATTTATTTACCTA
[T,G]
TTTTGAGCCTGATTTTCCTGATCCCACCTGTGCTCAGGGGGCTAAGAAACACTGGTAATG
ACCTCTAATTTCAAAGCTCACTGTCATTACTTATTTATGGACTGTCCAAAAAGATTTTTT
CCACTTTCTTCCAATGCCTTATTTCTTCCTTACCTTTACTGCTTCTGACATTTGAAAACA
GGGTCTCTGATTCTCAGAAATGTGAGCAATGGTGAGATTTAGCATGAAGGTGACTTTCTT
TAAAATACCAGCTATCCAGAGCTAGGTACAGTGGCAGGCACCTGTAGTATCAGCTACTTG

107310 AGCTTTATCCTCCCTTCAGAGAACAGTGTTTTCATCCCAGGTCTCATCCATGGCTTCACC
CTACTTCTATCATTAAGGCATCCTATTCTCCTTCAGTCAACTTCTTCCTCCTCCTCATTT
TCTTGGTGACTTGGTCATTGCAGATGAGGAAAAACATGAAGAAATCAATTAATCTTCAAG
TTTAACCACCTTTAGAGACTACCCTTGTGAAAGATTAATTGTGTAACAGTGTGGTTAAGA
ATGTGACTTCTGGAGCCAGATTGCCTTCATTCAAAACACACTTCACTCATTTCCTAGCCC
[C,T]
GAGAGCTTTGACAAGTTGCCTAAACTTTGTCTTAGTTTTTCCAGGGATCAAAAGAATACT
TACTTAGAAAAAAAATCTTACTTACAAAAGAAATCTTACAGGGATCAAAAGAATACTTAA
TTAGGGTCATTGTAAAGACTGACCTGATACGTGTGAAGTACTTGATGCAATGACTGTCAC
AAAGAAATCACTCAATAAAAGTCTAATATTAGTACAATTCTTCTGAGGCAGTCATGGCTT
TCTTTCCTTGGAAAGGAAGCTGGGACTGCTTCATCTTGTTTTATGTTTCTTTGTCTATGC

108663 ACTTTCCATGTGGAGCTCATATTTGAAGACCTCATTTGCCTTCTCCATCTCCATTTATAA
TATTTCATCCCTGATGGGCTGTCGCTTGGGCCTCATGTGGAAATTGTAGCCACTGTGAAG
GGTAACCACCTATCTCTCTGGTGCCCCCTATGCGCATCCCTACAAGTGAGCTGTGTATCA
CACCATGCTGCTTACATTTTTATGCAACACGATTCAGTAACAGGCAGAAACTTTTATTCT
TACTGACTCATATTCTTTATATTCATCTGAAAAGATTGACATTTAAAGGAGCCAATTGTA
[C,A]

FIGURE 3BBBB

AATGGGAAATCCACTGTGTGAATATTTCTTGTACATCAGAATTTGCCTTAAAAATGTTTT
TAACTTAGAGCACATCTGTACTGTTCTCCCCAAATGTCCCATTTACTAGTTCAGAGCAAG
ATGACATTAGGTCTTGGGTGACTCCTGACCCACTATCCTAATGTATATTTTCATTTCCTA
CCAATGTAAGTACCCCATCCAATTCTATCAATACCATAGTGTCTAAAATTCTTGTATTTT
TCTTATTCAGGAAATGCTACAACCAGAGGAACAGTAATGTCTGCCTGACATATCAGAGAA

108876 TCAGTAACAGGCAGAAACTTTTATTCTTACTGACTCATATTCTTTATATTCATCTGAAAA
GATTGACATTTAAAGGAGCCAATTGTACAATGGGAAATCCACTGTGTGAATATTTCTTGT
ACATCAGAATTTGCCTTAAAAATGTTTTTAACTTAGAGCACATCTGTACTGTTCTCCCCA
AATGTCCCATTTACTAGTTCAGAGCAAGATGACATTAGGTCTTGGGTGACTCCTGACCCA
CTATCCTAATGTATATTTTCATTTCCTACCAATGTAAGTACCCCATCCAATTCTATCAAT
[A,T]
CCATAGTGTCTAAAATTCTTGTATTTTTCTTATTCAGGAAATGCTACAACCAGAGGAACA
GTAATGTCTGCCTGACATATCAGAGAAAATGACAATTATGTCATCATCTGTCACTTAGGT
TTCTTAATACCATCCTGTTACAAGGAATAGAGGCAAAAACTCAGCGTAGGAGGTGAGAAA
AAACTGAGGCTGCCATCTTAACAGCCTTTTCATTGCAGAGTCTCAAAATGTACCAAAAGA
TGAAGTGGACAGTGTCCTTTTAAAACAACATACAGTGTAGAATACAGTAACTTATCCCCA

110733 CAACTGACGTGTAATGAGTACTCACCAGAGTTGAGATGTTCTGCTAAGCCAGGCCCTCTT
TTAAAAATGTAATCTCAAACTTTATTAGGTCTCATAATCACCTGGAAGGCTTATTTAAAT
ATTGGCGCCCAACCCACAGAGTTTCTGATTTGTTATAATAGAGTTGAGGGGGGACGGGGC
GTAAGAATCTGCATATCTAACAAGTTCCCAGGTGATGCTGATGCTGCTGATCTGGGCACT
ACATTGTAGGAATCAATTGGCTCTAAAACCTTCTCTACCTTCCACTTCTACATGAGCATA
[C,G]
ATAATCTTGTAGCTGAGTCAGCTTGGAAATCTATGCAGACTAAAGTAGACAGTTGCATGT
CTGGCTGCTCATCTGAATCACCTGTGGAATTTGTTGTTTTTAATACAGATACCTGGCTCT
CCTACAAGTCCCACTGAATTGGAGTTTCAGGAGACCGAAGCCCAGGCACATGTATTTTGC
AAAACTACACTGAAGTTTCTGATAATGACGGATATCAACAATTAAACGCTTACTTCTTGC
CAAATGCTGTGCTAAGTCTCCTGTAATCATTCTTTCATTTAATATTTCTAATAACCTCTT

111546 AGAAAAAGAAAAAACAGAGACAACCTACGCTATGATAAAGTTATTGAAATCAGGCATTGG
TGCCACTCCAGCAAGAATGAGTGGCTACCTTTTTTTTAGATGAGTGCTACCTTTACTTTA
CTGAAATATCATGACATAAACAAAGCCAAAACACTTTCTGCACAAAATAAAATCCTGGTG
ATAAAGGCAGTGGGATTTATGCTTAGCAGCAGGCTGGATACTATCAGGGAGCAGACAAAG
AAGTTTGATACAGGGCTTGTGGACTGTGGGCCCTGGAAGAATCTGATGACATGCCCTCCA
[A,G]
TTACAGCTGTATCTCATCAAAACCACAGACACATGTAAATGGAAATGCCAACACTTCAAG
ATTCTCTGAAAGCAGTTGACTGTCATGCCAACAGCTAACATAATAGGCTTGTTTGCCTGA
GCTTTTGGCACGGCCCTTTTGTTCCCTTTAGCTGTAAATGCAGGGACCCTAGAGCACCTC
ATAGAGTGTGTTCCCTGCCACGTATAAGTATTAGACCCACACTATATTGCTTTGAGTGTT
AAAGCTGAAAGAGACCCTAGAGATCATTTAGTCTACTCCTTCTTTTTTTATGTGAAGGAA

116728 ATTCTCCAGGTTTCCTGGGTTTCCATATTAAGGGCTATTTTCTTGGAACCAAATCAGAAA
ATGTGCATCTGGGTTTCCAGGGTTGGTTTCCATGGTGAGAGAAGTACGGGGAGGCCACCT
TTCTTTCCTCTCCCCAGTGGTTTTAAGTACAATATCTGTATAATGTAATTTTTTCAAAGT
TGGCATTTCTAGTCTTCTCACAAGATAGAACTGGGAAATTGGAACCTAGGAAAAATTCTG
TGCACCTTCCACTTTTACCCTTGTAATTAACAATGACTAATATTTCTTGAAATCTTTCCC
[T,C]
GGACCAGACAAGGTGTTAAATGTTTTACATTCATTTATTTGTTTATTTTTCTCAGCAGCC
CCATGGGGTGGACTATACTTATCACTACTTTATAATGAGAAAAATCAGAAGCTAAATAAT
TTGGCCGAGATCACATGGCTAATAATTGAAAAGTCTAGATTTAAATCAAGCTCTGTCTGA
TTTCAGAAATCAAGCTTTTTCTTAAAAGGAAGATTAATGAGAAATAAAAATATATATTTG
TAAATATTTTTATCTGTGGTTTTTAAATGGTTCTAAGTCAACTTAGTTAGGCTAACATAT

118403 GTAACCTAAATTTTCATTTTATAATGTAACAATAATGATAGCATCATATAGTGAACATTT
ATTGTTCCAAGCACTTTGCTAAGTTTTTAACATTTATTATTAAACTCTCAACCCCATAAA
ATAGGTTTTACTATTGTTTAGATTTTACAAGTTAAAAAAAAATCAGGCCCAGAGAGAGAG
AAAGTGATGTGTTCATAATCACACAGCCAGTGATTGGCAGAGCATGAAATTAAACCCAAG
TCTAGAAACATGCCGTGCCTGAGACATGGACGATGATGTGACAATGATGAAGGTAGAATG
[G,T]
CTGACATTGCTAAGCTCTTCCTAAATGTTAAGCACTGTTGTAACTGCATGCATTGTCATT
TAAACTAAAAACAGTTCTGTGAGGCCACTACTATCGTTACAGTTTTATTATTGCATAATA

FIGURE 3CCCC

TATTAACATATAATTAATGTAGTATATTGTATATATAGTACTATTGTTATAGTATATATT
GTTCTCACTTCAGAAATTAGCAGACTGAAAGGTTAAGAAACTTGTTGACTGTGAAGCTGG
AGACAGTCATAGGGGTCTGATGCCAGAGCCCTAACTCTTAACATGCTGCAGTACTGTCCC

118491 AACATTTATTATTAAACTCTCAACCCCATAAAATAGGTTTTACTATTGTTTAGATTTTAC
AAGTTAAAAAAAAATCAGGCCCAGAGAGAGAGAAAGTGATGTGTTCATAATCACACAGCC
AGTGATTGGCAGAGCATGAAATTAAACCCAAGTCTAGAAACATGCCGTGCCTGAGACATG
GACGATGATGTGACAATGATGAAGGTAGAATGTCTGACATTGCTAAGCTCTTCCTAAATG
TTAAGCACTGTTGTAACTGCATGCATTGTCATTTAAACTAAAAACAGTTCTGTGAGGCCA
[C,G]
TACTATCGTTACAGTTTTATTATTGCATAATATATTAACATATAATTAATGTAGTATATT
GTATATATAGTACTATTGTTATAGTATATATTGTTCTCACTTCAGAAATTAGCAGACTGA
AAGGTTAAGAAACTTGTTGACTGTGAAGCTGGAGACAGTCATAGGGGTCTGATGCCAGAG
CCCTAACTCTTAACATGCTGCAGTACTGTCCCTTTGTTCATGTCAATAAACATGCCTCTG
CTAAAATAGAAACCCACTTCTCTTAATCAATTTTTTATTGTTGAATGTTAGGTTGTTTCT

118888 TCACTTCAGAAATTAGCAGACTGAAAGGTTAAGAAACTTGTTGACTGTGAAGCTGGAGAC
AGTCATAGGGGTCTGATGCCAGAGCCCTAACTCTTAACATGCTGCAGTACTGTCCCTTTG
TTCATGTCAATAAACATGCCTCTGCTAAAATAGAAACCCACTTCTCTTAATCAATTTTTT
ATTGTTGAATGTTAGGTTGTTTCTCATTTTGAAATACAGATAGAGCATCCCAAATCCAAA
ATGCTCCAAAATCCAAAACATTTTGAACACCAACATGACACTCAAAGGAAATGCTCATTG
[A,G]
AGTATTTTGGATTGATTTGGGGATTTGGGATGGCCAACCAGTATAGTGCAAATATTTCAA
AATCTGAAAAAAAAAATTGAAATGCAGAACACTTCTGGTCCCAAGTATTTCAAATAGGGG
ATACTCAACCTGTACATTTAAATTTGTAGTAAAAATCCTGTTAGCAGAATTATGTCCTGG
AACTTAGTTATTTCTTTGTGATAAATTTTCATTCAATAATAATAGTGTATTCTCTTACTG
AAAATCACTCAAAGAAAATTTTGTGTTCTCACCACAGAAAACAGTAATGTGGGTAATGTG

125444 GGAGAATCACTTGAGCCCAGGAGGTAGAGGCTGTAGTGAGCCAAGATCATGCCACTGCAC
TCCAGCCTGAGCTACAGAGTGAGACCCCATCATTAAACAAAACAAAACAAAAAACAAACA
AACAAAAAACAAGCAAGTTATGTGCTTCCAAAATACAATGATACCATAGCTGTGGGATAG
AGAATCCCATTCCAACATTTCAAAAGAGAAATGGGAAAGAAGGAAGGGGCATCAGCTCCT
AAACAAGTCCAGAACATATCAAAGCAAATTCTATTATATCTTAAAACTCGAGAATAATCT
[-,A,T]
CTTTGAGTTGTTGGTTTGCCCTCTAGATCTACACAGGCATGGGAGCAATCACTCTCATGG
CTGGGGATGGGGAGAGGGGACTTGCTTAAGTGGCTCTCTACAAAGGCACTACCCACATGG
CTCTCTGTGAAGGCTCTGTCTACACAGCTCTGTTGAGTGGTGGTCCTGCCCTTCGAAACA
GAGGTGGAGGCAACCCTGCTCCCCAAGCCAGTGCACTCTGGACCTGTAGTGGGAATGGCA
GCCCTGATGATCTGTGAATCGCCCTCATGATCCTTCTTCCTTTTACTTGAAGGATAGCAC

125810 GATGGGGAGAGGGGACTTGCTTAAGTGGCTCTCTACAAAGGCACTACCCACATGGCTCTC
TGTGAAGGCTCTGTCTACACAGCTCTGTTGAGTGGTGGTCCTGCCCTTCGAAACAGAGGT
GGAGGCAACCCTGCTCCCCAAGCCAGTGCACTCTGGACCTGTAGTGGGAATGGCAGCCCT
GATGATCTGTGAATCGCCCTCATGATCCTTCTTCCTTTTACTTGAAGGATAGCACATGTT
CACAGCTGGATAGCATTACGGTCCCAGCCTGTAAAATCCAAGAAGTCTGACAGCCTTTCT
[T,C]
CATAAATTCAAACTGGCAGCATCTGCTAGTATAATCCCATCTTTATTTCTAGCTTCTGTT
GTGATAACTACTTGATTGTTCAGCTACACTCTAGTGTGCTCTTCAGAACAGGCTTGCTCA
TTTTCTGCAATATGGATAGAAATCTTCAATTTCTGGTTGCTTTTTGCTTAATTATTTTTT
CTTCAATTCAAACATTCCCTTTAACATTTTACTATAAGCAGACAGAAGGAACCAAGTTAC
TCCTTCAAAGTTTTGCTTAGAAATCTCCTCGGCTGGCCTGGTGCAGTGGCTCATGCCTAT

126092 AAGTCTGACAGCCTTTCTTCATAAATTCAAACTGGCAGCATCTGCTAGTATAATCCCATC
TTTATTTCTAGCTTCTGTTGTGATAACTACTTGATTGTTCAGCTACACTCTAGTGTGCTC
TTCAGAACAGGCTTGCTCATTTTCTGCAATATGGATAGAAATCTTCAATTTCTGGTTGCT
TTTTGCTTAATTATTTTTTCTTCAATTCAAACATTCCCTTTAACATTTTACTATAAGCAG
ACAGAAGGAACCAAGTTACTCCTTCAAAGTTTTGCTTAGAAATCTCCTCGGCTGGCCTGG
[T,C]
GCAGTGGCTCATGCCTATAATCCCAGCACTTTAGAAGGCTGAGGCGGGCAGATCACCTGA
GGTCAGTAATTCGAGTCCAACCTGATCAACATGGAGAAACCCCATCTGTACTAAAAATAC
AAAATTAGCCGGGCATGGTGGTGGATGCCTGTAATCCCAGCTACTCAGGAGGCTGAGGCA
GGAGAATCACTTGAACCTGGGAGGTAGATGTTGCAGTGAGCTGAGAACACAACATTGTAC

FIGURE 3DDDD

TCCAGCCTGGGCAATGAGAGCGAAACTCCATCTCAAAAAAAAAAAAAAAAAAAAAGAAATC

127506 CATTCTTTCTGCTGCTGTCAATAGCCCTCTTCTTTGGTCCCACAACACACCATCATGATT
TCTGCATTAAAAATGCCATCTCCCAAGTAATTAACCTATTCACAGTAAGAACAGTTGTTA
GAAGTTGGGGTTATTTCATCATGGTCCAATGGCTTTATCTTGCTCAGGAAATCAAAGATG
AGTGTTTCTAAAGCAAAAAAAAGGAGGATCTCACAATTGTATCTGTTTCATTCACTCTGC
AGGGTCCATTTTACACCCAAACATTCATTAGTTCATTGTTTGTACTCCTGCCTTTCCTGA
[G,A]
GAAGTCATTGTAGCACTATTTCTTAAGTATATTCAAATTTGGATAAGTTAGTCAAATTGA
TGTGAAAGGACCACCCTTGTAAGCCAAATGTGTAAGTCCTACATAGGGATATTACCTGTT
TTTATCTCCTGATGGGCTTTTTTTTTTTCAAGTTTCTAAATAAATCCAGTGAACAAGTAG
ATACGCTACTCATGATTATATAGGAAAACAGAGAAGAGAAACATACACTTACTTAAAAGT
AGAAACATATCTGCTCTTTCCCACTTCACCCTTAATTTTTTTCTCCCCAGCCAATTTACT

127878 CACCCTTGTAAGCCAAATGTGTAAGTCCTACATAGGGATATTACCTGTTTTTATCTCCTG
ATGGGCTTTTTTTTTTTCAAGTTTCTAAATAAATCCAGTGAACAAGTAGATACGCTACTC
ATGATTATATAGGAAAACAGAGAAGAGAAACATACACTTACTTAAAAGTAGAAACATATC
TGCTCTTTCCCACTTCACCCTTAATTTTTTTCTCCCCAGCCAATTTACTCACCTTCTGTG
GCTGTGCTTCTGTGTTAGACCCTTGCTAGCTGCTTCTGGGGTTCAGAGCAATTGTGCTCT
[G,T]
CCCTCATCTTTTATGACACACCTAGCAAAACAGAAGCAGAGGAGCGAGTTGAAACAGACA
AACGACTATCTGTTATTCTTCAAACATGCCTAGGATTGTATTTAACTATCACCTATCTAA
AAGAGGTATTCTCGCCTGCCTGGAAAGAATTTTGCTAAGAAAATTGTTTCTCTTCTTCCC
ATATTATTTTACCTCTATGCTAGTTCCCTGTGATTTGATATGTCAACTTTGACAAATTCA
TTTTTCTAAAGCACAGATATGACCTTTTTTGTTAAGAAAAAGAAACTACTGTTGCTCCCC

139738 GCTGTGGTTTGTTTTTAATTCATCTCTAAGTATATTCTGATATCTCATGTGATTTCTCTT
TTTGACTCTTTTTTTAAGAGTTTGTTGTTTAATTTCCACATTTTTGTGAATTTTCCAGTT
TTCCTTCTGTTATTGATTCCTACCTTCATTCCAATTATTTCAGTCTTTTTAAATTTTTTG
ATACCTGTTTTGTGGTTTCCTTCCATGGTTTCCTTTAACTCTGAGCATATTCAAGACGGT
TGTTTTAAAATCTCACTCTAGAAAGCTCAATGTTTGAGCTTCCTCAGGACAATTTCTATC
[T,C]
GTTGATTTTAAGTCTTTGAATGGCAATATTTTCCTGTTTCTTTGTGTGCCTTGTGATTTT
TTTTCTGTTGCTATTGAAAACTCGACATTTAAATATGATAATGTGGTAACTCTGGAAATC
AGGTTCCTCCTTTCTTCATGGTTTGCTATTTTTTGATTGTTGAAGGCTGTAGTTATCCAT
TGTTTAGCGACTTCTCCAAACAATGTTTGCAGAGATTGTCTGCTTTGTTGTGTCATCACT
GAAGTTTCTGTTACTTTAGCCTGTGCTCAGCTAATGTTTTGACTGAGATTTAACACCAAG

140261 CTTTGTTGTGTCATCACTGAAGTTTCTGTTACTTTAGCCTGTGCTCAGCTAATGTTTTGA
CTGAGATTTAACACCAAGAGCATTTTTAAGTTGTTTTTCTTTTCTTAATTTAGTGTTCAC
TTGGTTCCAGTAAACCTTTGAGTGCTTTCCGGAGTTTTGACAAAGTTGGTTTTGACAGTA
TCTGCTTGTTTTTTTGATGTTTCTGTTCAGAGATGGGGCTTGGAACTGCTTACATCAGCA
TTTTTCTCTAGATTCTTCTAATCTTGTACCCCAGGTTCAAAAATAAAAGGTACTTTGCTT
[C,T]
AAAACAAAGAATAGTCTTTCTTCCAAGAAGAATCAGAAAGATTATGAACTATTTTTCTGA
TTCTTCACTCTATTTTCTCTCTTTTACATTAAGGCTTTTAAAACATGAGTCAATCTTACC
TTATTATATTATTAACATGCTCGTTCATTCATTCATTCATTTATTCAGATGACTGTAAAA
TTCCTGCTTTGTTAGGAAATATTTCTGACTAGGTGGTTAATGCTATGGTTAGATACACAA
AGTGCTGTGGGAATTGCTCACTGGACCTGAGTGAAGGGTTAGGATAGGCTTTCCAGAGGA

141590 AATGGGAATAGCATTGAATCTATAAATTACTTTAGGCAGTATGGCCATTTTTATGATATT
GATTCTATCTGGGAACCTGGAATGTTTTTCCATTTGTTTGTGTCCTCTCTGATTTCCTTG
AGCAGTGGTTTGTATTTCTCCTTGAAGAGGTCCTTCATTTCCCTTGTTAGCTATATTCCT
AGGTGTTTTATTGTTTTGTAGCAGTTGTGAATGGGAGTTCATTCATGATTTGTCTCTCTG
CTTGCCTGTTGTTGGTGTATAGGAATGCTAGCAATCTTTGCACATTCATTTTATATCCTG
[T,G]
GTTTCAGTATTTTAAAAACTTACTTCAGGTGATTCTATGTGTGCAACCATGATTGAGATA
CACTGTTATAGAATCTAGGATGTGATAAACTAGAAGAACATAACTAAAGTTTTGCATTTT
TCGGGTGTCTCAGTTTCCTCATTTATAGATGGAGTTGGTATGTGTACCAAGTTCATAGGC
TTGTTCTGAGTAAATTAGTGCATGTAAAGTGCTCCACAGAATGTTAGCTGTTGTGATGCT
TTACTTTCCATTGCACTTCCTGACTCCTAGCCTTTCTTTTCCTTGGCTCTTTTTATGCTC

FIGURE 3EEEE

142613 ACAAGTTGAACATGAACCCTTTAAGGGTAATGGGGTCTGAAGTGTCACACTAAAAGGTCA
TCTGCAAGTATGTATTTCATATCTTTGTTTAAATAAAATAGTTACATAGTAGAGGGAAAA
AAAATCCATGTGGATTTTGCATTTCACTCAATTATAACCTTGATTTTTAATGCTAAAAAT
TATTTTTCCTAAAATCTTGGGGTAAAAGTGTTGCTCCAAAGAGCTTTTATCAGATTATGT
TTATCCTGTAGCTGCCTGTCCCCTGTGACCGATACTGGAAACCCTCAGGATTACAAATGC
[C,T]
TCCGTTTGCAAGTAAGAGTGAAATACAGCAGAACTGTGTCTTCTCCTTTGTCTTGTTCCC
CATCTCTCTTCTGTGCTTTGTATTGTTTCCTCTCCTGTCACCTAAACAGGCACTCTGAAA
GAAAACTCTCCAGTACTGGAGAACTTAGCATATTCTAATTCCTAGGTTAAAAAAAAATAA
TAAATGACTGAATGATTTTTTTTAAAGAATATTTTCCATCAGAAGAAATTTGGAAGTATT
TTGTTGCAGAATTTTAAAACATTTGATCTGGGTCTAATTCTGTCCTGGGACTGGTAATCA

142774 GATTTTTAATGCTAAAAATTATTTTTCCTAAAATCTTGGGGTAAAAGTGTTGCTCCAAAG
AGCTTTTATCAGATTATGTTTATCCTGTAGCTGCCTGTCCCCTGTGACCGATACTGGAAA
CCCTCAGGATTACAAATGCCTCCGTTTGCAAGTAAGAGTGAAATACAGCAGAACTGTGTC
TTCTCCTTTGTCTTGTTCCCCATCTCTCTTCTGTGCTTTGTATTGTTTCCTCTCCTGTCA
CCTAAACAGGCACTCTGAAAGAAAACTCTCCAGTACTGGAGAACTTAGCATATTCTAATT
[C,A]
CTAGGTTAAAAAAAAATAATAAATGACTGAATGATTTTTTTTAAAGAATATTTTCCATCA
GAAGAAATTTGGAAGTATTTTGTTGCAGAATTTTAAAACATTTGATCTGGGTCTAATTCT
GTCCTGGGACTGGTAATCATCTTTTTTTGAGGCTAAATTTTCTCATTTTGATGAAAAAGT
CATCAATAGATGTTGAAAGCTGGACAGTGCAGTGTCAAAGCAAATGCTTTGCATGTCTGC
AAGAAAGTCACAAATAAAGAAGGCTCTGCTGACTAAAAGAGAAAGATACTTAATCAACTC

143288 GTCAAAGCAAATGCTTTGCATGTCTGCAAGAAAGTCACAAATAAAGAAGGCTCTGCTGAC
TAAAAGAGAAAGATACTTAATCAACTCCAGTACCATTGTTGAGGGGAACATTCTATCAGG
ATTCAGTATAGAGAGATATTTTTAGGCTATTCACAAAATCCAGGTAGAACCTCCAAGCTA
CATTTACAATAATACTAGCTTTTAGATTAATTGTTGTTTTTTAAATATGTATTAGCCTCT
TATACAAATATAAGGAGTTACAAATTATTATTACAATAATCTTGGCTTTCGTGATTGTCC
[G,A]
ATGTATTTACACGTACCGAGAGCTTTATTTCTCCGTATAGTTTCAAGTTACTGTCTCGTG
TCCTTTCATTTCACCTTGCAGGACTCCTTTGAGCATTTCTTACAGGGAAGTTCTAGTGGT
AATAAACTCCCTCCACTTTTATCTGGAAACATCTTAGTTTCTCTCTCACTTTTCAAGAAC
AGTTCTGCCAGATAGAGGACCCTTGGTTGATAGGTTTTTTTCTTTTAGCACTTTGAATAT
ATCAGCCCACTGCCTTCTGGCCTCCAAAGTTTCTGATAAGAAATCTGCCCGTCATCTTAT

145610 TTTCCACCCTGACTCTCACAGGCTGTGTGCAAACTGCTCCGGAACATGTGTGTGCTCAGC
TCCCTCCCATGGGGCTGGAGGATGAGGGATGGGTAGCTGCTGCTGTGCTAAGAGCTTAAG
TTGGTCATAATTAACTGCGCTTTGCCACCCAAGCCTTCCCTGAAAGTTGCAAGCTTTCAA
TAGACTCCAGAGTTCTAAAATAGTGACATTAGACAGATTCTGCCAGTGCAATCGCTGTCT
AGGAGGGGAGACAGATTCCTGGTGCTTCCTGTTTTGCCAGCTTCCCGGAATCTTCTTCAC
[A,C]
TAGCATCCATTTTGAAGATACTACTTACTTCTCAATTTGGGGCTATTCATTGAATAGACT
GTCACCAGGTTATTGGCTGTTTGAAGATTCTCATTTGTCTGCTAACTATACCTCTATTTT
TTTTCTACGTTCACCTGGAAGACATGTCTTCTTCAAGAGCACCTTGACTCTGTCCAGAAG
GAGTTCATAATTTTCAACAGAGAAAAGTAAGTAATTCCTGGGAGAACAACAGCCCCAGAA
ATGGTGGCATGTTTCAGCCAGACTTTACTTGCAGAGAAAATATATTTTTAACATTTTAAA

148360 GAAGTGAACAGGCTTGGTGGGGGATTGTTTTCACCTCTTGGCTACTCAGAGTACCTAAAC
CTGTCCTTACTTATGGAGAGCATGTGTCACACCAAGATGGCAGTAAGCTGGCAACTGCGA
AGACCTGACTGATGCCCATTTGGGAAGCCAGGCAAGTGAAAATGGACCGAAGAAACAGAG
ATGGCTGTCTTTTATGCAGGGCTTTTCCATAAAGAGGTTACACTGGGGCAACCAAGTATG
TGTAGAAAGCCAGAGCTAAACTTCAGCTTGGCATTCACAGTTTTCTCTTCACTGAGCTAA
[T,C]
AGGCCCAGAGTTTCGGGCAGAGCTGTGAAATAGTGCTTCTCTAATAGCAACCATATTATT
GTTACATAATTAAAAGCCAGCTCTTTTGTTGTTTGTTTGATTCCTTTTCCCTACAGTTCC
CACATCATTTGTCTGTGCTATTCTGTTTTTCTCCAAACACTATAAACTTGAAGCAATTGC
CCTGACTCGATTTCAGAGAAGGGGATG

Chromosome map:

Chromosome 5

FIGURE 3FFFF

SEQUENCE LISTING

```
<160> NUMBER OF SEQ ID NOS: 8

<210> SEQ ID NO 1
<211> LENGTH: 1485
<212> TYPE: DNA
<213> ORGANISM: Homo sapiens
```

-continued

<400> SEQUENCE: 1

```
ccatgggagc gaacacttca agaaaaccac cagtgtttga tgaaaatgaa gatgtcaact      60
ttgaccactt tgaaattttg cgagccattg ggaaaggcag ttttggggag gtctgcattg     120
tacagaagaa tgataccaag aagatgtgcg caatgaagta catgaataaa caaaagtgcg     180
tggagcgcaa tgaagtgaga aatgtcttca aggaactcca gatcatgcag ggtctggagc     240
accctttcct ggttaatttg tggtattcct tccaagatga ggaagacatg ttcatggtgg     300
tggacctcct gctgggtgga gacctgcgtt atcacctgca acagaacgtc cacttcaagg     360
aagaaacagt gaagctcttc atctgtgagc tggtcatggc cctggactac ctgcagaacc     420
agcgcatcat tcacagggat atgaagcctg acaatatttt acttgacgaa catgggcacg     480
tgcacatcac agatttcaac attgctgcga tgctgcccag gggagacacag attaccacca     540
tggctggcac caagccttac atggcacctg agatgttcag ctccagaaaa ggagcaggct     600
attcctttgc tgttgactgg tggtccctgg gagtgacggc atatgaactg ctgagaggcc     660
ggagaccgta tcatattcgc tccagtactt ccagcaagga aattgtacac acgtttgaga     720
cgactgttgt aacttaccct tctgcctggt cacaggaaat ggtgtcactt cttaaaaagc     780
tactcgaacc taatccagac caacgatttt ctcagttatc tgatgtccag aacttcccgt     840
atatgaatga tataaactgg gatgcagttt ttcagaagag gctcattcca ggtttcattc     900
ctaataaagg caggctgaat tgtgatccta cctttgaact tgaggaaatg attttggagt     960
ccaaacctct acataagaaa aaaaagcgtc tggcaaagaa ggagaaggat atgaggaaat    1020
gcgattcttc tcagacatgt cttcttcaag agcaccttga ctctgtccag aaggagttca    1080
taattttcaa cagagaaaaa gtaaacaggg actttaacaa aagacaacca aatctagcct    1140
tggaacaaac caaagaccca caaggtgagg atggtcagaa taacaacttg taaaggcctc    1200
atgtcttctt cttgggacaa tctcatgcca gaaacttcta attacatatg tcaagaaaag    1260
ctgacagtag ctcctgccac tccacacacc atgacttaga aatgtgaat gaatatattt     1320
caaaaaaggc agcacaacac agtgaagggt cctgggcctg agctcctgga aagtcatttc    1380
acatcaatca actgtgtgat ctagagcaag tcacttagcc actttctgtg ctttacttta    1440
tttatctaaa atgagagggt tatactaaaa aaaaaaaaaa aaaaa                    1485
```

<210> SEQ ID NO 2
<211> LENGTH: 396
<212> TYPE: PRT
<213> ORGANISM: Homo sapiens

<400> SEQUENCE: 2

```
Met Gly Ala Asn Thr Ser Arg Lys Pro Pro Val Phe Asp Glu Asn Glu
 1               5                  10                  15

Asp Val Asn Phe Asp His Phe Glu Ile Leu Arg Ala Ile Gly Lys Gly
            20                  25                  30

Ser Phe Gly Glu Val Cys Ile Val Gln Lys Asn Asp Thr Lys Lys Met
        35                  40                  45

Cys Ala Met Lys Tyr Met Asn Lys Gln Lys Cys Val Glu Arg Asn Glu
    50                  55                  60

Val Arg Asn Val Phe Lys Glu Leu Gln Ile Met Gln Gly Leu Glu His
65                  70                  75                  80

Pro Phe Leu Val Asn Leu Trp Tyr Ser Phe Gln Asp Glu Glu Asp Met
                85                  90                  95

Phe Met Val Val Asp Leu Leu Leu Gly Gly Asp Leu Arg Tyr His Leu
```

-continued

```
            100                 105                 110

Gln Gln Asn Val His Phe Lys Glu Glu Thr Val Lys Leu Phe Ile Cys
        115                 120                 125

Glu Leu Val Met Ala Leu Asp Tyr Leu Gln Asn Gln Arg Ile Ile His
    130                 135                 140

Arg Asp Met Lys Pro Asp Asn Ile Leu Leu Asp Glu His Gly His Val
145                 150                 155                 160

His Ile Thr Asp Phe Asn Ile Ala Ala Met Leu Pro Arg Glu Thr Gln
                165                 170                 175

Ile Thr Thr Met Ala Gly Thr Lys Pro Tyr Met Ala Pro Glu Met Phe
            180                 185                 190

Ser Ser Arg Lys Gly Ala Gly Tyr Ser Phe Ala Val Asp Trp Trp Ser
        195                 200                 205

Leu Gly Val Thr Ala Tyr Glu Leu Leu Arg Gly Arg Arg Pro Tyr His
    210                 215                 220

Ile Arg Ser Ser Thr Ser Ser Lys Glu Ile Val His Thr Phe Glu Thr
225                 230                 235                 240

Thr Val Val Thr Tyr Pro Ser Ala Trp Ser Gln Glu Met Val Ser Leu
                245                 250                 255

Leu Lys Lys Leu Leu Glu Pro Asn Pro Asp Gln Arg Phe Ser Gln Leu
            260                 265                 270

Ser Asp Val Gln Asn Phe Pro Tyr Met Asn Asp Ile Asn Trp Asp Ala
        275                 280                 285

Val Phe Gln Lys Arg Leu Ile Pro Gly Phe Ile Pro Asn Lys Gly Arg
    290                 295                 300

Leu Asn Cys Asp Pro Thr Phe Glu Leu Glu Glu Met Ile Leu Glu Ser
305                 310                 315                 320

Lys Pro Leu His Lys Lys Lys Lys Arg Leu Ala Lys Lys Glu Lys Asp
                325                 330                 335

Met Arg Lys Cys Asp Ser Ser Gln Thr Cys Leu Leu Gln Glu His Leu
            340                 345                 350

Asp Ser Val Gln Lys Glu Phe Ile Ile Phe Asn Arg Glu Lys Val Asn
        355                 360                 365

Arg Asp Phe Asn Lys Arg Gln Pro Asn Leu Ala Leu Glu Gln Thr Lys
    370                 375                 380

Asp Pro Gln Gly Glu Asp Gly Gln Asn Asn Asn Leu
385                 390                 395


<210> SEQ ID NO 3
<211> LENGTH: 148567
<212> TYPE: DNA
<213> ORGANISM: Homo sapiens
<220> FEATURE:
<221> NAME/KEY: misc_feature
<222> LOCATION: (1)...(148567)
<223> OTHER INFORMATION: n = A,T,C or G

<400> SEQUENCE: 3

tccctctctc ataccattta attggttgct tcctaattaa tgactctctt tgctctctat     60

ttaatgattc ttgctaaagt ccataaggca ctttgccagc agttggtttt tagtatgaaa    120

agtagcattt ccttaatgag tctgagtctg ccttccaaat gaagggttta cttacatttt    180

cctaatggga aaacgagctt ttcttctacg cttccttagg ggtttcataa gttctttttc    240

aataactcat ccttaacact ttctccaatt ctgcctgtaa tcaatattcc cttcacatgt    300

aaagagctca ggaggaaatc aactattttt ttaaaaatac gcaataagga aattctgcta    360
```

-continued

```
ctcttagaaa tagcaggagc taacattcat tctttgcata tcatgtgcta ggcattgtgc    420
caattacctt atatacattg tctcattata tgtatccatg accatatatg tgctaagcat    480
gaaattttct taagccagat agctgagtag aattttaaaa tattattttg tacaaaatct    540
agacctttac cccatttggg ggatagatct gaagatctgg gctcatgttt ccatgtggtg    600
acaatctgtt tgatctgagc acaattactt tatttggatg gagccattgc caccattgtc    660
tgcccaatgc actaatgtta aatgcccagt ctggctcact catttgcatc atctgcctgg    720
ctcctatagg gatcccagct tgtcactcct gaggtagaca ctgtcatttc ccccattcta    780
gaggtgagag gttacataac tgggccaaag gcattatcag tgtcagtttt aggactggaa    840
cacaggatgc tgcctctctt taccattatg ttttaaagtg gagcaaagcc gtagttttca    900
ggatcttttc ttgttcacac atatcattta atttgagcct cagagcggct aacagttttg    960
agcacttatg ctatgaaaat gttttgtgta ttcagttaaa tgtatgcata tcatacattt   1020
atgtaactca atacatatat ataaatgtga tataacatac gtatgatata acagagttat   1080
atatatgtgt attatttaac ttaatatata atgagttaag tgtatgcata tcatagattt   1140
atgtaactca atatataaag agttatataa tacaacagag ttgatatata tataaatgtt   1200
gtatataaac ataatatata cgttaatata tattaacaaa gagttgtata atacaacaca   1260
gagttaataa tatataaata caacacaaag agttatatat gtgtgtatta tacatttaac   1320
ttaatatata atgagttaaa tgtatgtctg tcccattcaa ctctccattg aggaaagtac   1380
cattatcttc cccaagttca gaagaagaaa acagagaaat atattgaaat tcagcaattt   1440
gctggtgtgg tcaagtccaa cccagaactt gcttctttta cattgtagta ccctccaggg   1500
tatgcagaaa cagatagcta gtgcatcttt atgactaaaa aagaaaattt ttgttgttga   1560
ttacccagta acaacaagac agtataaaat cagcatattt tctcaacaat attttcattt   1620
tatagttgtt gaataaagta ttgctgactt cattttaaac ttttctacat actttgaaaa   1680
atatgttgct ttcctcccat tttgtaagtc taggtctgct attgatgagc catgcagtgt   1740
tttctcctgt tgcttgatgt ttttattctg aaatcatggt tggttttcaa acacaaaagt   1800
tttcactaca gtgatacaga tgaggtttat gtttccgcca cagtctatac tcagggtgcc   1860
tagagtatag catattatta gggtactatt tcttttccta tcctagatat ccaactaagg   1920
cttcgggaca tgttttgagc gaagatgggt gtttctgccc ggatagtata aatcgaggat   1980
ccaggtctgg gcagattcaa ccatgggagc gaacacttca agaaaaccac cagtgtttga   2040
tgaaaatgaa gatggtaaga aatatgggat agtggcatat aaaaaataga attttgcaaa   2100
attcaagtat atgcttctag tttcataagt taagcataag catggtctgt agggccttga   2160
aggaaaaagg caaagctgca tgagtgagtc tgaggacttt gtaggctcat agctaggttt   2220
taccttccac tttccatggg acctttggca gctttcctaa tctccactat accaatgtcc   2280
tttgtccaaa gggagctgca gttgggcatg tggtggatag ttaaatgatt tgtttgtcct   2340
ctgtgctgtt ccttggcagt tgaagttacc cccattgctc attgttacag aaaatacatt   2400
atcaacatgt acatgaatga taaccagtgc tcataatatt atagaatgaa gctgtgcctt   2460
ctgaatttcc aactgccaag cttttgtgta ctagacaaat cccataatgc tacgtcatag   2520
aaaaaagaat cagttgtatt ggagaaaagg gaaactttcc aggccagact cagcaagaca   2580
agaataaagg catgagtcct cctgattctc ccatcagtga ggcatgctgg aactgggcaa   2640
tgcctcctca tgtccctctt ccttcctata tgttaagtct gaacagcatt ggcgtatgca   2700
```

-continued

```
ggtggcagct gtttataggt tgtctggggg aaaaaaatgc cccaagcccc aggtagtaag   2760
ttgtccagac ctctgagagg gagctcttcc gagtaattcc cagagagctc tgctaattgg   2820
aacagggagg aaaagaatgg actgaaattc aggaaatctg acaccagtcc tactaccagt   2880
tacttgctag gcccaagcag cttatttact gactctatct tcaattttgt tatcaataaa   2940
gtgaggagat aggttccttc ccactcaaga agtttatcat tttgagatcc taaagcaact   3000
ttgtgaattc tgaagaagct tctaaatcat caaggaaagt ttattgggtt agaatgcaag   3060
tttgattgct gaaatgaaaa ctacaaataa cagtggctta agccaaatgg aaatgtttat   3120
ctttctcatg tgacaatcta ggcataagta atccaggtga tgtgtggttc cagcagctta   3180
gggactctga cgccaactac ttgccttttt ccctctcttc ccatttctag agtggtaccc   3240
tcagagtggc taaccaacac aacaaattcc agccagtgag aaaggtggaa agtaggagag   3300
gttatgccca cttatttata ggatttgctc tggcttgtca ctttcgttca cttccactta   3360
cctagataca agaaagactg ggaaattcag tttgttatct tgggtggcca tgaaccttct   3420
aaaaataagg agttctgttt tattacaaaa gaaaagaaga attaggagtt tgtcatgatt   3480
ggggacaact acgtctgctg tagttggggc aaacaatctt agttttgaat cttgggatgg   3540
aaatactttt aaaaacaaaa tatgggccag gcgcggtggc tcacgcctgt aatcccagca   3600
ctttgggagg ccgaggcggg cggatcacga ggtcaggaga tcgagaccat cctggctaac   3660
acggtgaaac cccgtctcta ctaaaaaata caaaaaatta gccgggcgtg gtggtggacg   3720
cctgtagtcc cagctactcg ggaggctgag gcaggagaat ggcgggaacc cgggaggtgg   3780
agcttgcagt gagccgagat ccggccactg cactccagcc tgggcgacag agcgagactc   3840
catctcaaaa caaacaaaca aacaaacaag caaaaaaacc caaaatatat ggctgatcag   3900
gacgccttgt ttcaagctat tcactatcag tttggaggcc cattcttact atttctacag   3960
aatagttcat aggaactttg aaattatata gctggaaagg ggtcttaaga aaactttttt   4020
ttcatggcta ttgtgattgc cttgctttaa cttatcaaat agtaaaagca aagatctaga   4080
gactagtgat attacttaat ttttctgtct ctaaaatgga aagacaaata ggcttgcttt   4140
tcatttagtt ggtttcctct gcttcctctg gactcagagc taatgttgta catgaggctg   4200
gtcgtcagag aatagggtgg aaaagagagg ccagctgcat acttttaact tgctgggcta   4260
catttgaagg tagtagaata gcattatgat gagaaaacac agaaatgcat aactcttcct   4320
tgattcagcc aggctttgtt cttgcgggat gcccaagaaa gctacataac caaagaattg   4380
tgacaattgg gaaataagat acccctttttt agttacttta aaggactcta gaaaaactag   4440
gttgaaggag agttaggctt agggaccaga caggtctttc ttaacaccct ctaggtcacc   4500
accttttctg ttgtctggct tctcagccca atgagatgaa cccactgcag cacccataaa   4560
ggaaagatct gagcatagca acaagtctgt gcctcccaaa ggtgctaggc tctctgtctg   4620
tttatgcaga cagttgcaag gcaaaggaag taggagggca agtccaccta ctataaacct   4680
gtcactctct agacatgaag aatagaggag gaaacaagtt ggtccttgct ctgtcattgt   4740
gaaccccatg ttctgatgat ggaaggctga caataaaaag gtaaataata cataaaccag   4800
ataatttcac agtgccttaa agtgccacca aggaaatgac tcctagtgat cttacagaca   4860
gtgacagtga tggtgaggag gccactttag atagggtggc tgcggttgtc tttctaagga   4920
ggtgacattt gggctgaagc ctgaaagatg agaagaagcc atctatgaaa tgacatgaaa   4980
agaatagttc aagaacagga aaaacaagtc caaaatccaa ataatgacaa aatcaggatt   5040
gaatagttgc ctatatctta acgttctctc atgagcacta gtttgccaaa gagactgcat   5100
```

-continued

```
ttattgccat gttaacttat ttcttcaaaa gatgattgat ttgaggagaa aaagtatgcc   5160
attctaggga atttactttg ctttaaaatt cagtacattt tgtaaagttc atttgactct   5220
tcacataaat ctggattgag cacaaggtaa aattgtatct gattgctgtg aagctcctga   5280
ccaagaaaaa gcaaccaaaa agcactgatt aaccaaacaa cattaatgct tatgtcattt   5340
ttgatatcca tatttttata tacataatca taatgtataa tcaaactggg ccagtatcaa   5400
gggcactaaa atgagccaac ttaattattt aaaaaatatt gctgaaaaga atcccaatat   5460
gtgattttta aaaagttttt taaaattttt aaaaagattt tttaaaagat ttttaaaaat   5520
attttcttca aactgtttaa tatttccaat atatagatat gagaaaaaca tttaaccaat   5580
aattttccca agtaatgttt caagaattct ctcttatgga aaaagtgttt ttgttcactt   5640
tgaaggtaat taaggagcaa gataagaggt tattggatgt cccttgagat aagctattct   5700
tgccagaatt catcctgaca cttgtatttc atgttgttcc atctgatatc tgatcttgaa   5760
cacataattt tattagttac ttatgttgat ctttattcag caaaaacaaa gtaggagatt   5820
ttcaggctag gcatggttgc ttacgcctgt aatcccagca cttcaggagg ccgaggcggg   5880
cagatcacga ggtcaagaga tcgaaaccat cctggccaac atggtgaaac cccatctcta   5940
ctaaaaaata caaaaaaaat tagctgggca tgccagtgtg cgcctgtagt cccagctatt   6000
caggaggctg aggcaggaga atctcttgaa cctgggaggt gaagtttgca gtgagctgag   6060
attgctccac tgcactccag cctggcaaca gagcaagact ctgtccaaaa aaaaacggct   6120
tgcttatttg attatataag atatctttca taaattagat ctcaaattat actattgttt   6180
tgcagtttta gcttttatgt tttagggcaa atcttaagtc ctaattactt ttttttttatt   6240
attgtggtaa aatgtatata acaaaatgta ccatttaatc attttagaat atacggttta   6300
tgacattaag cacattcacg ttatcatgca accatcacca ctacccatcc tcagaacatt   6360
tctcttctcg aattgaaact tggtacctct gaaacaataa catccacatt ccatcccctc   6420
cccagtccct gttaaacaac catttgactt tatgtctcta tgaatttaac tactctatgt   6480
acctcatata aatggaacat ataagatttg ttcttttgca tctggtttat ttcatttagc   6540
atatattttt aaggttcatc catgttgcag catgtgtcaa gattctcttt ctttttaagt   6600
ctgagtcgta ttccattgta tggatatacc acattttgtt tatcttttca ttagttgaca   6660
ttgattgtcc tcacctttttg atttttgtga ataaggctgc tataaacatt ggtgtgcaaa   6720
tatctgttca agtccctgtt ttcaattctt cagggtatat acctagaagt ggaagcactg   6780
gatcatataa ttccttgttt gactctctga ggaaccatca tactgtcttc tacctaatta   6840
tgctttgtgt tttagtaatg ggacacagcc tggcatgatg ggctagagta ttggaaaggc   6900
atgcacaggt tcaagtctca gctgtgccac gtgccagtaa tctacatgtt tctatgagaa   6960
gagtcaaaga ggatatagcc tggtcaacca ttatcagaca ctggagtcag tttgactaat   7020
tatatggtgt tctaaggaaa cttgaggtac cacaagaaaa gtctccaaat ctaaataatt   7080
actaatgaat taattgaggg ggaaacttat ttaacctttg taagcctcag tttctttgta   7140
tgtaaaatgc aggtaataat tgggcatact tcattaggtc tttgtgagga ttgaataaat   7200
aatgcaagta aaacacttag caaagtattt cccataaagt aaccactcaa ttaatgctaa   7260
ttaagtgtta tttactaaca tcagagtttc ctagtgtgaa ctctttgaag tactttaagt   7320
tctgagaaaa acaaaattaa ttaaatgcaa ctctgtcgat tccacagtta attagaccta   7380
ttcatgtttc tattgactgg attaacagaa cggcagattt tatggattct gttaaaacct   7440
```

-continued atataaaaac actttaaaag aagccaagtt attgactgca caaaaacata atctcatctg 7500
atatcttttt tatccccctg aggttattgt gtttttgttt aaggcaaaat caagaactaa 7560
ttgggatgaa aataactaaa gtttactttg tctgatttaa gtcccaaact gactaataag 7620
taatcccatt tgatcaacag attcagtgaa aactgtcccc cattctcaac taccatatgg 7680
atattctgag aaataattaa tgatgcagaa aaacattttt tgttttctga aataaaagaa 7740
tagacgtgca agtgacactt ctttttaatg cttacaacct ttttttaaaa atctacttta 7800
ttttctctat ctgaatgcac tagattttgt ttgtttgttt ttgtggttgg ttggtatggt 7860
tttgcttatt gaggttttca ggctgattta gaaaaaagaa atttttacag gagagagtgg 7920
acttgtttac aattcagagt tgaggcaaca aaaaaaaatc ttgcagtcat tatgagtaat 7980
atgtgtatcc aagtttatac aaagaatgta aaggtgataa agttggctta gttaaatcaa 8040
gagacagcct tcttctagaa tattatagct aagaaaattt ggacttaagt ttaaaaagct 8100
gctctaaaga gttcatcaat gccctgagtt tgcagagagt tcaattattg cattattctt 8160
tggacttgct gaaaactcag tgttctactt ttatttggca acaccatctc ctaggatatg 8220
tggctgtttc cagttttcca gcatcttcag tgacagaggc aatgggatcc tttaaaatgt 8280
tgggccaaga aaattggcca cagatttgca atccaaaaga aataggaggt tgctaaattg 8340
attccagcta tgaaggacat cgaaaatttc ttttgttatt tgactgtcta tcatggtcta 8400
tttgcactca atttaatagg caaatgaatt tccgactttc ccttagcagc cttgagtaat 8460
gctgtctcgt atttattatt ttgcattaga atggttggaa aagttaaagg aaaatttccc 8520
tagcaagaat tggcttctta aaaaaataag tcatcttgga caacctaaca tttagtaaag 8580
gcatttgtca taaataacct caagtccaat ttatggcaag ggttttaatt tgtaagggct 8640
ttatttctcc atacaaaggg attggagaaa caaactagaa agccagaaaa cagaccacaa 8700
acactgagct agtggttcca actggagtgt tccctgagca gtgacttatg aatacttgtt 8760
tagaagaatc aactcaaaca aatttaggaa agtcacatcc tgcctttaga gcttccagtg 8820
tttgttagca tattaaagtc tctgaaatga cctacaatat tgaaatctca gtcttctgct 8880
atttttaata tttatttcaa aatgaaataa tttttgtgaa aaacatttta atgtctgtgg 8940
ctcataatat tctgtggatc tcagtttggg aaatgaaaga ttataatcgt atctactctt 9000
tatctgttgg aaacatcttt ccatttattt ttcctgctgg tttaatggca acaaattttt 9060
acatgtgaaa tatttgtaat gtgatttata tgaaaaaatg taattttctt attacacgat 9120
caaaagtggt tatgctcctc tgtaagtttt tccttacaag tttttatgtt gcataattta 9180
tatctatttg gtttaatgag tacaacacaa gatagctcag tttaattctg ggatgttgga 9240
tgtttctagt taaagtacaa gttggatttg atgaaaattc attgcttctt tatgattttt 9300
taaaactcaa gaacatgtta gttaaagagt gtcttctgaa caaattcttg tgaagtagtt 9360
gctgattatt aagtaacact catgctaccg taacttttta tactatccaa agctatagac 9420
atttttaatt ttcaacttgc aactacctag gttgaaaaat taaatctgca agccagtttc 9480
attattcaga caatttggtt atcacttcaa gcctactatc ttcaaagaaa atgggagtgc 9540
aggccttcat gggagctgac ttctgctgta tggccttgca aatgtcaact cgattagagt 9600
gaccagtgtt agccctcaat tcacaaactc aggtcccatg aaatatacac ggatttctac 9660
tatgcattac tatgtgacca ttcatggaag tttcgtttgg aaacacagac attaaaaagc 9720
cagtcatgga ataacattct tgttaaaaca ggacattggc aaaaaggact agaaaacttc 9780
tggctataga ttttgaatcc aatagccttg cataggcttt tctgtttcct cctaaactat 9840

-continued

```
gtcttctgtc ctttctggag gcatatttat agtaaaataa acaaaattaa ccttgtttta   9900
cacttgagta acctatacct ttggttattt acgagaatta cttaaagcag agttggcaac   9960
tttttctgtg atgggcctga tactaaatat tttacacttt ccaagtaata cagtctctgt  10020
cacaactact caactctgcc actgtagcat aaaagcacac ttagacaatg cagaaacaaa  10080
tgaacatggc tttgttccaa taaaacttta tttatggaca ctgaaatgtg aatttcaaaa  10140
atattttttg cataagatca aatattattc ttttgatttt tttccaatca ataaaaagtg  10200
taaaaattgg ccgggcatgg tggctcatgc ctgtaatccc agcactttgg gaggccgagg  10260
tgggcagatc acctgaggtc acgagttcga gaccagcctg accaacatgg agaaaccctg  10320
tctatattaa aaatacaaaa ttagctgggt gtggtggggc ctacctgtaa tcccagctac  10380
tcgggaggct gaggcaggag aatcgcttga atgcaggagg cagaggttgc ggtgagccca  10440
gattgcacca ttgcactcca gccggggcaa caagagcaaa actccgtctc aaaaaaaaaa  10500
aaaaaaaaaa gtgtaaaaac cattcttagt tcatgagcta tacaaaaata gatagtgagt  10560
tagatttggc ccatggggct tattttgctg actcctgctc taagcatctt gcagacattt  10620
cttcatatgc cctaggagat ttctgatatc ccctcataat accctggcct tacaccaaga  10680
ctacaatctg ttctttgcag atgcttaata aattcattct tccctgtcat tcagttgatc  10740
tgtgtgagcc agtggaaata cttgggccaa taaatctagt gtgtttgagg gtaaaatatg  10800
ctatttttgt aagatatatt atttaatggc cacacaacct aaattcaatt aaatggttac  10860
aacctgtaac gcatttaaaa tatgactagg cagaatttgc ttcctactaa agacatttat  10920
tcgattgagg agcatccaac agttgatgtt gatcccccca tcctgcccca ctgttctact  10980
ttgcaatttg tttgaaagaa attgtcaata tatttctgac ttctgagcaa atccatgaat  11040
cgggatccag caacaggaaa agaagctgtt gctgcccatt gcttggtttt ggcaccagga  11100
atggataaat cccagacttc ctggggcacg tgttttataa aagggaagtg ctgacagtgc  11160
aaacagctgc catcaattgg ccttggagac tacttccctg gagaagctcc aattatattc  11220
ttaaaggacc caccaagctc ttcaagtgtt agtggcaacc atttgctgcc aaccatttga  11280
aatgatgaag taattttttt ttattagtgg atcctaagtg ataggctcta gaactgatct  11340
tcaaccttaa ctaatatcat ggcatcagag ggctacagat taaatcagtg gttcccagtc  11400
actctctgtg gacaagtagc aactacgaca aagcttttct tagtctatgg tggaagagaa  11460
aaattaggac aatgtaataa gcatcccata aacttattaa acctattaaa atttaatttt  11520
aagattatgt catttttttgt atgtgtgtat gcttagtatt tatggattgt ggaaatagaa  11580
tttttttttt atagtgagaa cctaggtaag tgacttacct ctctgatccc ccatttctc  11640
atatgtagaa gggggctaat aatagtatct gtctcatagt ttttgtgaga ataaaaaaat  11700
tgtccaggta aaatgcttag ctggtgactg gcacacagta attgctcaat aaatgttagc  11760
tattattgct atcattatat aatcatcatg gtttccaatg cctttacttg gcaaataaaa  11820
gaacaaaagt cacccgatat tgatctccct tttcttccct agttttctgg ggggtgggag  11880
gcagagaccg aatttctga tctgtgaaat ctgaatttat cattgtaatt ttccataagt  11940
gctatgtaga gaactcattt aagttgctgg gatgaaaaaa aatcaaaagt ggcctattgt  12000
gctgggtgca gtggttcacg cctgcaatcc cagcactttg ggaggctgag gggggtggat  12060
cgcctgaggt caggagttca agaccagcct ggccaacatg gtgaaacctt gactctacta  12120
aaaatacaaa aattagcctg gcatgatggt gggcacctgt aatcccagct actcaggagg  12180
```

-continued

```
ctgaggcagg agaatccctt gaacccagga ggtggaggat tcagtgagcc gagatctact  12240
gcactccagc ctgggcaaca gagtaagcct ctgtctcgaa aaaaaaaaaa aaaaaaaaaa  12300
aaaaagtggc ctcatcttca tttcagtgaa agatgatagt atctggactc acagtgtggc  12360
agtgcagacg gaaagctgag agtttattca acatttattt tcaatataaa ataattaggt  12420
gttactgatg gcttgaatgt ggggtaagat ggaaagaaca aaatcaagga taaatcctag  12480
gtttttgctt gagtagttat gtggatgact gtgacatttt actaagatgg agatgcgtgg  12540
gaacggaggg gtttgggacc ctgctcacat acagtctaga gttcactttt ggaggcatac  12600
agtgattatg ggacagctaa atgatggtgc caagtaggag ctggagtaga gtatccagca  12660
atgagtggaa acatctggga tggagacaga aagacacggg tattaattct acggggatgg  12720
ctaagtctgc tctgagagac agtgtggaga ccaaggagaa gaggaatcct aatatttaga  12780
aacaaggcag tggatagcaa tctagctatg gaaagtggaa ggaaagagat agttgatcat  12840
ccagttcaac actactcttg ttgtagttca cttatgttga atgcttctgt gtgactaagt  12900
cggtgagaaa aatctatggg agtaggcaac atggaggatg ttggtattca caaaagcagt  12960
ttagtggagt gtggaggcct gagccagact agaatgagtt aggagtagat ggaagataag  13020
aatgcagata tgggcccagc gcggtggctc acgcctgtaa tcccagcact ttgggaggcc  13080
aaggtgagca gatcacaagg tcaggagatc gagaccatcc tggctaacac cgtgaaaccc  13140
catctctact aaaaatacaa aaaattagcc gggcctggtg gcgggtgcct gtagtcccag  13200
ctactcggga ggctgaggca ggagaatggc gtgaacccgg gaggtggagc tggcagtgag  13260
ccgagatggt gccactgcac tccagcctgg gcaacagagc aagactccat ctcaaaaaaa  13320
aaaaaaaaaa aagaatgcag atatggcaag tatagacaag cttcaagaag tttggtctaa  13380
aaggaagcgg agaaataaac aaagagatga tgcctaatat aattcagcta aatgtaatat  13440
aatggatttt tttaagatga ggtactagag catgtaatat aaatctatta aattgggtgg  13500
ccaggaacca ggactggctc atcagcatgg accaggctag acgcacaggg ccttatatcc  13560
agaaggacat cacctttggg ttttaatgct ctgcacttgc tgtctccaaa ttctaactgt  13620
ctcttaggct ctcatcaaca cccacctcca tatccagata ttgagtacct cagggagttc  13680
aatttggaag caaatgatgt gaaaatgtac tttactatcc agtaacattc ttgttaggga  13740
gtgttggcag agattgtcga acaaccataa tgcattttat cattcgatca gtctacaatt  13800
taaacatagc aggactggac agaggcacag gaagattaag ccactgacct taagtcagac  13860
agtcacatgg gtagatccgg aatcttgatc taaaatgaat accatttttt cagttatagc  13920
tatcttccca ggatggccaa ccagaatgca tatataaaat ttcaaaaaca aacattggga  13980
attgctcttc agcaagaata catcaaacac ccattatgtg cctaactcta aatcttactt  14040
tcagagagct aaaaacaatt tcatttcaca gtgacattca tcttcgcttc tgccgtaact  14100
cacatgcata tgccttagac cacattatta atgaagtatt gggggggttcc atctagagca  14160
ccttttcttc cctggagtta atcatccagt tcagcaccac tcttgagctt tgcttagctt  14220
cttctaccca tttggatttt aaggacaaca attccaatgg cctttatcca tgtatttaac  14280
aattcattat gagccaggtg aagtggatca cacctctaat cccaacactt tgggaggctg  14340
aggcaggtgg atcgctggag cccaggagtt cacaaccagc ctgggcaaca tggtgagact  14400
ccatctctac catttttttt ttaattagtt gggtatggtg gcaggagatc aaggctacgg  14460
tgagctgtaa ttgcaccact gcacactagc ctgggcaaca gagcaagacc ctgtctcacc  14520
aaaaacaaaa acaatttatt tcatcatcat tgtcatcatc attgtcactg ctcactcttc  14580
```

-continued aacatttttt aggtcaactt aattaatatg ataccttgtg ggataatttt tatttatttt 14640
tataaaatat tgaagttttt gccactttga taacttcttc attttctgtc cagagtataa 14700
cataccaggg aaaaggctct aaaataaggc ttgaggtatt aaaaagatct tctgtttaag 14760
tcttatgttc ctaatcaata actagaattg gcctgattgc tttcctcagt gggttttctg 14820
gtagtcctga tatgatatcg aggctgtcat atagtcctga aatatcctat cattaacatt 14880
tgtggtggta tctgatataa aggtagatga acttcattgc agctattctt aggaaatgcg 14940
tatttaaatg catagttaaa agcaagattt acaattatag aaggaatgca aatgagttgt 15000
agaaagctca taaaataaaa atcaagaaga aagaattacc catcatgcct cagcccagtg 15060
ataaccactg ctaatatttt tggctgtttt catttgcaac cccatctcca ttctagcagc 15120
cctcatccct cctacccact atgtttttca ctatatttct tgtttaaatt tacttaatta 15180
tttgttaatt atgtttttcc tctcactaga aagtgaactc catgagggcc agggattttt 15240
gctattttgt tcacttttgt atccttagca cctactttgt tgattaagtg aatgcattaa 15300
tgatctattt ttaatctgtg tatgtgtata aaagacactt gatatatctg ggatgatatt 15360
caatatactt ttgtatcctc attttcacca taggtagttt atgtcaattc cttgaaattt 15420
gttgattttc ttgaataatt tagcagttgt acaattctaa aacataaata taatttgctt 15480
aaatatacat accattttaa acatatttaa atgtgaaaat acagttgagt tctcttagat 15540
tgcaattttg taacttttga taatcctttg atcctgaaaa aaattttttg gcatgaggga 15600
agagatgaat atttcttttg gagtatttaa atcatctctg caataatcct ttgatcctga 15660
aaaaaaattt gtggcatgag ggaagagaag aatatttctt ttggagtgtt taaatcatct 15720
ctacaattaa taatatctaa agcagtttgg ttggtttatt taggtaggat taattttcag 15780
tatgaatatt atttaaaaaa caaatatagt cagttgaatt gctgtggagg tttctgtacg 15840
atttactcaa agctggctct ttttctgtac gcactaccac gcccggctaa tttttgcatt 15900
tttttggtag agatgggggt ttcaccatgt tggccaggct ggtcttgaac tcctgatctc 15960
aagtgatcca cccacctcag cctctcaagg tgctgggatt acaggcataa gccaccatgc 16020
ccagcctgca tttatcctta catgatggtg aaaaataatg tttgtacttc cttcagaata 16080
atttcaagaa ggatccctgg agtcagctaa tgattagagt caggactgtg ccttagttga 16140
tggcccatat agcactactg aacatgccag agcttttgct tatccatact ggaggaggga 16200
gtgcttagaa ggcaaacgta tatcatttta ttttcattca aaatgtactg atagcaaaga 16260
atttcaatgg ctggcagatt cagttaagga caaaaataat tcacagcaga aactttttct 16320
tggtctccct cctccaagtg ctaagcatgg cacaagtaga tatcatggaa ttctagaacc 16380
ctctcttcat agatcttaaa aactactctc tttccctgct tgagtacttt ctcaaatctg 16440
tgtctgtgtg caaattttcc ttctaaggac accagccata ccggattcag ggcccactct 16500
actccatttt gatactgtac catcttaacc gaacatgtta tatctgcaac aaccccattc 16560
tcaaataaat ttcacagtct gacatactag gggttaggac ttcaacctat ctttttggga 16620
gacacctttg gtttgactgc ttcttcaact cttaccagct ctatgagctt gagcaggtta 16680
catactcttt tcaagtctta gtgcttcact tgtattttgg ggctaataag gattatacga 16740
aataatgcag gttaaatgcc tagcactttg ctttacatac taagggttcc caagtgcttt 16800
attattaggt ttctgaatgt tatatataaa gtttcagtgc tgcaaaagga atagcactcg 16860
aatataacat tttcttttta attctcagca aggcaacgta cttctatata gaagggtgca 16920

-continued

```
ccccttacaga tagaataatg gtgggcgcac acttggacaa gggaggagaa ggggttctta  16980
tcccccacgc acgtggcccc tgctcctgtg tcgttcccct attggctagg gttagaccac  17040
acaggctaac ctaattctga ttggctaatt taaagagaat gacggggtga gggctttggc  17100
agagtcaggg cagagcagat agcaggtaat cggactgagt tagggtggag caggtgatct  17160
gaatgagtca gggtggagca atcaaaaagg ttgctttatg aggaagttac gtttaaaagt  17220
agaaggcagg ctgggcgcgg tggctcacgc ctgtaatccc agcactttgg gaggcagagg  17280
tgggcggatc acgaggtcag gagatgcaga ccatcctggc taacacggtg aaaccccgtc  17340
tctactaaaa atacaaaaaa attagctggg cgtggtggca ggcacctgta gtcccagcta  17400
ctcaggaggc tgaggcggga gaatggcatg aacccaggag gcggagcttg cagtgaggcg  17460
agatcctgcc attgcacgcc agcctgggcg acagagactc cacctcaaaa acaaaacaaa  17520
aaagtagaag gcaaagaatt gaacatactg acatattaag tctttgaaaa gaaatttaga  17580
actcatatct aacaatccct ccccttgtat ttccttacag ctttcttttc aaactttttt  17640
ttaatatgcc ttggcttagt agttttgctt cattttccaa aagaagaagc ttctctggat  17700
aaggtggagg ttagttaagg gaggtttcag taagtgacat ttttatgagc ctctgcatct  17760
acttacggat gcacagtatg acacagcacc cgacaagaat aagtccacct attacggctg  17820
cgagggaagt aagaattgag gctattattc cttctcattt accaaactac ttttctagcc  17880
atcttataaa ggggtcattt acccctgagt tgctggctaa cttattggat agagcagtca  17940
gaccatgcag tgcctttcta atacttccat taggggcagt gttgtttggg atgaaggtgc  18000
aacattgagt tttaattatg atgcaaacta cccctctttc tgctactatc atgtctaagg  18060
ctattttatt ttgccaagcc atctggctag tagcccctaa ttgctcagct attccattaa  18120
cagcatctct agtgtagtta ataaatcact gttggttgta gtagctgtag tttatccaat  18180
ctacattttt attaattgtc actcaccaaa atattgactt aaatcctgcg gctatttgat  18240
tttgggcttt aaattgatct ggtattcctc atgggaccct aattgtgtct aaatagacgt  18300
gagagttgaa agacccataa ggggcttctc tcgctttacg atgtcttatt tttccttcct  18360
ctggttgatg aaatgccagg gtgaaaggga tagccaattg gactaaagca caagtgccac  18420
tccagttatt tggcagagtg tccagtaaag gtccaccaca ataccaccac acatccacac  18480
atccgctcgg ggatgaataa gggctgactg attgataagc tcttgaaaat tcttaagctc  18540
actgcatccc ttcaggtctc caaggaacgc taagtttcct ccctgtcatg agagacacta  18600
agtgaactag ttttgggaga cagaagctgg atggcccttg gggctgacc  tgcagggtac  18660
cagacttcgg gatatagcag agagagagct tggaacgact tattactcca ggctgtagaa  18720
tccctggaaa agagctacca tgcagcccat gcctggttga ctggaggacc accctagtgg  18780
aaaggggaca atctggaata cttgatccat tctaaccagg catttgcatc ttggtatcct  18840
gtcttagttg ccaaagtttg ctttaagtct ttgttttttt gttgttttgt tttgtttttt  18900
gagacggagt ttcgctactt gttgcccagg ctggagtgca atggcgcaat cttggctcac  18960
tgcaacctct gcttcccagg ttcaagcaat tctcctgtct cagcctcccg agtagctggg  19020
attacaggca tgcaccacca tgcctggcta agtttgtatt tttagtagag acggtggttt  19080
ctccatgttg gtcaggctgg tcttgaactc ccaacctcag gtgatccccc tgcctcggcc  19140
tcccaaagtg ctgggattac aggcgtgagc caccgagcct gacctgtttt aagtctttag  19200
tttttacaat agctatcttg gtcttgttgt tagatggagg aggagcaact gttccgttgt  19260
gagaggtttt ggaagaaggc ttacaggaag gtgcaggcgg tggggatcaa agaaatgcat  19320
```

-continued

```
tttaaataat ctaatagggt ttgtccctga aacctcagcc cctatagcat aaaactgact  19380
taaagaaggg aactggctta gaaaagggga agaaatttga gagtttgaga taataacctg  19440
tagagaatta tagataataa cctgtatagg tttagctgac agctgggggg agggctgtct  19500
ctttagtaaa atgagtgtat ggttttagta aattacaaaa actggttggg gcaatccctt  19560
cttgctattt agtggtccac agaacattgg accaactaca gcataaaagc tctacgtcgg  19620
gggcggggcg gggggtagga ctctgggttg acattggggt ctttattgaa atttccccgg  19680
attaaatggt cccaattcac taatgcccag tctgatgaca gtcaggaggc acagaggtat  19740
tttttctgaa atagagaggt gtctttgact tggcaaatcc ccacagggta taacaaggca  19800
agcattaagt gcaatagttt gaggcaaaat tgacttggtt atgttaataa ctagatggtc  19860
agcaatagag ccagtaaaga agaaagagta atagaataga taaaagagag ttaaattttt  19920
cttagcttta gtttggcagg gctttcccct ggggctgtgg cccacaactc tggagggggc  19980
ggcgctttct tgactcgggt gtgatgagtc catccctttt tcactgtaga aacagcagtc  20040
ttggtggtga gcagcacaag gtagggtcct tcccaggctg gctcgagttt tccttctttc  20100
cacccttgga taagaacgtg atcttcaggc tggtgttggt ttaccggaaa ttctaggggt  20160
ggtacctgtg ctaaaagact tttagttttg agggaaagga aaatggaaga taaaccaagt  20220
atataatttc taagaaatgg accttttgtt ttaaatgtgg ggacatcagc agtggacttt  20280
atagtccttg gtgccttttt actgagaaat ttcctttagc acctattttt attagatttt  20340
agaccaaaga aggccaaaca ccattttata tttaacagtg cttcctgtat gattcttata  20400
ccagataagc taagtttcac ctttatatta gcaagttgtt aaacttaatt ttaataaaac  20460
tttgtagaca tatttatcca atttttaatg tctgaccata atgtatgatt cttatagact  20520
ctttttaacc ttttataatt tttgttaaag agcaggttag tgctttaaga aatacctgtt  20580
gtgcttttat tttaatgtcc agttcacaga aaaactgtat gataccoctt aaactttagc  20640
caatatgttt acacacagaa tttcctttat aattaacatt tcaaaacttg cttaaacctt  20700
taaaacaaaa tatttgttta tttttaaact tttaatgtag gtaaaaatcc acattcttat  20760
ggctccttat aatcctttta ccaaaggcat attttacttt ccttatacac cttgcacata  20820
aactgtttct tcaatagctt tacattcagg aggcttaatt acttttaaat tatacaacat  20880
ttcttacata aattcccttt taaaactttt ttttccttca caactttcac agacaattct  20940
ttgacatgcc tcaactttct gacttgttgt aaacatccct ttctttaaac aactagttaa  21000
tttattttag gacaagaatt tactatataa cattcttttt acataaattc tccctctcct  21060
tttttttttt aagataatca ttcttctcca aagccaactt cctttatgtc tgtggacaag  21120
actgtctaag gccacaagat ttgaagttag gataatacat gttacactgt taacttttag  21180
ctaaatttac ttttgttgaa aacctctaag tttgggattt caattattct ttgctattaa  21240
taagaccttg tttagtcaaa attaactcag aattggtata gatggctttt ttttattatt  21300
attattattc tgtaagtact ttaaggcttg gctgagtgca aacagctctc acgtttgaac  21360
agcaccaatt attaggcagt tttcctaact ctgcttctac aagtgtttcc ttatcacttc  21420
ctgaatactc attgtgtctt tttccctcaa tcacccggga ggaacctgtc ctgaagggat  21480
ttagatcccc tgttaggcaa acctgctggg ttaaggggaa ttttcagtgg ttaatgttaa  21540
atcatctttt tctaacagta atagccccat actttaagat ttttgagtta gtaagctaca  21600
ttttcacttt ttatatattt tttgacttag ggtagttctg aactggtgag gtgtgctcac  21660
```

-continued

```
aatgaggttt cctctaaaag ttacttttct acttccttct gttagcaaag cagttgcggc  21720
tacagattga atgtattcag gccatccgcg ggttactggg ttaaggattt ttgataggaa  21780
ggctactggt tgtcagtggc ctcagtgctt tcaggctatg cccttgttta tacttacaac  21840
aaggtggtac tggagtgtta tagggtcacc gagaagacct tcgattatca gttataggtt  21900
ttaaatttac cctggctttt ttttttttat tattatactt taagtcctag ggtacatgtg  21960
cacaacgtgc aggtttgtta catatttata catgtgccac gttggtgtgc tgcacctatt  22020
aactaaggaa tagggtacac tgtttttttct ttactacttc tatctctttc tttccctctc  22080
tgactttctg tctctttctt tctgactccc tctttgtagc tctgcctctc tttctctctc  22140
tctgcctctc tcctctctgt ctctctcttc tctgtctctg tcctgtttct ctctctctct  22200
tgtttctctc tcctctgtct ctctcctctc tccctctctt ctgtctctct ctcctgtctc  22260
tctctttctc tctcctctct ctctctcccc tcttgtctct cactcctggc tgtctctctc  22320
tctctcctct ctgtctctct ctctcctctc tgtgtctctt tgtcctctct ctctttctct  22380
ctcctctgtc tctttgtcct ctctctttct ctctcctgtc tctcctctct ctctctcccc  22440
tctctcctgt ctctcgctct cctctgtctc tggctctgtc tcctctctgg ccctctctct  22500
ctcttctctg gctctctctc ctggctctct cctctctgac tctctctctc tctcctctct  22560
ctctccnnnn nnnnnnnnnn nnnnnnnnnn nnnnnnnnnn nnnnnnnnnn nnnnnnnnnn  22620
nnnnnnnnnn nnnnnnnnnn nnnnnnnnnn nnnnnnnnnn nnnnnnnnnn nnnnnnnnnn  22680
nnnnnnnnnn nnnnnnnnnn nnnnnnnnnn nnnnnnnnnn nnnnnnnnnn nnnnnnnnnn  22740
nnnnnnnnnn nnnnnnnnnn nnnnnnnnnn nnnnnnnnnn nnnnnnnnnn nnnnnnnnnn  22800
nnnnnnnnnn nnnnnnnnnn nnnnnnnnnn nnnnnnnnnn nnnnnnnnnn nnnnnnnnnn  22860
nnnnnnnnnn nnnnnnnnnn nnnnnnnnnn nnnnnnnnnn nnnnnnnnnn nnnnnnnnnn  22920
nnnnnnnnnn nnnnnnnnnn nnnnnnnnnn nnnnnnnnnn nnnnnnnnnn nnnnnnnnnn  22980
nnnnnnnnnn nnnnnnnnnn nnnnnnnnnn nnnnnnnnnn nnnnnnnnnn nnnnnnnnnn  23040
nnnnnnnnnn nnnnnnnnnn nnnnnnnnnn nnnnnnnnnn nnnnnnnnnn nnnnnnnnnn  23100
nnnnnnnnnn nnnnnnnnnn nnnnnnnnnn nnnnnnnnnn nnnnnnnnnn nnnnnnnnnn  23160
nnnnnnnnnn nnnnnnnnnn nnnnnnnnnn nnnnnnnnnn nnnnnnnnnn nnnnnnnnnn  23220
nnnnnnnnnn nnnnnnnnnn nnnnnnnnnn nnnnnnnnnn nnnnnnnnnn nnnnnnnnnn  23280
nnnnnnnnnn nnnnnnnnnn nnnnnnnnnn nnnnnnnnnn nnnnnnnnnn nnnnnnnnnn  23340
nnnnnnnaaa aaaggttgct ttacgaggaa gttaaattta aaagtagaag gcaaagaatt  23400
gaacatactg acatattaat tctttgaaaa gaaatttata actgatatct aacactgaag  23460
gaggcttatg cttagggttt tatgttagga gtttggttta gagcatagca tcttttattt  23520
agaagaaatc taattcttaa tatggaattc acaagtagga ttatgaggaa ccctgaaaat  23580
tatatacaaa gtttattttg tgtatttgaa ttattttttc tctttggaaa aggcatgtat  23640
tcaccaaagg agtccatgct atccccccca agctaagact gcttctgctc atcctcagcg  23700
attcatagtt gccttaggat acatttatag gggaccctca attttaaaaa cttagcactg  23760
aatcagagag aaaacttgag aggcatttgc gaggttaaat gagagtgacc gatgctgtac  23820
aagagtaggt ctcgaaatgt ggtacttttc ttgggttatc tcgtcttatt ctcatcacaa  23880
atggtgaaga aatggtcagc cacattaaag agcagatact gagattcagc aagtgagaaa  23940
acctgtcctg gttcacacag ccaggaagag gcagaggcag aatcctcacc ccacttctgt  24000
ttgcctccaa agctcaagga gagtgagctt tacccttcat atttactcat cctcttacta  24060
```

-continued

```
atttgactct taagataatc ctgagattta aaccagaaaa ctattatgat ccccttattt  24120
gaatgagaat atatgtctaa aaatgatttt taaaaacact attaaaggtc acaaagccag  24180
tgaatgataa agggattggt acctctggct cctatagtta gttcatcctt caaagaacaa  24240
aaatagcccc catttattga gtgcctacta aactctagat atgtttttaa tatatgctat  24300
ctcatttaat acctaccaca ttcctgtaag gtaggtatca ttcattatac ctattttaca  24360
gatcaggaaa aaacaaaaca aaacaaaaaa aaacaagact ttctagggaa agatgctgaa  24420
tagaacacat tcttctacat ccattccttt ctgaagatct tcctaatatg acaggtaggg  24480
atttgtctta agatttaaac ccacaaggta tgaagagaca ggcagaagag cttcactatc  24540
aacgttgcag aaactggaaa ggagacagag aactagaagc aacataactg agtcctaagc  24600
ttctagaagg ggaaggtgag aaataaccag acccatgccg tagaaccctc caaagactcg  24660
ggaattggca ctgtcatgtg cctctagagc tagaggtgaa ggggaagagc taaagtaaat  24720
gacattgttt ggatatctat ttaaaaacta gtcatgtccc ttctaccaac ttggaaaaag  24780
acaaaaaaaa attctccact ccatactatg gtttatcctc tgaagaagaa gttttcttag  24840
tggggaagtt gagtgcagaa gatgccttgc tgaaaatgga gggatcgggt agataaatgc  24900
atactggata ctggggcacc cagcctcctc ttcccacttg gctctgataa tactggcagc  24960
caaggactca ccctccagta aagagaacga cagaatattt tctggagatt ttgaccaatc  25020
caagaaggaa gatttaaaat tatcaacatt ggagattttc taattcaaca tccaggccac  25080
agctagaagc aacactatag aagtttattg ctggcaagag ccacatactc agaatgtcca  25140
aacaggggtt taggtctcca cacttaaata tgagcagaca accaaggatt ctcaggcttt  25200
tggggaagcc ctctaatatg actgatagag actaaaacaa atgaacaggg aaaaagttag  25260
caaaaagtat aagaaaggta agagaaagct atgaaaacca aaaaacaaat aaccagacaa  25320
aaaacaaaca aacaaaatag ataccaagaa aatagctttt ggagagcaaa aatttgcttt  25380
gggaaaaaaa ttacagcatg aatggaaaaa tccaaagaag atttagaaga tatatttaaa  25440
gaaaatttcc agaataatga gcaaacaaag atataaaata agggtaaata taagaacatt  25500
taacggccag gtgaggagtt ctagtttcta aataataggt atagaaagag agaaagagaa  25560
aatggaaggg gcaataatta ttacatattt taagaaaaag agtccagaat tgaagaacat  25620
aagttttcag attaaaggag cctattaaat gcccagcaca atgaataaat cataacatat  25680
caaaacattc aacacaagta tataagacta gaagtttcta gagaagaaaa ctgttacatc  25740
aaaaggatca ggcatcaaaa tagctctaga cttctcaaca gcaatgtgtg aaaaggtaga  25800
agataagagc aaagccttca aattctgaag gaaacaattt ccaacctaga attcaatagt  25860
cagccaaact attagtcaag tgtgaataca ataaaaatat ttttcatgga tatataatat  25920
ttcaaaaaat atatctccca tgcaatcctt cttacaaagc tgttttaaaa tgtgcttcag  25980
taaaacaaga aagaaggggg cactgcatgc aagagccagg aatctatcct taaagaggca  26040
tgaaggaaat ccccagggtg atggtgaagg gaataccagg aagacagctg tgcaggaata  26100
gagataaata gtccagactg gattatgtct gaggagagac attttcagga agatgacaat  26160
gtgcctgatg cacctgagca ttatgaaagg gaactagaca actggagaag ggtttgggat  26220
tggattggga aggagatgta gaaaagtcaa catgtgtaaa caagactgtt actaattcca  26280
gggaaagcca aaaattgtgc aagaaaagaa aactaatcat agtttactac aactcaattg  26340
agcctaccat ttctgtattc ataataatgg aaataccgaa tattgatcta attaaaatta  26400
```

-continued ttatgccaga tgtattagaa agatggaggc atgttgggat aaaaccaaag gagcaagaac 26460
atgagctaaa tccccatcta ccaccttgaa tattcaataa ctaatgccta aaatgaaaaa 26520
gaaaggacaa taaaattata ctctttaggg acatggtgga gatcacccaa tgcatatcta 26580
aagagaggta aaagtggttg ctccttggct gggagagatt agaagggggg taagtagatc 26640
ataggactgc cattttctcc tttttaaaaa ataacaaatc ttttagaact atttgattat 26700
ttaagctata taaagatata gatagttatg gacacaaaac ttgaaaaaat gaaaacatta 26760
aaaagactga aatagagcaa aatatgaatc atggttatct ttagatggtt ttgtttttct 26820
tctttatact ttgctgtatt ttttatactg atagcatatt cgttttatat atatgtgtgt 26880
atatatatat tttacaatta tatatacaat tttatatatt ttatatatat atttatatat 26940
atactcttca ttgtaaacaa gaaattgaag ttcagaaaag tcagataaat ttcctaattt 27000
caaatatctt gtaaatggta gagctaggat tccactgcaa gtctgtctga tgtgaagcat 27060
ttttatcttt catcaaagca ttcaatcttc gttaaaatcc gagaggcaaa attgtcatgc 27120
ctcaccattc tctcccatct ctgaaggtcc atagtgcctc ttttgtacac catacaaaat 27180
aacacttgat tggtttcatt atttgtttac ttatttgtct atctatacat ttattcatat 27240
tcatctaatt ttagaaagat gagagaatgg attccaaagg tacatagatt atagcaaaat 27300
aaaataaagt tacaaaaatg aaacaaggga catttgatta ttcaggtttt gttttgtcag 27360
actgctaaat gaggcacact cagttttcct tctctgcttg gggagggtaa gtgtcctggg 27420
actgagtccc aagcttctta tgtttttcca tcagtgccta ggaaagtcct gggtacacag 27480
atactcaatg aatgtttgtt ggtttgactt gccagcaaag ccgtggctcc tagggaagtg 27540
acttcagctt ctttatcttc ttggtgtgac tatcttaaaa gggagtaagt gagcctttct 27600
ttgtaactga ctgtatttga gaatgcagca tgacagacaa aacattcatc tcattcatgg 27660
agaattgtaa aatccagcag aagagctctc tttttaacca gtgcttacaa tttgtccttt 27720
ttcacccttc cttggcaaat cacgcaatat tccttcttaa aaatgggtaa agtgccagcc 27780
gaacttagaa gagggactga ttctatctct attctgacca ggtatacggt agactgtaat 27840
ttaatgtcag cacctttctg ttgccataat gaggtatatt tatttctgtt caaagatcat 27900
gcagccctga caaagcaaat accctctgac tcccactgtt aattatcctt cagttgctac 27960
agggttttca tccatgtcct cacttaggag agttggcggt tgtgaagcag atggagtcca 28020
caatctcagt ggcagttctt aatgctttga gctcaaagtg tgagtaagtc gatgagtgag 28080
gcttttaaga tgtaaatcca atatctgcag agaaatctga agctgtaata ttagaacaac 28140
attcaaatga ggacttcatt gactagctca ttaagaagtc ctttgataat agcatgttgg 28200
taagactttt cttagaaggt acatattata aatgatgatg tgctaagaaa tcaacataaa 28260
ggaaaataga aaaattttcc ccaaatccat cctttttctg tagaacttta atgatgatac 28320
ctcattcctt tgtaacttaa ttttaaaaag ttaattatgc acctactatg atacgtccaa 28380
aatgttttta ggtgatgtgg atatagcgaa gaacaagaca cacccagtgt cttccttcat 28440
ggagtctata ttcttggcac tgttggtcct gtgtgaagtc ctaacattat tttgcttaat 28500
gttttggcaa gagaggcaac attggctggg cgtgatggct catacctgta atcccagcac 28560
tttgggaggc tgaggtggat ggatcacctg aggtagggag ttcaagacca gcctgataac 28620
atagagaaac cctgcctctc ctaaaaatac aaaattagcc aggcatggtg gtgcgtgtct 28680
gtaatcccag ctactctgga ggctgaggca ggagaatcac ttaaacctgg gaggcagagg 28740
ttgtggtgag ccgagattgt gccattgcac ttgtactcca gcctgggcaa caagattgaa 28800

-continued

```
actccatctc aaaaaaaaaa aaccaacagg caacattctg ggctgaaaca aaggtaattc  28860
atctggtaac aatagcaata acataaatag cagtaataat tatacattat tgagttccta  28920
ttctctgcca aaaatggttg ataagcacct ttgatatggc ttattttacc tagtcctcat  28980
tataacctta gaaggtatat tgtatctggt caaaattgaa agaagaaatt gaaactcaca  29040
gagggtaaat aattaaagtt catagctagt aagtagtaca gacaaaccca aaagcagagt  29100
ttcatgctca tagtcaccat aatgtattca gaaactttta ggactcatca caatattaaa  29160
atcatggaac ttggagccac aaaaagtcag atttaagtcc aaaccctgac cctgggtaat  29220
ttaacttttc tgggtttatg taacatatct ataaagtagc aataataata ttaccacctc  29280
atgctgtttt ggtaaaaagt aaataagata atgtatatta aggtatttgg atagtgccta  29340
tagatgtata tatgctactt aatagacagt aatgtaatta ttaactatga cctaagatgt  29400
ggcacagtgc aggtagcaga agttctatca ttaatcattt acagatactt attaaattgc  29460
ttcaaaccca taaggataga ggcaagatgg agggggaagt ctaagaaatt gattgagtca  29520
acatttatat aaatacttat ctactgagag cttcttcacc tcagggtttg ggtcacttta  29580
aatgcatcct ccctgacctc ctctgcctgg ctacctttgg aactccaacc cattctgcaa  29640
gacccagtta aaatgctgcc cattcctgaa gctttcttat tttctaaagt aggaagagat  29700
ttctcccacc ttagaactcc tataaacatc tgcagactag ttctaggcag cctttaacaa  29760
aatcctcatg ggatctttga aaatacagat tcccaggtcc agcctccaga gaatctgatt  29820
cagataaggc caatgaatct gaatttaaaa acatgtattt gtgtgatttt gatgggtgga  29880
cacacttgag aatcacgtca ggaccattta tgtggctctc aattacatat acactacttt  29940
atattgcagt tgtttattta tgttatattg cagttattta tttatgtttc atctcttttc  30000
ctgagaaatt accttcctga taatccaatg cagagataaa ttaagaaaat ctgtaggaaa  30060
gaatagatca tcaagtccct tgcaacattc ttctgaggtt gtaataatct cctctaggat  30120
gctttgctgg atttccctgg actaggttgt cttttcctgc tactttctcc cattacaggt  30180
ctccctacgg cagcactgct tatatcactt ggaacttgaa tctattttgg taaaaaaaaa  30240
gttaaaaatt aaattatcag aaggatattg gggatgcctg cagagtaatc aaaataggat  30300
ctatattgtt atagagccag gcacattaat gccatcagct ttagcccttt atgttgtgat  30360
tttactttat tccaaatgtc agctttatcc tgttggatgt gctgatcttt tttctctaca  30420
ttcagccagt tccattctca tgttctggaa gcttgtgaca gagggggaat atgcatttca  30480
agatcagaag atccagagtg aaaatgattg gaatggcctg agtcacagtt ccaatcctag  30540
aacaaggcat cttgctaggg atgtgagaga tgataagtga cagatacagt gacagcaagt  30600
ggttgatggg atctgagttg tgagagaggg tctgtgaaaa atgaaagacc tgcataagaa  30660
gaggagaagc agaaatatga acattgttgt gagtcaggtc tttacccaac tctgtgctgc  30720
ttattctact tttttgtgca agattgatta tgtgtgttta atagaatgca gtaaagaaca  30780
gtgttggagg gcagctgtgg agtccacttg agtgggactc taccactctg ccacttacct  30840
actttgtggc cttgagaaag gtacttaatt tccctgggtt gcagtttgtt cacctaaaaa  30900
cgtggcaata atagtaatac tgtttcagag ttggcgcaaa attaggataa tatatgtaac  30960
atatttagaa taatgatggg tattccttat gtaaatgtta gatgttagct actgtgaatt  31020
tttctgttgt tccactagac tgtaggaccc ctgaaggcag gcaaccttgg gcttctttct  31080
cccagcacct agcacaatgg ctgttactta gtaagcagtc agtaatggtg tgttgttgtc  31140
```

-continued

```
agtgaacaca gactgagttc agtgagcaat gtcttggaaa gcctctactg cacctaggac  31200
tttcagctat actgagacag aaaaatgaaa tcctctctgg actggaaagc agaagccaga  31260
catgtaggca accaaactgt aactgtttcc atgtcgaatt gactttgcct ttagcgaatc  31320
atagcactga ggagtgtcac gtttaagcag caaatttgta tagcaaatta acatgccaaa  31380
aaaggcatgc aagactttta cttgattttt ttcccctcct ctctggggaa tttatcttat  31440
ttgggtctta tcttggaatt tatcttatct tgaacttatt cagactgcat tggtttaatt  31500
tgctatcaac tggggctata tagtgcactg gaatttaatg tgttgtatat gtgaaatatt  31560
taccaaataa ccacataacc aagatatgga ggacctactt taagaggaga ttcttgcaaa  31620
gcaccttaaa agcatacact caataatcac aatggcatga ctgcatacag ggagataatc  31680
agttgtttta acttttaatt taagcagtag cagaatgact ttttgggaac ttaggaattt  31740
ggaaaccttt ttattctatg tattgaatat caactatgta atttagtcta aggttatatg  31800
ctagaaacat ttcaaaaacg aaagcagcag caatgacatc aaaaatgcat gtcaaaagca  31860
aatggtttta aatagaaata catcatttta acaatcttga agtttaaaag atcctataaa  31920
aatcacaaac ccagaaggac aaacaagaaa agattgatac atttaactac ataaaattta  31980
aaactacatt actgaaaaaa aatctgagac agggtctctg tcacccaggc tggggtgcag  32040
tggtgcgatc acagcttact gcagccttga cttcccaggc ttaagggctc atgtaatcct  32100
cccatcttag cctcccaagt agatgggacc acaggcatgc atcaccacac tcgactaatg  32160
tttaattttt ttgttgttga gacagtctcc ctatgttgct caggctggtc tctaactcct  32220
gggctcaagt gattctcctg cctcagcctc tcaaagtgct agaattacag gtatgaacca  32280
ctgagcctgg ctttaaaagt ttttaaaatc aaaagccaaa tggacaacct agaaaaaata  32340
ctcctgagat atgttaaaca gagttaattt acttgccatt tttaagtgtg cttacatatc  32400
aaaaaatcta ataactcatt aaagatatgt aaaatatata caaaggcagt ttgctgaaaa  32460
aatacacata taaatatatg cagcttcact cagcattcaa gaaataaagt aaatcaataa  32520
ttcaatcttt ttcacttgtc agatgaagaa cagttaatgt agtagtgttg gcaaggtggt  32580
ggacaaaaag ttatttttat atgtttttga tatcaagaag atttgatgca acatctttga  32640
agagccagtt aataatatct gtaaaattag aaaattaaca tattctttgc ccagcatttc  32700
tacttttatc aactttgctt gtaaacagac acagaagccc atcaagaatg ctcaaggtag  32760
ttttggtaat catagataat tttttttttt ttttgacggt gtcttgctct gtcacccagg  32820
ctggagtgca atggcacaat cttggctcac tgcaatgtcc gcctcctggg ttcaagggtg  32880
ttgcaggaag tcagggaccc caaacggagg gactggctaa aaccatggca gaagaacatg  32940
gactgtgaag atttcatgga catttattag atcccccaaa ttaatacttt tataatttct  33000
tatgcctgtc tttactgcaa tctctgannn nnnnnnnnnn nnnnnnnnnn nnnnnnnnnn  33060
nnnnnnnnnn nnnnnnnnnn nnnnnnnnnn nnnnnnnnnn nnnnnnnnnn nnnnnnnnnn  33120
nnnnnnnnnn nnnnnnnnnn nnnnnnnnnn nnnnnnnnnn nnnnnnnnnn nnnnnnnnnn  33180
nnnnnnnnnn nnnnnnnnnn nnnnnnnnnn nnnnnnnnnn nnnnnnnnnn nnnnnnnnnn  33240
nnnnnnnnnn nnnnnnnnnn nnnnnnnnnn nnnnnnnnnn nnnnnnnnnn nnnnnnnnnn  33300
nnnnnnnnnn nnnnnnnnnn nnnnnnnnnn nnnnnnnnnn nnnnnnnnnn nnnnnnnnnn  33360
nnnnnnnnnn nnnnnnnnnn nnnnnnnnnn nnnnnnnnnn nnnnnnnnnn nnnnnnnnnn  33420
nnnnnnnnnn nnnnnnnnnn nnnnnnnnnn nnnnnnnnnn nnnnnnnnnn nnnnnnnnnn  33480
nnnnnnnnnn nnnnnnnnnn nnnnnnnnnn nnnnnnnnnn nnnnnnnnnn nnnnnnnnnn  33540
```

-continued

```
nnnnnnnnnn nnnnnnnnnn nnnnnnnnnn nnnnnnnnnn nnnnnnnnnn nnnnnnnnnn  33600
nnnnnnnnnn nnnnnnnnnn nnnnnnnnnn nnnnnnnnnn nnnnnnnnnn nnnnnnnnnn  33660
nnnnnnnnnn nnnnnnnnnn nnnnnnnnnn nnnnnnnnnn nnnnnnnnnn nnnnnnnnnn  33720
nnnnnnnnnn nnnnnnnnnn nnnnnnnnnn nnnnnnnnnn nnnnnnnnnn nnnnnnnnnn  33780
nnnactccct ccccttttga aaatccctaa taaaaacttg ctggttttac agctcggggg  33840
catcacggaa cctaccgaca tgtgatgtct cccccagatg tccagcctta aaatttctct  33900
cttttgtact ctgtcccttt atttttcaac gcagctgatg cttagggaaa atagaaaaga  33960
acctacgtga ctatcagggg caggttcccc gacacaaggg attttcctcc ctcagcctcc  34020
tgagtagctg ggattatagg cacacaccac cacacccggc taatttttgt atttttagta  34080
gagactgggt ttcaccatgt tggccagggt ggtctcaaac tcctgacctc tggtcatcca  34140
cccgcctcag cctcccaaag tgctgggatt acaggcgtta gccactgcac tcagcaatca  34200
cagataatta aaccatcttt caaaatccat caataagtta aatattttat ggtacattta  34260
cacaataaaa tacaaattag ctacttaaaa ataatgagat ctatatgtga tggtatgaat  34320
ggacagaggc aatgtgttat acagaaaggg tttaacaatg tatgctccca ttggaatgat  34380
agtatgttgc tattgctgtt aggaaggagt acatatatgc agagagaatc tcttaaaggg  34440
tacacaagga tttgttaata atggttgctt catggaactg gaactgcaaa cttggaagag  34500
gaagatagct tagttttcac tgaataattg ttgtacttaa aaaaatttgt aatttttagt  34560
tttcagtgga ccagatattt tgcttctggt ttataatgtc tcatcttcaa agtcagctga  34620
gttaggttta attagctcca ttttacagac agagacattg ttatttgaaa gattgagtaa  34680
ctagtctaag gttacacagc tggtgtcctc gttgcctgtt cagtagaaag gtttacataa  34740
acagcaaggt gtgctgttct caatagactc acttatgttc atgatttggt acttgctcaa  34800
gctggaatca atttttagaa aaaataaaat cttttgcaaa gatttttacc tcaaaaatag  34860
aaaaaaaggg cattcctgcc ttaccttcta caagggtctt ctctgaaatt ccaagcatca  34920
gggtgttata acagactcta aaaagggttt cctttttttct ttcctttaac attgcttatt  34980
gcacagcata ttgagacaga gaagatggta agtgaaataa aacaaaggaa ataaaaagta  35040
tcatcactgg gtttcagaat cagcatggtt tatgctaagg gaaagacttg gaaaccttga  35100
ttcaacatat aattctaaaa agagacagga agaaatccca ccttgtttcc tctgattcta  35160
cctttgggat gggtaggtat gttatacaat aagaataaca ttgagatgac tgctataaaa  35220
atagtggtta agagcctggg tccagaatga gaaaggtgga tattgaattt acctgagtgc  35280
aactaggcag actcaagtga gttgatttta cccactcctc cactcaaata ctgggtatgg  35340
ctttgcaaaa acattcaacc agttatccac atagttggtc ttaactttcc atgtgactat  35400
aatgaatata aacttgctaa tgagcagagt gtgattttag tgtttaaact attttttccc  35460
gaataatagt tcctagatgc agttaatgag ccttattggg tacccacaca aaggagatag  35520
aattgtctgt tggacttttt gaaaaacttt cttggtttta aaaaaggtac atttctaaag  35580
gatttttatg tgtagttttg actaaacaag tctttgcctt actttctgtt tttaaaatct  35640
aacctcaaca ttaatatgtc actatactgg ttataaccat aacaaattat ttcatctctc  35700
tgagcctgag taccctcaac tgtatacact ataaggatgt gaagatagaa agtgacataa  35760
aaatgaaaca tgtactgacc accctcataa acagatccct catacatata gaatgtctgt  35820
gcctggttga ttagtgaagg aatgtgtact cacccaaaag aaaaactctg aaataagtac  35880
```

-continued

```
ttttagatat ttactttttc aatattccaa gtaattatca caacattaag gtgcattcag  35940
ctttgtgtgt taacgtggta tacctccagg caacttttag gatactgtac agatacaatg  36000
gctgtgaagg ctgggatgaa aagacctgtg cgaagcagga ctgaggcact taaggaaggc  36060
ctcagagtta catctccttt gcctgttttc ttgcaggcca catacccctag cccagccctg  36120
tcagcatgag tgagaaccag gctctgcctt tgcccacact aaaccactac cttcaaggcc  36180
ccacaaagac ccagtgtctc cagacggtct ttctgtcttc ttaacactca gagctccatg  36240
aaccagaatg aaagttttgg aacatgatcc aagtaaaaga ctcaagaagt aaacaccact  36300
aaggttaact ttgctttaga ggttagagaa aacactgcaa ggacaccaca ccagagacta  36360
tgaaaacccc aaatgtattg aaatgatgct gattccattt acctccatat tgcctgataa  36420
tacccaggtg ctaccatggc agcttaaggt ggtatttgct gggagctatg atactcttta  36480
agaagtaata gcactactag taaaagcagt tagttccagg caatattcta tgcacatgac  36540
ccatttcatc ttcttataaa cctcatgaag aatatattat tttcatcctc attttataga  36600
tgcagaaagg gaagcataga cgtaaatttc caagattaca cagctattta ttgttggaac  36660
tgagatttga attcaggttg tctgtcttca gggactgtgc tcttaatctc agtggtcatc  36720
aaacttttct gtaaagagcc atccagtaaa tattgtgggt ttatatacat tctctattgc  36780
atatccattg gttttcaaaa ataatcctat acaaattcaa aaaccattct tagctcatag  36840
actacacaaa aacagattgc aagtccagtt tggcatttac tgttcctatt gatcaagggt  36900
ttaagaacat agtgagtaca ctattccaca ttccccttag gcaaatcctg tatgtttata  36960
gtactgttag atttctgttg acaaaataat ccacaattct gacttcatct ctctctctct  37020
ctctctttct gattttgttt gaatttatga ggtttagttg cattttcaag ttagtcttcc  37080
tgctaacgag tgattctttt gttgaacatt taaaaaggga ctgtcaggat tgaataagag  37140
aacctcttcc agtcactttt ttttttgaga aaggatctca cctgttgccc aggctggtgt  37200
gcagtggtgc aatcacagat aactgcagcc tcaacctctt aggttcaagt tccccctgcc  37260
tcaatttctg agtagctggg actacagatg tgcaccacca tgcctagcaa atttttaatt  37320
ttttgtagag atggggcctc actacattac ccaagctagt cttgaactcc tgggctcaag  37380
caatgctcct gcctcggcct cccaaagtgc tgggattaca ggtgtgagtg actgcatcca  37440
gcctcttata gtcactttta atctatcatt ggctttccca ttagattgta ctgttataca  37500
aggaagtgac ttcagacagt atggcactag actagaggct gtgtttttct ttaataaagg  37560
cataaatgag atgaattgct ctaaggcttt aggcttgtcc cttttctgag aagtgacctt  37620
tgggaggtca catttagtta aagcagtttt gctagtataa atttaccagg atcctgacat  37680
gtaatcctgt atcattttca gtaaggttaa aatggtatat gaaaggaggt ggttcacgaa  37740
atggattaat atcaacatgg aacttcatgc tttctaggta cctgctgcat ccttggagat  37800
tcaaaatgtc atcatggcat tctaggctag actggcagtg gagaaatcac tgtgagttat  37860
tggatttgct caagataaaa tcttgaattt gcaaataaat cctggtcagc ttttttttaac  37920
actcttgtgg taaataatac acaactcaga ttcatgtaat gggtgtaaga aaatcattgc  37980
tttggttatt tcagtatgaa actcaagaga aaacttactg aagtgttttt aaaattattc  38040
tgaccacaac ccaaggtaaa acataagcca aaaaacatat catgacatag taaatgaagc  38100
caggattgta tatatatgtc tactcaagta tatgaaatgg aaacaacagt ttcagaggca  38160
gtactatgct tactacattt gaggcatttc tggtattttc tattctattt aattaaattt  38220
ttagtacttc ttattttagc tacatttatt tcataactca ttaatgggtt ttgactcaca  38280
```

-continued

```
gctcaaaaac actgccttag agaatccaaa tgttcacact atccatattt ataagaagta  38340
attgttctgg ggttcttgtg tattcttata gcttagtttg atttatttgc taagacctgg  38400
ctaagtgaga actgcaaaga gttatgcctt caactaccta agccaggaat tttctgaggt  38460
ggcaggggaa ccagggtgag cagaaggaca tatcatcccc accctcatta agcttatgct  38520
atagtggatg aaataaactc agaagtcaag gagtttcaga agagaagtca ttcccttgag  38580
taactatgtt aagtacgtaa acagctttag tagtgctttc ttagtacaag gtgttttctt  38640
ctgatctagg agagtcagtc caattttttt cttttgagaa aatggaggct caaagagtct  38700
gtcatttatc tccagtctct tcattatttt gagtccaagt acaggattat ttgtaatata  38760
catgctgcct cacatgacta agtgggtttt gtgatagaaa gggaatttgg agttgagaag  38820
agaaagtgat gattaagtca catcattaaa atgtttgact ctcagatatc ttggaaagac  38880
tttgaaggca ctctagccaa actttttcct tcagaaggag cttatctaat tattctagat  38940
aatagagaaa aactaggtct tttaaagaga caaattatat accatttagt gtttcacaat  39000
attttctgaa taaacttaaa atcccttatt tggaatttaa ctcatctaaa tccttatttc  39060
aaaaaccagg aaacagagtc aaacattttc tcagttatca aggcagtaaa ccaaagattg  39120
tcacctgcac aggagaatct atgatttgtt cttctcatca ttatacattt cacgagcatt  39180
gactcaaaaa accatgctac ctataaacta atcaacaatt gcttcttcta gggactgaaa  39240
ttttaaaatt tcagacgtgg aggatcgact ctacttcaaa gcaaaattca gtggacttct  39300
gcacacatat ccattctaat ctgttacaag tctgcacttt ggagattagt tcatgctaca  39360
cacttagagg tgtaatattt tcctacttgg gaaaattgaa attacttaga tacaaaagag  39420
tggttgtagt aagaaaatag gcaaggagaa cattttaaag tgctgatcct cggtaaagcc  39480
atacatagga tgcacctggg agcagatctt tctgaagtca ttctgtgctc agagatgttt  39540
ctccttacct tgctgcctat gtcaaattct ctgtgatatg ttcttagagc cccatgacct  39600
ctcttcttaa cttgcagtgg gagcttgaat tttccattta tttttgtgac catttagtct  39660
ataagagtct ccgtctttac agggccctca cctgactaca gactccataa aggcagagat  39720
tctattttta ctctattatt actgtattcc cagcactaag cactaggatt aatacatagt  39780
aagtgttcaa cagatgttta ctggatgatt agattggcat tttaaggtag tctgagatca  39840
cgttttagac aagatacttc agtttagtcc aatctttatt atttattagc tactaaagag  39900
aaattgataa ttactcatga tattcttctt ttttgtttta cagtcaactt tgaccacttt  39960
gaaattttgc gagccattgg gaaaggcagt tttgggaagg tgagaacaaa ttgaaatgat  40020
taaccaccag cagggttatg tagcccaggg aacagagggt ccagaaatgt tcacattatt  40080
gagttgctgg gaccacaagg aaagataatt aagtgaaaat gtttttgtaa tggattttta  40140
taaaattgtc accacagttt aagaaaagcg tgtgacaggc agctacataa tgaacatata  40200
ctgttgtcag aataatctca ttaaactcaa atctgtttac tctcagtaaa ctttaaggct  40260
tttctctcta ccctaaagga gatgaagatt tcagaatcat tttcagattc taccagctgt  40320
atgcccagta atagttatct tgtttatgga agagttactt attttcatgt gggaaagaag  40380
tcatccgatt tctatttgtt tcctcatttg tctaatgttt ttatcttaag aaaaatacat  40440
attcagttta atttttttg caagaaactt ctgtattcaa accctgatta ctagtttctc  40500
aatggagacg tactttaaga gaataatatt tcatataaaa cttgcatttt aaaatcattt  40560
tctgtttact ttttcaggca ttatacagac ctctaaagaa atttcaaaaa catggacatc  40620
```

-continued atatttagtg tttttccagt ccttaaagtc ctttttggtt atatcatgta tgggttgtaa 40680
acagaaattc tttgcacagt attattcagc ttgacagttc agtcatgtct atttcagtca 40740
ctcaaagcag gattaaggat gttacttgtt attggaatat tcctgacatg gaggcagcta 40800
ttttcaccaa aatgctgtct taaaagccca aaaagcaata ccaggcaaaa ttgtttgaga 40860
aaaaagagat ccaagaattg aactggtgca tagaaaagaa aatgaaattt ttaatctaaa 40920
atcagagcta agtgggagct tttaacatca tataatttgc aaatgttaag gatccaagcc 40980
acagcaaaga acatgtcttg ttctgtctct catcaccatg atccattatc tccctaatca 41040
ctctctcact cgggttttca ccattaggtc tgcattgtac agaagaatga taccaagaag 41100
atgtacgcaa tgaagtacat gaataaacaa aagtgcgtgg agcgcaatga agtgagaaat 41160
gtcttcaagg aactccagat catgcagggt ctggagcacc ctttcctggt taatttgtgg 41220
tgagtaattt tactggacct ctgaatagag acactcctgt tatcggtggg ctaggggagg 41280
tccccaaatg cctctgggac ctcagccctg gctggtatcc aggctcttga cacaattgca 41340
agaaagagtt caaggatgag ttggaaaaca gtgaaagtac agagatttat tgcaaagtgg 41400
aaaagtacac actcaagaga ggggagcatg ggtgaactcc agcgaatgtc atgtaagggg 41460
gggtttgagg ctgctgccat aatgggtttc tttaaccaag gggtgaaaca ttcatgatga 41520
ttcctgaaaa aagatggaga tttcttggaa ctgtggtgcc agctattttt acaccaaata 41580
tgaatgttcc tggaactgtc atggtgctgg tgggtgtatg atttagtatg ttaatgagtg 41640
tatgatgagg tcctaggtga aacctaggtc aaatccagca caatggagag gacccacaga 41700
ctctctgaag gaaacgactg ctcctgcagg acccaggcaa ctcccccaaa actgtgagta 41760
ccccaactgt ggaggtggga aagagagacc ctcctctccc aaacacacac ccccactgga 41820
gaagctgaag gtctgtttgc tggagaagtt tctgacttta cctggagctg agtggacttg 41880
aagagcccag tgaaatacac ggggagaaga agcagcagaa aggccctggg agcttgctgg 41940
gtccacaagc aggccattcc tgcctggcac cacagggatc caatgggaga ggagcggggg 42000
taaaattcca tagggagaag caaatctcta gctgaacttg gtgacaattt gaacagggtg 42060
agaaagcgcc tggccagaac tcaggagagg gcacaaatcc agtgtgcaga ctccgggggc 42120
aggggataaa ccaagctctt ttatttccca gctgggagcg gggagcctgg ggcaggtttt 42180
caagcaggta ttgcttctct acttagaaac aacctgggag ctgtgttggc gggggagggg 42240
ggttggggat gggggagggg ggtggtggaa agcacggtgg gagtgagacc ggcccttcgg 42300
ttttcatggg agctgggtga ggcctgtgac tgccagcttt tccccacttc ctgacaatct 42360
gcatgtttct gcagagacag ccataatcct cctaggtaca caactccagt gacctgggaa 42420
tcccaccccc attccccaca gcagcagcag cagcaaggcc cacccaaagg agtctgagct 42480
cagagacacc tagccctgcc cccacctgat ggtccttcct actcactctg gtatcggaaa 42540
acaaagggca tataatcttg ggagttctag ggccctgccc actgccagtt tctccccata 42600
ataccaaagc tgatgctctc tggaaaagca ccacctcctg gcaggaggac aacagcacaa 42660
aaatagaata ttaaccaaag ctaagaaccc ttacagagtc cattgtactc cctgccacct 42720
ccaccagaat aggcactggt atccacagct gagagactca tagatggttc acatcacagg 42780
actctgtgca gacgacttcc agtaccagcc tggagctggg taggctagct gggtggctag 42840
acccagaata gagataacaa tcactgcagt tcagctcaca agaaaccata tccataggaa 42900
aggaggagag tactacatca aaggaacacc cagtgggacg aaagagtctg aacaagactt 42960
tccctctgaa agagcctacc caagtgagaa ggaaccagta atatgacaaa acaaggctct 43020

-continued

```
tgatgccccc caaaaatcac actagttcac cagcaatgga tccaaaccaa gaagaaatcc  43080
ctgatttacc tgaaaaagaa ttcaggaggt tagctattaa gctaatcagg gaggaaccag  43140
agaaaggtga agctcagtgc aagggaatcc aaaatatgat acaagaagtg aagggagaaa  43200
tattcaagca aatagatagc ttaaagaaaa aacaatacaa aattcaggaa actttagaca  43260
cactttaaaa attgcaaaat gctctagaaa gtgtcagcaa tagaattgaa caagtagaag  43320
aaagaaattc agagctcgaa gacaaagtct tcaaattaac ccaatcaaac aaagacaaag  43380
caaaaagaat aagaaaatat aaacaaaact cccaagaagt ctgatattat gttaaatgac  43440
caaacctaag aataatgggt gtccctgagg aagaagagaa ttttaaaagc ttggaaaaca  43500
tatctgaggg aataattgag gaaaacttcc ccggccttgc tagaaatcta gacatccaaa  43560
tacaagaagc acaaaaaaca cctgggtaat tcatcgcaaa aaggtatttg cttaggcaca  43620
ctgtcatcag attatccaaa gttaagatga aggaaagaat cttaagagat atgagacaga  43680
agcaccagga aacctacaaa ggaaaaccta ttagattaac agcagatttc tcagcagaaa  43740
ccctacaagc tagaagggat tggagcccta tctctggcct cctcaaaaca attattagcc  43800
aagaattttg tatccagtga aactaagcat catatatgaa ggaaagatac agtcattttc  43860
agacaaacaa atgctgagag aaattgccat taccaagtca ccactacaag aaccgctaaa  43920
aggagctcta aatcttaaaa caaatcctgg aaacacatca aaatggaacc tctttaaagc  43980
ataaatcaca gaggatctac aaaataaaaa tacaagttaa aaagcaaaaa caaaaccaaa  44040
aaaatctgca ggacccagga gaccaccccc aaaaaaatgt gagtgctcca actgtggaag  44100
taggaaagga agagcatcct ttcctgaaca cacaccccca ctggagaagc tgaaggtctg  44160
tttgtgggaa gaacagcttt agctcttttt tggtttttttg gaaaaaaacc caaagtacac  44220
aggcaacaaa gagcatgatg aatgccaacg gtaccctcac atttcaatac taacattgga  44280
atgtaaatgg cctaaatgct ccacttaaaa gatacagaat cacagaatgg ataagaactc  44340
accaacctac tatgtgctgc cttcaggaga ctcacctagt acataagtac tcacataaac  44400
ataaagtaaa ggtgtgggga aaggaatttc atgcaaatgg acaccaaaag cgaggagggg  44460
tagctattct tatatcagac aaaacaaact ttaaagtaac agcagttaaa agagagacaa  44520
agagggacat tatataatgg taaaaggcct tgttcaacag gaaaatgtca caatcctaaa  44580
catataagca cctaacactg gagctcccaa atttataaaa caattactaa ttgacctaag  44640
aaatgagaca gacagcaaca caataatagt gaaggatttt aatactccac tgacagcact  44700
agacaggtca tcaagagaga aagtcaacaa agaaacaatg gatttaaact ataccttgaa  44760
acaaatggat ttaacagata tatacagaac atttcatcca acaactgcag aatacacatt  44820
ctattcaaca gagcatggaa gtttctccaa gatagaccat atgataggcc atataatgag  44880
cctcaataaa tttaagaata ttcatattat atcaacattc tctcagacca cagtggaata  44940
aaactggaaa tgaactccaa aaggaaactt caaaaccatg caaatacatg gaaattaaat  45000
aacctgctcc tgaatggcat tgggtcaaaa acaaaatcaa gatgaaaatt taaaaattct  45060
tcaaactgaa tgacaataat gacacaacct atcaaaacct ctaggataca gcaaaggcgg  45120
tgctaaaagc aaagttgata gccctaaacg cccacattga aaagactgaa agagcacaaa  45180
ctgacactct aaggtcacac ctgaagggac tagagaaaca agaataaacc aaacccaaac  45240
ccggcagaag aaaggaaata accaagatca aagcagaact aaatgaaatt gaaacaaaaa  45300
aaaaaaaaga aagataaata aaacaaaaag atggttcttt gaaaagataa acaaaattgg  45360
```

-continued

```
tagactattg gcaagattaa ccaagaaaac aagggagaaa atctaaataa cctcacaaag  45420
aaatgaaaca agagatatta caactgacac cactgaaata caaaagatca ttcaaggcta  45480
ctatgaacac ctttatgcac ataaactaga aaacctagaa gatatggata aattcctgga  45540
aaaatataac tctcctagct taaatcagga agaattaaat accctgaaca gatcaatagc  45600
aagcagcgag attgaaacgg taatttaaaa attaccaaga aaaatgccca ggaccagatg  45660
gattcacagc agaattatat cagacattca aagaagaatt ggtaccaatt cttttgacac  45720
taaggaaacc tcccctaatt catcctatga agccagcatc accctaatac caaaaccatg  45780
aaagaacata acctaaaaag aaaactgcag accaatatca ttgatgaaca cagatgctga  45840
aatccttaac aaaatactag ctaactgaat ccaacagcat atcaaaaaga taatccacca  45900
tgatcaagtg ggtttcatat cagggatgca ggaatggctt aacatacaca agtcaataaa  45960
tgtgacacac cacataaaca gaatttttta aaaaatcaca tgatcatctc agtaggtgca  46020
gaaaaagcat tcaacaaaat ccagcatcct tttatgatta aaaccctcag caaaatcagc  46080
atacaaggga cataggcctt aatgtaataa aagccatcta tgacaaaccc acagccaaca  46140
taaaactgaa cacattccct ctgagaacca gaatgagaca agtatgccca ctctcactgc  46200
tcctcttcaa tgtagtactg gaagtcctag ccagagcaat aagacaagag aaagaaataa  46260
aggtcatcta aatcagtaaa gaggaagtca aactgtcact gcttattggc gatatgatcg  46320
tttaacttga aaaccctaag gactcttcca gaaagctcct agaactgata aaagaattca  46380
gcaaagtttc cggatacaag attaatgtac acaaatcagt agctctccta tacaccaaca  46440
gcaaccaagt agagaaccaa atcaagaact caatcccttt tacaatagct gcaaaaaaaa  46500
caaaacaaaa caagacaaaa caaaaaaaca aaaaaaaaca aatacttagg aatatactta  46560
accaaggagt agaaagacct ctacaaggga aaattacaaa acactgctgg aaggaatcat  46620
agatgacaca aacaaatgga aacatgtccc atgctcatgg atgagtaaaa tcagtattgt  46680
gaaaaataac catactgcca aaagcaatct ataaattcaa tgcaatttcc atcaaaatac  46740
caccatcatt cttcacagaa ttagaaaaaa caattctaaa attcatatgg aaccaaaaaa  46800
gaacctgcat agccaaagca agactaagca aaaagatcaa atctggaggc atcacactac  46860
ctgatttcaa actataccat aagcccacag tcaccaaaac agcatggtac tggtacaaaa  46920
ataggcacat agaccaatgg aacagaatag agaacacaga aataaactca aatacttaca  46980
gccaactgat ctttgataaa gcaaatgaaa acataaagtg ggaaaaggac accctttca  47040
acaaatggtg ctgggataat tgaatagcca caagtaggag aatgaaactg gatcgtcatc  47100
tctcacctta tacaaaaatc aactgaagat ggattaagga cttaaaccta agacctgaaa  47160
ctataaaaat tctagaagat aacattggaa aaacccttct agacattggc ttaagcaagg  47220
gtttcatgac caagaaccca aaagcaaatg caataaaaac aaagataaat tgctggtacc  47280
taattaaact aaagagcttt tgcatggcaa acggaagtca gcaaacagcc cacagagtgg  47340
aagaaaatct tcacaatcta tacatctgac aaaggatgaa tatccagaat cctacaatga  47400
actcaagtaa atcagtaagg aaaaaacaat cctatcaaaa agtgggctaa ggacatgaat  47460
agacagttct caaaagaaga tatacaaatg gccagcaaac atatgaaaaa atgctcaaca  47520
tcactaatga tcagggaaat gcaaatcaaa accataatgt gattccacct tactcctgca  47580
agaatggtta taataaaaaa aaaatcaaaa aacagcagat gttggcatgg atgcagtgaa  47640
cagggaacac tttctacact gctggtggga atgtaaacta gtacagccac tattgaaaac  47700
agtgtggaaa ttacttaaag aactaaaagt agaactacca tttgatccag caatccctct  47760
```

-continued actgggtatc tactcagagg aaaataagtc attattcaaa aaagatactt acacatgcat 47820
gtttacagag cacagagttg caacccaaat gcccatcaat caatgagtgg ataaagaaac 47880
tgtggtatat gtatacatga tggaatacta tgcagccata aaaaggaatg aactaacagc 47940
atttgcagtg acctggatga gattggagac tattattcta agtgacgtaa ttcaggaatt 48000
gaaaaccaaa catcatatgt tctcactgat atgtggaagc taagctatga ggatgcaaag 48060
caatgagaat gatacaatgg actttggaga cttaggggga agagtgggag gggggcgagg 48120
gatacaagac tacaaatgtg gtgtagtgta tactgctcag gtgatgggtg caacaaaatc 48180
tcacaatcac cactaaagaa cttacccatg taaccaaaac caccttttacc ccaataactt 48240
atggaaaaat aatccagcac cacattaggt ttagtcggac ttagccagct tggcttacac 48300
cctggttttt caggttctta tcattcccag tttatgcagc tgtttcaaca ttttcctttt 48360
gctagtcatg tgaaactgct gtctggaatt ttcttttctc ctgctaccac cctttattat 48420
tcctgtctca ctttcatctt catccctact gttacataaa tgcatcttga tttctaggca 48480
agcatttgtc aaattctcat taggatcttc ctcagggtct tttgttctcc ttagtttctt 48540
tggctttata gtgaaagaac atttttcttt tattgtcact aacaaatact tcttggtcag 48600
ttgtcacagt tccccttgtc cttgaggtca atatatatat atttttaaac attgtaatta 48660
aatatgctga ctgggaagga gttcagatgt cttactagtt attagatact ttctttcccc 48720
atgaactgca cgggaggaac tttggttaca aagcttggcc tcatcagctg acttgaggtt 48780
gatatttaga atttatacga agcactttct cccttaaaat aactggcaat aaaactgttg 48840
ctttgtagcg tatttcttag gcagccacat atatacctgt aagttagaca aggataggtg 48900
cttcctttgt caacaaatag cttttgcaga gctgaagcta acttgtatca atgactagac 48960
attaagtgac tgtgatctgc gctccaagct atttccataa tccaaggcat agaaaatggc 49020
agagaagctt gcagtatctg ttacctcctg ttcttttctt gtgtgtcaag gtctttgtgt 49080
gtcaccttcc attttatttt acattttaat gcgtccatta tgttaagtgg tgtttcttaa 49140
agctaattca ggatgactgt tatttaaata tgcataccaa gaagttctga cttaccagca 49200
aagaaaaaaa agggtcttta ttcagagaat gctaatggaa aaataattga ggttttactc 49260
tgtgtttagg gacatccttc tggagaaatc agtacataaa acctgcctcc atccatcttt 49320
aattattaca gttcatttaa tatacaattt gctcaaagcc tctatgccac agttgaaaag 49380
aagatggttt tatgtgactt ggaaataggt ctattacagt ttatgcacta ctcggatatg 49440
gtagagtcta atttcagctt aagctcagtg tatttaatca gtatcttaga gtggcctatt 49500
caaaatgctg ccatgtaaaa agctaaaatg gatgcagctc tttcttccct acccttagca 49560
atcatcaaat tgcctttctt cccctctctc tgcatcctga gaatgacaag atactgtcac 49620
ttcacaacct ccctttgttc aaagtcacat ttttcttctt aaaaagttta accaactaat 49680
tttttttttt ttaagaccag ggacccatga taaggcctta gcattttacc ttctcatatt 49740
tgtctttcat cgctgtgtgg gcaaagttga tttcattctg ttcctttttt taagaaaatg 49800
ggtattgtga ggctttaagc tggccaaaga tgatagattt tgctgtttgc taatttggtg 49860
tcattccaga caacattctg ttctccatgc atactgacct ggtgataaca tgacatataa 49920
cctattcttt ccttctcact tctcacattg aacctcacag tggaacacta ggcatcatta 49980
acaatgatag aagaaagaga ggagacttac ctccacccag tgattctggt actacattca 50040
aaactagaaa ctaactggga gggggaattc ttaaagtaca acagcaactc cctttgtctt 50100

-continued

```
ccaaaccatg agaaaaatct tcacaaatct gtatcattct tcctaataaa tgctttttgt  50160
tttagtaagt acaatatatt caatgtaagt ttatctttcc acatttataa accatcttgc  50220
agtgcttttg aaggtgtgat tgtgagtgta ttagtcagtt ctcacattgc tataaagaaa  50280
tacctgagac tgggtaattt ttaaagaaaa gaagtttaag tggctcatgg ttctgcaggc  50340
tgtgcaggaa gcatagtggc ttctgctttg ggaggactc aggaagcttc caatcattgt  50400
ggaaggcaaa aaggggagca gggcatctca catggtggga gcaggagcaa gagagaggag  50460
gagagagtca ctacacactt ttaaatgacc agctctctta agacctctat cacgagaaca  50520
gcaccaagag gatggtgtga aaccattcat gaggatccac ccccatgatc caatcacctc  50580
ccaccaggcc ccacctccag cattggggat tacaattcaa catgagattt gggtggggat  50640
agagatgcaa accatatcag tgagtaattt acttcatcat ttttaagtca catggttata  50700
agatagggtt aatgtgtgta actttacatt tataaatgaa atgaataaag tgctatggcc  50760
agtacccagc acatagtaac aggtgtctta caaatattcg ttctttcctt ccttacttca  50820
tgaagttatg acattctgaa cttgcccatc tcctatggtt cattgtggac atccaaagga  50880
caaatctaaa tggtgcttgg ccccaggaca tcatggaaag ctgtatgtgc agtgtcaagg  50940
gggttatctt caactcattc tctataagag catatgttgc ttgttttgtt ttgttttcta  51000
tcctcattct gcaannnnnn nnnnnnnnnn nnnnnnnnnn nnnnnnnnnn nnnnnnnnnn  51060
nnnntatctt taccacccga aagcattaaa agcttaagaa gcattgtatt atttataaag  51120
taacagcaat acttttaaaa tttctgcctt ctttgtgtac tctattttat ggatatgctg  51180
tgtaggcctc tcaataatac tttcaataat ctcattcatg ctaaaatgcc cctagcttct  51240
ggagatttat aaaattctag ttttcaggct gagggtaaac aaattgttcc ttttttaagt  51300
gagttaagat taaaaagttt gtgtgtgtga ataggtataa atgtatacat acatatgcat  51360
atatttatac atttatacct atacacacac aaacatatgt ttttcaatat catatatatg  51420
tattatatat atgaatatca catatatatg tgtgtgtata tatatatgtg atatttgaaa  51480
actcttctgc tcattgcagt caacttgaaa aacagaaaat tacctagaaa aatgaaaatt  51540
cttcaataat tcttatcacc ttgtaacaat cacttctaac atgttggtgt atgcttttca  51600
gtaaaatgtc tgcatttgat tttctgtttt tgatcatgca ttagcctcaa tcattccttc  51660
tttcacctat atgtttactg agcatcgaaa acaagttata atttgattgc taggtgaaat  51720
acaagatgca cagttatatt tgaatttcag ataaacaacc aataattttt agtatatggc  51780
ccaaatatca cgagatatat ttttactgaa aatttttatt tatctgaatc tgaagtttaa  51840
ttatgcatgt tgtactttta ttggttaaat ctggcaatct taactgtagt agaaacccat  51900
gctatgggga tatcttggtg agcagaaata gacggagccc tgatattaat caaatggcac  51960
atgaatatat aaactgtgag aagtatataa agagagtaag tatgaagaac tgtgtgtgtg  52020
gtgtgtgggt atgtatgtgt tggggtttca gagaaagaag gtaagtagtc tgggggcagg  52080
gacgttaagg aggaaagaac atttggaaat aaaattcaac ctgacttgcc tccagggacc  52140
tggctacact caggaacagt cttcaaatgt aggccatgtt atcaagtgaa tgctgccaga  52200
cagggctggc atccaggaaa agtaaataaa atcttcttgt gcgtctgtct ctgagggctc  52260
ttcacaaagc cctggcaacc cacagcctga aaacaaatag gccccagtct ttcccagcat  52320
agttgattcc ccaggtggct tttgttaatt gagattaaac ctgtagctgc acacaactcc  52380
tcagggcctc tatctcttta ctcatgtctt tgtccctgtg gatagaaggg gtccacatgt  52440
ggtttcagga aattaggaca ccagatcatc tgttttaact ggaaagaact acctgtactg  52500
```

-continued agagtgtgac aaggtccttt cagactctga acatagccca ataaatggta tcaaccttaa 52560
ataacgagat tctgaaaata tgattaagta tcgagtttgc tggagcccag agcttgagga 52620
tgcccacctg ggagcacaga ttcactttgc ccagaatgta cactccaatt agcagcagtt 52680
ataagtgggg ttttaagaaa aaaagacaag gcagttccta agttatttac caaaaattta 52740
cattaaaata atgtaagcta ttgatggact atgcattatt ctttatatca caaattacag 52800
gaacacaaag ataatgggtg aggcagctag tcaggaacaa aatggcttta aaatactgtc 52860
cttgagcatg ggtttgaggc tgtgactgac atcccatact catgtttctc taaacctaat 52920
aaattgtgca tatctcatat agctcagact gctctgagct atttttgttt tctcatttcc 52980
cccctttca tcaagatttt gcaaagaaag cattgtggat gaacttaagc agttttggct 53040
ccttttatgt tcaggaactt agtcctgcat tgctaggaag tcttattccc agatggtcct 53100
gtcccacatt tgggggaagg ggaaaggatg agtcttagtg gggattttaa caccatcaga 53160
agcaaaattg ggatggcatc gcagggtgcc acaaatgaga cctcacccaa gtcactaatt 53220
tatgtagcta ctgttgcttg tgggatcatc tccaggcttc agaataccat gcagttagtt 53280
ttctcggaat aagtaaaaca atgagctata catagtagaa atataataca cataacaatt 53340
acaattaaaa aaaaaaaaga atttctatgc ctgaatgaaa aaaatatcta ttccattgga 53400
aagtcaacta aaaacatcat gaagaaaatt aaaatccagt cctttcttag agacttgttg 53460
tagcaggaaa taattcaaga tttagatcaa attgtaggaa aataataaaa actagaaaac 53520
aatggtcagg gctgaattta aaaacaggtg tgctataatt ttcttctgaa ccataatttc 53580
tctctcttca gttcactatt tctacccaag ataaatgtta tcaggaccaa catacttgta 53640
aaataagctt tagtattata tttggcctaa ttatttgcat taagtgcaac aaaaataatg 53700
aatggccatg tacgcatttt taagttggct ttgctggaac tttttcataa ggaatctcag 53760
attagacttt taaaagcctc tctaaactag atattgaagc caataattca ccatcaaact 53820
gcctgtagca tctacataaa ttgggtgaat ttctcccttc ttcaggttct gaaatatatt 53880
gaggtttcta ggcctgtcaa atgatgacat tctttactta ctgcaaggtc aaaaaacttg 53940
tgagggtacc atgtagacaa ggtatcaggt cagttttcca aaaggactat tgatttggct 54000
ctataaagtc aacttcaatt catcaaagca gtttggtcat atctgaaagt atgtcatttc 54060
acccaaagcc ttggtaaaat gaccagcctt agtaaaatga ccagtgtctc caactgtgta 54120
ctgttacaga agaaaacagg ttcttactga acttacacaa ataacaatat tgccataaat 54180
aaagagtatt cacaaatagt ttccaaattc tggaggaatc aggtagagag taagatgttt 54240
caattttgct cataaaagta tactttactt aattgttgta agctctaaat agctcaaaaa 54300
aaattcttga ctttggaaaa caaaacaaaa agaatcagca atgttccaaa caaaaaaagt 54360
cattaaaaaa atttcagtcc tggccaggtg cagtggctga tgcctataat cccagcattt 54420
tgggaggcca aggcaggtgg atcacctgag gtcgggagtt caagaccagc ctgaccaaca 54480
tggagaaacc ctctaaaaat acaaaattag ccgacgtggg tggcacatgc ctgtaatccc 54540
agctactcgg gaggctgagg cagaagaatt gcttgaacct gggaggtgga ggttgcgttg 54600
agctgagatc acatcattgc actccagcct gggcaacaag agtgaaactt catctcaaaa 54660
aaaaaaagaa aaatttagtt ctctatcagt tcagttccat gtagttaact cttgttctgt 54720
ttgatattgg gttagcaatc ttcacgaact gatgaacttt tatattagaa ttctgaaagt 54780
ttttacataa tccattgata tgatttccaa aaccttcaga aacttgtatt cgagagtact 54840

-continued tctcagaatc cttttcatga atttccttga aggataagca aattttggac tgtagctgat 54900
tataaaccac tttttatgaa gaatctaagt aaaataataa ttgtctgtag atgacaaaag 54960
acttaaagca gtcttagtta aagacacaat tgaccaggaa atttggttat gcctgtagca 55020
tacaacaact tgacataaca atcgtaatta ttactgatca tatataccaa aacatattgg 55080
aacttttgga atctcattca attttggaac agatattaat catattaata catttataca 55140
aatatattca aagaaagtta aacatcattt cttatttgac aatgctttct gtatgattta 55200
aacatatcaa ataagcctga tctgcctctc tgtaacttct aggggacctc atatctgaaa 55260
agttatttcg aggtaaaaaa aaaaaaaaaa aaaaaaagga ctaaatttta atttgaaata 55320
tgattttgga aagtttgtca aatatcaaag gtttaaaaaa cttactcaaa atattttttac 55380
aggtcactgt aaaataatag tcatttattt agccaaagtg ataattccaa gatttcaaaa 55440
gcaaaaactt ttactatttg gtagaaagga gactgcgttc ccaatcaaga gacctaatag 55500
ggacagcatg aggcaaactc ttccctcctt tttataagga atctcagatt ttaccttaaa 55560
aagcctctca aggctaggta tctttgagag gttacctttt tttttttctg tttttctttt 55620
tgaagtttaa tcaaaaggca aacaaatctt ttactgtctc ttattaatac tatataaaat 55680
tcttattcaa aggagaatgc caaatttata ttagtgtgtt gtcaatacta aagctaattt 55740
taattaaaca ttataaacaa atccatacaa tctcagtcag ctttgactgc agaagataag 55800
attttcataa atcttttata acctattaca attttctatt aaagagaaga tcaatgtttc 55860
aagaaaaccc tgtggttcca aaagaggggc ccagactctg gccttgcacc agtgagcttt 55920
tgagattaat gttcactttt tagaaaaact tataaacaat tctcttctaa ttttagccaa 55980
cttgatcaca cacaaaattc ctttcacaag attaatcttc cataaaccca caacttgctt 56040
aaaccttcag ttttgtccta tacttctttt attttgagac ggagtctcac tctgcccagc 56100
ctggagtgca gtggcatgat ctcggctcgc tgcaacctcc gcctcctggg ttcaagcaat 56160
tcttctgcct cagcctcccg agtagctgaa actacaggca tgcaccacca tgccgggcta 56220
atttttgtat ttttagtaca gacggggttt caccatattg gccaggctgg tatacttctt 56280
ttttagattg gcattctatc ttaggacaaa atctactttc ctttctccct tatcattttg 56340
accacacaat gctctctttc atgcaaatga aaaattactg tcatttcaac tccctttacc 56400
aaaaacacat cttaatttct ttatatacct tatgtataga attgtctctc ttatatctag 56460
tcattttttt tttctttttt cttttttttct ttttgagatg gagtctcact ctgtcgcaca 56520
gactggagtg caatggtgcg atcttggctc actgcaacct ctgcctcctg ggttcaagca 56580
attctcttgc ttcagcctcc caagtagctg ggactacagg catgtgccac cacacctggc 56640
tattttttttg tatttttagg agagacaggg tttcactgtg tttgccaggg tggtctcgat 56700
ctcctgaccg catgatctgc ccgcctcggc ctcccaaagt gctgggataa caggcatgag 56760
ccaccgcgtc tggccatatc tagtcattta aattacatac gataactaca attttaactc 56820
ttaggaacgc taatttacag tgaaatctga ggaagtaatt ttgagctgtt ttatgccagt 56880
atttatagat gaaaaccatt tcataatttt tataaagttg tttcctcaat tattttgttt 56940
attaacagat ctaaatatat ttagcttttc tacaccatat aactcagaca ttttatggtt 57000
acacaatgct taatttaaca tgactttacg atttagttac tgaaaaagat ttttgaaact 57060
gaaaagttca tttatacact tctatctcat ttacattcat ttaatttagt ttattcattc 57120
ttaacaatta tgcttgaata gttcattaaa caaaagtagc caccatcaag ttatttcttt 57180
gttaatcatt tttatagcct gcaaatgtca ggcagttgcc acctaagcaa gaacccgaaa 57240

-continued gctaaaacag agatattttg ctgatcagaa ggcacggtgg ctttcattaa accaacagta 57300
ttaactggtc ttatttaccg aagatttacc caagttatgt gaactaaaag ggatttgagt 57360
tattttctat ttttctgata aaatatttaa gtgtttcctt tctcttttgg ccaattagaa 57420
ctcattcata tatttttgta ataaatttta catacacatg acacatataa acatgcagac 57480
acacacaggc agattttata gctttgtaag tttcttcatt tgccagtttt caatagtttc 57540
tctcccacct ttagactgtc aagccctaaa caattgttag ctaggcaacc ttaaatttgt 57600
acttctaaag ggatgactct tagctgaaac aaagtaaaaa aaaataaaaa ttacacttca 57660
aaaacacaga gcggagctca aactaaggga gcaggtgtat ataggtaaag gtccagttaa 57720
gacaagatgg ccaaggaaag catcttaagt aaaggtagga cttgtataga tttaaaccaa 57780
tgttaaattt ctcatgactc agctctccct ctcctccagg tgcacagagg cagaaaccct 57840
tacaaatgga gatttccttt atcaatgtaa atttcaatat agccagctaa atgccagcaa 57900
ggtatatttt ggagaactgt tagaggcagt gaatctgtat gtgtctgcag caacttcaat 57960
tcttgcctac tctcaaaata aaaaattcaa ctgaggggca taaggtagaa tgaaagacag 58020
aggcaatttt tagagcaaaa gggaaagttt attttaaaag ttttagagca ggaattaaag 58080
gaagtaaagt acacttggaa gagggccaga tgggcagctt gagagattca agcacacggt 58140
ttgacctttg acttggagtt ttatatgttg gcaggcttct cgggggttgt tgcttctccc 58200
ctgattcttc ctttggggtg gactgtccgc atgtgcagca gcctgccggc acttgggaga 58260
ggccgcatgt gcagtgtgtt tactgaagtt atgtgcatgc ttacttgagg catctttttt 58320
tccttaccag ttgactgttc ctagaggaag gtcatatacc agttaaactc taccattttt 58380
gcctcttagt gtgcatgctt gagcctactc gcccacctcc tgagatctta tcaggaacct 58440
actgatcatc agtttcaggg tttttctatc tactgggaga ttgccttttc ctggcgccgg 58500
ctgcaaccaa atattatttg agagagacag tttaacaacc acctgaccat cacctaatgg 58560
ttgtctgaca ttccttggtg gaggttgggg gtgatctcct gccttgccca tgtctgcctg 58620
cctactgtaa cagaccaact tagttaaata ggtgggcttt tcaacttagt ttgtttcttg 58680
gtgagatgac tgacatcatt gtgaagctct ttaatgaaca gggcaaagaa agccttctct 58740
atgcctggac tcggcatgga cagctctggg aaagaagaaa gcctatttta cctgagggcc 58800
tatcttttat aaatattttg ttcaaattct ttcttttaaa acaaaggttc tttttcaatg 58860
acttaccaaa ccaatacacc ttaaccaagg ttatgtctaa accaaggatc aactaggcat 58920
ttccaaagag tggcaaagta gtcctcacaa gatccagaac caaagacagc tcaaagaaac 58980
aaatgtcttg ctcactgcaa atagaataca acccatattt ctgtccagcc gtattttcaa 59040
ggatctcagc ttctctgttg agcacctact cacggaggcc ccaaagccct atatgcccca 59100
cagatagaga caggaaatca aaagctgtct ctggaaggga aaagaatcaa taacaaatgg 59160
gtacctcaga aggtcaagag ttatacaaat gattttaaac aaataggact gctttcctga 59220
ctgggaatca aacctgggct gcagtcatga aagcagaatc ttagctggta gaccacagag 59280
tggagtgctt ttttgtaaat ccttcaggag atccaagcag gcagtttgag catataaagg 59340
atttcaactc atttcagatc tgatcacagc tggaatgctg tttagctaat ttcctgcatg 59400
ttaatatttc aaagatatga tgagatttgt atctgcaagg gattgtgaag tccagcaggg 59460
catttgaagg atattgtctg ggccgggcat ggtgacttaa atgtgctggc ttaaaatccc 59520
agcactttgg gaggccaagg cgggtgaatc acttgaggtc aggagtttga gaccagtctg 59580

-continued

```
gttcacatgg tgaaatccca tctctactaa aaaatacaaa aaattagctg aatgtggtgg  59640
cacgtgcctg taatctcagc tactcaggag gcttaggcag gagaattgct tgaacctggg  59700
aggtagaggc tgtagtgagc tgagatcaca ccactgcact ctatcctggt gacagagcaa  59760
gactctgtct caaaaaaaaa aaaaaaaata ctatctgatg ttgggtcaag aaatcatcag  59820
tgtcattcat tagacctggt atagacaaaa gtttgttgga tctgtatttt tataatctct  59880
gtagtatcat tcttgttctg tagttgtttc atttgttctc tctgtttaaa aattatcttc  59940
ctaggagatg gatgggagct gagggaatga gcagaaaggg atgagtttag atcacaggag  60000
taggaggaga tggagcagtt agaggtgaaa gagaaaacct ccaaaatctt attaaattta  60060
gaaatagttt caaacatact tttgttcacc tcttgaatgg aggcaatttt ttcttttagg  60120
atttctttta gaaacttgta ggtactattg gaagtaagtc tctcactcaa tttggttcta  60180
aaactagctt tttctaattg tgtgtgcaaa caaactaatt taggtatttt aaaaggtacc  60240
acattttggc cattgtcagt tggaatcatt ctgagttatg ctctactagt tttctaaata  60300
tttgcatgaa gaggcatggt aagtattcag tatgaatcga gctggcattt ctaatggtgg  60360
atctcttctt aaggaggaaa cctcagtttt agatagttga actgccttca gaatctggcc  60420
agttttaaaa actacagttg ttttttctta agccacaaag atttacttat ttttcaagag  60480
aaactatatt cttcttggcc aaattttgta ttagaggaaa ggttacaaac tctaatgaat  60540
aagacaaaga aaaccttaac ttcagagaaa agtgaaaatc acaaaacaaa gtaaatataa  60600
tctctagaga ataacacatg aaactcctgt ctttcagtag agtttcaatt ccaatcccgc  60660
agagttaaga atgtgtatgg cttgaataaa gtctgaatcc tcaactaacc tgggagtatt  60720
tggataccga gatggctgcc agatctggtg aggttgggtg aaccaagctg ttgattctgg  60780
tactgttaca ggaaagcagt cctgatccat accccaagag agggttcttg gatctcacgc  60840
aagaaagaat tcagggcaag tttgcagagt aaggtgaaag caagtttatt aagaaagtaa  60900
aggaacaaaa gaatggctac tccatagaca gagcagccct gaggactgct ggttgatcat  60960
ttttatggtt tttttaataa tatgccaaac aaggggtgga ttattccctt cccttttttag  61020
atcatatagg gtaacttcct gacattgcca tggcatttgt aaactgtcat ggtgctggtg  61080
ggagtgtagc attgaggacg accagagatc actctcatcg tcatcttggt tttggccggc  61140
ttctttgccg caacttgttt tatcaggaag gtcttcatga cccgtatctt gtgctgacct  61200
cctatctcat cctgtgactt agaatgcctt aactgtctgg aaatgcagct cagtaggttt  61260
cagcctcatt ttacccagct cctatttaag atggagttgc tctggttcac acgcctctga  61320
cagtaccaac attccaattg tcacgaactt gaggggatca ctgaagctcc actttagatc  61380
ccatctgggg tggtaaaatg tcaacgtgaa acaagattca gaaaatatga ttaagtatag  61440
catttattgg ggctcaaagc ttgaaaattg ttatccggga gcatagattc aagttgccct  61500
gaatatactc caattaacag cagcgacaag tgggtttcta cggaaaaaag aagaggcagt  61560
ttctaacttg ttcgccaaaa atttacgtta aagtaacgta agctattgat aggctacacg  61620
ttattctttg tatcacaaat tccaggatca cgatgataat gagccaggca gctagtcaga  61680
aacaaaatcc caggcatcag tgtggggata tgactgaagt cccatactcc tgtctctctg  61740
ggcctgacac attttgcata gttcatatag ctcagccttc tctgagctat ttctctcttc  61800
tcagtggctt tcctggaagc agcctccatc atatgtgact cagagtgcta gcatttcttc  61860
atgggtttat aaaccataag aactcaaggt ggccttcaga gccacagcat caacaatatt  61920
aacttcccta ttagtagtgt tctattactt tgggttttac atatattatc tcatttattc  61980
```

-continued atcataacaa cctggttgat agggattatt attcccattc tattcctgaa gaaactgagg 62040
ctcaaaggag ctaaaatatt ttcctatagt cacacagcta ggaagtggca gagcgaggac 62100
tcaaacccaa gaatcctgac ttcaaagcct ctgctcttcc tgctgcacta taccatccct 62160
atacacatct ctgagactcc tgtaaaaata tgtaaggaac aggatttatt tcatttattg 62220
tctttcatat cccacaagaa tacaaactgt gtaaggcagg tatgtctgta tgttttttat 62280
cactgcctca ttccccatct tccacaacag tgcctaccgc acagtaagtg ctcgataaat 62340
atcttttaaa tgagcatgtg aatgaatgtg tgttagtgtt agggctaagg cctttggctt 62400
ctggttaatt gcccttttttg ccattatgcc aatgtcattt gcacactcac aaacataccc 62460
tcatataatc atatgcactt cagtttcttt gcaggtcctg ggttcagaca aatctgagtt 62520
tgaatttctg ttccaccact gggtaactga gtgaatttgg tcagttatgt ttggtatttt 62580
acttagtttc ctcacctgta attaggaata acaggaatac tcatgtcagt actactttga 62640
atgacagtga taagaatatg tacttcaagc acctcacaaa gtacgtggtt gataaatggt 62700
gactttacac aacaactgag tgacacttct tctggcacag gggccaaggg aaaatttccc 62760
cttcaccctc tgaaggttca ctgagaatca actgataaaa ggcagattaa taggagaaaa 62820
agcacacaaa atttgtttgc aatatggaaa ttcacagaaa ggggtagatg gttgacactt 62880
ttatgccatc ttgaggttac agaaagagct tggaaaaata gattatgggt gaagggagag 62940
aaagaaagtc ctggggcaaa ggtggtcctt gttatgtaga tgaaatctca caagtagcaa 63000
ctctcagaaa gaatagatga tagtctgtgg ttgggagatc tgatcatggg gaggtcctca 63060
gagaatgcct ggttgtttat ttcactaatg tatttttttt tcctatagat acaaatcatc 63120
tccatgaaag gtagcttttc agggttattc ctgtgtgcat gccttcttct gaagcaccat 63180
ctcaagatat gtcaaataag tgtatttggg gtgaaatatt tttggtttcc tttgctagaa 63240
atgaaatgtc cctgcttccc catagccaga aaagattctt gagtggacaa ctgcacctaa 63300
acttgaacct gagcactaga aagtcttttg ttttattcta tgtttttata aatttaaatc 63360
taattttttg aatataaaat aatacatatt ttgtaaatgt ggaaacacag aaagttctaa 63420
tgaaaaaata aaaacctgta tttcatcacg cagaaatatc tgctgtatta gttttccgtt 63480
gctgcggtaa caaattgcca caaacctggt ggcttgagac atcatagatt tagtatctta 63540
caattctgga agtcagaagt ccaaaatcag tctccctagg ctaaaatcaa tgtgtcacca 63600
gggctgtgtt tcttccagag cctccaggtg agaatctgtt tcattatctt ttctagcttc 63660
ttgaggctgc ctgtattctc ggcttgtggc cccttccttt atcttcaaag ccagcagcat 63720
actatcttca aacctctctc tgactctgac ttcatgttct ccttattcat cttttaaggc 63780
cccttgtgat tacattgggc ctacttggat aatgcaggat cacctctcta tctgatgatg 63840
ggccttaaag tccctttttgc cacaaaagaa aacatatttg caggttctgg agattataat 63900
gtggacagct ttggggagcc tttattctgc ttattacaaa cactattagt atttagtgca 63960
attcattccc attgttttcc ctatattttt caacatattt cactttttac tatctatgcc 64020
attcacaaga ttgcttattt caagcaacgt tttattgtaa ttgttttctg ttatcaacat 64080
aaagtaatca aaagggtcag aatctagttt aaagtgagtt tattcgagta caaagtttga 64140
ggacaagccc cccaggaaac agaattcaag gaatggaagt cagagttcca aagtgtagac 64200
attggggatc atttatagac aaagttcagg gaagtttaac agaatttcac catctttcta 64260
tgtaaggttt aatgcatagt tacaacaatc tgattagtca aagtggtctt tttcttttga 64320

-continued

```
gaaatgtata tttaaacatt ctactctgaa gatgtaattg tcatggggcc ttgggcacca  64380
tcatgtctga gttaggtaca agactatagg gaggcagtta atctataaca aagatcagtg  64440
attggaaagg ggaggtctgg tctcttctag tcatttatag aataagaaca atgaggaaga  64500
gaggtaagct ataatctaag atgcagaatt gcagacatgc catgcgactc actcagtttc  64560
cagggcttaa cttccccctt gtcaaaatca atttagaaga tcctgaaatt ttattttatt  64620
ttatacttat attattaaac atgttttatt agaatgtttc attgttgtgg ggagaattcc  64680
taaatttcct aagcataaac actctttgtt tcttttcagt atatatttct tcccagtaca  64740
tgttatttgg acctaagtct tctgggatgg caatagagat gcaatggagg tcaaattcca  64800
tcctttttag aggaatctat acaaattaga gctagtaagg atataaaaga tcattttatc  64860
aggtgcatca tccctaaaca tacatacaca tttacacaca taatgtaaaa tcctgttaaa  64920
agaagacgct tcccaatatt caagggctgt atagacgtgc ttttagatta agaattagat  64980
gcattatgac agattttgct atgtaacaaa ctgccccaaa acttattaac tcaaaacagc  65040
aagtattgat gtctcatgat tctgtagatt ggccaggaag ttcttccagt ctgggctgtt  65100
atgtgagtca gtgattcaaa actatccatc taggccttga aggcgggggc tagcctaacc  65160
tttttcttct gccatgagac taaccctggc ttcttcacgt gcgggtggaa gggttcctaa  65220
cagcaacagc tgacaaactt aatgagcaag cactttttca gcctctgcca cagtcacatt  65280
ttctatccta ttggctaaag taaatcacga agtcaggctc agattcaagg ggtgtagaaa  65340
taggctccac ttctgatgag tggcacggca aagtcaacat tgcaaaaagc caggcagaga  65400
tattactgtg gccagttttg caaacaatcc accgtaatac ataaaatatg tttaagcagt  65460
ccacaaaatg atcaaggaaa tggtagaaac tataaacact gcaagaactc agagccacat  65520
gatgttattg agtccttgta gtgctctgaa agggttcaag gaagaagttg ttttggcata  65580
tgaccctgat gaacttgcaa aagtagagaa gaagggagca cagtttctga agaagaactt  65640
agtagagaag tgttattctg tggccagtac gcagtaattg ttccacctag agatgttgac  65700
tgactgatga acaggaagct gagtctttat aatgcagata ttcacatatt catttactca  65760
tcctttattg aaaacaacgc aaggagccac tagaaaattt aagctcaaaa gaaactcact  65820
ggatggatat ggggtaaaga ttcagaagca cagctgaagt agcaggtttc acaaagatta  65880
gggacaaagg gcaatctgga aatctaggta gcaggaacta ttgaatagac tcttaagctg  65940
tctgggcgga catgagtcag ctccaaccaa ttttctaacc ttgtgtcacc cactcaagat  66000
tgaaagtcct gggagagaat ccaactggcc ttgctcagaa aacattcctg cccccttagct  66060
caaagaaaga ataaaataaa tgactcctgg attgttagcc taagcaactt agatgatcat  66120
gtcattcatt tagatgggga gattggagga ggagcagatt cattgtgaaa atcaggaaaa  66180
ctcttttagc tctgttaatt ttgaactgcc ccttagtaat tcagatagag ctcttgaata  66240
ggcagtaagt gaatctggag ttcaaaggga aattcaggga gtataaagtc caacaaaaca  66300
aaaatatggg aatcactggc tgttagatgc catttagacc agggacttga agggagcacc  66360
ttgggaaaga gactagatgg aacagaaagt ctgaggacta aagacattgc tctctaatag  66420
ttctggtaga ggaggaagat tcaggaaact agacagaaag acaacagtca tgaagctaat  66480
caacaagcta tgggtaagtc aggggagtct gccatcctgg aatcttccag agagaaaagt  66540
ttttcagaaa ggaaggaggg aaaaccattt cagatgctgc tgcaaggtca agaagaagaa  66600
gacaaaaaga gcagacccct tacttgagaa gataaatatt gtgaccttgt cccagtgttt  66660
tgggaggctg aggcaggagg atcacttgag gtcaggagtt tgaggccagc ctaggcaaca  66720
```

-continued

```
tagtgagaac tcatctctac aaaatataag aataaaataa ttagctgagt aatctcagct  66780
tctttggagg ctgaggtggg aggatccctt gggccaggag tttgaagtga ttactccact  66840
gcactccagc ctgggtgaca gggcaagact ctgctctaaa aaactaaaaa aaaaattaaa  66900
aaaatatatt gagattgttg cagaactttc tccttaggtc agctaaaact gggctcttgt  66960
cacatgacca gggaagatta ggcttgcaga cacatagaag ggtgaggaaa acatttattg  67020
ggagaaaagg aaaaagaaag aaaaaccctc agcaaagcga gagggagtct tgccaacaac  67080
ctcctgcctc acagataggt taccacacgg aaactgaaga ggccaggctc ctccccctgc  67140
aaacagcgcg aacttcccct ggctccaccc acttccctca gtgcgcaagt gggcattatt  67200
tagagagaat gagccaggaa agcgcgggct tcatccagga ccagcagtcc ggtttttcag  67260
ccttcaggct gttttagact tggaggctgg gtttctccgg gacccttggc tgtctcctgt  67320
ctctatcaag atcttaataa gagccaactc cacatggtgg gacaaaagac caaagggagt  67380
aaagggagag gcttaatgag aaaatgagaa attaaatcat ttaatgagtg attttatttt  67440
ccaagtagag gaggagaggt acaaaatgag ttttgagatt catgttgtga caggtagcaa  67500
tagtgtcttg ccatttctgt attgtattcc attgtataaa tactccatgg ttcatttacg  67560
tttttttacca ttgataggca tttggatcgt ttgcaatttg agactttcgc agagtactac  67620
tattaacatt cttatttgtt cttttggcaa actccaaaat atgtgtactt ttgtacacat  67680
gtaaacccta ggacccagtg gagcgtagta cttgatttta cgncgtgtag attagagtgc  67740
aacagatctt tagtatactt tagctgagta gagtagcaga taatgctgga cgaagacgat  67800
tgtcgtgctc gtgtagtaac ctgttctagt cttgcgtgag agcacctctc tagccgctgt  67860
gacgtcgtac ctagtgttca agtagctgag gagcagtgtc acagtaggac gtccgcacca  67920
gagtttagtt cgggtcgact atgatgtatg tgtactagta gtgtagtata gtagtacacg  67980
agtcgtagag gagtagcctt agagannnnn nnnnnnnnnn nnnnnnnnnn nnnnnnnnnn  68040
nnnnnnnnnn nnnnnattgg aatcctcccc tgtgctctaa agatgtgtac ttcttatttt  68100
tctacacata ttttggaata taaacttaag aattaaatca ctgggtccta gggtttacat  68160
aggtttagct ggcaaacaat tttccaaaga gcttgtgcca gtttatactc acatccgcaa  68220
tgtatgaaaa gtcaagttgc tccaaagcat caccaacact ggatattatc agtttattta  68280
actctgggtg ttccagcaaa tgtgtaatgg tatctccctg tggttttaat ttgcattttt  68340
ctggtgactt atgagtttgg gcatattttt gcttattgac catttataat ccctttgttg  68400
ggaagtgctt gtttgactct tttaaccatc tttctatcgg ttgcctcttt ttcttattga  68460
tccatgaaag ctctttatat attctatata caagtctttt taaaagtttt ttaaaaactt  68520
ttatttagca cataccaagt caggtgttgt tccaggtgct gaaatggagg agaaggaaat  68580
tttcagaaga tatgtggcaa agagaaaaaa gcgttaacct ttgtgatttg tgttatttgt  68640
tactatcaag ttggcaataa taaatattta ttataatttg taacacatat ttaaaatgta  68700
ttatatataa tattttatat tgtatcatat ataaaatcaa cagattttaa ttaattcaaa  68760
attcagtatc ttcactgaca tgtgttagct tcctagcact ggaatgtcat ttgcttgctt  68820
acatataaag gtataataaa attttaaatc ttctgctcag ataaagaagt agtgaattat  68880
ctaagatgtt tggaatgact taacataaat atttctaaag ggaaagggat aaatcacata  68940
atttttctgc atggaaacca aataaaacaa ataaaaagaa agatgcgttt atcagtaggg  69000
aaagtgtcta gaaaaagtac atataactat gcctgacaat aggcatatag cctacatgta  69060
```

-continued

```
attgatacat tttagaagaa agtgtggaat catttttaat attatgtatg tagaactcta  69120
ccctgagtca ggagtttctt gtcatatgtt gaggagggta gaacagagtt actaacacta  69180
aatgagacat tgaataacct atcttttgtt tttatgggta aaaaatatag cgaccataat  69240
ataccagaag taaaagaaat acaaattaat atctaattta ttatatatat ggaatgagct  69300
gtgaaacttc accaagaagt ctttctttgg ggcatataaa ctatttgcac aatctctgac  69360
cttctttttc actgcaataa tggttttttt tttaacaata aaaaatgttt ggacttaatg  69420
tggtacaatt tatcaatctt tttctttatg cgtagtgatt tctgtgttct ctttaagaaa  69480
tttttgtctg gctggggaca gtgactcacg cttgtaatcc cagcactgtg gaaggccgag  69540
gcaggcagat cacttgaggc caggagcttg agacaagcct ggccaacatg gtgaaacacc  69600
atctctatta aaaatacaaa tattagccgg gcgtaatggc acatgcctgt aaatcccagc  69660
tacttgggaa gctgaggcat gagaatccca tgaatcctag aggtggaggt tgcagtgtgc  69720
cgagatcatg gcgccaatgc actccaggtt gggcgacaga tccagacgct gtctcaaaaa  69780
aaaaaaaaaa aaaaaaaaaa tctttgccta tgccaacgtg gagctattct atcctgtttc  69840
ctagaagctt cactgtttta gctttcacat ttagatctac agtctaggat caagttttat  69900
tttgtcttca tataaataag taattgaccc ttagccattt gttgataagc ttatactttc  69960
cttacgtcac cacagaacca catttgttat taatcaagtc accatctatg tatgggtttc  70020
ctgactctgt tccattgatt catttgtata ctcttgcata tttatcactc tgttttaatt  70080
actgtagttt tatactggat tttcagtaat tcatctttgg attatgttgg ctacagttgg  70140
ttctttaaaa ttccatataa atttcataag tagcttttca atttgtattt taaagctgct  70200
ggtatgtata ttgggtacat ggagtctata gattaattca gggataacta acatcttttt  70260
aaaatatcaa atttccaatt catacatttt atatatatat atatatgtgt gtgtacatgc  70320
atatacatat atatgcgtat acatttcctt atttatgtag atattcctta atttctctct  70380
ttggttttag tttttcatgt agaggtctag cgtatttgtc tttagactga tgactaggta  70440
tttgataaga ttacaagtgg tattatttat caaaattgta tttcttgcta gtttggtgct  70500
tatatactaa aatacaattg attattaata ttgactttgt gttcagtgac ctggctaaat  70560
tctcttatta attatactag ttgtcccata ggtttcttg gattttcaat atttacattc  70620
atgtgattta ctaatagtgg caggttcatt tcttcccttt caatcttgcc ttttctttcc  70680
atgcatattg cacatgcatt gagaacaatg ttgaataaaa gtagtgataa tggacatctt  70740
tgtctctttt tcccgagttc acagggaagg ttttcaatat atcaagagtt tataaaatat  70800
ttgctgtagg ctatttgtag atatccttta tcacaataag aaagtttctt ttctgtccta  70860
agtcactaga agtttttttt ttttttaaca tgaatgagta caatatttta tcaaatactt  70920
ttgttttact gaggtcattt ctattgtgag tgaagcaagt tgatttgtaa atattaaagc  70980
aatcttgatt tccaaaagta aatgctagtt ggtcatgttc tattatcctc ttgtgtatat  71040
tactggctac aataaaatat ttgtttttta tattttttat attattattc atacattatt  71100
tatgtatgtt atttattatt tataaatatg tattctattt atatatattc ctacatatat  71160
tttaggatgt acatagacaa gtttgaatgg taacaagaat gagccaactg agaggaagaa  71220
attggtaatg tagtaaagag cggggatgat tgccaagtca ggtcctgcag gtggtgagat  71280
gaatgtgact cagggcacag gtgaatgagc tgaccttagg tggaagtggg gacccttcct  71340
tcatgtacta ggagagaaag cagagtttga agtctgtatg tgtgtgagct gctgggcttc  71400
tcagagggca gatgaaatag ttcttatgcc attgcctgtg ttttccctgt ggtatatgag  71460
```

-continued

```
gccatccact gagaatgaag gtggtcagag tataggaaat tttgagatgc cgagaagatc  71520
tgtgaaatta gtagagaatt agaataggat tttctaagta tccatttgag acttgtagtt  71580
ataattaaac aagaatctat cctgcagatt tgtatttttc tccttagatt gcacttaata  71640
gatcaccagt tcatttttgt tgctgtttaa aagcatattg agtttaagca ggattggagt  71700
ttaattgggt gaggtattct cactgtgact aagtttgatg aattgaaaag cgtagttgta  71760
gaaaggaaac tcaagaagga aattcttggg gaaacttaaa gaatcgtata tatgcaatgt  71820
cactttttaa gacaactaat atttttaaga atttactact tttgaggtgc tgtactaata  71880
tattacatgt ataatttcat atatcttcaa ctactagttc ctgtaaataa gtatgctgat  71940
gatgacacgt tccatttctt tcgatagcca caaaaacagg aagtgatgac aaagctggat  72000
tctaactcct gactcccaaa ttctctaaga ccctcagcat taacatatat tttattttaa  72060
tgttattata tatgtatcat tacttttaca actcttaaac caaacatttt aaaattagct  72120
acaactgcaa aatcaactta aaaatttcaa agagccattt aacatgataa attaaaatat  72180
tttagtaaaa caaaatcacc actgatactt taatattctt aggtctgaga aaaaccatta  72240
tgtcgtatta ttcctgcgtt cctggtagcg tttctactgc tggacatcag aaatagagaa  72300
tagtagagcc cctgagataa gagcagagac aggggaaaag caaaacattt ctgaagaggc  72360
agttggtcta gtttggctat aatcactaga cgggtaaagg aacattgggt gcattaaaag  72420
tagagagcct gggatgaagg cgtgaaggct gagtaagaat ctcttcactt ggtagtaatt  72480
ctagttcatc cccctctgac ctgcaattct gaacatggtg tagcttggtc aataaggaaa  72540
taaattgcct ttctggctgg agaggcaaag ggtagacaat acattgtgcc agctgaactt  72600
cctgtctctc cgctctggag aagagccagt cacaatgtat gactcagcac gccgggcacc  72660
tctcccacgc cagccaggcc tgcccagcca cttgctgaat cacaagtggc catttccaat  72720
cccatcagtg acccaagctc tccaacttag actagtttct ctgtgatcgg tctatgattg  72780
tcatggagca caaaaagtat taacttctaa catttatttt tctttcctgg atgcttgatg  72840
aactttataa gcaagagact gatttaattg ttcctcatta tcatctgagc atgccgtctt  72900
ggcttgccct tttatatgga gagcaaaatg ttgttattcc cctttgcctg attactggct  72960
gtattattct ctgaggtggc catctcaaga gattctgtag aaaataataa tagcaaaatt  73020
tctcccttga gaagcttcat aaattaaatc tccagagcca gtatatgtaa gccgacagat  73080
tatgaaatat gatttaatgc tctgtccaga gaaaggtcag ggcttcagaa aaatcatcat  73140
aatatcaaga aaaactaatc tgcaacctgt tatatgattt ttaaaaatca ccccccatct  73200
tttttactgt gcaaactgta gatttttgtt tattttattt gaggctatag tttatgtctt  73260
gaatcacaca catatgagta ttactttctg tgaagttttc atgacccctg caatcaaact  73320
tgggtccttc tgttagtttc tatcacagta tccttcactt ttctttcaca attcttgcca  73380
tattctataa ctacatattt gtttgttaaa tatttgttta tcttttatag atgattggct  73440
tcaggaagag ggaaaccatg tccttttgtt cagtccttta ttctcagcac cttgcacaac  73500
atgaatatac aaaaaatatt tgtaaaatga ccatcgaatg aacaagtgct cattaagtac  73560
caagctatat gccaggggtt gctgatggtt agaaatgagc agggcacaaa attctttgtt  73620
caattagtga gcaattcagg caaaaagaaa atattaatgg tgattataca atataatgca  73680
atgcagccat ctgccactag atttactgaa gtgttttgtt ttgtttttaa gagacagagt  73740
cttgctctgt cacccagact ggagtacagt gggtaaaatc atagctcact tcagtctcga  73800
```

-continued actcctgggc tcaaggaatc ctctcacctc aacctcttaa gtagctggga ctacaggtgc 73860
atgccactat actggctaat ttaaaaacag aagccaacaa acaaaaaaca cacctttttta 73920
agactgggtc tcactatgtt gcccaggctg gccttgaact cctggcctca agcgatcatc 73980
ctgccttcca aagtgctacc ttctagagta ttgggattac aagcgtgagt catctgcacc 74040
aggcctgaag cattctgtaa tggagaaata cctgggtgct atggaagggc agagggggaa 74100
acacagagga gtaacatcta gtttacgttt gtcaaggaga ggccaggaaa gactaactac 74160
aggggagata aactccaacc aagagtcttt aagtcttcca agacttacgt acaagtttct 74220
tattgctaaa atggaagttt taatgaacat ttatttattt atttgagatg ggtttcact 74280
cttgttgccc aggctggtgt gcaatggcac aatcttggct tactgcaacc tctgcccccc 74340
aggttcaggt gattatcctg cctcagcctc caaagtagct ggaatacagg agcctgccac 74400
catgcccagc taattttttt ttgtatttgt agtagagacg gggttttgcc atattggcca 74460
tgcttgtctc aaactcctga tctcaggtga tccacccacc tcggccttcc aaagtgctgg 74520
gattacaggt gtgaaccact gcccccggcc tgaacactta ctataaatat tatatggtag 74580
ttctctcaaa ttcattctgt ttactgccca aaagagctac ataaattcta agttgtccac 74640
atttatgaat tttagatata tggctgttta ttctggataa acacacaaaa tacacaagag 74700
tgggtgcgat cacttatatg tgttaaagaa ggcattcaag gtgcattttt tctttggaaa 74760
agctttgtaa ggctgcttat gagacagaga agtaagtatt ttataaattc caaagcttct 74820
tggtctattg atgagttttt ctgctgttaa aaacctctga aaatttgaca acgtactcta 74880
gagagagaaa gcgctgaaat aggcactgac gtactgctgg tggcaattca aaatgatatg 74940
caccctatgg agataaattt ggcaatatca agcaaacatt acatatacct ttgccctttg 75000
ttttgacaaa tctttgtttt agcaaaccct cttctataca tctataatga cattagactg 75060
cccagaatac aagaaggcaa ccacagtggg ccagtactac tactgggcta gatgtggtgg 75120
ctcacacctg taaccacaac attttgggag gctaaggtag gaaggctgct tgaggccagc 75180
ctgggcaaca tagtgagacc tcatctctac aaaaaaaaaa aaaaaaaaaa aattagccag 75240
tcatggtggt acatgcctgt agtctcagct actcaggagg ctgagatgga aggacaggtt 75300
gagccttgga agtggaggct gcggggaact atgaatatgc cacagcactc cagcctgtgc 75360
tacagagaga gactccgtct taaaaaacaa aacaaaataa caacaacaac aaacaaagat 75420
agatgcatag agtttttcac tgttgcacta tttatattag ccaaaaaccg ggaaacaacc 75480
tgaatattca tcaagtgggg acaggttgag taatcatgtg acatacataa attgcagcac 75540
tgcacacttg agaaaagaag tgagaaatgt ctctatttcc tagtgtggtt tgctctccag 75600
agtatactgt taagtgaaaa aagcactgtg gcctcaaatt tatctataga ttctatacaa 75660
tccccatcaa aatctcagct ggcttctttg cagaaattca caagctgatc ttaaaatgtg 75720
tatagaaatc caagggactc aaaattcaat aaattcaaag actagccaaa acaatcttga 75780
aaaagaagag caaagttgga gggctcatac ttttcagttt cgaaagttgt tatgaagcta 75840
caataatcaa gatagggtgg tcctggcata aggataaaca tggaacagaa ttgagcatct 75900
aaaaataaag cctcatattt ccagtcaatt gacttttaac cagggtgcca agaaaattca 75960
atgggggaag aatttgtctt ttcaacaact ggtgctggga caactgtata tccaaatgta 76020
aaagaatgaa attggaaccc tacctcacac catgtacaaa attagctcaa aatggaaaac 76080
agaggtaaat ataagaactt aatgtataaa attcttcgaa gaaaatacag aagtagatga 76140
tcaagacctt gtaatcacta attgttcctc agatatgacc ccaaaagaac aagtactaaa 76200

-continued aaaaaaagta gacaaattgg acaccatcaa aattgaaaac ttttatgctt tttatacttc 76260
aaagtcacta tcaaaaaagt gaaaagtcac cccagagaat ggggagaaaa tatttgcaaa 76320
tcatatatct actaaaggat gtgcatttac aatatacaaa ggggccaggc gctgtggctc 76380
atgcctgtaa tcccagcaaa tcgggaggcc aaggtgggtg gatcacctga ggtcaggagt 76440
tcaagaccag cctgatcaac atggtgaaac cctgtctcta ctaaaaatat aaaaattagc 76500
tgggtgtggt gtcaggtacc tgtatcccca gctacttggg aggctgaggc aggagaatca 76560
cttgaacctg ggaggtagag gttgcagggc gtggagattg tgccattgca ctccagcctg 76620
ggcaacaaga gcgaaactcc atatcaaaaa aaacaaaaaa aaacaaaaaa aaacaaaaaa 76680
aaaaaaagaa caaagatttc ttccaagtca ataataaaaa cagaaaatgc aatttaaaaa 76740
tggataaaga atctgagtag ttttacatta aaagataaat aaatggtcag tgagcacttc 76800
aaaagatcct gagcattact aaacattaga gaaatgcaaa tcaaaatcac aatgagatgt 76860
catttcatac ctattgcttt ctttttcttt tttttttttt ttgagacaga atcttgctct 76920
atcttccagg ctggagtgca gtgtgtgtga tcatgaaaat ggctcactgc agcctcaaca 76980
tcctgggctc aagtcatcct cctgcctcag cctcttgagt agctgggact gcaggcatgt 77040
gccaccgcac cagacaattt tttttttctt ttgtagacac agtgtctcac tatgttgccc 77100
aggctggtct gaaactcctg ggttgaagca atctttctgc ctcagccccc caaagtgctg 77160
taagtatagg tgtgagccac cacactgggc cagtactatt ctttaaaaaa tgggaaataa 77220
caagtgttgg agaggatgta gagaaactgg agcctttgta cattgatagt gggaatgtaa 77280
tgtggtacag ccactgaaga aaacagttgg acagttcttc aaaaagttaa acatagagtt 77340
tccatttgat ccaacaattc cgttactcaa tatttactca aaataattga aagcagggac 77400
tcaaatagat acttgcacac cagtgttcac agcagcatta ttcataatag tcaaaaggta 77460
gaaataaccc gaatgtccat caacagatga atggataaac accacatagt atgtgcctat 77520
gatggaatat tactcagcct tataaaggag taaaattctg atatacacta caacatggat 77580
gaaccttgaa atcttataat aaatgaaata atccagacac aaaaggacca atattatatg 77640
attccactta gatgagatgc ctagaacaga caaattcata gaaacagaaa ataaaataga 77700
ggttaccagg agttggagag gaggaataag gagttattat taaatgggta tagagtttct 77760
gttagcaatg atgaaaatgt tctaaaaatg gacagtggtg atggttgtag aacattctga 77820
acgtacatag tgccactgaa ttgtacttaa agtggttaaa atgataaatt atatgatatg 77880
tatattttac cacaatagaa aaaaatacaa gaagttacca gtggggaaaa ggagggatta 77940
cagaagacag ggataacagc acgacttttc tcagtatacc ttgtttttcg tatttgactt 78000
tgaaaatatg tacatacttt atataactag aaaacaaaat taaatcttaa aacaatccca 78060
aaaatggaat gtaaaaaaaa tgaaaccaat taatctaagt atatatccag tttgtggcat 78120
aaccacacaa aaatgaacta ttccaagtga cttttgaaca gaaaattact atataccatc 78180
agtagaatat atcctaataa caagaaagaa cagcaaaaat atcttaaagt gttttcagta 78240
atggcattgt tgggggtaat gttgatactg ttattttgaa agtgttgagt gtatacagtg 78300
ggatagaacc aacaagtatt tataatgata tcattgagaa ccaagatttt cattgaggga 78360
gaagactgat gaagttaaga atttctgtaa tcttgaatgt aaactgaaag cattattatg 78420
aaatgtgtga tgtgtttatc ttagtttacc tttgaatatg tgtatattta taactataca 78480
tctatagcag cagacacttc tgtcacccag attgtctgaa acaggaaata tacaagatag 78540

-continued

```
ccagcaatat gttttcatat tctacagtta caaagctgtc aaaacttact agggttatgt  78600
caaacaaaac atgatctaac atgactatgt tcctactggc tgaagaatga acattatgaa  78660
ctgaacatca ataagaataa tgacatcaaa cccaggagtt cattataata tatttttaag  78720
tatattgatt gcttttggag ggttctagga aacaaacaaa tcattttgaa aagtggtaaa  78780
taaaggaaag acttcagttc aagaccagtc tgagcaacat agtaagaccc catctctaca  78840
aaaaattaaa atatcagctg agcattgtgg tgtacatctt tagtcctagc cacttgaagg  78900
ctgaggctgg aggattgcct gagcccagga gttcaaggct gcagtgaact atgatggcac  78960
cactgtggtc cagccagggt taaatagcaa gaccctgttt ctggcgaaaa aaaaaaaaaa  79020
aaaaaaaagg aagacttaaa catacctttc ctatatgaac tgtgcctcgg agtaactaaa  79080
taattgatta aagcaagttt ctctgtataa aagtactcca gctaaaacat taaggagaaa  79140
tgatagaatt caaatatcac aacccctaag gaatttttgc atcaagacaa caataattaa  79200
tgactgataa caccacacac agaatacaga cttattaatt gtataactcc tgatcaagtg  79260
cataccacta tctgtgaaat agttttgcca aaaaaaaaaa aaaaaatcta acctaaactt  79320
gaacaagcct ctagatctaa ccaccaattt ttacaaacta caaagaattg tggaatgtat  79380
agattgacgt gacatgaagg caatcggcaa agtccagact gtgaaaatac tacagcaaac  79440
atttagggtc tttttttctt tttctttctt tttttttttt tttttttttt ttttgagaga  79500
gtctccctct gtttcccagg ctagagtgca gtggtgtgat ctcggctcac tgcaacctcc  79560
gccgcccagg ttcaagtgat tctcctacct cagcctcctg agtagctgag attataggtg  79620
cgcgccacca tgcccagcta atttttgtat ttttagtaga gacgggtttc accatgttgg  79680
taagcctggt ctcaaactcc tgacctcgtg atccacccgc ttcagcctcc caaagtgctg  79740
ggattgcagg cgtgagccac tgcacccagc ccacccttgg tttttttcaa caaaaaatta  79800
ctagaaataa aagaataata gttggtcaag gaagctgtag aataagaaag actgccacat  79860
acatcaatgg cagtgggcgg gctttgtttg aatccaactc tagcatgcaa acatttgata  79920
aaaatttctt tatttaaaaa gaaaagttta caaaacaatc agaaaaaata aaaaagattg  79980
aggatctcag gacaactact agcctagata atttataaag attagataac tgactcattt  80040
ttattagttt ctttcctaat aaggcaatat gtattagata tatcagagta gaaggaaata  80100
tttttcttac atctatttgg ctttttaaat ataaacatat ataagtaaaa accaaaatga  80160
tttataatcc caccatttat gtaactatct tattttcaaa aaaaattatg caaatactag  80220
catttgtgtg cttttttttcc ttttgtgttt gtgtgtttat atccttttta aatatatcct  80280
ttttatgtac ctaagcagct gtatactata ctgcatacta tagtgtgaac tttgttcttt  80340
tccttcgtct ttacaacata ttgtggaaaa cgttccatat cagaatatag atatgccttt  80400
ttgtagccat tgaaatgcaa agaaaaaaag aatatagatc tgtctcattt tttaaaaatg  80460
ctgtataatc tgtagcacga atttactata atttattcgc atgctccctt atcgatgggc  80520
atgtaaattg tgttaatttt atatgatata atgagtatcc ttatatgtat atcttggcac  80580
agtttttcga gtgtatccat aaagtttctt gcaatgaaat tatagggcaa caagggtgtg  80640
gtggctcttg tctgtaattt caacactttg agaggctacg gcaggaggat tacttgaggc  80700
caggagtttg agaccagcgt ggacaacata gtgagccctc acctctacta aaaattaaaa  80760
aaaaaaaaaa gaaaaagttt ggtatggtga tatgtacctg tagtcccaga tacccaggag  80820
gctgaggtgg gaggatcatt tgaacctggg atgtcaaggc tacagtgagc tatgactgtg  80880
ccactgcact gcagcctgga tgacacagtg agaccctgtc tcaaaaaaaa aaaaaaaaat  80940
```

-continued

```
tacaggccaa atccatatgc ttttaaagga tatttttgaa ttgttctcaa aaagaggctt  81000
caccaaatta ccatccaggg tatacaagat acccatttct ccatgtcctt accaacagtg  81060
gctctcatca agccttggtg gaaatgctct catactgata ctttaacgac taaaagtcat  81120
gacatatctg cttaggttgt aaattgcctc cctctaaact tatacagaga gaatttagag  81180
tgttgtctca gcttggttcc agtgttatcc aagccattaa cctttgtttt gccttagatt  81240
gtcacattgt ggtatttcag ttaaaaaaca aaaacacaac tggtactttt tttttttttt  81300
tttttttgag acggagtctc gctgtgtcgc ccaggctgga gtgcagtggc gtgatcttgg  81360
ctcactgcaa gctccgcctc ctgggttcaa gccattctcc tgcctcagcc tcccgagtag  81420
ctggacctac gggtgcatgc caccaccccc ggctaatttt ttgtattttt agtagagaca  81480
gggtttcacc atgttagcca ggatggtctc ggtctcctga cctcgtgatc cgcccgcctc  81540
ggcctcccaa agtgctggga ttacaggcat gagccactgt gcctggccac aatggggtat  81600
tgtttttata gactgttgaa atctgccttt ggaaaccatg ggtttgctgt gttgttatgg  81660
tgaatgaatt aggtgcacaa tactagtttt taaaaaatga acttcacact aggtacacct  81720
tgaaaaatta ttccagagct ataagaagag ctataagaag aaaaatatga tgggtcattg  81780
ctccaaagaa aggttttaaa atgtaaattt gtacttaatg aataggacag tgtaccctaa  81840
cctcctcctt gctattcttc agggatctct tctaacaagg gctaatgctt cacctaagct  81900
gtgaaaagcc tgctgtgagc actccctgtt cagggtcaga aaaacacaat gaactgttct  81960
atcattttag gttctaggac aatgttctct tgcttttcct tgctcagaat ggacccttgc  82020
tggggtagca tcagaatgag gatctggtgc aacagttctg caataggaag taggttcccc  82080
tactatcatg gttttcaagc ttttttgact gcagcccata acgagaaata atgtttttca  82140
tcataaccca gtagatatac tcacagagac acagtatatt cataaaaaaa atcataacgt  82200
ttaaccttat gttaatagca tttatcctat gttattcaat ctattttatt tctttttaaa  82260
aaatgctcat cacagttaac taaactgatt tcacaactcc ttaaaggaat ttgactcaca  82320
atttgaaaaa cactgcattg tagaatattt tagagtctct tcccaaccct cagagtcaga  82380
tttatttcaa gatggcccct gtaagacagc ttcaagcttg tgagtgactt tcttttttct  82440
ttttacttct ttaccattta ccatgactcc caaataagtg actcttttgg cttatttggt  82500
aaccatgcta atttctacac atagaaccta gagcatttac ataagaccca cccaaagctt  82560
gtgttttaac cttgcttctc tcctttcttt ctttgattca ttgattatgt tttctattgc  82620
tatctgttca atctgtgttt caggcagtgt acaggtactg aggcaacaat ggtgagtaaa  82680
agcaagcatg catcctgaga tatactggga atgaaagaag ctaatccaaa agcatacagg  82740
aaaatatttt caaactttga taaattctgt gtaagcatat ggcattgcac gtaacagggg  82800
aaccgcattt aatatggagt gttggaaaag gcttctgtga gaagtgacac ttgagctaag  82860
actagaaaag tgaaaagaat ataaccaggt actggacagc atcatgagtg caggcacagg  82920
tgacatcgta tcacaagctt ctaaggctga agggggcgtg aattgctagc tggagagtgg  82980
aaggaaaaga tcttcaagat aaagctggaa aaataaacag ggccaggcct cataggtttc  83040
tgtagaccat ggaaagaggt gaaggttatt ttgagcctgg atgacatgat aaaactcaca  83100
ttgtaaaaat ataactgcaa ggtagagaat ggattgaaga ggtccaagat tacgcagaca  83160
gagctatgaa cagcctattg caatggtctg ggtcaagcat gatggagtag ggttggaata  83220
gggtggtgaa cttttattag ttatcttcct tactgagcac actttgcaat gaatttcaaa  83280
```

-continued tgcactggga ccagacttgt taattttgga gctgtcgact aacaaataag taagccatga 83340
taacccacca aagaaagttg cagaaatgca agagcaaggc tgtgatgaat ggttgaggta 83400
caaggaagct cttactcact cattttaaaa aatcagatga tatgaagttg aatattcaag 83460
atattgccca attgtgttat gttcacatat tttactgggc atagttctgg ataataaaat 83520
atttatcttc tctccctctg agaattaaaa atctgagatg gaggcctctg atgtgccaaa 83580
ggagaaagat gatttttaag agccaaacgt gcctccatga ttaaatacat ttatatttct 83640
actggccaag gaaagcatgt tgcctcttgc ctgggcctct tctgtctttg attaataatc 83700
ccctgcacat tcgaacactg ttattaactt gccacattgg cacctttatc actttgttct 83760
ttgaataaaa agagcttaac ccaagtccca gtaaaaatgt tcattcaggc tgaatttaag 83820
aaatatattc tgctcccttg gagttaaatg gaataatagg agaagagtcc acttgactgt 83880
taccaggttt ctgaactaca cctggcagcc taacatagtc aacagcaggg agtgaatcac 83940
atctgctctg tatgctaacc cggtctgagt aggtggtttg cattggcatc taattatttt 84000
tatggttagt actctcttct cctgactttt ggtaccaaac cctcacacac ctcattatcc 84060
ctattgcatc tgccactcat cctaaaaggc cttgcttaca tcccacaatc aatcattctt 84120
tctcttacct tagcggagaa cagcctgagg tgcagcaggt cccagatatg attacagttt 84180
caccagttca atattgttta ctgaatggcc tgtaaaacac agtgaatata atttgtgttg 84240
ctgcagttgg aaggcttaca taccacattg cctagaacca aagacctttc ctcatgccca 84300
atacaccaat ggcagagatg accagccagt cactgcatcg agatgaagaa tagtatctcc 84360
caaaaggcaa taccaagcat atgtttctca ggcttttaca aaacactttt taagtttctg 84420
tctaaactcc tctaagagct aaatttttcc aagacgtatt ctgtgtaaat cagtcttcag 84480
tgataaacaa aattttattt attgaactat caggtgctat taatgctaat tagaatgtta 84540
ccacctcaga ttaatgcttc gttgaatttc tttttttttct ggtgtttgta agtattcctt 84600
ttctccttca gcacaatgat aattataaag aagaaaatgt actaagtgca tttctcccat 84660
catttgatat tttacattta tttcctcagc aaataatttg tcacaaggaa gtaatgtgca 84720
tccctgggca ctgcttgcag gcacttaatt cttgattcaa atgaaacttt aaaatgtttt 84780
atccatgatg ttatgtctaa agaaacatgt caaagaaaca tgtcagagaa cttgactttg 84840
aatagaaatc atggctgtgc tttgagggaa acaaaataaa tcacagaggt aggaatgcat 84900
agttacaagc tactgtttgt acacagcaga gaccaattct actctctgtt ctcatttcct 84960
cttctaattc ctcatcccta cactccttcc tgtgtgaagc ccatgtctga tcctgcctaa 85020
ttcagtgact gggggtcact gcagatgcgt gcacagggtc ctgttatggg atccggattc 85080
tgccgccttc tccagacaca agtttcccct catacctgtt gttccagcaa atccaagcta 85140
ttctcctttc cccacttgca ctaggttctt tccctagtct gtgcttgcat gcatcctatt 85200
tttctctggt atttttcaaa ttttactttg gcacctggag aacgttttgg caccaccatt 85260
tgtcaggtgt ttaactttgt gcatttcctc gtgtgaatgg gagcgtaggt ccagcatcgt 85320
gaggaaggac tggggtcaca ctcacagagt gtgtcagagc ccacaaagtc actcagtaga 85380
aacatcagga gatgttagcg ttatttttca gttattacta tgatcaccat tcctcaaaat 85440
tgagctctgg ttttacctct cctgacaagc tttcctttac ttccccatcc caaagacaga 85500
gtgaattact tccttgtact gtgtgcttag ttcttcattg cccttcttat gtgttttcct 85560
tatcattaat gtgggacatg atctgttata atgttgctgg gcaatgatgt tgttagtata 85620
gaaaaatggg catgaggata gttcaaggag ttcccataac tcatatttta tgggccttct 85680

-continued

```
gcaatatatg gttaggatac aaccattagc aataaatgga taacttgggt tctcttcatt  85740
ttctgtgttt tattgctaca tgaataaaca gttattgagt gcttactgta tgtcaagcat  85800
gacaataagt attataatta ccctgtttat tcatcagtat gatcaaatgt ggttattatt  85860
cccatgtgac ccatgaggaa actaaaggcc taaggtgata gagctagtga tagaccacct  85920
actcccaaag tctgagctct tagctcaaga acactctgct ctgatctgta gggtctcatt  85980
tgtctctgag actctttaat gtgtaaatat atttgataag ttttctcttc taatgtaatt  86040
ccaggtattc cttccaagat gaggaagaca tgttcatggt ggtggacctc ctgctgggtg  86100
gagacctgcg ttatcacctg caacagaacg tccacttcaa ggaagaaaca gtgaagctct  86160
tcatctgtga gctggtcatg gccctggact acctgcagaa ccagcgcatc attcacaggt  86220
cagtcaagtc caaggagatg gccatgaacg taacgcaagg agagaatcca caactggcta  86280
ccttcaataa attcttattg aacatgacat ttaatccccg tttaattctt gaaacagtac  86340
cctgaggtag gttgattgtc ttcattttgc agattttgta aaagactgaa cacatagagc  86400
ttaatttgcc aaaggtcaca gtaaacaaca agatcacaat caatgaattt tggtactatt  86460
ttataactaa gcttagacaa aaaggagaaa aggtgacata tagaaaccta ataaatatta  86520
agtaaataat taaatggagg tagcacatgg agggaaagaa atagaatgaa aagaaagaaa  86580
gttctttggg aaaaaagctt gagtctttct aatatttgct gtcctgcagt ctatattaaa  86640
ttaatcccta atgtatgtac tgcaaatgga ggtagaaaaa gcaatagcaa tgtcttctgc  86700
atttagagca ttagtagtaa ataaagacat acaaataaca taagaaacca taaagctata  86760
gagataatac agagaaaagg ataatacttt atagtaaaga aatttgtagt ttcaatgatg  86820
attttatata tagtatctca tttgatctct gaaataacct gagataaatg atcagagcag  86880
atataattag actagaatta catatgaaaa aatcatggct tgtatacatt aaattatcac  86940
ccagtttact tatatgaatt gtaaacatat caaacatcaa aacatctact aatcaacatc  87000
aaaacaacta gtgtttactg gttgatgact tactatgtgc caggcactcc taggtacttt  87060
atgtacatta gtttattaaa tcctcaaaac tcagcaaaga ttccacattt cattataata  87120
ttcccattac acagataaag aaactgtctc aaaggtttgc caaggacaaa cagctaacaa  87180
atagcgtagc caggatttaa acctagatct ctctgacctc aaagtcagaa ttctatgata  87240
ccaattcaca ttacttacac atatgaaata tatgcattaa ttgattatac atcattaaat  87300
gaaaaatcag tacatgtgac tctgctgctg tcatctctaa tccttgaaga atttgctgag  87360
attttaagta caattatgtc tcaattagta aaaagttggc tagataaaat atttgaccac  87420
caccagttga cattgacctg taatttattt tttaaacctt tatatatata tatatattta  87480
gagagatggg gtttcaccat gttgcccagt ctggtctcca acttttggcc tcaagttgtc  87540
ctcctgcctc agcctcccaa aatgctggga ttacaggagt gagccactgt actcagccta  87600
taatttatct tgatgagtac agagcctata gatgaaggtg aagcatcaga atttatagat  87660
tctctgtgca ggtaccacag gccagttctt ttatttattt ttattttttt gggccttggc  87720
cctctacatt tagtttttat ttaatgttcc ttctttggaa gggcctgctt gtattggaag  87780
tgtgctcttc aggcaccaga taaatgaaag cagaccagtt aattacgtag gatctcagaa  87840
gtgaatttgc acacctggtg tttttttcaa taactagaaa tcctgttctc aagcactcat  87900
cttcccatac tggttttctg gtccctcata gctctttctg aagagagact gttcatactt  87960
gttagtctat ggagtccctc tcaaaacttt cctgctcgtt cattctccca aaaattgcca  88020
```

-continued accacagcct atcttggttg tgacatcaca gatatcagaa agaaggcagt gaccttgaga 88080
aaccagcatg gcctcagagc cttttcactc tctctccttt tcctgtttga aattgggttc 88140
tgtcccttct ttctttaggc ttcatgttct tggtcatcaa aagaccaatt ctctgagcat 88200
tttctccatg tacttagaac tgtgttccaa gaggaattca ggagggaaaa acaacaacaa 88260
aaatattgat acaatttttc cccaaggagc ttactaacac ccaatactgt ttttctgttc 88320
tttccctctc tttttttctc accgttatca tcattttgcc acttaaatca taaaccaagg 88380
attaactttc tggtttttttg cccttcaatc acatccacag ttattactta gtgcccgttc 88440
tcagaagggc ctttttgtac tgaaatgtct cctcaccatg gtaaaggtat ggaaggcaaa 88500
caggatgaca ttttgagtgc agtgttaaat tgaggtgaca tccttctggt gtcaaaaact 88560
attcaggtgc atttctgtaa cctctatgca cctctccccc cacctcccag gtgttatatt 88620
ttacaggctg tcataccctt ttgtacctct cctgaggagt tgtgacattt ggtgtataat 88680
taattcattt gtctccttta taaaattgtg aactctgcat gttttgcttt tcattgtata 88740
accagtatgt gaaaaaaata tgagccacat gaatgaatga ttgaccagaa gttcaggctt 88800
acaagtagga aatattcaaa tataggacat taaatccaaa ggcctcagac ctacttgtac 88860
cttggtcttt acattaatca tgttatttat catccaaacc aggatactct gagagctaaa 88920
gaggatgcta ttaatattaa tagcactggg aagagtcaaa agccataaat aatctaggca 88980
attcaggacc tatgtcaaca tcattaaggc ttttcaaggc agtgtttttt ggtttttttat 89040
tttttgtaga gacagggtct ccctatgttg cctaggctgg ccttgaactc ctgggctcaa 89100
gcaatcctcc tgcctcagcc tcccaaaact ctgggattac aggtgtgagt caccatgccc 89160
agcttcaaat agacatttta attctgacag tgttctgata accaggattt tctgctctca 89220
gaataccaga tatcaatttg aaatggtgtc aaatagcttt ttaaaaagtg tacatggtaa 89280
aagaagcagt gatccctttg tttaaggaat ttaaatgata ataactttgt caatctgaga 89340
ctaagaactc ctgggccaga gagtgcaaaa agcaatacag aagagataca ggcttctgaa 89400
tactgtaatt cttttttaaa cctccttctt caaaagaatc agcccgattc atgttgtact 89460
tgaattcaag ataacaaaac accttttagt tacttagaaa gattagattg taaaatatgt 89520
gctgagttcc tagaaattaa aagtgagaat gaaaaaaaga atcaatgaaa gtacagtaga 89580
tctcccggac aaggagagac catctgcata aaactgaaga tataaaatat gtgacttcct 89640
acttttagat taaaatctac attttgcctt tggacatggt agaagattca aaattacccg 89700
taaacagtca gcactacgtg gaagtaggag cagcagtagg ctgctgtttg cttagggttt 89760
cctgggtacc aggctgcctg ctaagcactt gtgagttatt tcactcagtc ttcccatagc 89820
tccaggaggt ttatggcact ttgtccccat ttcaccttcg atgaaactct ggttctgaaa 89880
aattacttgc ccaagtttgc atggctatta agtagggaaa gcatcatgtt taggaaatgc 89940
agagctcttc accactctcc agcctgcaga tgctcagcat ggctgcagct ctgaggggag 90000
cgcgggacac ctatgcatgg ccacctgcct caggcaccca cagacgaaag tggtacatgt 90060
ggaacggaca gacagagaac agcctaaaat tggaagctaa attgtgtgag aaagacaagt 90120
acttcagaga agatagtgtg gagtcgcaaa ataagtttca tgagagctca tacagaaaac 90180
agcctaaaac tagaagctaa attgcgtaag aaagacaagt acttcagaga agttggttgg 90240
gagtaagaaa gcaagtctca tgagagctct gaggggtgta aatgggactt ttaacagcca 90300
aagcacacag caagtctagc ctagcaagag gagctcaatg gatggaagtc ctcacttgtt 90360
tccctgtgtt aacatagaag gggtcttttt taaaattttg ttttcacttc agcttttctg 90420

-continued

```
ccagaaatgt ctagtgtagt gatgttttaa aaaaaaccta agtatctgtt tccgccacaa  90480
atccccatta agacataaat ggagttttat tttgtggatg tttaaaaatc catggacttg  90540
aacttttggt agtttcccaa atatgtagaa tattcagcta gttttcttca atttcagaat  90600
ctttcttttc tatcattgtt aaagacacag ggttgcataa taaccattaa gtttgaattg  90660
tgcaattaga caactttctt attagtcaag aagtcaaact ttttgtgtga gtacagcttg  90720
aaaatcagct ttagtttcca aagaatggcc agtttgaagt ataatattct cttttgctta  90780
cttgaaatct gcaaataaat gctttaaatt agggacaaag tgattatttg cttttattta  90840
aaaaataagg gaaacaaaac tcattacaat ctcttctaca gggttagtac tattctattt  90900
gttgattgcc tcagcctctc caatgaacaa tctggtggaa agtaattatt taatattata  90960
atccaaagac aaatttctgt ttactccctt gtcagatctt aaagtagact caattatgaa  91020
tttaagctaa tgagatggat tgtatgggac aattaaatag taagtcattt tgggtcaaaa  91080
taccatttga gaggatggtt gattgttttt tccctctgag aattaccccc cactataacg  91140
aggttataac tcactgtttg ctaaattttt ataggaatga gataaaaaat ctgattagag  91200
taatttgtgc aagtaattac agtacaacag agagagttgc aaaaatttca tttcccattg  91260
agtaccgaaa tgttgaagag aaataaaaga agatttatgg ctgtgtagaa aaacacagga  91320
tggtattttt atttatcacc tttgccttct ttgctgttct cattggaacc aataactgat  91380
tccagattca tcttagggac tgtataagat gcagatagaa attatttctc acacatgacc  91440
tcttgggctg gagtagctgc ttatgagatg ttcctatcat tcttctagaa atcagtacct  91500
tgacagtgaa gaaaaaaatc ttaggaataa tgcttctagt ccaaatattt attcaaaaat  91560
tatttactgg gtacctattt gccagtgttc tgaatgccag gctcccatgg ggaagaagac  91620
aatccccctg tcataagaag ttgttaatat tatagtgtga aaaatagtca agtaaacact  91680
tcaacattaa tatcaaaagg cttttaaatg ttgtggcatg tgccataaag aatgaaagct  91740
gttatgtgca tatcctgagc gatgcatgtg tgcctgcatg cacgtgcacg cacgcacaca  91800
cacacacaat atgcttagtt gcgtcttccc aatgctcatg gttatacctc taattgtagc  91860
ctctggacca tgatattcta tataaaaagc tgtctcccct ctccaatctt aagccctcat  91920
aagtggatac tacacctcac ttatgtttta atctccagca acttgcactg gatctaaact  91980
agagtgcttg ctggataatt caatgactga acaaatgaat gaggacagta tgtatatgta  92040
accattgggt gagtgcagaa ggtaaaagtt gctgtggagg atgtcgtctt cagcaaattc  92100
tcaaatttat tccacacatt cctctgtgca tccacaacat gtggggttct ggtctgcctt  92160
tccactatgc tggattagtt ttgtatgctg tgtaacaaat tcctacagtc ccagtgacca  92220
gaaagaacat acctttatca gctcgcagtt tctttgggac aggtgtctgg gcacagtcta  92280
gttgagttct cggcacagct gccattaaga tgtcagccag aactgggttc tcttctggag  92340
gctgaactgg gcaagaatcc acttccaagc tcagtcagaa tgttggcagg aggtatttcc  92400
ttgtggctgt aggacccatg gtggctactt tctttaaatt taacaaggag aagaataccg  92460
tagagtaagt tggctagaaa gaaaacagag tacacatact tgaatgatga tatataacat  92520
tgtaacataa ctcagtcaca gaagtaagac catcacatct gccatgtaat gtcggttaga  92580
aacaaaccat ggaaccagcc catgctgagg ggctggaaat tatgcaaggg tgtgaacacc  92640
aaaagctggg aatcctgggg gtcaccgtac acagtctgtt cacatttcct ctaaagaagt  92700
tgcactgcat cacagttcca taccaatttc tgctatgacc ttaaatatag ccctgaactt  92760
```

-continued

```
ccctgtcaag gaagaagtga ggaggtttca acaagtgatc agtaatgatt cttttatgtc  92820
taagattcta ggatgatttc ctctctgccc tggtaggctg ctcttcaaag tatgacctcc  92880
tcattgtttc tctgctctac cacacactca ttcccctcca agaaggctgc ccacctgtaa  92940
tgacctgtct acagagcctg tgatagtgac ttgtgataaa tggctattag cacatttacc  93000
aatcaaggtc ctgtttgcaa ttcggttgtg ggtcaaaatt atgtttgttt taactgaggt  93060
ctttagttta tttcaggcag agatctgggc tggagtgtca cctttgtgtc taattctcac  93120
acactgtact atcttagcag tcacatttta ttttcttgag atgataattt ataggaaaaa  93180
ataagacatt tctgcagcta atcattttag tcaatgatca ttgagtgaca ggtgagctcc  93240
taataaataa atttgccaac acagtgacac ctcaggtttc tgaagcctgt gggaatgagt  93300
catctggaaa gatgtttttc taattcctgg aagtatttca gagattttta actatttaat  93360
ttatactaca aagcacctat gtcacttttt taatgactta ataggagcta tcacttattg  93420
tttacaccaa gaactgcgta ctgtgctaat tggcaggttc cacacaccac ctaacttgat  93480
aatcaacaat tctctgaggg gattaagcaa cttgccaata tacagtcagt atatggggac  93540
cagattcaaa tgtagaatta ccttcttcaa aggccctgtt ctaggtatag acgctcttac  93600
tttcactctt ataataataa gatatcctca aggtcagatg agctgttcag tgctgtttac  93660
caaatagcat aaaacttcag tttagataca tattttagtg ggtaggtact atatgttaat  93720
ttgtgctccc tcagaaagat ttgttgaagt cctaacctcc agtgcctcag actgtcatct  93780
tttttggaaa gagggttttt acccagataa tcaagttaga atgaggccat tagtgtaggc  93840
cctaatccag tatgactggt gtccttatga aaagaggaac tttggacaca gaggaacata  93900
caaagagtga agatgatgtg gatgtagaga gacacaggga ggatgacagg tgaagatggg  93960
ggattgatgt gatgggtcca ccagccaagg aatgccagag attgccagca aacccacaga  94020
agctggaaga ggcctgggag gagtctccct gagaagtttc agagggagca tgggccctgc  94080
tggcatcttg attttggact ttctaccttc agaactgtga gaaaattaat ttctgtgttc  94140
ttcaagccac tgtttgtggt actttgtgac agcagctcta acaaatgaat gtagtaaata  94200
tgtttctatt gttttctttg ctgctaattt tttaatcttt gcttctctag taggtgctac  94260
tcagagcacc ttctgtcctc actcctaaca tgctgcttac aatacattat gggatagaag  94320
accaagtgac aaaacttgtt tgtattgttt gtaaaattaa actaaaccaa gagaatattc  94380
agtaagtcaa gtccattggc tttagtatag ggtaacctat tttaatgttg ccagagactg  94440
tctttgctta cttttgtatt tcaggtttgg gaagatattt tcagtatctg taggcttttt  94500
ttttttttat accacttctc ctgtccaagg tgtgttgttt tgcttttata tatctattag  94560
gaaagttaaa tcttttccat tttaccaaag ctacatgtcc agtatgagaa catttaaagt  94620
ctaaaaatta tctgattact tatattgtat gtgttctgct tgatgctggc tttctttcag  94680
tgtattgata aaagtttcta tttgttgcag tggaataata gactttggtt ttaggctatc  94740
atctgtggag tgcttaagaa aatgcccttt ctttttgttt tggtaaatct tcttttcagt  94800
agaccacaag cccttgcaaa tgttctcttt ttctaactct ggtagcagaa ggaccacttg  94860
agcctcaaaa caaaacggca gtgcagtaat gagggtatta ggttgatgtg ttctattcag  94920
cacctgctcc cgagctaccg aataatgaat gagcatgaat tacacattgt gaaaacagga  94980
gaatctgcct tctttgtgtt gtatgcatca agcagtttca aaagggcttt gcaattgtgt  95040
ttctcacaca aagccaccca tttgtgaaaa cccatgtgta aaggcaaaga gaactgtctg  95100
tgtacaggtt aacatttaac tagactggca gagcttttaa taatttctat aaggttaatg  95160
```

-continued

```
gcttcgttaa tatgcaacct gtgatttggt ccaagttaaa ttttactttg cccagaatac  95220
attataatat aaagcttaag ctttattctt tcaggtttag tcatttaaca cataatattg  95280
atcaattatg catgttggac acagagctct gaatagagct ttgaaatata aaactatggt  95340
tttagtcctc ttagagctat gatgtttggt aggttaggtg aagtagacac atttttgact  95400
tataaatttt cagcttacaa tgggtttatc agggcgtaac ccattgcaag ttgggagcat  95460
ctgtacgatg gtatagatat atataatgca tatagtttta tatcctttta agacaaaata  95520
tgaagatatt ttatttgctc aaatcttgtt acacagtttt ccactgtgat attcacatgc  95580
tgacagagag gctatttgca tggtgtttgt caccagcaat gaacagcagc atttgagtta  95640
tgtagtggct ctgccagtta ccagtggggc aacttgggca agacactaag cacctctgaa  95700
cctcatttgt tttatcagta aaatgaagat agctatacat acttcacagg ctgtggtgat  95760
gatatattct aatgaatata cagtcttaaa taaaaacatt caataaattc tagctactca  95820
tttatattaa tttattatac ccatttgctt tgagttatct tctttgcaat aagctgtggg  95880
aaaaacttac tgttccttct catactccag gatacatcat cacccaaatc attacacatt  95940
cttatataac gcaaacatta agaaagaaca ataatcttac taaaaagcag agtgtggtat  96000
ggtagagaga ttaagaggct ttggaatagt tacatcaggg atcaattagt gagctgtgtg  96060
actttaggca aattaataaa ctgaatttct ttaaattttg ttaaataggt ataataacat  96120
tatatataag aaagcaggaa aaatatgaac agctcctatt ataatgcttg caaaatcagg  96180
agtgcttaat aaatggaagc cacactgcga ttttccagat aattgtgaaa caactacggg  96240
ccattacaaa accataggaa attagaagtg aggagtaatt tggagactga caagctctac  96300
cttcatctaa aggcagaatt tcttctgcag tctccctaac aaggaatcgt tatacctcag  96360
ggatgggata gtcactacca cataaagtag ttcattttca gacatgcata accttagaaa  96420
gttcttctct tgatttacaa ttagcctcat agttctgttg ctgcctattg gagttttact  96480
acgtgtacag tcaggcaggg cttccattca gtcaccaccc attagtactg ttgtactagt  96540
aatttatgga tggcgtccat tcttactggt ccatgtccca ttctgatttg tgtttgtgcc  96600
atttttaagt gttttgaata ttaaccctgg tatcagataa acatggagtc ctgacttttt  96660
ccataatcat gaataacagt ggaatagtta catcagattt gtgtgccact gtggtcccat  96720
ctatgaaata gggataataa ttgtacctag ttcataaggt tgtttgagga tagtgtggaa  96780
taaagtataa aaagggctta gcctggtttc tcaaatattg caataaatga aacttagcat  96840
catgatgctg tcacaatggt tcaatgataa ttgaaaacat cgattcatca tttagcatcc  96900
tcagcttatc agtttctcac tatctagctc ttcttacact ggacacttcc taattattct  96960
ttcaatgttt tctggaagtt agttgaataa ttactgtgca ccagatacta cacagtagtc  97020
ccccttgatg catgagggat acattcaaga cccccagtgg atacctgaat acgcagatat  97080
ttccaaaccc atatatacta tgttttttcc cttttgtaca tacctatggt aaagtttgat  97140
tcatagagta agagattaac aataactaat aatagaacaa ttataacaat atgcagagta  97200
aaagtatgtg aatgcagtcc ctctctcaaa gcatctgatt gtaccgtact tacctatttt  97260
tgaaccacag ttgactgtgg gtaaaaagga aaactgcaga taaggggga ttactatact  97320
acgagtttta catgtaccat ttaactaaat cattacgact ctataaagta gatatgatta  97380
ttgtcctcag ttacaaatgt ggagggctga gtctcagaac gttctattac cgacatggtt  97440
ttggtcccaa cagaaaacct cataatggtt taaacaataa aagagattta ttatcttata  97500
```

-continued aaatcagaaa atccagatgt gtgctggact tggagggtat cttgattcaa caattcagca 97560
gtatcaccaa ctagctggtt tctttcactc tcttctctct tttccatgtg gccacttcat 97620
cctcagcttg ttcctccatg tgattgcaag aaagctgcct gctgcccagg gctccatgct 97680
aaattcttta aatctaaaga atcacactcc ttctcaaaac tttccccagg acagcaagga 97740
agctttttcc tcagaagccc agaacataat tctttctgat actcagtggc ttaaattggg 97800
tcaccagccc atccctgaac caataacagg gcctgtggga tgggataact cctacttagg 97860
cctgactcac ataatccttc cctacagtca gggtggagta ggtttcccaa agcacacaaa 97920
atacagtgtg tgtgtgtatg tgtgtgtgtg tgcgcacgtg catgcgtgcg cgtgtgtgcg 97980
cgcatgtgtg catgaatgtg tgtgttacag agaagtgaaa atacccagtt gaaaactgaa 98040
atgatgatta agagaatgaa gaatgcgtat tagaaaggca atcaaaatga ccattagtaa 98100
gctgcacagt cgagatctga gccttggtca tttgactaca gaattaatac tcttaaacct 98160
ccactatcta ctgcttccca aatcaaccta gaaatccctg gggttggata ggaccatttg 98220
tgtttgagac tattaccaac attactaagt actatactaa tatactcatg caacctaaag 98280
catatatatg tgaagtgtgt atatgtaccc atatatatac atacacactc atatactaca 98340
cacagtatag cctatacagg gctcatgttt aatcagcata cactggtctg gccctatcag 98400
ttgtatttca gtgtattggc tgatgaagag gtcatgccta agctttgctg ctactccagc 98460
ccctttccca atctccccct catcccccac cccttccctc ccttgaccca gcaactgaag 98520
tgctaactcc tggcccagga gaggtccttc agggcactgc tcctgggctt ccatcagcat 98580
cccttctgat gaaaggatga ctgtgctgtt ctggttgtta aatattttgt ccatcacctc 98640
tggctatttg taaatatata tacttacatg gaatactata tatgcccact atatttcagt 98700
aaactttact atgctaagct ctagagagtt tagatcattt gtccaagatt acataatgag 98760
tgactgggat tacaaccaaa gattgtgaag tacaatctta ggaggatgat acctagtctt 98820
taatcatcta accctgacag cctttcactt ctgcccccta ttccaaactg tttttcctta 98880
taattttccc tcactcgctc ttaacatggg tctgtttttt gagaccaata gcccatctgt 98940
gacaccctaa ataatatgtt acagaattat atgtataata tttttcccct ctccagaact 99000
tggcgatggc ccaatctgag agactgttat gtggcaaata attaaataca aactatggac 99060
catcaaaagg ccatgggaca ctgaaggagt tgattttggt ttcgatatac cgatttcctt 99120
gtttgctatt ttcatgtaca tgtaccggta taggattgca gggtgagcaa cttgactcca 99180
ggggaggcgc aatgaaggga tgtaattagc ctgttaaccc tgctaatgtc ttgtaaagtc 99240
attcaagtga gaagagtaga tacatcaatt cttccttgga tcctgccaca aggagcattg 99300
tatttccact ctgctattta tagttctcac agctggaatc agctggttca gcaggacatg 99360
gctctttttt atttaatcaa accaagatgc aatgaagaat ttccaaagta tgcatcctag 99420
aatttccctt tatcaccccc aaaattccat agtccctctg aaatcatagg ctcgtaacag 99480
gcataaatca cttcttattt attactctta ctctaataca tacacataca cttactggaa 99540
agtcaagttt cttagttggc caatggtaaa tgtggcgcat ctggcacaca gggtttgttt 99600
gggttgtttt gggggtgggg attggttgtt ttgctttgtt ttgttttctc ttctcttctt 99660
aggggaaaaa gacatgcagg gcttagtatt ccaacaattt gagaaaccag ggggctggga 99720
ttcattcatt tttatgacaa atagttactc gagcacctac tttattcttg ggtactttta 99780
tgagtccagg ggctgctgca ttgaacaata cagaaaagaa gtcctttcac ttagaactta 99840
cgtcctagtg ggggttgggg gttgggggtt gagagaatga agcattctta caaagaatgt 99900

-continued

```
taaaagcgaa ctatgggcag gaattgagga tatgagtttt gatgtataaa gaaaaagtga  99960
caaggtcaat aattggtggt cttagtgtga tagatatgcc agtttggaaa ttgtattgaa 100020
taaatgctag tcaggggcta ggctgtagtt atgaaaagga gatgattaag gaagtgagaa 100080
taaggaaact attggtgtgg gacggatgaa aagattattg gaggcaagtc aaggaactga 100140
gaggccaggg tgttagatgg agcattcatg tagacactga agtcaccaag aataataaat 100200
aacaagtaag agggaattca tcattagcta tctgcttatg atatggatgt gtttttgctg 100260
tgtccccatc caaatctcat cttgaattgt agttcccata atctccattt gtcataggaa 100320
gaatgcagta ggagttaatt gagtcatggg ggtgggtttt tccaatgctg ttcttgtgat 100380
agtgggtgag tctcatgaga tatgatggtt ttataaaggg caattcccct gcacatggtc 100440
tcttgcctgc ctccacgtaa gaggtgcctt tgcttctcca tcaccttctg ccatgattgt 100500
gagggctccc cagccatgtg gaactgtgag tctgttaaac ctctttttct ttataaatta 100560
cccagtcttg ggtatgtctt tattagcagt gtgagaatag actaataaag ccaattggta 100620
tgaggagtgg ggcactgctg taaagatacc caaaaatgtg gaagcaactt tggaactggg 100680
taacaggcag ggttggaac agtttggagg gctcagaaga agataggaaa atgtgggaaa 100740
gtgtggaact tcctagagac ttgttgaatg gctttgacca aaatgctgat agtgatatga 100800
atgaaaaagt ccaggctgag gtggcctcat gtggagataa ggaacttacc aggaactaga 100860
gcaaaagtga ttcctgctgt gctttagcaa agagactggt gacatttttc ccctgccata 100920
gagatctgtg taactttgaa cttgagagag ataatttagg gtatctgatg gaagaaattt 100980
ctaaacagca aagcattcaa gaggtgacgt gggtgctctt aaaaacatta agttttattc 101040
attcacaaag atatggtttg gaattagaac tcatgtttta aagaaaagca gggaataaaa 101100
gttcagaaaa tttatagcct gatgatggaa tagaaaagaa aaacctattt tctgaggaga 101160
aattcaaact ggctgcggaa atttgcatca gtaatgagga gcaaaatgtt aatggccaag 101220
acgatgggga aaatgtctcc agggcatgtc agaggtagcc cctcctatca caagccctga 101280
gtcctgggag gaaaaatggt ttcatgggct gggcccaggg ccttgctgct ttcgtagtct 101340
caggacttgc tgccctgcat cccagctgtt tctaaagggg ccaacataca gttcagacca 101400
ttgcttcaga gggtgtaagc agcaagcctt ggtggcttac gcatggtgtt gggcctgtgg 101460
atgcacagaa gtcaagaatt gaggtttggg aacctctgcc tggatttcag aggatgtatg 101520
gaaatgccta gatgtcccga cagagttgtg ctacatgggc agagccctta tggagaacct 101580
ctgctagggc agcgtggaag ggaaatatgg ggtgggaacc cacacacaga gttcccacta 101640
gggcaccacc tagtggagct gtgagaagaa ggtcaccatc ttccagacac cagaatggta 101700
gctccaccaa cagtttgcac catgtgcctg gaaaagctgc agacatacaa tgccagccaa 101760
tgaacgcagc caggaagggg gctgcaccct ggaaagccac agaggtggag ctgcccaagg 101820
ttgtgggagc ccacatgtta catcagcgtg acctggatgt gagacatgga gtcaaagatt 101880
attttggagc tttaagatta tactgccctg ctggatttca gacttgcatg aggcctgtag 101940
ccactttgtt ttggccaatt cctcttattt ggaatgagtg tatttaccca ctgcctgtaa 102000
ccccattgta tctaagaagt aactaactta cttttgattt tacaggctca taggcagaag 102060
ggacttgcct tgtcttagat gagacattgg actgtggact tttgagttat tgctgaaatg 102120
agttaagact ttggggaatt cccagaactg agggttcctc cccattgtag accatatagg 102180
tagcttccag acgttgccaa ggcatttgta aactgtcatg gtgctagtga gagtgtcttt 102240
```

-continued tagcatgctc atgtattata attagtgtat aatgagcagt gaggatgacc agagatcact 102300
tttgtcacca tcttggtttt ggccagcttc ttcactgcat cttatttcta tcagtggggt 102360
ctttgtgacc tgtaccttgc aaaaacagtc ctgctgatta ctaaattcct atctcaccta 102420
ttcaagatgg agtcactctg gtctgaatgc ccctgataag agaatccaca gtgttcaatt 102480
ctccccagtt gattctgaag catatccagg tttattagcc actaagtaaa aatatattat 102540
agactactgt caatgaaaga aacattttgt aagttatttc atatttattt ttacttgaga 102600
agactgaaaa ggtaaagaag tgatgctaaa atttagaact agaaaatctc aacttgctct 102660
agtaggaatt ttaatagagc acactaagtt tcttttcatt ttctctctcc tggtatgtga 102720
ataaacaacc ttccatactg caatttaccc tgtagtgaat tagatgttac cctattatat 102780
tttggagaaa ctatatagtt agaatctaag cttagataac ttatttttat gtttacaaat 102840
ccactttctc ttatacattt ttcttaaatt tttctcatat tctttctctg aatttgtggt 102900
aaaaataccc ctttcccatt ctatgtcatg gttctttacg aagctttctc atcctctcca 102960
tcccgaggga actatgtctc atttatcttt aggttttctg tatcttacta cagtgactta 103020
ccagagtagg taaatatctg atgaataaat gaatacaaga tttaattaag aagtaatcac 103080
attaaactaa ttgttccctc tctgatctct gtaatattaa gtttcaaagt agtttctggg 103140
aaaagtagtt aacacaatga tgtatggatt caataaataa gaaaaatggt gctcagggat 103200
ttaacagaaa gctcataaaa tgtcaaatcc acagcaatta atttctccca gtaagtcctc 103260
ataaattcag gccaagaaat ttgatactga tcttgcctct ctcaactctc atccatcttt 103320
ggtagggctc ctctgggcct ctttttcacc tggcaaacag tacctgatac tcattggatg 103380
cagatctgaa agaggtggaa agagcccgac acctggttta tctctagctt tatggtgcag 103440
agagtatttg atggtgtgca cagtgctctg tatatactgt taggatcagc cttcttgagt 103500
gcactggaat ttctctgggt gtcattaagt tcttcattta ctgaccatga ggcactggga 103560
tagaatatga tattaatcaa gaaaccatcc ctgacatcat gatccacttg gaaaacttgc 103620
agaaattaga aaaatttttt gagtaggcat tttgctttgt tgcccaggct ggagtgcaat 103680
ggctagtcag ggcacagttg tgcaatgcag cctcaaactc ctgggctcag gtgatatccc 103740
tcttccacct cctgagtggc tgggactata agtacacacc actgtgcctg gcaagaattt 103800
ttttttttag gatgttataa ggcctatagt tatttaatta ttaatcctgg ggtagttagt 103860
gaaaagattt ggaccagtct tttacacact gatgtacagc aagataacta tagttagtaa 103920
cattgtatta tataccagaa atttgctata tcaaagtatc atgttggcca cttcaaacac 103980
acaatttttg gtttaaaatg actaaaaaaa ttaaaatagc aaagtaaaaa aaattcacag 104040
gagagcacaa aacccacctt cttccaatga agggagtagt ctggtggtta atacttggag 104100
gatagaatga tagagtttgc aaagccttgg tgaatattat agtaaggaac actcctgaat 104160
caaaaaatcg cattgtactt tataacagcc ctcacttttc cactctcaga tttttactgc 104220
ctttccctaa tgtaccatta aagcccttca gcctaaattc atagactcca ttagagaaga 104280
aattctgaaa caggttttgg gaacacattc tcagcctagt caaatagctt tcatgctgct 104340
agaataaaaa taccttaatc tttgacagac caagtctgtc agcttactct ttacttaaaa 104400
atattaatga gtaacaagtc ccatatccat aaacagaacc aagtgtgtga taaactgtga 104460
taaatgttat ggtggaagaa gtatcccatg tggtcagaat atatgggatt aggggggatt 104520
tgacccagaa atgaaaaatc aggaaggctt cctgcaggaa atggcatctg agctgtgggg 104580
ttaagggtga atctgtgttg tctgagtgca ctggtgagag gactctaatt taggcaaagc 104640

-continued aacagcaggt gtggatgtga ggaggcaaaa ggagacaggg ggtggttata taactacatt 104700
atcaaccata tttttcccat ttatagtctt taagctcaca tcatctgtgc aattctagag 104760
ttacacaaga aaatgatgct taatactact aacattactt tatggcaatg taaatgcttt 104820
atatgatcca atggaccaat atctacatgc ttagatacaa catgctatag gaagtttaga 104880
gtctgagttt ttgaatgaga gaggccttgg ttcagagccc atttcttcca tttactagcc 104940
tgtgaccttg ggttaagctt cagttttctg atttaaaaat tggggatttt ctgtctcata 105000
aatttactgt gagaattgaa tgagaagatg agtattgaga agctagtaca ctgtttcaac 105060
tccagttagc tttcttaagc ctttttgccc ctacccctta gttctgttcg ttttattgtg 105120
agcaactttc ttttttcttt ttactcctct agggatatga agcctgacaa tattttactt 105180
gacgaacatg gtaagtgagt gatttgtttg caatcaagta catgacatgc atgtagaaaa 105240
gttgattgtt cccagcagag gggtattaca catgaaaaag gtattttgtt ctattcattc 105300
gagctctact tacaaactcc tcatagacaa tatgggggaa ctttattact tatggcaggt 105360
tatagtacaa caatacaccc ttaaatcaca ttgaatttac ctaatgagaa aatcatagtc 105420
tactcaattt tcttccacta ctatatttct tcaagaaaac catcacaact tttcagtgtt 105480
agctggcctt aatataacac gcaatcacct atttttttata atgatacaga aggcctcaag 105540
ctgagagcat ttggccagca atagcatcta cctagacatt aatgacatta ttttgttctc 105600
attgcatcta cttttttgca ttccttctta taaaaggcaa attggtttta catttgcaaa 105660
ttggttttta catttactta atatcacaga agaattctta cattttaggg tcattgtaaa 105720
gactgaccta atacatgtaa actacttgat gcagtgactg tcacgaagaa atcactcaat 105780
agaagtctaa tattggtaca atttttatga ggtggtcatg ggtttctccc cttggaaagg 105840
aagctggaac tgcttcatct tgttttatgc ggctttgtct atgctggcac ataactagta 105900
tgtaccaatg tatctcagaa aagatatcaa gttttctgtt taaaaatttc agtttgagaa 105960
aaatcagtta aagaaaaaca taaaaaaagat aaaagtatat gtgttatcta gatttgtgat 106020
atagggatat ggcaataatc aagatggtga taagtgaatg ctgaatttca agaactactg 106080
attacaccct ctagaataag cttttgcccg tgatgattaa atgtgtacga tttcttccta 106140
atatttattt ttgtgtatat tgggatttat tagaatatca gggaagatct gcagggcaca 106200
aaaactgtat gttataaatg ttaacagtgt caataagatc tttgttatgt ctttagaagg 106260
ctgctagatg aggagagtcc tagatcttaa aggctcctta ttcaattttt acaaaaagga 106320
tttgcaagtg gaactgaaac tccaagtacc atctattgct cattatttat ttacctattt 106380
ttgagcctga ttttcctgat cccacctgtg ctcagggggc taagaaacac tggtaatgac 106440
ctctaatttc aaagctcact gtcattactt atttatggac tgtccaaaaa gattttttcc 106500
actttcttcc aatgccttat ttcttcctta cctttactgc ttctgacatt tgaaaacagg 106560
gtctctgatt ctcagaaatg tgagcaatgg tgagatttag catgaaggtg actttcttta 106620
aaataccagc tatccagagc taggtacagt ggcaggcacc tgtagtatca gctacttggg 106680
aggctgaggc aggaggatcg cttgagccca ggagtttgaa tccagcctgg gcagcacaga 106740
gagaccctgt ttcttgttgg gggaaaaaca attaccactg gcttctcttc tagcctatag 106800
aggccacctt tgtgcaactt agggagaagt gctccccctg cccaccacag cttcctgaca 106860
gcacatggcc caccaaggag aacccaagtt aggattgagt cctcacttgc tccctcagct 106920
gggtgccttt gtgcatgatt tctgctgttc caccatttat agaggcctta aatgaaggca 106980

-continued

```
tataggtcct atcaatccaa cactttccca gctttatcct cccttcagag aacagtgttt 107040
tcatcccagg tctcatccat ggcttcaccc tacttctatc attaaggcat cctattctcc 107100
ttcagtcaac ttcttcctcc tcctcatttt cttggtgact tggtcattgc agatgaggaa 107160
aaacatgaag aaatcaatta atcttcaagt ttaaccacct ttagagacta cccttgtgaa 107220
agattaattg tgtaacagtg tggttaagaa tgtgacttct ggagccagat tgccttcatt 107280
caaaacacac ttcactcatt tcctagcccc gagagctttg acaagttgcc taaactttgt 107340
cttagttttt ccagggatca aaagaatact tacttagaaa aaaaatctta cttacaaaag 107400
aaatcttaca gggatcaaaa gaatacttaa ttagggtcat tgtaaagact gacctgatac 107460
gtgtgaagta cttgatgcaa tgactgtcac aaagaaatca ctcaataaaa gtctaatatt 107520
agtacaattc ttctgaggca gtcatggctt tctttccttg gaaaggaagc tgggactgct 107580
tcatcttgtt ttatgtttct ttgtctatgc taacacatac ctaatacgta ccaaatctct 107640
accagataga atctgtaaaa gttgtccttc ccaaataatt attttgattt aagaagtgat 107700
ataccaaata ttctgcttgt ctacttctta gatcttgtgt ttaaaccatt ttgtttatcc 107760
cttcatcctc aggtaactac actttccgtg tacattctgc tgtctttcat gtgtgcaggg 107820
ggcaagggtg cagtcatgac attttattct tggtggagct ggggctctgt tgcctacaga 107880
atacaagcca tcattccagt gtgccagaga gagagtctca gtctgcccct attacctggt 107940
gtcttattta caatgactgc tttcattctc aaggcttttt aaaatttggt cagtgaatta 108000
agaagaggct tttctgtatt atattcctac cctgaactca acttgaaaat caattgcttt 108060
gggaaggatt gtatatgaat ggtacagaag tgagcaaaca aaaaagactg agagccattt 108120
tctaaacatt gccttaggga tctctttctg gagataataa ttttttgaa gttatttact 108180
tcgtttgttc agattctgaa aaagtaggac tctcagacat tactcaagga acataattaa 108240
ccacttttcc atgaacaaat tcctgttgtt cacctctccc cagctcgtta tgtagagctg 108300
atcttgtgag aatcagctga atcacaaatc aatgcctgcc ttttagagtg tctgctggtg 108360
tgactttcca tgtggagctc atatttgaag acctcatttg ccttctccat ctccatttat 108420
aatatttcat ccctgatggg ctgtcgcttg ggcctcatgt ggaaattgta gccactgtga 108480
agggtaacca cctatctctc tggtgccccc tatgcgcatc cctacaagtg agctgtgtat 108540
cacaccatgc tgcttacatt tttatgcaac acgattcagt aacaggcaga aacttttatt 108600
cttactgact catattcttt atattcatct gaaaagattg acatttaaag gagccaattg 108660
tacaatggga aatccactgt gtgaatattt cttgtacatc agaatttgcc ttaaaaatgt 108720
ttttaactta gagcacatct gtactgttct ccccaaatgt cccatttact agttcagagc 108780
aagatgacat taggtcttgg gtgactcctg acccactatc ctaatgtata ttttcatttc 108840
ctaccaatgt aagtacccca tccaattcta tcaataccat agtgtctaaa attcttgtat 108900
ttttcttatt caggaaatgc tacaaccaga ggaacagtaa tgtctgcctg acatatcaga 108960
gaaaatgaca attatgtcat catctgtcac ttaggtttct taataccatc ctgttacaag 109020
gaatagaggc aaaaactcag cgtaggaggt gagaaaaaac tgaggctgcc atcttaacag 109080
ccttttcatt gcagagtctc aaaatgtacc aaaagatgaa gtggacagtg tccttttaaa 109140
acaacataca gtgtagaata cagtaactta tccccattta attactccct aggtagtgcc 109200
taaggatata cattttcagc aaggatctca gaaaaatgtg ggcacatat tctaaacacc 109260
tgcgagtagc agagacttaa aagttgggag cagtgccaac tgattggtta tggtgcccta 109320
gagcactgcg ttgatgaaag agatcctcag gctgtgcaca ggagcagcaa gaaagagtgt 109380
```

-continued

```
aaatgatgac aacaatgatg gctgaattca atggcatcat aaaatgaatt cagatttttt 109440
atatgatcct ctatcccaag caatagaggc aaaaaaaaaa aggcagaaac cctctcctag 109500
agtggtaaat taggaagttc tgaggcttgc acctgaaaaa cttttcacta aagtagtgat 109560
tctcaactgg gcgtaatttt gctctactcc ttctccctgc agaggacatt tggtaatttc 109620
tggagacatt tttgattatc aggattccag ccagggttgg gaggtgatat cagcagctag 109680
tgggtagagg ccgggatgct agcatgcatc ctgcaatgca caggacagtt cgcactacaa 109740
aaaattatca ggtccaatat ttcaatggtg ctgaggttga gaaactctgc tctaaggctc 109800
actcaaggcc tgggctaatg aaaaaagcca gagaagtcct tcattcccaa ggcaattcct 109860
gtgtccttca gtcagcagga gactgaaccc tttcctgtga tccagcagtc aaatttcatt 109920
ttcaaaacac agaagggaac ctggcagata ggtcaccatg gtaaggagaa gcaagtcatg 109980
gctgtagccg gacctgggac taaggcttag ggccagcact ctgtgaagtt ctgccttcat 110040
tgtttagctc agaagcacca ggttacaaga tccagtagaa cctgaccctc aaataatttc 110100
tccctctcct taaataggca tcctggaagt ggactagaac tctgagccaa tcagaaatta 110160
actgttttag gttattcagt tctttgatct tgtgatacag cacacaaagt ttttggtaga 110220
ttcatagtct gacaaaggga ttctagacaa aattctaggt cttaactcca gctctgtaac 110280
ttttgagtct tttgaaccta gccataaatg actcatatat aaaatagggc ctacctcact 110340
aggctaaagg agaaattttg tgcaacaaca ttttgaaaac tgaatcatgc aagtgtaaac 110400
agcatttaaa aggaaaatac tcaacattct ttcaactgac gtgtaatgag tactcaccag 110460
agttgagatg ttctgctaag ccaggccctc ttttaaaaat gtaatctcaa actttattag 110520
gtctcataat cacctggaag gcttatttaa atattggcgc ccaacccaca gagtttctga 110580
tttgttataa tagagttgag gggggacggg gcgtaagaat ctgcatatct aacaagttcc 110640
caggtgatgc tgatgctgct gatctgggca ctacattgta ggaatcaatt ggctctaaaa 110700
ccttctctac cttccacttc tacatgagca tacataatct tgtagctgag tcagcttgga 110760
aatctatgca gactaaagta gacagttgca tgtctggctg ctcatctgaa tcacctgtgg 110820
aatttgttgt ttttaataca gatacctggc tctcctacaa gtcccactga attggagttt 110880
caggagaccg aagcccaggc acatgtattt tgcaaaacta cactgaagtt tctgataatg 110940
acggatatca acaattaaac gcttacttct tgccaaatgc tgtgctaagt ctcctgtaat 111000
cattctttca tttaatattt ctaataacct cttgagaaga ctatgattat ctttccaact 111060
ttacagagag gataagtgac gttttcaagg taacacagct agttagtggt agaacctaga 111120
cttgaagcca agcagtctga ctccaagaaa caggctcttc accacagtct ccagactcac 111180
ctgatttgta ttaaactttg tgaatcactg atccaacact atgagcagga cccatgggga 111240
gaaagagaaa aagaaaaaac agagacaacc tacgctatga taaagttatt gaaatcaggc 111300
attggtgcca ctccagcaag aatgagtggc taccttttt ttagatgagt gctaccttta 111360
ctttactgaa atatcatgac ataaacaaag ccaaaacact ttctgcacaa aataaaatcc 111420
tggtgataaa ggcagtggga tttatgctta gcagcaggct ggatactatc agggagcaga 111480
caaagaagtt tgatacaggg cttgtggact gtgggccctg gaagaatctg atgacatgcc 111540
ctccaattac agctgtatct catcaaaacc acagacacat gtaaatggaa atgccaacac 111600
ttcaagattc tctgaaagca gttgactgtc atgccaacag ctaacataat aggcttgttt 111660
gcctgagctt ttggcacggc ccttttgttc cctttagctg taaatgcagg gaccctagag 111720
```

-continued cacctcatag agtgtgttcc ctgccacgta taagtattag acccacacta tattgctttg 111780
agtgttaaag ctgaaagaga ccctagagat catttagtct actccttctt tttttatgtg 111840
aaggaaaatt tagatccacc ttggaaaagg acttagagtc tactatgtgt tagaggctga 111900
gttcaaggca gaacccaggc ctcctggctc ccagtctagt gctctttata gaatcccttt 111960
aaaaatgaag ttgactggcc gggcgcagtg gctcacgcct gtaatcccaa cactttcaga 112020
ggccgaggca agcagatcac gaggtcaaga gatcgtagaa caccctgacc aacatggtga 112080
aatcccatct ctactaaaaa tacaaaaatt agctgagcat ggttgtgcat gcctgtaatc 112140
ccagcaactc gggaggctga ggcaggagaa tcacttgaac ccgggaggcg gagattgcag 112200
tgagccgaga gcacaccata acactccagc ctggcaacag agtgagactc cacttcaaaa 112260
aaaaaaaatt aaattaaatt taaaaaaaac ctaaagttaa accccgcccc ccacccaccg 112320
ccccccgcta tcccttgata acagttattt tgctgggaac tgatgaggcc aacctgaatt 112380
atcagacaaa aaatatgtac aaaaatattt tagaaaaact gaagaaaagg gatgctttct 112440
tggctaggaa ataaatattt gtatccatat tcatgccagt tttgtagtaa taatatttgc 112500
ctcttacttt tcttttcttt tttttttgag atagtctcac tctgtcaccc aggctggagt 112560
gcagtggtgt gatctcagct cactgcaacc tctgcctccc aggttcatgt gattctcctg 112620
cctcagcctc ccaagtagct gggattacag gcacccatca ccacgcccag ctaatttttt 112680 atttttttatt tttagtagag acagggtttc accattttgg ccaggctggt ctcgaactcc 112740
tgacctcaag tgatctgccc acctcagcct tccaaagtgc taggattaca ggggtgagcc 112800
accacgccca gcctatttgc ctctttaaaa aaaataatcc cataagggat gtttggaaac 112860
gtgatacttt gagtatctct tggctgtctc cttcatagta ttcataggct aaagtaactt 112920
aaaatgtcac caacagacaa aagatgccta actagaatta cctgaccaca aattcttaac 112980
tactaagggt aaaacttttc tgaggctgaa ctacaggctt acaatcagag actaatcatt 113040
gcatatcatg aaatggagaa ttgttggttt aagaccatat cggccttgag gatggactgc 113100
aactggccta caagaattaa cagactaatt gggtgttttc agttaaaagc atgattgtgc 113160
cactgggttg aatgggactt aactttctgt gtggttcttc tctctctgca gggcacgtgc 113220
acatcacaga tttcaacatt gctgcgatgc tgcccaggga gacacagatt accaccatgg 113280
ctggcaccaa gccttacatg ggtatgggtt tcatgagtgt cttttttttt tctttcctgt 113340
aaataccatt tattacaggt ggaatcatct gtggggattt gcagctagaa ctggtaagtt 113400
cctctctgac tttacctgtg gagcttctga tttcatgggt cttctccact agcaagcacc 113460
caagatgact ttgataggaa aggaccattg attacatttt gaaaacttac ttcgtgtgtc 113520
aaggaagacc gtttgtaccc acttcctaac aaaaatatta actaattcaa taaataccta 113580
ctaactgtct ctgtgtgctt agcactgttt cagatgccgg tgaccctgta gaaagcaaca 113640
cagacaaggt cttcagatcc tggagcttac attctagtgg gagcagattt ataaaaaaaa 113700
aagaaccaaa caaggccggg catggtggct cacgcctgta atcccagcac tttgggaggc 113760
tgaagtaggc agatcatgag gtcaaaagat tgagaccatc ctggccaaca tggtgaaacc 113820
ctgtctctac taaaaataca aaaattagct gggtgtggta gcatgcgcct gtagtcccag 113880
ctactcgggg ggctgaggca ggagaatcgc ttgaatctgg gaggcggagg ttgcagtgag 113940
tcgagatcgc gccattgcac tccagcctgg cgacaaagcg agatttcgtc tcaaaacaaa 114000
caaacaaaca aacaaacaaa gaagtaggaa acagtaataa gcaaaatgat aataagtggc 114060
aaagtattat tttaaccatt atttacataa tactgcatta catacataga gctataaact 114120

-continued ttacaaaata cattcccagc tataatttta gatttacttg tagtgccaca acaatcccat 114180
gaattcttct gtttaaagat aaggaaattc tggagctgga tggtggcatg catctgtggt 114240
cccagctgct ttggaagcca aggcaggagc attgctcgag tccaggagtt ggaggctgca 114300
gtgagctatg atcatgccac tgtactccag cctgagtgat aaagtgagac tctgtctcta 114360
aaaacaaata aattattttt aaaaataaat aaaggtgagg aaattctgcc tcagaaagtt 114420
taaatgtctt tgcattattt tgtgtgtagc gaggtgagga actggttttt gccttgacaa 114480
ttcagcattt actaaggggt gaccaaaaag agagtgttag atgcaaaatt gtcagttggt 114540
ttcacgtata gttgtggtaa caaatcaact acaaaaactc taagttcacc tgttgggagc 114600
agccatctat atagacacca gaactagttg ttagcagaac cagctttact tcccgtccag 114660
cctcaacaat gcaaggagag agctagtgtc ctcgaggggg cacacagtat tcagaaagag 114720
ggagttctcc ctcccttttc cctgtggttg ctcctaaggc aagtgagtca gatctcaaga 114780
gaattatctg taaactctta gagtgactgc aagaaaagat acctggaatt taattcttga 114840
ttagatatct gtgtagttac tggacttgtg actggtcctg gagttaacac agcctggttg 114900
gccatggaag tttgatgagt ttgggggcta gtctttctgg ggatcatagc agcaggagac 114960
aggtatgcag tgaatgtgat ttgtcttggg gagaagggag gtggattagc tacaggctgt 115020
gatccacctt cacatgggac cctccaatga ccaagaatat agcctggaag ggagggaggc 115080
tcctgtcagt gtgacttcct gaaaacacca caagtcccaa tagagctcaa catatcagaa 115140
tcactgagag tggagtctag gcatagtgtg atttaaagct cttagcgtaa ttcctccgtg 115200
tagctaggag tcacaacttc caccacagac ccctaaagag agattactct gcagggtagc 115260
acatgtgtga ggacccctct gcctcgacta cccttctttc atgtcctaaa acaaatagtg 115320
ctttctagga aaagatagaa ggacgtgtgt gagagccaga tcaatcctcc acctccatac 115380
cggggtggct gaaaccagcc cagcagggtg agtgaaggag ctttgaatca gatataagaa 115440
tagttttaaa attcacagaa ctgaattgta aagcatctaa agtaaatgta ataagcaaat 115500
aggactaaaa cttattaggc aacagactga gatatcatta ggcgagctcc ttatccagca 115560
aaaacaggaa gttagacact gcacagttgc tgtcaaatga cagaagacta aaaactactc 115620
atgcttggcg gggtgcggtg gctcacacct gtaatcccag cactttggga gaccgaggca 115680
ggcggatcac aagatcaaga gatcgagacc agcctggcca acatggtgaa accccatctc 115740
tactaaaaat acaaaaatta gctgggcatg gtggcgtgca tctgtagtca tagctactcg 115800
ggaggctgag gcaggaaaat cacttgaacc tgggaggcgg aggttgcagt gagccgagac 115860
tgtgtcactg cactccagcc tggcgacaga gtgagactcc atctcaaaag aaaaaacaaa 115920
caacaacaac aacaaaaaac ctactcatgc tttaccctaa ttagttaaga tgcttaaagc 115980
aggtgatgtg gtgatgttgc tgtttaaact ggtgggatta agtcgggtgg aatgaattgt 116040
ttcagctaga tatggtcaga gtaattcaaa ggtaaaatat ttcaacttga aatcaaggac 116100
aagagcaatg ccattttctt ttaatatttc attctcttcc cccatgtaac tagagagaga 116160
gagagagaga ggaaaagaga accccctaca tgcagagcca cctcactttc caacagaaat 116220
cttctatgag aaaaaaaaat gagccttatt ttctatgata tttgaacaac tgcaaatttc 116280
atggctttca attaccagtg gggggaataa atctcttttg tcacttctaa aataatggac 116340
atatataatt cagcctattt tctgcctaaa acctatggta ctcaaatgat aaaaaagcat 116400
atccaagcct gctgctctga tgagtttatt ctccaggttt cctgggtttc catattaagg 116460

-continued gctattttct tggaaccaaa tcagaaaatg tgcatctggg tttccagggt tggtttccat 116520
ggtgagagaa gtacggggag gccacctttc tttcctctcc ccagtggttt taagtacaat 116580
atctgtataa tgtaattttt tcaaagttgg catttctagt cttctcacaa gatagaactg 116640
ggaaattgga acctaggaaa aattctgtgc accttccact tttacccttg taattaacaa 116700
tgactaatat ttcttgaaat ctttccctgg accagacaag gtgttaaatg ttttacattc 116760
atttatttgt ttatttttct cagcagcccc atggggtgga ctatacttat cactacttta 116820
taatgagaaa aatcagaagc taaataattt ggccgagatc acatggctaa taattgaaaa 116880
gtctagattt aaatcaagct ctgtctgatt tcagaaatca agctttttct taaaaggaag 116940
attaatgaga aataaaaata tatatttgta aatattttta tctgtggttt ttaaatggtt 117000
ctaagtcaac ttagttaggc taacatattc gaaatgtttc ttgccttatt ccaaaatgat 117060
tatgtgattg ccacactcct ccttttggat aggagtcttt cccagacgta ttgtgggtag 117120
aagtctgctg tctcttttta aaaattatgc tcccaatggt ttggtaaaat ctaccaaatc 117180
tatcagcacc cattttatag tgctttcata ggatactaag tagcaattca ccagaaagaa 117240
caaaaagaat tctaaaaaga aagaaaacta accaaaatac tgaatgaaga ttggagaaat 117300
attcatctac taatacaaga tgctgagcat attttaaatc agttccatag ctctgtaaat 117360
aataagacag tatgccagtt cttcaccacc ttccatcaag caaggaaagt tttgcttttt 117420
acaatttatt gtcctctacc tctgtgctcc ctctggtccc tccattattc cttctctctt 117480
ctcctttgtc tgtatgaata taatccagat tacttagagt taaccaatta aaaccttctc 117540
cgccgggcgc ggtggctcac cctgtaatcc cagcactttg ggaggccgag gcgggcagat 117600
cacaaggtca ggaaatcgag atcatcctgg ctaacacggt gaaaccccgt ctctactaaa 117660
aaaaatacac aaaaaaatta gccgggcgtg gtggcaggtg cctgtagttc cagctactcg 117720
ggaggctgag gcaggagaat ggcgcgaacc cgggaggcgg agctcgcagt gagcagagat 117780
cgcgccactg cactccaggc tgggcgacag agcgagattc cgtctcaaaa aaaataaaat 117840
gaataaaata aaaaataaaa ataaaaataa aacattctcc tccaaattat atatgtatgt 117900
atgtgtatat atgtatatgt atgtgtgtga gtgtgtgtgt gtatatatat atatatatat 117960
aaataagttc actatggact agcaagcaaa aggaaagtaa taatcccttt gccaatagat 118020
atttatggtt tatttccaga catttttttcc taagcacaaa cacatactgt ttacattttt 118080
taaatattcg atcatgctaa atgtaaccta aattttcatt ttataatgta acaataatga 118140
tagcatcata tagtgaacat ttattgttcc aagcactttg ctaagttttt aacatttatt 118200
attaaactct caaccccata aaataggttt tactattgtt tagattttac aagttaaaaa 118260
aaaatcaggc ccagagagag agaaagtgat gtgttcataa tcacacagcc agtgattggc 118320
agagcatgaa attaaaccca agtctagaaa catgccgtgc ctgagacatg gacgatgatg 118380
tgacaatgat gaaggtagaa tgtctgacat tgctaagctc ttcctaaatg ttaagcactg 118440
ttgtaactgc atgcattgtc atttaaacta aaaacagttc tgtgaggcca ctactatcgt 118500
tacagtttta ttattgcata atatattaac atataattaa tgtagtatat tgtatatata 118560
gtactattgt tatagtatat attgttctca cttcagaaat tagcagactg aaaggttaag 118620
aaacttgttg actgtgaagc tggagacagt catagggggtc tgatgccaga gccctaactc 118680
ttaacatgct gcagtactgt ccctttgttc atgtcaataa acatgcctct gctaaaatag 118740
aaacccactt ctcttaatca attttttatt gttgaatgtt aggttgtttc tcattttgaa 118800
atacagatag agcatcccaa atccaaaatg ctccaaaatc caaaacattt tgaacaccaa 118860

-continued catgacactc aaaggaaatg ctcattgaag tattttggat tgatttgggg atttgggatg 118920
gccaaccagt atagtgcaaa tatttcaaaa tctgaaaaaa aaaattgaaa tgcagaacac 118980
ttctggtccc aagtatttca aataggggat actcaacctg tacatttaaa tttgtagtaa 119040
aaatcctgtt agcagaatta tgtcctggaa cttagttatt tctttgtgat aaattttcat 119100
tcaataataa tagtgtattc tcttactgaa aatcactcaa agaaaatttt gtgttctcac 119160
cacagaaaac agtaatgtgg gtaatgtgag gtaaggcaca tgttaattag ctctattcag 119220
ccattctaaa atgtatttat ttcaaaaaat agtgtcatat acaatatatg caatttttac 119280
ttcttaatta aaattaatta atttgattaa ttaaaagagc aaaagaattt ctggtcaaag 119340
cctttacatg ttaatagatt tctgttctga aaattcatat taacttgtac ttgctctgga 119400
agtgtctgaa gatattcatt tccctgcatt cttatcagtg ctacactatc aatatcttta 119460
attgtcccaa aaaaggtagg taaaaatgat atgacattat gatattacca cagtatttct 119520
ttgacttctt ttgtcaattg cctgttcaaa ttctttgctc attttctatt aaggtgttaa 119580
tacttttatc ctattccaat agttcttatt gattatataa ataattcttg ccttttatat 119640
atttggaata tgaaatccta gggtatcata tttgttgtac atttcattac aaatataatt 119700
tctcattttt aatttgttgc tgttttatgg cctagttttg acatgaaaag cttgctaaaa 119760
atattatcaa gccactcatc tttttacttt gctttctaac tttgatgctt ttcttagcaa 119820
gaccttctta ccagatttta gatgtgtttg cttaatattt ttattctgat tatggtttca 119880 ttttttttact taactcagtt gtatattatt ttgactgaac ggatgtggca aggatctgac 119940
tttatttttg tatgattatt aaataattgt tttgagacta tgtattaaat aagtcccttt 120000
ccatgctgat ttgaaatatg ttcatcataa actaaataca tttttgtgct aatatctata 120060
ttctgtagat ttcaaatctt gtagctttat aggttaatac atgggatgcg ggactctttc 120120
tttattcttt tccaaaaata ttacttccac aatttttttc ttgtagatga aatttagaat 120180
catttttgta aagttccatg aattaatccc attaaatgta tagattagtg ttgggtccct 120240
ttctttatgt cctgaccaaa atttaatacc cacgtttaaa aaaatctgaa aaccaaatga 120300
tggaaatcca aatatttaat aaatatatta aaatgtagtc aagcttatta gtaaacaaga 120360
caatgccaat ttaaaccaca gtgaaatact attacacact caccagattg gcaataaagg 120420
gtcagttatt gccaagtgtg ggtaaggatg ttcaacaaaa ggaaccctga tctaatactg 120480
gtcatagtgt gaatttatac aacactttgg taaatagttt ggagttactg tggtacacag 120540
aaaagttaca cattcttatc accaacagtt cccctgccag gaatacactc taaagagata 120600
tgcacttata ggaatactca catgtatagg aacgttcatg acagcattgt tcacaatagt 120660
cccaaactga aaataaccca aatggctatc aacaatggga taggtaggta aattacagta 120720
tattcatata gcactaaaag tgaacaaact taactacatg tagcaacttg gataaatctt 120780
atacacatac cattgagtaa gaaaagtaag acaccaaaga atacaaggaa tacgatttga 120840
tttaatagga tttaatttaa tggaatttaa tagaatacaa ggcatagatt ttttttgct 120900 ttgttagtgt ttcctttatt ataaagcact gaaataaata aataggtagc tagccaattt 120960
atccacagtt tctgggagct atataagata ggcaaagcta aactattgtc taaaaatatg 121020
tacatagata ttgatctata tagaaaaaca agaaaattat taacataaaa tttagcacag 121080
tgacttctag ggttatgaac agaacaggac acagtgatgg ggacaagatt ctatttcttg 121140
acctgtatca tgtttatgtg gacatttgct tataactgtt tgctaattct gcagtgtttt 121200

-continued atttactttt ctgaatatat gtatagaaat acataatgag caataccaaa caaaatactc 121260
agtggctttt ttgaaggaca cttagccctt ctctgactct cttagtactc tcttaggtgc 121320
agggaatctt ctggaagggt tggtgaaagc ccttcaatat cttcctgctc tggtttctca 121380
gctatttgag ggctcaaata attactcgtc tgttatgttt ttgtatgttg tcataaggtt 121440
tcttcttaat gttccaccaa aatgcttcag tgccttgcat accatgaata ttttctgaat 121500
gaataaatgt gtattaaaat gttttaatgc ctgaaaatag accaggtaga agaggatgaa 121560
aaagaatact ggataaataa agctggaaga aagaaagaaa gtgaaaagaa tactcatgta 121620
aaccccaagg ataatccaat atgacagata cataacttgt atagagtaat gtttattcta 121680
ttaggcattt tcttagcaca gtggctctga ttatccctca aagttctttg tagcttctct 121740
gagtgacgtg tctgtcaccc atcacctggg gactatctga tatgacttgt tgtgagatac 121800
tgagaaggga gagcagaaat atagtccatc ctgtctgtgg gagtagtgtg gggtcagggc 121860
cattacctcc caaattgcac tgggggctgt gacttgcaga aaggatgcag tgattcatga 121920
aaggtgaatg cactagggaa atagccctcc ttattcctgc tgcatcaagc tcttatagtc 121980
agggccagtc ccgggcattg ggatgtaaac actctacctc tctagttgga tgttgttcac 122040
aggattttac ttaaaaagaa catgagtgca ctgggtaggg aaaacctgtg tgtgcaggac 122100
ccatgtcata ccagtttcct ttgcccagag ccagcacttt atacaggagg cttgggatca 122160
accatacaaa tctttcaact aggtcaatta ttatgaatgt ttgcctctct agaagcctac 122220
ccaatgtttc tgagcacttt ataagtgcta ggcaccatac tgagattttg acatggatta 122280
tcactgttaa tttctaactc tataaagatt gccttattgg ctgggtgcag tgactcacac 122340
ctgtaatccc agtactttag gaggccaaag caggtggatc acctaagccc aggagttcaa 122400
gaccagtctg ggcaacatgg caagacccta tctctacaaa aagcacaaaa attttaccaa 122460
atgtggtggt acccacctgt agtcccagct acttgggagg ccaaggttgg aggatcactt 122520
gagtctggga ggtcgaggct gcagtgagcc atgattgtat cactgcaatc cagcctgggc 122580
aatggagtga gattctgtct caaaaaaaaa aaaaaaaaga aaaaaaaaag aaagaaagaa 122640
agaaagaaaa aaaaggaaaa gaaaagggaa agattgcctt attgttctgc ttttgctgtt 122700
tctcaggctc tgccaacttg ctcaaggtca cagtaagtgg tgaaggtaga atttgaaccc 122760
agagagcaca gctccagagc taatgatcac aactattgct tgagcaattg atttgttcat 122820
tcattcaaca aatttctctc cagtgattct gaatgccaga ttctgtatta gacagtagga 122880
atatggtggt gagcatgcag aagcattccc tgcctttgct ttgtgcttca ttctccctat 122940
tacatccctc aggagttagg tttattctta gaagggtaag taaaaggttc atagtgtgtc 123000
aaagtgctta gagaatgcat aacttggggt cctctctggg ggtaaaattg actgtagctc 123060
tgccttccac tggaatcaat tgaaagaact acagttacaa agtgtaaaga acccacagct 123120
gttgtaaaac cttacactct ccagaatgct tgctccctct tttctccctc cctcatcccc 123180
aacagatggc tgcaagtgct tcccttgctg cttccaggtg actctgagat agagagatta 123240
tccaatgtat gctgtaccaa attctgcacg ttgtctgcga ctgttataga aatttagatc 123300
ctttagttga aaccttccca atcaaaacaa ataacatctt cttagccttc ttgatttcag 123360
ggtgagccac atatttgagg cccaatagga cccaaatttt aatcggtgca tgatctaaat 123420
aagcgaagag tttatccatg aaggcctatg catgcctgtg tgtgttgact gatgaatgag 123480
gctactgaga gagattagaa aattagaaat gtttgcctgc tgtgagcaat ctagcaacgg 123540
atgataaaca tccataaaag tgtttatatt tttgatcctg gtaattctcc tttggaggaa 123600

-continued catgttgaga aaatataata ctaatgtctc agggaatcaa actggtttaa tttttcgtgt 123660
ttttcagcac ctgagatgtt cagctccaga aaaggagcag gctattcctt tgctgttgac 123720
tggtggtccc tgggagtgac ggcatatgaa ctgctgagag gccgggtact gtagtagcat 123780
ttcctctttg gttatttttc cagcaagttc tattttagaa tgaaagaatg tattgtttgc 123840
taagatccaa gcagttcact tgaaagctga aatcagctat gccatgtgat gttgataaca 123900
ccccttgaga tttctgcata ggttaattca tttgtcccgc atatgggacc aaccatgtca 123960
attaccatta aattacacag ttaaaagtaa aggaataata tggatattat aaactcccaa 124020
agaggggaaa tcaatacacc tcactaaata tcttgtgtaa atatctgtgt ttgtttaaag 124080
aaagtcattt tgcagtcata gtacaggact ctaattcaga catacctcac caaggctagt 124140
gtgaattatt aatacaacac aattcatgct ctgtcttgtt ggatttctat cacttggctc 124200
ctgggttctg ggttcagtga caaattagag tcatttcctt ttaaaggaaa catttcttaa 124260
actaagaatc tctttcccag aaaaaagaga tgaaaagaaa gcaaatatgc tgaaacatat 124320
tttatacaat ttgtgcaaac tattacataa tagaaataca ctccttaggt tatatctcag 124380
tcagctctgc ttaccataat aaaatactgc agacaggatg gcttaaataa cagacatcta 124440
ttttcttggt tatggaggtt ggaagtctga gattaagatg ccagaatggt tgggttatgg 124500
tgaaatctct ttttggcttg cagatagcag cctttttttct gtgtcctcac atggcagaga 124560
gagatctttg tcttcttata agtctactaa tcccatcacg agggacctac ccccataaac 124620
taacctaacc cttattccct ctcagaggct ccatttccaa ataccatcaa attgagggtt 124680
aaggcttcaa catctgaatt ttgagtggga cacaaacatt cagtccatga cattctatcc 124740
ttgacccctc caatattcat gtccttctca tatgcaaaat acatacattc aacagtccca 124800
aaagtcttaa cttattccca tatcaactct aaagtctgaa gtccaaaatc tcatctaaac 124860
atcatagaaa ttgtgtatgg gtgagactcg aggtatgatt catcctaagg caaaatttct 124920
cctcagctat gtacctataa aagcagacaa gtggccaggc actggctcat gcctgtaatc 124980
ccaacacttt aagaggtagg aggcaggagg attccttgag cccaggagtg tgagaccagc 125040
ctgggccaca tgggagaccc tgtgtctaca acaccttttt tttttaatta gccaggcatg 125100
gtggggcaag ccagtggtcc caactactca ggtggttgag gtgggagaat cacttgagcc 125160
caggaggtag aggctgtagt gagccaagat catgccactg cactccagcc tgagctacag 125220
agtgagaccc catcattaaa caaaacaaaa caaaaaacaa acaaacaaaa aacaagcaag 125280
ttatgtgctt ccaaaataca atgataccat agctgtggga tagagaatcc cattccaaca 125340
tttcaaaaga gaaatgggaa agaaggaagg ggcatcagct cctaaacaag tccagaacat 125400
atcaaagcaa attctattat atcttaaaac tcgagaataa tcttctttga gttgttggtt 125460
tgccctctag atctacacag gcatgggagc aatcactctc atggctgggg atggggagag 125520
gggacttgct taagtggctc tctacaaagg cactacccac atggctctct gtgaaggctc 125580
tgtctacaca gctctgttga gtggtggtcc tgcccttcga aacagaggtg gaggcaaccc 125640
tgctccccaa gccagtgcac tctggacctg tagtgggaat ggcagccctg atgatctgtg 125700
aatcgccctc atgatccttc ttccttttac ttgaaggata gcacatgttc acagctggat 125760
agcattacgg tcccagcctg taaaatccaa gaagtctgac agcctttctt cataaattca 125820
aactggcagc atctgctagt ataatcccat ctttatttct agcttctgtt gtgataacta 125880
cttgattgtt cagctacact ctagtgtgct cttcagaaca ggcttgctca ttttctgcaa 125940

-continued tatggataga aatcttcaat ttctggttgc tttttgctta attatttttt cttcaattca 126000
aacattccct ttaacatttt actataagca gacagaagga accaagttac tccttcaaag 126060
ttttgcttag aaatctcctc ggctggcctg gtgcagtggc tcatgcctat aatcccagca 126120
ctttagaagg ctgaggcggg cagatcacct gaggtcagta attcgagtcc aacctgatca 126180
acatggagaa accccatctg tactaaaaat acaaaattag ccgggcatgg tggtggatgc 126240
ctgtaatccc agctactcag gaggctgagg caggagaatc acttgaacct gggaggtaga 126300
tgttgcagtg agctgagaac acaacattgt actccagcct gggcaatgag agcgaaactc 126360
catctcaaaa aaaaaaaaaa aaaaaagaaa tctcctcagc taaatatctc atttcatcac 126420
tcacaatttc taccttctgc aaaatagtag aacacagttc agacaagctc cttgccactt 126480
tataacaaga atcacctttc ctccagtttc caataacatg ttcctcattt ctgtcagacc 126540
tcaccagaat caccettaat atccatattt ctagtgcata catccacagt cttccagctc 126600
aataactagt tccaaagtca cttccacatt ttaaggcatt tgttccagca gcattccaat 126660
tctcaatacc aaaattttag tctgcaatat ctgccttcac aaaataccac agaattggtg 126720
gcttaggcaa cagaaattta ttttctcagt tatggagtct agaattctga gattaacgtg 126780
ccatcatggt tgggttctgg tgagggcttt cttcctgact tgcagacagc ttctttcttg 126840
ccctcacatg acggagagag agataatctc tttctcttct ttttgtaata aggccactaa 126900
tcctatcctg agggctccac ccttatgacc taatctaacc ctaattacct cccaagggct 126960
tcatctccaa ataccatcat attgaaggtt agggattaaa tttagaaatt ttggggggat 127020
acattcagtc tgtaacaggt tgtatactct caaggtccca gtgatggatg caatcagtga 127080
ttcctctaag accaaagagt tgaagacctg actttaggag cttgtttatc ccacagaact 127140
aaagaattgg gtatctcaag tcatcatcca gatactgcag ctctcctctc ctaacttttt 127200
ggagtcattc tttctgctgc tgtcaatagc cctcttcttt ggtcccacaa cacaccatca 127260
tgatttctgc attaaaaatg ccatctccca agtaattaac ctattcacag taagaacagt 127320
tgttagaagt tggggttatt tcatcatggt ccaatggctt tatcttgctc aggaaatcaa 127380
agatgagtgt ttctaaagca aaaaaaagga ggatctcaca attgtatctg tttcattcac 127440
tctgcagggt ccattttaca cccaaacatt cattagttca ttgtttgtac tcctgccttt 127500
cctgaggaag tcattgtagc actatttctt aagtatattc aaatttggat aagttagtca 127560
aattgatgtg aaaggaccac ccttgtaagc caaatgtgta agtcctacat agggatatta 127620
cctgttttta tctcctgatg ggcttttttt ttttcaagtt tctaaataaa tccagtgaac 127680
aagtagatac gctactcatg attatatagg aaaacagaga agagaaacat acacttactt 127740
aaaagtagaa acatatctgc tctttcccac ttcaccctta attttttttct ccccagccaa 127800
tttactcacc ttctgtggct gtgcttctgt gttagaccct tgctagctgc ttctggggtt 127860
cagagcaatt gtgctctgcc ctcatctttt atgacacacc tagcaaaaca gaagcagagg 127920
agcgagttga aacagacaaa cgactatctg ttattcttca aacatgccta ggattgtatt 127980
taactatcac ctatctaaaa gaggtattct cgcctgcctg gaaagaattt tgctaagaaa 128040
attgtttctc ttcttcccat attattttac ctctatgcta gttccctgtg atttgatatg 128100
tcaactttga caaattcatt tttctaaagc acagatatga ccttttttgt taagaaaaag 128160
aaactactgt tgctccccag tgctacacac acacacacac acacatacac atacacaccc 128220
ttcacaagcc ttatctgcac ccccgcccac tccccacaac aaacttcaga tgtcttagct 128280
tggcattctt cggaattagg tcaacgtttc agattttgct tccatttgtg tatttctgac 128340

-continued ccttcatgaa ctcattttgg cctcttagaa cttcttcctc ttctcaaagc atctcttggg 128400
ttttttaacc tcttgttcct tcgcctataa agagagtttc caaggcaaac cttggtcttc 128460
tttaaaaatc actctgcgta agatttgaaa tcactaaatg aagttttaat aaaggatata 128520
tcttcattgc agggcttttc aaaatcttta tagccaagta ttttggtcat ttctaagaaa 128580
ggacacacta ttaaactatt ccagttcgtg ttggggaggt ttttctagat ctctttatat 128640
tcaaattcta ttcatacttt atcacctatg acaaaatagc actttctcta aagaaacatt 128700
ctctgacctc cctatctaaa gtgatccgaa tctcttccaa acatttattt actttatgta 128760
tcctgtgaat ctttggaatc taagcttatt agaaaatata gaaaaccacg aaaatgaaag 128820
caaaaatcag ctgtagtctc taaggcaaag aacatttcca attaagaaat taaactccct 128880
ttgactttta aaccccatct tagcagtttg ttgcattcac ttccaacttg tttctgttct 128940
cataaggata ctctatcttc agatagatag atatagatag atgtgttgtt ttagcaaaaa 129000
tagaagtatg ttttaccttg ttgagccttt tttttttca tttcataaga taaaatgtac 129060
agctttctag atcagaacac ctaaatctat tttcttttta aggattaaat ctataggcat 129120
atcaattttt atttttatc tcttgtatat tattaggttg ttaattcatt aaaggtaaag 129180
tatgtatctt atataggtta gtattattca cagtatttaa ctgtttttt tttcctcagg 129240
agagtcttgc tctgtccccc aggctggagt gcaatggccc aatctcggct cactgcaacc 129300
accccctcct ctgtccaatc aaccctcccg cctgagcctc ccaagtagct gggactacag 129360
gcatatgcca ccatgcctgg aaattttttg tattttttgt agagttgggg tcttaccatg 129420
ttgcccaggc tagtcttgaa ctcctgggct caagcaatcc acctgccttg gccctgcaaa 129480
gtggtgggat tacaggtgtg agccgccgca cctggtcaca atatttaact ttaaataggt 129540
atataataca tggttatttt cactcacatc catgtgaaga gaccaccaaa caggctttgt 129600
gtgagcaaca aggctatttc acctgggttt caggtgggct gagtccgaaa agagaatcag 129660
cgaagggaga taggagtggg gccgttttat aagatttggg taggtaaagg aaaaaggggg 129720
gttgttctct ggtgggcagg ggtgaggatc acaaggtgct cagcgggggga cgttttgagc 129780
caggatgagc caggagaagg aatttcacaa ggtagtgtca tcagttaagg caggaaccgg 129840
ccattttcac ttcttttgtg gtggaatatc atcagttaag gcaggaacca gccatctgga 129900
tgtgtatgtg caggtcacag gggatatgat ggcttagctt gggctcagag gcctgacagt 129960
tattgaatga atggagaaac aaatcactta gacaccttct aggaaaaaat gaccaactat 130020
gctacctgca attacgtttc aaaatgtagc ttatctgaag aaaaggaagt aacatttaat 130080
tacaagcatc aatacaactc aagcacagag gaagtgtgct aaacaatttc ctccatacgt 130140
acaaattttt atttacagaa aagtatatgt cttaatgaga aaatgtgctc gaaaacattc 130200
tcatcatttc tgagtttggt ttcagtctta atgaatgtgt cccttaacta ttaatctgct 130260
ttgtcatctc tctaactccc tactatctca ttgccattgc aaaggcaaag gtccacatct 130320
tttatagttt catattatcc aaaagtgtta acttaggata gatgtgtaca tagttttgta 130380
ctcattgtac atgcttagct gcaattcttt tgcctttgca cttctgaaat acaaccatat 130440
tcacaacaca tcatttgttc ccttataaca tttcaccttt tccactttgt ttattctcta 130500
tatgctcact gttagtttag atgctgcctt aggcttttat gatatatact gtgactgcat 130560
actgtaattt ttctctatag catgtatccc atttatttaa gtgtgtgtgt gtgtgtgtat 130620
acagtctata taataaattt acatgcttcc ttaagtagac tgtaggcccc accaacatag 130680

-continued aaaccatatg tgtcttgttc ttcattgtac cctcaatgcc taagaaaggt gctggaacat 130740
ggtaggcatt caataaataa ttggtaaata aataaatata caattctggt agttgattaa 130800
ttcaaattaa ttttaaaatt tagaactgta aaagtaaatt aaaaaataag ataaagacaa 130860
tgtgattatt ttttaataaa ccaacaggtc atggagattt taaaaattaa attcagtcat 130920
atggccttgt aaagtaacta gagaaaaatg tacacactta aaccagctgc ttgtggcatt 130980
catcagttaa ttcatttgtt tataaaatca ttttattttc taggtggccc agaaacagta 131040
ggttgagaag cagcaatgaa ttaaaatcaa gaagaaacac agaaaaaagt aaaaacacat 131100
gtgcatacac atataagcct agaagcttga gtatactaag cctaatctga ttcttaatga 131160
taaacatggt ctgaatcata tggagtaacc taaccctttg gctactaaat taccaataaa 131220
cattgataat ggtgataaag catctagcac tcctttactg atattgagtt aatgagttat 131280
ttctactata taattaccaa gacatatgat atagctatgg tcctttattt agtgttgagg 131340
gggtaaatat ggcagttgtt tttagatctt acttaaaaag caaaaatgtt tgaattaatc 131400
tccctttcaa gggccacctc ctggcacttc atggttccat gaatagctga cattgacttg 131460
ccatgtgtaa aattaagctt ttcttcccat cacttttctt gaggactcat tttgctgttc 131520
actattcatt cacatttaca tatgcccatt tttacctttg tgtcaataat gataaaaatc 131580
tctctcttat attgtgtcta atactattag ccactcactc tgttgagaaa tttacacata 131640
ttatctcctt taatttttcc agcaatctca tgaggtagct cattttacag atgaagtaac 131700
aagctcagaa attgagtgga gaagtttagc accaaatcct tttaacctca aacacatgat 131760
tattttatat tacctcttaa cactgattta ctacagggaa aaacttaaac cctttcattt 131820
cccccaattt aggtcatcca tcaacagtca tttattaaat atcttaaaag ggccaggcat 131880
gtgatcaatg tgtatatcca tattaactgt gctgtggcta gttaatcgaa tatggaaatt 131940
ttgttcatta aataaacatg tattgtgcac ctactgaatg cttggtctca tgaacaagaa 132000
tgatataatc tctggctgtg agtatcttac agttcacata agagacatga aatttcagtg 132060
ttggtgagtc ccctacaaaa taatatagat aaaggctgtc ctctagtgta aagctgtgaa 132120
aactacagct aatccacagt tttcttttgt ttaatttctt ttctttttaa attacttttc 132180
ttcaaaatta aaactgtaga agaacctggt tcttcccccca aaattttttt taaaagcttc 132240
tgcctcatca caaaattctc caccctgcca tactctgtgg aaccagggac tcatagcatt 132300
tgtgggactg gagttgatgt tttctgagca gttttctgtc ctgagcttcc tcattatgtt 132360
gcagtgaaag ggatggtatg gtaaaattct ggatttactt gcaatcaacc cttacataat 132420 aatttttttag acttccattt attgaggact tgtccagtat ttcgtgttaa tacttatata 132480
ataccttata aaacaatttc aaatcagcat ctcagaggct gattcagtcc acttgaatgt 132540
tttgtttggc tcagtggagt gttcaacttt aaaatttatg gtattttaga agcgaccata 132600
aattcctagt gtctctttaa gaaaaagtag gggtctggc aacacaggac cacctacaca 132660
tatggcaacg caagagtcag ctggacaggg ttagaaattg atatagatat tttatcggtt 132720
gaaagtttag cttggaaaca tttggaaatt ttttttttct tttgtcctat acaaatgaag 132780
acttttactt cttttctccc ttaagagacc gtatcatatt cgctccagta cttccagcaa 132840
ggaaattgta cacacgtttg agacgactgt tgtaacttac ccttctgcct ggtcacagga 132900
aatggtgtca cttcttaaaa aggtaagaag gaagactgca tgtccaaacg aagtaacaaa 132960
aggaagcagg ctctctggct taagtttaga agttagtata caatattggg gacagtcatg 133020
atagtataca tttgtagagt gtattttcta gctgttagct ttcaaataca tggcttcatt 133080

-continued

```
aactcaactc agattcccct tggatgtccc aaagccatct taaactcaaa ggacttcttt 133140
atgctttgtc tttcctgaat atcttctcag gaaattactc tcagtgactg gcttctctat 133200
ccaaatccac ttacgccagc cagcaaccag gactcatctt gtcatactgc gtattcaatt 133260
nnnnnnnnnn nnnnnnnnnn nnnnnnnnnn nnnnnnnnnn nnnnnnnnnn nnnnnnnnnn 133320
nnnnnnnnnn nnnnnnnnnn nnnnnnnnnn nnnnnnnnnn nnnnnnnnnn nnnnnnnnnn 133380
nnnnnnnnnn nnnnnnnnnn nnnnnnnnnn nnnnnnnnnn nnnnnctagc cttataacgg 133440
gtttgtccac atacactttt accactccat tctattcccc atgcagcccc acagtggtct 133500
gttaaaggac agtccaggat attttcctta ttcttagaat aaagattaaa ataattttgt 133560
ggtacaaaag ttcaaaatac ctctcaagcc ttgttttgga cttttggact tttgtccccc 133620
ctttgactac acataaactg ctttggcctt tttcttcttc ttttctttct tttctccttc 133680
ttcactttta cataccagtc ttcctctcac cacaggacct ttgcacatgc cagtacctat 133740
tcctggaaca gtgcctccaa tcctagttcc tccagttcct ccttgagagc agtactactc 133800
aatgtggttc actggttcta gtccatgaat tttttctgca ggtctattgt aagtaaagaa 133860
cttgagagaa gcatttagaa acttttatag caattggaca ctgctgtagc atctaaacac 133920
atgatcaatg gacttatctt attgaagagg gtccaagctt gtttgacggt tgttgaactc 133980
aagtcacaag gtgtctatgt ggggtgctgc atactggcaa tgcataataa gaccacatac 134040
tgatttcagt ggattggaaa ttgaaacagt acaaaaacaa acaaaaataa ctgacccttc 134100
tacatagttt gggaagcaca actttagctc ttagctcaaa tatcaccttc ttggtgtaag 134160
ttcacataac actatctttc cttcatagca tttttcagtt taaaattata cccagcattt 134220
gtgtgatcct tggttacgta ccattttctt cttagcttca tgagggtagg gaccatgtct 134280
gacatgtgtt accattgtat tctcagcatc taacacaaag cctgagaagt gaaatttgac 134340
aagtattcaa ataaatgagg tccacagctt tcatcagatt ttcaaggtac ccatcttcat 134400
caaacagatg aagaacagtt atagcgggag gtcaaaagtg tatattgagt gatgatacaa 134460
aacaagaatg aggggcccaa gaggaatggg cttggccttt tttttttttt tttttttttt 134520
tttttttgag gagaaaattg caccagttgt ggctggtaat ggaaaatagc tttagtggct 134580
aaggagtcat catttgtgtc tcttgttttt ggagtcaagt tccttatttt ggaataggga 134640
cattgcatca gtaatgtcaa agacatagaa tgggggatca tttttcataa gcaaattctg 134700
cttagttcca agacagccct gcttcactcc acaaattaca ccctgaggtt gcatggttgt 134760
catcttcaga agcattctca agtgggactg acaatgccta tttgagccac acaattgctg 134820
tgatgttggc tcaggaatgg ttaagggggc aaaaatcttt tatctcaatt agtaaaatct 134880
agaactataa cagttacttt agttacacct tatctatgcc gcccccaatg tattttaatt 134940
agttgtaaaa acagctacaa ttcttagtag gaaatgagtt ctacttgtga aatgtatcaa 135000
catttgtcac cataggtttt ctactaggta ctttgtataa atagcctccc actaatcctg 135060
attacaatcg tatgaaatac attattacca ctttttttaa acacatgggt aaactannnn 135120
nnnnnnnnnn nnnnnnnnnn nnnnnnnnnn nnnnnnnnnn nnnnnnnnnn nnnnnnnnnn 135180
nnnnnnnnnn nnnnnnnnnn nnnnnnnnnn nnnnnnnnnn nnnnnnnnnn nnnnnnnnnn 135240
nnnnnnnnnn nnnnnnnnnn nnnnnnnnnn nnnnnnnnnn nnnnnnnnnn nnnnnnnnnn 135300
nnnnnnnnnn nnnnnnnnnn nnnnnnnnnn nnnnnnnnnn nnnnnnnnnn nnnnnnnnnn 135360
nnnnnnnnnn nnnnnnnnnn nnnnnnnnnn nnnnnnnnnn nnnnnnnnnn nnnnnnnnnn 135420
```

-continued nnnnnnnnnn nnnnnnnnnn nnnnnnnnnn nnnnnnnnnn nnnnnnnnnn nnnnnnnnnn 135480
nnnnnnnnnn nnnnnnnnnn nnnnnnnnnn nnnnnnnnnn nnnnnnnnnn nnnnnnnnnn 135540
nnnnnnnnnn nnnnnnnnnn nnnnnnnnnn nnnnnnnnnn cattccaggt ttattcctaa 135600
tgtgagtcaa tcctaacaaa gccaaataac tcccattcag tgcgcattac ccggtgtgcc 135660
agattcacac attgtctcat tagataatca caccagtgtt gttaagagag ccccaattcc 135720
cattttacag tatgagagaa ttgagacatg cacagggtaa gtttgtcacc aaaggtcaca 135780
aagctagcaa gtagtcaagc tgggattcta atccaggtgt atttgcgact gaagttctag 135840
cttttaacca ctttttatgg tctgttttta ttgaaaggaa gtcctagttc cccaaatagt 135900
cattctcatg aatctgctgg ggtttttttt aagttttctt tgattctaaa gatgcagaag 135960
tttgtgtccc tagagatctg agtcaaagaa ttgaaaattg ttggagttgg ggtgaggaat 136020
ttattttagc atttgcccct catcctttgt ttgttctgtc tcagggattt atatttgtaa 136080
ggactgataa ccaaagacat ataattccca ttggatggat agccaaacca atggacttct 136140
gtggtctact gcattatgct ggtaagagcc agagtccaga agcttaggcc aaaggtccca 136200
agtgaggcca ctagctcctt ctctctgcct agaactgaaa ttatatgttc agttgtaggt 136260
atattgggca gaataagagg cttctaaagg ggcctgtaga accaattcag ttttctgttt 136320
tggctgtcat ggcagctcag gcctgcaatc tcagcacttt aggaggccga ggcaggagga 136380
tcaggggttc aagatcagcc ttggcaacat ggcaagaccg tgtctctaca gaaaaagaaa 136440
aaaaaattag gcaggcgtgg tggtacttgg gtgtagtctc agctacctag gaggctgagg 136500
tagaaagatc acttaagccc aggagtttga ggctgcatga gcagtgattg tgccactgca 136560
ctctagcctg ggtaacagag tgagaccctg tctcaaaaaa aaaaaaaaat tactcttaag 136620
cccatatgag gcatttgctg tgggaatgtg agagtgtgat ccttcatgta cacacagcag 136680
gaggcatgct ccaatgagag ggtaaggaga aagtacaaag tgagagaaag gagaaagcag 136740
ggtggtggaa ttgtacctta tggagcaaca ggagggtagg tctgagttct tacctctccg 136800
ctttgtgggg tccattaggg gcaacttgta ccataattga cacatgacac aatgaaggtc 136860
taggcacccc aactcttgct tccccctcct tctatgtgtt gcgtccctgc aattagccat 136920
caatgctggc tcaaaagaag ttctacgtta tgcttctctg actttagtgt gaatcggaat 136980
catctgggaa gctcattaaa gtgcaagttc ttggacctca cattctgaaa ttctgatttg 137040
ggaagtctgg ttggagaact gggaagctga gcaagcaact taggtgattc tgagttacat 137100
gattattaga gcgcactttc ggaaacataa cccaaaattt attttccact ttagaaaaat 137160
aactgtaagt cggcttttgt ttttactcat tgaggcctaa ttgagagttt agaaaaataa 137220
acgaagaata tgaaaaacga tgctggcaat aaataacgta aaacttagag tgggaatccc 137280
agtgtattat tcatggactg ctccgttaag actaagtatt attttccgta ttaggtctgc 137340
tgtgtttttc agaatgatac agtaatctga ggattgagcc aactgtcttc cttgcagaaa 137400
ggcaggctga attgtgatcc tacctttgaa cttgaggaaa tgattttgga gtccaaacct 137460
ctacataaga aaaaaaagcg tctggcaaag aaggagaagg atatgaggaa atgcgattct 137520
tctcaggtaa gcaggtcccc accaaactca gggtcatggg tatccccatg atggctgcaa 137580
tatcttcgag agcttctact gggaggtcat ttcagcttcc tgcttttgct gcttagtgaa 137640
ataggagaag tagatcagcc gggtttctaa aagggcagac cagagctcct ctgaggatcc 137700
tagcagcaac attttacttg taggctttcc gtctagagtt ctgccattaa cttgactcag 137760
ttatttctct cttccagttc tcaattcaaa atttacaaat ttcctgggag aggaactgtc 137820

-continued attggccaag cttaggtcag gggatgattc ataaaattat ggtaaagggg caggtttcaa 137880
agtacacaca tggttgtttt ggacctcact cctgctttga ggagtttctg ggagcagcca 137940
accctagaga tgatgtctgt tctttgccac aagcagaatt ttatgatatc aagcctcaca 138000
gaagagtgtc tgttcacagg aatgacggaa ttctaacatg gtggagcact attgctggat 138060
ttcaggctga gttaaattaa ctttgtaact aagtatatta ttctctgtca gagtcagagc 138120
tcagatttca gtgaagtaac ttgcaaacac tcagtaggat tttatactca catgtggctc 138180
tatgaattat aatgatgatg aagtaataaa gttactttgc ctctaaaggt catctatcta 138240
tccacacgac catttccatt cctccatcaa tccctgcctc cctccatcca ttcatttagg 138300
ctactttttt ttagtagcta tgatctgcca ggtcctgtgc taaagactgg agtgagaaat 138360
gattgagata taatttctat actcagtgct gtcccttttc tcaaagattg tgtagtcttg 138420
tggtaaagat ggctctgcaa acaaataagt atcctccatc tccttaattt ctctagtagt 138480
caggggccac tatatatttc aatggacaat taaccaacgt tcacatctct gtcctgtttg 138540
atcacagaac tggcttctcg tcagattccc ttcaggaaat attttctagg accctccaag 138600
gaatgcttag ctgtgctgct aacccgtctt gcatattgct tgtctctgaa ctgtcttctt 138660
cccaatggtc tgttcctcat gatcatgtca taaccaaccc gcttctccag acttgctcct 138720
tcccctgacc tagcagaact tggctcaagg tggatacagg cctctctgat aacaggacct 138780
aacatgtgat aaaaaccaag agatcctttt tattacaagt ttttaaagtt ttagaaataa 138840
ctgagcaatt taggaataac ttttgaccat acgtaccatg ctcaacatga tctgcccatc 138900
tttcctgcca catccttgta ctatcccact ctgaccctca cttaaaaccc tccaacctca 138960
caggccctgc aagtgtctca ctctcaagca ctgaaccttt tgttcttctt caaggccttt 139020
gcccttgctc ttccctgttc ctagaatggt cttccctttc atcttcacat agggggcttc 139080
ctctcattct ttatacctta aatatcacct tgtcatttct gttgttgaat tataggatgt 139140
tttttacata ttctggatat tggaccctta tcaaatatgt gaactgcaaa tagtttctcc 139200
cttagtcatt ctacgaagcc agcattaccc tgataccaaa ctggacaaag acatcacaaa 139260
aaatgataat tacaaactga catctgttat gaatatagat gcaaaaatcc ttaacatatt 139320
agcaaggtgt tcagttaggc ttttgactta agatgtttct tctttttttaa tattggtgtt 139380
tatagctata aagttccttc tgagcactgc cttcacctat cccataagtt ttgggatgct 139440
gtggtttgtt tttaattcat ctctaagtat attctgatat ctcatgtgat ttctcttttt 139500
gactcttttt ttaagagttt gttgtttaat ttccacattt ttgtgaattt tccagttttc 139560
cttctgttat tgattcctac cttcattcca attatttcag tctttttaaa tttttttgata 139620
cctgttttgt ggtttccttc catggtttcc tttaactctg agcatattca agacggttgt 139680
tttaaaatct cactctagaa agctcaatgt ttgagcttcc tcaggacaat ttctatccgt 139740
tgattttaag tctttgaatg gcaatatttt cctgtttctt tgtgtgcctt gtgatttttt 139800
ttctgttgct attgaaaact cgacatttaa atatgataat gtggtaactc tggaaatcag 139860
gttcctcctt tcttcatggt ttgctatttt ttgattgttg aaggctgtag ttatccattg 139920
tttagcgact tctccaaaca atgtttgcag agattgtctg ctttgttgtg tcatcactga 139980
agtttctgtt actttagcct gtgctcagct aatgttttga ctgagattta acaccaagag 140040
catttttaag ttgtttttct tttcttaatt tagtgttcac ttggttccag taaacctttg 140100
agtgctttcc ggagttttga caaagttggt tttgacagta tctgcttgtt tttttgatgt 140160

-continued ttctgttcag agatggggct tggaactgct tacatcagca tttttctcta gattcttcta 140220
atcttgtacc ccaggttcaa aaataaaagg tactttgctt caaaacaaag aatagtcttt 140280
cttccaagaa gaatcagaaa gattatgaac tatttttctg attcttcact ctattttctc 140340
tcttttacat taaggctttt aaaacatgag tcaatcttac cttattatat tattaacatg 140400
ctcgttcatt cattcattca tttattcaga tgactgtaaa attcctgctt tgttaggaaa 140460
tatttctgac taggtggtta atgctatggt tagatacaca aagtgctgtg ggaattgctc 140520
actggacctg agtgaagggt taggataggc tttccagagg aggcaacatt tgatctggtt 140580
cctccagatt gagcagaggt aggtgagcat acaggaaagg acaagagcat ttcaaggctg 140640
gcacatctca gggcacaggc agatcttaat gttacagagg aaataaaatg acaggtggtt 140700
tctgatcata ggaattaccc atgctgtgtt caaaaggctt gtgacattac tcatcctccc 140760
tgcctttagt cttatctaga gccattcact gaaggcattc cttcagcaaa atctaacaag 140820
aacatacacc atatcagtat catattagct atagcttagc cccatttctg ccccactgtg 140880
tgtagctcag agtcaccttg ttactctaga gccaaattca tcactgttta ggtacccaca 140940
ttagaaaaga gtcaagtgtt ggcaagggaa ttccaatcaa gccacaagcc tggaaaagga 141000
gctctctatt ctgagctctc tgagttctct attctgttta attggtctat gcgtctgtcg 141060
ttgtaccagt accatgctgt tttggttact gtagctttgt agtatagttt gaagtcaggt 141120
agtgtagtag tgtaataatg cctccagtct tttttttttt tttttttttt tttttttttt 141180
tttttttttt gcttaggatt gtcttgacta ttcaagccct tatttggttc catatacatt 141240
tgaaaatagt tttttttttct aattctgtga agaatgccaa cagtcattta atgggaatag 141300
cattgaatct ataaattact ttaggcagta tggccatttt tatgatattg attctatctg 141360
ggaacctgga atgtttttcc atttgtttgt gtcctctctg atttccttga gcagtggttt 141420
gtatttctcc ttgaagaggt ccttcatttc ccttgttagc tatattccta ggtgttttat 141480
tgttttgtag cagttgtgaa tgggagttca ttcatgattt gtctctctgc ttgcctgttg 141540
ttggtgtata ggaatgctag caatctttgc acattcattt tatatcctgg gtttcagtat 141600
tttaaaaact tacttcaggt gattctatgt gtgcaaccat gattgagata cactgttata 141660
gaatctagga tgtgataaac tagaagaaca taactaaagt tttgcatttt tcgggtgtct 141720
cagtttcctc atttatagat ggagttggta tgtgtaccaa gttcataggc ttgttctgag 141780
taaattagtg catgtaaagt gctccacaga atgttagctg ttgtgatgct ttactttcca 141840
ttgcacttcc tgactcctag cctttctttt ccttggctct ttttatgctc atgtcagatg 141900
cctctattgt ttctttcccc ccagaatatc ctccacttta tcttgctctg ctcaacatct 141960
ttaaagtata gaatcaacag actgccatgc cacccagtct gtctgacaat tgaggcaaat 142020
tccctaagtc ctcttgttct ccttctgaga tttccacctg ctctaacccc ttccaatatt 142080
tcagatgccg tctccagcta tgataattta atcagtgttt gctctgctca tccttgatat 142140
gtgagtccta agattttaag cgatcatttc ccttctaagt catgtatgac ccattagtcc 142200
ctccattctt ttttcttacc cctcatttca tattctcttt atggctactc ctgttgatgt 142260
atccatttgg ccacacttct taaacttctc cacctaaagc agaggaaaaa gaacaagttg 142320
aacatgaacc ctttaagggt aatggggtct gaagtgtcac actaaaaggt catctgcaag 142380
tatgtatttc atatctttgt ttaaataaaa tagttacata gtagagggaa aaaaaatcca 142440
tgtggatttt gcatttcact caattataac cttgattttt aatgctaaaa attatttttc 142500
ctaaaatctt ggggtaaaag tgttgctcca aagagctttt atcagattat gtttatcctg 142560

-continued tagctgcctg tcccctgtga ccgatactgg aaaccctcag gattacaaat gcctccgttt 142620
gcaagtaaga gtgaaataca gcagaactgt gtcttctcct ttgtcttgtt ccccatctct 142680
cttctgtgct ttgtattgtt tcctctcctg tcacctaaac aggcactctg aaagaaaact 142740
ctccagtact ggagaactta gcatattcta attcctaggt taaaaaaaaa taataaatga 142800
ctgaatgatt tttttaaag aatattttcc atcagaagaa atttggaagt attttgttgc 142860
agaattttaa aacatttgat ctgggtctaa ttctgtcctg ggactggtaa tcatcttttt 142920
ttgaggctaa attttctcat tttgatgaaa aagtcatcaa tagatgttga aagctggaca 142980
gtgcagtgtc aaagcaaatg ctttgcatgt ctgcaagaaa gtcacaaata aagaaggctc 143040
tgctgactaa aagagaaaga tacttaatca actccagtac cattgttgag gggaacattc 143100
tatcaggatt cagtatagag agatattttt aggctattca caaaatccag gtagaacctc 143160
caagctacat ttacaataat actagctttt agattaattg ttgtttttta aatatgtatt 143220
agcctcttat acaaatataa ggagttacaa attattatta caataatctt ggctttcgtg 143280
attgtccaat gtatttacac gtaccgagag ctttatttct ccgtatagtt tcaagttact 143340
gtctcgtgtc ctttcatttc accttgcagg actcctttga gcatttctta cagggaagtt 143400
ctagtggtaa taaactccct ccacttttat ctggaaacat cttagtttct ctctcacttt 143460
tcaagaacag ttctgccaga tagaggaccc ttggttgata ggttttttc ttttagcact 143520
ttgaatatat cagcccactg ccttctggcc tccaaagttt ctgataagaa atctgcccgt 143580
catcttatga tgtacttgac aaatttttc tctcttgctg ctttcaagat tctctccttg 143640
tctttggctt tagaaagttt gcttatattg gctggacatg gtggctcaca cctgtaatcc 143700
cagcactttg ggaggctgag gcaggcggat cacttgaggc caggagtttg agatcagcct 143760
ggccaacatg atgaaacccc tgcctctact taaaattcaa aaattagcta agtgtagtgg 143820
tgcacacctg taatcccagc tacttgggtg gctaaggcaa gagaatctct tgaacccaag 143880
aggaggaggt tgcagtgagc tgagagcatg ccacttcact ccagtctggg caacagagca 143940
aaagtctgtc agaaaaaaaa aaaaaggaaa gtttgattat attatgtgtc aatgtgggtc 144000
tttttgaatt catcttactt gggatacact gtgccttttt ggatttgggg gctcatgcct 144060
ttcagctatg atttctttaa gtattctgtt ttccttttc tctctcttct cctcctggga 144120
cttccacagt acgtacactg gtttgcttga tggtgttcca tacattcctg taggccaggg 144180
atgtccaatc ttttggcttc cctgggccac gttggaagaa gaggaattgt cttaggccac 144240
acataaaata cactaacact aacgatagct gatgagctaa agaaaaatca ccctcaaaaa 144300
aatctcctaa tgttttaaga aagtttacaa atttgtgttg ggccacattc aaagccatcc 144360
tgaggcacat gtggcccatg ggctgtgggt tggacaagct tgctataggc tctgttcatt 144420
attcttcaat ctttttctt tctgttcctc agactcagta atttccactg tcctgtcatc 144480
aagtttgata ctgattcctt ccttgcctgc tcaattttgc cgttgaaacc ctgtagcaaa 144540
tttttaaatt ttagttattg cacttttcag ctcaagaatt cctttttagt ttctttttag 144600
gttttctata tttttattaa tactttagtt ttgtttgcac atcattttct tgattttctc 144660
tatatcttcc tttagctctt tgagcatctt taagatagtt gttttgatgt ctttatctag 144720
tagatctact gttaggtctt tttaagggat aggttttttg gtttatgttt tttactgtga 144780
atgagccata cttctctatt tcctggcatg ccttgttatt ttttgtattg gacacttgaa 144840
tctaataatg tgataaatct aggaaaatca gatttctccc atccccaggg tttgctgttt 144900

-continued tttgttattg tttttatttt tatttttat tattgttgta agctgtctcc atgccaagga 144960
tcagctgagg tgtaaacata agatcttctt aggtcttttc tgagcctgca cccttccctg 145020
gtcatgtgca gtcactttct aattttccct acacatgcag ttgtttttga atgtcccagc 145080
ctttcacgtg tggctcccaa aaggaggaaa ggagaaaaat gaagagggtg aaaaggtgct 145140
ggccctttaa ttctcccaga agtcacttca gcctgaggga gagtggctgg caacattgtg 145200
ggggaggtgc aacaacaatg gccatcaagc attttgtttg cacctctgtg atcagaagca 145260
gcagtgtcgg aagcacagat cctcagaatt tggagaacac agttcttgct ttccaccctg 145320
actctcacag gctgtgtgca aactgctccg gaacatgtgt gtgctcagct ccctcccatg 145380
gggctggagg atgagggatg ggtagctgct gctgtgctaa gagcttaagt tggtcataat 145440
taactgcgct ttgccaccca agccttccct gaaagttgca agctttcaat agactccaga 145500
gttctaaaat agtgacatta gacagattct gccagtgcaa tcgctgtcta ggagggggaga 145560 cagattcctg gtgcttcctg ttttgccagc ttcccggaat cttcttcaca tagcatccat 145620
tttgaagata ctacttactt ctcaatttgg ggctattcat tgaatagact gtcaccaggt 145680
tattggctgt ttgaagattc tcatttgtct gctaactata cctctatttt ttttctacgt 145740
tcacctggaa gacatgtctt cttcaagagc accttgactc tgtccagaag gagttcataa 145800
ttttcaacag agaaaagtaa gtaattcctg ggagaacaac agccccagaa atggtggcat 145860
gtttcagcca gactttactt gcagagaaaa tatattttta acattttaaa aattattttc 145920
taattgggaa aatgatgcaa tctattatag aaaatgtaga aaccttttt gtaaggtatt 145980 taacattttt taattgataa attagcctag catcaagttt ttgtttgtga gaagggaaga 146040
ggaattagga tttaaacact taaaaatcaa agccttttaa aagatttcct tggctcatgc 146100
ttatttataa attattgggc ttaatattat ttcaaaagct taaacctttc attttatttt 146160
tcaaagaata aaacatcttt ttttttcttt tctttttaag agtaaacagg gactttaaca 146220
aaagacaacc aaatctagcc ttggaacaaa ccaaagaccc acaaggtgag gatggtcaga 146280
ataacaactt gtaaaggcct catgtcttct tcttgggaca atctcatgcc agaaacttct 146340
aattacatat gtcaagaaaa gctgacagta gttcttgcca ctccacacac catgacttag 146400
aaaatgtgaa tgaatatatt tcaaaaaagg cagcacaaca cagtgaaggg tcctgggcct 146460
gagctcctgg gatgtcattt cacatcaatc aactgtgtga tctagagcaa gtcacttagc 146520
cactttctgt gctttacttt atttatctaa aatgagaggg ttatactaga cgagccatac 146580
cctgcctttt tagtgctata gttgttattc taaaccgcct ttatttttat tttaaaatta 146640
atatatgaat atagatttat ttttccactc cttctaatta tgcagtgaca aatggacaaa 146700
tggacacagg actcagtgag acttttcaga cctcgaaagt ttcataaagt ggtcagaatg 146760
ccccaggcta cttggataaa gataaggaat tctatcaggg aggcatgaat ggaatcagat 146820
taaaagtaac agagatggat gagggccttc cagtgatatg cgtgaatcag cattagatcc 146880
gcttatctca gctggcagga gcctgctgtg cacaccactt cccagctccc tcttcaacaa 146940
tgtgaaagtg gtaacttgaa attggtaata atgggagcat ttacaccacg gaaactggta 147000
aatgctcgtt ttttccctcc taacaagtga attgctaaat attagcccac cactccttcc 147060
aagaagcatg ttccttgagg gctaattgtc ctctgaagat tagcagagac ctgtatctgg 147120
agaggatcag aaaagaatgt catcacactg aaagtatgtc caccttgcag ttcagaaaag 147180
ttgcatctta tatggggttt attgtctaag ttagaaatga atttagaaga tagtaaaatt 147240
taccgttgaa aaacccctta aattacccat aaagtatatg ggaagtatct tttctcagta 147300

-continued

```
aagcccaata cagtgtcacc tttcactaat gaaacaagcc attgcttttg ttttgttttg 147360
acttagttat ttttattttt ggtctcattt tggctaatac cagatgagct aaaatgttga 147420
acaaattata cttgttttta tagactagaa ttactctttt ttttcttttc aggcagagtc 147480
tcactctgtc acccaggctg gagtgcagtg gcatgatctc tgctcactac atctgcctcc 147540
cgggttcaag tgattcttgt gtctcagcct cctaagtagc tgggatcgca tgtgtgtgcc 147600
accatgtgta gctaattttt tgtattttta gtagagatag gattttgcta agctggccag 147660
gttggtttca aactcctggt ctcaagtgat ccgcccacct tggcctccca aagtgctggg 147720
attacaggcg tgagccacca aacctggcct tagaattact cttagaacag tggaatgccc 147780
acacatccaa gacaggcaag ttcatggaga ctaagggaac agtggtatca tgtctccctt 147840
ctcccttgtg cttactacaa gaatggcagg cagaattccc tacttattta aaatatcact 147900
gatgtctcac tctttttctt tatattttat ttattgattt gccacaaagt ttaattcacc 147960
taagtgagac gtgcatatga tgtaactcca ctgtacagat acacagatct ttacagaaga 148020
actattttg gcaacccta tgcccctggg tagggtccag aagtgaacag gcttggtggg 148080
ggattgtttt cacctcttgg ctactcagag tacctaaacc tgtccttact tatggagagc 148140
atgtgtcaca ccaagatggc agtaagctgg caactgcgaa gacctgactg atgcccattt 148200
gggaagccag gcaagtgaaa atggaccgaa gaaacagaga tggctgtctt ttatgcaggg 148260
cttttccata aagaggttac actggggcaa ccaagtatgt gtagaaagcc agagctaaac 148320
ttcagcttgg cattcacagt tttctcttca ctgagctaat aggcccagag tttcgggcag 148380
agctgtgaaa tagtgcttct ctaatagcaa ccatattatt gttacataat taaaagccag 148440
ctcttttgtt gtttgtttga ttccttttcc ctacagttcc cacatcattt gtctgtgcta 148500
ttctgttttt ctccaaacac tataaacttg aagcaattgc cctgactcga tttcagagaa 148560
ggggatg                                                           148567
```

```
<210> SEQ ID NO 4
<211> LENGTH: 404
<212> TYPE: PRT
<213> ORGANISM: Mus Musculus

<400> SEQUENCE: 4

Met Gly Gly Asn His Ser His Lys Pro Pro Val Phe Asp Glu Asn Glu
 1               5                  10                  15
Glu Val Asn Phe Asp His Phe Gln Ile Leu Arg Ala Ile Gly Lys Gly
            20                  25                  30
Ser Phe Gly Lys Val Cys Ile Val Gln Lys Arg Asp Thr Lys Lys Met
        35                  40                  45
Tyr Ala Met Lys Tyr Met Asn Lys Gln Lys Cys Val Gln Glu Arg Asp
    50                  55                  60
Glu Val Arg Asn Val Phe Arg Glu Leu Gln Ile Met Gln Gly Leu Glu
65                  70                  75                  80
His Pro Phe Leu Val Asn Leu Trp Tyr Ser Phe Gln Asp Glu Glu Asp
                85                  90                  95
Met Phe Met Val Val Asp Leu Leu Leu Gly Gly Asp Leu Arg Tyr His
            100                 105                 110
Leu Gln Gln Asn Val His Phe Thr Glu Gly Thr Val Lys Leu Tyr Ile
        115                 120                 125
Cys Glu Leu Ala Leu Ala Leu Glu Tyr Leu Gln Arg Tyr His Ile Ile
    130                 135                 140
His Arg Asp Ile Lys Pro Asp Asn Ile Leu Leu Asp Glu His Gly His
145                 150                 155                 160
Val His Ile Thr Asp Phe Asn Ile Ala Thr Val Leu Lys Gly Ser Glu
                165                 170                 175
Lys Ala Ser Ser Met Ala Gly Thr Lys Pro Tyr Met Ala Pro Glu Val
            180                 185                 190
Phe Gln Val Tyr Val Asp Gly Gly Pro Gly Tyr Ser Tyr Pro Val Asp
        195                 200                 205
```

-continued

```
Trp Trp Ser Leu Gly Val Thr Ala Tyr Glu Leu Leu Arg Gly Trp Arg
    210                 215                 220
Pro Tyr Glu Ile His Ser Ala Thr Pro Ile Asp Glu Ile Leu Asn Met
225                 230                 235                 240
Phe Lys Val Glu Arg Val His Tyr Ser Ser Thr Trp Cys Glu Gly Met
                245                 250                 255
Val Ser Leu Leu Lys Lys Leu Leu Thr Lys Asp Pro Glu Ser Arg Leu
            260                 265                 270
Ser Ser Leu Arg Asp Ile Gln Ser Met Thr Tyr Leu Ala Asp Met Asn
        275                 280                 285
Trp Asp Ala Val Phe Glu Lys Ala Leu Met Pro Gly Phe Val Pro Asn
    290                 295                 300
Lys Gly Arg Leu Asn Cys Asp Pro Thr Phe Glu Leu Glu Glu Met Ile
305                 310                 315                 320
Leu Glu Ser Lys Pro Leu His Lys Lys Lys Lys Arg Leu Ala Lys His
                325                 330                 335
Arg Ser Arg Asp Ser Thr Lys Asp Ser Cys Pro Leu Asn Gly His Leu
            340                 345                 350
Gln Gln Cys Leu Glu Thr Val Arg Lys Glu Phe Ile Ile Phe Asn Arg
        355                 360                 365
Glu Lys Leu Arg Arg Gln Gln Gly His Asp Gly Gln Leu Ser Asp Leu
    370                 375                 380
Asp Gly Arg Ile Gly Ser Gln Thr Ser Ser Lys Leu Gln Asp Gly Arg
385                 390                 395                 400
Asn Asn Asn Ile
```

<210> SEQ ID NO 5
<211> LENGTH: 403
<212> TYPE: PRT
<213> ORGANISM: Human

<400> SEQUENCE: 5

```
Met Gly Gly Asn His Ser His Lys Pro Pro Val Phe Asp Glu Asn Glu
 1               5                  10                  15

Glu Val Asn Phe Asp His Phe Gln Ile Leu Arg Ala Ile Gly Lys Gly
            20                  25                  30

Ser Phe Gly Lys Val Cys Ile Val Gln Lys Arg Asp Thr Lys Lys Met
        35                  40                  45

Tyr Ala Met Lys Tyr Met Asn Lys Gln Lys Cys Ile Glu Arg Asp Glu
    50                  55                  60

Val Arg Asn Val Phe Arg Glu Leu Gln Ile Met Gln Gly Leu Glu His
65                  70                  75                  80

Pro Phe Leu Val Asn Leu Trp Tyr Ser Phe Gln Asp Glu Glu Asp Met
                85                  90                  95

Phe Met Val Val Asp Leu Leu Leu Gly Gly Asp Leu Arg Tyr His Leu
            100                 105                 110

Gln Gln Asn Val His Phe Thr Glu Gly Thr Val Lys Leu Tyr Ile Cys
        115                 120                 125

Glu Leu Ala Leu Ala Leu Glu Tyr Leu Gln Arg Tyr His Ile Ile His
    130                 135                 140

Arg Asp Ile Lys Pro Asp Asn Ile Leu Leu Asp Glu His Gly His Val
145                 150                 155                 160

His Ile Thr Asp Phe Asn Ile Ala Thr Val Val Lys Gly Ala Glu Arg
                165                 170                 175

Ala Ser Ser Met Ala Gly Thr Lys Pro Tyr Met Ala Pro Glu Val Phe
            180                 185                 190

Gln Val Tyr Met Asp Arg Gly Pro Gly Tyr Ser Tyr Pro Val Asp Trp
        195                 200                 205

Trp Ser Leu Gly Ile Thr Ala Tyr Glu Leu Leu Arg Gly Trp Arg Pro
    210                 215                 220

Tyr Glu Ile His Ser Val Thr Pro Ile Asp Glu Ile Leu Asn Met Phe
225                 230                 235                 240
```

-continued

Lys Val Glu Arg Val His Tyr Ser Ser Thr Trp Cys Lys Gly Met Val
245 250 255

Ala Leu Leu Arg Lys Leu Leu Thr Lys Asp Pro Glu Ser Arg Val Ser
260 265 270

Ser Leu His Asp Ile Gln Ser Val Pro Tyr Leu Ala Asp Met Asn Trp
275 280 285

Asp Ala Val Phe Lys Lys Ala Leu Met Pro Gly Phe Val Pro Asn Lys
290 295 300

Gly Arg Leu Asn Cys Asp Pro Thr Phe Glu Leu Glu Glu Met Ile Leu
305 310 315 320

Glu Ser Lys Pro Leu His Lys Lys Lys Lys Arg Leu Ala Lys Asn Arg
325 330 335

Ser Arg Asp Gly Thr Lys Asp Ser Cys Pro Leu Asn Gly His Leu Gln
340 345 350

His Cys Leu Glu Thr Val Arg Glu Glu Phe Ile Ile Phe Asn Arg Glu
355 360 365

Lys Leu Arg Arg Gln Gln Gly Gln Gly Ser Gln Leu Leu Asp Thr Asp
370 375 380

Ser Arg Gly Gly Gly Gln Ala Gln Ser Lys Leu Gln Asp Gly Cys Asn
385 390 395 400

Asn Asn Leu

<210> SEQ ID NO 6
<211> LENGTH: 384
<212> TYPE: PRT
<213> ORGANISM: Mus Musculus

<400> SEQUENCE: 6

Ser Ala Arg Arg Pro Val Phe Asp Asp Lys Glu Asp Val Asn Phe Asp
1 5 10 15

His Phe Gln Ile Leu Arg Ala Ile Gly Lys Gly Ser Phe Gly Lys Val
20 25 30

Cys Ile Val Gln Lys Arg Asp Thr Glu Lys Met Tyr Ala Met Lys Tyr
35 40 45

Met Asn Lys Gln Gln Cys Ile Glu Arg Asp Glu Val Arg Asn Val Phe
50 55 60

Arg Glu Leu Glu Ile Leu Gln Glu Ile Glu His Val Phe Leu Val Asn
65 70 75 80

Leu Trp Tyr Ser Phe Gln Asp Glu Glu Asp Met Phe Met Val Val Asp
85 90 95

Leu Leu Leu Gly Gly Asp Leu Arg Tyr His Leu Gln Gln Asn Val Gln
100 105 110

Phe Ser Glu Asp Thr Val Arg Leu Tyr Ile Cys Glu Met Ala Leu Ala
115 120 125

Leu Asp Tyr Leu Arg Ser Gln His Ile Ile His Arg Asp Val Lys Pro
130 135 140

Asp Asn Ile Leu Leu Asp Glu Gln Gly His Ala His Leu Thr Asp Phe
145 150 155 160

Asn Ile Ala Thr Ile Ile Lys Asp Gly Glu Arg Ala Thr Ala Leu Ala
165 170 175

Gly Thr Lys Pro Tyr Met Ala Pro Glu Ile Phe His Ser Phe Val Asn
180 185 190

Gly Gly Thr Gly Tyr Ser Phe Glu Val Asp Trp Trp Ser Val Gly Val
195 200 205

-continued

```
Met Ala Tyr Glu Leu Leu Arg Gly Trp Arg Pro Tyr Asp Ile His Ser
    210                 215                 220

Ser Asn Ala Val Glu Ser Leu Val Gln Leu Phe Ser Thr Val Ser Val
225                 230                 235                 240

Gln Tyr Val Pro Thr Trp Ser Lys Glu Met Val Ala Leu Leu Arg Lys
                245                 250                 255

Leu Leu Thr Val Asn Pro Glu His Arg Phe Ser Ser Leu Gln Asp Met
            260                 265                 270

Gln Thr Ala Pro Ser Leu Ala His Val Leu Trp Asp Asp Leu Ser Glu
        275                 280                 285

Lys Lys Val Glu Pro Gly Phe Val Pro Asn Lys Gly Arg Leu His Cys
    290                 295                 300

Asp Pro Thr Phe Glu Leu Glu Glu Met Ile Leu Glu Ser Arg Pro Leu
305                 310                 315                 320

His Lys Lys Lys Lys Arg Leu Ala Lys Asn Lys Ser Arg Asp Ser Ser
                325                 330                 335

Arg Asp Ser Ser Gln Ser Glu Asn Asp Tyr Leu Gln Asp Cys Leu Asp
            340                 345                 350

Ala Ile Gln Gln Asp Phe Val Ile Phe Asn Arg Glu Lys Leu Lys Arg
        355                 360                 365

Ser Gln Glu Leu Met Ser Glu Pro Pro Pro Gly Pro Glu Thr Ser Asp
    370                 375                 380


<210> SEQ ID NO 7
<211> LENGTH: 316
<212> TYPE: PRT
<213> ORGANISM: Homo sapiens

<400> SEQUENCE: 7

Tyr Ser Phe Gln Asp Glu Glu Asp Met Phe Met Val Val Asp Leu Leu
 1               5                  10                  15

Leu Gly Gly Asp Leu Arg Tyr His Leu Gln Gln Asn Val His Phe Thr
            20                  25                  30

Glu Gly Thr Val Lys Leu Tyr Ile Cys Glu Leu Ala Leu Ala Leu Glu
        35                  40                  45

Tyr Leu Gln Arg Tyr His Ile Ile His Arg Asp Ile Lys Pro Asp Asn
    50                  55                  60

Ile Leu Leu Asp Glu His Gly His Val His Ile Thr Asp Phe Asn Ile
65                  70                  75                  80

Ala Thr Val Val Lys Gly Ala Glu Arg Ala Ser Ser Met Ala Gly Thr
                85                  90                  95

Lys Pro Tyr Met Ala Pro Glu Val Phe Gln Val Tyr Met Asp Arg Gly
            100                 105                 110

Pro Gly Tyr Ser Tyr Pro Val Asp Trp Trp Ser Leu Gly Ile Thr Ala
        115                 120                 125

Tyr Glu Leu Leu Arg Gly Trp Arg Pro Tyr Glu Ile His Ser Val Thr
    130                 135                 140

Pro Ile Asp Glu Ile Leu Asn Met Phe Lys Val Glu Arg Val His Tyr
145                 150                 155                 160

Ser Ser Thr Trp Cys Lys Gly Met Val Ala Leu Leu Arg Lys Leu Leu
                165                 170                 175

Thr Lys Asp Pro Glu Ser Arg Val Ser Ser Leu His Asp Ile Gln Ser
            180                 185                 190

Val Pro Tyr Leu Ala Asp Met Asn Trp Asp Ala Val Phe Lys Lys Ala
        195                 200                 205
```

-continued

```
Leu Met Pro Gly Phe Val Pro Asn Lys Gly Arg Leu Asn Cys Asp Pro
    210                 215                 220

Thr Phe Glu Leu Glu Glu Met Ile Leu Glu Ser Lys Pro Leu His Lys
225                 230                 235                 240

Lys Lys Lys Arg Leu Ala Lys Asn Arg Ser Arg Asp Gly Thr Lys Asp
                245                 250                 255

Ser Cys Pro Leu Asn Gly His Leu Gln His Cys Leu Glu Thr Val Arg
            260                 265                 270

Glu Glu Phe Ile Ile Phe Asn Arg Glu Lys Leu Arg Arg Gln Gln Gly
        275                 280                 285

Gln Gly Ser Gln Leu Leu Asp Thr Asp Ser Arg Gly Gly Gly Gln Ala
    290                 295                 300

Gln Ser Lys Leu Gln Asp Gly Cys Asn Asn Asn Leu
305                 310                 315


<210> SEQ ID NO 8
<211> LENGTH: 347
<212> TYPE: PRT
<213> ORGANISM: Caenorhabditis elegans

<400> SEQUENCE: 8

His Phe Ser Val Ile Arg Ser Ile Gly Arg Gly Ala Phe Gly Lys Val
1               5                   10                  15

Cys Ile Val Gln Glu Arg Lys Thr Lys Lys Tyr Phe Ala Leu Lys Tyr
            20                  25                  30

Met Asn Lys Arg Arg Cys Ile Glu Lys Gly Val Ala Ala Asn Val Ile
        35                  40                  45

Arg Glu Leu Thr Leu Leu Ser Lys Met Ser His Pro Phe Ile Val Asn
    50                  55                  60

Leu Trp Tyr Thr Phe Gln Asp Gly Asp Tyr Met Tyr Met Val Ser Asp
65                  70                  75                  80

Leu Leu Leu Gly Gly Asp Leu Arg Tyr His Leu Ser Gln Gln Gly Lys
                85                  90                  95

Phe Ala Glu Asp Arg Ala Lys Leu Tyr Leu Cys Glu Ile Cys Leu Ala
            100                 105                 110

Val Glu Tyr Leu His Glu Met Lys Ile Val His Arg Asp Ile Lys Pro
        115                 120                 125

Glu Asn Ile Leu Leu Asp Glu Gln Gly His Ala His Leu Thr Asp Leu
    130                 135                 140

Asn Leu Ala Thr Gln Leu Glu Asp Asp Gln Leu Ala Thr Ser Tyr Ser
145                 150                 155                 160

Gly Thr Arg Pro Tyr Met Ala Pro Glu Ile Tyr Ala Thr Tyr Leu Glu
                165                 170                 175

Ile Glu Asp Gly Tyr Asp Ser Arg Val Asp Trp Trp Ala Leu Gly Val
            180                 185                 190

Cys Phe Tyr Glu Met Leu Arg Gly Arg Thr Pro Phe Glu Phe Ser Ser
        195                 200                 205

Arg Thr Lys Pro Glu Glu Ala Tyr Val Ala Phe Arg Glu Ser Ser Ile
    210                 215                 220

Pro Tyr Pro Ala His Trp Pro Thr Asp Leu Ile Gln Phe Ile Asn Ser
225                 230                 235                 240

Met Leu Lys Phe Asp Lys Glu Lys Arg Leu Val Gly Leu Glu Ala Ile
                245                 250                 255

Lys Lys His Ser Tyr Thr Glu Arg Ile Asp Phe Lys Ser Val Phe Glu
```

-continued

```
        260                 265                 270

Lys Lys Pro Ser Pro Val Phe Ile Pro Cys Lys Glu Gly Leu Asn Cys
    275                 280                 285

Asp Pro Met Tyr Glu Leu Glu Glu Arg Ile Leu Val Ser Thr Pro Ile
    290                 295                 300

His Arg Arg Arg Thr Asn His Asn Asn Ser Ser Gly Arg Ser Ser Ser
305                 310                 315                 320

Glu Pro Gln Asn Ala Ala Leu Val Glu Val Ser Lys Ala Phe Ile Asp
                325                 330                 335

Phe Ser Arg His Asn Val Lys Ile Glu Pro Asn
            340                 345
```

ISOLATED HUMAN KINASE PROTEINS, NUCLEIC ACID MOLECULES ENCODING HUMAN KINASE PROTEINS, AND USES THEREOF

This application is a Divisional of U.S. application Ser. No. 10/254,869 filed Sep. 26, 2002, now U.S. Pat. No. 6,653,117 issued Nov. 25, 2003, which is a Divisional of U.S. application Ser. No. 09/801,876 filed Mar. 9, 2001, now U.S. Pat. No. 6,492,155 issued Dec. 10, 2002.

FIELD OF THE INVENTION

The present invention is in the field of kinase proteins that are related to the serine/threonine protein kinase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks N K (1992) *Annu. Rev. Cell. Biol.* 8:463–93). Regulation of PTK activity may therefore be an important strategy in controlling some types of cancer.

The kinases comprise the largest known protein group, a superfamily of enzymes with widely varied functions and specificities. Kinases are usually named after their substrates, or regulatory molecules, or after some aspect of a mutant phenotype. With regard to substrates, the protein kinases may be roughly divided into two groups those that phosphorylate tyrosine residues (protein tyrosine kinases (PTK) and those that phosphorylate serine or threonine residues (serine/threonine kinases (STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinase of the present invention is associated with the Ellis-van Creveld syndrome. The syndrome is an autosomal recessive skeletal dysplasia characterized by short limbs, short ribs, postaxial polydactyly and dysplastic nails and teeth. Congenital cardiac defects, most commonly a defect of primary atrial septation producing a common atrium, occur in 60% of affected individuals. The disease was mapped to chromosome 4p16 in nine Amish subpedigrees and single pedigrees from Mexico, Ecuador and Brazil. The kinase of the present invention is also associated with Weyers acrodental dysostosis, an autosomal dominant disorder with a similar but milder phenotype, has been mapped in a single pedigree to an area including the EvC critical region. A new gene (EVC), encoding a 992-amino-acid protein, that is mutated in individuals with EvC was also identified. A splice-donor change in an Amish pedigree and six truncating mutations and a single amino acid deletion in seven pedigrees were also identified. The heterozygous carriers of these mutations did not manifest features of EvC. Two heterozygous missense mutations associated with a phenotype were found, one in a man with Weyers acrodental dysostosis and another in a father and his daughter, who both have the heart defect characteristic of EvC and polydactyly, but not short stature, which suggested that EvC and Weyers acrodental dysostosis are allelic conditions. (Ruiz-Perez et al., Nat. Genet. 24 (3), 283–286 (2000)).

Kinase proteins, particularly members of the serine/threonine protein kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the serine/threonine protein kinase subfamily.

SUMMARY OF THE INVENTION

The present invention is based in part on the identification of amino acid sequences of human kinase peptides and proteins that are related to the serine/threonine protein kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in the brain hippocampus, breast mammary adenocarcinoma cell line, bladder carcinoma cell line, and the tissues of brain, fetal brain, fetal heart, kidney, uterus.

DESCRIPTION OF THE FIGURE SHEETS

FIG. 1 provides the nucleotide sequence of a cDNA molecule or transcript sequence that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in the brain hippocampus, breast mammary adenocarcinoma cell line, bladder carcinoma cell line, and the tissues of brain, fetal brain, fetal heart, kidney, uterus.

FIGS. 2A–2E provide the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIGS. 3A–3FFFF provide genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. 168 SNPs, including 14 indels, have been identified in the gene encoding the kinase protein provided by the present invention and are given in FIG. 3.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the serine/threonine protein kinase subfamily. Utilizing these sequences, additional genomic sequences were assembled and transcript and/or cDNA sequences were isolated and characterized. Based on this analysis, the present invention provides amino acid sequences of human kinase peptides and proteins that are related to the serine/threonine protein kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the serine/threonine protein kinase subfamily and the expression pattern observed. Experimental data as provided in FIG. 1 indicates expression in the brain hippocampus, breast mammary adenocarcinoma cell line, bladder carcinoma cell line, and the tissues of brain, fetal brain, fetal heart, kidney, uterus. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known serine/threonine protein kinase family or subfamily of kinase proteins.

Specific Embodiments

Peptide Molecules

The present invention provides nucleic acid sequences that encode protein molecules that have been identified as being members of the kinase family of proteins and are related to the serine/threonine protein kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in the brain hippocampus, breast mammary adenocarcinoma cell line, bladder carcinoma cell line, and the tissues of brain, fetal brain, fetal heart, kidney, uterus. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology,* 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the linase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987;

and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. As indicated by the data presented in FIG. 3, the map position was determined to be on chromosome 5 by ePCR.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. As indicated by the data presented in FIG. 3, the map position was determined to be on chromosome 5 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been found in the gene encoding the kinase protein of the present invention. SNPs were identified at 168 different nucleotide positions in introns and regions 5' and 3' of the ORF. Such SNPs in introns and outside the ORF may affect control/regulatory elements.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N. Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in the brain hippocampus, breast mammary adenocarcinoma cell line, bladder carcinoma cell line by a virtual northern blot. In addition, PCR-based tissue screening panel indicates expression in brain, fetal brain, fetal heart, kidney, uterus. A large percentage of pharmaceutical agents are being developed that modulate the activity of kinase proteins, particularly members of the serine/threonine protein kinase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the brain hippocampus, breast mammary adenocarcinoma cell line, bladder carcinoma cell line, and the tissues of brain, fetal brain, fetal heart, kidney, uterus. Such uses can readily be determined using the information provided herein, that which is known in the art, and routine experimentation.

The proteins of the present invention (including variants and fragments that may have been disclosed prior to the present invention) are useful for biological assays related to kinases that are related to members of the serine/threonine protein kinase subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in the brain hippocampus, breast mammary adenocarcinoma cell line, bladder carcinoma cell line by a virtual northern blot. In addition, PCR-based tissue screening panel indicates expression in brain, fetal brain, fetal heart, kidney, uterus.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in the brain hippocampus, breast mammary adenocarcinoma cell line, bladder carcinoma cell line, and the tissues of brain, fetal brain, fetal heart, kidney, uterus. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that kinase proteins of the present invention are expressed in the brain hippocampus, breast mammary adenocarcinoma cell line, bladder carcinoma cell line by a virtual northern blot. In addition, PCR-based tissue screening panel indicates expression in brain, fetal brain, fetal heart, kidney, uterus.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}S$-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in the brain hippocampus, breast mammary adenocarcinoma cell line, bladder carcinoma cell line, and the tissues of brain, fetal brain, fetal heart, kidney, uterus. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the brain hippocampus, breast mammary adenocarcinoma cell line, bladder carcinoma cell line, and the tissues of brain, fetal brain, fetal heart, kidney, uterus. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomic deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the brain hippocampus, breast mammary adenocarcinoma cell line, bladder carcinoma cell line, and the tissues of brain, fetal brain, fetal heart, kidney, uterus. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in the brain hippocampus, breast mammary adenocarcinoma cell line, bladder carcinoma cell line by a virtual northern blot. In addition, PCR-based tissue screening panel indicates expression in brain, fetal brain, fetal heart, kidney, uterus. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the brain hippocampus, breast mammary adenocarcinoma cell line, bladder carcinoma cell line, and the tissues of brain, fetal brain, fetal heart, kidney, uterus. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the brain hippocampus, breast mammary adenocarcinoma cell line, bladder carcinoma cell line, and the tissues of brain, fetal brain, fetal heart, kidney, uterus. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the brain hippocampus, breast mammary adenocarcinoma cell line, bladder carcinoma cell line, and the tissues of brain, fetal brain, fetal heart, kidney, uterus. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 5 by ePCR.

FIG. 3 provides information on SNPs that have been found in the gene encoding the kinase protein of the present invention. SNPs were identified at 168 different nucleotide positions in introns and regions 5' and 3' of the ORF. Such SNPs in introns and outside the ORF may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45C., followed by one or more washes in 0.2×SSC, 0.1% SDS at 50–65C, Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. 168 SNPs, including 14 indels, have been identified in the gene encoding the kinase protein provided by the present invention and are given in FIG. 3.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 5 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in the brain hippocampus, breast mammary adenocarcinoma cell line, bladder carcinoma cell line by a virtual northern blot. In addition, PCR-based tissue screening panel indicates expression in brain, fetal brain, fetal heart, kidney, uterus. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that kinase proteins of the present invention are expressed in the brain hippocampus, breast mammary adenocarcinoma cell line, bladder carcinoma cell line by a virtual northern blot. In addition, PCR-based tissue screening panel indicates expression in brain, fetal brain, fetal heart, kidney, uterus.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in the brain hippocampus, breast mammary adenocarcinoma cell line, bladder carcinoma cell line, and the tissues of brain, fetal brain, fetal heart, kidney, uterus. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in the brain hippocampus, breast mammary adenocarcinoma cell line, bladder carcinoma cell line by a virtual northern blot. In addition, PCR-based tissue screening panel indicates expression in brain, fetal brain, fetal heart, kidney, uterus. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in the brain hippocampus, breast mammary adenocarcinoma cell line, bladder carcinoma cell line, and the tissues of brain, fetal brain, fetal heart, kidney, uterus.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been found in the gene encoding the kinase protein of the present invention. SNPs were identified at 168 different nucleotide positions in introns and regions 5' and 3' of the ORF. Such SNPs in introns and outside the ORF may affect control/regulatory elements. As indicated by the data presented in FIG. 3, the map position was determined to be on chromosome 5 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been found in the gene encoding the kinase protein of the present invention. SNPs were identified at 168 different nucleotide positions in introns and regions 5' and 3' of the ORF. Such SNPs in introns and outside the ORF may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired linase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that kinase proteins of the present invention are expressed in the brain hippocampus, breast mammary adenocarcinoma cell line, bladder carcinoma cell line by a virtual northern blot. In addition, PCR-based tissue screening panel indicates expression in brain, fetal brain, fetal heart, kidney, uterus. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application W095/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application W095/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been found in the gene encoding the kinase protein of the present invention. SNPs were identified at 168 different nucleotide positions in introns and regions 5' and 3' of the ORF. Such SNPs in introns and outside the ORF may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1 982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11 d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., Nucleic Acids Res. 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kojan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different-vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule comprising a nucleotide sequence selected from the group consisting of:

(a) a transcript or cDNA sequence that encodes a polypeptide having an amino acid sequence comprising SEQ ID NO:2;

(b) SEQ ID NO:1;

(c) nucleotides 3–1190 of SEQ ID NO:1; and (d) a nucleotide sequence that is completely complementary to the nucleotide sequence of (a), (b) or (c).

2. An isolated nucleic acid molecule having a nucleotide sequence comprising SEQ ID NO:1 or the complement thereof.

3. An isolated nucleic acid molecule having a nucleotide sequence comprising nucleotides 3–1190 of SEQ ID NO:1 or the complement thereof.

4. An isolated transcript or cDNA nucleic acid molecule comprising a nucleotide sequence that encodes a polypeptide comprising SEQ ID NO:2, or the complement of said nucleotide sequence.

5. The isolated nucleic acid molecule of claim 1, further comprising a heterologous nucleotide sequence.

6. The isolated nucleic acid molecule of claim 5, wherein the heterologous nucleotide sequence encodes a heterologous amino acid sequence.

7. A vector comprising the nucleic acid molecule of any one of claims 1–6.

8. An isolated host cell containing the vector of claim 7.

9. A process for producing a polypeptide comprising culturing the host cell of claim 8 under conditions sufficient for the production of said polypeptide, and recovering said polypeptide.

10. The vector of claim 7, wherein said vector is selected from the group consisting of a plasmid, a virus, and a bacteriophage.

11. The vector of claim 7, wherein said nucleic acid molecule is inserted into said vector in proper orientation and correct reading frame such that a polypeptide comprising SEQ ID NO:2 is expressed by a cell transformed with said vector.

12. The vector of claim 11, wherein said isolated nucleic acid molecules is operatively linked to a promoter sequence.

* * * * *